(12) United States Patent
Scarlato et al.

(10) Patent No.: US 6,709,660 B1
(45) Date of Patent: Mar. 23, 2004

(54) MENINGOCOCCAL ANTIGENS

(75) Inventors: Vincenzo Scarlato, Siena (IT); Vega Masignani, Siena (IT); Rino Rappuoli, Siena (IT); Mariagrazia Pizza, Siena (IT); Guido Grandi, Siena (IT)

(73) Assignee: Chrion S.r.l., Siena (IT)

( * ) Notice: Subject to any disclaimer, the term of this patent is extended or adjusted under 35 U.S.C. 154(b) by 0 days.

(21) Appl. No.: 09/302,626

(22) Filed: Apr. 30, 1999

Related U.S. Application Data

(63) Continuation-in-part of application No. PCT/IB99/00103, filed on Jan. 14, 1999.

(30) Foreign Application Priority Data

Jan. 14, 1998 (GB) ............................................. 9800760
Sep. 1, 1998 (GB) ............................................. 9819015
Oct. 9, 1998 (GB) ............................................. 9822143

(51) Int. Cl.[7] .......................................... A61K 39/095
(52) U.S. Cl. ............................ 424/250.1; 424/185.1; 424/190.1; 424/234.1; 424/249.1; 530/300; 530/350
(58) Field of Search .......................... 424/250.1, 234.1, 424/185.1, 190.1, 249.1; 530/300, 350

(56) References Cited

U.S. PATENT DOCUMENTS 6,197,312 B1 * 3/2001 Peak et al.
6,200,578 B1 * 3/2001 St. Geme

FOREIGN PATENT DOCUMENTS

| EP | 0 467 714 A1 | 7/1991 |
|---|---|---|
| WO | 95/03413 | 2/1995 |
| WO | 95/33049 | 12/1995 |
| WO | 96/29412 | 9/1996 |
| WO | 96/30519 | 10/1996 |

OTHER PUBLICATIONS

Aldeen et al., "The meningococcal transferrin–binding proteins 1 and 2 are both surface exposed and generate bactericidal antibodies capable of killing homologous and heterologous strains", 1996, Vaccine, 14(1): 49–53.

Constantino et al., "Development and phase 1 clinical testing of a conjugate vaccine against meningococcus A and C", Vaccine, 10: 691–698.

Jafari et al., "Control and Prevention of Meningococcal Disease: Recommendations of the Advisory Committee on Immunization Practices (ACIP)", 1997, MMWR, 46(RR–5): 1–10.

Lieberman et al., "Safety and Immunogenicity of a Serogroups A/C *Neisseria meningitidis* Oligosaccharide–Protein Conjugate Vaccine in Young Children", 1996, JAMA, 275(19): 1499–1503.

Perkins et al., "Control and Prevention of Serogroup C Menengoccal Disease: Evaluation and Management of Suspected Outbreaks: Recommendations fo theAdvisory Committee on Immunization Practices (ACIP)", 1997, MMWR, 46(RR–5): 13–21.

Poolman, "Development of a Mengococcal Vaccine", 1995, Infections Agents and Disease, 4:13–28.

Rokbi et al., "Evaluation of Recombinant Transferrin–Binding Protein B Variants from *Neisseria meningitidis* for Their Ability To Induce Cross–Reactive and Bactericidal Antibodies against a Genetically Diverse Collection of Serogroup B Strains", 1997, Infection and Immunity, 65(1): 55–63.

Rokbi et al., "Heterogeneity of *tbpB*, the Transferrin–Binding Protein B Gene, among Serogroup B *Neisseria meningitidis* Strains of the ET–5 Complex", 1997, Clinical and Diagnostic Lab. Immun., 4(5): 522–529.

Romero et al., "Current Status of Meningococcal Group B Vaccine Candidates: Capsular or Noncapsular?", 1994, Clinical Microbio. Reviews, 7(4): 559–575.

Schuchat et al., "Bacterial Meningitis in the United States in 1995", 1997, New England J. of Medicine, 337(14): 970–976.

Zollinger, "New and Improved Vaccines Against Menigococcal Disease" in : New Generation Vaccines, $2^{nd}$ ed., 1997, pp. 469–488.

Wedege, E., et al., "Human antibody response to a group B serotype 2a meningococcal vaccine determined by immunoblotting," *Infection and Immunity*, Feb. 1986, 51(2), 571–578.

* cited by examiner

*Primary Examiner*—Jennifer E. Graser
(74) *Attorney, Agent, or Firm*—Roberta L. Robins; Alisa A. Harbin; Robert P. Blackburn

(57) ABSTRACT

The invention provides proteins from *Neisseria meningitidis* (strains A & B), including amino acid sequences, the corresponding nucleotide sequences, expression data, and serological data. The proteins are useful antigens for vaccines, immunogenic compositions, and/or diagnostics.

9 Claims, 8 Drawing Sheets

FIGURE 1
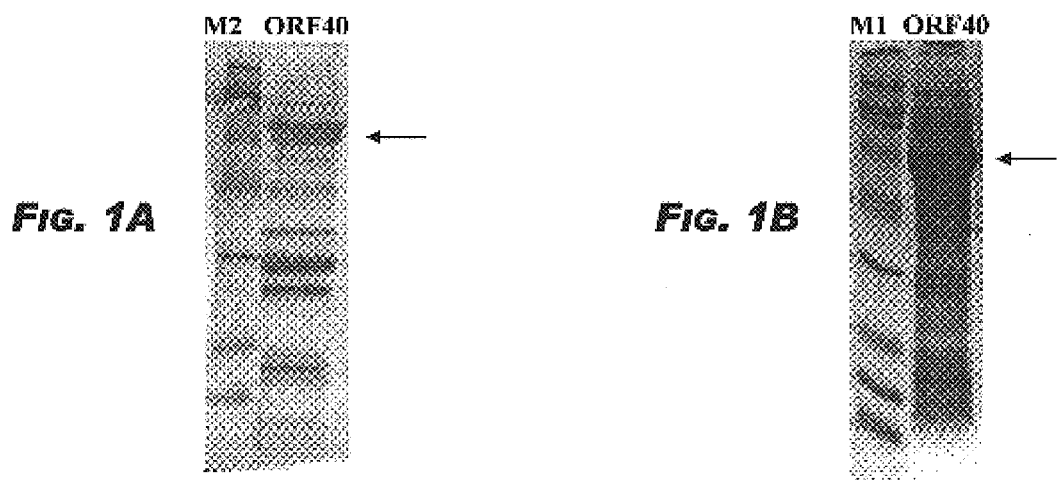
FIG. 1A   FIG. 1B
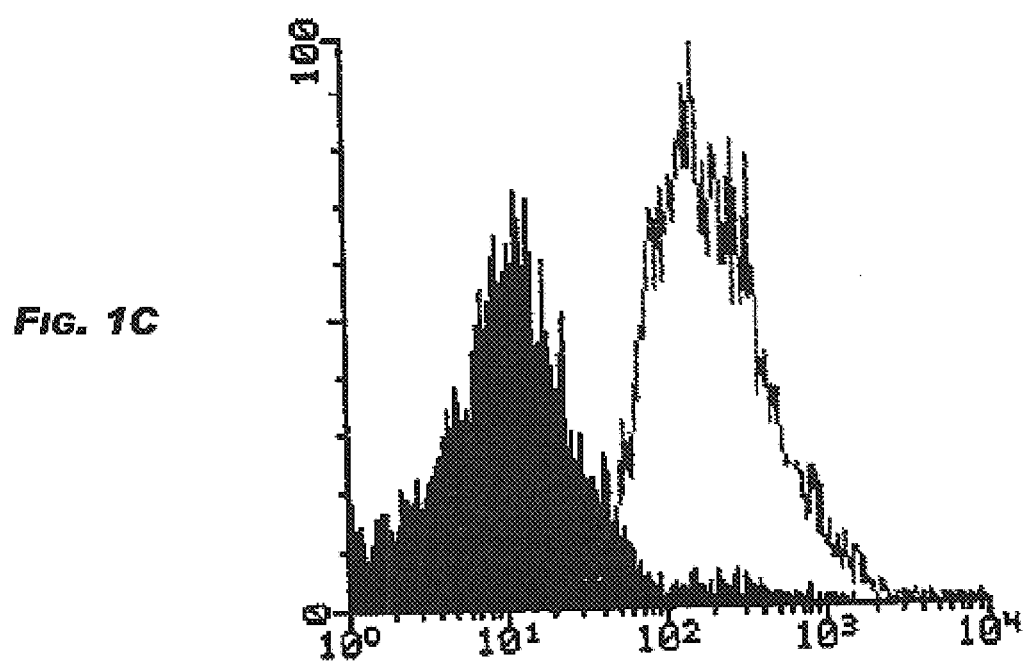
FIG. 1C
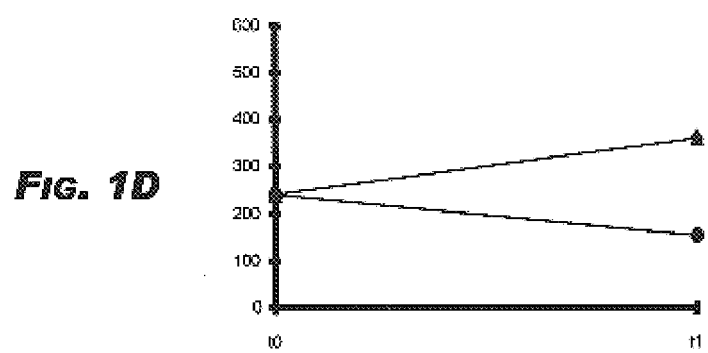
FIG. 1D

FIGURE 2
FIG. 2A
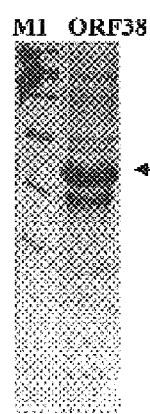
FIG. 2B
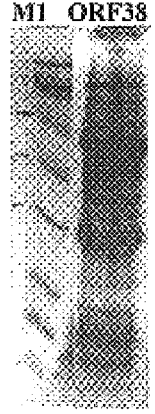
FIG. 2C
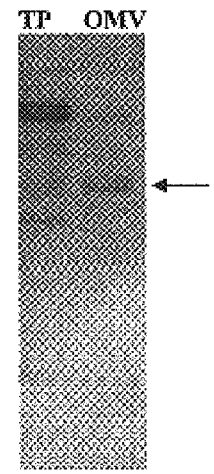
FIG. 2D
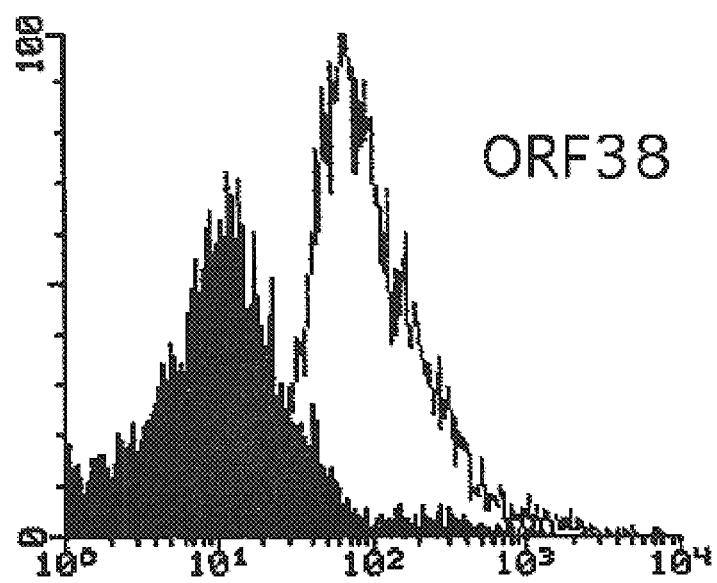

FIGURE 3
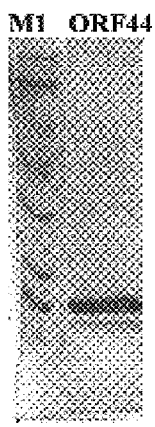
FIG. 3A
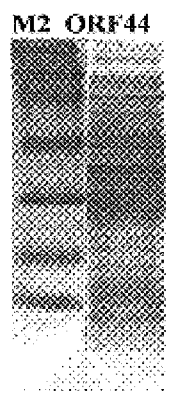
FIG. 3B
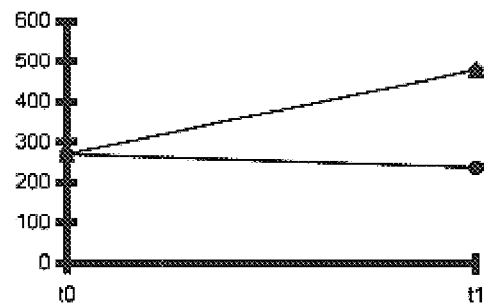
FIG. 3C
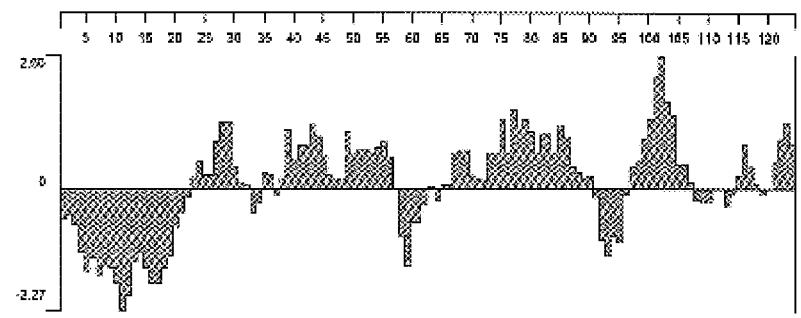
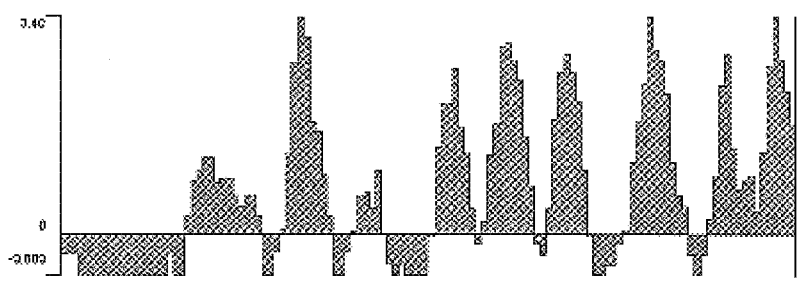
FIG. 3D

FIGURE 4
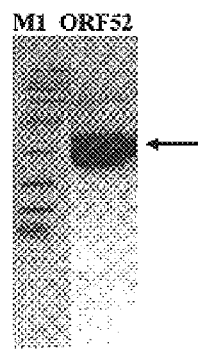
FIG. 4A
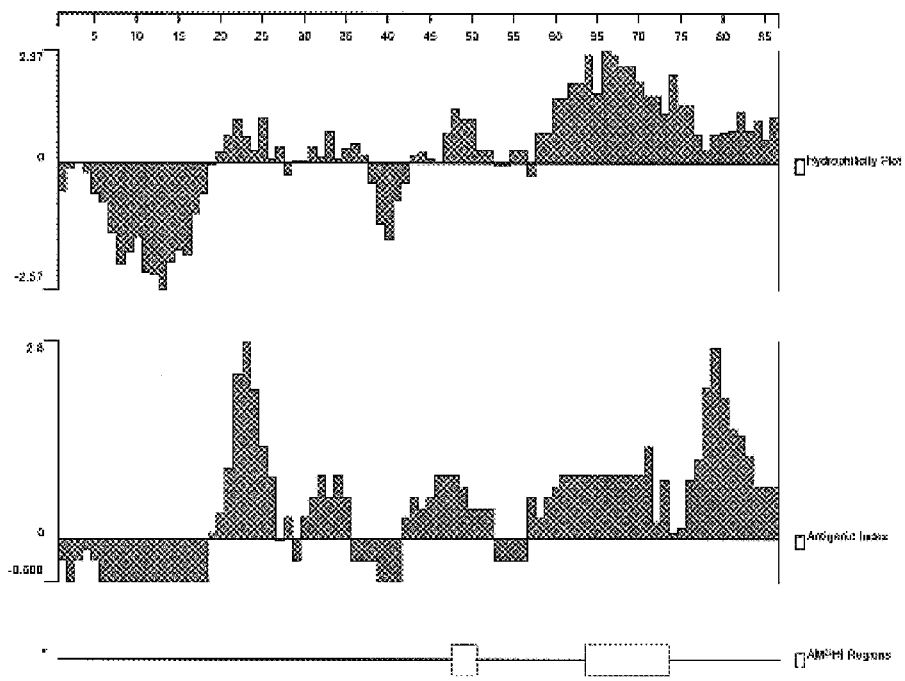
FIG. 4B

MENINGOCOCCAL ANTIGENS

This application is a continuation-in-part of international patent application PCT/IB99/00103, filed Jan. 14, 1999, from which priority is claimed under 35. U.S.C §120, and claims priority under 35. U.S.C §119 to Great Britain application nos. GB9800022143.5, filed on Oct. 9, 1998, GB9819015.0, filed on Sep. 1, 1998, and GB9800760.2, filed on Jan. 14, 1998, all of which are incorporated by reference herein in their entireties.

This invention relates to antigens from the bacterium *Neisseria meningitidis*.

BACKGROUND

*Neisseria meningitidis* is a non-motile, gram negative diplococcus human pathogen. It colonises the pharynx, causing meningitis and, occasionally, septicaemia in the absence of meningitis. It is closely related to *N.gonorrhoeae*, although one feature that clearly differentiates meningococcus from gonococcus is the presence of a polysaccharide capsule that is present in all pathogenic meningococci.

*N.meningitidis* causes both endemic and epidemic disease. In the United States the attack rate is 0.6–1 per 100,000 persons per year, and it can be much greater during outbreaks (see Lieberman et al. (1996) Safety and Immunogenicity of a Serogroups A/C *Neisseria meningitidis* Oligosaccharide-Protein Conjugate Vaccine in Young Children. *JAMA* 275(19):1499–1503; Schuchat et al (1997) Bacterial Meningitis in the United States in 1995. *N Engl J Med* 337(14):970–976). In developing countries, endemic disease rates are much higher and during epidemics incidence rates can reach 500 cases per 100,000 persons per year. Mortality is extremely high, at 10–20% in the United States, and much higher in developing countries. Following the introduction of the conjugate vaccine against *Haemophilus influenzae*, *N. meningitidis* is the major cause of bacterial meningitis at all ages in the United States (Schuchat et al (1997) supra).

Based on the organism's capsular polysaccharide, 12 serogroups of *N.meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries. The meningococcal vaccine currently in use is a tetravalent polysaccharide vaccine composed of serogroups A, C, Y and W135. Although efficacious in adolescents and adults, it induces a poor immune response and short duration of protection, and cannot be used in infants [eg. Morbidity and Mortality weekly report, Vol. 46, No. RR-5 (1997)]. This is because polysaccharides are T-cell independent antigens that induce a weak immune response that cannot be boosted by repeated immunization. Following the success of the vaccination against *H.influenzae*, conjugate vaccines against serogroups A and C have been developed and are at the final stage of clinical testing (Zollinger WD "New and Improved Vaccines Against Meningococcal Disease" in: *New Generation Vaccines*, supra, pp. 469–488; Lieberman et al (1996) supra; Costantino et al (1992) Development and phase I clinical testing of a conjugate vaccine against meningococcus A and C. *Vaccine* 10:691–698).

Meningococcus B remains a problem, however. This serotype currently is responsible for approximately 50% of total meningitis in the United States, Europe, and South America. The polysaccharide approach cannot be used because the menB capsular polysaccharide is a polymer of α(2–8)-linked N-acetyl neuraminic acid that is also present in mammalian tissue. This results in tolerance to the antigen; indeed, if an immune response were elicited, it would be anti-self, and therefore undesirable. In order to avoid induction of autoimmunity and to induce a protective immune response, the capsular polysaccharide has, for instance, been chemically modified substituting the N-acetyl groups with N-propionyl groups, leaving the specific antigenicity unaltered (Romero & Outschoorn (1994) Current status of Meningococcal group B vaccine candidates: capsular or non-capsular? *Clin Microbiol Rev* 7(4):559–575).

Alternative approaches to menB vaccines have used complex mixtures of outer membrane proteins (OMPs), containing either the OMPs alone, or OMPs enriched in porins, or deleted of the class 4 OMPs that are believed to induce antibodies that block bactericidal activity. This approach produces vaccines that are not well characterized. They are able to protect against the homologous strain, but are not effective at large where there are many antigenic variants of the outer membrane proteins. To overcome the antigenic variability, multivalent vaccines containing up to nine different porins have been constructed (eg. Poolman J T (1992) Development of a meningococcal vaccine. *Infect. Agents Dis.* 4:13–28). Additional proteins to be used in outer membrane vaccines have been the opa and opc proteins, but none of these approaches have been able to overcome the antigenic variability (eg. Ala'Aldeen & Borriello (1996) The meningococcal transferrin-binding proteins 1 and 2 are both surface exposed and generate bactericidal antibodies capable of killing homologous and heterologous strains. *Vaccine* 14(1):49–53).

A certain amount of sequence data is available for meningococcal and gonococcal genes and proteins (eg. EP-A-0467714, WO96/29412), but this is by no means complete. The provision of further sequences could provide an opportunity to identify secreted or surface-exposed proteins that are presumed targets for the immune system and which are not antigenically variable. For instance, some of the identified proteins could be components of efficacious vaccines against meningococcus B, some could be components of vaccines against all meningococcal serotypes, and others could be components of vaccines against all pathogenic Neisseriae.

THE INVENTION

The invention provides proteins comprising the *N.meningitidis* amino acid sequences disclosed in the examples.

It also provides proteins comprising sequences homologous (ie. having sequence identity) to the *N.meningitidis* amino acid sequences disclosed in the examples. Depending on the particular sequence, the degree of sequence identity is preferably greater than 50% (eg. 60%, 70%, 80%, 90%, 95%, 99% or more). These homologous proteins include mutants and allelic variants of the sequences disclosed in the examples. Typically, 50% identity or more between two proteins is considered to be an indication of functional equivalence. Identity between the proteins is preferably determined by the Smith-Waterman homology search algorithm as implemented in the MPSRCH program (Oxford Molecular), using an affine gap search with parameters gap open penalty=12 and gap extension penalty=1.

The invention further provides proteins comprising fragments of the *N.meningitidis* amino acid sequences disclosed in the examples. The fragments should comprise at least n consecutive amino acids from the sequences and, depending on the particular sequence, n is 7 or more (eg. 8, 10, 12, 14, 16, 18, 20 or more). Preferably the fragments comprise an epitope from the sequence.

The proteins of the invention can, of course, be prepared by various means (eg. recombinant expression, purification from cell culture, chemical synthesis etc.) and in various forms (eg. native, fusions etc.). They are preferably prepared in substantially pure form (ie. substantially free from other N.meningitidis or host cell proteins).

According to a further aspect, the invention provides antibodies which bind to these proteins. These may be polyclonal or monoclonal and may be produced by any suitable means.

According to a further aspect, the invention provides nucleic acid comprising the N.meningitidis nucleotide sequences disclosed in the examples. In addition, the invention provides nucleic acid comprising sequences homologous (ie. having sequence identity) to the N.meningitidis nucleotide sequences disclosed in the examples.

Furthermore, the invention provides nucleic acid which can hybridise to the N.meningitidis nucleic acid disclosed in the examples, preferably under "high stringency" conditions (eg. 65° C. in a at 0.1×SSC, 0.5% SDS solution).

Nucleic acid comprising fragments of these sequences are also provided. These should comprise at least n consecutive nucleotides from the N.meningitidis sequences and, depending on the particular sequence, n is 10 or more (eg 12, 14, 15, 18, 20, 25, 30, 35, 40 or more).

According to a further aspect, the invention provides nucleic acid encoding the proteins and protein fragments of the invention.

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (eg. expression vectors) and host cells transformed with such vectors.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (eg. as vaccines) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as N.gonorrhoeae) but are preferably N.meningitidis, especially strain A, strain B or strain C.

The invention also provides a method of treating a patient, comprising administering to the patient a therapeutically effective amount of nucleic acid, protein, and/or antibody according to the invention.

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridizing conditions to form duplexes; and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes.

Unlike the sequences disclosed in PCT/IB98/01665, the sequences disclosed in the present application are believed not to have any significant homologs in N.gonorrhoeae. Accordingly, the sequences. of the present invention also find use in the preparation of reagents for distinguishing between N.meningitidis and N.gonorrhoeae A summary of standard techniques and procedures which may be employed in order to perform the invention (eg. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I–IV* (D. M. Weir and C. C. Blackwell eds 1986).

Standard abbreviations for nucleotides and amino acids are used in this specification.

All publications, patents, and patent applications cited herein are incorporated in full by reference.

In particular, the contents of UK patent applications 9800760.2, 9819015.0 and 9822143.5 are incorporated herein.

Definitions

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" eg. a composition "comprising" X may consist exclusively of X or may include something additional to X, such as X+Y.

A "conserved" Neisseria amino acid fragment or protein is one that is present in a particular Neisserial protein in at least x% of Neisseria. The value of x may be 50% or more, e.g., 66%, 75%, 80%, 90%, 95% or even 100% (i.e. the amino acid is found in the protein in question in all Neisseria). In order to determine whether an animo acid is "conserved" in a particular Neisserial protein, it is necessary to compare that amino acid residue in the sequences of the protein in question from a plurality of different Neisseria (a reference population). The reference population may include a number of different Neisseria species or may include a single species. The reference population may include a number of different serogroups of a particular species or a single serogroup. A preferred reference population consists of the 5 most common Neisseria.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (eg. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753,235).

Expression Systems

The Neisserial nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the, TATA box. An upstream promoter element determines the rate at which transcription is initiated and can act in either orientation [Sambrook et al. (1989) "Expression of Cloned Genes in Mammalian Cells." In *Molecular Cloning. A Laboratory Manual, 2nd ed.*].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gormnan et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Ternmination and 3' end processing of eukaryotic RNA. In *Transcription and splicing* (ed. B. D. Hames and D. M. Glover); Proudfoot (1989) *Trends Biochem. Scip.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Usually, the above described components, comprising a promoter, polyadenylation signal, and transcription termination sequence are put together into expression constructs. Enhancers, introns with fimctional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufinan et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (eg. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler);, EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene*, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human cc-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA*, 82:8404; mouse IL-3, (Miyajima et al., (1987) *Gene* 58:273; and human glucocerebrosidase, Martin et al. (1988) *DNA*, 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, eg. proteins, lipids and polysaccharides.

In order to obtain protein expression, recombinant host cells derived from the transforrnants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861–3863 (1991). Descriptions of plant protein signal peptides may be found in addition to the references described above in Vaulcombe et al., *Mol. Gen. Genet.* 209:33–40 (1987); Chandler et al., *Plant Molecular Biology* 3:407–418 (1984); Rogers, *J. Biol. Chem.* 260:3731–3738 (1985); Rothstein et al., *Gene* 55:353–356 (1987); Whittier et al., Nucleic Acids Research 15:2515–2535 (1987); Wirsel et al., *Molecular Microbiology* 3:3–14 (1989); Yu et al., *Gene* 122:247–253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology,*. Malcolm B. Wilkins, ed., 1984 Pitman Publishing Limited, London, pp. 21–52. References that describe other metabolically-regulated genes: Sheen, *Plant Cell*, 2:1027–1038(1990); Maas et al., *EMBO J.* 9:3447–3452 (1990); Benkel and Hickey, *Proc. Natl. Acad. Sci.* 84:1337–1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr*, 11 (2):165–185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequenceencoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically, secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed rnutagenesis of the "intron" region may be conducted to prevent losing a portion of the genetic message as a false intron code, Reed and Maniatis, *Cell* 41:95–105, 1985.

The vector can be microinjected directly into plant cells by use of micropipettes to mechanically transfer the recombinant DNA. Crossway, *Mol. Gen. Genet*, 202:179–185, 1985. The genetic material may also be transferred into the plant cell by using polyethylene glycol, Krens, et al., *Nature*, 296, 72–74, 1982. Another method of introduction of nucleic acid segments is high velocity ballistic penetration by small particles with the nucleic acid either within the matrix of small beads or particles, or on the surface, Klein, et al., *Nature*, 327, 70–73, 1987 and Knudsen and Muller, 1991, *Planta*, 185:330–336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA*, 79, 1859–1863, 1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in Escherichia coli (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other-mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc. Natl. Acad. Sci.* 82:1074]. In addition, a hybrid promoter can also be comprised of a bacteriophage promoter and an *E. coli* operator region (EPO-A-0 267 851).

In addition to a fumctioning promoter sequence, an efficient ribosome binding site is also useful for the expression of foreign genes in prokaryotes. In *E. coli*, the ribosome binding site is called the Shine-Dalgamo (SD) sequence and includes an initiation codon (ATG) and a sequence 3–9 nucleotides in length located 3–11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various Bacillus strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: Bacillus subtilis [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amaann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], Streptomyces lividans [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, Bacillus], [Miller et al. (1988) *Proc. Natl. Acad. Sci.* 85:856; Wang et al. (1990) *J. Bacteriol.* 172:949, Campylobacter], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; Escherichia], [Chassy et al. (1987) *FEMS Microbiol. Lett.* 44:173 Lactobacillus]; [Fiedler et al. (1988) *Anal. Biochem* 170:38, Pseudomonas]; [Augustin et al. (1990) *FEMS Microbiol. Lett.* 66:203, Staphylococcus], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, Streptococcus].

v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also fuinction as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an niRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17–24], pC1/1 [Brake et al. (1984) *Proc. Natl. Acad. Sci USA* 81:4642–4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228–245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837, 148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141; Candida]; [Gleeson et al. (1986) *J. Gen. Microbiol.* 132:3459; Roggenkamp et al. (1986) *Mol. Gen. Genet* 202:302; Hansenula]; [Das et al. (1984) *J. Bacteriol.* 158:1165; De Louvencourt et al. (1983) *J. Bacteriol.* 154:1165; Van den Berg et al. (1990) *Bio/Technology* 8:135; Kluyveromyces]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; Pichia]; [Hinnen et al. (1978) *Proc. Natl. Acad. Sci. USA* Ito et al. (1983) *J. Bacteriol.* 153:163 Saccharomyces]; [Beach and Nurse (1981) *Nature* 300:706; Schizosaccharomyces]; [Davidow et al. (1985) *Curr. Genet.* 10:39; Gaillardin et al. (1985) *Curr. Genet.* 10:49; Yarrowia].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies. Antibodies against the proteins of the invention are useful for affinity chromatography, immunoassays, and distinguishing/identifying Neisserial proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50–200 μg/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2–18 hours. The serum is recovered by centrifugation (eg. 1,000 g for 10 minutes). About 20–50 ml per bleed may be obtained from rabbits.

Monoclonal antibodies are prepared using the standard method of Kohler & Milstein [*Nature* (1975) 256:495–96], or a modification thereof Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}$P and $^{125}$I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}$I, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (ie. to prevent infection) or therapeutic (ie. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, *cholera, H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containingvarious amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detoxam); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normnuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/ nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effecfive amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [eg. Robinson & Torres (1997) *Seminars in Immunology* 9:271–283; Donnelly et al. (1997) *Annu Rev Immunol* 15:617–648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picomavirus, poxvirus, or togavirus viral vector. See generally, Jolly (1994) *Cancer Gene Therapy* 1:51–64; Kimura (1994) *Human Gene Therapy* 5:845–852; Connelly (1995) *Human Gene Therapy* 6:185–193; and Kaplitt (1994) *Nature Genetics* 6:148–153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9–1 (see O'Neill (1985) *J. Virol*. 53:160) polytropic retroviruses eg, MCF and MCF-MLV (see Kelly (1983) *J. Virol*. 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19–25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Maryland or isolated from known sources using commnonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See (1993) *Cancer Res* 53:3860–3864; Vile (1993) *Cancer Res* 53:962–967; Ram (1993) *Cancer Res* 53 (1993) 83–88; Takamiya (1992) *J Neurosci Res* 33:493–503; Baba (1993) *J Neurosurg* 79:729–735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147–154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleofides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257–262. Another example of such an AAV vector is psub20l (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463–470. Additional AAV gene therapy vectors are described in U.S. Pat. No. 5,354, 678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667–1669 and in WO90/09441 and WO92/07945, HSV Us3::pgC-lacZ described in Fink (1992) *Human Gene Therapy* 3:11–19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc NatlAcad Sci* 86:317; Flexner (1989) *Ann NY Acad Sci* 569:86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S.

Pat. No. 5,166,057 and in Enami (1990) *Proc Natl Acad Sci* 87:3802–3805; Enami & Palese (1991) *J Virol* 65:2711–2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147–154 ligand linked DNA, for example see Wu (1989) *J Biol Chem* 264:16985–16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or filsion with cell membranes. Additional approaches are described in Philip (1994) *Mol Cell Biol* 14:2411–2418 and in Woffendin (1994) *Proc Natl Acad Sci* 91:1581–1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429–4432, insulin as described in Hucked (1990) *Biochem Pharmacol* 40:253–263, galactose as described in Plank (1992) *Bioconjugate Chem* 3:533–539, lactose or transferrin.

Naked DNA may also be employed. Exemplary naked DNA introduction methods are described in WO 90/11092 and U.S. Pat. No. 5,580,859. Uptake efficiency rnay be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for; high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236–240 (1975) W. H. Freeman, San Francisco; Szoka (1980) *Biochem Biophys Acta* 600: 1; Bayer (1979) *Biochem Biophys Acta* 550:464; Rivnay (1987) *Meth Enzymol* 20 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of plasmodium falciparum known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1–17; Straubinger (1983) *Meth. Enzymol.* 101:512–527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413–7416); mRNA (Malone (1989) *Proc. Natl. Acad. Sci. USA* 86:6077–6081); and purified transcription factors (Debs (1990) *J. Biol. Chem.* 265:10189–10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *Proc. Natl. Acad. Sci. USA* 75:4194–4198; WO90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512–527; Szoka (1978) *Proc. Natl. Acad. Sci. USA* 75:4194–4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) *Annu Rev. Biochem* 54:699; Law (1986) *Adv. Exp Med. Biol.* 151:162; Chen (1986) *J Biol Chem* 261:12918; Kane (1980) *Proc Natl Acad Sci USA* 77:2465; and Utermann (1984) *Hum Genet* 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454–5460 and Mahey (1979) *J Clin. Invest* 64:743–750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30:443. Lipoproteins can also be purchased from commercial suppliers, such as Biomedical Techniologies, Inc., Stoughton, Mass., USA. Further description of lipoproteins can be found in Zuckermann et al. PCT/US97/14465.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are usefuil include, for example, DEAE-dextran, polybrene. Lipofectin™, and lipofectAMINE™ are monomers that form polycationic complexes when combined with polynucleotides/polypeptides.

Immunodiagnostic Assays

Neisserial antigens of the invention can be used in immunoassays to detect antibody levels (or, conversely, anti-Neisserial antibodies can be used to detect antigen levels). Immunoassays based on well defined, recombinant antigens can be developed to replace invasive diagnostics methods. Antibodies to Neisserial proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment (s) to be studied can vary a magnitude of 10, from 0.1 to 1 $\mu$g for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 $\mu$g of yeast DNA, blotting for two hours, and hybridizing for 4–8 hours with a probe of $10^8$ cpm/$\mu$g. For a single-copy mammalian gene a conservative approach would start with 10 $\mu$g of DNA, blot overnight, and hybridize overnight in the presence of 10% dextran sulfate using a probe of greater than $10^8$ cpm/$\mu$g, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6(\%formamide)-600/n-1.5(\%mismatch).$$

where Ci is the salt concentration (monovalent ions) and n is the length of the hybrid in base pairs (slightly modified from Meinkoth & Wahl (1984) *Anal. Biochem.* 138: 267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (ie. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the Neisserial nucleotide sequences of the invention (including both sense and antisense strands). Though many different nucleotide sequences will encode the amino acid sequence, the native Neisserial sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the Neisserial sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional Neisserial sequence may also be helpful as a label to detect the formed duplex. For example, a non-complementary nucleotide sequence may be attached to the 5' end of the probe, with the remainder of the probe sequence being complementary to a Neisserial sequence. Alternatively, non-complementary bases or longer sequences can be interspersed into the probe, provided that the probe sequence has sufficient complementarity with the a Neisserial sequence in order to hybridize therewith and thereby form a duplex which can be detected.

The exact length and sequence of the probe will depend on the hybridization conditions, such as temperature, salt condition and the like. For example, for diagnostic applications, depending on the complexity of the analyte sequence, the nucleic acid probe typically contains at least 10–20 nucleotides, preferably 15–25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated eg. backbone modifications, such as phosphorothioates or methylphosphonates, can be used to increase in vivo half-life, alter RNA affinity, increase nuclease resistance etc. [eg. see Agrawal & Iyer (1995) *Curr Opin Biotechnol* 6:12–19; Agrawal (1996) *TIBTECH* 14:376–387]; analogues such as peptide nucleic acids may also be used [eg. see Corey (1997) *TIBTECH* 15:224–229; Buchardt et al. (1993) *TIBTECH* 11:384–386].

Alternatively, the polymerase chain reaction (PCR) is another well-known means for detecting small amounts of target nucleic acids. The assay is described in: Mullis et al. [*Meth. Enzytmnol.* (1987) 155: 335–350]; U.S. Pat. Nos. 4,683,195 and 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired Neisserial sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the Neisserial sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

BRIEF DESCRIPTION OF THE DRAWINGS

FIGS. 1A–E show biochemical data and sequence analysis pertaining to ORF 40. FIG. 1A shows the results of affinity purification and FIG. 1B shows the results of expression of the GST-fusion in *E. coli*, where M2 and M1 are molecular weight markers, and Arrows indicate the position of the main recombinant product. FIG. 1C shows the results of FACS analysis of the sera of mice that were immunized with the purified protein. FIG. 1D shows the results of bactericidal assay where a diamond (♦) shows preimmune data; a triangle (▲) shows GST control data; and a circle (●) shows data with recombinant *N.meningitidis* protein. FIG. 1E shows computer analysis showing a hydrophilicity plot (upper), an antigenic index plot (middle), and an AMPHI analysis (lower). The AMPHI program has been used to predict T-cell epitopes (Gao et al. (1989) *J. Immunol.* 143:3007; Roberts et al. (1996) *AIDS Res Hum Retrovir* 12:593; Quakyi et al. (1992) *Scad J. Immunol suppl.* 11:9) and is available in the Protean Package of DNASTAR, Inc. (1228 South Park Street, Madison, Wis. 53715 USA).

FIGS. 2A–E show biochemical data and sequence analysis pertaining to ORF 38–1. FIG. 2A shows the results of affinity purification and FIG. 2B shows the results of expression of the GST-fusion in *E. coli*, where M2 and M1 are molecular weight markers, and Arrows indicate the position of the main recombinant product. FIG. 2C shows the results of FACS analysis of the sera of mice that were immunized with the purified protein. FIG. 2D shows the results of bactericidal assay where a diamond (♦) shows preimmune data; a triangle (▲) shows GST control data; and a circle (●) shows data with recombinant *N.meningitidis* protein. FIG. 2E shows plots of hydrophilicity plot (upper), an antigenic index plot (middle), and an AMPHI analysis (lower).

FIGS. 3A–D show biochemical data and sequence analysis pertaining to ORF 44–1. FIG. 3A shows the results of affinity purification and FIG. 3B shows the results of expression of the GST-fusion in *E. coli*, where M2 and M1 are molecular weight markers, and Arrows indicate the position of the main recombinant product. FIG. 3C shows the results of bactericidal assay where a diamond (+) shows preimmune data; a triangle (▲) shows GST control data; and a circle (●) shows data with recombinant *N.meningitidis* protein. FIG. 3D shows plots of hydrophilicity plot (upper), an antigenic index plot (middle), and an AMPHI analysis (lower).

FIG. 4A shows the results of affinity purification of ORF 52, where M1 is a molecular weight marker, and the arrow indicates the position of the main recombinant product. FIG. 4B shows a hydrophilicity plot (upper), an antigenic index plot (middle), and an AMPHI analysis (lower).

FIG. 8 shows an alignment comparison of amino acid sequences for ORF 40 for several strains of Neisseria (zn07_1, SEQ ID NO:96; zn20_1, SEQ ID NO:104; zn21_1, SEQ ID NO:105; zn06_1, SEQ ID NO:95; zn19_1, SEQ ID NO:103; zn03_1, SEQ ID NO:93; zn18_1, SEQ ID NO:102; zn11_ass, SEQ ID NO:99; zn02_1, SEQ ID NO:92; zn04_1, SEQ ID NO:94; zn16_1, SEQ ID NO:101; zn14_1, SEQ ID NO:100; z2491, SEQ ID NO:91; zn10_1, SEQ ID NO:98; zn22_1, SEQ ID NO:106; zn23_1, SEQ ID NO: 107; zn28_ass, SEQ ID NO: 110; zn24_1, SEQ ID NO: 108; zn25_ass, SEQ ID NO:109; zn08_1, SEQ ID NO:97; zn29_ass, SEQ ID NO:111). Dark shading indicates regions of homology, and gray shading indicates the conservation of amino acids with similar characteristics. The Figure demonstrates a high degree of conservation among the various strains, further confirming its utility as an antigen for both vaccines and diagnostics.

EXAMPLES

Figure 1E:
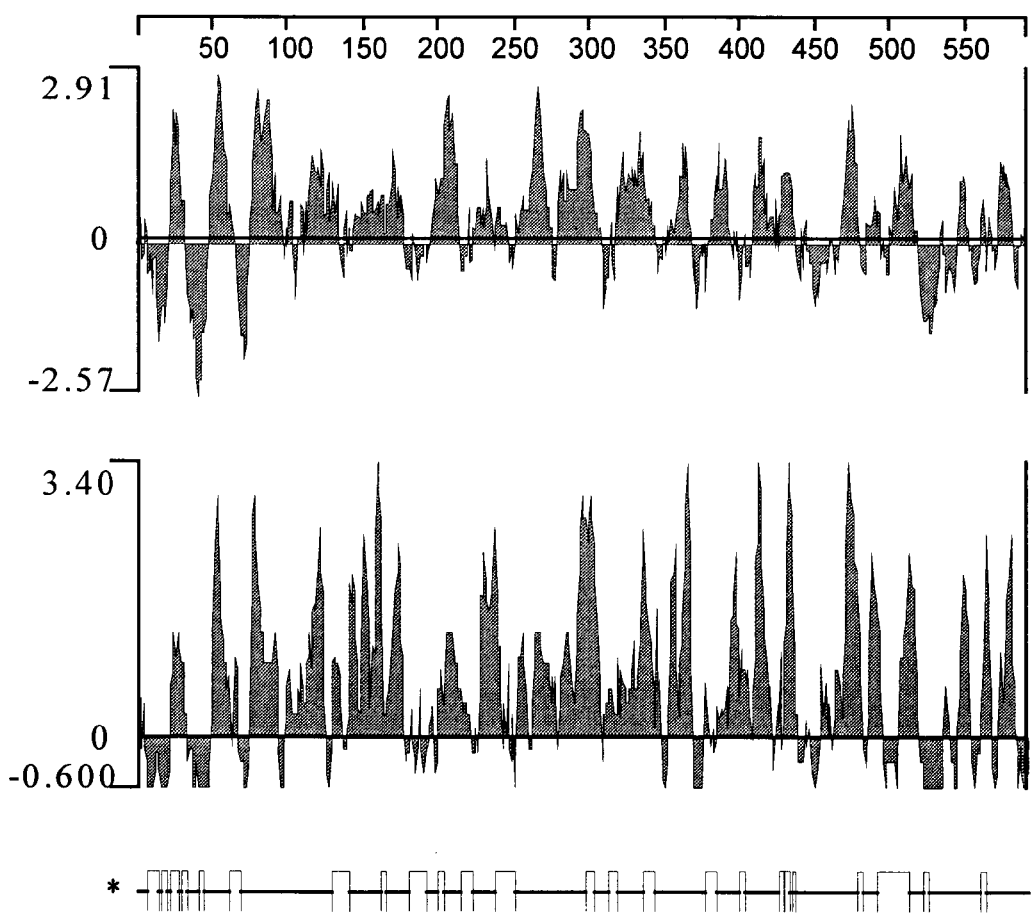

The examples describe nucleic acid sequences which have been identified in *N.meningitidis*, along with their putative translation products. Not all of the nucleic acid sequences are complete ie. they encode less than the full-length wild-type protein. It is believed at present that none of the DNA sequences described herein have significant homologs in *N.gonorrhoeae*.

The examples are generally in the following format:

a nucleotide sequence which has been identified in *N.meningitidis* (strain B)

the putative translation product of this sequence a computer analysis of the translation product based on database comparisons a corresponding gene and protein sequence identified in *N.meningitidis* (strain A)

a description of the characteristics of the proteins which indicates that they might be suitably antigenic results of biochemical analysis (expression, purification, ELISA, FACS etc.)

The examples typically include details of sequence homology between species and strains. Proteins that are similar in sequence are generally similar in both structure and function, and the homology often indicates a common evolutionary origin. Comparison with sequences of proteins of known function is widely used as a guide for the assignment of putative protein function to a new sequence and has proved particularly useful in whole-genome analyses.

Sequence comparisons were performed at NCBI (http://www.ncbi.nlm.nih.gov) using the algorithms BLAST, BLAST2, BLASTn, BLASTp, tBLASTn, BLASTx, & tBLASTx [eg. see also Altschul et al. (1997) Gapped BLAST and PSI-BLAST: a new generation of protein database search programs. *Nucleic Acids Research* 25:2289–3402]. Searches were performed against the following databases: non-redundant GenBank+EMBL+DDBJ+PDB sequences and non-redundant GenBank CDS translations+PDB+SwissProt+SPupdate+PIR sequences.

Dots within nucleotide sequences (eg. position 288 in Example 12) represent nucleotides which have been arbitrarily introduced in order to maintain a reading frame. In the same way, double-underlined nucleotides were removed. Lower case letters (eg. position 589 in Example 12) represent ambiguities which arose during alignment of independent sequencing reactions (some of the nucleotide sequences in the examples are derived from combining the results of two or more experiments).

Nucleotide sequences were scanned in all six reading frames to predict the presence of hydrophobic domains using an algorithm based on the statistical studies of Esposti et al. [Critical evaluation of the hydropathy of membrane proteins (1990) *Eur J Biochem* 190:207–219]. These domains represent potential transmembrane regions or hydrophobic leader sequences.

Open reading frames were predicted from fragmented nucleotide sequences using the program ORFFINDER (NCBI).

Underlined amino acid sequences indicate possible transmembrane domains or leader sequences in the ORFs, as predicted by the PSORT algorithm (http://www.psort.nibb.ac.jp). Functional domains were also predicted using the MOTIFS program (GCG Wisconsin & PROSITE).

Various tests can be used to assess the in vivo immunogenicity of the proteins identified in the examples. For example, the proteins can be expressed recombinantly and used to screen patient sera by immunoblot. A positive reaction between the protein and patient serum indicates that the patient has previously mounted an immune response to the protein in question ie. the protein is an immunogen. This method can also be used to identify immunodominant proteins.

The recombinant protein can also be conveniently used to prepare antibodies eg. in a mouse. These can be used for direct confirmation that a protein is located on the cell-surface. Labelled antibody (eg. fluorescent labelling for FACS) can be incubated with intact bacteria and the presence of label on the bacterial surface confirms the location of the protein.

In particular, the following methods (A) to (S) were used to express, purify and biochemically characterise the proteins of the invention:

A) Chromosomal DNA Preparation

*N.meningitidis* strain 2996 was grown to exponential phase in 100 ml of GC medium, harvested by centrifugation, and resuspended in 5 ml buffer (20% Sucrose, 50 mM Tris-HCl, 50 mM EDTA, pH8). After 10 minutes incubation on ice, the bacteria were lysed by adding 10 ml lysis solution (50 mM NaCl, 1% Na-Sarkosyl, 50 μg/ml Proteinase K), and the suspension was incubated at 37° C. for 2 hours. Two phenol extractions (equilibrated to pH 8) and one ChCl$_3$/isoamylalcohol (24:1) extraction were performed. DNA was precipitated by addition of 0.3M sodium acetate and 2 volumes ethanol, and was collected by centrifugation. The pellet was washed once with 70% ethanol and redissolved in 4 ml buffer (10 mM Tris-HCl, 1 mM EDTA, pH 8). The DNA concentration was measured by reading the OD at 260 nm.

B) Oligonucleotide Design

Synthetic oligonucleotide primers were designed on the basis of the coding sequence of each ORF, using (a) the meningococcus B sequence when available, or (b) the gonococcus/meningococcus A sequence, adapted to the codon preference usage of meningococcus as necessary. Any predicted signal peptides were omitted, by deducing the 5'-end amplification primer sequence immediately downstream from the predicted leader sequence.

The 5' primers included two restriction enzyme recognition sites (BamHI-NdeI, BamHI-NheI, or EcoRI-NheI, depending on the gene's own restriction pattern); the 3' primers included a XhoI restriction site. This procedure was established in order to direct the cloning of each amplification product (corresponding to each ORF) into two different expression systems: pGEX-KG (using either BamHI-XhoI or EcoRI-XhoI), and pET21b+ (using either NdeI-XhoI or NheI-XhoI).

| | | | |
|---|---|---|---|
| 5'-end primer tail: | CGCGGATCCCATATG | (BamHI-NdeI) | (SEQ ID NO:134) |
| | CGCGGATCCGCTAGC | (BamHI-NheI) | (SEQ ID NO:135) |
| | CCGGAATTCTAGCTAGC | (EcoRI-NheI) | (SEQ ID NO:136) |
| 3'-end primer tail: | CCCGCTCGAG | (XhoI) | (SEQ ID NO:137) |

As well as containing the restriction enzyme recognition sequences, the primers included nucleotides which hybridised to the sequence to be amplified. The number of hybridizing nucleotides depended on the melting temperature of the whole primer, and was determined for each primer using the formulae:

| | |
|---|---|
| $T_m = 4 (G+C) + 2 (A+T)$ | (tail excluded) |
| $T_m = 64.9 + 0.41 (\% GC) - 600/N$ | (whole primer) |

The average melting temperature of the selected oligos were 65–70° C. for the whole oligo and 50–55° C. for the hybridising region alone.

Table I shows the forward and reverse primers used for each amplification. Oligos were synthesized by a Perkin Elmer 394 DNA/RNA Synthesizer, eluted from the columns in 2 ml NH$_{40}$H, and deprotected by 5 hours incubation at 56° C. The oligos were precipitated by addition of 0.3M Na-Acetate and 2 volumes ethanol. The samples were then centrifuged and the pellets resuspended in either 100 μl or 1 ml of water. OD$_{260}$ was determined using a Perkin Elmer Lambda Bio spectrophotometer and the concentration was determined and adjusted to 2–10 μmol/μl.

TABLE I

PCR primers

| ORF | Primer | Sequence | Restriction sites |
|---|---|---|---|
| ORF 38 | Forward | CGCGGATCCCATATG-TCGCCGCAAAATTCCGA <SEQ ID 112> | BamHI-NdeI |
|  | Reverse | CCCGCTCGAG-TTTTGCCGCGTTAAAAGC <SEQ ID 113> | XhoI |
| ORF 40 | Forward | CGCGGATCCCATATG-ACCGTGAAGACCGCC <SEQ ID 114> | BamHI-NdeI |
|  | Reverse | CCCGCTCGAG-CCACTGATAACCGACAGA <SEQ ID 115> | XhoI |
| ORF 41 | Forward | CGCGGATCCCATATG-TATTTGAAACAGCTCCAAG <SEQ ID 116> | BamHI-NdeI |
|  | Reverse | CCCGCTCGAG-TTCTGGGTGAATGTTA <SEQ ID 117> | XhoI |
| ORF 44 | Forward | GCGGATCCCATATG-GGCACGGACAACCCC <SEQ ID 118> | BamHI-NdeI |
|  | Reverse | CCCGCTCGAG-ACGTGGGGAACAGTCT <SEQ ID 119> | XhoI |
| ORF 51 | Forward | GCGGATCCCATATG-AAAAATATTCAAGTAGTTGC <SEQ ID 120> | BamHI-NdeI |
|  | Reverse | CCCGCTCGAG-AAGTTTGATTAAACCCG <SEQ ID 121> | XhoI |
| ORF 52 | Forward | CGCGGATCCCATATG-TGCCAACCGCAATCCG <SEQ ID 122> | BamHI-NdeI |
|  | Reverse | CCCGCTCGAG-TTTTTCCAGCTCCGGCA <SEQ ID 123> | XhoI |
| ORF 56 | Forward | GCGGATCCCATATG-GTTATCGGAATATTACTCG <SEQ ID 124> | BamHI-NdeI |
|  | Reverse | CCCGCTCGAG-GGCTCCAGAAGCTGG <SEQ ID 125> | XhoI |
| ORF 69 | Forward | CGCGGATCCCATATG-CGGACGTGGTTGGTTTT <SEQ ID 126> | BamHI-NdeI |
|  | Reverse | CCCGCTCGAG-ATATCTTCCGTTTTTTTCAC <SEQ ID 127> | XhoI |
| ORF 82 | Forward | CGCGGATCCGCTAGC-GTAAATTTATTATTTTTAGAA <SEQ ID 128> | BamHI-NheI |
|  | Reverse | CCCGCTCGAG-TTCCAACTCATTGAAGTA <SEQ ID 129> | XhoI |
| ORF 114 | Forward | CGCGGATCCCATATG-AATAAAGGTTTACATCGCAT <SEQ ID 130> | BamHI-NheI |
|  | Reverse | CCCGCTCGAG-AATCGCTGCACCGGCT <SEQ ID 131> | XhoI |
| ORF 124 | Forward | CGCGGATCCCATATG-ACTGCCTTTTCGACA <SEQ ID 132> | BamHI-NheI |
|  | Reverse | CCCGCTCGAG-GCGTGAAGCGTCAGGA <SEQ ID 133> | XhoI |

C) Amplification

The standard PCR protocol was as follows: 50–200 ng of genomic DNA were used as a template in the presence of 20–40 µM of each oligo, 400–800 µM dNTPs solution, 1×PCR buffer (including 1.5 mM $MgCl_2$), 2.5 units TaqI DNA polymerase (using Perkin-Elmer AmpliTaQ, GIBCO Platinum, Pwo DNA polymerase, or Tahara Shuzo Taq polymerase).

In some cases, PCR was optimised by the addition of 10 µl DMSO or 50 µl 2M betaine.

After a hot start (adding the polymerase during a preliminary 3 minute incubation of the whole mix at 95° C.), each sample underwent a double-step amplification: the first 5 cycles were performed using as the hybridization temperature the one of the oligos excluding the restriction enzymes tail, ollowed by 30 cycles performed according to the hybridization temperature of the whole length oligos. The cycles were followed by a final 10 minute extension step at 72° C.

The standard cycles were as follows:

|  | Denaturation | Hybridisation | Elongation |
|---|---|---|---|
| First 5 cycles | 30 seconds 95° C. | 30 seconds 50–55° C. | 30–60 seconds 72° C. |
| Last 30 cycles | 30 seconds 95° C. | 30 seconds 65–70° C. | 30–60 seconds 72° C. |

The elongation time varied according to the length of the ORF to be amplified.

The amplifications were performed using either a 9600 or a 2400 Perkin Elmer GeneAmp PCR System. To check the results, 1/10 of the amplification volume was loaded onto a 1–1.5% agarose gel and the size of each amplified fragment compared with a DNA molecular weight marker.

The amplified DNA was either loaded directly on a 1% agarose gel or first precipitated with ethanol and resuspended in a suitable volume to be loaded on a 1% agarose gel. The DNA fragment corresponding to the right size band was then eluted and purified from gel, using the Qiagen Gel Extraction Kit, following the instructions of the manufacturer. The final volume of the DNA fragment was 30 µl or 50 µl of either water or 10 mM Tris, pH 8.5.

D) Digestion of PCR Fragments

The purified DNA corresponding to the amplified fragment was split into 2 aliquots and double-digested with:

NdeI/XhoI or NheI/XhoI for cloning into pET-21b+ and further expression of the protein as a C-terminus His-tag fusion BamHI/XhoI or EcoRI/XhoI for cloning into pGEX-KG and further expression of the protein as N-terminus GST fusion.

EcoRI/PstI, EcoRI/SalI, SalI/PstI for cloning into pGex-His and further expression of the protein as N-terminus His-tag fusion Each purified DNA fragment was incubated (37° C. for 3 hours to overnight) with 20 units of each restriction enzyme (New England Biolabs) in a either 30 or 40 µl final volume in the presence of the appropriate buffer. The digestion product was then purified using the QIAquick PCR purification kit, following the manufacturer's instructions, and eluted in a final volume of 30 or 50 µl of either water or 10 mM Tris-HCl, pH 8.5. The final DNA concentration was determined by 1% agarose gel electrophoresis in the presence of titrated molecular weight marker.

E) Digestion of the Cloning Vectors (pET22B, pGEX-KG, pTRC-His A, and pGex-His)

10 µg plasmid was double-digested with 50 units of each restriction enzyme in 200 µl reaction volume in the presence of appropriate buffer by overnight incubation at 37° C. After loading the whole digestion on a 1% agarose gel, the band corresponding to the digested vector was purified from the gel using the Qiagen QIAquick Gel Extraction Kit and the DNA was eluted in 50 µl of 10 mM Tris-HCl, pH 8.5. The DNA concentration was evaluated by measuring $OD_{260}$ of the sample, and adjusted to 50 µg/µl. 1 µl of plasmid was used for each cloning procedure.

The vector pGEX-His is a modified pGEX-2T vector carrying a region encoding six histidine residues upstream to the thrombin cleavage site and containing the multiple cloning site of the vector pTRC99 (Pharmacia).

F) Cloning

The fragments corresponding to each ORF, previously digested and purified, were ligated in both pET22b and pGEX-KG. In a final volume of 20 µl, a molar ratio of 3:1 fragrnent/vector was ligated using 0.5 µl of NEB T4 DNA ligase (400 units/µl), in the presence of the buffer supplied by the manufacturer. The reaction was incubated at room temperature for 3 hours. In some experiments, ligation was performed using the Boehringer "Rapid Ligation Kit", following the manufacturer's instructions.

In order to introduce the recombinant plasmid in a suitable strain, 100 µl E. coli DH5 competent cells were incubated with the ligase reaction solution for 40 minutes on ice, then at 37° C. for 3 minutes, then, after adding 800 µl LB broth, again at 37° C. for 20 minutes. The cells were then centrifuged at maximum speed in an Eppendorf microfuge and resuspended in approximately 200 µl of the supernatant. The suspension was then plated on LB ampicillin (100 mg /ml).

The screening of the recombinant clones was performed by growing 5 randomly-chosen colonies overnight at 37° C. in either 2 ml (PGEX or pTC clones) or 5 ml (pET clones) LB broth+100 µg/ml ampicillin. The cells were then pelletted and the DNA extracted using the Qiagen QIAprep Spin Miniprep Kit, following the manufacturer's instructions, to a final volume of 30 µl. 5 µl of each individual miniprep (approximately 1 g) were digested with either NdeI/XhoI or BamHI/XhoI and the whole digestion loaded onto a 1–1.5% agarose gel (depending on the expected insert size), in parallel with the molecular weight marker (1 Kb DNA Ladder, GIBCO). The screening of the positive clones was made on the base of the correct insert size.

G) Expression

Each ORF cloned into the expression vector was transformed into the strain suitable for expression of the recombinant protein product. 1 µl of each construct was used to transform 30 µl of E.coli BL21 (PGEX vector), E.coli TOP 10 (PTRC vector) or E.coli BL21-DE3 (pET vector), as described above. In the case of the pGEX-His vector, the same E.coli strain (W3110) was used for initial cloning and expression. Single recombinant colonies were inoculated into 2 ml LB+Amp (100 µg/ml), incubated at 37° C. overnight, then diluted 1:30 in 20 ml of LB+Amp (100 µg/ml) in 100 ml flasks, making sure that the $OD_{600}$ ranged between 0.1 and 0.15. The flasks were incubated at 30° C. into gyratory water bath shakers until OD indicated exponential growth suitable for induction of expression (0.4–0.8 OD for pET and pTRC vectors; 0.8–1 OD for pGEX and pGEX-His vectors). For the pET, pTRC and pGEX-His vectors, the protein expression was induced by addition of 1 mM IPTG, whereas in the case of pGEX system the final concentration of IPTG was 0.2 mM. After 3 hours incubation at 30° C., the final concentration of the sample was checked by OD. In order to check expression, 1 ml of each sample was removed, centrifuged in a microfuge, the pellet resuspended in PBS, and analysed by 12% SDS-PAGE with Coomassie Blue staining. The whole sample was centrifuged at 6000g and the pellet resuspended in PBS for further use.

H) GST-fusion Proteins Large-scale Purification

A single colony was grown overnight at 37° C. on LB+Amp agar plate. The bacteria were inoculated into 20 ml of LB+Amp liquid culture in a water bath shaker and grown overnight. Bacteria were diluted 1:30 into 600 ml of fresh medium and allowed to grow at the optimal temperature (20–37° C.) to $OD_{550}$ 0.8–1. Protein expression was induced with 0.2 mM IPTG followed by three hours incubation. The culture was centrifuged at 8000 rpm at 4° C. The supernatant was discarded and the bacterial pellet was resuspended in 7.5 ml cold PBS. The cells were disrupted by sonication on ice for 30 sec at 40W using a Branson sonifier B-15, frozen and thawed twice and centrifuged again. The supernatant was collected and mixed with 150 µl Glutatione-Sepharose 4B resin (Pharmacia) (previously washed with PBS) and incubated at room temperature for 30 minutes. The sample was centrifuged at 700 g for 5 minutes at 4° C. The resin was washed twice with 10 ml cold PBS for 10 minutes, resuspended in 1 ml cold PBS, and loaded on a disposable column. The resin was washed twice with 2 ml cold PBS until the flow-through reached $OD_{280}$ of 0.02–0.06. The GST-fusion protein was eluted by addition of 700 µl cold Glutathione elution buffer (10 mM reduced glutathione, 50 mM Tris-HCl) and fractions collected until the $OD_{280}$ was 0.1. 21 µl of each fraction were loaded on a 12% SDS gel using either Biorad SDS-PAGE Molecular weight standard broad range (M1) (200, 116.25, 97.4, 66.2, 45, 31, 21.5, 14.4, 6.5 kDa) or Amersham Rainbow Marker (M2) (220, 66, 46, 30, 21.5, 14.3 kDa) as standards. As the MW of GST is 26 kDa, this value must be added to the MW of each GST-fusion protein.

I) His-fusion Solubility Analysis

To analyse the solubility of the His-fusion expression products, pellets of 3 ml cultures were resuspended in buffer M1 [500 µl PBS pH 7.2]. 25 µl lysozyme (10 mg/ml) was added and the bacteria were incubated for 15 min at 4° C. The pellets were sonicated for 30 sec at 40W using a Branson sonifier B-15, frozen and thawed twice and then separated again into pellet and supernatant by a centrifugation step. The supernatant was collected and the pellet was resuspended in buffer M2 [8M urea, 0.5M NaCl, 20 mM imidazole and 0.1M $NaH_2PO_4$] and incubated for 4 hours at 4° C. After centrifugation, the supernatant was collected and the pellet was resuspended in buffer M3 [6M guanidinium-HCl, 0.5M NaCl, 20 mM imidazole and 0.1M $NaH_2PO_4$] overnight at 4° C. The supernatants from all steps were analysed by SDS-PAGE.

J) His-fusion Large-scale Purification

A single colony was grown overnight at 37° C. on a LB+Amp agar plate. The bacteria were inoculated into 20 ml of LB+Amp liquid culture and incubated overnight in a water bath shaker. Bacteria were diluted 1:30 into 600 ml fresh medium and allowed to grow at the optimal temperature (20–37° C.) to $OD_{550}$ 0.6–0.8. Protein expression was induced by addition of 1 mM IPTG and the culture further incubated for three hours. The culture was centrifuged at 8000 rpm at 4° C., the supernatant was discarded and the bacterial pellet was resuspended in 7.5 ml of either (i) cold buffer A (300 mM NaCl, 50 mM phosphate buffer, 10 mM imidazole, pH 8) for soluble proteins or (ii) buffer B (urea 8M, 10 mM Tris-HCl, 100 mM phosphate buffer, pH 8.8) for insoluble proteins.

The cells were disrupted by sonication on ice for 30 sec at 40W using a Branson sonifier B-15, frozen and thawed two times and centrifuged again.

For insoluble proteins, the supernatant was stored at −20° C., while the pellets were resuspended in 2 ml buffer C (6M guanidine hydrochloride, 100 mM phosphate buffer, 10 mM Tris-HCl, pH 7.5) and treated in a homogenizer for 10 cycles. The product was centrifuged at 13000 rpm for 40 minutes.

Supernatants were collected and mixed with 150 μl $Ni^{2+}$-resin (Pharmacia) (previously washed with either buffer A or buffer B, as appropriate) and incubated at room temperature with gentle agitation for 30 minutes. The sample was centrifuged at 700 g for 5 minutes at 4° C. The resin was washed twice with 10 ml buffer A or B for 10 minutes, resuspended in 1 ml buffer A or B and loaded on a disposable column. The resin was washed at either (i) 4° C. with 2 ml cold buffer A or (ii) room temperature with 2 ml buffer B, until the flow-through reached $OD_{280}$ of 0.02–0.06.

The resin was washed with either (i) 2 ml cold 20 mM imidazole buffer (300 mM NaCl, 50 mM phosphate buffer, 20 mM imidazole, pH 8) or (ii) buffer D (urea 8M, 10 mM Tris-HCl, 100 mM phosphate buffer, pH 6.3) until the flow-through reached the $O.D_{280}$ of 0.02–0.06. The His-fusion protein was eluted by addition of 700 μl of either (i) cold elution buffer A (300 mM NaCl, 50 mM phosphate buffer, 250 mM imidazole, pH 8) or (ii) elution buffer B (urea 8M, 10 mM Tris-HCl, 100 mM phosphate buffer, pH 4.5) and fractions collected until the $OD_{280}$ was 0.1. 21 μl of each fraction were loaded on a 12% SDS gel.

K) His-fusion Proteins Renaturation

10% glycerol was added to the denatured proteins. The proteins were then diluted to 20 μg/ml using dialysis buffer I (10% glycerol, 0.5M arginine, 50 mM phosphate buffer, 5 mM reduced glutathione, 0.5 mM oxidised glutathione, 2M urea, pH 8.8) and dialysed against the same buffer at 4° C. for 12–14 hours. The protein was further dialysed against dialysis buffer II (10% glycerol, 0.5M arginine, 50 mM phosphate buffer, 5 mM reduced glutathione, 0.5 mM oxidised glutathione, pH 8.8) for 12–14 hours at 4° C. Protein concentration was evaluated using the formula:

Protein (mg/ml)=$(1.55 \times OD_{280}) - (0.76 \times OD_{260})$

L) His-fusion Large-scale Purification 500 ml of bacterial cultures were induced and the fusion proteins were obtained soluble in buffer M1, M2 or M3 using the procedure described above. The crude extract of the bacteria was loaded onto a Ni-NTA superflow column (Qiagen) equilibrated with buffer M1, M2 or M3 depending on the solubilization buffer of the fusion proteins. Unbound material was eluted by washing the column with the same buffer. The specific protein was eluted with the corresponding buffer containing 500 mM imidazole and dialysed against the corresponding buffer without imidazole. After each run the columns were sanitized by washing with at least two column volumes of 0.5 M sodium hydroxide and reequilibrated before the next use.

M) Mice Immunisations

20 μg of each purified protein were used to immunise mice intraperitoneally. In the case of ORF 44, CD1 mice were imnmunised with $Al(OH)_3$ as adjuvant on days 1, 21 and 42, and immune response was monitored in samples taken on day 56. For ORF 40, CD1 mice were immunised using Freund's adjuvant, rather than $Al(OH)_3$, and the same immunisation protocol was used, except that the immune response was measured on day 42, rather than 56. Similarly, for ORF 38, CD1 mice were immunised with Freund's adjuvant, but the immune response was measured on day 49.

N) ELISA Assay (Sera Analysis)

The acapsulated MenB M7 strain was plated on chocolate agar plates and incubated overnight at 37° C. Bacterial colonies were collected from the agar plates using a sterile dracon swab and inoculated into 7 ml of Mueller-Hinton Broth (Difco) containing 0.25% Glucose. Bacterial growth was monitored every 30 minutes by following $OD_{620}$. The bacteria were let to grow until the OD reached the value of 0.3–0.4. The culture was centrifuged for 10 minutes at 10000 rpm. The supernatant was discarded and bacteria were washed once with PBS, resuspended in PBS containing 0.025% formaldehyde, and incubated for 2 hours at room temperature and then overnight at 4° C. with stirring. 100 μl bacterial cells were added to each well of a 96 well Greiner plate and incubated overnight at 4° C. The wells were then washed three times with PBT washing buffer (0.1% Tween-20 in PBS). 200 μl of saturation buffer (2.7% Polyvinylpyrrolidone 10 in water) was added to each well and the plates incubated for 2 hours at 37° C. Wells were washed three times with PBT. 200 μl of diluted sera (Dilution buffer: 1% BSA, 0.1% Tween-20, 0.1% $NaN_3$ in PBS) were added to each well and the plates incubated for 90 minutes at 37° C. Wells were washed three times with PBT. 100 μl of HRP-conjugated rabbit anti-mouse (Dako) serum diluted 1:2000 in dilution buffer were added to each well and the plates were incubated for 90 minutes at 37° C. Wells were washed three times with PBT buffer. 100 μl of substrate buffer for HRP (25 ml of citrate buffer pH5, 10 mg of O-phenildiamine and 10 μl of $H_2O$) were added to each well and the plates were left at room temperature for 20 minutes. 100 μl $H_2SO_4$ was added to each well and $OD_{490}$ was followed. The ELISA was considered positive when $OD_{490}$ was 2.5 times the respective pre-immune sera.

O) FACScan Bacteria Binding Assay Procedure

The acapsulated MenB M7 strain was plated on chocolate agar plates and incubated overnight at 37° C. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35–0.5. The culture was centrifuged for 10 minutes at 4000 rpm. The supernatant was discarded and the pellet was resuspended in blocking buffer (1% BSA, 0.4% $NaN_3$) and centrifuged for 5 minutes at 4000 rpm. Cells were resuspended in blocking buffer to reach $OD_{620}$ of 0.07. 100 μl bacterial cells were added to each well of a Costar 96 well plate. 100 μl of diluted (1:200) sera (in blocking buffer) were added to each well and plates incubated for 2 hours at 4° C. Cells were centrifuged for 5 minutes at 4000 rpm, the supernatant aspirated and cells washed by addition of 200 μl/well of blocking buffer in each well. 100 μl of R-Phicoerytrin conjugated $F(ab)_2$ goat anti-mouse, diluted 1:100, was added to each well and plates incubated for 1 hour at 4° C. Cells were spun down by centrifuigation at 4000 rpm for 5 minutes and washed by addition of 200 μl/well of blocking buffer. The supernatant was aspirated and cells resuspended in 200 μl/well of PBS, 0.25% formaldehyde. Samples were transferred to FACScan tubes and read. The condition for FACScan setting were: FL1 on, FL2 and FL3 off; FSC-H threshold:92; FSC PMT Voltage: E 02; SSC PMT: 474; Amp. Gains 7.1; FL-2 PMT: 539; compensation values: 0.

P) OMV Preparations

Bacteria were grown overnight on 5 GC plates, harvested with a loop and resuspended in 10 ml 20 mM Tris-HCl. Heat inactivation was performed at 56° C. for 30 minutes and the bacteria disrupted by sonication for 10 minutes on ice (50% duty cycle, 50% output). Unbroken cells were removed by centrifugation at 5000 g for 10 minutes and the total cell envelope fraction recovered by centrifugation at 50000 g at 4° C. for 75 minutes. To extract cytoplasmic membrane proteins from the crude outer membranes, the whole fraction was resuspended in 2% sarkosyl (Sigma) and incubated at room temperature for 20 minutes. The suspension was centrifuged at 1000 g for 10 minutes to remove aggregates, and the supernatant further ultracentrifuged at 50000 g for 75 minutes to pellet the outer membranes. The outer membranes were resuspended in 10 mM Tris-HCl, pH8 and the protein concentration measured by the Bio-Rad Protein assay, using BSA as a standard.

Q) Whole Extracts Preparation

Bacteria were grown overnight on a GC plate, harvested with a loop and resuspended in 1 ml of 20 mM Tris-HCl. Heat inactivation was performed at 56° C. for 30 minutes.

R) Western Blotting

Purified proteins (500 ng/lane), outer membrane vesicles (5 kg) and total cell extracts (25 μg) derived from MenB strain 2996 were loaded on 15% SDS-PAGE and transferred to a nitrocellulose membrane. The transfer was performed for 2 hours at 150 mA at 4° C., in transferring buffer (0.3% Tris base, 1.44% glycine, 20% methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

S) Bactericidal Assay

MC58 strain was grown overnight at 37° C. on chocolate agar plates. 5–7 colonies were collected and used to inoculate 7 ml Mueller-Hinton broth. The suspension was incubated at 37° C. on a nutator and let to grow until $OD_{620}$ was 0.5–0.8. The culture was aliquoted into sterile 1.5 ml Eppendorf tubes and centrifuged for 20 minutes at maximum speed in a microfuge. The pellet was washed once in Gey's buffer (Gibco) and resuspended in the same buffer to an $OD_{620}$ of 0.5, diluted 1:20000 in Gey's buffer and stored at 25° C.

50 μl of Gey's buffer/1% BSA was added to each well of a 96-well tissue culture plate. 25 μl of diluted mice sera (1:100 in Gey's buffer/0.2% BSA) were added to each well and the plate incubated at 4° C. 25 μl of the previously described bacterial suspension were added to each well. 25 μl of either heat-inactivated (56° C. waterbath for 30 minutes) or normal baby rabbit complement were added to each well. Immediately after the addition of the baby rabbit complement, 22 μl of each sample/well were plated on Mueller-Hinton agar plates (time 0). The 96-well plate was incubated for 1 hour at 37° C. with rotation and then 22 μl of each sample/well were plated on Mueller-Hinton agar plates (time 1) After overnight incubation the colonies corresponding to time 0 and time 1 hour were counted.

Table II gives a summary of the cloning, expression and purification results.

TABLE II

Cloning, expression and purification

| ORF | PCR/ cloning | His-fusion expression | GST-fusion expression | Purification |
|---|---|---|---|---|
| orf 38 | + | + | + | His-fusion |
| orf 40 | + | + | + | His-fusion |
| orf 41 | + | n.d. | n.d. | |
| orf 44 | + | + | + | His-fusion |
| orf 51 | + | n.d. | n.d. | |
| orf 52 | + | n.d. | + | GST-fusion |
| orf 56 | + | n.d. | n.d. | |
| orf 69 | + | n.d. | n.d. | |
| orf 82 | + | n.d. | n.d. | |
| orf 114 | + | n.d. | + | GST-fusion |
| orf 124 | + | n.d. | n.d. | |

Example 1

The following partial DNA sequence was identified in *N.meningitidis* <SEQ ID 1>:

```
  1  ..ACACTGTTGT TTGCAACGGT TCAGGCAAGT GCTAACCAAT GAAGAGCAAG

51    AAGAAGATTT ATATTTAGAC CCCGTACAAC GCACTGTTGC CGTGTTGATA

101    GTCAATTCCG ATAAAGAAGG CACGGGAGAA AAAGAAAAAG TAGAAGAAAA

151    TTCAGATTGG GCAGTATATT TCAACGAGAA AGGAGTACTA ACAGCCAGAG

201    AAATCACCyT CAAAGCCGGC GACAACCTGA AAATCAAACA AAACGGCACA

251    AACTTCACCT ACTCGCTGAA AAAAGACCTC AcAGATCTGA CCAGTGTTGG

301    AACTGAAAAA TTATCGTTTA GCGCAAACGG CAATAAAGTC AACATcACAA

351    GCGACACCAA AGGCTTGAAT TTTGCGAAAG AAACGGCTGG sACGAACGgC

401    GACACCACGG TTCATCTGAA CGGTATTGGT TCGACTTTGA CCGATACGCT

451    GCTGAATACC GGAGCGACCA CAAACGTAAC CAACGACAAC GTTACCGATG
```

-continued

```
501  ACGAGAAAAA ACGTGCGGCA AGCGTTAAAG ACGTATTAAA CGCTGGCTGG
551  AACATTAAAG GCGTTAAACC CGGTACAACA GCTTCCGATA ACGTTGATTT
601  CGTCCGCACT TACGACACAG TCGAGTTCTT GAGCGCAGAT ACGAAAACAA
651  CGACTGTTAA TGTGGAAAGC AAAGACAACG GCAAGAAAAC CGAAGTTAAA
701  ATCGGTGCGA AGACTTCTGT TATTAAAGAA AAAGAC...
```

This corresponds to the amino acid sequence <SEQ ID 2; ORF40>:

```
1    ..TLLFATVQAS ANQEEQEEDL YLDPVQRTVA VLIVNSDKEG TGEKEKVEEN
51     SDWAVYFNEK GVLTAREITX KAGDNLKIKQ NGTNFTYSLK KDLTDLTSVG
101    TEKLSFSANG NKVNITSDTK GLNFAKETAG TNGDTTVHLN GIGSTLTDTL
151    LNTGATTNVT NDNVTDDEKK RAASVKDVLN AGWNIKGVKP GTTASDNVDF
201    VRTYDTVEFL SADTKTTTVN VESKDNGKKT EVKIGAKTSV IKEKD...
```

Further work revealed the complete DNA sequence <SEQ ID 3>:

```
1    ATGAACAAAA TATACCGCAT CATTTGGAAT AGTGCCCTCA ATGCCTGGGT
51   CGTCGTATCC GAGCTCACAC GCAACCACAC CAAACGCGCC TCCGCAACCG
101  TGAAGACCGC CGTATTGGCG ACACTGTTGT TTGCAACGGT TCAGGCAAGT
151  GCTAACAATG AAGAGCAAGA AGAAGATTTA TATTTAGACC CCGTACAACG
201  CACTGTTGCC GTGTTGATAG TCAATTCCGA TAAAGAAGGC ACGGGAGAAA
251  AAGAAAAAGT AGAAGAAAAT TCAGATTGGG CAGTATATTT CAACGAGAAA
301  GGAGTACTAA CAGCCAGAGA AATCACCCTC AAAGCCGGCG ACAACCTGAA
351  AATCAAACAA AACGGCACAA ACTTCACCTA CTCGCTGAAA AAAGACCTCA
401  CAGATCTGAC CAGTGTTGGA ACTGAAAAAT TATCGTTTAG CGCAAACGGC
451  AATAAAGTCA ACATCACAAG CGACACCAAA GGCTTGAATT TTGCGAAAGA
501  AACGGCTGGG ACGAACGGCG ACACCACGGT TCATCTGAAC GGTATTGGTT
551  CGACTTTGAC CGATACGCTG CTGAATACCG GAGCGACCAC AAACGTAACC
601  AACGACAACG TTACCGATGA CGAGAAAAAA CGTGCGGCAA GCGTTAAAGA
651  CGTATTAAAC GCTGGCTGGA ACATTAAAGG CGTTAAACCC GGTACAACAG
701  CTTCCGATAA CGTTGATTTC GTCCGCACTT ACGACACAGT CGAGTTCTTG
751  AGCGCAGATA CGAAAACAAC GACTGTTAAT GTGGAAAGCA AGACAACGG
801  CAAGAAAACC GAAGTTAAAA TCGGTGCGAA GACTTCTGTT ATTAAAGAAA
851  AAGACGGTAA GTTGGTTACT GGTAAAGACA AAGGCGAGAA TGGTTCTTCT
901  ACAGACGAAG GCGAAGGCTT AGTGACTGCA AAAGAAGTGA TTGATGCAGT
951  AAACAAGGCT GGTTGGAGAA TGAAAACAAC AACCGCTAAT GGTCAAACAG
1001 GTCAAGCTGA CAAGTTTGAA ACCGTTACAT CAGGCACAAA TGTAACCTTT
1051 GCTAGTGGTA AAGGTACAAC TGCGACTGTA AGTAAAGATG ATCAAGGCAA
1101 CATCACTGTT ATGTATGATG TAAATGTCGG CGATGCCCTA AACGTCAATC
```

-continued

```
1151  AGCTGCAAAA CAGCGGTTGG AATTTGGATT CCAAAGCGGT TGCAGGTTCT
1201  TCGGGCAAAG TCATCAGCGG CAATGTTTCG CCGAGCAAGG GAAAGATGGA
1251  TGAAACCGTC AACATTAATG CCGGCAACAA CATCGAGATT ACCCGCAACG
1301  GTAAAAATAT CGACATCGCC ACTTCGATGA CCCCGCAGTT TTCCAGCGTT
1351  TCGCTCGGCG CGGGGGCGGA TGCGCCCACT TTGAGCGTGG ATGGGGACGC
1401  ATTGAATGTC GGCAGCAAGA AGGACAACAA ACCCGTCCGC ATTACCAATG
1451  TCGCCCCGGG CGTTAAAGAG GGGGATGTTA CAAACGTCGC ACAACTTAAA
1501  GGCGTGGCGC AAAACTTGAA CAACCGCATC GACAATGTGG ACGGCAACGC
1551  GCGTGCGGGC ATCGCCCAAG CGATTGCAAC CGCAGGTCTG GTTCAGGCGT
1601  ATTTGCCCGG CAAGAGTATG ATGGCGATCG GCGGCGGCAC TTATCGCGGC
1651  GAAGCCGGTT ACGCCATCGG CTACTCCAGT ATTTCCGACG GCGGAAATTG
1701  GATTATCAAA GGCACGGCTT CCGGCAATTC GCGCGGCCAT TTCGGTGCTT
1751  CCGCATCTGT CGGTTATCAG TGGTAA
```

This corresponds to the amino acid sequence <SEQ ID 4; ORF40-1>:

```
  1  MNKIYRIIWN SALNAWVVVS ELTRNHTKRA SATVKTAVLA TLLFATVQAS
 51  ANNEEQEEDL YLDPVQRTVA VLIVNSDKEG TGEKEKVEEN SDWAVYFNEK
101  GVLTAREITL KAGDNLKIKQ NGTNFTYSLK KDLTDLTSVG TEKLSFSANG
151  NKVNITSDTK GLNFAKETAG TNGDTTVHLN GIGSTLTDTL LNTGATTNVT
201  NDNVTDDEKK RAASVKDVLN AGWNIKGVKP GTTASDNVDF VRTYDTVEFL
251  SADTKTTTVN VESKDNGKKT EVKIGAKTSV IKEKDGKLVT GKDKGENGSS
301  TDEGEGLVTA KEVIDAVNKA GWRMKTTTAN GQTGQADKFE TVTSGTNVTF
351  ASGKGTTATV SKDDQGNITV MYDVNVGDAL NVNQLQNSGW NLDSKAVAGS
401  SGKVISGNVS PSKGKMDETV NINAGNNIEI TRNGKNIDIA TSMTPQFSSV
451  SLGAGADAPT LSVDGDALNV GSKKDNKPVR ITNVAPGVKE GDVTNVAQLK
501  GVAQNLNNRI DNVDGNARAG IAQAIATAGL VQAYLPGKSM MAIGGGTYRG
551  EAGYAIGYSS ISDGGNWIIK GTASGNSRGH FGASASVGYQ W*
```

Further work identified the corresponding gene in strain A of *N.meningilidis* <SEQ ID 5 >:

```
  1  ATGAACAAAA TATACCGCAT CATTTGGAAT AGTGCCCTCA ATGCCTGNGT
 51  CGCCGTATCC GAGCTCACAC GCAACCACAC CAAACGCGCC TCCGCAACCG
101  TGAAGACCGC CGTATTGGCG ACACTGTTGT TTGCAACGGT TCAGGCGAAT
151  GCTACCGATG AAGATGAAGA AGAAGAGTTA GAATCCGTAC AACGCTCTGT
201  CGTAGGGAGC ATTCAAGCCA GTATGGAAGG CAGCGGCGAA TTGGAAACGA
251  TATCATTATC AATGACTAAC GACAGCAAGG AATTTGTAGA CCCATACATA
301  GTAGTTACCC TCAAAGCCGG CGACAACCTG AAAATCAAAC AAAACACCAA
351  TGAAAACACC AATGCCAGTA GCTTCACCTA CTCGCTGAAA AAAGACCTCA
401  CAGGCCTGAT CAATGTTGAN ACTGAAAAAT TATCGTTTGG CGCAAACGGC
```

-continued

```
 451    AAGAAAGTCA ACATCATAAG CGACACCAAA GGCTTGAATT TCGCGAAAGA
 501    AACGGCTGGG ACGAACGGCG ACACCACGGT TCATCTGAAC GGTATCGGTT
 551    CGACTTTGAC CGATACGCTT GCGGGTTCTT CTGCTTCTCA CGTTGATGCG
 601    GGTAACCNAA GTACACATTA CACTCGTGCA GCAAGTATTA AGGATGTGTT
 651    GAATGCGGGT TGGAATATTA AGGGTGTTAA ANNNGGCTCA ACAACTGGTC
 701    AATCAGAAAA TGTCGATTTC GTCCGCACTT ACGACACAGT CGAGTTCTTG
 751    AGCGCAGATA CGNAAACAAC GACNGTTAAT GTGGAAAGCA AAGACAACGG
 801    CAAGAGAACC GAAGTTAAAA TCGGTGCGAA GACTTCTGTT ATTAAAGAAA
 851    AAGACGGTAA GTTGGTTACT GGTAAAGGCA AAGGCGAGAA TGGTTCTTCT
 901    ACAGACGAAG GCGAAGGCTT AGTGACTGCA AAAGAAGTGA TTGATGCAGT
 951    AAACAAGGCT GGTTGGAGAA TGAAAACAAC AACCGCTAAT GGTCAAACAG
1001    GTCAAGCTGA CAAGTTTGAA ACCGTTACAT CAGGCACAAA TGTAACCTTT
1051    GCTAGTGGTA AAGGTACAAC TGCGACTGTA AGTAAAGATG ATCAAGGCAA
1101    CATCACTGTT ATGTATGATG TAAATGTCGG CGATGCCCTA AACGTCAATC
1151    AGCTGCAAAA CAGCGGTTGG AATTTGGATT CCAAAGCGGT TGCAGGTTCT
1201    TCGGGCAAAG TCATCAGCGG CAATGTTTCG CCGAGCAAGG GAAAGATGGA
1251    TGAAACCGTC AACATTAATG CCGGCAACAA CATCGAGATT AGCCGCAACG
1301    GTAAAAATAT CGACATCGCC ACTTCGATGG CGCCGCAGTT TTCCAGCGTT
1351    TCGCTCGGCG CGGGGGCAGA TGCGCCCACT TTAAGCGTGG ATGACGAGGG
1401    CGCGTTGAAT GTCGGCAGCA AGGATGCCAA CAAACCCGTC CGCATTACCA
1451    ATGTCGCCCC GGGCGTTAAA GANGGGGATG TTACAAACGT CNCACAACTT
1501    AAAGGCGTGG CGCAAAACTT GAACAACCGC ATCGACAATG TGGACGGCAA
1551    CGCGCGTGCN GGCATCGCCC AAGCGATTGC AACCGCAGGT CTGGTTCAGG
1601    CGTATCTGCC CGGCAAGAGT ATGATGGCGA TCGGCGGCGG CACTTATCGC
1651    GGCGAAGCCG GTTACGCCAT CGGCTACTCC AGTATTTCCG ACGGCGGAAA
1701    TTGGATTATC AAAGGCACGG CTTCCGGCAA TTCGCGCGGC CATTTCGGTG
1751    CTTCCGCATC TGTCGGTTAT CAGTGGTAA
```

This encodes a protein having amino acid sequence <SEQ ID 6; ORF40a>:

```
  1    MNKIYRIIWN SALNAXVAVS ELTRNHTKRA SATVKTAVLA TLLFATVQAN
 51    ATDEDEEEEL ESVQRSVVGS IQASMEGSGE LETISLSMTN DSKEFVDPYI
101    VVTLKAGDNL KIKQNTNENT NASSFTYSLK KDLTGLINVX TEKLSFGANG
151    KKVNIISDTK GLNFAKETAG TNGDTTVHLN GIGSTLTDTL AGSSASHVDA
201    GNXSTHYTRA ASIKDVLNAG WNIKGVKXGS TTGQSENVDF VRTYDTVEFL
251    SADTXTTTVN VESKDNGKRT EVKIGAKTSV IKEKDGKLVT GKGKGENGSS
301    TDEGEGLVTA KEVIDAVNKA GWRMKTTTAN GQTGQADKFE TVTSGTNVTF
351    ASGKGTTATV SKDDQGNITV MYDVNVGDAL NVNQLQNSGW NLDSKAVAGS
401    SGKVISGNVS PSKGKMDETV NINAGNNIEI SRNGKNIDIA TSMAPQFSSV
```

```
-continued
451  SLGAGADAPT LSVDDEGALN VGSKDANKPV RITNVAFGVK XGDVTNVXQL

501  KGVAQNLNNR IDNVDGNARA GIAQAIATAG LVQAYLPGKS MMAIGGGTYR

551  GEAGYAIGYS SISDGGNWII KGTASGNSRG HFGASASVGY QW*
```

The originally-identified partial strain B sequence (ORF40 (SEQ ID NO:2)) shows 65.7% identity over a 254aa overlap with ORF40a (SEQ ID NO:138):

```
                                       10        20        30
orf40.pep                         TLLFATVQASANQEEQEEDLYLDPVQRTVA
                                  ||||||||||:|::|::||:|  :  |||:|
orf40a    SALNAXVAVSELTRNHTKRASATVKTAVLATLLFATVQANATDEDEEEEL--ESVQRSV-
                  20        30        40        50        60

40        50        60        70        80
orf40.pep  VLIVNSDKEGTGEKEKVEEN-SDWAVYFNEKGVLTAREITXKAGDNLKIKQN------GT
           |  ::::  ||:||  |  :  :::  :  |  :  ::      :| ||||||||||      ::
orf40a     VGSIQASMEGSGELETISLSMTNDSKEFVDPYIV----VTLKAGDNLKIKQNTNENTNAS
                  70        80        90       100       110       120

90       100       110       120       130       140
orf40.pep  NFTYSLKKDLTDLTSVGTEKLSFSANGNKVNITSDTKGLNFAKETAGTNGDTTVHLNGIG
           :|||||||||| | :| ||||||:||:||||  |||||||||||||||||||||||||||
orf40a     SFTYSLKKDLTGLINVXTEKLSFGANGKKVNIISDTKGLNFAKETAGTNGDTTVHLNGIG
                 130       140       150       160       170       180

150       160       170       180       190       200
orf40.pep  STLTDTLLNTGATTNVTNDNVTDDEKKRAASVKDVLNAGWNIKGVKPGTTA--SDNVDFV
           ||||||| :::|: :|    | : :   ||||:||||||||||||||||  |:|:  |:||||
orf40a     STLTDTLAGSSAS-HVDAGNXST-HYTRAASIKDVLNAGWNIKGVKGSTTGQSENVDFV
                 190       200       210       220       230       240

210       220       230       240
orf40.pep  RTYDTVEFLSADTKTTTVNVESKDNGKKTEVKIGAKTSVIKEKD
           |||||||||||||||| |||||||||||:|||||||||||||||
orf40a     RTYDTVEFLSADTXTTTVNVESKDNGKRTEVKIGAKTSVIKEKDGKLVTGKGKGENGSST
                 250       260       270       280       290       300
```

The complete strain B sequence (ORF40-1 (SEQ ID NO:4)) and ORF40a (SEQ ID NO:6) show 83.7% identity in 601 aa overlap:

```
                 10        20        30        40        50        60
orf40-1.pep MNKIYRIIWNSALNAWVVVSELTRNHTKRASATVKTAVLATLLFATVQASANNEEQEEDL
            |||||||||||||| |:||||||||||||||||||||||||||||||||||:|::|::||:|
orf40a     MNKIYRIIWNSALNAXVAVSELTRNHTKRASATVKTAVLATLLFATVQANATDEDEEEEL
                 10        20        30        40        50        60

70        80        90       100       110       119
orf40-1.pep YLDPVQRTVAVLIVNSDKEGTGEKEKVEEN-SDWAVYFNEKGVLTAREITLKAGDNLKIK
            :  ||||:|  ::::  ||:||  |  :  ::  :  |  :  ::      :||||||||||
orf40a     --ESVQRSV-VGSIQASMEGSGELETISLSMTNDSKEFVDPYIV----VTLKAGDNLKIK
                      70        80        90       100       110

120       130       140       150       160       170
orf40-1.pep QN------GTNFTYSLKKDLTDLTSVGTEKLSFSANGNKVNITSDTKGLNFAKETAGTNG
            ||      :::|||||||||| | :| ||||||:||:||||  |||||||||||||||||
orf40a     QNTNENTNASSFTYSLKKDLTGLINVXTEKLSFGANGKKVNIISDTKGLNFAKETAGTNG
                 120       130       140       150       160       170

180       190       200       210       220       230
orf40-1.pep DTTVHLNGIGSTLTDTLLNTGATTNVTNDNVTDDEKKRAASVKDVLNAGWNIKGVKPGTT
            ||||||||||||||||| :::|: :|    | : :   ||||:|||||||||||||||  |:|
orf40a     DTTVHLNGIGSTLTDTLAGSSAS-HVDAGNXST-HYTRAASIKDVLNAGWNIKGVKXGST
                 180       190       200       210       220       230

240       250       260       270       280       290
orf40-1.pep A--SDNVDFVRTYDTVEFLSADTKTTTVNVESKDNGKKTEVKIGAKTSVIKEKDGKLVTG
            :  |:||||||||||||||||||||| ||||||||||||:|||||||||||||||||||||
orf40a     TGQSENVDFVRTYDTVEFLSADTXTTTVNVESKDNGKRTEVKIGAKTSVIKEKDGKLVTG
```

```
                           240       250       260       270       280       290

300       310       320       330       340       350
orf40-1.pep    KDKGENGSSTDEGEGLVTAKEVIDAVNKAGWRMKTTTANGQTGQADKFETVTSGTNVTFA
               | ||||||||||||||||||||||||||||||||||||||||||||||||||||||||||
orf40a         KGKGENGSSTDEGEGLVTAKEVIDAVNKAGWRMKTTTANGQTGQADKFETVTSGTNVTFA
                           300       310       320       330       340       350

360       370       380       390       400       410
orf40-1.pep    SGKGTTATVSKDDQGNITVMYDVNVGDALNVNQLQNSGWNLDSKAVAGSSGKVISGNVSP
               ||||||||||||||||||||||||||||||||||||||||||||||||||||||||||||
orf40a         SGKGTTATVSKDDQGNITVMYDVNVGDALNVNQLQNSGWNLDSKAVAGSSGKVISGNVSP
                           360       370       380       390       400       410

420       430       440       450       460       470
orf40-1.pep    SKGKMDETVNINAGNNIEITRNGKNIDIATSMTPQFSSVSLGAGADAPTLSVDGD-ALNV
               |||||||||||||||||:|||||||||||||||||:|||||||||||||||||||  : ||||
orf40a         SKGKMDETVNINAGNNIEISRNGKNIDIATSMAPQFSSVSLGAGADAPTLSVDDEGALNV
                           420       430       440       450       460       470

480       490       500       510       520       530
orf40-1.pep    GSKKDNKPVRITNVAPGVKEGDVTNVAQLKGVAQNLNNRIDNVDGNARAGIAQAIATAGL
               ||| |||||||||||||| |||||| ||||||||||||||||||||||||||||||||||
orf40a         GSKDANKPVRITNVAPGVKXGDVTNVXQLKGVAQNLNNRIDNVDGNARAGIAQAIATAGL
                           480       490       500       510       520       530

540       550       560       570       580       590
orf40-1.pep    VQAYLPGKSMMAIGGGTYRGEAGYAIGYSSISDGGNWIIKGTASGNSRGHFGASASVGYQ
               ||||||||||||||||||||||||||||||||||||||||||||||||||||||||||||
orf40a         VQAYLPGKSMMAIGGGTYRGEAGYAIGYSSISDGGNWIIKGTASGNSRGHFGASASVGYQ
                           540       550       560       570       580       590 orf40-1.pep    WX
               ||
orf40a         WX
```

Computer analysis of these two amino acid sequences gave the following results:

Homology With Hsf Protein Encoded by the Type b Surface Fibrils Locus of *H.influenzae* (Accession Number U41852)

ORF40 (SEQ ID NO:2) and Hsf protein (SEQ ID NO:139) show 54% aa identity (SEQ ID NO:140) in 251 aa overlap:

```
Orf40    1 TLLFATVQASANQEEQEEDLYLDPVQRTVAVLIVNSDXXXXXXXXXXXXNSDWAVYFNEK   60
           TLLFATVQA+A  E++E     LDPV RT VL +SD            NS+W +YF+ K
Hsf     41 TLLFATVQANATDEDEE----LDPVVRTAPVLSFHSDKEGTGEKEVTE-NSNWGIYFDNK   95

Orf40   61 GVLTAREITXKAGDNLKIKQN------GTNFTYSLKKDLTDLTSVGTEKLSFSANGNKVN  114
           GVL A  IT KAGDNLKIKQN       ++FTYSLKKDLTDLTSV TEKLSF ANG+KV+
Hsf     96 GVLKAGAITLKAGDNLKIKQNTDESTNASSFTYSLKKDLTDLTSVATEKLSFGANGDKVD  155

Orf40  115 ITSDTKGLNFAKETAGTNGDTTVHLNGIGSTLTDTLLNTGAXXXXXXXXXXXXXEKKRAAS  174
           ITSD  GL AK     G+ VHLNG+ STL D + NTG             EK RAA+
Hsf    156 ITSDANGLKLAK-----TGNGNVHLNGLDSTLPDAVTNTGVLSSSSFTPNDV-EKTRAAT  209

Orf40  175 VKDVLNAGWNIKGVKPGTTASDNVDFVRTYDTVEFLSADTKTTTVNVESKDNGKKTEVKI  234
           VKDVLNAGWNIKG K     ++VD V  Y+ VEF++ D  T   V + +K+NGK TEVK
Hsf    210 VKDVLNAGWNIKGAKTAGGNVESVDLVSAYNNVEFITGDKNTLDVVLTAKENGKTTEVKF  269

Orf40  235 GAKTSVIKEKD                                                   245
              KTSVIKEKD
Hsf    270 TPKTSVIKEKD                                                   280
```

ORF40a also shows homology to Hsf:

```
gl|1666683 (U41852) hsf gene product [Haemophilus influenzae] Length = 2353
Score = 153 (67.7 bits), Expect = 1.5e-116, Sum P(11) = 1.5e-116
Identities = 33/36 (91%), Positives = 34/36 (94%)

Query:     16 VAVSELTRNHTKRASATVKTAVLATLLFATVQANAT    51   (SEQ ID NO:141)
```

```
                            -continued
          V VSELTR HTKRASATV+TAVLATLLFATVQANAT       (SEQ ID NO:142)

Sbjct:   17 VVVSELTRTHTKRASATVETAVLATLLFATVQANAT   52 (SEQ ID NO:143)

Score = 161 (71.2 bits), Expect = 1.5e-116, Sum P(11) = 1.5e-116
Identities = 32/38 (84%), Positives = 36/38 (94%)

Query:  101 VTLKAGDNLKIKQNTNENTNASSFTYSLKKDLTGLINV  138 (SEQ ID NO:144)

+TLKAGDNLKIKQNT+E+TNASSFTYSLKKDLT L +V      (SEQ ID NO:145)

Sbjct:  103 ITLKAGDNLKIKQNTDESTNASSFTYSLKKDLTDLTSV  140 (SEQ ID NO:146)

Score = 110 (48.7 bits), Expect = 1.5e-116, Sum P(11) = 1.5e-116
Identities = 21/29 (72%), Positives = 25/29 (86%)

Query:  138 VTEKLSFGANGKKVNIISDTKGLNFAKET           166 (SEQ ID NO:147)

V++KLS G NG KVNI SDTKGLNFAK++               (SEQ ID NO:148)

Sbjct: 1439 VSDKLSLGTNGNKVNITSDTKGLNFAKDS          1467 (SEQ ID NO:149)

Score = 85 (37.6 bits), Expect = 1.5e-116, Sum P(11) = 1.5e-116
Identities = 18/32 (56%), Positives = 20/32 (62%)

Query:  169 TNGDTTVHLNGIGSTLTDTLAGSSASHVDAGN        200 (SEQ ID NO:150)

T  D  +HLNGI STLTDTL  S A+    GN            (SEQ ID NO:151)

Sbjct: 1469 TGDDANIHLNGIASTLTDTLLNSGATTNLGGN       1500 (SEQ ID NO:152)

Score = 92 (40.7 bits), Expect = 1.5e-116, Sum P(11) = 1.5e-116
Identities = 16/19 (84%), Positives = 19/19 (100%)

Query:  206 RAASIKDVLNAGWNIKGVK                     224 (SEQ ID NO:153)

RAAS+KDVLNAGWN++GVK                         (SEQ ID NO:154)

Sbjct: 1509 RAASVKDVLNAGWNVRGVK                    1527 (SEQ ID NO:155)

Score = 90 (39.8 bits), Expect = 1.5e-116, Sum P(11) = 1.5e-116
Identities = 17/28 (60%), Positives = 20/28 (71%)

Query:  226 STTGQSENVDFVRTYDTVEFLSADTTTT            253 (SEQ ID NO:156)

S   Q EN+DFV TYDTV+F+S D  TT                (SEQ ID NO:157)

Sbjct: 1530 SANNQVENIDFVATYDTVDFVSGDKDTT           1557 (SEQ ID NO:158)
```

Based on homology with Hsf, it was predicted that this protein from *N.meningitidis*, and its epitopes, could be useful antigens for vaccines or diagnostics.

ORF40-1 (61 kDa) was cloned in pET and pGex vectors and expressed in *E.coli*, as described above. The products of protein expression and purification were analyzed by SDS-PAGE. FIG. 1A shows the results of affinity purification of the His-fuision protein, and FIG. 1B shows the results of expression of the GST-fusion in *E.coli*. Purified His-fusion protein was used to immunise mice, whose sera were used for FACS analysis (FIG. 1C), a bactericidal assay (FIG. 1D), and ELISA (positive result). These experiments confirm that ORF40-1 is a surface-exposed protein, and that it is a useful immunogen.

FIG. 1E shows plots of hydrophilicity, antigenic index, and AMPHI regions for ORF40-1.

Example 2

The following partial DNA sequence was identified in *N.meningitidis* <SEQ ID 7>

```
  1 ATGTTACGTt TGACTGCtTT AGCCGTATGC ACCGCCCTCG CTTTGGGCGC
 51 GTGTTCGCCG CAAAATTCCG ACTCTGCCCC ACAAGCCAAA GaACAGGCGG
101 TTTCCGCCGC ACAAACCGAA GgCGCGTCCG TTACCGTCAA AACCGCGCGC
151 GGCGACGTTC AAATACCGCA AAACCCCGAA CGCATCGCCG TTTACGATTT
201 GGGTATGCTC GACACCTTGA GCAAACTGGG CGTGAAAACC GGTTTGTCCG
251 TCGATAAAAA CCGCCTGCCG TATTTAGAGG AATATTTCAA AACGACAAAA
301 CCTGCCGGCA CTTTGTTCGA GCCGGATTAC GAAACGCTCA ACGCTTACAA
```

-continued

```
351 ACCGCAGCTC ATCATCATCG GCAGCCGCGC CgCCAAGGCG TTTGACAAAT
401 TGAAcGAAAT CGCGCCGACC ATCGrmwTGA CCGCCGATAC CGCCAACCTC
451 AAAGAAAGTG CCAArGAGGC ATCGACGCTG GCGCAAATCT TC..
```

This corresponds to the amino acid sequence <SEQ ID 8; ORF38>:

```
  1 MLRLTALAVC TALALGACSP QNSDSAPQAK EQAVSAAQTE GASVTVKTAR
 51 GDVQIPQNPE RIAVYDLGML DTLSKLGVKT GLSVDKNRLF YLEEYFKTTK
101 PAGTLFEPDY ETLNAYKPQL IIIGSRAAKA FDKLNEIAPT IXXTADTANL
151 KESAKEASTL AQIF..
```

Further work revealed the complete nucleotide sequence <SEQ ID 9>:

```
  1 ATGTTACGTT TGACTGCTTT AGCCGTATGC ACCGCCCTCG CTTTGGGCGC
 51 GTGTTCGCCG CAAAATTCCG ACTCTGCCCC ACAAGCCAAA GAACAGGCGG
101 TTTCCGCCGC ACAAACCGAA GGCGCGTCCG TTACCGTCAA AACCGCGCGC
151 GGCGACGTTC AAATACCGCA AAACCCCGAA CGCATCGCCG TTTACGATTT
201 GGGTATGCTC GACACCTTGA GCAAACTGGG CGTGAAAACC GGTTTGTCCG
251 TCGATAAAAA CCGCCTGCCG TATTTAGAGG AATATTTCAA AACGACAAAA
301 CCTGCCGGCA CTTTGTTCGA GCCGGATTAC GAAACGCTCA ACGCTTACAA
351 ACCGCAGCTC ATCATCATCG GCAGCCGCGC CGCCAAGGCG TTTGACAAAT
401 TGAACGAAAT CGCGCCGACC ATCGAAATGA CCGCCGATAC CGCCAACCTC
451 AAAGAAAGTG CCAAAGAGCG CATCGACGCG CTGGCGCAAA TCTTCGGCAA
501 ACAGGCGGAA GCCGACAAGC TGAAGGCGGA AATCGACGCG TCTTTTGAAG
551 CCGCGAAAAC TGCCGCACAA GGTAAGGGCA AAGGTTTGGT GATTTTGGTC
601 AACGGCGGCA AGATGTCGGC TTTCGGCCCG TCTTCACGCT TGGGCGGCTG
651 GCTGCACAAA GACATCGGCG TTCCCGCTGT CGATGAATCA ATTAAAGAAG
701 GCAGCCACGG TCAGCCTATC AGCTTTGAAT ACCTGAAAGA GAAAAATCCC
751 GACTGGCTGT TTGTCCTTGA CCGAAGCGCG GCCATCGGCG AAGAGGGTCA
801 GGCGGCGAAA GACGTGTTGG ATAATCCGCT GGTTGCCGAA CAACCGCTT
851 GGAAAAAAGG ACAGGTCGTG TACCTCGTTC CTGAAACTTA TTTGGCAGCC
901 GGTGGCGCGC AAGAGCTGCT GAATGCAAGC AAACAGGTTG CCGACGCTTT
951 TAACGCGGCA AAATAA
```

This corresponds to the amino acid sequence <SEQ ID 10; ORF38-1>:

```
  1 MLRLTALAVC TALALGACSP QNSDSAPQAK EQAVSAAQTE GASVTVKTAR
 51 GDVQIPQNPE RIAVYDLGML DTLSKLGVKT GLSVDKNRLP YLEEYFKTTK
101 PAGTLFEPDY ETLNAYKPQL IIIGSRAAKA FDKLNEIAPT IEMTADTANL
```

```
151 KESAKERIDA LAQIFGKQAE ADKLKAEIDA SFEAAKTAAQ GKGKGLVILV

201 NGGKMSAFGP SSRLGGWLHK DIGVPAVDES IKEGSHGQPI SFEYLKEKNP

251 DWLFVLDRSA AIGEEGQAAK DVLDNPLVAE TTAWKKGQVV YLVPETYLAA

301 GGAQELLNAS KQVADAFNAA K*
```

Computer analysis of this amino acid sequence reveals a putative prokaryotic membrane lipoprotein lipid attachment site (underlined).

Further work identified the corresponding gene in strain A of N.meningitidis <SEQ ID 11>:

```
  1 ATGTTACGTT TGACTGCTTT AGCCGTATGC ACCGCCCTCG CTTTGGGCGC

51 GTGTTCGCCG CAAAATTCCG ACTCTGCCCC ACAAGCCAAA GAACAGGCGG

101 TTTCCGCCGC ACAATCCGAA GGCGTGTCCG TTACCGTCAA AACGGCGCGC

151 GGCGATGTTC AAATACCGCA AAACCCCGAA CGTATCGCCG TTTACGATTT

201 GGGTATGCTC GACACCTTGA GCAAACTGGG CGTGAAAACC GGTTTGTCCG

251 TCGATAAAAA CCGCCTGCCG TATTTAGAGG AATATTTCAA AACGACAAAA

301 CCTGCCGGAA CTTTGTTCGA GCCGGATTAC GAAACGCTCA ACGCTTACAA

351 ACCGCAGCTC ATCATCATCG GCAGCCGCGC AGCCAAAGCG TTTGACAAAT

401 TGAACGAAAT CGCGCCGACC ATCGAAATGA CCGCCGATAC CGCCAACCTC

451 AAAGAAAGTG CCAAAGAGCG TATCGACGCG CTGGCGCAAA TCTTCGGCAA

501 AAAGGCGGAA GCCGACAAGC TGAAGGCGGA AATCGACGCG TCTTTTGAAG

551 CCGCGAAAAC TGCCGCGCAA GGCAAAGGCA AGGGTTTGGT GATTTTGGTC

601 AACGGCGGCA AGATGTCCGC CTTCGGCCCG TCTTCACGAC TGGGCGGCTG

651 GCTGCACAAA GACATCGGCG TTCCCGCTGT TGACGAAGCC ATCAAAGAAG

701 GCAGCCACGG TCAGCCTATC AGCTTTGAAT ACCTGAAAGA GAAAAATCCC

751 GACTGGCTGT TTGTCCTTGA CCGCAGCGCG GCCATCGGCG AAGAGGGTCA

801 GGCGGCGAAA GACGTGTTGA ACAATCCGCT GGTTGCCGAA ACAACCGCTT

851 GGAAAAAAGG ACAAGTCGTT TACCTTGTTC CTGAAACTTA TTTGGCAGCC

901 GGTGGCGCGC AAGAGCTACT GAATGCAAGC AAACAGGTTG CCGACGCTTT

951 TAACGCGGCA AAATAA
```

This encodes a protein having amino acid sequence <SEQ ID 12; ORF38a>:

```
  1 MLRLTALAVC TALALGACSF QNSDSAFQAK EQAVSAAQSE GVSVTVKTAR

51 GDVQIPQNPE RIAVYDLGML DTLSKLGVKT GLSVDKNRLP YLEEYFKTTK

101 FAGTLFEPDY ETLNAYKFQL IIIGSRAAKA FDKLNEIAPT IEMTADTANL

151 KESAKERIDA LAQIFGKKAE ADKLKAEIDA SFEAAKTAAQ GKGKGLVILV

201 NGGKMSAFGP SSRLGGWLHK DIGVPAVDEA IKEGSHGQPI SFEYLKEKNP

251 DWLFVLDRSA AIGEEGQAAK DVLNNPLVAE TTAWKKGQVV YLVFETYLAA

301 GGAQELLNAS KQVADAFNAA K*
```

The originally-identified partial strain B sequence (ORF38 (SEQ ID NO:8)) shows 95.2% identity over a 165aa overlap with ORF38a (SEQ ID NO:159):

```
                  10         20         30         40         50         60
orf38.pep  MLRLTALAVCTALALGACSPQNSDSAPQAKEQAVSAAQTEGASVTVKTARGDVQIPQNPE
           ||||||||||||||||||||||||||||||||||||:||:||||||||||||||||||||
orf38a     MLRLTALAVCTALALGACSPQNSDSAPQAKEQAVSAAQSEGVSVTVKTARGDVQXPQNPE
                  10         20         30         40         50         60

70         80         90        100        110        120
orf38.pep  RIAVYDLGMLDTLSKLGVKTGLSVDKNRLPYLEEYFKTTKPAGTLFEPDYETLNAYKPQL
           ||||||||||||||||||||||||||||||||||||||||||||||||||||||||||||
ort38a     RIAVYDLGMLDTLSKLGVKTGLSVDKNRLPYLEEYFKTTKPAGTLFEPDYETLNAYKPQL
                  70         80         90        100        110        120

130        140        150        160
orf38.pep  IIIGSRAAKAFDKLNEIAPTIXXTADTANLKESAKE-ASTLAQIF
           |||||||||||||||||||| |||||||||||||||  ::|||||
orf38a     IIIGSRAAKAFDKLNEIAPTIEMTADTANLKESAKERIDALAQIFGKKAEADKLKAEIDA
                 130        140        150        160        170        180 orf38a     SFEAAKTAAQGKGKGLVILVNGGKMSAFGPSSRLGGWLHKDIGVPAVDEAIKEGSHGQPI
                 190        200        210        220        230        240
```

The complete strain B sequence (ORF38-1 (SEQ ID NO: 10)) and OR38a (SEQ ID NO: 12) show 98.4% identity in 321 aa overlap:

```
orf38a.pep  MLRLTALAVCTALALGACSPQNSDSAPQAKEQAVSAAQSEGVSVTVKTARGDVQIPQNPE
            |||||||||||||||||||||||||:|||||||||||||:||:|||||||||||||||:|
orf38-1     MLRLTALAVCTALALGACSPQNSDSAFQAKEQAVSAAQTEGASVTVKTARGDVQIPQNFE orf38a.pep  RIAVYDLGMLDTLSKLGVKTGLSVDKNRLPYLEEYFKTTKPAGTLFEFDYETLNAYKPQL
            ||||||||:|||||||||||||||||||||||||||||||||||||||:|||||||||||
orf38-1     RIAVYDLGNLDTLSKLGVKTGLSVDKNRLPYLEEYFKTTKPAGTLFEPDYETLNAYKPQL orf38a.pep  IIIGSFAAKAFDKLNEIAFTIEMTADTANLKESAKERIDALAQIFGKKAEADKLKAEIDA
            |||||:||||||||||||:|||||||||||||||||||||||||||:|||||||||||||
orf38-1     IIIGSRAAKAFDKLNEIAPTIEMTADTANLKESAKERIDALAQIFGKQAEADKLKAEIDA orf38a.pep  SFEAAKTAAQGKGKGLVILVNGGKMSAFGPSSRLGGWLHKDIGVFAVDEAIKEGSHGQPI
            ||||||||||||||||||||||||||||||||||||||||||||:|||||:|||||||||
orf38-1     SFEAAKTAAQGKGKGLVILVNGGKMSAFGPSSRLGGWLHKDIGVPAVDESIKEGSHGQPI orf38a.pep  SFEYLKEKNFDWLFVLDRSAAIGEEGQAAKDVLNNFLVAETTAWKKGQVVYLVPETYLAA
            |||||||||:||||||||||||||||||||||||||:|||||||||||||||||||||||
orf38-1     SFEYLKEKNPDWLFVLDRSAAIGEEGQAAKDVLDNPLVAETTAWKKGQVVYLVPETYLAA orf38a.pep  GGAQELLNASKQVADAFNAAK
            |||||||||||||||||||||
orf38-1     GGAQELLNASKQVADAFNAAK
```

Computer analysis of these sequences revealed the following:
Homology With a Lipoprotein (Lipo) of *C.jejuni* (Accession Number X82427)

ORF38 (SEQ ID NO:160) and lipo (SEQ ID NO:162) show 38% aa identity (SEQ ID NO:161) in 96 aa overlap:

```
Orf38: 40  EGASVTVKTARGDVQIPQNPERIAVYDLGMLDTLSKLGVKTGLS-VDKNRLPYLEEYFKT   98
           EG S  VK + G+ + P+NP ++ + DLG+LDT   L +   ++ V      LP   + FK
Lipo: 51   EGDSFLVKDSLGENKTPKNPSKVVILDLGILDTFDALKLNDKVAGVFAKNLPKYLQQFKN  110

Orf38: 99  TKPAGTLFEPDYETLNAYKPQLIIIGSRAAKAFDKL                          134
                G + + D+E +NA KP LIII  R +K +DKL
Lipo: 111  KPSVGGVQQVDFEAINALKPDLIIISGRQSKFYDKL                          146
```

Based on this analysis, it was predicted that this protein from *N.meningitidis*, and its epitopes, could be useful antigens for vaccines or diagnostics.

ORF38-1 (32 kDa) was cloned in pET and pGex vectors and expressed in *E.coli*, as described above. The products of protein expression and purification were analyzed by SDS-PAGE. FIG. 2A shows the results of affinity purification of the His-fusion protein, and FIG. 2B shows the results of expression of the GST-fusion in *E.coli*. Purified His-fusion protein was used to immunise mice, whose sera were used for Western blot analysis (FIG. 2C) and FACS analysis (FIG. 2D). These experiments confirm that ORF38-1 is a surface-exposed protein, and that it is a useful imrnunogen.

Figure 2E:
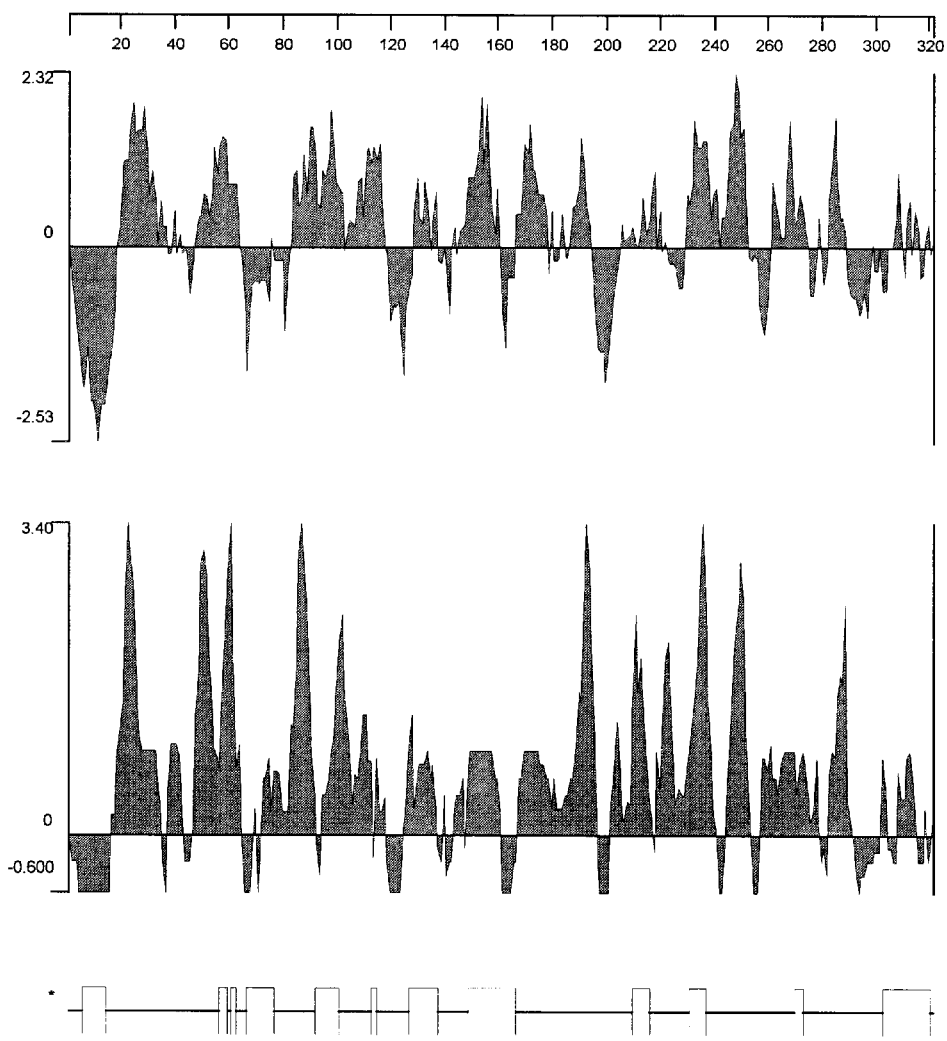

FIG. 2E shows plots of hydrophilicity, antigenic index, and AMPHI regions for ORF38-1.

Example 3

The following *N.meningitidis* DNA sequence was identified <SEQ ID 13>:

```
  1    ATGAAACTTC TGACCACCGC AATCCTGTCT TCCGCAATCG CGCTCAGCAG
 51    TATGGCTGCC GCCGCTGGCA CGGACAACCC CACTGTTGCA AAAAAAACCG
101    TCAGCTACGT CTGCCAGCAA GGTAAAAAAG TCAAAGTAAC CTACGGCTTC
151    AACAAACAGG GTCTGACCAC ATACGCTTCC GCCGTCATCA ACGGCAAACG
201    CGTGCAAATG CCTGTCAATT TGGACAAATC CGACAATGTG GAAACATTCT
251    ACGGCAAAGA AGGCGGTTAT GTTTTGGGTA CCGGCGTGAT GGATGGCAAA
301    TCCTACCGCA AACAGCCCAT TATGATTACC GCACCTGACA ACCAAATCGT
351    CTTCAAAGAC TGTTCCCCAC GTTAA
```

This corresponds to the amino acid sequence <SEQ ID 14; ORF44>:

```
  1    MKLLTTAILS SAIALSSMAA AAGTDNPTVA KKTVSYVCQQ GKKVKVTYGF
 51    NKQGLTTYAS AVINGKRVQM PVNLDKSDNV ETFYGKEGGY VLGTGVMDGK
101    SYRKQPIMIT AFDNQIVFKD CSPR*
```

Computer analysis of this amino acid sequence predicted the leader peptide shown underlined.

Further work identified the corresponding gene in strain A of *N.meningitidis* <SEQ ID 15>:

```
  1    ATGAAACTTC TGACCACCGC AATCCTGTCT TCCGCAATCG CGCTCAGCAG
 51    TATGGCTGCT GCTGCCGGCA CGAACAACCC CACCGTTGCC AAAAAAACCG
101    TCAGCTACGT CTGCCAGCAA GGTAAAAAAG TCAAAGTAAC CTACGGCTTT
151    AACAAACAGG GCCTGACCAC ATACGCTTCC GCCGTCATCA ACGGCAAACG
201    TGTGCAAATG CCTGTCAATT TGGACAAATC CGACAATGTG GAAACATTCT
251    ACGGCAAAGA AGGCGGTTAT GTTTTGGGTA CCGGCGTGAT GGATGGCAAA
301    TCCTATCGCA AACAGCCTAT TATGATTACC GCACCTGACA ACCAAATCGT
351    CTTCAAAGAC TGTTCCCCAC GTTAA
```

This encodes a protein having amino acid sequence <SEQ ID 16; ORF44a>:

```
  1    MKLLTTAILSSAIALSSMAA AAGTNNPTVA KKTVSYVCQQ GKKVKVTYGF
 51    NKQGLTTYAS AVINGKRVQM PVNLDKSDNV ETFYGKEGGY VLGTGVMDGK
101    SYRKQPIMIT APDNQIVFKD CSPR*
```

The strain B sequence (ORF44 (SEQ ID NO: 14)) shows 99.2% identity over a 124aa overlap with ORF44a (SEQ ID NO:16):

```
                   10         20         30         40         50         60
orf44.pep  MKLLTTAILSSAIALSSMAAAAGTDNPTVAKKTVSYVCQQGKKVKVTYGFNKQGLTTYAS
           ||||||||||||||||||||||||:||||||||||||||||||||||||||||||||||
orf44a     MKLLTTAILSSAIALSSMAAAAGTNNPTVAKKTVSYVCQQGKKVKVTYGFNKQGLTTYAS
                   10         20         30         40         50         60

70         80         90        100        110        120
orf44.pep  AVINGKRVQMPVNLDKSDNVETFYGKEGGYVLGTGVMDGKSYRKQPIMITAPDNQIVFKD
           ||||||||||||||||||||||||||||||||||||||||||||||||||||||||||||
orf44a     AVINGKRVQMPVNLDKSDNVETFYGKEGGYVLGTGVMDGKSYRKQPIMITAPDNQIVFKD
                   70         80         90        100        110        120 ort44.pep  CSPRX
           |||||
ort44a     CSPRX
```

Computer analysis gave the following results:
Homology With the LecA Adhesin of *Eikenella corrodens* (Accession Number D78153)
ORF44 (SEQ ID NO:163) and LecA (SEQ ID NO:165) protein show 45% aa identity (SEQ ID NO: 164) in 91 aa overlap:

```
Orf44   33   TVSYVCQQGKKVKVTYGFNKQGLTTYASAVINGKRVQMPVNLDKSDNVETFYGKEGGYVL   92
             +V+YVCQQG+++ V Y FN  G+ T A   +N + +++P NL  SDNV+T +   GY L
LecA   135   SVAYVCQQGRRLNVNYRFNSAGVPTSAELRVNNRNLRLPYNLSASDNVDTVF-SANGYRL  193

Orf44   93   GTGVMDGKSYRKQPIMITAPDNQIVFKDCSP  123
              T   MD  +YR Q I+++AP+ Q+++KDCSP
LecA   194   TTNAMDSANYRSQDIIVSAPNGQMLYKDCSP  224
```

Based on homology with the adhesin, it was predicted that this protein from *N.meningitidis*, and its epitopes, could be useful antigens for vaccines or diagnostics.

ORF44-4 (11.2 kDa) was cloned in pET and pGex vectors and expressed in *E.coli*, as described above. The products of protein expression and purification were analyzed by SDS-PAGE. FIG. 3A shows the results of affinity purification of the His-fusion protein, and FIG. 3B shows the results of expression of the GST-fusion in *E.coli*. Purified His-fusion protein was used to immunise mice, whose sere were used for ELISA, which gave positive results, and for a bactericidal assay (FIG. 3C). These experiments confirm that ORF44-1 is a surface-exposed protein, and that it is a usefuel immunogen.

FIG. 3D showa plots of hydrophilicity, antigenic index, and AMPHI regions for ORF44-1.

Example 4

The following partial DNA sequence was identified in *N.meningitidis* <SEQ ID 17>

```
  1..GGCACCGAAT TCAAAACCAC CCTTTCCGGA GCCGACATAC AGGCAGGGGT
 51   GGGTGAAAAA GCCCGAGCCG ATGCGAAAAT TATCCTAAAA GGCATCGTTA
101   ACCGCATCCA AACCGAAGAA AAGCTGGAAT CCAACTCGAC CGTATGGCAA
151   AAGCAGGCCG GAAGCGGCAG CACGGTTGAA ACGCTGAAGC TACCGAGCTT
201   TGAAGGGCCG GCACTGCCTA AGCTGACCGC TCCCGGCGGC TATATCGCCG
251   ACATCCCCAA AGGCAACCTC AAAACCGAAA TCGAAAAGCT GGCCAAACAG
301   CCCGAATATG CCTATCTGAA ACAGCTTCAG ACGGTCAAGG ACGTGAACTG
```

-continued

```
351   GAACCAAGTA CAGCTCGCTT ACGACAAATG GGACTATAAA CAGGAAGGCC

401   TAACCGGAGC CGGAGCCGCA ATTANCGCAC TGGCCGTTAC CGTGGTCACC

451   TCAGGCGCAG GAACCGGAGC CGTATTGGGA TTAANACGNG TGGCCGCCGC

501   CGCAACCGAT GCAGCATTT...
```

This corresponds to the amino acid sequence <SEQ ID 18; ORF49>:

```
  1 ..GTEFKTTLSG ADIQAGVGEK ARADAKIILK GIVNRIQTEE KLESNSTVWQ

51   KQAGSGSTVE TLKLPSFEGP ALPKLTAPGG YIADIPKGNL KTEIEKLAKQ

101   PEYAYLKQLQ TVKDVNWNQV QLAYDKWDYK QEGLTGAGAA IXALAVTVVT

151   SGAGTGAVLG LXRVAAAATD AAF..
```

Further work revealed the complete nucleotide sequence <SEQ ID 19>:

```
   1 ATGCAACTGC TGGCAGCCGA AGGCATTCAC CAACACCAAT TGAATGTTCA

51 GAAAAGTACC CGTTTCATCG GCATCAAAGT GGGTAAAAGC AATTACAGCA

101 AAAACGAGCT GAACGAAACC AAACTGCCCG TACGCGTTAT CGCCCAAACA

151 GCCAAAACCC GTTCCGGCTG GGATACCGTA CTCGAAGGCA CCGAATTCAA

201 AACCACCCTT TCCGGAGCCG ACATACAGGC AGGGGTGGGT GAAAAAGCCC

251 GAGCCGATGC GAAAATTATC CTAAAAGGCA TCGTTAACCG CATCCAAACC

301 GAAGAAAAGC TGGAATCCAA CTCGACCGTA TGGCAAAAGC AGGCCGGAAG

351 CGGCAGCACG GTTGAAACGC TGAAGCTACC GAGCTTTGAA GGGCCGGCAC

401 TGCCTAAGCT GACCGCTCCC GGCGGCTATA TCGCCGACAT CCCCAAAGGC

451 AACCTCAAAA CCGAAATCGA AAAGCTGGCC AAACAGCCCG AATATGCCTA

501 TCTGAAACAG CTTCAGACGG TCAAGGACGT GAACTGGAAC CAAGTACAGC

551 TCGCTTACGA CAAATGGGAC TATAAACAGG AAGGCCTAAC CGGAGCCGGA

601 GCCGCAATTA TCGCACTGGC CGTTACCGTG GTCACCTCAG GCGCAGGAAC

651 CGGAGCCGTA TTGGGATTAA ACGGTGCGGC CGCCGCCGCA ACCGATGCAG

701 CATTTGCCTC TTTGGCCAGC CAGGCTTCCG TATCGTTCAT CAACAACAAA

751 GGCAATATCG GTAACACCCT GAAAGAGCTG GGCAGAAGCA GCACGGTGAA

801 AAATCTGATG GTTGCCGTCG CTACCGCAGG CGTAGCCGAC AAAATCGGTG

851 CTTCGGCACT GAACAATGTC AGCGATAAGC AGTGGATCAA CAACCTGACC

901 GTCAACCTGG CCAATGCGGG CAGTGCCGCA CTGATTAATA CCGCTGTCAA

951 CGGCGGCAGC CTGAAAGACA ATCTGGAAGC GAATATCCTT GCGGCTTTGG

1001 TGAATACTGC GCATGGAGAG GCAGCAAGTA AAATCAAACA GTTGGATCAG

1051 CACTACATTG CCCATAAGAT TGCCCATGCC ATAGCGGGCT GTGCGGCAGC

1101 GGCGGCGAAT AAGGGCAAGT GTCAAGATGG TGCGATCGGT GCGGCGGTCG

1151 GTGAAATCCT TGGCGAAACC CTACTGGACG GCAGAGACCC TGGCAGCCTG

1201 AATGTGAAGG ACAGGGCAAA AATCATTGCT AAGGCGAAGC TGGCAGCAGG
```

```
-continued
1251 GGCGGTTGCG GCGTTGAGTA AGGGGGATGT GAGTACGGCG GCGAATGCGG

1301 CTGCTGTGGC GGTAGAGAAT AATTCTTTAA ATGATATACA GGATCGTTTG

1351 TTGAGTGGAA ATTATGCTTT ATGTATGAGT GCAGGAGGAG CAGAAAGCTT

1401 TTGTGAGTCT TATCGACCAC TGGGCTTGCC ACACTTTGTA AGTGTTTCAG

1451 GAGAAATGAA ATTACCTAAT AAATTCGGGA ATCGTATGGT TAATGGAAAA

1501 TTAATTATTA ACACTAGAAA TGGCAATGTA TATTTCTCTG TAGGTAAAAT

1551 ATGGAGTACT GTAAAATCAA CAAAATCAAA TATAAGTGGG GTATCTGTCG

1601 GTTGGGTTTT AAATGTTTCC CCTAATGATT ATTTAAAAGA AGCATCTATG

1651 AATGATTTCA GAAATAGTAA TCAAAATAAA GCCTATGCAG AAATGATTTC

1701 CCAGACTTTG GTAGGTGAGA GTGTTGGTGG TAGTCTTTGT CTGACAAGAG

1751 CCTGCTTTTC GGTAAGTTCA ACAATATCTA AATCTAAATC TCCTTTTAAA

1801 GATTCAAAAA TTATTGGGGA AATCGGTTTG GGAAGTGGTG TTGCTGCAGG

1851 AGTAGAAAAA ACAATATACA TAGGTAACAT AAAAGATATT GATAAATTTA

1901 TTAGTGCAAA CATAAAAAAA TAG
```

This corresponds to the amino acid sequence <SEQ ID 20; ORF49-1>:

```
  1 MQLLAAEGIH QHQLNVQKST RFIGIKVGKS NYSKNELNET KLPVRVIAQT

51 AKTRSGWDTV LEGTEFKTTL SGADIQAGVG EKARADAKII LKGIVNRIQT

101 EEKLESNSTV WQKQAGSGST VETLKLPSFE GPALPKLTAP GGYIADIPKG

151 NLKTEIEKLA KQPEYAYLKQ LQTVKDVNWN QVQLAYDKWD YKQEGLTGAG

201 AAIIALAVTV VTSGAGTGAV LGLNGAAAAA TDAAFASLAS QASVSFINNK

251 GNIGNTLKEL GRSSTVKNLM VAVATAGVAD KIGASALNNV SDKQWINNLT

301 VNLANAGSAA LINTAVNGGS LKDNLEANIL AALVNTAHGE AASKIKQLDQ

351 HYIAHKIAHA IAGCAAAAAN KGKCQDGAIG AAVGEILGET LLDGRDPGSL

401 NVKDRAKIIA KAKLAAGAVA ALSKGDVSTA ANAAAVAVEN NSLNDIQDRL

451 LSGNYALCMS AGGAESFCES YRPLGLPHFV SVSGEMKLPN KFGNRMVNGK

501 LIINTRNGNV YFSVGKIWST VKSTKSNISG VSVGWVLNVS PNDYLKEASM

551 NDFRNSNQNK AYAEMISQTL VGESVGGSLC LTRACFSVSS TISKSKSPFK

601 DSKIIGEIGL GSGVAAGVEK TIYIGNIKDI DKFISANIKK *
```

Computer analysis predicts a transmembrane domain and also indicates that ORF49 has no significant amino acid homology with known proteins. A corresponding ORF from *N.meningitidis* strain A was, however, identified:

ORF49 (SEQ ID NO:18) shows 86.1% identity over a 173aa overlap with an ORF (ORF49a (SEQ ID NO:166)) from strain A of *N.meningitidis*:

```
                                         10         20         30
orf49.pep                         GTEFKTTLSGADIQAGVGEKARADAKIILK
                                  ||||||||:|||||||| ||||:||||||
orf49a    SKNELNETKLPVRVVAQXAATRSGWDTVLEGTEFKTTLAGADIQAGVXEKARVDAKIILK
                   40         50         60         70         80         90

40         50         60         70         80         90
orf49.pep GIVNRIQTEEKLESNSTVWQKQAGSGSTVETLKLPSFEGPALPKLTAPGGYIADIPKGNL
          ||||||:|||:||||||||||||||| |||:|||||||:|: |||:|||||:||||||||
orf49a    GIVNRIQSEEKLETNSTVWQKQAGRGSTIETLKLPSFESPTPPKLSAPGGYIVDIPKGNL
```

-continued

```
                100       110       120       130       140       150

100       110       120       130       140       150
orf49.pep  KTEIEKLAKQPEYAYLKQLQTVKDVNWNQVQLAYDKWDYKQEGLTGAGAAIXALAVTVVT
           ||||||:||||||||||||::|::||||||||:|||||  ||||| ||||||||
orf49a     KTEIEKLSKQPEYAYLKQLQVAKNINWNQVQLAYDRWDYKQEGLTEAGAAIIALAVTVVT
                160       170       180       190       200       210

160       170
orf49.pep  SGAGTGAVLGLXRVAAAATDAAF
           ||||||||||||  :  |||||||||
orf49a     SGAGTGAVLGLNGAXAAATDAAFASLASQASVSFINNKGDVGKTLKELGRSSTVKNLVVA
                220       230       240       250       260       270
```

ORF49-1 (SEQ ID NO:168) and ORF49a (SEQ ID NO:167) show 83.2% identity in 457 aa overlap:

```
orf49.pep  XQLLAEEGIHKHELDVQKSRRFIGIKVGXSNYSKNELNETKLPVRVVAQXAATRSGWDTV
            |||  ||||:|:||||  ||||||||  ||||||||||||||||||:|  |||||||||
orf49-1    MQLLAAEGIHQHQLNVQKSTRFIGIKVGKSNYSKNELNETKLPVRVIAQTAKTRSGWDTV orf49.pep  LEGTEFKTTLAGADIQAGVXEKARVDAKIILKGIVNRIQSEEKLETNSTVWQKQAGRGST
           |||||||||:|||||||||  |||:||||||||||||||:|||||:|||||||||| |||
orf49-1    LEGTEFKTTLSGADIQAGVGEKARADAKIILKGIVNRIQTEEKLESNSVWTQKQAGSGST orf49.pep  IETLKLPSFESPTPPKLSAPGGYIVDIPKGNLKTEIEKLSKQPEYAYLKQLQVAKNINWN
           :|||||||||:|: |||:||||||:||||||||||||||||||||||||||||::|::|||
orf49-1    VETLKLPSFEGPALPKLTAPGGYIADIPKGNLKTEIEKLAKQPEYAYLKQLQTVKDVNWN orf49.pep  QVQLAYDRWDYKQEGLTEAGAAIIALAVTVVTSGAGTGAVLGLNGAXAAATDAAFASLAS
           |||||||:|||||||| ||||||||||||||||||||||||||||| ||||||||||||||
orf49-1    QVQLAYDKWDYKQEGLTGAGAAIIALAVTVVTSGAGTGAVLGLNGAAAAATDAAFASLAS orf49.pep  QASVSFINNKGDVGKTLKELGRSSTVKNLVVAAATAGVADKIGASALXNVSDKQWINNLT
           ||||||||||:::|:|||||||||||||:||:|||||||||||||||||:||||||||||||
orf49-1    QASVSFINNKGNIGNTLKELGRSSTVKNLMVAVATAGVADKIGASALNNVSDKQWINNLT orf49.pep  VNLANAGSAALINTAVNGGSLKDXLEANILAALVNTAHGEAASKIKQLDQHYIVHKIAHA
           |||||||||||||||||||||||| ||||||||||||||||||||||||||||||:||||||
orf49-1    VNLANAGSAALINTAVNGGSLKDNLEANILAALVNTAHGEAASKIKQLDQHYIAHKIAHA orf49.pep  IAGCAAAAANKGKCQDGAIGAAVGEIVGEALTNGKNPDTLTAKEREQILAYSKLVAGTVS
           |||||||||||||||||||||||||||:||: ||: :|::| :|::|: |:|: :||:||:|:
orf49-1    IAGCAAAAANKGKCQDGAIGAAVGEILGETLLDGRDPGSLNVKDRAKIIAKAKLAAGAVA orf49.pep  GVVGGDVNAAANAAEVAVKNNQLSDXEGREFDNEMTACAKQNXPQLCRKNTVKKYQNVAD
           ::   |||::|||||   |||:||:|: : | ::::::  |
orf49-1    ALSKGDVSTAANAAAVAVENNSLNDIQDRLLSGNYALCMSAGGAESFCESYRPLGLPHFV orf49.pep  KRLAASIAICTDISRSTECRTIRKQHLIDSRSLHSSWEAGLIGKDDEWYKLFSKSYTQAD orf49-1    SVSGEMKLPNKFGNRMVNGKLIINTRNGNVYFSVGKIWSTVKSTKSNISGVSVGWVLNVS
```

The complete length ORF49a nucleotide sequence <SEQ ID 21> is:

```
  1 NTGCAACTGC TGGCAGAAGA AGGCATCCAC AAGCACGAGT TGGATGTCCA

51 AAAAAGCCGC CGCTTTATCG GCATCAAGGT AGGTNAGAGC AATTACAGTA

101 AAAACGAACT GAACGAAACC AAATTGCCTG TCCGCGTCGT CGCCCAAANT

151 GCAGCCACCC GTTCAGGCTG GGATACCGTG CTCGAAGGTA CCGAATTCAA

201 AACCACGCTG GCCGGTGCCG ACATTCAGGC AGGTGTANGC GAAAAAGCCC

251 GTGTCGATGC GAAAATTATC CTCAAAGGCA TTGTGAACCG TATCCAGTCG

301 GAAGAAAAAT TAGAAACCAA CTCAACCGTA TGGCAGAAAC AGGCCGGACG

351 CGGCAGCACT ATCGAAACGC TAAAACTGCC CAGCTTCGAA AGCCCTACTC

401 CGCCCAAATT GTCCGCACCC GGCGGNTATA TCGTCGACAT TCCGAAAGGC
```

-continued

```
 451 AATCTGAAAA CCGAAATCGA AAAGCTGTCC AAACAGCCCG AGTATGCCTA
 501 TCTGAAACAG CTCCAAGTAG CGAAAAACAT CAACTGGAAT CAGGTGCAGC
 551 TTGCTTACGA CAGATGGGAC TACAAACAGG AGGGCTTAAC CGAAGCAGGT
 601 GCGGCGATTA TCGCACTGGC CGTTACCGTG GTCACCTCAG GCGCAGGAAC
 651 CGGAGCCGTA TTGGGATTAA ACGGTGCGNC CGCCGCCGCA ACCGATGCAG
 701 CATTCGCCTC TTTGGCCAGC CAGGCTTCCG TATCGTTCAT CAACAACAAA
 751 GGCGATGTCG GCAAAACCCT GAAAGAGCTG GCAGAAGCA GCACGGTGAA
 801 AAATCTGGTG GTTGCCGCCG CTACCGCAGG CGTAGCCGAC AAAATCGGCG
 851 CTTCGGCACT GANCAATGTC AGCGATAAGC AGTGGATCAA CAACCTGACC
 901 GTCAACCTAG CCAATGCGGG CAGTGCCGCA CTGATTAATA CCGCTGTCAA
 951 CGGCGGCAGC CTGAAAGACA NTCTGGAAGC GAATATCCTT GCGGCTTTGG
1001 TCAATACCGC GCATGGAGAA GCAGCCAGTA AAATCAAACA GTTGGATCAG
1051 CACTACATAG TCCACAAGAT TGCCCATGCC ATAGCGGGCT GTGCGGCAGC
1101 GGCGGCGAAT AAGGGCAAGT GTCAGGATGG TGCGATAGGT GCGGCTGTGG
1151 GCGAGATAGT CGGGGAGGCT TTGACAAACG GCAAAAATCC TGACACTTTG
1201 ACAGCTAAAG AACGCGAACA GATTTTGGCA TACAGCAAAC TGGTTGCCGG
1251 TACGGTAAGC GGTGTGGTCG GCGGCGATGT AAATGCGGCG GCGAATGCGG
1301 CTGAGGTAGC GGTGAAAAAT AATCAGCTTA GCGACNAAGA GGGTAGAGAA
1351 TTTGATAACG AAATGACTGC ATGCGCCAAA CAGAATANTC CTCAACTGTG
1401 CAGAAAAAAT ACTGTAAAAA AGTATCAAAA TGTTGCTGAT AAAAGACTTG
1451 CTGCTTCGAT TGCAATATGT ACGGATATAT CCCGTAGTAC TGAATGTAGA
1501 ACAATCAGAA AACAACATTT GATCGATAGT AGAAGCCTTC ATTCATCTTG
1551 GGAAGCAGGT CTAATTGGTA AAGATGATGA ATGGTATAAA TTATTCAGCA
1601 AATCTTACAC CCAAGCAGAT TTGGCTTTAC AGTCTTATCA TTTGAATACT
1651 GCTGCTAAAT CTTGGCTTCA ATCGGGCAAT ACAAAGCCTT TATCCGAATG
1701 GATGTCCGAC CAAGGTTATA CACTTATTTC AGGAGTTAAT CCTAGATTCA
1751 TTCCAATACC AAGAGGGTTT GTAAAACAAA ATACACCTAT TACTAATGTC
1801 AAATACCCGG AAGGCATCAG TTTCGATACA AACCTANAAA GACATCTGGC
1851 AAATGCTGAT GGTTTTAGTC AAGAACAGGG CATTAAAGGA GCCCATAACC
1901 GCACCAATNT TATGGCAGAA CTAAATTCAC GAGGAGGANG NGTAAAATCT
1951 GAAACCCANA CTGATATTGA AGGCATTACC CGAATTAAAT ATGAGATTCC
2001 TACACTAGAC AGGACAGGTA AACCTGATGG TGGATTTAAG GAAATTTCAA
2051 GTATAAAAAC TGTTTATAAT CCTAAAAANT TTTNNGATGA TAAAATACTT
2101 CAAATGGCTC AANATGCTGN TTCACAAGGA TATTCAAAAG CCTCTAAAAT
2151 TGCTCAAAAT GAAAGAACTA AATCAATATC GGAAAGAAAA AATGTCATTC
2201 AATTCTCAGA AACCTTTGAC GGAATCAAAT TTAGANNNTA TNTNGATGTA
2251 AATACAGGAA GAATTACAAA CATTCACCCA GAATAATTTA A
```

This encodes a protein having amino acid sequence <SEQ ID 22>:

```
  1 XQLLAEEGIH KHELDVQKSR RFIGIKVGXS NYSKNELNET KLPVRVVAQX
 51 AATRSGWDTV LEGTEFKTTL AGADIQAGVX EKARVDAKII LKGIVNRIQS
101 EEKLETNSTV WQKQAGRGST IETLKLPSFE SPTPPKLSAP GGYIVDIPKG
151 NLKTEIEKLS KQPEYAYLKQ LQVAKNINWN QVQLAYDRWD YKQEGLTEAG
201 AAIIALAVTV VTSGAGTGAV LGLNGAXAAA TDAAFASLAS QASVSFINNK
251 GDVGKTLKEL GRSSTVKNLV VAAATAGVAD KIGASALXNV SDKQWINNLT
301 VNLANAGSAA LINTAVNGGS LKDXLEANIL AALVNTAHGE AASKIKQLDQ
351 HYIVHKIAHA IAGCAAAAAN KGKCQDGAIG AAVGEIVGEA LTNGKNPDTL
401 TAKEREQILA YSKLVAGTVS GVVGGDVNAA ANAAEVAVKN NQLSDXEGRE
451 FDNEMTACAK QNXPQLCRKN TVKKYQNVAD KRLAASIAIC TDISRSTECR
501 TIRKQHLIDS RSLHSSWEAG LIGKDDEWYK LFSKSYTQAD LALQSYHLNT
551 AAKSWLQSGN TKPLSEWMSD QGYTLISGVN PRFIPIPRGF VKQNTPITNV
601 KYPEGISFDT NLXRHLANAD GFSQEQGIKG AHNRTNXMAE LNSRGGXVKS
651 ETXTDIEGIT RIKYEIPTLD RTGKPDGGFK EISSIKTVYN PKXFXDDKIL
701 QMAQXAXSQG YSKASKIAQN ERTKSISERK NVIQFSETFD GIKFRXYXDV
751 NTGRITNIHP E*
```

Based on the presence of a putative transmembrane domain, it is predicted that these proteins from *N.meningitidis*, and their epitopes, could be useful antigens for vaccines or diagnostics.

Example 5

The following partial DNA sequence was identified in *N.meningitidis* <SEQ ID 23>

```
  1    CGGATCGTTG TAGGTTTGCG GATTTCTTGC GCCGTAGTCA CCGTAGTCCC
 51    AAGTATAACC CAAGGCTTTG TCTTCGCCTT TCATTCCGAT AAGGGATATG
101    ACGCTTTGGT CGGTATAGCC GTCTTGGGAA CCTTTGTCCA CCCAACGCAT
151    ATCTGCCTGC GGATTCTCAT TGCCGCTTCT TGGCTGCTGA TTTTTCTGCC
201    TTCGCGTTTT TCAACTTCGC GCTTGAGGGC TTCGGCATAT TTGTCGGCCA
251    ACGCCATTTC TTTCGGATGC AGCTGCCTAT TGTTCCAATC TACATTCGCA
301    CCCACCACAG CACCACCACT ACCACCAGTT GCATAG
```

This corresponds to the amino acid sequence <SEQ ID 24; ORF50>:

```
  1    RIVVGLRISC AVVTVVPSIT QGFVFAFHSD KGYDALVGIA VLGTFVHPTH
 51    ICLRILIAAS WLLIFLPSRF STSRLRASAY LSANAISFGC SCLLFQSTFA
101    PTTAPPLPPV A*
```

Computer analysis predicts two transmembrane domains and also indicates that ORF50 has no significant amino acid homology with known proteins.

Based on the presence of a putative transmembrane domain, it is predicted that this protein from *N.meningitidis*, and its epitopes, could be useful antigens for vaccines or diagnostics.

Example 6

The following partial DNA sequence was identified in *N.meningitidis* <SEQ ID 25>

```
   1    AAGTTTGACT TTACCTGGTT TATTCCGGCG GTAATCAAAT ACCGCCGGTT
  51    GTTTTTTGAA GTATTGGTGG TGTCGGTGGT GTTGCAGCTG TTTGCGCTGA
 101    TTACGCCTCT GTTTTTCCAA GTGGTGATGG ACAAGGTGCT GGTACATCGG
 151    GGATTCTCTA CTTTGGATGT GGTGTCGGTG GCTTTGTTGG TGGTGTCGCT
 201    GTTTGAGATT GTGTTGGGCG GTTTGCGGAC GTATCTGTTT GCACATACGA
 251    CTTCACGTAT TGATGTGGAA TTGGGCGCGC GTTTGTTCCG GCATCTGCTT
 301    TCCCTGCCTT TATCCTATTT CGAGCACAGA CGAGTGGGTG ATACGGTGGC
 351    TCGGGTGCGG GAATTGGAGC AGATTCGCAA TTTCTTGACC GGTCAGGCCC
 401    TGACTTCGGT GTTGGATTTG GCGTTTTCGT TTATCTTTCT GGCGGTGATG
 451    TGGTATTACA GCTCCACTCT GACTTGGGTG GTATTGGCTT CGTTG.....
1451    .......... .......... .......... .......... ..........
1501    .......... .......... .......... .......... ..ATTTGCGC
1551    CAACCGGACG GTGCTGATTA TCGCCCACCG TCTGTCCACT GTTAAAACGG
1601    CACACCGGAT CATTGCCATG GATAAAGGCA GGATTGTGGA AGCGGGAACA
1651    CAGCAGGAAT TGCTGGCGAA CG..AACGGA TATTACCGCT ATCTGTATGA
1701    TTTACAGAAC GGGTAG
```

This corresponds to the amino acid sequence <SEQ ID 26; ORF39>:

```
   1    KFDFTWFIPA VIKYRRLFFE VLVVSVVLQL FALITPLFFQ VVMDKVLVHR
  51    GFSTLDVVSV ALLVVSLFEI VLGGLRTYLF AHTTSRIDVE LGARLFRHLL
 101    SLPLSYFEHR RVGDTVARVR ELEQIRNFLT GQALTSVLDL AFSFIFLAVM
 151    WYYSSTLTWV VLASL..... .......... .......... ..........
 501    .......... ....ICANRT VLIIAHRLST VKTAHRIIAM DKGRIVEAGT
 551    QQELLANXNG YYRYLYDLQN G*
```

Further work revealed the complete nucleotide sequence <SEQ ID 27>:

```
   1    ATGTCTATCG TATCCGCACC GCTCCCCGCC CTTTCCCCCC TCATCATCCT
  51    CGCCCATTAC CACGGCATTG CCGCCAATCC TGCCGATATA CAGCATGAAT
 101    TTTGTACTTC CGCACAGAGC GATTTAAATG AAACGCAATG GCTGTTAGCC
 151    GCCAAATCTT TGGGATTGAA GGCAAAGGTA GTCCGCCAGC CTATTAAACC
 201    TTTGGCTATG GCGACTTTAC CCGCATTGGT ATGGTGTGAT CACGGCAACC
 251    ATTTCATTTT GGCCAAAACA GACGGTGAGG GTGAGCATGC CCAATTTTTG
```

-continued

```
 301   ATACAGGATT TGGTTACGAA TAAGTCTGCG GTATTGTCTT TTGCCGAATT
 351   TTCTAACAGA TATTCGGGCA AACTGATATT GGTTGCTTCC CGCGCTTCGG
 401   TATTGGGCAG TTTGGCAAAG TTTGACTTTA CCTGGTTTAT TCCGGCGGTA
 451   ATCAAATACC GCCGGTTGTT TTTTGAAGTA TTGGTGGTGT CGGTGGTGTT
 501   GCAGCTGTTT GCGCTGATTA CGCCTCTGTT TTTCCAAGTG GTGATGGACA
 551   AGGTGCTGGT ACATCGGGGA TTCTCTACTT TGGATGTGGT GTCGGTGGCT
 601   TTGTTGGTGG TGTCGCTGTT TGAGATTGTG TTGGGCGGTT TGCGGACGTA
 651   TCTGTTTGCA CATACGACTT CACGTATTGA TGTGGAATTG GGCGCGCGTT
 701   TGTTCCGGCA TCTGCTTTCC CTGCCTTTAT CCTATTTCGA GCACAGACGA
 751   GTGGGTGATA CGGTGGCTCG GGTGCGGGAA TTGGAGCAGA TTCGCAATTT
 801   CTTGACCGGT CAGGCGCTGA CTTCGGTGTT GGATTTGGCG TTTTCGTTTA
 851   TCTTTCTGGC GGTGATGTGG TATTACAGCT CCACTCTGAC TTGGGTGGTA
 901   TTGGCTTCGT TGCCTGCCTA TGCGTTTTGG TCGGCATTTA TCAGTCCGAT
 951   ACTGCGGACG CGTCTGAACG ATAAGTTCGC GCGCAATGCA GACAACCAGT
1001   CGTTTTTAGT AGAAAGCATC ACTGCGGTGG GTACGGTAAA GGCGATGGCG
1051   GTGGAGCCGC AGATGACGCA GCGTTGGGAC AATCAGTTGG CGGCTTATGT
1101   GGCTTCGGGA TTTCGGGTAA CGAAGTTGGC GGTGGTCGGC CAGCAGGGGG
1151   TGCAGCTGAT TCAGAAGCTG GTGACGGTGG CGACGTTGTG GATTGGCGCA
1201   CGGCTGGTAA TTGAGAGCAA GCTGACGGTG GGGCAGCTGA TTGCGTTTAA
1251   TATGCTCTCG GGACAGGTGG CGGCGCCTGT TATCCGTTTG GCGCAGTTGT
1301   GGCAGGATTT CCAGCAGGTG GGGATTTCGG TGGCGCGTTT GGGGGATATT
1351   CTGAATGCGC CGACCGAGAA TGCGTCTTCG CATTTGGCTT TGCCCGATAT
1401   CCGGGGGGAG ATTACGTTCG AACATGTCGA TTTCCGCTAT AAGGCGGACG
1451   GCAGGCTGAT TTTGCAGGAT TTGAACCTGC GGATTCGGGC GGGGGAAGTG
1501   CTGGGGATTG TGGGACGTTC GGGGTCGGGC AAATCCACAC TCACCAAATT
1551   GGTGCAGCGT CTGTATGTAC CGGAGCAGGG ACGGGTGTTG GTGGACGGCA
1601   ACGATTTGGC TTTGGCCGCT CCTGCCTGGC TGCGGCGGCA GGTCGGCGTG
1651   GTCTTGCAGG AGAATGTGCT GCTCAACCGC AGCATACGCG ACAATATCGC
1701   GCTGACGGAT ACGGGTATGC CGCTGGAACG CATTATCGAA GCAGCCAAAC
1751   TGGCGGGCGC ACACGAGTTT ATTATGGAGC TGCCGGAAGG CTACGGCACC
1801   GTGGTGGGCG AACAAGGGGC CGGCTTGTCG GGCGGACAGC GGCAGCGTAT
1851   TGCGATTGCC CGCGCGTTAA TCACCAATCC GCGCATTCTG ATTTTTGATG
1901   AAGCCACCAG CGCGCTGGAT TATGAAAGTG AACGAGCGAT TATGCAGAAC
1951   ATGCAGGCCA TTTGCGCCAA CCGGACGGTG CTGATTATCG CCCACCGTCT
2001   GTCCACTGTT AAAACGGCAC ACCGGATCAT TGCCATGGAT AAAGGCAGGA
2051   TTGTGGAAGC GGGAACACAG CAGGAATTGC TGGCGAAGCC GAACGGATAT
2101   TACCGCTATC TGTATGATTT ACAGAACGGG TAG
```

This corresponds to the amino acid sequence <SEQ ID 28; ORF39-1>:

```
  1    MSIVSAPLPA LSALIILAHY HGIAANPADI QHEFCTSAQS DLNETQWLLA

51    AKSLGLKAKV VRQPIKRLAM ATLPALVWCD DGNHFILAKT DGEGERAQFL

101    IQDLVTNKSA VLSFAEFSNR YSGKLILVAS RASVLGSLAK FDFTWFIPAV

151    IKYRRLFFEV LVVSVVLQLF ALITPLFFQV VMDKVLVHRG FSTLDVVSVA

201    LLVVSLFEIV LGGLRTYLFA HTTSRIDVEL GARLFRHLLS LPLSYFEHRR

251    VGDTVARVRE LEQIRNFLTG QALTSVLDLA FSFIFLAVMW YYSSTLTWVV

301    LASLPAYAFW SAFISPILRT RLNDKFARNA DNQSFLVESI TAVGTVKAMA

351    VEPQMTQRWD NQLAAYVASG FRVTKLAVVG QQGVQLIQKL VTVATLWIGA

401    RLVIFSKLTV GQLIAFNMLS GQVAAPVIRL AQLWQDFQQV GISVARLGDI

451    LNAPTENASS HLALPDIRGE ITFEHVDFRY KADGRLILQD LNLRIRAGEV

501    LGIVGRSGSG KSTLTKLVQR LYVFEQGRVL VDGNDLALAA PAWLRRQVGV

551    VLQENVLLNR SIRDNIALTD TGMPLERIIE AAKLAGAHEF IMELPEGYGT

601    VVGEQGAGLS GGQRQRIAIA RALITNPPIL IFDEATSALD YESERAIMQN

651    MQAICANRTV LIIAHRLSTV KTAHRIIAMD KGRIVEAGTQ QELLAKFNGY

701    YRLYDLQNG *
```

Computer analysis of this amino acid sequence gave the following results:
Homology With a Predicted ORF From *N.meningitidis* (Strain A)

ORF39 (SEQ ID NO:169) shows 100% identity over a 165aa overlap with an ORF (ORF39a (SEQ ID NO:170)) from strain A of *N.meningitidis*:

```
orf39.pep                                    KFDFTWFIPAVIKYRRLFFEVINVSVV-
              LQL
                                             ||||||||||||||||||||||||||||
orf39a       AVLSFAEFSNRYSGKLILVASRASV-
              LGSLAKFDFTWFIPAVIKYRRLFFEVLVVSVVLQL
              110       120       130       140       150       160

40        50        60        70        80        90
orf39.pep    FALITPLFFQVVMDKVLVHRGFSTL
              DVVSVALLVVSLFEIVLGGLRTYLFAHTTSRIDVE
              |||||||||||||||||||||||||||||||||||||||||||||||||||||||||
orf39a       FALITPLFFQVVMDKVLVHRGFSTL
              DVVSVALLVVSLFEIVLGGLRTYLFAHTTSRIDVE
              170       180       190       200       210       220

100       110       120       130       140       150
orf39.pep    LGARLFRHLLSLPLSYFEHRRVGDTVARVRELEQIRNFLTGQA
              LTSVLDLAFSIFLAVM
              |||||||||||||||||||||||||||||||||||||||||||||||||||||||||
orf39a       LGARLFRHLLSLFLSYFEHRRVGDTVARVRELEQIRNFLTGQA
              LTSVLDLAFSIFLAVM
              230       240       250       260       270       280

160       170       180       190       200       210
orf39.pep    WYYSSTLTW
              VVLASLXXXXXXXXXXXXXXXXXXXXXXXXXXXXXXXICANRTVLIIAHRLSTV
              ||||||||||||||||
orf39a       WYYSSTLTW
              VVLASLFAYAFWSAFISPILRTRLNDKFARNADNQSFLVESITAVGTVKAM
              290       300       310       320       330       340
```

ORF39-1 (SEQ ID NO:28) and ORF39a (SEQ ID NO:30) show 99.4% identity in 710 aa overlap:

```
orf39-1.pep  MSIVSAFLFALSALIILAHYHGIAANFADIQHEFCTSAQSDLNETQWLLAAKSLGLKAKV
             ||||||:|:|||||||||||||||:|||||||||||||||||||||||||||||||||
orf39a       MSIVSAPLPALSALIILAHYHGIAANPADIQHEFCTSAQSDLNETQWLLAAKSLGLKAKV orf39-1.pep  VRQPIKRLAMATLFALVWCDDGNHFILAKTDGEGEHAQFLIQDLVTNKSAVLSFAEFSNR
             ||||||||||||:|||||||||||:||||||| |||||:|||||:||||||||||||||
orf39a       VRQPIKRLAMATLPALVWCDDGNRFILAKTDGGGEHAQYLIQDLTTNKSAVLSFAEFSNR orf39-1.pep  YSGKLILVASRASVLGSLAKFDFTWFIPAVIKYRRLFFEVLVVSVVLQLFALITPLFFQV
             |||||||||||||||||||||||||||:||||||||||||||||||||||||||||||
orf39a       YSGKLILVASRASVLGSLAKFDFTWFIFAVIKYRRLFFEVLVVSVVLQLFALITPLFFQV orf39-1.pep  VMDKVLVHRGFSTLDVVSVALLVVSLFEIVLGGLRTYLFAHTTSRIDVELGARLFRHLLS
             ||||||||||||||||||||||||||||||||||||||||||||||||||||||||||
orf39a       VMDKVLVHRGFSTLDVVSVALLVVSLFEIVLGGLRTYLFAHTTSRIDVELGARLFRHLLS orf39-1.pep  LPLSYFERRRVGDTVARVRELEQIRNFLTGQALTSVLDLAFSFIFLAVMWYYSSTLTWVV
             | ||||| ||||||||||||||||||||||||||||||||||||||||||||||||||
orf39a       LFLSYFEHRRVGDTVARVRELEQIRNFLTGQALTSVLDLAFSFIFLAVMWYYSSTLTWVV orf39-1.pep  LASLPAYAPWSAFISPILRTRLNDKFARNADNQSFLVESITAVGTVKAMAVEPQMTQRWD
             ||||||||:|||||| |||||||||||||||||||||||||||||||||||:|||||||
orf39a       LASLPAYAFWSAFISFILRTRLNDKFARNADNQSFLVESITAVGTVKAMAVEFQMTQRWD orf39-1.pep  NQLAAYVASGFRVTKLAVVGQQGVQLIQKLVTVATLWIGARLVIESKLTVGQLIAFNMLS
             ||||||||||||||||||||||||||||||||||||||||||||||||||||||||||
orf39a       NQLAAYVASGFRVTKLAVVGQQGVQLIQKLVTVATLWIGARLVIESKLTVGQLIAFNMLS orf39-1-pep  GQVAAFVIRLAQLWQDFQQVGISVARLCDILNAPTENASSHLALPDIRGEITFEHVDFRY
             |||||||||||||||||||||||||| ||||||||||||||||:|||||||||||||||
orf39a       GQVAAFVIRLAQLWQDFQQVGISVARLGDILNAPTENASSHLALFDIRGEITFEHVDFRY orf39-1.pep  KADGRLILQDLNLRIRAGEVLGIVGRSGSGKSTLTKLVQRLYVPEQGRVLVDGNDLALAA
             ||||||||||||||||||||||||||||||||||||||||||| |||||||||||||||
orf39a       KADGRLILQDLNLRIRAGEVLGIVGRSGSGKSTLTKLVQRLYVPAQGRVLVDGNDLALAA orf39-1.pep  PAWLRRQVGVVLQENVLLNRSIRDNIALTDTGMFLERIIEAAKLAGAHEFIMELFEGYGT
             ||||||||||||:|||||||||||||||||||||||||||||||||||||||||:||||
orf39a       PAWLRRQVGVVLOENVLLNRSIRDNIALTDTGMFLERIIEAAKLAGAHEFIMELPEGYGT orf39-1.pep  VVGEQGAGLSGGQRQRIAIARALITNPRILIFDEATSALDYESERAIMQNMQAICANRTV
             ||||||||||||||||||||||||||||||||||||||||||||||||||||||||||
orf39a       VVGEQGAGLSGGQRQRIAIARALITNPRILIFDEATSALDYESERAIMQNMQAICANRTV orf39-1.pep  LIIAHRLSTVKTAHRIIAMDKGRIVEAGTQQELLAKPNGYYRYLYDLQNGX
             |||||||||||||||||||||||||||||||||||:|||||||||||||
orf39a       LIIAHRLSTVKTAHRIIAMDKGRIVEAGTQQELLAKFNGYYRYLYDLQNGX
```

The complete length ORF39a nucleotide sequence <SEQ ID 29>is:

```
  1    ATGTCTATCG TATCCGCACC GCTCCCCGCC CTTTCCGCCC TCATCATCCT
 51    CGCCCATTAC CACGGCATTG CCGCCAATCC TGCCGATATA CAGCATGAAT
101    TTTGTACTTC CGCACAGAGC GATTTAAATG AAACGCAATG GCTGTTAGCC
151    GCCAAATCTT TGGGATTGAA GGCAAAGGTA GTCCGCCAGC CTATTAAACG
201    TTTGGCTATG GCGACTTTAC CCGCATTGGT ATGGTGTGAT GACGGCAACC
251    ATTTTATTTT GGCTAAAACA GACGGTGGGG GTGAGCATGC CCAATATCTA
301    ATACAGGATT TAACTACGAA TAAGTCTGCG GTATTGTCTT TTGCCGAATT
351    TTCTAACAGA TATTCGGGCA AACTGATATT GGTTGCTTCC CGCGCTTCGG
401    TATTGGGCAG TTTGGCAAAG TTTGACTTTA CCTGGTTTAT TCCGGCGGTA
451    ATCAAATACC GCCGGTTGTT TTTTGAAGTA TTGGTGGTGT CGGTGGTGTT
501    GCAGCTGTTT GCGCTGATTA CGCCTCTGTT TTTCCAAGTG GTGATGGACA
```

```
 551      AGGTGCTGGT ACATCGGGGA TTCTCTACTT TGGATGTGGT GTCGGTGGCT
 601      TTGTTGGTGG TGTCGCTGTT TGAGATTGTG TTGGGCGGTT TGCGGACGTA
 651      TCTGTTTGCA CATACGACTT CACGTATTGA TGTGGAATTG GGCGCGCGTT
 701      TGTTCCGGCA TCTGCTTTCC CTGCCTTTAT CCTATTTCGA GCACAGACGA
 751      GTGGGTGATA CGGTGGCTCG GGTGCGGGAA TTGGAGCAGA TTCGCAATTT
 801      CTTGACCGGT CAGGCGCTGA CTTCGGTGTT GGATTTGGCG TTTTCGTTTA
 851      TCTTTCTGGC GGTGATGTGG TATTACAGCT CCACTCTGAC TTGGGTGGTA
 901      TTGGCTTCGT TGCCTGCCTA TGCGTTTTGG TCGGCATTTA TCAGTCCGAT
 951      ACTGCGGACG CGTCTGAACG ATAAGTTCGC GCGCAATGCA GACAACCAGT
1001      CGTTTTTAGT AGAAAGCATC ACTGCGGTGG GTACGGTAAA GGCGATGGCG
1051      GTGGAGCCGC AGATGACGCA GCGTTGGGAC AATCAGTTGG CGGCTTATGT
1101      GGCTTCGGGA TTTCGGGTAA CGAAGTTGGC GGTGGTCGGC CAGCAGGGGG
1151      TGCAGCTGAT TCAGAAGCTG GTGACGGTGG CGACGTTGTG GATTGGCGCA
1201      CGGCTGGTAA TTGAGAGCAA GCTGACGGTG GGGCAGCTGA TTGCGTTTAA
1251      TATGCTCTCG GGACAGGTGG CGGCGCCTGT TATCCGTTTG GCGCAGTTGT
1301      GGCAGGATTT CCAGCAGGTG GGGATTTCGG TGGCGCGTTT GGGGGATATT
1351      CTGAATGCGC CGACCGAGAA TGCGTCTTCG CATTTGGCTT TGCCCGATAT
1401      CCGGGGGGAG ATTACGTTCG AACATGTCGA TTTCCGCTAT AAGGCGGACG
1451      GCAGGCTGAT TTTGCAGGAT TTGAACCTGC GGATTCGGGC GGGGGAAGTG
1501      CTGGGGATTG TGGACGTTC GGGGTCGGGC AAATCCACAC TCACCAAATT
1551      GGTGCAGCGT CTGTATGTAC CGGCGCAGGG ACGGGTGTTG GTGGACGGCA
1601      ACGATTTGGC TTTGGCCGCT CCTGCTTGGC TGCGGCGGCA GGTCGGCGTG
1651      GTCTTGCAGG AGAATGTGCT GCTCAACCGC AGCATACGCG ACAATATCGC
1701      GCTGACGGAT ACGGGTATGC CGCTGGAACG CATTATCGAA GCAGCCAAAC
1751      TGGCGGGCGC ACACGAGTTT ATTATGGAGC TGCCGGAAGG CTACGGCACC
1801      GTGGTGGGCA ACAAGGGGC CGGCTTGTCG GCGGACAGC GGCAGCGTAT
1851      TGCGATTGCC CGCGCGTTAA TCACCAATCC GCGCATTCTG ATTTTTGATG
1901      AAGCCACCAG CGCGCTGGAT TATGAAAGTG AACGAGCGAT TATGCAGAAC
1951      ATGCAGGCCA TTTGCGCCAA CCGGACGGTG CTGATTATCG CCCACCGTCT
2001      GTCCACTGTT AAAACGGCAC ACCGGATCAT TGCCATGGAT AAAGGCAGGA
2051      TTGTGGAAGC GGGAACACAG CAGGAATTGC TGGCGAAGCC GAACGGATAT
2101      TACCGCTATC TGTATGATTT ACAGAACGGG TAG
```

This encodes a protein having amino acid sequence <SEQ ID 30>:

```
  1       MSIVSAPLPALSALIILAHYHGIAANFADIQHEFCTSAQS DLNETQWLLA
 51       AKSLGLKAKV VRQPIKRLAM ATLFALVWCD DGNHFILAKT DGGGEHAQYL
101       IQDLTTNKSA VLSFAEFSNR YSGKLILVAS RASVLGSLAK FDFTWFIPAV
151       IKYRRLFFEVLVVSVVLQLFALITPLFFQV VMDKVLVHRG FSTLDVVSVA
201       LLVVSLFEIVLGGLRTYLFA HTTSRIDVEL GARLFRHLLS LFLSYFEHRR
```

```
251    VGDTVARVRE LEQIRNFLTG QALTSVLDLAFSFIFLAVMW YYSSTLTWVVn

301    LASLPAYAFWSAFISPILRT RLNDKFARNA DNQSFLVESI TAVGTVKAMA

351    VEPQMTQRWD NQLAAYVASG FRVTKLAVVG QQGVQLIQKL VTVATLWIGA

401    RLVIESKLTV GQLIAFNMLS GQVAAPVIRL AQLWQDFQQV GISVARLGDI

451    LNAPTENASS HLALFDIRGE ITFEHVDFRY KADGRLILQD LNLRIRAGEV

501    LGIVGRSGSG KSTLTKLVQR LYVPAQGRVL VDGNDLALAA FAWLRRQVGV

551    VLQENVLLNR SIRDNIALTD TGMPLERIIE AAKLAGAHEF IMELPEGYGT

601    VVGEQGAGLS GGQRQRIAIA RALITNFRIL IFDEATSALD YESERAIMQN

651    MQAICANRTV LIIAHRLSTV KTAMRIIAMD KGRIVEAGTQ QELLAKPNGY

701    YRYLYDLQNG *
```

ORF39a is homologous to a cytolysin from *A.pleuropneumoniae*:

```
sp|P26760|RT1B_ACTPL RTX-I TOXIN DETERMINANT B (TOXIN RTX-I SECRETION ATP-
BINDING PROTEIN) (APX-IB) (HLY-IB) (CYTOLYSIN IB) (CLY-IB)
>gi|97137|pir||D43599 cytolysin IB - Actinobacillus pleuropneuxnoriae (serotype 9)
>gi|38944 (X61112) ClyI-B protein Actinabacillus pleuropneumoniae Length = 707
Score = 931 bits (2379), Expect = 0.0
Identities = 472/690 (68%), Positives = 540/690 (77%) Gaps =3/690 (0%)

Query: 20   YHGIAANPADIQMEFCTSAQSDLNETQWXXXXXXXXXXXXXVVRQFIKRLAMATLPALVWC   79
            YH/IA/NP/+++H+F   + L+ T W              V++ I RIA   LPALVW
Sbjct: 20   YHNIAVNPEELKHKFDLEGKG-LDLTAWLLAAKSLELKAKQVKKAIDRLAFIALFALVWR   78

Query: 80   DDGNHFILAKTDGGGEHAQYLIQDLTTNKSAVLSFAEFSNRYSGKLILVASRASVLGSLA  139
            +DG HFIL K D   E +YLI DL T+   +L  AEF + Y GKLILVASRAS++G LA
Sbjct: 79   EDGKHFILTKIDN--EAKKYLIFDLETHNPRILEQAEFESLYQGKLILVASRASIVGKLA  136

Query: 140  KFDFTWFIPAVIKYRRXXXXXXXXXXXXXXXXXXITPLFFQVVMDKVLVHRGFXXXXXXXX  199
            KFDFTWFIPAVIKYR+                  ITFLFFQVVMDKVLVHRGF
Sbjct: 137  KFDFTWFIPAVIKYRKIFIETLIVSIFLQIFALITFLFFQVVMDKVLVHRGFSTLNVITV  196

Query: 200  XXXXXXXFEIVLGGLRTYLFAHTTSRIDVELGARLFRHLLSLPLSYFEHRRVGDTVARVR  259
                   FEIVL GLRTY+FAH+TSRTDVELGARLFRHLL+LP+SYFE+RRVGDTVARVR
Sbjct: 197  ALAIVVLFEIVLNGLRTYIFAHSTSRIDVELGARLFRHLLALFISYFENRRVGDTVARVR  256

Query: 260  ELEQIRNFLTGQALTSVLDLAFSFIFLAVMWYYSSTLTWVVLASLFAYAFWSAFISFILR  319
            EL+QIRNFLTGQALTSVLDL FSFIF AVMWYYS LT V+L SLP Y  WS FISPILR
Sbjct: 257  ELDQIRNFLTGQALTSVLDLMFSFIFFAVMWYYSFKLTLVILGSLPFYMGWSIFISPILR  316

Query: 320  TRLNDKFARNADNQSFLVESITAVGTVKANAVEFQMTQRWDNQLAAYVASGFRVTKLAVV  379
            RL++KFAR ADNQSFLVES+TA+ T+KA+AV PQMT  WD QLA YV++GFRVT LA +
Sbjct: 317  RRLDEKFARGADNQSFLVESVTAINTIKALAVTPQMTNTWDKQLASYVSAGFRVTTLATI  376

Query: 380  GQQGVQLIQKLVTVATLWIGARLVIESKLTVGQLIAFNMLSGQVAAPVIRLAQLWQDFQQ  439
            GQQGVQ IQK+V V TLW+GA LVI   L++GQLIAFNMLSGQV AFVIRLAQLWQDFQQ
Sbjct: 377  GQQGVQFIQKVVMVITLWLGAHLVISGDLSIGQLIAFNMLSGQVIAFVIRLAQLWQDFQQ  436

Query: 440  VGISVARLGDILNAFTENASSHLALFDIRGEITFEHVDFRYKADGRLILQDLNLRIRAGE  499
            VGISV RLGD+LN+FTE+    LALP+I+G+ITF ++ FRYK D  +IL D+NL I+ GE
Sbjct: 437  VGISVTRLGDVLNSPTESYQGKLALPEIKGDITFRNIRFRYKFDAFVILNDVNLSIQQGE  496

Query: 500  VLGIVGRSGSGKSTLTKLVQRLYVFAQGRVLVDGNDLALAAPAWLRRQVGVVLQENVLLN  559
            V+GIVGRSGSGKSTLTKL+QR Y+P  G+VL+DG+DLALA P WLRRQVGVVLQ+NVLLN
Sbjct: 497  VIGIVGRSGSGKSTLTKLIQRFYIFENGQVLIDGHDLALADPNWLRRQVGVVLQDNVLLN  556

Query: 560  RSIRDNIALTDTGMPLERIIEAAKLAGAHEFIMELPEGYGTVVGEQGAGLSGGQRQRIAI  619
            RSIRDNIAL D GMF+E+I+  AAKLAGAHEFI EL EGY T+VGEQGAGLSGGQRQRIAI
Sbjct: 557  RSIRDNIALADPGMPMEKIVHAAKLAGAHEFISELREGYNTIVGEQGAGLSGGQRQRIAI  616

Query: 620  ARALITNFRILIFDEATSALDYESERAIMQNMQAICANRTVLIIAHRLSTVKTAMRIIAM  679
            ARAL+ NP+ILIFDEATSALDYESE  IM+NM  IC  RTV+IIAHRLSTVK A RII M
```

```
                                    -continued
Sbjct: 617  ARALVNNPKILIFDEATSALDYESEHIIMRNMHQICKGRTVIIIAHRLSTVKNADRIIVM    676

Query: 680  DKGRIVEAGTQQELLAKPNGYYRYLYDLQN                                  709  (SEQ ID NO:171)
            +KG+IVE G  +ELLA PNG Y YL+ LQ+                                      (SEQ ID NO:172)
Sbjct: 677  EKGQIVEQGKHKELLADPNGLYHYLHQLQS                                  706  (SEQ ID NO:173)
```

Homology With the HlyB Leucotoxin Secretion ATP-binding Protein of *Haemophilus actinomycetemcomitans* (Accession Number X53955)

ORF39 (SEQ ID NO:174) and HlyB (SEQ ID NO:176) protein show 71% and 69% amino acid identity (SEQ ID NO:175) in 167 and 55 overlap at the N- and C-terminal regions, respectively:

```
Orf39    1  KFDFTWFIPAVIKYRRXXXXXXXXXXXXXXXXXXITPLFFQVVMDKVLVHRGFXXXXXXXX   60
            KFDFTWFIPAVIKYR+                  ITPLFFQVVMDKVLVHRGF
HlyB   137  KFDFTWFIPAVIKYRKIFIETLIVSIFLQIFALITPLFFQVVMDKVLVMRGFSTLNVITV   196

Orf39   61  XXXXXXXFEIVLGGLRTYLFAHTTSRIDVELGARLFRHLLSLPLSYFEHRRVGDTVARVR   120
                   FEI+LGGLRTY+FAH+TSRIDVELGARLFRHLL+LP+SYFE RRVGDTVARVR
HlyB   197  ALAIVVLFEIILGGLRTYVFAHSTSRIDVELGARLFRHLLALPISYFEARRVGDTVARVR   256

Orf39  121  ELEQIRNFLTGQALTSVLDLAFSFIFLAVMWYYSSTLTWVVLASLIC                167
            EL+QIRNFLTGQALTS+LDL FSFIF AVMWYYS  LT VVL SL C
HlyB   257  ELDQIRNFLTGQALTSILDLLFSFIFFAVMWYYSFKLTLVVLGSLPC                303

Orf39  166  ICANRTVLIIAHRLSTVKTAHRIIAMDKGRIVEAGTQQELLANXNGYYRYLYDLQ        220
            IC NRTVLIIAHRLSTVK A RII MDKG I+E G  QELL +  G Y YL+ LQ
HlyB   651  ICQNRTVLIIAHRLSTVKNADRIIVHDKGEIIEQGKHQELLKDEKGLYSYLHQLQ        705
```

Based on this analysis, it is predicted that this protein from *N.meningitidis*, and its epitopes, could be useful antigens for vaccines or diagnostics.

Example 7

The following partial DNA sequence was identified in *N.meningitidis* <SEQ ID 31>

```
  1  ATGAAATACT TGATCCGCAC CGCCTTACTC GCAGTCGCAG CCGCCGGCAT
 51  CTACGCCTGC CAACCGCAAT CCGAAGCCGC AGTGCAAGTC AAGGCTGAAA
101  ACAGCCTGAC CGCTATGCGC TTAGCCGTCG CCGACAAACA GGCAGAGATT
151  GACGGGTTGA ACGCCCAAAk sGACGCCGAA ATCAGA ...
```

This corresponds to the amino acid sequence <SEQ ID 32; ORF52>:

```
  1  MKYLIRTALL AVAAAGIYAC QPQSEAAVQV KAENSLTAMR LAVADKQAEI
 51  DGLNAQXDAE IR..
```

Further work revealed the complete nucleotide sequence <SEQ ID 33>:

```
  1  ATGAAATACT TGATCCGCAC CGCCTTACTC GCAGTCGCAG CCGCCGGCAT
 51  CTACGCCTGC CAACCGCAAT CCGAAGCCGC AGTGCAAGTC AAGGCTGAAA
101  ACAGCCTGAC CGCTATGCGC TTAGCCGTCG CCGACAAACA GGCAGAGATT
```

-continued
```
151 GACGGGTTGA ACGCCCAAAT CGACGCCGAA ATCAGACAAC GCGAAGCCGA

201 AGAATTGAAA GACTACCGAT GGATACACGG CGACGCGGAA GTGCCGGAGC

251 TGGAAAAATG A
```

This corresponds to the amino acid sequence <SEQ ID 34; ORF52-1>:

```
  1 MKYLIRTALL AVAAAGIYAC QFQSEAAVQV KAENSLTAMR LAVADKQAEI

51 DGLNAQIDAE IRQREAEELK DYRWIHGDAE VPELEK*
```

Computer analysis of this amino acid sequence predicts a prokaryotic membrane lipoprotein lipid attachment site (underlined).

ORF52-1 (7 kDa) was cloned in the pGex vectors and expressed in E.coli, as described above. The products of protein expression and purification were analyzed by SDS-PAGE. FIG. 4A shows the results of affinity purification of the GST-fusion. FIG. 4B shows plots of hydrophilicity, antigenic index, and AMPHI regions for ORF52-1.

Based on this analysis, it is predicted that this protein from N.meningitidis, and its epitopes, could be useful antigens for vaccines or diagnostics.

Example 8

The following DNA sequence was identified in N.meningitidis <SEQ ID 35>

```
  1 ATGGTTATCG GAATATTACT CGCATCAAGC AAGCATGCTC TTGTCATTAC

51 TCTATTGTTA AATCCCGTCT TCCATGCATC CAGTTGCGTA TCGCGTTsGG

101 CAATACGGAA TAAAAtCTGC TGTTCTGCTT TGGCTAAATT TGCCAAATTG

151 TTTATTGTTT CTTTAGGaGC AGCTTGCTTA GCCGCCTTCG CTTTCGACAA

201 CGCCCCCACA GGCGCTTCCC AAGCgTTGCC TACCGTTACC GCACCCGTGG

251 CGATTCCCGC GCCCGCTTCG GCAGCCTGA
```

This corresponds to the amino acid sequence <SEQ ID 36; ORF56>:

```
  1 MVIGILLASS KHALVITLLL NPVFHASSCV SRXAIRNKIC CSALAKFAKL

51 FIVSLGAACL AAFAFDNAPT GASQALPTVT APVAIPAPAS AA*
```

Further work revealed the complete nucleotide sequence <SEQ ID 37>:

```
  1 ATGGCTTGTA CAGGTTTGAT GGTTTTTCCG TTAATGGTTA TCGGAATATT

51 ACTTGCATCA AGCAAGCCTG CTCCTTTCCT TACTCTATTG TTAAATCCCG

101 TCTTCCATGC ATCCAGTTGC GTATCGCGTT GGGCAATACG GAATAAAATC

151 TGCTGTTCTG CTTTGGCTAA ATTTGCCAAA TTGTTTATTG TTTCTTTAGG

201 AGCAGCTTGC TTAGCCGCCT TCGCTTTCGA CAACGCCCCC ACAGGCGCTT

251 CCCAAGCGTT GCCTACCGTT ACCGCACCCG TGGCGATTCC CGCGCCCGCT

301 TCGGCAGCCT GA
```

This corresponds to the amino acid sequence <SEQ ID 38; ORF56-1>:

```
  1  MACTGLMVFP LMVIGILLAS SKPAPFLTLL LNFVFHASSC VSRWAIPNKL
 51  CCSALAKFAK LFIVSLGAAC LAAFAFDNAP TGASQALPTV TAPVAIPAPA
101  SAA*
```

Computer analysis of this amino acid sequence predicts a leader peptide (underlined) and suggests that ORF56 might be a membrane or periplasmic protein.

Based on this analysis, it is predicted that this protein from *N.meningitidis*, and its epitopes, could be useful antigens for vaccines or diagnostics.

Example 9

The following partial DNA sequence was identified in *N.meningitidis* <SEQ ID 39>

```
  1  ATGTTCAGTA TTTTAAATGT CTTTCTTCAT TGTATTCTGG CTTGTGTAGT
 51  CTCTGGTGAG ACGCCTACTA TATTTGGTAT CCTTGCTCTT TTTTACTTAT
101  TGTATCTTTC TTATCTTGCT GTTTTTAAGA TTTTCTTTTC TTTTTTCTTA
151  GACAGAGTTT CACTCCGGTC TCCCAGGCTG GAGTGCAAAT GGCATGACCC
201  TTTGGCTCAC TGGCTCACGG CCACTTCTGC TATTCTGCCG CCTCAGCCTC
251  CAGGG ...
```

This corresponds to the amino acid sequence <SEQ ID 40; ORF63>:

```
1     MFSILNVFLH CILACVVSGE TPTIFGILAL FYLLYLSYLA VFKIFFSFFL
51    DRVSLRSPRL ECKWHDPLAH WLTATSAILP PQPPG...
```

Computer analysis of this amino acid sequence predicts a transmembrane region.

```
1 ..VRTWLVFWLQ RLKYPLLLWI ADMLLYRLLG GAEIECGRCP VPPMTDWQHF
51   LPAMGTVSAW VAVIWAYLMI ESEKNGRY*
```

Based on this analysis, it is predicted that this protein from *N.meningitidis*, and its epitopes, could be useful antigens for vaccines or diagnostics.

Example 10

The following partial DNA sequence was identified in *N.meningitidis* <SEQ ID 41>

```
  1 ..GTGCGGACGT GGTTGGTTTT TTGGTTGCAG CGTTTGAAAT ACCCGTTGTT
 51   GCTTTGGATT GCGGATATGT TGCTGTACCG GTTGTTGGGC GGCGCGGAAA
101   TCGAATGCGG CCGTTGCCCT GTGCCGCCGA TGACGGATTG GCAGCATTTT
151   TTGCCGGCGA TGGGAACGGT GTCGGCTTGG GTGGCGGTGA TTTGGGCATA
201   CCTGATGATT GAAAGTGAAA AAAACGGAAG ATATTGA
```

This corresponds to the amino acid sequence <SEQ ID 42; ORF69>:

Computer analysis of this amino acid sequence predicts a transmembrane region.

A corresponding ORF from strain A of *N.meningitidis* was also identified:

Homology With a Predicted ORF from *N.meningitidis* (Strain A)

ORF69 (SEQ ID NO:42) shows 96.2% identity over a 78aa overlap with an ORF (ORF69a (SEQ ID NO:44)) from strain A of *N.meningitidis*:

```
                    10        20        30        40        50        60
orf69.pep  VRTWLVFWLQRLKYPLLLWIADMLLYRLLGGAEIECGRCPVPPMTDWQHFLPAMGTVSAW
           |||||||||||||||| ||||||||||||||||||||||||||||||||||:|:|||:||
orf69a     VRTWLVFWLQRLKYPLLLCIADMLLYRLLGGAEIECGRCPVPPMTDWQHFLPTMGTVAAW
                    10        20        30        40        50        60

70        79
orf69.pep  VAVIWAYLMIESEKNGRYX
           |||||||||||||||||||
orf69a     VAVIWAYLMIESEKNGRYX
                    70
```

The ORF69a nucleotide sequence <SEQ ID 43> is:

```
  1    GTGCGGACGT GGTTGGTTTT TTGGTTGCAG CGTTTGAAAT ACCCGTTGTT
 51    GCTTTGTATT GCGGATATGC TGCTGTACCG GTTGTTGGGC GGCGCGGAAA
101    TCGAATGCGG CCGTTGCCCT GTACCGCCGA TGACGGATTG GCAGCATTTT
151    TTGCCGACGA TGGGAACGGT GGCGGCTTGG GTGGCGGTGA TTTGGGCATA
201    CCTGATGATT GAAAGTGAAA AAAACGGAAG ATATTGA
```

This encodes a protein having amino acid sequence <SEQ ID 44>:

```
  1    VRTWLVFWLQ RLKYPLLLCI ADMLLYRLLG GAEIECGRCP VPPMTDWCHF
 51    LPTMGTVAAW VAVIWAYLMIESEKNGRY*
```

Based on this analysis, it is predicted that this protein from *N.meningitidis*, and its epitopes, could be useful antigens for vaccines or diagnostics.

Example 11

The following DNA sequence was identified in *N.meningitidis* <SEQ ID 45>

```
  1    ATGTTTCAAA ATTTTGATTT GGGCGTGTTC CTGCTTGCCG TCCTCCCCGT
 51    GCTGCCCTCC ATTACCGTCT CGCACGTGGC GCGCGGCTAT ACGGCGCGCT
101    ACTGGGGAGA CAACACTGCC GAACAATACG GCAGGCTGAC ACTGAACCCC
151    CTGCCCCATA TCGATTTGGT CGGCACAATC ATCgTACCGC TGCTTACTTT
201    GATGTTCACG CCCTTCCTGT TCGGCTGGGC GCGTCCGATT CCTATCGATT
251    CGCGCAACTT CCGCAACCCG cGCCTTGCCT GGCGTTGCGT TGCCGCGTCC
301    GGCCCGCTGT CGAATCTAGC GATGGCTGTw CTGTGGGGCG TGGTTTTGGT
351    GCTGACTCCG TATGTCGGCG GGGCGTATCA GATGCCGTTG GCTCAAATGG
401    CAAACTACGG TATTCTGATC AATGCGATTC TGTTCGCGCT CAACATCATC
451    CCCATCCTGC CTTGGGACGG CGGCATTTTC ATCGACACCT TCCTGTCGGC
501    GAAATATTCG CAAGCGTTCC GCAAAATCGA ACCTTATGGG ACGTGGATTA
551    TCCTACTGCT GATGCTGACC sGGGTTTTGG GTGCGTTTAT wGCACCGATT
601    sTGCGGmTGc GTGATTGCrT TTGTGCAGAT GTwCGTCTGA CTGGCTTTCA
651    GACGGCATAA
```

This corresponds to the amino acid sequence <SEQ ID 46; ORF77>:

```
  1    MFQNFDLGVF LLAVLPVLPS ITVSHVARGY TARYWGDNTA EQYGRLTLNP
 51    LPHIDLVGTI IVPLLTLMFT PFLFGWARPI PIDSRNFRNP RLAWRCVAAS
101    GPLSNLAMAV LWGVVLVLTP YVGGAYQMPL AQMANYGILI NAILFALNII
151    PILPWDGGIF IDTFLSAKYS QAFRKIEPYG TWIILLLMLT XVLGAFIAPI
201    XRXRDCXCAD VRLTGFQTA*
```

Further work revealed the complete nucleotide sequence <SEQ ID 47>:

```
  1    ATGTTTCAAA ATTTTGATTT GGGCGTGTTT CTGCTTGCCG TCCTGCCCGT
 51    GCTGCTCTCC ATTACCGTCA GGGAGGTGGC GCGCGGCTAT ACGGCGCGCT
101    ACTGGGGAGA CAACACTGCC GAACAATACG GCAGGCTGAC ACTGAACCCC
151    CTGCCCCATA TCGATTTGGT CGGCACAATC ATCGTACCGC TGCTTACTTT
201    GATGTTCACG CCCTTCCTGT TCGGCTGGGC GCGTCCGATT CCTATCGAPT
251    CGCGCAACTT CCGCAACCCG CGCCTTGCCT GGCGTTGCGT TGCCGCGTCC
301    GGCCCGCTGT CGAATCTAGC GATGGCTGTT CTGTGGGGCG TGGTTTTGGT
351    GCTGACTCCG TATGTCGGCG GGGCGTATCA GATGCCGTTG GCTCAAATGG
401    CAAACTACGG TATTCTGATC AATGCGATTC TGTTCGCGCT CAACATCATC
451    CCCATCCTGC CTTGGGACGG CGGCATTTTC ATCGACACCT TCCTGTCGGC
501    GAAATATTCG CAAGCGTTCC GCAAAATCGA ACCTTATGGG ACGTGGATTA
```

-continued

```
551    TCCTACTGCT GATGCTGACC GGGGTTTTGG GTGCGTTTAT TGCACCGATT

601    GTGCGGCTGG TGATTGCGTT TGTGCAGATG TTCGTCTGA
```

This corresponds to the amino acid sequence <SEQ ID 48; ORF77-1>:

```
  1    MFQNFDLGVF LLAVLPVLLS ITVREVARGY TARYWGDNTA EQYGRLTLNP

51    LPHIDLVGTI IVPLLTLMFT PFLFGWARPI PIDSRNFRNP RLAWRCVAAS

101    GPLSNLAMAV LWGVVLVLTP YVGGAYQMPL AQMANYGILI NAILFALNII

151    PILPWDGGIF IDTFLSAKYS QAFRKIFPYG TWIILLLMLT GVLGAFIAPI

201    VRLVIAFVQM FV*
```

Computer analysis of this amino acid sequence reveals a putative leader sequence and several transmembrane domains.

A corresponding ORF from strain A of N.meningitidis was also identified:

Homology With a Predicted ORF From N.meningitidis (Strain A)

ORF77 (SEQ ID NO:46) shows 96.5% identity over a 173aa overlap with an ORF (ORF77a (SEQ ID NO:50)) from strain A of N.meningitidis:

```
                    10         20         30         40         50         60
orf77.pep    MFQNFDLGVFLLAVLPVLPSITVSHVARGYTARYWGDNTAEQYGRLTLNPLPHIDLVGTI
                                       ||||||||||||||||||||||||||||||||
orf77a                                 RGYTARYWGDNTAEQYGRLTLNPLPHIDLVGTI
                                                10        20        30

70         80         90        100        110        120
orf77.pep    IVPLLTLMFTPFLFGWARPIPIDSRNFRNPRLAWRCVAASGPLSNLAMAVLWGVVLVLTP
             ||||||||||||||||||||||||||||||||||||||||||||||||||||||||||||
orf77a       IVPLLTLMFTPFLFGWARPIPIDSRNFRNPRLAWRCVAASGPLSNLAMAVLWGVVLVLTP
                 40        50        60        70        80        90

130        140        150        160        170        180
orf77.pep    YVGGAYQMPLAQMANYGILINAILFALNIIPILPWDGGIFIDTFLSAKYSQAFRKIEPYG
             |||||||||||||||| ||||||| |||||||||||||||||||||||| ||||||||||
orf77a       YVGGAYQMPLAQMANYXILINAILXALNIIPILPWDGGIFIDTFLSAKXSQAFRKIEFYG
                 100       110       120       130       140       150

190        200        210        220
orf77.pep    TWIILLLMLTXVLGAFIAPIXRXRDCXCADVRLTGFQTAX
             |||| ||||| |||| ||||
orf77a       TWIIXLLMLTGVLGAXIAPIVQLVIAFVQMFVX
                 160       170       180
```

ORF77-1 (SEQ ID NO:48) and ORF77a (SEQ ID NO:50) show 96.8% identity in 185 aa overlap:

```
                      10         20         30         40         50         60
orf77-1.pep   MFQNFDLGVFLLAVLPVLLSITVREVARGYTARYWGDNTAEQYGRLTLNPLPHIDLVGTI
                                         ||||||||||||||||||||||||||||||||
orf77a                                   RGYTARYWGDNTAEQYGRLTLNPLPHIDLVGTI
                                                  10        20        30

70         80         90        100        110        120
orf77-1.pep   IVPLLTLMFTPFLFGWARPIPIDSRNFRNPRLAWRCVAASGPLSNLAMAVLWGVVLVLTP
              ||||||||||||||||||||||||||||| ||||||||||||||||||||||||||||||
orf77a        IVPLLTLMFTPFLFGWARPIPIDSRNFRNFRLAWRCVAASGPLSNLAMAVLWGVVLVLTP
```

```
                   -continued
          40        50        60        70        80        90

130       140       150       160       170       180
orf77-1.pep YVGGAYQMPLAQMANYGILINAILFALNIIPILPWDGGIFIDTFLSAKYSQAFRKIEPYG
            ||||||||||||||| |||||||| |||||||||||||||||||| ||||||||||||
orf77a      YVGGAYQMPLAQMANYXILINAILXALNIIPILPWDGGIFIDTFLSAKXSQAFRKIEPYG
              100       110       120       130       140       150

190       200       210
orf77-1.pep TWIILLLMLTGVLGAFIAPIVRLVIAFVQMFVX
            ||||  |||||||||||  |||||:|||||||||
orf77a      TWIIXLLMLTGVLGAXIAPIVQLVIAFVQMFVX
              160       170       180
```

A partial ORF77a nucleotide sequence <SEQ ID 49> was identified:

```
  1    CGCGGCTATA CAGCGCGCTA CTGGGGTGAC AACACTGCCG AACAATACGG
 51    CAGGCTGACA CTGAACCCCC TGCCCCATAT CGATTTGGTC GGCACAATCA
101    TCGTACCGCT GCTTACTTTG ATGTTTACGC CCTTCCTGTT CGGCTGGGCG
151    CGTCCGATTC CTATCGATTC GCGCAACTTC CGCAACCCGC GCCTTGCCTG
201    GCGTTGCGTT GCCGCGTCCG GCCCGCTGTC GAATCTGGCG ATGGCTGTTC
251    TGTGGGGCGT GGTTTTGGTG CTGACTCCGT ATGTCGGTGG GGCGTATCAG
301    ATGCCGTTGG CNCAAATGGC AAACTACNNN ATTCTGATCA ATGCGATTCT
351    GTNCGCGCTC AACATCATCC CCATCCTGCC TTGGGACGGC GGCATTTTCA
401    TCGACACCTT CCTGTCGGCN AAATANTCGC AAGCGTTCCG CAAAATCGAA
451    CCTTATGGGA CGTGGATTAT CCNGCTGCTT ATGCTGACCG GGGTTTTGGG
501    TGCGTNTATT GCACCGATTG TGCAGCTGGT GATTGCGTTT GTGCAGATGT
551    TCGTCTGA
```

This encodes a protein having amino acid sequence <SEQ ID 50>:

```
  1    RGYTARYWGD NTAEQYGRLT LNPLFHIDLV GTIIVPLLTL MFTPFLFGWA
 51    RPIPIDSRNF RNPRLAWRCV AASGPLSNLA MAVLWGVVLV LTPYVGGAYQ
101    MPLAQNANYX ILINAILXAL NIIPILPWDG GIFIDTFLSA KXSQAFRKIE
151    PYGTWIIXLL MLTGVLGAXI APIVQLVIAF VQMFV*
```

Based on this analysis, it is predicted that this protein from *N.meningitidis*, and its epitopes, could be useful antigens for vaccines or diagnostics.

Example 12

The following partial DNA sequence was identified in *N.meningitidis* <SEQ ID 51>

```
  1    ATGAACCTGA TTTCACGTTA CATCATCCGT CAAATGGCGG TTATGGCGGT
 51    TTACGCGCTC CTTGCCTTCC TCGCTTTGTA CAGCTTTTTT GAAATCCTGT
101    ACGAAACCGG CAACCTCGGC AAAGGCAGTT ACGGCATATG GGAAATGCTG
151    GGCTACACCG CCCTCAAAAT GCCCGCCCGC GCCTACGAAC TGATTCCCCT
```

-continued

```
201      CGCCGTCCTT ATCGGCGGAC TGGTCTCCCT CAGCCAGCTT GCCGCCGGCA
251      GCGAACTGAC CGTCATCAAA GCCAGCGGCA TGAGCACCAA AAAGCTGCTG
301      TTGATTCTGT CGCAGTTCGG TTTTATTTTT GCTATTGCCA CCGTCGCGCT
351      CGGCGAATGG GTTGCGCCCA CACTGAGCCA AAAAGCCGAA AACATCAAAG
401      CCGCCGCCAT CAACGGCAAA ATCAGCACCG GCAATACCGG CCTTTGGCTG
451      AAAGAAAAAA ACAGCGTGAT CAATGTGCGC GAAATGTTGC CCGACCAT..
```

This corresponds to the amino acid sequence <SEQ ID 52; ORF112>:

```
  1      MNLISRYIIR QMAVMAVYAL LAFLALYSFF EILYETGNLG KGSYGIWEML
 51      GYTALKMPAR AYELIPLAVL IGGLVSLSQL AAGSELTVIK ASGMSTKKLL
101      LILSQFGFIF AIATVALGEW VAPTLSQKAE NIKAAAINGK ISTGNTGLWL
151      KEKNSVINVR EMLPDH...
```

Further work revealed further partial nucleotide sequence <SEQ ID 53>:

```
  1      ATGAACCTGA TTTCACGTTA CATCATCCGT CAAATGGCGG TTATGGCGGT
 51      TTACGCGCTC CTTGCCTTCC TCGCTTTGTA CAGCTTTTTT GAAATCCTGT
101      ACGAAACCGG CAACCTCGGC AAAGGCAGTT ACGGCATATG GGAAATGCTG
151      gGCTACACCG CCCTCAAAAT GCCCGCCCGC GCCTACGAAC TGATTCCCCT
201      CGCCGTCCTT ATCGGCGGAC TGGTCTCCCT CAGCCAGCTT GCCGCCGGCA
251      GCGAACTGAC CGTCATCAAA GCCAGCGGCA TGAGCACCAA AAAGCTGCTG
301      TTGATTCTGT CGCAGTTCGG TTTTATTTTT GCTATTGCCA CCGTCGCGCT
351      CGGCGAATGG GTTGCGCCCA CACTGAGCCA AAAAGCCGAA AACATCAAAG
401      CCGCCGCCAT CAACGGCAAA ATCAGCACCG GCAATACCGG CCTTTGGCTG
451      AAAGAAAAAA ACAGCrTkAT CAATGTGCGC GAAATGTTGC CCGACCATAC
501      GCTTTTGGGC ATCAAAATTT GGGCGCGCAA CGATAAAAAC GAATTGGCAG
551      AGGCAGTGGA AGCCGATTCC GCCGTTTTGA ACAGCGACGG CAGTTGGCAG
601      TTGAAAAACA TCCGCCGCAG CACGCTTGGC GAAGACAAAG TCGAGGTCTC
651      TATTGCGGCT GAAGAAAACT GGCCGATTTC CGTCAAACGC AACCTGATGG
701      ACGTATTGCT CGTCAAACCC GACCAAATGT CCGTCGGCGA ACTGACCACC
751      TACATCCGCC ACCTCCAAAA CAACAGCCAA AACACCCGAA TCTACGCCAT
801      CGCATGGTGG CGCAAATTGG TTTACCCCGC CGCAGCCTGG GTGATGGCGC
851      TCGTCGCCTT TGCCTTTACC CCGCAAACCA CCCGCCACGG CAATATGGGC
901      TTAAAACTCT TCGGCGGCAT CTGTsTCGGA TTGCTGTTCC ACCTTGCCGG
951      ACGGCTCTTT GGGTTTACCA GCCAACTCGG...
```

This corresponds to the amino acid sequence <SEQ ID 54; ORF112-1>:

```
  1    MNLISRYIIR QMAVMAVYAL LAFLALYSFF EILYETGNLG KGSYGIWEML
 51    GYTALKMPAR AYELIPLAVL IGGLVSLSQL AAGSELTVIK ASGMSTKKLL
101    LILSQFGFIF AIATVALGEW VAPTLSQKAE NIKAAAINGK ISTGNTGLWL
151    KEKNSXTNVR EMLPDHTLLG IKIWARNDKN ELAEAVEADS AVLNSDGSWQ
201    LKNIRRSTLG EDKVEVSIAA EENWPISVKR NLMDVLLVKP DQMSVGELTT
251    YIRHLQNNSQ NTRIYAIAWW RKLVYPAAAW VMALVAFAFT PQTTRHGNMG
301    LKLFGGICXG LLFHLAGRLF GFTSQL...
```

Computer analysis of this amino acid sequence predicts two transmembrane domains.

A corresponding ORF from strain A of *N.meningitidis* was also identified:

Homology With a Predicted ORF From *N.meningitidis* (Strain A)

ORF112 (SEQ ID NO:52) shows 96.4% identity over a 166aa overlap with an ORF (ORF112a (SEQ ID NO: 177)) from strain A of *N.meningitidis*:

```
                   10         20         30         40         50         60
orf112.pep  MNLISRYIIRQMAVMAVYALLAFLALYSFFEILYETGNLGKGSYGIWEMLGYTALKMPAR
            ||||||||||||||||||||||||||||||||||||||||||||||||||| |||||| ||
orf112a     MNLISRYIIRQMAVMAVYALLAFLALYSFFEILYETGNLGKGSYGIWEMXGYTALKMXAR
                   10         20         30         40         50         60

70         80         90        100        110        120
orf112.pep  AYELIPLAVLIGGLVSLSQLAAGSELTVIKASGMSTKKLLLILSQFGFIFAIATVALGEW
            ||||:||||||||||| |||||||||||:|||||||||||||||||||||||||||||||
orf112a     AYELMPLAVLIGGLVSXSQLAAGSELXVIKASGMSTKKLLLILSQFGFIFAIATVALGEW
                   70         80         90        100        110        120

130        140        150        160
orf112.pep  VAPTLSQKAENIKAAAINGKISTGNTGLWLKEKNSVINVREMLPDH
            |||||||||||||||||||||||||||||||||||:|||||||||
orf112a     VAPTLSQKAENIKAAAINGKISTGNTGLWLKEKNSIINVREMLPDHTLLGIKIWARNDKN
                  130        140        150        160        170        180 orf112a     ELAEAVEADSAVLNSDGSWQLKNIRRSTLGEDKVEVSIAAEEXWPISVKRNLMDVLLVKP
                  190        200        210        220        230        240
```

A partial ORF112a nucleotide sequence <SEQ ID 55> was identified:

```
  1    ATGAACCTGA TTTCACGTTA CATCATCCGT CAAATGGCGG TTATGGCGGT
 51    TTACGCGCTC CTTGCCTTCC TCGCTTTGTA CAGCTTTTTT GAAATCCTGT
101    ACGAAACCGG CAACCTCGGC AAAGGCAGTT ACGGCATATG GAAATGNTG
151    GGNTACACCG CCCTCAAAAT GNCCGCCCGC GCCTACGAAC TGATGCCCCT
201    CGCCGTCCTT ATCGGCGGAC TGGTCTCTNT CAGCCAGCTT GCCGCCGGCA
251    GCGAACTGAN CGTCATCAAA GCCAGCGGCA TGAGCACCAA AAAGCTGCTG
301    TTGATTCTGT CGCAGTTCGG TTTTATTTTT GCTATTGCCA CCGTCGCGOT
351    CGGCGAATGG GTTGCGCCCA CACTGAGCCA AAAAGCCGAA AACATCAAAG
401    CCGCGGCCAT CAACGGCAAA ATCAGTACCG GCAATACCGG CCTTTGGCTG
451    AAAGAAAAAA ACAGCATTAT CAATGTGCGC GAAATGTTGC CCGACCATAC
```

-continued

```
 501    CCTGCTGGGC ATTAAAATCT GGGCCCGCAA CGATAAAAAC GAACTGGCAG
 551    AGGCAGTGGA AGCCGATTCC GCCGTTTTGA ACAGCGACGG CAGTTGGCAG
 601    TTGAAAAACA TCCGCCGCAG CACGCTTGGC GAAGACAAAG TCGAGGTCTC
 651    TATTGCGGCT GAAGAAAANT GGCCGATTTC CGTCAAACGC AACCTGATGG
 701    ACGTATTGCT CGTCAAACCC GACCAAATGT CCGTCGGCGA ACTGACCACC
 751    TACATCCGCC ACCTCCAAAN NNACAGCCAA ACACCCGAA TCTACGCCAT
 801    CGCATGGTGG CGCAAATTGG TTTACCCCGC CGCAGCCTGG GTGATGGCGC
 851    TCGTCGCCTT TGCCTTTACC CCGCAAACCA CCCGCCACGG CAATATGGGC
 901    TTAAAANTCT TCGGCGGCAT CTGTCTCGGA TTGCTGTTCC ACCTTGCCGG
 951    NCGGCTCTTC NGGTTTACCA GCCAACTCTA CGGCATCCCG CCCTTCCTCG
1001    NCGGCGCACT ACCTACCATA GCCTTCGCCT TGCTCGCCGT TTGGCTGATA
1051    CGCAAACAGG AAAAACGCTA A
```

This encodes a protein having amino acid sequence <SEQ ID 56>:

```
  1    MNLISRYIIR QMAVMAVYAL LAFLALYSFF EILYETGNLG KGSYGIWEMX
 51    GYTALKMXAR AYELMPLAVL IGGLVSXSQL AAGSELXVIK ASGMSTKKLL
101    LILSQFGFIF AIATVALGEW VAPTLSQKAE NTKAAAINGK ISTGNTGLWL
151    KEKNSIINVR EMLFDHTLLG IKIWARNDKN ELAEAVEADS AVLNSDGSWQ
201    LKNIRRSTLG EDKVEVSIAA EEXWPISVKR NLMDVLLVKP DQMSVGELTT
251    YIRHLQXXSQ NTRIYAIAWW RKLVYPAAAW VMALVAFAFT PQTTRHGNMG
301    LKXFGGICLG LLFHLAGRLF XFTSQLYGIP PFLXGALPTI AFALLAVWLI
351    RKQEKR*
```

ORF112a (SEQ ID NO:56) and ORF112-1 (SEQ ID NO:54) show 96.3% identity in 326 aa overlap:

```
orf112a.pep MNLISRYIIRQMAVMAVYALLAFLALYSFFEILYETGNLGKGSYGIWEMXGYTALKMXAR
            |||||||||||||||||||||||||||||||||||||||||||||||| ||||||| ||
orf112-1    MNLISRYIIRQMAVMAVYALLAFLALYSFFEILYETGNLGKGSYGIWEMLGYTALKMPAR orf112a.pep AYELMPLAVLIGGLVSXSQLAAGSELXVIKASGMSTKKLLLILSQFGFIFAIATVALGEW
            ||||:||||||||||| |||||||||:|||||||||||||||||||||||||||||||||
orf112-1    AYELIPLAVLIGGLVSLSQLAAGSELTVIKASGMSTKKLLLILSQFGFIFAIATVALGEW orf112a.pep VAPTLSQKAENIKAAAINGKISTGNTGLWLKEKNSIINVREMLPDRTLLGIKIWARNDKN
            ||||||||||||||||||||||||||||||||||| |||||||| |||||||||||||||
orf112-1    VAPTLSQKAENIKAAAINGKISTGNTGLWLKEKNSXINVREMLPDHTLLGIKIWARNDKN orf112a.pep ELAEAVEADSAVLNSDGSWQLKNIRRSTLGEDKVEVSIAAEEXWPISVKRNLMDVLLVKP
            |||||||||||||||||||||||||||||||||||||||||| |||||||||||||||||
orf112-1    ELAEAVEADSAVLNSDGSWQLKNIRRSTLGEDKVEVSIAAEENWPISVKRNLMDVLLVKP orf112a.pep DQMSVGELTTYIRHLQXXSQNTRIYAIAWWRKLVYPAAAWVMALVAFAFTPQTTRHGNNG
            ||||||||||||||||  ||||||||||||||||||||||||||||||||||||||||
orf112-1    DQMSVGELTTYIRHLQNNSQNTRIYAIAWWRKLVYPAAAWVMALVAFAFTPQTTRHGNMG orf112a.pep LKXFGGICLGLLFHLAGRLFXFTSQLYGIPPFLXGALPTIAFALLAVWLIRKQEKRX
            || ||||| |||||||||||  |||||
orf112-1    LKLFGGICXGLLFHLAGRLFGFTSQL
```

Based on this analysis, it is predicted that this protein from *N.meningitidis*, and its epitopes, could be useful antigens for vaccines or diagnostics.

Example 13

The following partial DNA sequence was identified in *N.meningitidis* <SEQ ID 57>

```
  1  GCAGTAGCCG AAACTGCCAA CAGCCAGGGC AAAGGTAAAC AGGCAGGCAG
 51  TTCGGTTTCT GTTTCACTGA AAACTTCAGG CGACCTTTGC GGCAAACTCA
101  AAACCACCCT TAAAACTTTG GTCTGCTCTT TGGTTTCCCT GAGTATGGTA
151  TTGCCTGCCC ATGCCCAAAT TACCACCGAC AAATCAGCAC CTAAAAACCA
201  GCAGGTCGTT ATCCTTAAAA CCAACACTGG TGCCCCCTTG GTGAATATCC
251  AAACTCCGAA TGGACGCGGA TTGAGCCACA ACCGCTA.TA CGCATTTGAT
301  GTTGACAACA AAGGGGCAGT GTTAAACAAC GACCGTAACA ATAATCCGTT
351  TGTGGTCAAA GGCAGTGCGC AATTGATTTT GAACGAGGTA CGCGGTACGG
401  CTAGCAAACT CAACGGCATC GTTACCGTAG GCGGTCAAAA GGCCGACGTG
451  ATTATTGCCA ACCCCAACGG CATTACCGTT AATGGCGGCG GCTTTAAAAA
501  TGTCGGTCGG GGCATCTTAA CTACCGGTGC GCCCCAAATC GGCAAAGACG
551  GTGCACTGAC AGGATTTGAT GTGCGTCAAG GCACATTGgA CCGTAGrAGC
601  AGCAGGTTGG AATGATAAAG GCGGAGCmrm yTACACCGGG GTACTTGCTC
651  GTGCAGTTGC TTTGCAGGGG AAATTwmmGG GTAAA.AACT GGCGGTTTCT
701  ACCGGTCCTC AGAAAGTAGA TTACGCCAGC GGCGAAATCA GTGCAGGTAC
751  GGCAGCGGGT ACGAAACCGA CTATTGCCCT TGATACTGCC GCACTGGGCG
801  GTATGTACGC CGACAGCATC ACACTGATTG CCAATGAAAA AGGCGTAGGC
851  GTCTAA
```

This corresponds to the amino acid sequence <SEQ ID 58; ORF114>:

```
  1  AVAETANSQG KGKQAGSSVS VSLKTSGDLC GKLKTTLKTL VCSLVSLSNV
 51  LPAHAQITTD KSAPKNQQVV ILKTNTGAPL VNIQTPNGRG LSHNRXYAFD
101  VDNKGAVLNN DRNNNPFVVK GSAQLILNEV RGTASKLNGI VTVGGQKADV
151  IIANPNGITV NGGGFKNVGR GILTTGAPQI GKDGALTGFD VVKAHWTVXA
201  AGWNDKGGAX YTGVLARAVA LQGKXXGKXL AVSTGPQKVD YASGEISAGT
251  AAGTKPTIAL DTAALGGMYA DSITLIANEK GVGV*
```

Further work revealed the complete nucleotide sequence
<SEQ ID 59>:

```
   1    ATGAATAAAG GTTTACATCG CATTATCTTT AGTAAAAAGC ACAGCACCAT
  51    GGTTGCAGTA GCCGAAACTG CCAACAGCCA GGGCAAAGGT AAACAGGCAG
 101    GCAGTTCGGT TTCTGTTTCA CTGAAAACTT CAGGCGACCT TTGCGGCAAA
 151    CTCAAAACCA CCCTTAAAAC TTTGGTCTGC TCTTTGGTTT CCCTGAGTAT
 201    GGTATTGCCT GCCCATGCCC AAATTACCAC CGACAAATCA GCACCTAAAA
 251    ACCAGCAGGT CGTTATCCTT AAAACCAACA CTGGTGCCCC CTTGGTGAAT
 301    ATCCAAACTC CGAATGGACG CGGATTGAGC CACAACCGCT ATACGCAGTT
 351    TGATGTTGAC AACAAAGGGG CAGTGTTAAA CAACGACCGT AACAATAATC
 401    CGTTTGTGGT CAAAGGCAGT GCGCAATTGA TTTTGAACGA GGTACGCGGT
 451    ACGGCTAGCA AACTCAACGG CATCGTTACC GTAGGCGGTC AAAAGGCCGA
 501    CGTGATTATT GCCAACCCCA ACGGCATTAC CGTTAATGGC GGCGGCTTTA
 551    AAAATGTCGG TCGGGGCATC TTAACTACCG GTGCGCCCCA AATCGGCAAA
 601    GACGGTGCAC TGACAGGATT TGATGTGCGT CAAGGCACAT TGACCGTAGG
 651    AGCAGCAGGT TGGAATGATA AAGGCGGAGC CGACTACACC GGGGTACTTG
 701    CTCGTGCAGT TGCTTTGCAG GGGAAATTAC AGGGTAAAAA CCTGGCGGTT
 751    TCTACCGGTC CTCAGAAAGT AGATTACGCC AGCGGCGAAA TCAGTGCAGG
 801    TACGGCAGCG GGTACGAAAC CGACTATTGC CCTTGATACT GCCGCACTGG
 851    GCGGTATGTA CGCCGACAGC ATCACACTGA TTGCCAATGA AAAAGGCGTA
 901    GGCGTCAAAA ATGCCGGCAC ACTCGAAGCG GCCAAGCAAT TGATTGTGAC
 951    TTCGTCAGGC CGCATTGAAA ACAGCGGCCG CATCGCCACC ACTGCCGACG
1001    GCACCGAAGC TTCACCGACT TATCTCTCCA TCGAAACCAC CGAAAAAGGA
1051    GCGGCAGGCA CATTTATCTC CAATGGTGGT CGGATCGAGA GCAAAGGCTT
1101    ATTGGTTATT GAGACGGGAG AAGATATCAG CTTGCGTAAC GGAGCCGTGG
1151    TGCAGAATAA CGGCAGTCGC CCAGCTACCA CGGTATTAAA TGCTGGTCAT
1201    AATTTGGTGA TTGAGAGCAA AACTAATGTG AACAATGCCA AAGGCCCGGC
1251    TACTCTGTCG GCCGACGGCC GTACCGTCAT CAAGGAGGCC AGTATTCAGA
1301    CTGGCACTAC CGTATACAGT TCCAGCAAAG GCAACGCCGA ATTAGGCAAT
1351    AACACACGCA TTACCGGGGC AGATGTTACC GTATTATCCA ACGGCACCAT
1401    CAGCAGTTCC GCCGTAATAG ATGCCAAAGA CACCGCACAC ATCGAAGCAG
1451    GCAAACCGCT TTCTTTGGAA GCTTCAACAG TTACCTCCGA TATCCGCTTA
1501    AACGGAGGCA GTATCAAGGG CGGCAAGCAG CTTGCTTTAC TGGCAGACGA
1551    TAACATTACT GCCAAAACTA CCAATCTGAA TACTCCCGGC AATCTGTATG
1601    TTCATACAGG TAAAGATCTG AATTTGAATG TTGATAAAGA TTTGTCTGCC
1651    GCCAGCATCC ATTTGAAATC GGATAACGCT GCCCATATTA CCGGCACCAG
1701    TAAAACCCTC ACTGCCTCAA AAGACATGGG TGTGGAGGCA GGCTCGCTGA
1751    ATGTTACCAA TACCAATCTG CGTACCAACT CGGGTAATCT GCACATTCAG
1801    GCAGCCAAAG GCAATATTCA GCTTCGCAAT ACCAAGCTGA ACGCAGCCAA
1851    GGCTCTCGAA ACCACCGCAT TGCAGGGCAA TATCGTTTCA GACGGCCTTC
```

-continued

```
1901  ATGCTGTTTC TGCAGACGGT CATGTATCCT TATTGGCCAA CGGTAATGCC

1951  GACTTTACCG GTCACAATAC CCTGACAGCC AAGGCCGATG TCAATGCAGG

2001  ATCGGTTGGT AAAGGCCGTC TGAAAGCAGA CAATACCAAT ATCACTTCAC

2051  CTTCAGGAGA TATTACGTTG GTTGCCGGCA ACGGTATTCA GCTTGGTGAC

2101  GGAAAACAAC GCAATTCAAT CAACGGAAAA CACATCAGCA TCAAAACAA

2151  CGGTGGTAAT GCCGACTTAA AAAACCTTAA CGTCCATGCC AAAAGCGGGG

2201  CATTGAACAT TCATTCCGAC CGGGCATTGA GCATAGAAAA TACCAAGCTG

2251  GAGTCTACCC ATAATACGCA TCTTAATGCA CAACACGAGC GGGTAACGCT

2301  CAACCAAGTA GATGCCTACG CACACCGTCA TCTAAGCATT ACCGGCAGCC

2351  AGATTTGGCA AAACGACAAA CTGCCTTCTG CCAACAAGCT GGTGGCTAAC

2401  GGTGTATTGG CACTCAATGC GCGCTATTCC CAAATTGCCG ACAACACCAC

2451  GCTGAGAGCG GGTGCAATCA ACCTTACTGC CGGTACCGCC CTAGTCAAGC

2501  GCGGCAACAT CAATTGGAGT ACCGTTTCGA CCAAAACTTT GGAAGATAAT

2551  GCCGAATTAA AACCATTGGC CGGACGGCTG AATATTGAAG CAGGTAGCGG

2601  CACATTAACC ATCGAACCTG CCAACCGCAT CAGTGCGCAT ACCGACCTGA

2651  GCATCAAAAC AGGCGGAAAA TTGCTGTTGT CTGCAAAAGG AGGAAATGCA

2701  GGTGCGCCTA GTGCTCAAGT TTCCTCATTG GAAGCAAAAG GCAATATCCG

2751  TCTGGTTACA GGAGAAACAG ATTTAAGAGG TTCTAAAATT ACAGCCGGTA

2801  AAAACTTGGT TGTCGCCACC ACCAAAGGCA AGTTGAATAT CGAAGCCGTA

2851  AACAACTCAT TCAGCAATTA TTTTCCTACA CAAAAAGCGG CTGAACTCAA

2901  CCAAAAATCC AAAGAATTGG AACAGCAGAT TGCGCAGTTG AAAAAAAGCT

2951  CGCCTAAAAG CAAGCTGATT CCAACCCTGC AAGAAGAACG CGACCGTCTC

3001  GCTTTCTATA TTCAAGCCAT CAACAAGGAA GTTAAAGGTA AAAACCCAA

3051  AGGCAAAGAA TACCTGCAAG CCAAGCTTTC TGCACAAAAT ATTGACTTGA

3101  TTTCCGCACA AGGCATCGAA ATCAGCGGTT CCGATATTAC CGCTTCCAAA

3151  AAACTGAACC TTCACGCCGC AGGCGTATTG CCAAAGGCAG CAGATTCAGA

3201  GGCGGCTGCT ATTCTGATTG ACGGCATAAC CGACCAATAT GAAATTGGCA

3251  AGCCCACCTA CAAGAGTCAC TACGACAAAG CTGCTCTGAA CAAGCCTTCA

3301  CGTTTGACCG GACGTACAGG GGTAAGTATT CATGCAGCTG CGGCACTCGA

3351  TGATGCACGT ATTATTATCG GTGCATCCGA AATCAAAGCT CCCTCAGGCA

3401  GCATAGACAT CAAAGCCCAT AGTGATATTG TACTGGAGGC TGGACAAAAC

3451  GATGCCTATA CCTTCTTAAA AACCAAAGGT AAAAGCGGCA AAATCATCAG

3501  AAAAACCAAG TTTACCAGCA CCCGCGACCA CCTGATTATG CCAGCCCCCG

3551  TCGAGCTGAC CGCCAACGGC ATAACGCTTC AGGCAGGCGG CAACATCGAA

3601  GCTAATACCA CCCGCTTCAA TGCCCCTGCA GGTAAAGTTA CCCTGGTTGC

3651  GGGTGAAGAG CTGCAACTGC TGGCAGAAGA AGGCATCCAC AAGCACGAGT

3701  TGGATGTCCA AAAAAGCCGC CGCTTTATCG GCATCAAGGT AGGCAAGAGC

3751  AATTACAGTA AAAACGAACT GAACGAAACC AAATTGCCTG TCCGCGTCGT

3801  CGCCCAAACT GCAGCCACCC GTTCAGGCTG GGATACCGTG CTCGAAGGTA

3851  CCGAATTCAA AACCACGCTG GCCGGTGCGG ACATTCAGGC AGGTGTAGGC
```

```
-continued
3901  GAAAAAGCCC GTGCCGATGC GAAAATTATC CTCAAAGGCA TTGTGAACCG
3951  TATCCAGTCG AAGAAAAAT TAGAAACCAA CTCAACCGTA TGGCAGAAAC
4001  AGGCCGGACG CGGCAGCACT ATCGAAACGC TGAAACTGCC CAGCTTCGAA
4051  AGCCCTACTC CGCCCAAACT GACCGCCCCC GGTGGCTATA TCGTCGACAT
4101  TCCGAAAGGC AATTTGAAAA CCGAAATCGA AAGCTGGCC AAACAGCCCG
4151  AGTATGCCTA TCTGAAACAG CTCCAAGTAG CGAAAAACGT CAACTGGAAC
4201  CAGGTGCAAC TGGCTTACGA TAAATGGGAC TATAAGCAGG AAGGCTTAAC
4251  CAGAGCCGGT GCAGCGATTG TTACCATAAT CGTAACCGCA CTGACTTATG
4301  GATACGGCGC AACCGCAGCG GGCGGTGTAG CCGCTTCAGG AAGTAGTACA
4351  GCCGCAGCTG CCGGAACAGC CGCCACAACG ACAGCAGCAG CTACTACCGT
4401  TTCTACAGCG ACTGCCATGC AAACCGCTGC TTTAGCCTCC TTGTATAGCC
4451  AAGCAGCTGT ATCCATCATC AATAATAAAG GTGATGTCGG CAAAGCGTTG
4501  AAAGATCTCG GCACCAGTGA TACGGTCAAG CAGATTGTCA CTTCTGCCCT
4551  GACGGCGGGT GCATTAAATC AGATGGGCGC AGATATTGCC CAATTGAACA
4601  GCAAGGTAAG AACCGAACTG TTCAGCAGTA CGGGCAATCA AACTATTGCC
4651  AACCTTGGAG GCAGACTGGC TACCAATCTC AGTAATGCAG GTATCTCAGC
4701  TGGTATCAAT ACCGCCGTCA ACGGCGGCAG CCTGAAAGAC AACTTAGGCA
4751  ATGCCGCATT AGGAGCATTG GTTAATAGCT TCCAAGGAGA AGCCGCCAGC
4801  AAAATCAAAA CAACCTTCAG CGACGATTAT GTTGCCAAAC AGTTCGCCCA
4851  CGCTTTGGCT GGGTGTGTTA GCGGATTGGT ACAAGGAAAA TGTAAAGACG
4901  GGGCAATTGG CGCAGCAGTT GGGGAAATCG TAGCCGACTC CATGCTTGGC
4951  GGCAGAAACC CTGCTACACT CAGCGATGCG GAAAAGCATA AGGTTATCAG
5001  TTACTCGAAG ATTATTGCCG GCAGCGTGGC GGCACTCAAC GGCGGCGATG
5051  TGAATACTGC GGCGAATGCG GCTGAGGTGG CGGTAGTGAA TAATGCTTTG
5101  AATTTTGACA GTACCCCTAC CAATGCGAAA AAGCATCAAC QGCAGAAGCC
5151  CGACAAAACC GCACTGGAAA AAATTATCCA AGGTATTATG CCTGCACATG
5201  CAGCAGGTGC GATGACTAAT CCGCAGGATA AGGATGCTGC CATTTGGATA
5251  AGCAATATCC GTAATGGCAT CACAGGCCCG ATTGTGATTA CCAGCTATGG
5301  GGTTTATGCT GCAGGTTGGA CAGCTCCGCT GATCGGTACA GCGGGTAAAT
5351  TAGCTATCAG CACCTGCATG GCTAATCCTT CTGGTTGTAC TGTCATGGTC
5401  ACTCAGGCTG CCGAAGCGGG CGCGGGAATC GCCACGGGTG CGGTAACGGT
5451  AGGCAACGCT TGGGAAGCGC CTGTGGGGGC GTTGTCGAAA GCGAAGGCGG
5501  CCAAGCAGGC TATACCAACC CAGACAGTTA AAGAACTTGA TGGCTTACTA
5551  CAAGAATCAA AAAATATAGG TGCTGTAAAT ACACGAATTA ATATAGCGAA
5601  TAGTACTACT CGATATACAC CAATGAGACA AACGGGACAA CCGGTATCTG
5651  CTGGCTTTGA GCATGTTCTT GAGGGGCACT TCCATAGGCC TATTGCGAAT
5701  AACCGTTCAG TTTTTACCAT CTCCCCAAAT GAATTGAAGG TTATACTTCA
5751  AAGTAATAAA GTAGTTTCTT CTCCCGTATC GATGACTCCT GATGGCCAAT
5801  ATATGCGGAC TGTCGATGTA GGAAAAGTTA TTGGTACTAC TTCTATTAAA
5851  GAAGGTGGAC AACCCACAAC TACAATTAAA GTATTTACAG ATAAGTCAGG
```

```
                       -continued
5901     AAATTTGATT ACTACATACC CAGTAAAAGG AAACTAA
```

This corresponds to the amino acid sequence <SEQ ID 60; ORF114-1>:

```
   1 MNKGLHRIIF SKKHSTMVAV AETANSQGKG KQAGSSVSVS LKTSGDLCGK

51 LKTTLKTLVC SLVSLSMVLP AHAQITTDKS APKNQQVVIL KTNTGAPLVN

101 IQTPNGRGLS HYNRYTQFDVD NKGAVLNNDR NNNPFVVKGS AQLILNEVRG

151 TASKLNGIVT VGGQKADVII ANPNGITVNG GGFKNVGRGI LTTGAPQIGK

201 DGALTGFDVR QGTLTVGAAG WNDKGGADYT GVLARAVALQ GKLQGKNLAV

251 STGPQKVDYA SGEISAGTAA GTKPTIALDT AALGGMYADS ITLIANEKGV

301 GVKNAGTLEA AKQLIVTSSG RIENSGRIAT TADGTEASPT YLSIETTEKG

351 AAGTFISNGG RIESKGLLVI ETGEDISLRN GAVVQNNGSR FATTVLNAGH

401 NLVIESKTNV NNAKGPATLS ADGRTVIKEA SIQTGTTVYS SSKGNAELGN

451 NTRITGADVT VLSNGTISSS AVIDAKDTAH IEAGKPLSLE ASTVTSDIRL

501 NGGSIKGGKQ LALLADDNIT AKTTNLNTPG NLYVHTGKDL NLNVDKDLSA

551 ASIHLKSDNA AHITGTSKTL TASKDMGVEA GSLNVTNTNL RTNSGNLHIQ

601 AAKGNIQLRN TKLNAAKALE TTALQGNIVS DGLHAVSADG HVSLLANGNA

651 DFTGHNTLTA KADVNAGSVG KGRLKADNTN ITSSSGDITL VAGNGIQLGD

701 GKQRNSINGK HISIKNNGGN ADLKNLNVHA KSGALNIHSD RALSIENTKL

751 ESTHNTHLNA QRERVTLNQV DAYAHRHLSI TGSQIWQNDK LPSANKLVAN

801 GVLALNARYS QIADNTTLRA GAINLTAGTA LVKRGNINWS TVSTKTLEDN

851 AELKPLAGRL NIEAGSGTLT IEPANRISAH TDLSIKTGGK LLLSAKGGNA

901 GAPSAQVSSL EAKGNIRLVT GETDLRGSKI TAGKNLVVAT TKGKLNIEAV

951 NNSFSNYFPT QKAAELNQKS KELEQQIAQL KKSSPKSKLI PTLQEERDRL

1001 AFYIQAINKE VKGKKPKGKE YLQAKLSAQN IDLISAQGIE ISGSDITASK

1051 KLNLHAAGVL PKAADSEAAA ILIDGITDQY EIGKPTYKSH YDKAALNKPS

1101 RLTGRTGVSI HAAAALDDAR IIIGASEIKA PSGSIDIKAH SDIVLEAGQN

1151 DAYTFLKTKG KSGKIIRKTK FTSTRDHLIM PAPVELTANG ITLQAGGNIE

1201 ANTTRFNAPA GKVTLVAGEE LQLLAEEGIH KHELDVQKSR RFIGIKVGKS

1251 NYSKNELNET KLPVRVVAQT AATRSGWDTV LEGTEFKTTL AGADIQAGVG

1301 EKARADAKII LKGIVNRIQS EEKLETNSTV WQKQAGRGST IETKLPSFE

1351 SPTPPKLTAP GGYIVDIPKG NLKTEIEKLA KQPEYAYLKQ LQVAKNVNWN

1401 QVQLAYDKWD YKQEGLTRAG AAIVTIIVTA LTYGYGATAA GGVAASGSST

1451 AAAAGTAATT TAAATTVSTA TAMQTAALAS LYSQAAVSII NNKGDVGKAL

1501 KDLGTSDTVK QIVTSALTAG ALNQMGADIA QLNSKVRTEL FSSTGNQTIA
```

```
-continued
1551 NLGGRLATNL SNAGISAGIN TAVNGGSLKD NLGNAALGAL VNSFQGEAAS

1601 KIKTTFSDDY VAKQFAHALA GCVSGLVQGK CKDGAIGAAV GEIVADSMLG

1651 GRNPATLSDA EKHKVISYSK IIAGSVAALN GGDVNTAANA AEVAVVNNAL

1701 NFDSTPTNAK KHQPQKPDKT ALEKIIQGIM PAHAAGAMTN PQDKDAAIWI

1751 SNIRNGITGP IVITSYGVYA AGWTAPLIGT AGKLAISTCM ANPSGCTVMV

1801 TQAAEAGAGI ATGAVTVGNA WEAPVGALSK AKAAKQAIPT QTVKELDGLL

1851 QESKNIGAVN TRINIANSTT RYTPMRQTGQ PVSAGFEHVL EGHFHRPIAN

1901 NRSVFTISPN ELKVILQSNK VVSSPVSMTP DGQYMRTVDV GKVIGTTSIK

1951 EGGQPTTTIK VFTDKSGNLI TTYPVKGN*
```

Computer analysis of this amino acid sequence predicts a transmembrane region and also gives the following results: Homology With a Predicted ORF From *N.meningitidis* (Strain A)

ORF114 (SEQ ID NO:58) shows 91.9% identity over a 284aa overlap with an ORF (ORF114a (SEQ ID NO:178)) from strain A of *N.meningitidis*:

```
                              10         20         30         40
orf114.pep                AVAETANSQGKGKQAGSSVSVSLKTSGDLCGKLKTTLKTLVC
                          |||||||||||||||||||||||||||||||||||||||||
orf114a     MNKGLHRIIFSKKHSTMVAVAETANSQGKGKQAGSSVSVSLKTSGDLCGKLKTTLKTLVC
                    10         20         30         40         50         60

50         60         70         80         90        100
orf114.pep    SLVSLSMVLPAHAQITTDKSAPKNQQVVILKTNTGAPLVNIQTPNGRGLSHNRXYAFDVD
              |||||||      ||||||||||||||| |||||||||||||||||||||||||| | |||
orf114a       SLVSLSMXXXXXXQITTDKSAPKNXQVVILKTNTGAPLVNIQTPNGRGLSHNRYTQFDVD
                    70         80         90        100        110        120

110        120        130        140        150        160
orf114.pep    NKGAVLNNDRNNNPFVVKGSAQLILNEVRGTASKLNGIVTVGGQKADVIIANPNGITVNG
              ||||||||||||||:|||||||||||||||||||||||||||||||||||||||||||||
orf114a       NKGAVLNNDRNNNPFLVKGSAQLILNEVRGTASKLNGIVTVGGQKADVIIANPNGITVNG
                    130        140        150        160        170        180

170        180        190        200        210        220
orf114.pep    GGFKNVGRGILTTGAPQIGKDGALTGFDVVKAHWTVXAAGWNDKGGAXYTGVLARAVALQ
              ||||||||||||| |||||||||||||||||  || ||||||||||| ||||||||||||
orf114a       GGFKNVGRGILTIGAPQIGKDGALTGFDVRQGTLTVGAAGWNDKGGADYTGVLARAVALQ
                    190        200        210        220        230        240

230        240        250        260        270        280
orf114.pep    GKXXGKXLAVSTGPQKVDYASGEISAGTAAGTKPTIALDTAALGGMYADSITLIANEKGV
              || || |||||||||||||||||||||||||||||||||||||||||||||||| ||||
orf114a       GKLQGKNLAVSTGPQKVDYASGEISAGTAAGTKPTIALDTAALGGMYADSITLIAXEKGV
                    250        260        270        280        290        300 orf114.pep    GVX
              |||
orf114a       GVKNAGTLEAAKQLIVTSSGRIENSGRIATTADGTEASPTYLXIETTEKGAXGTFISNGG
                    310        320        330        340        350        360
```

The complete length ORF114a nucleotide sequence <SEQ ID 61> is:

```
  1    ATGAATAAAG GTTTACATCG CATTATCTTT AGTAAAAAGC ACAGCACCAT

51    GGTTGCAGTA GCCGAAACTG CCAACAGCCA GGGCAAAGGT AAACAGGCAG

101    GCAGTTCGGT TTCTGTTTCA CTGAAAACTT CAGGCGACCT TTGCGGCAAA

151    CTCAAAACCA CCCTTAAAAC CTTGGTCTGC TCTTTGGTTT CCCTGAGTAT

201    GGNATTNCNN NNCNNTNCCC AAATTACCAC CGACAAATCA GCACCTAAAA
```

-continued

```
 251  ACCANCAGGT CGTTATCCTT AAAACCAACA CTGGTGCCCC CTTGGTGAAT
 301  ATCCAAACTC CGAATGGACG CGGATTGAGC CACAACCGCT ATACGCAGTT
 351  TGATGTTGAC AACAAAGGGG CAGTGTTAAA CAACGACCGT AACAATAATC
 401  CGTTTCTGGT CAAAGGCAGT GCGCAATTGA TTTTGAACGA GGTACGCGGT
 451  ACGGCTAGCA AACTCAACGG CATCGTTACC GTAGGCGGTC AAAAGGCCGA
 501  CGTGATTATT GCCAACCCCA ACGGCATTAC CGTTAATGGC GGCGGCTTTA
 551  AAAATGTCGG TCGGGGCATC TTAACTATCG GTGCGCCCCA AATCGGCAAA
 601  GACGGTGCAC TGACAGGATT TGATGTGCCT CAAGGCACAT TGACCGTAGG
 651  AGCAGCAGGT TGGAATGATA AAGGCGGAGC CGACTACACC GGGGTACTTG
 701  CTCGTGCAGT TGCTTTGCAG GGAAATTAC AGGGTAAAAA CCTGGCGGTT
 751  TCTACCGGTC CTCAGAAAGT AGATTACGCC AGCGGCGAAA TCAGTGCAGG
 801  TACGGCAGCG GGTACGAAAC CGACTATTGC CCTTGATACT GCCGCACTGG
 851  GCGGTATGTA CGCCGACAGC ATCACACTGA TTGCCANTGA AAAAGGCGTA
 901  GGCGTCAAAA ATGCCGGCAC ACTCGAAGCG GCCAAGCAAT TGATTGTGAC
 951  TTCGTCAGGC CGCATTGAAA ACAGCGGCCG CATCGCCACC ACTGCCGACG
1001  GCACCGAAGC TTCACCGACT TATCTNNCNA TCGAAACCAC CGAAAAAGGA
1051  GCNNCAGGCA CATTTATCTC CAATGGTGGT CGGATCGAGA GCAAAGGCTT
1101  ATTGGTTATT GAGACGGGAG AAGATATCAN CTTGCGTAAC GGAGCCGTGG
1151  TGCAGAATAA CGGCAGTCGC CCAGCTACCA CGGTATTAAA TGCTGGTCAT
1201  AATTTGGTGA TTGAGAGTAA AACTAATGTG AACAATGCCA AAGGCTCGNC
1251  TAATCTGTCG GCCGGCGGTC GTACTACGAT CAATGATGCT ACTATTCAAG
1301  CGGGCAGTTC CGTGTACAGC TCCACCAAAG GCGATACTGA NTTGGGTGAA
1351  AATACCCGTA TTATTGCTGA AAACGTAACC GTATTATCTA ACGGTAGTAT
1401  TGGCAGTGCT GCTGTAATTG AGGCTAAAGA CACTGCACAC ATTGAATCGG
1451  GCAAACCGCT TTCTTTAGAA ACCTCGACCG TTGCCTCCAA CATCCGTTTG
1501  AACAACGGTA ACATTAAAGG CGGAAAGCAG CTTGCTTTAC TGGCAGACGA
1551  TAACATTACT GCCAAAACTA CCAATCTGAA TACTCCCGGC AATCTGTATG
1601  TTCATACAGG TAAAGATCTG AATTTGAATG TTGATAAAGA TTTGTCTGCC
1651  GCCAGCATCC ATTTGAAATC GGATAACGCT GCCCATATTA CCGGCACCAG
1701  TAAAACCCTC ACTGCCTCAA AAGACATGGG TGTGGAGGCA GGCTTGCTGA
1751  ATGTTACCAA TACCAATCTG CGTACCAACT CGGGTAATCT GCACATTCAG
1801  GCAGCCAAAG GCAATATTCA GCTTCGCAAT ACCAAGCTGA ACGCAGCCAA
1851  GGCTCTCGAA ACCACCGCAT TGCAGGGCAA TATCGTTTCA GACGGCCTTC
1901  ATGCTGTTTC TGCAGACGGT CATGTATCCT TATTGGCCAA CGGTAATGCC
1951  GACTTTACCG GTCACAATAC CCTGACAGCC AAGGCCGATG TCNATGCAGG
2001  ATCGGTTGGT AAAGGCCGTC TGAAAGCAGA CAATACCAAT ATCACTTCAT
2051  CTTCAGGAGA TATTACGTTG GTTGCCGNNN NCGGTATTCA GCTTGGTGAC
2101  GGAAAACAAC GCAATTCAAT CAACGGAAAA CACATCAGCA TCAAAAACAA
2151  CGGTGGTAAT GCCGACTTAA AAAACCTTAA CGTCCATGCC AAAAGCGGGG
2201  CATTGAACAT TCATTCCGAC CGGGCATTGA GCATAGAAAA TACNAAGCTG
```

```
                     -continued
2251    GAGTCTACCC ATAATACGCA TCTTAATGCA CAACACGAGC GGGTAACGCT

2301    CAACCAAGTA GATGCCTACG CACACCGTCA TCTAAGCATT ANCGGCAGCC

2351    AGATTTGGCA AAACGACAAA CTGCCTTCTG CCAACAAGCT GGTGGCTAAC

2401    GGTGTATTGG CANTCAATGC GCGCTATTCC CAAATTGCCG ACAACACCAC

2451    GCTGAGAGCG GGTGCAATCA ACCTTACTGC CGGTACCGCC CTAGTCAAGC

2501    GCGGCAACAT CAATTGGAGT ACCGTTTCGA CCAAGACTTT GGAAGATAAT

2551    GCCGAATTAA AACCATTGGC CGGACGGCTG AATATTGAAG CAGGTAGCGG

2601    CACATTAACC ATCGAACCTG CCAACCGCAT CAGTGCGCAT ACCGACCTGA

2651    GCATCAAAAC AGGCGGAAAA TTGCTGTTGT CTGCAAAAGG AGGAAATGCA

2701    GGTGCGCNTA GTGCTCAAGT TTCCTCATTG GAAGCAAAAG GCAATATCCG

2751    TCTGGTTACA GGAGNAACAG ATTTAAGAGG TTCTAAAATT ACAGCCGGTA

2801    AAAACTTGGT TGTCGCCACC ACCAAAGGCA AGTTGAATAT CGAAGCCGTA

2851    AACAACTCAT TCAGCAATTA TTTTCNTACA CAAAAAGNGN NNGNNCTCAA

2901    CCAAAAATCC AAAGAATTGG AACAGCAGAT TGCGCAGTTG AAAAAAAGCT

2951    CGCNTAAAAG CAAGCTGATT CCAACCCTGC AAGAAGAACG CGACCGTCTC

3001    GCTTTCTATA TTCAAGCCAT CAACAAGGAA GTTAAAGGTA AAAACCCAA

3051    AGGCAAAGAA TACCTGCAAG CCAAGCTTTC TGCACAAAAT ATTGACTTGA

3101    TTTCCGCACA AGGCATCGAA ATCAGCGGTT CCGATATTAC CGCTTCCAAA

3151    AAACTGAACC TTCACGCCGC AGGCGTATTG CCAAAGGCAG CAGATTCAGA

3201    GGCGGCTGCT ATTCTGATTG ACGGCATAAC CGACCAATAT GAAATTGGCA

3251    AGCCCACCTA CAAGAGTCAC TACGACAAAG CTGCTCTGAA CAAGCCTTCA

3301    CGTTTGACCG GACGTACGGG GGTAAGTATT CATGCAGCTG CGGCACTCGA

3351    TGATGCACGT ATTATTATCG GTGCATCCGA AATCAAAGCT CCCTCAGGCA

3401    GCATAGACAT CAAAGCCCAT AGTGATATTG TACTGGAGGC TGGACAAAAC

3451    GATGCCTATA CCTTCTTANA AACCAAAGGT AAAAGCGGCA NAATNATCAG

3501    AAAAACNAAG TTTACCAGCA CCNGCGANCA CCTGATTATG CCAGCCCCNG

3551    TCGAGCTGAC CGCCAACGGT ATCACGCTTC AGGCAGGCGG CAACATCGAA

3601    GCTAATACCA CCCGCTTCAA TGCCCCTGCA GGTAAAGTTA CCCTGGTTGC

3651    GGGTGAAAAG NTGCAACTGC TGGCAGAAGA AGGCATCCAC AAGCACGAGT

3701    TGGATGTCCA AAAAAGCCGC CGCTTTATCG GCATCAAGGT AGGTNAGAGC

3751    AATTACAGTA AAAACGAACT GAACGAAACC AAATTGCCTG TCCGCGTCGT

3801    CGCCCAAANT GCAGCCACCC GTTCAGGCTG GGATACCGTG CTCGAAGGTA

3851    CCGAATTCAA AACCACGCTG GCCGGTGCCG ACATTCAGGC AGGTGTANGC

3901    GAAAAAGCCC GTGTCGATGC GAAAATTATC CTCAAAGGCA TTGTGAACCG

3951    TATCCAGTCG GAAGAAAAAT TAGAAACCAA CTCAACCGTA TGGCAGAAAC

4001    AGGCCGGACG CGGCAGCACT ATCGAAACGC TAAAACTGCC CAGCTTCGAA

4051    AGCCCTACTC CGCCCAAATT GTCCGCACCC GGCGGNTATA TCGTCGACAT

4101    TCCGAAAGGC AATCTGAAAA CCGAAATCGA AAAGCTGTCC AAACAGCCCG

4151    AGTATGCCTA TCTGAAACAC CTCCAAGTAG CGAAAAACAT CAACTGGAAT

4201    CAGGTGCAGC TTGCTTACGA CAGATGGGAC TACAAACAGG AGGGCTTAAC
```

```
-continued
4251   CGAAGCAGGT GCGGCGATTA TCGCACTGGC CGTTACCGTG GTCACCTCAG
4301   GCGCAGGAAC CGGAGCCGTA TTGGGATTAA ACGGTGCGNC CGCCGCCGCA
4351   ACCGATGCAG CATTCGCCTC TTTGGCCAGC CAGGCTTCCG TATCGTTCAT
4401   CAACAACAAA GGCGATGTCG GCAAAACCCT GAAAGAGCTG GGCAGAAGCA
4451   GCACGGTGAA AAATCTGGTG GTTGCCGCCG CTACCGCAGG CGTAGCCGAC
4501   AAAATCGGCG CTTCGGCACT GANCAATGTC AGCGATAAGC AGTGGATCAA
4551   CAACCTGACC GTCAACCTAG CCAATGNCGG GCAGTGCCGC ACTGAttaa
```

This encodes a protein having amino acid sequence <SEQ ID 62>:

```
   1   MNKGLHRIIF SKKHSTMVAV AETANSQGKG KQAGSSVSVS LKTSGDLCGK
  51   LKTTLKTLVC SLVSLSMXXX XXXQITTDKS APKNXQVVIL KTNTGAPLVN
 101   IQTPNGRGLS HNRYTQFDVD NKGAVLNNDR NNNPFLVKGS AQLILNEVRG
 151   TASKLNGIVT VGGQKADVII ANPNGITVNG GGFKNVGRGI LTIGAPQIGK
 201   DGALTGFDVR QGTLTVGAAG WNDKGGADYT GVLARAVALQ GKLQGKNLAV
 251   STGPQKVDYA SGEISAGTAA GTKPTIALDT AALGGMYADS ITLIAXEKGV
 301   GVKNAGTLEA AKQLIVTSSG RIENSGRIAT TADGTEASPT YLXIETTEKG
 351   AXGTFISNGG RIESKGLLVI ETGEDIXLRN GAVVQNNGSR PATTVLNAGH
 401   NLVIESKTNV NNAKGSXNLS AGGRTTINDA TIQAGSSVYS STKGDTXLGE
 451   NTRIIAENVT VLSNGSIGSA AVIEAKDTAH IESGKPLSLE TSTVASNIRL
 501   NNGNIKGGKQ LALLADDNIT AKTTNLNTPG NLYVHTGKDL NLNVDKDLSA
 551   ASIHLKSDNA AHITGTSKTL TASKDMGVEA GLLNVTNTNL RTNSGNLHIQ
 601   AAKGNIQLRN TKLNAAKALE TTALQGNIVS DGLHAVSADG HVSLLANGNA
 651   DFTGHNTLTA KADVXAGSVG KGRLKADNTN ITSSSGDITL VAXXGIQLGD
 701   GKQRNSINGK HISIKNNGGN ADLKNLNVHA KSGALNIHSD RALSIENTKL
 751   ESTHNTHLNA QHERVTLNQV DAYAHRHLSI XGSQIWQNDK LPSANKLVAN
 801   GVLAXNARYS QIADNTTLRA GAINLTAGTA LVKRGNINWS TVSTKTLEDN
 851   AELKPLAGRL NIEAGSGTLT IEPANRISAH TDLSIKTGGK LLLSAKGGNA
 901   GAXSAQVSSL EAKGNIRLVT GXTDLRGSKI TAGKNLVVAT TKGKLNIEAV
 951   NNSFSNYFXT QKXXXLNQKS KELEQQIAQL KKSSXKSKLI PTLQEERDRL
1001   AFYIQAINKE VKGKKPKGKE YLQAKLSAQN IDLISAQGIE ISGSDITASK
1051   KLNLHAAGVL PKAADSEAAA ILIDGITDQY EIGKPTYKSH YDKAALNKPS
1101   RLTGRTGVSI HAAAALDDAR IIIGASEIKA PSGSIDIKAH SDIVLEAGQN
1151   DAYTFLXTKG KSGXXIRKTK FTSTXXHLIM PAPVELTANG ITLQAGGNIE
1201   ANTTRFNAPA GKVTLVAGEX XQLLAEEGIH KHELDVQKSR RFIGIKVGXS
1251   NYSKNELNET KLPVRVVAQX AATRSGWDTV LEGTEFKTTL AGADIQAGVX
1301   EKARVDAKII LKGIVNRIQS EEKLETNSTV WQKQAGRGST IETLKLPSFE
1351   SPTPPKLSAP GGYIVDIPKG NLKTEIEKLS KQPEYAYLKQ LQVAKNINWN
1401   QVQLAYDRWD YKQEGLTEAG AAIIALAVTV VTSGAGTGAV LGLNGAXAAA
```

```
                                   -continued
1451     TDAAFASLAS QASVSFINNK GDVGKTLKEL GRSSTVKNLV VAAATAGVAD

1501     KIGASALXNV SDKQWINNLT VNLANXGQCR TD*
```

ORF114-1 (SEQ ID NO: 179) and ORF 114a (SEQ ID NO:62) show 89.8% identity in 1564 aa overlap

```
orf114a.pep  MNKGLHRIIFSKKHSTMVAVAETANSQGKGKQAGSSVSVSLKTSGDLCGKLKTTLKTLVC
             ||||||||||||||||||||||||||||||||||||||||||||||||||||||||||||
orf114-1     MNKGLHRIIFSKKHSTMVAVAETANSQGKGKQAGSSVSVSLKTSGDLCGKLKTTLKTLVC orf114a.pep  SLVSLSMXXXXXXQITTDKSAPKNXQVVILKTNTGAPLVNIQTPNGRGLSHNRYTQFDVD
             |||||||       |||||||||||| |||||||||||||||||||||||||||||||||
orf114-1     SLVSLSMVLPAHAQITTDKSAPKNQQVVILKTNTGAPLVNIQTPNGRGLSHNRYTQFDVD orf114a.pep  NKGAVLNNDRNNNPFLVKGSAQLILNEVRGTASKLNGIVTVGGQKADVIIANPNGITVNG
             |||||||||||||||:||||||||||||||||||||||||||||||||||||||||||||
orf114-1     NKGAVLNNDRNNNPFVVKGSAQLILNEVRGTASKLNGIVTVGGQKADVIIANPNGITVNG orf114a.pep  GGFKNVGRGILTIGAPQIGKDGALTGFDVRQGTLTVGAAGWNDKGGADYTGVLARAVALQ
             |||||||||||| |||||||||||||||||||||||||||||||||||||||||||||||
orf114-1     GGFKNVGRGILTTGAPQIGKDGALTGFDVRQGTLTVGAAGWNDKGGADYTGVLARAVALQ orf114a.pep  GKLQGKNLAVSTGPQKVDYASGEISAGTAAGTKPTIALDTAALGGMYADSITLIAXEKGV
             ||||||||||||||||||||||||||||||||||||||||||||||||||||||| ||||
orf114-1     GKLQGKNLAVSTGPQKVDYASGEISAGTAAGTKPTIALDTAALGGMYADSITLIANEKGV orf114a.pep  GVKNAGTLEAAKQLIVTSSGRIENSGRIATTADGTEASPTYLXIETTEKGAXGTFISNGG
             ||||||||||||||||||||||||||||||||||||||||| ||||||| ||||||||||
orf114-1     GVKNAGTLEAAKQLIVTSSGRIENSGRIATTADGTEASPTYLSIETTEKGAAGTFISNGG orf114a.pep  RIESKGLLVIETGEDIXLRNGAVVQNNGSRPATTVLNAGHNLVIESKTNVNNAKGSXNLS
             |||||||||||||||| ||||||||||||||||||||||||||||||||||||||| :||
orf114-1     RIESKGLLVIETGEDISLRNGAVVQNNGSRPATTVLNAGHNLVIESKTNVNNAKGPATLS orf114a.pep  AGGRTTINDATIQAGSSVYSSTKGDTXLGENTRIIAENVTVLSNGSIGSAAVIEAKDTAH
             | |||:|::|:||:|::||||:||:: ||:||||  : :|||||||:|:|||:||||||
orf114-1     ADGRTVIKEASIQTGTTVYSSSKGNAELGNNTRITGADVTVLSNGTISSSAVIDAKDTAH orf114a.pep  IESGKPLSLETSTVASNIRLNNGNIKGGKQLALLADDNITAKTTNLNTPGNLYVHTGKDL
             ||:||||||:|||:|||:|||||:|||||||||||||||||||||||||||||||||||
orf114-1     IEAGKPLSLEASTVTSDIRLNGGSIKGGKQLALLADDNITAKTTNLNTPGNLYVHTGKDL orf114a.pep  NLNVDKDLSAASIHLKSDNAAHITGTSKTLTASKDMGVEAGLLNVTNTNLRTNSGNLHIQ
             |||||||||||||||||||||||||||||||||||||||||| |||||||||||||||||
orf114-1     NLNVDKDLSAASIHLKSDNAAHITGTSKTLTASKDMGVEAGSLNVTNTNLRTNSGNLHIQ orf114a.pep  AAKGNIQLRNTKLNAAKALETTALQGNIVSDGLHAVSADGHVSLLANGNADFTGHNTLTA
             ||||||||||||||||||||||||||||||||||||||||||||||||||||||||||||
orf114-1     AAKGNIQLRNTKLNAAKALETTALQGNIVSDGLHAVSADGHVSLLANGNADFTGHNTLTA orf114a.pep  KADVXAGSVGKGRLKADNTNITSSSGDITLVAXXGIQLGDGKQRNSINGKHISIKNNGGN
             ||||  |||||||||||||||||||||||||  ||||||||||||||||||||||||||
orf114-1     KADVNAGSVGKGRLKADNTNITSSSGDITLVAGNGIQLGDGKQRNSINGKHISIKNNGGN orf114a.pep  ADLKNLNVHAKSGALNIHSDRALSIENTKLESTHNTHLNAQHERVTLNQVDAYAHRHLSI
             ||||||||||||||||||||||||||||||||||||||||||||||||||||||||||||
orf114-1     ADLKNLNVHAKSGALNIHSDRALSIENTKLESTHNTHLNAQHERVTLNQVDAYAHRHLSI orf114a.pep  XGSQIWQNDKLPSANKLVANGVLAXNARYSQIADNTTLRAGAINLTAGTALVKRGNINWS
             :|||||||||||||||||||||||| ||||||||||||||||||||||||||||||||||
orf114-1     TGSQIWQNDKLPSANKLVANGVLALNARYSQIADNTTLRAGAINLTAGTALVKRGNINWS orf114a.pep  TVSTKTLEDNAELKPLAGRLNIEAGSGTLTIEPANRISAHTDLSIKTGGKLLLSAKGGNA
             ||||||||||||||||||||||||||||||||||||||||||||||||||||||||||||
orf114-1     TVSTKTLEDNAELKPLAGRLNIEAGSGTLTIEPANRISAHTDLSIKTGGKLLLSAKGGNA orf114a.pep  GAXSAQVSSLEAKGNIRLVTGXTDLRGSKITAGKNLVVATTKGKLNIEAVNNSFSNYFXT
             || |||||||||||||||||| |||||||||||||||||||||||||||||||||||| |
orf114-1     GAPSAQVSSLEAKGNIRLVTGETDLRGSKITAGKNLVVATTKGKLNIEAVNNSFSNYFPT
```

-continued

```
orf114a.pep  QKXXXLNQKSKELEQQIAQLKKSSXKSKLIPTLQEERDRLAFYIQAINKEVKGKKPKGKE
             ||   |||||||||||||||||||| |||||||||||||||||||||||||||||||||
orf114-1     QKAAELNQKSKELEQQIAQLKKSSPKSKLIPTLQEERDRLAFYIQAINKEVKGKKPKGKE orf114a.pep  YLQAKLSAQNIDLISAQGIEISGSDITASKKLNLHAAGVLPKAADSEAAAILIDGITDQY
             ||||||||||||||||||||||||||||||||||||||||||||||||||||||||||||
orf114-1     YLQAKLSAQNIDLISAQGIEISGSDITASKKLNLHAAGVLPKAADSEAAAILIDGITDQY orf114a.pep  EIGKPTYKSHYDKAALNKPSRLTGRTGVSIHAAAALDDARIIIGASEIKAPSGSIDIKAH
             ||||||||||||||||||||||||||||||||||||||||||||||||||||||||||||
orf114-1     EIGKPTYKSHYDKAALNKPSRLTGRTGVSIHAAAALDDARIIIGASEIKAPSGSIDIKAH orf114a.pep  SDIVLEAGQNDAYTFLXTKGKSGXXIRKTKFTSTXXHLIMPAPVELTANGITLQAGGNIE
             ||||||||||||||| |||||| |||||||||||    ||||||||||||||||||||||
orf114-1     SDIVLEAGQNDAYTFLKTKGKSGKIIRKTKFTSTRDHLIMPAPVELTANGITLQAGGNIE orf114a.pep  ANTTRFNAPAGKVTLVAGEXXQLLAEEGIHKHELDVQKSRRFIGIKVGXSNYSKNELNET
             |||||||||||||||||||   ||||||||||||||||||||||||| |||||||||||
orf114-1     ANTTRFNAPAGKVTLVAGEELQLLAEEGIHKHELDVQKSRRFIGIKVGKSNYSKNELNET orf114a.pep  KLPVRVVAQXAATRSGWDTVLEGTEFKTTLAGADIQAGVXEKARVDAKIILKGIVNRIQS
             |||||||||:||||||||||||||||||||||||||||| |||:||||||||||||||||
orf114-1     KLPVRVVAQTAATRSGWDTVLEGTEFKTTLAGADIQAGVGEKARADAKIILKGIVNRIQS orf114a.pep  EEKLETNSTVWQKQAGRGSTIETLKLPSFESPTPPKLSAPGGYIVDIPKGNLKTEIEKLS
             |||||||||||||||||||||||||||:|||:|||||||||||||||||||||||||||:
orf114-1     EEKLETNSTVWQKQAGRGSTIETLKLFSFESFTFFKLTAPGGYIVDIPKGNLKTEIEKLA orf114a.pep  KQPEYAYLKQLQVAKNINWNQVQLAYDRWDYKQEGLTEAGAAIIALAVTVVTSGAGTGAV
             |||||||||||||||:|||||||||||:|||||||||||:||||::: | ::| | |: |:
orf114-1     KQPEYAYLKQLQVAKNVNWNQVQLAYDKWDYKQEGLTRAGAAIVTIIVTALTYGYGATAA orf114a.pep  LGLNGA--------------XAAATD---------AAFASLASQASVSFINNKGDVGKTL  1477
             |: ::               :||||          ||:|||  |||:||:||||||||:|
orf114-1     GGVAASGSSTAAAAGTAATTTAAATTVSTATAMQTAALASLYSQAAVSIINNKGDVGKAL  1500 orf114a.pep  KELGRSSTVKNLVVAAATAGVADKIGA----------SALXNVSDKQWINNL----TVNL  1523
             |:||   |:|||::::|  |||:  :::||             :  | : : :|  | ||    ::||
orf114-1     KDLGTSDTVKQIVTSALTAGALNQMGADIAQLNSKVRTELFSSTGNQTIANLGGRLATNL  1560 orf114a.pep  ANXGQCRTDX
             :|  |
orf114-1     SNAGISAGINTAVN...
```

Homology with pspA Putative Secreted Protein of *N.meningitidis* (Accession Number AF030941)

ORF114 (SEQ ID NO:180) and pspA (SEQ ID NO:182) protein show 36% aa identity (SEQ ID NO:181) in 302aa overlap:

```
Orf114:    1 AVAETANSQGKGKQAGSSVSVSL----KTSGDXXXXXXXXXXXXXXXXXXXXXXXPAHAQ   56
             AVAE + GK Q   + SV +      S                            PA A
pspA:     19 AVAENVHRDGKSMQDSEAASVRVTGAASVSSARAAFGFRMAAFSVMLALGVAAFSPAPAS   78

Orf114:   57 -ITTDKSAFKNQQVVILKTNTGAPLVNIQTFNGRGLSHNRXYAFDVDNKGAVLNNDRNN-  114
              I  DKSAPKNQQ VIL+T  G P VNIQTP+ +G+S NR   FDVD KG +LNN R+N
pspA:     79 GIIADKSAFKNQQAVILQTANGLPQVNIQTPSSQGVSVNRFKQFDVDEKGVILNNSRSNT  138

Orf114:  115 ----------NPFVVKGSAQLILNEV-RGTASKLNGIVTVGGQKADVIIANPNGITVNGG  163
                       NP + +G A++I+N++     S LNG + VGG++A+V++ANP+GI VNGG
pspA:    139 QTQLGGWIQGNPHLARGEARVIVNQIDSSNFSLLNGYIEVGGKRAEVVVANPSGIRVNGG  198

Orf114:  164 GFKNVGRGILTTGAPQIGKDGALTGFDVVKAHWTVXAAGWNDKGGAXYTGVLARAVALQG  223
              G N    LT+G P +  +G LTGFDV         G D   A YT +L+RA  +
pspA:    199 GLINAASVTLTSGVPVL-NNGNLTGFDVSSGKVVIGGKGL-DTSDADYTRILSKAAEINA  256

Orf114:  224 KXXGKXLAVSTGPQKVDYASGEISAGTAAGTK----PTIALDTAALGGMYADSITLIANE  279
                GK + V +G  K+D+             +A  +     PT+A+DTA LGGMYAD ITLI+ +
pspA:    257 GVWGKDVKVVSGKNKLDFDGSLAKTASAPSSSDSVTPTVAIDTATLGGMYADKITLISTD  316

Orf114:  280 KG                                                          281
              G
p5pA:    317 NG                                                          318
```

ORF114a is also homologous to pspA:

```
gi|26|23258 (AF030941), putative secreted protein [Neisseria meningitidis]
Length
= 2273
Score = 261 bits (659), Expect = 3e-68
Identities = 203/663 (30%), Positives = 314/663 (46%), Gaps = 76/663 (11%)

Query: 1    MNKGLHRIIFSKKHSTMVAVAETANSQGKGKQAGSSVSVSLK-----TSGDXXXXXXXXX    55
            MNK  +++IF+KK S M+AVAE + GK Q + SV +       +S
Sbjct: 1    MNKRCYKVIFNKKRSCMMAVAENVHRDGKSMQDSEAASVRVTGAASVSSARAAFGFRMAA  60

Query: 56   XXXXXXXXXXXXXXXXXXXQITTDKSAPKNXQVVILKTNTGAPLVNIQTPNGRGLSHNRYT  115
                               I   DKSAPKN Q VIL+T  G P VNIQTP+ +G+S NR+
Sbjct: 61   FSVMLALGVAAFSPAPASGIIADKSAPKNQQAVILQTANGLPQVNIQTPSSQGVSVNRFK  120

Query: 116  QFDVDNKGAVLNNDRNN-----------NPFLVKGSAQLILNEV-RGTASKLNGIVTVGG  163
            QFDVD KG +LNN R+N            NP L +G A++I+N++    S LNG + VGG
Sbjct: 121  QFDVDEKGVILNNSRSNTQTQLGGWIQGNPHLARGEARVIVNQIDSSNPSLLNGYIEVGG  180

Query: 164  QKADVIIANPNGITVNGGGFKNVGRGILTIGAPQIGKDGALTGFDVRQGTLTVGAAGWND  223
            ++A+V++ANP+GI VNGGG  N      LT G P + +G LTGFDV   G + G    D
Sbjct: 181  KRAEVVVANPSGIRVNGGGLINAASVTLTSGVPVL-NNGNLTGFDVSSGKVVIGGKGL-D  238

Query: 224  KGGADYTGVLARAVALQGKLQGKNLAVSTGPQKVDYASGEISAGTAAGTK----PTIALD  279
                 ADYT +L+RA  +  +  GK++ V +G  K+D+        +A +    PT+A+D
Sbjct: 239  TSDADYTRILSRAAEINAGVWGKDVKVVSGKNKLDFDGSLAKTASAFSSSDSVTPTVAID  298

Query: 280  TAALGGMYADSITLIAXEKGVGVKNAGTLEAAK-QLIVTSSGRIENSGRIATTADGTEAS  338
            TA LGGMYAD ITLI+ + G  ++N G + AA    + +++ G++ NSG I         +A+
Sbjct: 299  TATLGGMYADKITLISTDNGAVIRNKGRIFAATGGVTLSADGKLSNSGSI-------DAA  351

Query: 339  PTYLXTETTEKGAXGTFTSNGGRIESKGLLVIETGEDIXLRNGAVVQNNGSRPATTVLNA  398
              + +T +        G IS      V++  + I  +   G+     GS        + +
Sbjct: 352  EITISAQTVD--------NRQGFIRSGKGSVLKVSDGINNQAGLI----GSAGLLDIRDT  399

Query: 399  GHNLVIESKTNVNNAKGS----XNLSAGGRTTINDATIQAGSSVYSSTKGDTXLGENTRI  454
            G      +S ++NN G+      ++S   ++ ND  + A   V S+    D    G+
Sbjct: 400  G-----KSSLHTNNTDGTIIAGKDVSLQAKSLDNDGILTAARDV-SVSLHDDFAGKRDIE  453

Query: 455  IAENVTVLSNGSTGSAAVIEAKDTAHIESGKPLSLETSTVASNTRLNNGNIKGGKQLALL  514
             +T   G + +  +I+A DT + + +      +   + +S R         G      L+
Sbjct: 454  AGRTLTFSTQGRLKNTRIIQAGDTVSLTAAQIDNTVSGKIQSGNRTGLNGKNGITNRGLI  513

Query: 515  ADDNIT-----AKTTNLNTPGNLYVMTGKDLNLNVDKDLSAASIHLKSDNAANTTGTSKT  569
             + IT       AK+ N T G +Y   G + + D  L+                 AA
Sbjct: 514  NSNGITLLQTEAKSDNAGT-GRIY---GSRVAVKADTLLNREETVNGETKAA-------V  562

Query: 570  LTASKDMGVEAGXXXXXXXXXXXXXSGNLHIQAA---KGNIQLRNTKL-NAAKALETTALQ  625
             + A + + A               SG+LHI +A     +Q  NT L N  A+E+++
Sbjct: 563  IAARERLDTGAREIENREAALLSSSGDLHIGSALNGSRQVQGANTSLHNRSAAIESS---  619

Query: 626  GNI                                                           628 (SEQ ID NO:183)
            GNI                                                               (SEQ ID NO:184)
Sbjct: 620  GNI                                                           622 (SEQ ID NO:185)

Score = 37.5 bits (85), Expect = 0.53
Identities = 87/432 (20%), Positives = 159/432 (36%), Gaps = 62/432 (14%)

Query: 239  LQGKLQGKNLAVSTGPQKVDYASGEISAGTAAGTKPTIALDTAALGGMYADSITLIAXEK  298
            LQG LQGKN+ + G    +   G  I AA  K     A   A + +S T     +
Sbjct: 1023 LQGDLQGKNIFAAAGSDITN--TGSIGAENALLLK--------ASNNIESRSETRSNQE  1072

Query: 299  GVGVKNAGTLEAAKQLIVTSSGRI--ENSGRIATTADGTEASPTYLXIETTEKGAXG-TF  355
                V+N G + A  L   +G +  +   I TA              E T+    G T
Sbjct: 1073 QGSVRNIGRV-AGIYLTGRQNGSVLLDAGNNIVLTAS----------ELTNQSEDGQTV  1120

Query: 356  ISNGGRIESKGLLVIETGEDIXLRNGAVVQNNGSRPATTVLNAGHNLVIESK-------T  408
            ++  GG IS   +    I + V++   +T+   G NL + +K
Sbjct: 1121 LNAGGDIRSDTTGISRNQNTIFDSDNYVIRKEQNEVGSTIRTRG-NLSLNAKGDIRIRAA  1179

Query: 409  NVNNAKGSXNLSAGGRTTINDATIQAGSS--------VYSSTKGDTXLGENTRIIAENVT  460
             V + +G L+AG       D ++AG +           Y+  G     + TR +
Sbjct: 1180 EVGSEQGRLKLAAG-----RDIKVEAGKAHTETEDALKYTGRSGGGIKQKMTRHLKNQNG  1234

Query: 461  VLSNGSIGSAAVIEAKDTAHIESGKPLSLETSTVASNIRLNNGNIKGGKQLALLADDNIT  520
             +G++    +I       +G + +   T+ S   NN +K +    + A+ N
Sbjct: 1235 QAVSGTLDGKEIILVSGRDITVTGSNIIADNHTILS--AKNNIVLKAAETRSRSAEMNKK  1292

Query: 521  AKTTNLNTPG-NLYVRTGKDLNLNVDKDLSAASIHLKSDN-------AAHITGTSKTLTA  572
```

```
                        -continued
            K+  + + G      + KD    N  + +S      + S N         H T T   T+++
Sbjct: 1293 EKSGLMGSGGIGFTAGSKKDTQTNRSETVSHTESVVGSLNGNTLISAGKHYTQTGSTISS 1352

Query:  573 SK-DMGVEAGXXXXXXXXXXXXXSGNLHIQAAKG-----NIQLRNTKLNAAAALETTALQG  626
            + D+G+ +G                 +  + KG      ++ + NT + A A++     G
Sbjct: 1353 PQGDVGISSGKISIDAAQNRYSQESKQVYEQKGVTVAISVPVVNTVMGAVDAVKAVQTVG 1412

Query:  627 NIVSDGLHAVSA                                                 638 (SEQ ID NO:186)
            +  ++A++A                                                       (SEQ ID NO:187)
Sbjct: 1413 KSKNSRVNAMAA                                                1424 (SEQ ID NO:188)
```

Figure 5:
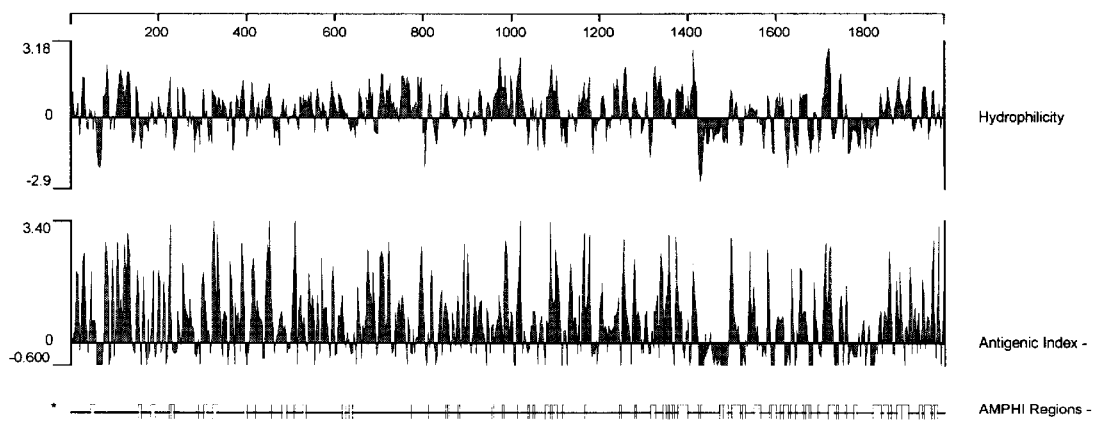
FIG. 5 shows a hydrophilicity plot (upper), an antigenic index plot (middle), and an AMPHI analysis (lower) for ORF 114.

Amino acids 1–1423 of ORF114-1 were cloned in the pGex vector and expressed in *E.coli*, as described above. ST-fusion expression was visible using SDS-PAGE, and FIG. 5 shows plots of hydrophilicity, antigenic index, and AMPHI regions for ORF114-1.

Based on these results, including the homology with the putative secreted protein of *N.meningitidis* and on the presence of a transmembrane domain, it is predicted that this protein from *N.meningitidis*, and its epitopes, could be useful antigens for vaccines or diagnostics.

Example 14

The following partial DNA sequence was identified in *N.meningitidis* <SEQ ID 63>

```
   1  CGCTTCATTC ATGATGAAGC AGTCGGCAGC AACATCGGCG GCGGCAAAAT
  51  GATTGTTGCA GCCGGGCAGG ATATCAATGT ACGCGGCAnA ACCCTTATTT
 101  CTGATAAGGG CATTGTTTTA AAAGCAGGAC ACGACATCGA TATTTCTACT
 151  GCCCATAATC CCTATACCGC CAATCAATAC CACCACACCA wAAAwTCAGG
 201  CGTCATGGGT ACTGGCGGAT TGGGCTTTAC TATCGGTAAC CGGAAAACTA
 251  CCGATGACAC TGATCGTACC AATATTGTsC ATACAGGCAG CATTATAGGC
 301  AGCCTGAaTG GAGACACCGT TACAGTTGCA GGAAACCGCT ACCGACAAAC
 351  CGGCAGTACC GTCTCCAGCC CCGAGGGGCC CAATACCGTC ACAGCCAAAw
 401  GCATAGATGT AGAGTTCGCA AACAACCGGT ATGCCACTGA CTACGcCCAT
 451  ACCCAgGGAA CAAAAAGGCC TTACCGTCGC CCTCAATGTC CCGGTTGTCC
 501  AAGCTGCACA AAACTTCATA CAAGCAGCCC AAAATGTGGG CAAAAGTAAA
 551  AATAAACGCG TTAATGCCAT GGCTGCAGCC AATGCTGCAT GGCAGAGTTA
 601  TCAAGCAACC CAACAAATGC AACAATTTGC TCCAAGCAGC AGTGCGGGAC
 651  AAGGTCAAAA CTACAATCAA AGCCCAGTA TCAGTGTGTC CATTAC.TAC
 701  GGCGAACAGA AAAGTCGTAA CGAGCAAAAA AGACATTACA CCGAAgCGGC
 751  AgCAAGTCAA ATTATCGGCA AAGGGCAAAC CACACTTGCG GCAACAGGAA
 801  GTGGGGAGCA GTCCAATATC AATATTACAG GTTCCGATGT CATCGGCCAT
 851  GCAGGTACTC C.CTCATTGC CGACAACCAT ATCAGACTCC AATCTGCCAA
 901  ACAGGACGGC AGCGAGCAAA GCAAAAACAA AAGCAGTGGT TGGAATGCAG
 951  GCGTACGTnn CAAAATAGGC AACGGCATCA GGTTTGGAAT TACCGCCGGA
1001  GGAAATATCG GTAAAGGTAA AGAGCAAGGG GGAAGTACTA CCCACCGCCA
1051  CACCCATGTC GGCAGCACAA CCGGCAAAAC TACCATCCGA AGCGGCGGGg
1101  GATACCACCC TCAAAGGTGT GCAGCTCATC GGCAAAGGCA TACAGGCAGA
1151  TACGCGCAAC CTGCATATAG AAAGTGTTCA AGATACTGAA ACCTATCAGA
1201  GCAAACAGCA AAACGGCAAT GTCCAAGTTt ACTGTCGGTT ACGGATTCAG
1251  TGCAAGCGGC AGTTACCGCC AAAGCAAAGT CAAAGCAGAC CATGCCTCCG
1301  TAACCGGGCA AAgCGGTATT TATGCCGGAG AAGACGGCTA TCAAATyAAA
1351  GTyAGAGACA ACACAGACCT yAAGGGCGGT ATCATCACGT CTAGCCAAAG
```

-continued

```
1401    CGCAGAAGAT AAGGGCAAAA ACCTTTTTCA GACGGCCACC CTTACTGCCA

1451    GCGACATTCA AAACCACAGC CGCTACGAAG GCAGAAGCTT CGGCATAGGC

1501    GGCAGTTTCG ACCTGAACGG CGGCTGGGAC GGCACGGTTA CCGACAAACA

1551    AGGCAGGCCT ACCGACAGGA TAAGCCCGGC AGCCGGCTAC GGCAGCGACG

1601    GAGACAGCAA AAACAGCACC ACCCGCAGCG GCGTCAACAC CCACAACATA

1651    CACATCACCG ACGAAGCGGG ACAACTTGCC CGAACAGGCA GGACTGCAAA

1701    AGAAACCGAA GCGCGTATCT ACACCGGCAT CGACACCGAA ACTGCGGATC

1751    AACACTCAGG CCATCTGAAA AACAGCTTCG AC...
```

This corresponds to the amino acid sequence <SEQ ID 64; ORF116>:

```
  1    RFIHDEAVGS NIGGGKMIVA AGQDINVRGX SLISDKGIVL KAGHDIDIST

51    AHNRYTGNEY HESXXSGVMG TGGLGFTIGN RKTTDDTDRT NIVHTGSIIG

101    SLNGDTVTVA GNRYRQTGST VSSFEGRNTV TAKXIDVEFA NNRYATDYAH

151    TQEQKGLTVA LNVPVVQAAQ NFIQAAQNVG KSKNKRVNAM AAANAAWQSY

201    QATQQMQQFA PSSSAGQGQN YNQSPSISVS IXYGEQKSRN EQKRHYTEAA

251    ASQIIGKGQT TLAATGSGEQ SNINITGSDV IGHAGTXLIA DNHIRLQSAK

301    QDGSEQSKNK SSGWNAGVRX KIGNGIRFGI TAGGNIGKGK EQGGSTTHRH

351    THVGSTTGKT TIRSGGDTTL KGVQLIGKGI QADTRNLHIE SVQDTETYQS

401    KQQNGNVQVT VGYGFSASGS YRQSKVKADH ASVTGQSGIY AGEDGYQIKV

451    RDNTDLKGGI ITSSQSAEDK GKNLFQTATL TASDIQNHSR YEGRSFGIGG

501    SFDLNGGWDG TVTDKQGRPT DRISPAAGYG SDGDSKNSTT RSGVNTHNIH

551    ITDEAGQLAR TGRTAKETEA RIYTGIDTET ADQHSGHLKN SFD...
```

Computer analysis of this amino acid sequence gave the following results:
Homology With pspA Putative Secreted Protein of *N.meningitidis* (Accession Number AF030941)
ORF116 (SEQ ID NO:189) and pspA (SEQ ID NO:191) protein show 38% aa identity (SEQ ID NO:190) in 502aa overlap:

```
Orf116:    6  EAVGSNIGGGKMTVAAGQDINVRGXSLISDKGIVLKAGHDIDISTAHNRYTGNEYHESXX    65
              +AV   + G ++I+ +G+DI V G ++I+D   +L A ++I +  A R     E ++
PspA:   1235  QAVSGTLDGKEIILVSGRDITVTGSNIIADNHTILSAKNNIVLKAAETRSRSAEMNKKEK  1294

Orf116:   66  XXXXXXXXXXXXXNRKXXXXXXXRTNIVHTGSIIGSLNGDTVTVAGNRYRQTGSTVSSPE   125
                           ++K         + HT S++GSLNG+T+   AG   Y QTGST+SSP+
PspA:   1295  SGLMGSGGIGFTAGSKKDTQTNRSETVSHTESVVGSLNGNTLISAGKHYTQTGSTISSPQ  1354

Orf116:  126  GRNTVTAKXIDVEFANNRYATDYAHTQEQKGLTVALNVPXXXX---XXXXXXXXXXGKS    182
              G    +++  I ++ A NRY+ +    EQKG+TVA++VP                GKS
PspA:   1355  GDVGISSGK:SIDAAQNRYSQESKQVYEQKGVTVAISVPVVNTVMGAVDAVKAVQTVGKS  1414

Orf116:  183  KNKRVXXXXXXXXXXXWQSYQATQQMQQFA--PSSSAGQGQNYNQSPSISVSIXYGEQKSRN   240
              KN RV           +   +   +  A P  +AGQG          ISVS+YGEQK+  +
PspA:   1415  KNSRVNAMAANALNKGVDSGVALYNAARNPKKAAGQG---------ISVSVTYGEQKNTS  1466

Orf116:  241  EQKRHYTEAAASQIIGKGQTTLAATGSGEQSNINITGSDVIGHAGTXLIADNHIRLQSAK   300
              E +   T+    +I G G+ +L A+G+G+  S I  ITGSDV  GT L A+N +++++A+
PspA:   1467  ESRIKGTQVQEGKITGGGKVSLTASGAGKDSRITITGSDVYGGKGTRLKAENAVQIEAAR  1526
```

-continued

```
Orf116:  301  QDGSEQSKNKSSGWNAGVRXKIGNGIRFGITAXXXXXXXXXXXXXSTTHRHTHVGSTTGKT  360
              Q   E+S+NKS+G+NAGV   I  GI FG TA             T +R++H+GS   +T
PspA:   1527  QTHQERSENKSAGFNAGVAIAINKGISFGFTAGANYGKGYGNGDETAYRNSHIGSKDSQT  1586

Orf116:  361  TIRSGGDTTLKGVQLIGKGIQADTRNLHIESVQDTETYQSKQQNGNVQVTVGYGFSASGS  420
                 I SGGDT +KG QL GKG+     +LHIES+QDT  ++ KQ+N + QVTVGYGFS  GS
PspA:   1587  AIESGGDTVIKGGQLKGKGVGVTAESLHIESLQDTAVFKGKQENVSAQVTVGYGFSVGGS  1646

Orf116:  421  YRQSKVKADRASVTGQSGIYAGEDGYQIKVRDNTDLKGGITTSSQSAEDKGKNLFQTATL  480
              Y +SK  +D+ASV  QSGI+AG DGY+I+V    T L G   + S    DK KNL +T+ +
PspA:   1647  YNRSKSSSDYASVNEQSGIFAGGDGYRIRVNGKTGLVGAAVVSD---ADKSKNLLKTSEI  1703

Orf116:  481  TASDIQNHSRYEGRSFGIGGSF                                        502
                    DIQNH+      + G+ G F
PspA:   1704  WHKDIQNHASAAASALGLSGGF                                        1725
```

Based on homology with pspA, it is predicted that this protein from *N.meningitidis*, and its epitopes, could be useful antigens for vaccines or diagnostics.

Example 15

The following partial DNA sequence was identified in *N.meningitidis* <SEQ ID 65>

```
  1   ACGACCGGCA GCCTCGGCGG CATACTGGCC GGCGGCGGCA CTTCCCTTGC
 51   CGCACCGTAT TTGGACAAAG CGGCGGAAAA CCTCGGTCCG GCGGGCAAAG
101   CGGCGGTCAA CGCACTGGGC GGTGCGGCCA TCGGCTATGC AACTGGTGGT
151   AGTGGTGGTG CTGTGGTGGG TGCGAATGTA GATTGGAACA ATAGGCAGCT
201   GCATCCGAAA GAAATGGCGT TGGCCGACAA ATATGCCGAA GCCCTCAAGC
251   GCGAAGTTGA AAAACGCGAA GGCAGAAAAA TCAGCAGCCA AGAAGCGGCA
301   ATGAGAATCC GCAGGCAGAT ATGCGTTGGG TGGACAAAGG TTCCCAAGAC
351   GGCTATACCG ACCAAAGCGT CATATCCCTT ATCGGAATGA
```

This corresponds to the amino acid sequence <SEQ ID 66; ORF 118>:

```
  1   TTGSLGGILA GGGTSLAAPY LDKAAENLGP AGKAAVNALG GAAIGYATGG
 51   SGGAVVGANV DWNNRQLHPK EMALADKYAE ALKREVEKRE GRKISSQEAA
101   MRIRRQICVG WTKVPKTAIP TKASYPLSE*
```

Computer analysis of this amino acid sequence reveals two putative transmembrane domains.

Based on this analysis, it is predicted that this protein from *N.meningitidis*, and its epitopes, could be useful antigens for vaccines or diagnostics.

Example 16

The following partial DNA sequence was identified in *N.meningitidis* <SEQ ID 67>

```
  1  CAATGCCGTC TGAAAAGCTC ACAATTTTAC AGACGGCATT TGTTATGCAA
 51  GTACATATAC AGATTCCCTA TATACTGCCC AGrkGCGTGC GTgGCTGAAG
101  ACACCCCCTA CGCTTGCTAT TTGrAACAGC TCCAAGTCAC CAAAGACGTC
151  AACTGGAACC AGGTACwACT GGCGTACGAC AAATGGGACT ATAAACAGGA
201  AGGCTTAACC GGAGCCGGAG CAGCGATTAT TGCGCTGGCT GTTACCGTGG
251  TTACTGCGGG CGCGGGAgCC GGAGCCGCAC TGGGCTTAAA CGGCGCGGCc
301  GCAGCGGCAA CCGATGCCGC ATTCGCCTCG CTGGCCAGCC AGGCTTCCGT
351  ATCGCTCATC AaCAACAAAG GCAATATCGG TAaCACCCTG AAAGAGCTGG
401  GCAGAAGCAG CACGGTGAAA AATCTGATGG TTGCCGTCGc tACCGCAgGC
451  GTagCcgaCA AAATCGGTGC TTCGGCACTG AACAATGTCA GCGATAAGCA
501  GTGGATCAAC AACCTGACCG TCAACCTGGC CAATGCGGGC AGTGCCGCAC
551  TGATTAATAC CGCTGTCAAC GGCGGCAGCc tgAAAGACAA TCTGGAAGCG
601  AATATCCTTG CGGCTTTGGT GAATACTGCG CATGGAGAAG CAGCCAGTAA
651  AATCAAACAG TTGGATCAGC ACTACATTAC CCACAAGATT GCCCaTGCCA
701  TAGCGGGCTG TGCGGCTGCG GCGGCGAATA AGGGCAAGTG TCAGGATGGT
751  GCGATAgGTG CGGCTGTGGG CGAGATAGTC GGGGAgGCTT TGACAAACGG
801  CAAAAATCCT GACACTTTGA CAGCTAAAgA ACGCGaACAG ATTTTGGCAT
951  ACAGCAAACT GGTTGCCGGT ACCGTAAGCG GTGTGGTCGG CGGCGATGTA
901  AATGCGGCGG CGAATGCGGC TGAGGTAGCG GTGAAAAATA ATCAGCTTAG
951  CGACAAAtGA
```

This corresponds to the amino acid sequence <SEQ ID 68; ORF41>:

```
  1  QCRLKSSQFY RRHLLCKYIY RFPIYCPXAC VAEDTPYACY LXQLQVTKDV
 51  NWNQVXLAYD KWDYKQEGLT GAGAAIIALA VTVVTAGAGA GAALGLNGAA
101  AAATDAAFAS LASQASVSLI NNKGNIGNTL KELGRSSTVK NLMVAVATAG
151  VADKIGASAL NNVSDKQWIN NLTVNLANAG SAALINTAVN GGSLKDNLEA
201  NILAALVNTA HGEAASKIKQ LDQHYITHKI AHAIAGCAAA AANKGKCQDG
251  AIGAAVGEIV GEALTNGKNP DTLTAKEREQ ILAYSKLVAG TVSGVVGGDV
301  NAAANAAEVA VKNNQLSDK*
```

Further work revealed the complete nucleotide sequence <SEQ ID 69>:

```
  1  ATGCAAGTAA ATATTCAGAT TCCCTATATA CTGCCCAGAT GCGTGCGTGC
 51  TGAAGACACC CCCTACGCTT GCTATTTGAA ACAGCTCCAA GTCACCAAAG
101  ACGTCAACTG GAACCAGGTA CAACTGGCGT ACGACAAATG GGACTATAAA
151  CAGGAAGGCT TAACCGGAGC CGGAGCAGCG ATTATTGCGC TGGCTGTTAC
201  CGTGGTTACT GCGGGCGCGG GAGCCGGAGC CGCACTGGGC TTAAACGGCG
251  CGGCCGCAGC GGCAACCGAT GCCGCATTCG CCTCGCTGGC CAGCCAGGCT
301  TCCGTATCGC TCATCAACAA CAAAGGCAAT ATCGGTAACA CCCTGAAAGA
```

-continued

```
 351    GCTGGGCAGA AGCAGCACGG TGAAAAATCT GATGGTTGCC GTCGCTACCG
 401    CAGGCGTAGC CGACAAAATC GGTGCTTCGG CACTGAACAA TGTCAGCGAT
 451    AAGCAGTGGA TCAACAACCT GACCGTCAAC CTGGCCAATG CGGGCAGTGC
 501    CGCACTGATT AATACCGCTG TCAACGGCGG CAGCCTGAAA GACAATCTGG
 551    AAGCGAATAT CCTTGCGGCT TTGGTGAATA CTGCGCATGG AGAAGCAGCC
 601    AGTAAAATCA AACAGTTGGA TCAGCACTAC ATTACCCACA AGATTGCCCA
 651    TGCCATAGCG GGCTGTGCGG CTGCGGCGGC GAATAAGGGC AAGTGTCAGG
 701    ATGGTGCGAT AGGTGCGGCT GTGGGCGAGA TAGTCGGGGA GGCTTTGACA
 751    AACGGCAAAA ATCCTGACAC TTTGACAGCT AAAGAACGCG AACAGATTTT
 801    GGCATACAGC AAACTGGTTG CCGGTACGGT AAGCGGTGTG GTCGGCGGCG
 851    ATGTAAATGC GGCGGCGAAT GCGGCTGAGG TAGCGGTGAA AATAATCAG
 901    CTTAGCGACA AGAGGGTAG AGAATTTGAT AACGAAATGA CTGCATGCGC
 951    CAAACAGAAT AATCCTCAAC TGTGCAGAAA AAATACTGTA AAAAAGTATC
1001    AAAATGTTGC TGATAAAAGA CTTGCTGCTT CGATTGCAAT ATGTACGGAT
1051    ATATCCCGTA GTACTGAATG TAGAACAATC AGAAAACAAC ATTTGATCGA
1101    TAGTAGAAGC CTTCATTCAT CTTGGGAAGC AGGTCTAATT GGTAAAGATG
1151    ATGAATGGTA TAAATTATTC AGCAAATCTT ACACCCAAGC AGATTTGGCT
1201    TTACAGTCTT ATCATTTGAA TACTGCTGCT AAATCTTGGC TTCAATCGGG
1251    CAATACAAAG CCTTTATCCG AATGGATGTC CGACCAAGGT TATACACTTA
1301    TTTCAGGAGT TAATCCTAGA TTCATTCCAA TACCAAGAGG GTTTGTAAAA
1351    CAAAATACAC CTATTACTAA TGTCAAATAC CCGGAAGGCA TCAGTTTCGA
1401    TACAAACCTA AAAAGACATC TGGCAAATGC TGATGGTTTT AGTCAAAAAC
1451    AGGGCATTAA AGGAGCCCAT AACCGCACCA ATTTTATGGC AGAACTAAAT
1501    TCACGAGGAG GACGCGTAAA ATCTGAAACC CAAACTGATA TTGAAGGCAT
1551    TACCCGAATT AAATATGAGA TTCCTACACT AGACAGGACA GGTAAACCTG
1601    ATGGTGGATT TAAGGAAATT TCAAGTATAA AAACTGTTTA TAATCCTAAA
1651    AAATTTTCTG ATGATAAAAT ACTTCAAATG GCTCAAAATG CTGCTTCACA
1701    AGGATATTCA AAAGCCTCTA AAATTGCTCA AAATGAAAGA ACTAAATCAA
1751    TATCGGAAAG AAAAAATGTC ATTCAATTCT CAGAAACCTT TGACGGAATC
1801    AAATTTAGAT CATATTTTGA TGTAAATACA GGAAGAATTA CAAACATTCA
1851    CCCAGAATAA
```

This corresponds to the amino acid sequence <SEQ ID 70; ORF41-1>:

```
  1    MQVNIQIPYI LPRCVRAEDT PYACYLKQLQ VTKDVNWNQV QLAYDKWDYK
 51    QEGLTGAGAA IIALAVTVVT AGACAGAALG LNGAAAAATD AAEASLASQA
101    SVSLINNKGN IGNTLKELGR SSTVKNLMVA VATAGVADKI GASALNNVSD
151    KQWTNNLTVN LANAGSAALI NTAVNGGSLK DNLEANILAA LVNTAHGEAA
201    SKIKQLDQHY ITHKIAHAIA GCAAAAANKG KCQDGAIGAA VGEIVGEALT
```

```
-continued
251   NGKNPDTLTA  KEREQILAYS  KLVAGTVSGV  VGGDVNAAAN  AAEVAVKNNQ

301   LSDKEGREFD  NEMTACAKQN  NPQLCRKNTV  KKYQNVADKR  LAASIAICTD

351   ISRSTECRTI  RKQHLIDSRS  LHSSWEAGLI  GKDDEWYKLF  SKSYTQADLA

401   LQSYHLNTAA  KSWLQSGNTK  PLSEWMSDQG  YTLISGVNPR  FIPIPRGFVK

451   QNTPITNVKY  PEGISFDTNL  KRHLANADGF  SQKQGIKGAH  NRTNFMAELN

501   SRGGRVKSET  QTDIEGITRI  KYEIPTLDRT  GKPDGGFKEI  SSIKTVYNPK

551   KFSDDKILQM  AQNAASQGYS  KASKIAQNER  TKSISERKNV  IQFSETFDGI

601   KFRSYFDVNT  GRITNIHPE*
```

Computer analysis of this of this amino acid sequence predicts a transmembrane domain, and homology with an ORF from *N.meningitidis* (strain A) was also found.

ORF41 (SEQ ID NO:192) shows 92.8% identity over a 279aa overlap with an ORF (ORF41a (SEQ ID NO:193)) from strain A of *N.meningitidis*:

```
                10        20        30        40        50        60      69
orf41.pep   YPPHLLCKYIYRFPIYCPXACVAEDTPYACYLXQLQVTKDVNWNQVXLAYDKNDYKQEGL
                                         ||  ||||:|::|||||  ||||:||||||||
orf41a                                   YLKQLQVAKNINWNQVQLAYDRWDYKQEGL
                                                     10        20        30

70        80        90       100       110       120     129
orf41.pep   TGAGAAIIALAVTVVTAGAGAGAALGLNGAAAAATDAAFASLASQASVSLINNKGNIGNT
            |  ||||||||||||:|||:||:|||||| ||||||||||||||||||||:||||::|:|
ort41a      TEAGAAIIALAVTVVTSGAGTGAVLGLNGAXAAATDAAFASLASQASVSFINNKGDVGKT
                      40        50        60        70        80        90

130       140       150       160       170       180     189
orf41.pep   LKELGRSSTVKNLMVAVATAGVADKIGASALNNVSDKQWINNLTVNLANAGSAALINTAV
            ||||||:||:|||:||||||||||||||||||| |||||||||||||||||||||||||||
orf41a      LKELGPSSTVKNLVVAAATAGVADKIGASALXNVSDKQWINNLTVNLANAGSAALINTAV
                     100       110       120       130       140       150

190       200       210       220       230       240     249
orf41.pep   NGGSLKDNLEANILAALVNTAHGEAASKIKQLDQHYITHKIAHAIAGCAAAAANKGKCQD
            ||||||| |||||||||||||||||||||||||||||:|||||||||||||||||||||
orf41a      NGGSLKDXLEANILAALVNTAHGEAASKIKQLDQHYIVHKIAHAIAGCAAAAANKGKCQD
                     160       170       180       190       200       210

250       260       270       280       290       300     309
orf41.pep   GAIGAAVGEIVGEALTNGKNPDTLTAKEREQILAYSKLVAGTVSGVVGGDVNAAANAAEV
            ||||||||||||||||||||||||||||||||||||||||||||||||||||||||||||
orf41a      GAIGAAVGEIVGEALTNGKNPDTLTAKEREQILAYSKLVAGTVSGVVGGDVNAAANAAEV
                     220       230       240       250       260       270

310       320
orf41.pep   AVKNNQLSDKX
            |||||||||
orf41a      AVKNNQLSDXEGREFDNEMTACAKQNXPQLCRKNTVKKYQNVADKRLAASIAICTDISRS
                     280       290       300       310       320       330
```

A partial ORF41a nucleotide sequence <SEQ ID 71> is:

```
  1   TATCTGAAAC AGCTCCAAGT AGCGAAAAAC ATCAACTGGA ATCAGGTGCA

51   GCTTGCTTAC GACAGATGGG ACTACAAACA GGAGGGCTTA ACCGAAGCAG

101   GTGCGGCGAT TATCGCACTG GCCGTTACCG TGGTCACCTC AGGCGCAGGA

151   ACCGGAGCCG TATTGGGATT AAACGGTGCG NCCGCCGCCG CAACCGATGC

201   AGCATTCGCC TCTTTGGCCA GCCAGGCTTC CGTATCGTTC ATCAACAACA

251   AAGGCGATGT CGGCAAAACC CTGAAAGAGC TGGGCAGAAG CAGCACGTGC
```

```
 301    AAAAATCTGG TGGTTGCCGC CGCTACCGCA GGCGTAGCCG ACAAAATCGG
 351    CGCTTCGGCA CTGANCAATG TCAGCGATAA GCAGTGGATC AACAACCTGA
 401    CCGTCAACCT AGCCAATGCG GGCAGTGCCG CACTGATTAA TACCGCTGTC
 451    AACGGCGGCA GCCTGAAAGA CANTCTGGAA GCGAATATCC TTGCGGCTTT
 501    GGTCAATACC GCGCATGGAG AAGCAGCCAG TAAAATCAAA CAGTTGGATC
 551    AGCACTACAT AGTCCACAAG ATTGCCCATG CCATAGCGGG CTGTGCGGCA
 601    GCGGCGGCGA ATAAGGGCAA GTGTCAGGAT GGTGCGATAG GTGCGGCTGT
 651    GGGCGAGATA GTCGGGGAGG CTTTGACAAA CGGCAAAAAT CCTGACACTT
 701    TGACAGCTAA AGAACGCGAA CAGATTTTGG CATACAGCAA ACTGGTTGCC
 751    GGTACGGTAA GCGGTGTGGT CGGCGGCGAT GTAAATGCGG CGGCGAATGC
 801    GGCTGAGGTA GCGGTGAAAA ATAATCAGCT TAGCGACNAA GAGGGTAGAG
 851    AATTTGATAA CGAAATGACT GCATGCGCCA AACAGAATAN TCCTCAACTG
 901    TGCAGAAAAA ATACTGTAAA AAAGTATCAA AATGTTGCTG ATAAAAGACT
 951    TGCTGCTTCG ATTGCAATAT GTACGGATAT ATCCCGTAGT ACTGAATGTA
1001    GAACAATCAG AAAACAACAT TTGATCGATA GTAGAAGCCT TCATTCATCT
1051    TGGGAAGCAG GTCTAATTGG TAAAGATGAT GAATGGTATA AATTATTCAG
1101    CAAATCTTAC ACCCAAGCAG ATTTGGCTTT ACAGTCTTAT CATTTGAA7A
1151    CTGCTGCTAA ATCTTGGCTT CAATCGGGCA ATACAAAGCC TTTATCCGAA
1201    TGGATGTCCG ACCAAGGTTA TACACTTATT TCAGGAGTTA ATCCTAGATT
1251    CATTCCAATA CCAAGAGGGT TTGTAAAACA AAATACACCT ATTACTAATG
1301    TCAAATACCC GGAAGGCATC AGTTTCGATA CAAACCTANA AAGACATCTG
1351    GCAAATGCTG ATGGTTTTAG TCAAGAACAG GGCATTAAAG GAGCCCATAA
1401    CCGCACCAAT NTTATGGCAG AACTAAATTC ACGAGGAGGA NGNGTAAAAT
1451    CTGAAACCCA NACTGATATT GAAGGCATTA CCCGAATTAA ATATGAGATT
1501    CCTACACTAG ACAGGACAGG TAAACCTGAT GGTGGATTTA AGGAAATTTC
1551    AAGTATAAAA ACTGTTTATA ATCCTAAAAA NTTTTNNGAT GATAAAATAC
1601    TTCAAATGGC TCAANATGCT GNTTCACAAG GATATTCAAA AGCCTCTAAA
1651    ATTGCTCAAA ATGAAAGAAC TAAATCAATA TCGGAAAGAA AAAATGTCAT
1701    TCAATTCTCA GAAACCTTTG ACGGAATCAA ATTTAGANNN TATNTNGATG
1751    TAAATACAGG AAGAATTACA AACATTCACC CAGAATAA
```

This encodes a protein having the partial amino acid sequence <SEQ ID 72>:

```
  1    YLKQLQVAKN INWNQVQLAY DRWDYKQEGL TEAGAAIIAL AVTVVTSGAG
 51    TGAVLGLNGA XAAATDAAFA SLASQASVSF INNKGDVGKT LKELGRSSTV
101    KNLVVAAATA GVADKIGASA LXNVSDKQWI NNLTVNLANA GSAALINTAV
151    NGGSLKDXLE ANILAALVNT AHGEAASKIK QLDQRYIVHK IAHAIAGCAA
201    AAANKGKCQD GAIGAAVGEI VGEALTNGKN PDTLTAKERE QILAYSKLVA
251    GTVSGVVGGD VNAAANAAEV AVKNNQLSDX EGREFDNEMT ACAKQNX+190
       QL
```

```
301   CRKNTVKKYQ NVADKRLAAS IAICTDISRS TECRTIRKQH LIDSRSLHSS

351   WEAGLIGKDD EWYKLFSKSY TQADLALQSY HLNTAAKSWL QSGNTKFLSE

401   WMSDQGYTLI SGVNPRFIPI PRGFVKQNTP ITNVKYPEGI SFDTNLXRHI

451   ANADGFSQEQ GIKGAHNRTN XMAELNSRGG XVKSETXTDI EGITRIKYEI

501   PTLDRTGKPD GGFKEISSIK TVYNPKXFXD DKILQMAQXA XSQGYSKASK

551   IAQNERTKSI SERKNVIQFS ETFDGIKFRX YXDVNTGRIT NIHPE*
```

ORF41a (SEQ ID NO:72) and ORF41-1 (SEQ ID NO:70)
show 94.8% identity in 595 aa overlap:

```
                                  10        20        30
orf41a.pep                YLKQLQVAKNINWNQVQLAYDRWDYKQEGLTEAGAA
                          ||||||:|::|||||||||||:||||||||:|||||
orf41-1    MQVNIQIPYILPRCVRAEDTPYACYLKQLQVTKDVNWNQVQLAYDKWDYKQEGLTGAGAA
                    10        20        30        40        50        60

40        50        60        70        80        90
orf41a.pep ITALAVTVVTSGAGTGAVLGLNGAXAAATDAAFASLASQASVSFINNKGDVGKTLKELGR
           |||||||||||:|||:||:||||| |||||||||||||||||||||:||||::|:||||
orf41-1    IIALAVTVVTAGAGAGAALGLNGAAAAATDAAFASLASQASVSLINNKGNIGNTLKELGR
                    70        80        90       100       110       120

100       110       120       130       140       150
orf40a.pep SSTVKNLVVAAATAGVADKIGASALXNVSDKQWINNLTVNLANAGSAALINTAVNGGSLK
           ||||||:||:|||||||||||||||| |||||||||||||||||||||||||||||||||
orf41-1    SSTVKNLMVAVATAGVADKIGASALNNVSDKQWINNLTVNLANAGSAALINTAVNGGSLK
                   130       140       150       160       170       180

160       170       180       190       200       210
orf41a.pep DXLEANILAALVNTAHGEAASKIKQLDQHYIVHKIAHAIAGCAAAAANKGKCQDGAIGAA
           |  |||||||||||||||||||||||||||:|||||||||||||||||||||||||||||
orf41-1    DNLEANILAALVNTAHGEAASKIKQLDQHYITHKIAHAIAGCAAAAANKGKCQDGAIGAA
                   190       200       210       220       230       240

220       230       240       250       260       270
orf41a.pep VGEIVGEALTNGKNPDTLTAKEREQILAYSKLVAGTVSGVVGGDVNAAANAAEVAVKNNQ
           ||||||||||||||||||||||||||||||||||||||||||||||||||||||||||||
orf41-1    VGEIVGEALTNGKNPDTLTAKEREQILAYSKLVAGTVSGVVGGDVNAAANAAEVAVKNNQ
                   250       260       270       280       290       300

280       290       300       310       320       330
orf41a.pep LSDXEGREFDNEMTACAKQNXPQLCRKNTVKKYQNVADKRLAASIAICTDISRSTECRTI
           ||| ||||||||||||||||| ||||||||||||||||||||||||||||||||||||||
orf41-1    LSDKEGREFDNEMTACAKQNNPQLCRKNTVKKYQNVADKRLAASIAICTDISRSTECRTI
                   310       320       330       340       350       360

340       350       360       370       380       390
orf41a.pep RKQHLIDSRSLHSSWEAGLIGKDDEWYKLFSKSYTQADLALQSYHLNTAAKSWLQSGNTK
           ||||||||||||:|||||||||||||||||||||||||||||||||||||||||||||||
orf41-1    RKQHLIDSRSLRSSWEAGLIGKDDEWYKLFSKSYTQADLALQSYHLNTAAKSWLQSGNTK
                   370       380       390       400       410       420

400       410       420       430       440       450
orf41a.pep PLSEWMSDQGYTLISGVNFRFIPIPRGFVKQNTPITNVKYPEGISFDTNLXRHLANADGF
           |||||||||||||||||||:||||||||||||||||||||||||||||||| |:||||||
orf41-1    PLSEWMSDQGYTLISGVNPRFIPIPRGFVKQNTPITNVKYPEGISFDTNLKRRLANADGF
                   430       440       450       460       470       480

460       470       480       490       500       510
orf41a.pep SQEQGIKGAHNRTNXMAELNSRGGXVKSETXTDIEGITRIKYEIPTLDRTGKPDGGFKEI
           ||:||||||||||| ||||||||| |||||| ||||||||||||| ||||||||||||||
orf41-1    SQKQGIKGAHNRTNFMAELNSRGGRVKSETQTDIEGITRIKYEIFTLDRTGKPDGGFKEI
                   490       500       510       520       530       540

520       530       540       550       560       570
orf41a.pep SSIKTVYNPKXFXDDKILQMAQXAXSQGYSKASKIAQNERTKSISERKNVIQFSETFDGI
           ||||||||||| |:|||||||||| |||||||||||||||||||||||||||||||||||
orf41-1    SSIKTVYNPKKFSDDKILQMAQNAASQGYSKASKIAQNERTKSISERKNVIQFSETFDGI
                   550       560       570       580       590       600
```

```
                      -continued
                580         590
orf41a.pep   KFRXYXDVNTGRITNIHPEX
             ||| | ||||||||||||||
orf41-1      KFRSYFDVNTGRITNIHPEX
                610         620
```

Figure 6:
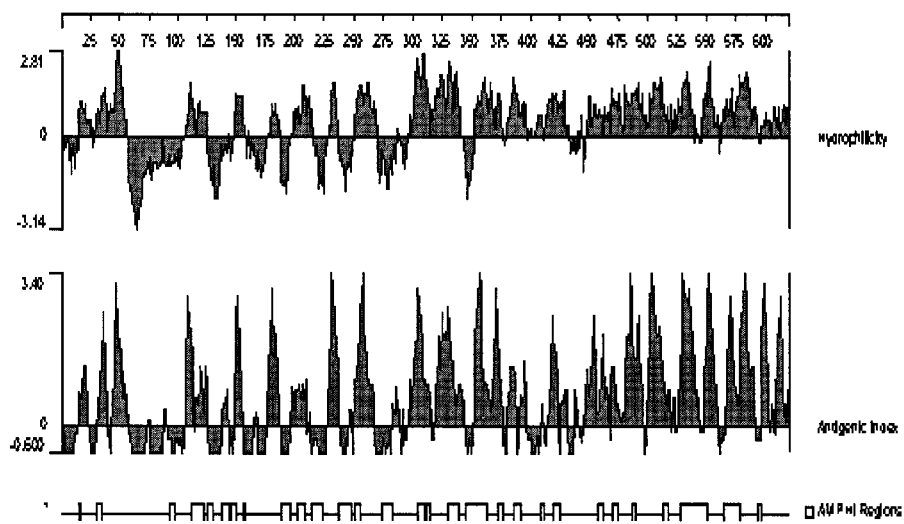
FIG. 6 shows a hydrophilicity plot (upper), an antigenic index plot (middle), and an AMPHI analysis (lower) for ORF 41.

Amino acids 25-619 of ORF41-1 were amplified as described above. FIG. 6 shows plots of hydrophilicity, antigenic index, and AMPHI regions for ORF41-1.

Based on this analysis, it is predicted that this protein from *N.meningitidis*, and its epitopes, could be useful antigens for vaccines or diagnostics.

Example 17

The following DNA sequence was identified in *N.meningitidis* <SEQ ID 73>

```
  1    ATGGCAATCA TTACATTGTA TTATTCTGTC AATGGTATTT TAAATGTATG
 51    TGCAAAAGCA AAAAATATTC AAGTAGTTCC CAATAATAAG AATATGGTTC
101    TTTTTGGGTT TTTGGsmrGC ATCATCGGCG GTTCAACCAA TGCCATGTCT
151    CCCATATTGT TAATATTTTT GCTTAGCGAA ACAGAAAATA AAAATcgTAT
201    CGTAAAATCA AGCAATCTAT GCTATCTTTT GGCGAAAATT GTTCAAATAT
251    ATATGCTAAG AGACCAGTAT TGGTTATTAA ATAAGAGTGA ATACGdTTTA
301    ATATTTTTAC TGTCCGTATT GTCTGTTATT GGATTGTATG TTGGAATTCG
351    GTTAAGGACT AAGATTAGCC CAaATTTTTT TAAAATGTTA ATTTTTATTG
401    tTTTATTGGT ATTGGCtCTG AAAATCGGGC AttCGGGTTT AAtCAAACTT
451    TAA
```

This corresponds to the amino acid sequence <SEQ ID 74; ORF51>:

```
  1    MAIITLYYSV NGILNVCAKA KNIQVVANNK NMVLFGFLXX IIGGSTNAMS
 51    PILLIFLLSE TENKNRIVKS SNLCYLLAKI VQIYMLRDQY WLLNKSEYXL
101    IFLLSVLSVI GLYVGIRLRT KISPNFFKML IFIVLLVLAL KIGHSGLIKL
151    *
```

Further work revealed the complete nucteotide sequence <SEQ ID 75>:

```
  1    ATGCAAGAAA TAATGCAATC TATCGTTTTT GTTGCTGCCG CAATACTGCA
 51    CGGAATTACA GGCATGGGAT TTCCGATGCT CGGTACAACC GCATTGGCTT
101    TTATCATGCC ATTGTCTAAG GTTGTTGCCT TGGTGGCATT ACCAAGCCTG
151    TTAATGAGCT TGTTGGTTCT ATGCAGCAAT AACAAAAAGG GTTTTTGGCA
201    AGAGATTGTT TATTATTTAA AAACCTATAA ATTGCTTGCT ATCGGCAGCG
251    TCGTTGGCAG CATTTTGGGG GTGAAGTTGC TTTTGATACT TCCAGTGTCT
301    TGGCTGCTTT TACTGATGGC AATCATTACA TTGTATTATT CTGTCAATGG
351    TATTTTAAAT GTATGTGCAA AAGCAAAAAA TATTCAAGTA GTTGCCAATA
```

-continued

```
401     ATAAGAATAT GGTTCTTTTT GGGTTTTTGG CAGGCATCAT CGGCGGTTCA

451     ACCAATGCCA TGTCTCCCAT ATTGTTAATA TTTTTGCTTA GCGAAACAGA

501     AAATAAAAAT CGTATCGTAA AATCAAGCAA TCTATGCTAT CTTTTGGCGA

551     AAATTGTTCA AATATATATG CTAAGAGACC AGTATTGGTT ATTAAATAAG

601     AGTGAATACG GTTTAATATT TTTACTGTCC GTATTGTCTG TTATTGGATT

651     GTATGTTGGA ATTCGGTTAA GGACTAAGAT TAGCCCAAAT TTTTTTAAAA

701     TGTTAATTTT TATTGTTTTA TTGGTATTGG CTCTGAAAAT CGGGCATTCG

751     GGTTTAATCA AACTTTAA
```

This corresponds to the amino acid sequence <SEQ ID 76; ORF51-1>:

```
  1     MQEIMQSIVF VAAAILHGIT GMGFPMLGTT ALAFIMPLSK VVALVALPSL

51     LMSLLVLCSN NKKGFWQEIV YYLKTYKLLA IGSVVGSILG VKLLLILPVS

101     WLLLLMAIIT LYYSVNGILN VCAKAKNIQV VANNKNMVLF GFLAGIIGGS

151     TNAMSPILLI FLLSETENKN RIVKSSNLCY LLAKIVQIYM LRDQYWLLNK

201     SEYGLIFLLS VLSVIGLYVG IRLRTKISPN FFKNLIFIVL LVLALKIGHS

251     GLIKL*
```

Computer analysis of this amino acid sequence reveals three putative transmembrane domains. A corresponding ORF from strain A of N.meningitidis was also identified:
Homology With a Predicted ORF From N.meningitidis (Strain A)

ORF51 (SEQ ID NO:74) shows 96.7% identity over a 150aa overlap with an ORF (ORF51a (SEQ ID NO: 194)) from strain A of N.meningitidis:

```
                                    10        20        30
orf51.pep                           MAIITLYYSVNGILNVCAKAKNIQVVANNK
                                    ||||||||||||||||||||||||||||||
orf51a     YKLLAIGSVVGSILGVKLLLILPVSWLLLIMAIITLYYSVNGILNVCAKAKNIQVVANNK
                 80        90       100       110       120       130

40        50        60        70        80        90
orf51.pep  NMVLFGFLXXIIGGSTNAMSPILLIFLLSETENKNRIVKSSNLCYLLAKIVQIYMLRDQY
           ||||||||  ||||||||||||||||||||||||||:|||||||||||||||||||||||
orf51a     NMVLFGFLAGIIGGSTNAMSPILLIFLLSETENKNRIAKSSNLCYLLAKIVQIYMLRDQY
                140       150       160       170       180       190

100       110       120       130       140       150
orf51.pep  WLLNKSEYXLIFLLSVLSVIGLYVGIRLRTKISPNFFKMLIFIVLLVLALKIGHSGLIKL
           ||||||||| |||||||||||||||||||||||||||||||||||||||||:||||||
orf51a     WLLNKSEYGLIFLLSVLSVIGLYVGIRLRTKISPNFFKMLIFIVLLVLALKIGYSGLIKL
                200       210       220       230       240       250
```

ORF51-1 (SEQ ID NO:76) and ORF51a (SEQ ID NO:78) show 99.2% identity in 255 aa overlap:

```
orf51a.pep  MQEIMQSIVFVAAAILHGITGMGFPMLGTTALAFIMPLSKVVALVALPSLLMSLLVLCSN
            ||||||||||||||||||||||||||||||||||||||||||||||||||||||||||||
orf51-1     MQEIMQSIVFVAAAILHGITGMGFPMLGTTALAFIMPLSKVVALVALPSLLMSLLVLCSN orf51a.pep  NKKGFWQEIVYYLKTYKLLAIGSVVGSILGVKLLLILPVSWLLLLMAIITLYYSVNGILN
            ||||||||||||||||||||||||||||||||||||||||||||||||||||||||||||
```

```
orf51-1     NKKGFWQEIVYYLKTYKLLAIGSVVGSILGVKLLLILPVSWLLLLMAIITLYYSVNGILN orf51a.pep  VCAKAKNIQVVANNKNMVLFGFLAGIIGGSTNAMSPILLIFLLSETENKNRIAKSSNLCY
            ||||||||||||||||||||||||||||||||||||||||||||||||||||:||||||
orf51-1     VCAKAKNIQVVANNKNMVLFGFLAGIIGGSTNAMSPILLIFLLSETENKNRIVKSSNLCY orf51a.pep  LLAKIVQIYMLRDQYWLLNKSEYGLIFLLSVLSVIGLYVGIRLRTKISPNFFKMLIFIVL
            ||||||||||||||||||||||||||||||||||||||||||||||||||||||||||||
orf51-1     LLAKIVQIYMLRDQYWLLNKSEYGLIFLLSVLSVIGLYVGIRLRTKISPNFFKMLIFIVL ort51a.pep  LVLALKIGYSGLIKLX
            ||||||||:|||||||
ort51-1     LVLALKIGHSGLIKLX
```

The complete length ORF51 a nucleotide sequence <SEQ ID 77> is:

```
  1    ATGCAAGAAA TAATGCAATC TATCGTTTTT GTTGCTGCCG CAATACTGCA
 51    CGGAATTACA GGCATGGGAT TTCCGATGCT CGGTACAACC GCATTGGCTT
101    TTATCATGCC ATTGTCTAAG GTTGTTGCCT TGGTGGCATT ACCAAGCCTG
151    TTAATGAGCT TGTTGGTTCT ATGCAGCAAT AACAAAAAGG GTTTTTGGCA
201    AGAGATTGTT TATTATTTAA AAACCTATAA ATTGCTTGCT ATCGGCAGCG
251    TCGTTGGCAG CATTTTGGGG GTGAAGTTGC TTTTGATACT TCCAGTGTCT
301    TGGCTGCTTT TACTGATGGC AATCATTACA TTGTATTATT CTGTCAATGG
351    TATTTTAAAT GTATGTGCAA AAGCAAAAAA TATTCAAGTA GTTGCCAATA
401    ATAAGAATAT GGTTCTTTTT GGGTTTTTGG GAGGCATCAT CGGCGGTTCA
451    ACCAATGCCA TGTCTCCCAT ATTGTTAATA TTTTTGCTTA GCGAAACAGA
501    GAATAAAAAT CGTATCGCAA AATCAAGCAA TCTATGCTAT CTTTTGGCAA
551    AAATTGTTCA AATATATATG CTAAGAGACC AGTATTGGTT ATTAAATAAG
601    AGTGAATACG GTTTAATATT TTTACTGTCC GTATTGTCTG TTATTGGATT
651    GTATGTTGGA ATTCGGTTAA GGACTAAGAT TAGCCCAAAT TTTTTTAAAA
701    TGTTAATTTT TATTGTTTTA TTGGTATTGG CTCTGAAAAT CGGGTATTCA
751    GGTTTAATCA AACTTTAA
```

This encodes a protein having amino acid sequence <SEQ ID 78>:

```
  1    MQEIMQSIVF VAAAILHGIT GMGFPMLGTT ALAFIMPLSK VVALVALPSL
 51    LMSLLVLCSN NKKGFWQEIV YYLKTYKLLA IGSVVCSILG VKLLLILPVS
101    WLLLLMAIIT LYYSVNGILN VCAKAKNIQV VANNKNMVLF GFLAGIIGGS
151    TNAMSPILLI FLLSETENKN RIAKSSNLCY LLAKIVQIYM LRDQYWLLNK
201    SEYGLIFLLS VLSVIGLYVG IRLRTKISPN FFKMLIFIVLLVLALKIGYS
251    GLIKL*
```

Based on this analysis, it is predicted that this protein from *N.meningitidis*, and its epitopes, could be useful antigens for vaccines or diagnostics.

Example 18

The following partial DNA sequence was identified in *N.meningitidis* <SEQ ID 79>

```
  1    ATGAGACATA TGAAAATACA AAATTATTTA CTAGTATTTA TAGTTTTACA
 51    TATAGCCTTG ATAGTAATTA ATATAGTGTT TGGTTATTTT GTTTTTCTAT
101    TTGATTTTTT TGCGTTTTTG TTTTTTGCAA ACGTCTTTCT TGCTGTAAAT
151    TTATTATTTT TAGAAAAAAA CATAAAAAAC AAATTATTGT TTTTATTGCC
201    GATTTCTATT ATTATATGGA TGGTAATTCA TATTAGTATG ATAAATATAA
251    AATTTTATAA ATTTGAGCAT CAAATAAAGG AACAAAATAT ATCCTCGATT
301    ACTGGGGTGA TAAAACCACA TGATAGTTAT AATTATGTTT ATGACTCAAA
351    AAACACCTTA TATTGATGTA GTTGCATCTG ATGTTAAAAA TAAATCCATA
401    AAACACCTTA TATTGATGTA GTTGCATCTG ATGTTAAAAA TAAATCCATA
451    AGATTAAGCT TGGTTTGTGG TATTCATTCA TATGCTCCAT GTGCCAATTT
501    TATAAAATTT GTCAGG..
```

This corresponds to the amino acid sequence <SEQ ID 80; ORF82>:

```
  1    MRHMKIQNYL LVFIVLHIAL IVINIVFGYF VFLFDFFAFL FFANVFLAVN
 51    LLFLEKNIKN KLLFLLPISI IIWMVIHISM INIKFYKFEH QIKEQNISSI
101    TGVIKPHDSY NYVYDSNGYA KLKDNHRYGR VIRETPYIDV VASDVKNKSI
151    RLSLVCGIHS YAPCANFIKF VR..
```

Further work revealed the complete nucleotide sequence <SEQ ID 81>:

```
  1    ATGAGACATA TGAAAAATAA AAATTATTTA CTAGTATTTA TAGTTTTACA
 51    TATAGCCTTG ATAGTAATTA ATATAGTGTT TGGTTATTTT GTTTTTCTAT
101    TTGATTTTTT TGCGTTTTTG TTTTTTGCAA ACGTCTTTCT TGCTGTAAAT
151    TTATTATTTT TAGAAAAAAA CATAAAAAAC AAATTATTGT TTTTATTGCC
201    GATTTCTATT ATTATATGGA TGGTAATTCA TATTAGTATG ATAAATATAA
251    AATTTTATAA ATTTGAGCAT CAAATAAAGG AACAAAATAT ATCCTCGATT
301    ACTGGGGTGA TAAAACCACA TGATAGTTAT AATTATGTTT ATGACTCAAA
351    TGGATATGCT AAATTAAAAG ATAATCATAG ATATGGTAGG GTAATTAGAG
401    AAACACCTTA TATTGATGTA GTTGCATCTG ATGTTAAAAA TAAATCCATA
451    AGATTAAGCT TGGTTTGTGG TATTCATTCA TATGCTCCAT GTGCCAATTT
501    TATAAAATTT GCAAAAAAAC CTGTTAAAAT TTATTTTTAT AATCAACCTC
551    AAGGAGATTT TATAGATAAT GTAATATTTG AAATTGGTGA TGGAAACAAA
601    AGTTTGTACT TGTTAGATAA GTATAAAACA TTTTTTCTTA TTGAAAACAG
651    TGTTTGTATC GTATTAATTA TTTTATATTT AAAATTTAAT TTGCTTTTAT
701    ATAGGACTTA CTTCAATGAG TTGGAATAG
```

This corresponds to the amino acid sequence <SEQ ID 82; ORF82-1>:

```
  1    MRHMKNKNYL LVFIVLHIAL IVINIVFGYF VFLFDFFAFL FFANVFLAVN

51    LLFLEKNIKN KLLFLLPISI IIWMVIHISM INIKFYKFEH QIKEQNISSI

101    TGVIKPHDSY NYVYDSNGYA KLKDNHRYGR VIRETPYIDV VASDVKNKSI

151    RLSLVCGIHS YAPCANFIKF AKKPVKIYFY NQPQGDFIDN VIFEINDGNK

201    SLYLLDKYKT FFLIENSVCI VLIILYLKFN LLLYRTYFNE LE*
```

Computer analysis of this amino acid sequence reveals a predicted leader peptide.

A corresponding ORF from strain A of *N.meningitidis* was also identified:

Homology With a Predicted ORF From *N.meningitidis* (Strain A)

ORF82 (SEQ ID NO:80) shows 97.1% identity over a 172aa overlap with an ORF (ORF82a (SEQ ID NO:195)) from strain A of *N.meningitidis*:

```
                    10        20        30        40        50        60
orf82.pep  MRHMKIQNYLLVFIVLHIALIVINIVFGYFVFLFDFFAFLFFANVFLAVNLLFLEKNIKN
           |||||:||||||||||||:|||||||||||||||||||||||||||||||||||||||||
orf82a     MRHMKNKNYLLVFIVLHITLIVINIVFGYFVFLFDFFAFLFFANVFLAVNLLFLEKNIKN
                    10        20        30        40        50        60

70        80        90       100       110       120
orf82.pep  KLLFLLPISIIWMVIHISMINIKFYKFEHQIKEQNISSITGVIKPHDSYNYVYDSNGYA
           ||||||||||||||||||||||||||||||||||||||||||||||||||||||||||||
orf82a     KLLFLLPISIIWMVIHISMINIKFYKFEHQIKEQNISSITGVIKPHDSYNYVYDSNGYA
                    70        80        90       100       110       120

130       140       150       160       170
orf82.pep  KLKDNHRYGRVIRETPYIDVVASDVKNKSIRLSLVCGIHSYAPCANFIKFVR
           |||||||||||||||||||||||||||||||||||||||||||||||::
orf82a     KLKDNHRYGRVIRETPYIDVVASDVKNKSIRLSLVCGIHSYAPCANFIKFAKKPVKIYFY
                   130       140       150       160       170       180
```

ORF82a (SEQ ID NO:84) and ORF82-1 (SEQ ID NO:82) show 99.2% identity in 242 aa overlap:

```
orf82a.pep  MRHMKNKNYLLVFIVLHITLIVINIVFGYFVFLFDFFAFLFFANVFLAVNLLFLEKNIKN
            ||||||||||||||||||:|||||||||||||||||||||||||||||||||||||||||
orf82-1     MRHMKNKNYLLVFIVLHIALIVINIVFGYFVFLFDFFAFLFFANVFLAVNLLFLEKNIKN orf82a.pep  KLLFLLPISIIWMVIHISMINIKFYKFEHQIKEQNISSITGVIKPHDSYNYVYDSNGYA
            ||||||||||||||||||||||||||||||||||||||||||||||||||||||||||||
orf82-1     KLLFLLPISIIWMVIHISMINIKFYKFEHQIKEQNISSITGVIKPHDSYNYVYDSNGYA orf82a.pep  KLKDNHRYGRVIRETPYIDVVASDVKNKSIRLSLVCGIHSYAPCANFIKFAKKPVKIYFY
            ||||||||||||||||||||||||||||||||||||||||||||||||||||||||||||
orf82-1     KLKDNHRYGRVIRETPYIDVVASDVKNKSIRLSLVCGIHSYAPCANFIKFAKKPVKIYFY orf82a.pep  NQPQGDFIDNVIFEINDGKKSLYLLDKYKTFFLIENSVCIVLIILYLKFNLLLYRTYFNE
            |||||||||||||||||||:||||||||||||||||||||||||||||||||||||||||
orf82-1     NQPQGDFIDNVIFEINDGNKSLYLLDKYKTFFLIENSVCIVLIILYLKFNLLLYRTYFNE orf82a.pep  LEX
            |||
orf82-1     LEX
```

The complere length ORF82a nucleotide sequence <SEQ ID 83> is:

```
  1    ATGAGACATA TGAAAAATAA AAATTATTTA CTAGTATTTA TAGTTTTACA

51    TATAACCTTG ATAGTAATTA ATATAGTGTT TGGTTATTTT GTTTTTCTAT
```

-continued

```
101    TTGATTTTTT TGCGTTTTTG TTTTTTGCAA ACGTCTTTCT TGCTGTAAAT
151    TTATTATTTT TAGAAAAAAA CATAAAAAAC AAATTATTGT TTTTATTGCC
201    GATTTCTATT ATTATATGGA TGGTAATTCA TATTAGTATG ATAAATATAA
251    AATTTTATAA ATTTGAGCAT CAAATAAAGG AACAAAATAT ATCCTCGATT
301    ACTGGGGTGA TAAAACCACA TGATAGTTAT AATTATGTTT ATGACTGAAA
351    TGGATATGCT AAATTAAAAG ATAATCATAG ATATGGTAGG GTAATTAGAG
401    AAACACCTTA TATTGATGTA GTTGCATCTG ATGTTAAAAA TAAATCCATA
451    AGATTAAGCT TGGTTTGTGG TATTCATTCA TATGCTCCAT GTGCCAATTT
501    TATAAAATTT GCAAAAAAAC CTGTTAAAAT TTATTTTTAT AATCAACCTC
551    AAGGAGATTT TATAGATAAT GTAATATTTG AAATTAATGA TGGAAAAAAA
601    AGTTTGTACT TGTTAGATAA GTATAAAACA TTTTTTCTTA TTGAAAACAG
651    TGTTTGTATC GTATTAATTA TTTTATATTT AAAATTTAAT TTGCTTTTAT
701    ATAGGACTTA CTTCAATGAG TTGGAATAG
```

This encodes a protein having amino acid sequence <SEQ ID 84>:

```
1      MRHMKNKNYL LVFIVLHITL IVINIVFGYF VFLFDFFAFL FFANVFLAVN
51     LLFLEKNIKN KLLFLLPISI IIWMVIHISM INIKFYKFEH QIKEQNISSI
101    TGVIKPHDSY NYVYDSNGYA KLKDNHRYGR VIRETPYIDV VASDVKNKSI
151    RLSLVCGIHS YAPCANFIKF AKKPVKIYFY NQPQGDFIDN VIFElNDGKK
201    SLYLLDKYKT FFLIENSVCI VLIILYLKFN LLLYRTYFNE LE*
```

Based on this analysis, it is predicted that this protein from *N.meningitidis*, and its epitopes, could be useful antigens for vaccines or diagnostics.

Example 19

The following partial DNA sequence was identified in *N.meningitidis* <SEQ ID 85>

```
1      ACCCCCAACA GCGTGACCGT CTTGCCGTCT TTCGGCGGAT TCGGGCGTAC
51     CGGCGCGACC ATCAATGCAG CAGGCGGGGT CGGCATGACT GCCTTTTCGA
101    CAACCTTAAT TTCCGTAGCC GAGGGCGCGG TTGTAGAGCT GCAGGCCGTG
151    AGAGCCAAAG CCGTCAATGC AACCGCCGCT TGCATTTTTA CGGTCTTGAG
261    TAAGGACATT TTCGATTTCC TTTTTATTTT CCGTTTTCAG ACGGCTGACT
251    TCCGCCTGTA TTTTCGCCAA AGCCATGCCG ACAGCGTGCG CCTTGACTTC
301    ATATTTAAAA GCTTCCGCGC GTGCCAGTTC CAGTTCGCGC GCATAGTTTT
351    GAGCCGACAA CAGCAGGGCT TGCGCCTTGT CGCGCTCCAT CTTGTCGATG
401    ACCGCCTGCA GCTTCGCAAA TGCCGACTTG TAGCCTTGAT GGTGCGACAC
451    AGCCAAGCCC GTGCCGACAA GCGCGATAAT GGCAATCGGT TGCCAGTAAT
501    TCGCCAGCAG TTTCACGAGA TTCATTCTCG ACCTCCTGAC GCTTCACGCT
551    GA
```

This corresponds to the amino acid sequence <SEQ ID 86; ORF124>:

```
  1    ..TPNSVTVLPS FGGFGRTGAT INAAGGVGMT AFSTTLISVA EGAVVELQAV

51    RAKAVNATAA CIFTVLSKDI FDFLFIFRFQ TADFRLYFRQ SHADSVRLDF

101    IFKSFRACQF QFARIVLSRQ QQGLRLVALH LVDDRLQLRK CRLVALMVRH

151    SQARADKRDN GNRLPVIRQQ FHEIHSRPPD ASR*
```

Computer analysis of this amino acid sequence predicts a transmembrane domain.

Further work revealed the complete nucleotide sequence <SEQ ID 87>:

```
  1    ATGACTGCCT TTTCGACAAC CTTAATTTCC GTAGCCGAGG GCGCGGTTGT

51    AGAGCTGCAG GCCGTGAGAG CCAAAGCCGT CAATGCAACC GCCGCTTGCA

161    TTTTTACGGT CTTGAGTAAG GACATTTTCG ATTTCCTTTT TATTTTCCGT

151    TTTCAGACGG CTGACTTCCG CCTGTTTTTT CGCCAAAGCC ATGCCGACAG

201    CGTGCGCCTT GACTTCATAT TTTTTAGCTT CCGCGCGTGC CAGTTCCAGT

251    TCGCGCGCAT AGTTTTGAGC CGACAACAGC AGGGCTTGCG CCTTGTCGCG

301    CTCCATCTTG TCGATGACCG CCTGCTGCTT CGCAAATGCC GACTTGTAGC

351    CTTGATGGTG CGACACAGCC AAGCCCGTGC CGACAAGCGC GATAATGGCA

401    ATCGGTTGCC AGTTATTCGC CAGCAGTTTC ACGAGATTCA TTCTCGACCT

451    CCTGACGCTT CACGCTGA
```

This corresponds to the amino acid sequence <SEQ ID 88; ORF124-1>:

```
  1    MTAFSTTLIS VAEGAVVELQ AVRAKAVNAT AACIFTVLSK DIFDFLFIFR

51    FQTADFRLFF RQSHADSVRL DFIFFSFRAC QFQFARIVLS RQQQGLRLVA

101    LHLVDDRLLL RKCRLVALMV RHSQARADKR DNGNRLPVIR QQFHEIHSRP

151    PDASR*
```

A corresponding ORF from strain A of *N.meningitidis* was also identified:

Homology With a Predicted ORF From *N.meningitidis* (Strain A)

ORF124 (SEQ ID NO:86) shows 87.5% identity over a 152aa overlap with an ORF (ORFI24a (SEQ ID NO:90)) from strain A of *N.meningitidis*:

```
                    10         20         30         40         50         60
orf124.pep  TPNSVTVLPSFGGFGRTGATINAAGGVGMTAFSTTLISVAEGAVVELQAVRAKAVNATAA
                                         ||||||||||||:||||| |||||:|||
orf124a                                  MTAFSTTLISVAEGALVELQAVMAKAVNTTAA
                                                  10         20         30

70         80         90        100        110        120
orf124.pep  CIFTVLSKDIFDFLFIFRFQTADFRLYFRQSHADSVRLDFIFKSFRACQFQFARIVLSRQ
            |||||||||||||||||||||||||:||||||:||||||| |||: |||| :|||||
orf124a     CIFTVLSKDIFDFLFIFRFQTADFRLFFRQSHADGVRLDFIFFSFRTRLFQFAGVVLSRQ
                    40         50         60         70         80         90
```

```
                -continued
              130       140       150       160       170       180
orf124.pep  QQGLRLVALHLVDDRLQLRKCRLVALMVRHSQARADKRDNGNRLPVIRQQFHEIHSRPPD
            ||||||||||:::|||  |||  ||||||||| |:||||||:||||||||||||||||||
orf124a     QQGLRLVALHFLNDRLLLRKSRLVALMVRHRQTRADKRDDGNRLPVIRQQFHEIHSRPPD
              100       110       120       130       140       150 orf124.pep  ASRX
            :
orf124a     VX
```

ORF124a (SEQ ID NO:90) and ORF124-1 (SEQ ID NO:88) show 89.5% identity in 152 aa overlap:

```
orf124-1.pep  MTAFSTTLISVAEGAVVELQAVRAKAVNATAACIFTVLSKDIFDFLFIFRFQTADFRLFF
              ||||||||||||||:||||||  |||||:|||||||||||||||||||||||||||||||
orf124a       MTAFSTTLISVAEGALVELQAVMAKAVNTTAACIFTVLSKDIFDFLFIFRFQTADFRLFF orf124-1.pep  RQSHADSVRLDFIFFSFRACQFQFARIVLSRQQQGLRLVALHLVDDRLLLRKCRLVALMV
              ||||||:|||||||||||||:   ||||  :|||||||||||||:::|||||| |||||||
orf124a       RQSHADGVRLDFIFFSFRTRLFQFAGVVLSRQQQGLRLVALHFLNDRLLLRKSRLVALMV orf124-1.pep  RHSQARADKRDNGNRLPVIRQQFHEIHSRPPDASRX
              || |:||||||:|||||||||||||||||||||||:
orf124a       RHRQTRADKRDDGNRLPVIRQQFHEIHSRPPDVX
```

The complete length ORF124a nucleotide sequence <SEQ ID 89> is:

```
  1    ATGACCGCCT TTTCGACAAC CTTAATTTCC GTAGCCGAGG GCGCGCTTGT
 51    AGAGCTGCAA GCCGTGATGG CCAAAGCCGT CAATACAACC GCCGCCTGCA
101    TTTTTACGGT CTTGAGTAAG GACATTTTCG ATTTCCTTTT TATTTTCCGT
151    TTTCAGACGG CTGACTTCCG CCTGTTTTTT CGCCAAAGCC ATGCCGACGG
201    CGTGCGCCTT GACTTCATAT TTTTTAGCTT CCGCACGCGC CTGTTCCAGT
251    TCGCGGGCGT AGTTTTGAGC CGACAACAGC AGGGCTTGCG CCTTGTCGCG
301    CTTCATTTTC TCAATGACCG CCTGCTGCTT CGCAAAAGCC GACTTGTAGC
351    CTTGATGGTG CGACACCGCC AAACCCGTGC CGACAAGCGC GATGATGGCA
401    ATCGGTTGCC AGTTATTCGC CAGCAGTTTC ACGAGATTCA TTCTCGACCT
451    CCTGACGTTT GA
PS
```

This encodes a protein having amino acid sequence <SEQ ID 90>:

```
  1    MTAFSTTLIS VAEGALVELQ AVMAKAVNTT AACIFTVLSK DIFDFLFIFR
 51    FQTADFRLFF RQSHADGVRL DFIFFSFRTR LFQFAGVVLS RQQQGLRLVA
101    LHFLNDRLLL RKSRLVALMV RHRQTRADKR DDGNRLPVIR QQFHEIHSRP
151    PDV*
```

Figure 7:
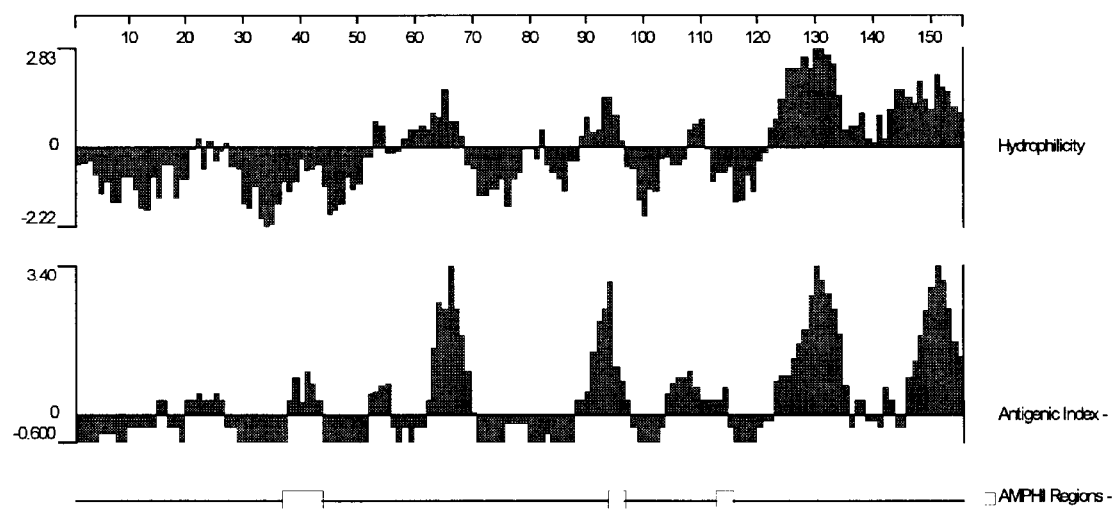
FIG. 7 shows a hydrophilicity plot (upper), an antigenic index plot (middle), and an AMPHI analysis (lower) for ORF 124.

ORF124-1 was amplified as described above. FIG. 7 shows plots of hydrophilicity, antigenic index, and AMPHI regions for ORF 124-1.

Based on this analysis, it is predicted that this protein from *N.meningitidis*, and its epitopes, could be useful antigens for vaccines or diagnostics.

Example 20

Table III lists several Neisseria strains which were used to assess the conservation of the sequence of ORF 40 among different strains.

TABLE III

List of Neisseria Strains Used for Gene Variability Study of ORF 40

| Identification number | Strains | Source/reference |
|---|---|---|
| | Group B | |
| zn02_1 | BZ198 | R. Moxon/Seiler et al., 1996 |
| zn03_1 | NG3/88 | R. Moxon/Seiler et al., 1996 |
| zn04_1 | 297-0 | R. Moxon/Seiler et al., 1996 |
| zn06_1 | BZ147 | R. Moxon/Seiler et al., 1996 |
| zn07_1 | BZ169 | R. Moxon/Seiler et al., 1996 |
| zn08_1 | 528 | R. Moxon/Seiler et al., 1996 |
| zn10_1 | BZ133 | R. Moxon/Seiler et al., 1996 |
| zn11_1ass | NGE31 | R. Moxon/Seiler et al., 1996 |
| zn14_1 | NGH38 | R. Moxon/Seiler et al., 1996 |
| zn16_1 | NGH15 | R. Moxon/Seiler et al., 1996 |
| zn18_1 | BZ232 | R. Moxon/Seiler et al., 1996 |
| zn19_1 | BZ83 | R. Moxon/Seiler et al., 1996 |
| zn20_1 | 44/76 | R. Moxon/Seiler et al., 1996 |
| zn21_1 | MC58 | R. Moxon |
| | Group A | |
| zn22_1 | 205900 | R. Moxon |
| zn23_1 | F6124 | R. Moxon |
| z2491_1 | Z2491 | R. Moxon/Maiden et al., 1998 |
| | Group C | |
| zn24_1 | 90/18311 | R. Moxon |
| zn25_1ass | 93/4286 | R. Moxon |
| | Others | |
| zn28_1ass | 860800 (group Y) | R. Moxon/Maiden et al., 1998 |
| zn29_1ass | E32 (group Z) | R. Moxon/Maiden et al., 1998 |

References:
Seiler A. et al., Mol. Microbiol., 1996, 19(4): 841–856.
Maiden et al., Proc. Natl. Acad. Sci. USA, 1998, 95: 3140–3145.

The amino acid sequences for each listed strain are as follows:

```
>Z2491 <SEQ ID 91>
MNKIYRIIWNSALNAWVAVSELTRNHTKRASATVKTAVLATLLFATVQANATDEDEEEEL
ESVQRSVVGSIQASMEGSGELETISLSMTNDSKEFVDPYIVVTLKAGDNLKIKQNTNENT
NASSFTYSLKKDLTGLINVETEKLSFGANGKKVNIISDTKGLNFAKETAGTNGDTTVHLN
GIGSTLTDTLAGSSASHVDAGNQSTHYTRAASIKDVLNAGWNIKGVKTGSTTGQSENVDF
VRTYDTVEFLSADTKTTTVNVESKDNGKRTEVKIGAKTSVIKEKDGKLVTGKGKGENGSS
TDEGEGLVTAKEVIDAVNKAGWRMKTTTANGQTGQADKFETVTSGTNVTFASGKGTTATV
SKDDQGNITVMYDVNVGDALNVNQLQNSGWNLDSKAVAGSSGKVISGNVSPSKGKMDETV
NINAGNNIEISRNGKNIDIATSMAPQFSSVSLGAGADAPTLSVDDEGALNVGSKDANKPV
RITNVAPGVKEGDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVGYQW*
>ZN01_1 <SEQ ID 92>
MNKIYRIIWNSALNAWVVVSELTRNHTKRASATVATAVLATLLFATVQANATDDDDLYLE
PVQRTAVVLSFRSDKEGTGEKEGTEDSNWAVYFDEKRVLKAGAITLKAGDNLKIKQNTNE
NTNDSSFRYSLKKDLTDLTSVETEKLSFGANGNKVNITSDTKGLNFAKETAGTNGDPTVH
LNGIGSTLTDTLLNTGATTNVTNDNVTDDEKKRAASVKDVLNAGWNIKGVKPGTTASDNV
DFVRTYDTVEFLSADTKTTTVNVESKDNGKKTEVKIGAKTSVIKEKDGKLVTGKGKDENG
SSTDEGEGLVTAKEVIDAVNKAGWRMKTTTANGQTGQADKFETVTSGTNVTFASGKGTTA
TVSKDDQGNITVKYDVNVGDALNVNQLQNSGWNLDSKAVAGSSGKVISGNVSPSKGKMDE
TVNINAGNNIEITRNGKNIDIATSMAPQFSSVSLGAGADAPTLSVDDEGALNVGSKDTNK
```

-continued

PVRITNVAPGVKEGDVTNVAQLKGVAQNLNNRIDNVDGNARAGIAQAIATAGLVQAYLPG

KSMMAIGGDTYRGEAGYAIGYSSISDGGNWIIKGTASGNSRGHFGASASVGYQW*

>ZN03_1 <SEQ ID 93>

MNKIYRIIWNSALNAWVAVSELTRNHTKRASATVATAVLATLLFATVQASTTDDDDLYLE

PVQRTAPVLSFHADSEGTGEKEVTEDSNWGVYFDKKGVLTAGTITLKAGDNLKIKQNTDE

NTNASSFTYSLKKDLTDLTSVETEKLSFGANGKKVNITSDTKGLNFAKETAGTNGDTTVH

LNGIGSTLTDTLLNTGATTNVTNDNVTDDEKKRAASVKDVLNAGWNIKGVKPGTTASDNV

DFVRTYDTVEFLSADTKTTTVNVESKDNGKKTEVKIGAKTSVIKEKDGKLVTGKDKGENG

SSTDEGEGLVTAKEVIDAVNKAGWRMKTTTANGQTGQADKFETVTSGTKVTFASGNGTTA

TVSKDDQGNITVKYDVNVGDALNVNQLQNSGWNLDSKAVAGSSGKVISGNVSPSKGKMDE

TVNINAGNNIEITRNGKNIDIATSMTPQFSSVSLGAGADAPTLSVDDEGALNVGSKDANK

PVRITNVAPGVKEGDVTNVAWLKGVAQNLNNHIDNVDGNARAGIAQAIATAGLVQAYLPG

KSMMAIGGGTYRGEAGYAIGYSSISDGGNWIIKGTASGNSRGHFGASASVGYQW*

>ZN04_1 <SEQ ID 94>

MNKIYRIIWNSALNAWVVVSELTRNHTKRASATVATAVLATLLFATVQANATDDDDLYLE

PVQRTAVVLSFRSDKEGTGEKEGTEDSNWAVYFDEKRVLKAGAITLKAGDNLKIKQNTNE

NTNDSSFRYSLKKDLTDLTSVETEKLSFGANGNKVNITSDTKGLNFAKETAGTNGDPTVH

LNGIGSTLTDTLLNTGATTNVTNDNVTDDEKKRAASVKDVLNAGWNIKGVKPGTTASDNV

DFVRTYDTVEFLSADTKTTTVNVESKDNGKKTEVKIGAKTSVIKEKDGKLVTGKGKDENG

SSTDEGEGLVTAKEVIDAVNKAGWRMKTTTANGQTGQADKFETVTSGTNVTFASGKGTTA

TVSKDDQGNITVKYDVNVGDALNVNQLQNSGWNLDSKAVAGSSGKVISGNVSPSKGKMDE

TVNINAGNNIEITRNGKNIDIATSMAPQFSSVSLGAGADAPTLSVDDEGALNVGSKDTNK

PVRITNVAPGVKEGDVTNVAWLKGVAQNLNNRIDNVDGNARAGIAQAIATAGLVQAYLPG

KSMMAIGGDTYRGEAGYAIGYSSISDGGNWIIKGTASGNSRGHFGASASVGYQW*

>ZN06_1

MNKIYRIIWNSALNAWVVVSELTRNHTKRASATVETAVLATLLFATVQASANNEEQEEDL

TLDPVQRTAVLIVNSDKEGTGEKEKVEENSDWAVYGNEKGVLTAREITLKAGDNLKIKQ

NGTNFTYSLKKDLTDLTSVGTEKLSFSANGNKVNITSDTKGLNFAKETAGTNGDTTVHLN

GIGSTLTDTLLNTGATTNVTNDNVTDDEKKRAASVKDVLNAGWNIKGVKPGTTASDNVDF

VRTYDTVEFLSADTKTTTVNVESKDNGKKTEVKIGAKTSVIKEKDGKLVTGKDKGENGSS

TDEGEGLVTAKEVIDAVNKAGWRMKTTTANGQTGQADKFETVTSGTNVTFASGKGTTATV

SKDDQGNITVMYDVNVGDALNVNQLQNSGWNLDSKAVAGSSGKVISGNVSPSKGKMDETV

NINAGNNIEITRNGKNIDIATSMTPQFSSVSLGAGADAPTLSVDGDALNVGSKKDNKPVR

ITNVAPGVKEGDVTNVAWLKGVAQNLNNRIDNVDGNARAGIAQAIATAGLVQAYLPGKSM

MAIGGGTYRGEAGYAIGYSSISDGGNWIIKGTASGNSRGHFGASASVGYQW*

>XN07_1 <SEQ ID 96>

MNKIYRIIWNSALNAWVVVSELTRNHTKRASATVKTAVLATLLFATVQASANNEEQEEDL

YLDPVQRTAVLIVNSDKEGTGEKEKVEENSDWAVYFNEKGVLTAREITLKAGDNLKIKQ

NGTNFTYSLKKDLTDLTSVGTEKLSFSANGNKVNITSDTKGLNFAKETAGTNGDTTVHLN

GIGSTLTDTLLNTGATTNVTNDNVTDDEKKRAASVKDVLNAGWNIKGVKPGTTASDNVDF

-continued

VRTYDTVEFLSADTKTTTVNVESKDNGKKTEVKIGAKTSVIKEKDGKLVTGKDKGENGSS
TDEGEGLVTAKEVIDAVNKAGWRMKTTTANGQTGQADKGETVTSGTNVTFASGKGTTATV
SKDDQGNITVMYDVNVGDALNVNQLQNSGWNLDSKAVAGSSGKVISGNVSPSKGKMDETV
NINAGNNIEITRNGKNIDIATSMTPQFSSVSLGAGADAPTLSVDGDALNVGSKKDNKPVR
ITNVAPGVKEGDVTNVAWLKGVAQNLNNRIDNVDGNARAGIAQAIATAGLVQAYLPGKSM
MAIGGGTYRGEAGYAIGYSSISDGGNWIIKGTASGNSRGHFGASASVGYQW*

>ZN08_1 <SEQ ID 97>

MNKIYRIIWNSALNAWVVVSELTRNHTKRASATVETAVLATLLFATVQANATDTDEDDEL
EPVVRSALVLQFMIDKEGNGEIESTGDIGWSIYYDDHNTLHGATVTLKAGDNLKIKQNTD
ENTNASSFTYSLKKDLTDLTSVGTEELSFGANGNKVNITSDTKGLNFAKKTAGTNGDTTV
HLNGIGSTLTDTLAGSSASHVDAGNQSTHYTRAASIKDVLNAGWNIKGVKTGSTTGQSEN
VDFVRTYDTVEFLSADTKTTTVNVESKDNGKRTEVKIGAKTSVIKEKDGKLVTGKGKGEN
GSSTDEGEGLVTAKEVIDAVNKAGWRMKTTTANGQTGQADKFETVTSGTNVTGASGKGTT
ATVSKDDQGNITVKYDVNVGDALNVNQLQNSGWNLDSKAVAGSSGKVISGNVSPSKGKMD
ETVNINAGNNIEITRNGKNIDIATSMTPQFSSVSLGAGADAPTLSVDDEGALNVGSKDAN
KPVRITNVAPGVKEGDVTNVAQLKGVAWNLNNHIDNVDGNARAGIAQAIATAGLVQAYLP
GKSMMAIGGGTYRGEAGYAIGYSSISDGGNWIIKGTASGNSRGHFGASASVGYQW*

>ZN10_1
MNKIYRIIWNSALNAWVAVSELTRNKTKRASATVKTAVLATLLFATVQANATDEDEEEEL
ESVQRSVVGSIQASMEGSGELETISLSMTNDSKEFVDPYIVVTLKAGDNLKIKQNTNENT
NASSFTYSLKKDLTGLINVETEKLSFGANGKKVNIISDTKGLNFAKETAGTNGDTTVHLN
GIGSTLTDTLAGSSASHVDAGNQSTHYTRAASIKDVLNAGWNIKGVKTGSTTGQSENVDF
VRTYDTVEFLSADTKTTTVNVESKDNGKRTEVKIGAKTSVIKEKDGKLVTGKGKGENGSS
TDEGEGLVTAKEVIDAVNKAGWRMKTTTANGQTGQADKFETVTSGTNVTFASGKGTTATV
SKDDQGNITVMYDVNVGDALNVNQLQNSGWNLDSKAVAGSSGKVISGNVSPSKGKMDETV
NINAGNNIEISRNGKNIDIATSMAPQFSSVSLGAGADAPTLSVDDEGALNVGSKDANKPV
RITNVAPGVKEGDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVGYQW*

>XN11_ASS <SEQ ID 99>

MNKIYRIIWNSALNAWVVVSELTRNHTKRASATVATAVLATLLFATVQASTTDDDDLYLE
PVQRTAPVLSFHADSEGTGEKEVTEDSNWGVYFDKKGVLTAGTITLKAGDNLKIKQNTDE
NTNASSFTYSLKKDLTDLTSVETEKLSFGANGKKVNITSDTKGLNFAKETAGTNGDTTVH
LNGIGSTLTDTLLNTGATTNVTNDNVTDDEKKRAASVKDVLNAGWNIKGVKPGTTASDNV
DFVRTYDTVEFLSADTKTTTVNVESKDNGKKTEVKIGAKTSVIKEKDGKLVTGKDKGENG
SSTDEGEGLVTAKEVIDAVNKAGWRMKTTTANGQTGQADKFETVTSGTKVTFASGNGTTA
TVSKDDQGNITVKYDVNVGDALNVNQLQNSGWNLDSKAVAGSSGKVISGNVSPSKGKMDE
TVNINAGNNIEITRNGKNIDIATSMTPQFSSVSLGAGADAPTLSVDDEGALNVGSKDANK
PVRITNVAPGVKEGDVTNVAWLKGVAQNLNNHIDNVDGNARAGIAQAIATASLVQAYLPG
KSMMAIGGGTYRGEAGYAIGYSSISDGGNWIIKGTASGNSRGHFGASASVGYQW*

>ZN14_1

-continued

```
MNKIYRIIWNSALNAWVAVSELTRNHTKRASATVKTAVLATLLFATVQANATDEDEEEEL
EPVVRSALVLQFMIDKEGNGENESTGNIGWSIYYDNHNTLHGATVTLKAGDNLKIKQNTN
KNTNENTNDSSFTYSLKKDLTDLTSVETEKLSFGANGNKVNITSDTKGLNFAKETAGTNG
DTTVHLNGIGSTLTDTLLNTGATTNVTNDNVTDDKKKRAASVKDVLNAGWNIKGVKPGTT
ASDNVDFVHTYDTVEFLSADTKTTTVNVESKDNGKRTEVKIGAKTSVIKEKDGKLVTGKG
KGENGSSTDEGEGLVTAKEVIDAVNKAGWRMKTTTANGQTGQADKFETVTSGTNVTFASG
KGTTATVSKDDQGNITVKYDVNVGDALNVNQLQNSGWNLDSKAVAGSSGKVISGNVSPSK
GKMDETVNINAGNNIEITRNGKNIDIATSMTPQFSSVSLGAGADAPTLSVDDKGALNVGS
KDANKPVRITNVAPGVKEGDVTNVAQLKGVAQNLNNRIDNVDGNARAGIAQAIATAGLVQ
AYLPGKSMMAIGGGTYRGEAGYAIGYSSISDGGNWIIKGTASGNSRGHFGASASVGYQW*
>SN16_1 <SEQ ID 101>
MNKIYRIIWNSALNAWVVVSELTRNHTKRASATVATAVLATLLFATVQANATDDDDLYLE
PVQRTAVVLSFRSDKEGTGEKEGTEDSNWAVYFDEKRVLKAGAITLKAGDNLKIKQNTNE
NTNENTNDSSFTYSLKKDLTDLTSVETEKLSFGANGNKVNITSDTKGLNFAKETAGTNGD
PTVHLNGIGSTLTDTLLNTGATTNVTNDNVTDDEKKRAASVKDVLNAGWNIKGVKPGTTA
SDNVDFVRTYDTVEFLSADTKTTTVNVESKDNGKKTEVKIGAKTSVIKEKDGKLVTGKGK
DENGSSTDEGEGLVTAKEVIDAVNKAGWRMKTTTANGQTGQADKFETVTSGTKVTFASGN
GTTATVSKDDQGNITVKYDVNVGDALNVNQLQNSGWNLDSKAVAGSSGKVISGNVSPSKG
KMDETVNINAGNNIEITRNGKNIDIATSMTPQFSSVSLGAGADAPTLSVDDEGALNVGSK
DANKPVRITNVAPGVKEGDVTNVAWLKGVAQNLNNRIDNVDGNARAGIAQAIATAGLAQA
YLPGKSMMAIGGGTYRGEAGYAIGYSSISDTGNWVIKGTASGNSRGHFGASASVGTQW*
>SN18_1 <SEQ ID 102>
MNKIYRIIWNSALNAWVAVSELTRNHTKRASATVATAVLATLLFATVQASTTDDDDLYLE
PVQRTAPVLSFHADSEGTGEKEVTEDSNWGVYFDKKGVLTAGTITLKAGDNLKIKQNTDE
NTNASSFTYSLKKDLTDLTSVETEKLSFGANGKKVNITSDTKGLNFAKETAGTNGDTTVH
LNGIGSTLTDTLLNTGATTNVTNDNVTDDEKKRAASVKDVLNAGWNIKGVKPGTTASDNV
DFVRTYDTVEFLSADTKTTTVNVESKDNGKKTEVKIGAKTSVIKEKDGKLVTGKDKGENG
SSTDEGEGLVTAKEVIDAVNKAGWRMKTTTANGQTGQADKFETVTSGTKVTFASGNGTTA
TVSKDDQGNITVKYDVNVGDALNVNQLQNSGWNLDSKAVAGSSGKVISGNVSPSKGKMDE
TVNINAGNNIEITRNSKNIDIATSMTPQFSSVSLGAGADAPTLSVDDEGALNVGSKDANK
PVRITNVAPGVKEGDVTNVAWLKGVAQNLNNHIDNVDGNARAGIAQAIATAGLVQAYLPG
KSMMAIGGGTYRGEAGYAIGYSSISDGGNWIIKGTASGNSRGHGASASVGYQW*
>SN19_1 <SEQ ID 103>
MNKIYRIIWNSALNAWVVVSELTRNHTKRASATVKTAVLATLLFATVQASANNEEQEEDL
YLDPVQRTVAVLIVNSDKEGTGEKEKVEENSDWAVYGNEKGVLTAREITLKAGDNLKIKQ
NGTNFTYSLKKDLTDLTDVGTEKLSFSANGNKVNITSDTKGLNFAKETAGTNGDTTVHLN
GIGSTLTDTLLNTGATTNVTNDNVTDDEKKRAASVKDVLNAGWNIKGVKPGTTASDNVDF
VRTYDTVEFLSADTKTTTVNVESKDNGKKTEVKIGAKTSVIKEKDGKLVTGKDKGENGSS
TDEGEGLVTAKEVIDAVNKAGWRMKTTTANGQTGQADKFETVTSGTNVTFASGKGTTATV
SKDDQGNITVMYDVNVGDALNVNHLQNSGWDLDSKAVAGSSGKVISGNVSPSKGKMDETV
```

-continued

NINAGNNIEITRNGKNIDIATSMTPQFSSVSLGAGADAPTLSVDGDALNVGSKKDNKPVR

ITNVAPGVKEGDVTNVAQLKGVAQNLNNRIDNVDGNARAGIAQAIATAGLVQAYSPGKSM

MAIGGGTYRGEAGYAIGYSSISDGGNWIIKGTASGNSRGHFGASASVGYQW*

>ZN20_1 <SEQ ID NO104>

MNKIYRIIWNSALNAWVVVSELTRNHTKRASATVKTAVLATLLFATVQASANNEEQEEDL

YLDPVQRTVAVLIVNSDKEGTGEKEKVEENSDWAVYGNEKGVLTAREITLKAGDNLKIKQ

NGTNFTYSLKKDLTDLTSVGTEKLSFSANGNKVNITSDTKGLNFAKETAGTNGDTTVHLN

GIGSTLTDTLLNTGATTNVTNDNVTDDEKKRAASVKDVLNAGWNIKGVKPGTTASDNVDF

VRTYDTVEFLSADTKTTTVNVESKDNGKKTEVKIGAKTSVIKEKDGKLVTGKDKGENGSS

TDEGEGLVTAKEVIDAVNKAGWRMKTTTANGQTGQADKFETVTSGTNVTFASGKGTTATV

SKDDQGNITVMYDVNVGDALNVNQLQNSGWNLDSKAVAGSSGKVISGNVSPSKGKMDETV

NINAGNNIEITRNGKNIDIATSMTPQFSSVSLGAGADAPTLSVDGDALNVGSKKDNKPVR

ITNVAPGVKEGDVTNVAQLKGVAQNLNNRIDNVDGNARAGIAQAIATAGLVQAYLPGKSM

MAIGGGTYRGEAGYAIGYSSISDGGNWIIKGTASGNSRGHFGASASVGYQW*

>ZN21_1 <SEQ ID 105>

MNKIYRIIWNSALNAWVVVSELTRNHTKRASATVKTAVLATLLFATVQASANNEEQEEDL

YLDPVQRTVAVLIVNSDKEGTGEKEKVEENSDWAVYFNEKGVLTAREITLKAGDNLKIKQ

NGTNFTYSLKKDLTDLTSVGTEKLSFSANGNKVNITSDTKGLNFAKETAGTNGDTTVHLN

GIGSTLTDTLLNTGATTNVTNDNVTDDEDDRAASVKDVLNAGWNIKGVKPGTTASDNVDF

VRTYDTVEFLSADTKTTTVNVESKDNGKKTEVKIGAKTSVIKEKDGKLVTGKDKGENGSS

TDEGEGLVTAKEVIDAVNKAGWRMKTTTANGQTGQADKFETVTSGTNVTFASGKGTTATV

SKDDQGNITVMYDVNVGDALNVNQLQNSGWNLDSKAVAGSSGKVISGNVSPSKGKMDETV

NINAGNNIEITRNGKNIDIATSMTPQFSSVSLGAGADAPTLSVDGDALNVGSKKDNKPVR

ITNVAPGVKEGDVTNVAQLKGVAQNLNNRIDNVDGNARAGIAQAIATAGLVQAYLPGKSM

MAIGGGTYRGEAGYAIGYSSISDGGNWIIKGTASGNSRGHFGASASVGYQW*

>SN22_1 <SEQ ID 106>

MNKIYRIIWNSALNAWVAVSELTRNHTKRASATVKTAVLATLLFATVQANATDEDEEEEL

ESVQRSVVGSIQASMEGSGELETISLSMTNDSKEFVDPYIVVTLKAGDNLKIKQNTNENT

NASSFTYSLKKDLTGLINVETEKLSFGANGKKVNIISDTKGLNFAKETAGTNGDTTVHLN

GIGSTLTDTLAGSSASHVDAGNQSTHYTRAASIKDVLNAGWNIKGVKTGSTTGQSENVDF

VRTYDTVEFLSADTKTTTVNVESKDNGKRTEVKIGAKTSVIKEKDGKLVTGKGKGENGSS

TDEGEGLVTAKEVIDAVNKAGWRMKTTTANGQTGQADKFETVTSGTNVTFASGKGTTATV

SKDDQGNITVMYDVNVGDALNVNQLQNSGWNLDSKAVAGSSGKVISGNVSPSKGKMDETV

NINAGNNIEISRNGKNIDIATSMAPQFSSVSLGAGADAPTLSVDDEGALNVGSKDANKPV

RITNVAPGVKEGDVTNVAQLKGVAQNLNNRIDNVDGNARAGIAQAIATAGLVQAYLPGKS

MMAIGGGTYRGEAGYAIGYSSISDGGNWIIKGTASGNSRGHFGASASVGYQW*

>ZN23_1 <SEQ ID 107>

MNKIYRIIWNSALNAWVAVSELTRNHTKRASATVKTAVLATLLFATVQANATDEDEEEEL

ESVQRSVVGSIQASMEGSGELETISLSMTNDSKEFVDPYIVVTLKAGDNLKIKQNTNENT

NASSFTYSLKKDLTGLINVETEKLSFGANGKKVNIISDTKGLNFAKETAGTNGDTTVHLN

-continued

GIGSTLTDTLAGSSASHVDAGNQSTHYTRAASIKDVLNAGWNIKGVKTGSTTGQSENVDF
VRTYDTVEFLSADTKTTTVNVESKDNGKRTEVKIGAKTSVIKEKDGKLVTGKGKGENGSS
TDEGEGLVTAKEVIDAVNKAGWRMKTTTANGQTGQADKFETVTSGTNVTFASGKGTTATV
SKDDQGNITVMYDVNVGDALNVNQLQNSGWNLDSKAVAGSSGKVISGNVSPSKGKMDETV
NINAGNNIEISRNGKNIDIATSMAPQFSSVSLGAGADAPTLSVDDEGALNVGSKDANKPV
RITNVAPGVKEGDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVGYQW*

>ZN24_1 <SEQ ID 108>

MNKIYRIIWNSALNAWVVVSELTRNHTKRASATVATAVLATLLSATVQANATDTDEDEEL
ESVVRSALVLQFMIDKEGNGEIESTGDIGWSIYYDDHNTLHGATVTLKAGDNLKIKQSGK
DFTYSLKKELKDLTSVETEKLSFGANGNKVNITSDTKGLNFAKETAGTNGDPTVHLNGIG
STLTDTLAGSSASHVDAGNQSTHYTRAASIKDVLNAGWNIKGVKTGSTTGQSENVDFVRT
YDTVEFLSADTKTTTVNVESKDNGKRTEVKIGAKTSVIKEKDGKLVTGKGKGENGSSTDE
GEGLVTAKEVIDAVNKAGWRMKTTTANGQTGQADKFETVTSGTKVTFASGNGTTATVSKD
DQGNITVKYDVNVGDALNVNQLQNSGWNLDSKAVAGSSGKVISGNVSPSKGKMDETVNIN
AGNNIEITRNGKNIDIATSMTPQFSSVSLGAGADAPTLSVDDEGALNVGSKDANKPVRIT
NVAPGVKEGDVTNVAWLKGVAQNLNNRIDNVDGNARAGIAQAIATAGLAQAYLPGKSMMA
IGGGTYRGEAGYAIGYSSISDTGNWVIKGTASGNSRGHFGTSASVGYQW*

>ZN25_ASS <SEQ ID 109>

MNKIYRIIWNSALNAWVVVSELTRNHTKRASATVATAVLATLLSATVQANATDTDEDEEL
ESVVRSALVLQFMIDKEGNGEIESTGDIGWSIYYDDHNTLHGATVTLKAGDNLKIKQSGK
DFTYSLKKELKDLTSVETEKLSFGANGNKVNITSDTKGLNFAKETAGTNGDPTVHLNGIG
STLTDTLAGSSASHVDAGNQSTHYTRAASIKDVLNAGWNIKGVKTGSTTGQSENVDFVRT
YDTVEFLSADTKTTTVNVESKDNGKRTEVKIGAKTSVIKEKDGKLVTGKGKGENGSSTDE
GEGLVTAKEVIDAVNKAGWRMKTTTANGQTGQADKFETVTSGTKVTFASGNGTTATVSKD
DQGNITVKYDVNVGDALNVNQLQNSGWNLDSKAVAGSSGKVISGNVSPSKGKMDETVNIN
AGNNIEITRNGKNIDIATSMTPQFSSVSLGAGADAPTLSVDDEGALNVGSKDANKPVRIT
NVAPGVKEGDVTNVAQLKGVAQNLNNRIDNVDGNARAGIAQAIATAGLAQAYLPGKSMMA
IGGGTYRGEAGYAIGYSSISDTGNWVIKGTASGNSRGHFGTSASVGYQW*

>ZN28_ASS <SEQ ID 110>

MNKIYRIIWNSALNAWVAVSELTRNHTKRASATVKTAVLATLLFATVQANATDEDEEEEL
ESVQRSVVGSIQASMEGSGELETISLSMTNDSKEFVDPYIVVTLKAGDNLKIKQNTNENT
NASSFTYSLKKDLTGLINVETEKLSFGANGKKVNIISDTKGLNFAKETAGTNGDTTVHLN
GIGSTLTDMLLNTGATTNVTNDNVTDDEKKRAASVKDVLNAGWNIKGVKPGTTASDNVDF
VRTYDTVEFLSADTKTTTVNVESKDNGKKTEVKIGAKTSVIKEKDGKLVTGKGKGENGSS
TDEGEGLVTAKEVIDAVNKAGWRMKTTTANGQTGQADKFETVTSGTNVTFASGKGTTATV
SKDDQGNITVMYDVNVGDALNVNQLQNSGWNLDSKAVAGSSGKVISGNVSPSKGKMDETV
NINAGNNIEITRNGKNIDIATSMTPQFSSVSLGAGADAPTLSVDDKGALNVGSKDANKPV
RITNVAPGVKEGDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVGYQW*

-continued

>ZN29_ASS <SEQ ID 111>

MNKIYRIIWNIALNAWVVVSELTRNHTKRASATVATAVLATLLSATVQANATDEEDNEDL

EPVVRTAPVLSFHSDKEGTGEKEEVGASSNLTVYFDKNRVLKAGTITLKAGDNLKIKQNT

NENTNENTNASSFTYSLKKDLTGLINVETEKLSFGANGKKVNIISDTKGLNFAKETAGTN

GDPTVHLNGIGSTLTDTLAGSSASHVDAGNQSTHYTRAASIKDVLNAGWNIKGVKTGSTT

GQSENVDFVRTYDTVEFLSADTKTTTVNVESKDNGKRTEVKIGAKTSVIKEKDGKLVTGK

GKGENGSSTDEGEGLVTAKEVIDAVNKAGWRMKTTTANGQTGQADKFETVTSGTKVTFAS

GNGTTATVSKDDQGNITVKYDVNVGDALNVNQLQNSGWNLDSKAVAGSSGKVISGNVSPS

KGKMDETVNINAGNNIEITRNGKNIDIATSMTPQFSSVSLGAGADAPTLSVDDEGALNVG

SKDANKPVRITNVAPGVKEGDVTNVAWLKGVAQNLNNRIDNVDGNARAGIAQAIATAGLV

QAYLPGKSMMAIGGGTYRGEAGYAIGYSSISDGGNWIIKGTASGNSRGHFGASASVGYQW

*

FIG. 8 shows the results of aligning the sequences of each of these strains. Dark shading indicates regions of homology, and gray shading indicates the conservation of amino acids with similar characteristics. As is readily discernible, there is significant conservation among the various strains of ORF 40, further confirming its utility as an antigen for both vaccines and diagnostics.

It will be appreciated that the invention has been described by means of example only, and that modifications may be made whilst remaining within the spirit and scope of the invention.

What is claimed is:

1. An isolated or recombinant protein comprising an amino acid sequence selected from the group consisting of SEQ ID NOS: 2, 4, and 6.

2. An isolated or recombinant protein comprising an immunogenic fragment having 60% or greater sequence identity to the contiguous sequence of amino acids depicted in SEQ ID NOS: 2, 4, or 6.

3. A composition comprising a protein of claim 1 or 2.

4. A diagnostic composition comprising a protein of claim 1 or 2.

5. A pharmaceutical composition according to claim 3.

6. An isolated or recombinant protein of claim 2, where in the protein has 80% or greater sequence identity to the contiguous sequence of amino acids depicted in SEQ ID NOS: 2, 4, or 6.

7. An isolated or recombinant protein of claim 2, wherein the protein has 90% or greater sequence identity to the contiguous sequence of amino acids depicted in SEQ ID NOS: 2, 4, or 6.

8. An isolated or recombinant protein of claim 2, wherein the protein has 95% or greater sequence identity to the contiguous sequence of amino acids depicted in SEQ ID NOS: 2, 4, or 6.

9. A pharmaceutical composition according to claim 4.

* * * * *

SEQUENCE LISTING

<160> NUMBER OF SEQ ID NOS: 195

<210> SEQ ID NO 1
<211> LENGTH: 736
<212> TYPE: DNA
<213> ORGANISM: Neisseria meningitidis

<400> SEQUENCE: 1

```
acactgttgt ttgcaacggt tcaggcaagt gctaaccaat gaagagcaag aagaagattt     60
atatttagac cccgtacaac gcactgttgc cgtgttgata gtcaattccg ataaagaagg    120
cacgggagaa aaagaaaaag tagaagaaaa ttcagattgg gcagtatatt tcaacgagaa    180
aggagtacta acagccagag aaatcaccyt caaagccggc gacaacctga aaatcaaaca    240
aaacggcaca aacttcacct actcgctgaa aaaagacctc acagatctga ccagtgttgg    300
aactgaaaaa ttatcgttta gcgcaaacgg caataaagtc aacatcacaa gcgacaccaa    360
aggcttgaat tttgcgaaag aaacggctgg sacgaacggc gacaccacgg ttcatctgaa    420
cggtattggt tcgactttga ccgatacgct gctgaatacc ggagcgacca caaacgtaac    480
caacgacaac gttaccgatg acgagaaaaa acgtgcggca agcgttaaag acgtattaaa    540
cgctggctgg aacattaaag gcgttaaacc cggtacaaca gcttccgata acgttgattt    600
cgtccgcact tacgacacag tcgagttctt gagcgcagat acgaaaacaa cgactgttaa    660
tgtggaaagc aaagacaacg gcaagaaaac cgaagttaaa atcggtgcga agacttctgt    720
tattaaagaa aaagac                                                     736
```

<210> SEQ ID NO 2
<211> LENGTH: 245
<212> TYPE: PRT
<213> ORGANISM: Neisseria meningitidis
<220> FEATURE:

```
<221> NAME/KEY: SITE
<222> LOCATION: (70)
<223> OTHER INFORMATION: unknown

<400> SEQUENCE: 2
```

| | | | | | | | | | | | | | | | |
|---|---|---|---|---|---|---|---|---|---|---|---|---|---|---|---|
| Thr | Leu | Leu | Phe | Ala | Thr | Val | Gln | Ala | Ser | Ala | Asn | Gln | Glu | Glu | Gln |
| 1 | | | | 5 | | | | | 10 | | | | | 15 | |
| Glu | Glu | Asp | Leu | Tyr | Leu | Asp | Pro | Val | Gln | Arg | Thr | Val | Ala | Val | Leu |
| | | | 20 | | | | | 25 | | | | | 30 | | |
| Ile | Val | Asn | Ser | Asp | Lys | Glu | Gly | Thr | Gly | Glu | Lys | Glu | Lys | Val | Glu |
| | | 35 | | | | | 40 | | | | | 45 | | | |
| Glu | Asn | Ser | Asp | Trp | Ala | Val | Tyr | Phe | Asn | Glu | Lys | Gly | Val | Leu | Thr |
| 50 | | | | | 55 | | | | | 60 | | | | | |
| Ala | Arg | Glu | Ile | Thr | Xaa | Lys | Ala | Gly | Asp | Asn | Leu | Lys | Ile | Lys | Gln |
| 65 | | | | | 70 | | | | | 75 | | | | | 80 |
| Asn | Gly | Thr | Asn | Phe | Thr | Tyr | Ser | Leu | Lys | Lys | Asp | Leu | Thr | Asp | Leu |
| | | | | 85 | | | | | 90 | | | | | 95 | |
| Thr | Ser | Val | Gly | Thr | Glu | Lys | Leu | Ser | Phe | Ser | Ala | Asn | Gly | Asn | Lys |
| | | | | 100 | | | | | 105 | | | | | 110 | |
| Val | Asn | Ile | Thr | Ser | Asp | Thr | Lys | Gly | Leu | Asn | Phe | Ala | Lys | Glu | Thr |
| | | | 115 | | | | | 120 | | | | | 125 | | |
| Ala | Gly | Thr | Asn | Gly | Asp | Thr | Thr | Val | His | Leu | Asn | Gly | Ile | Gly | Ser |
| | 130 | | | | | 135 | | | | | 140 | | | | |
| Thr | Leu | Thr | Asp | Thr | Leu | Leu | Asn | Thr | Gly | Ala | Thr | Thr | Asn | Val | Thr |
| 145 | | | | | 150 | | | | | 155 | | | | | 160 |
| Asn | Asp | Asn | Val | Thr | Asp | Asp | Glu | Lys | Lys | Arg | Ala | Ala | Ser | Val | Lys |
| | | | | 165 | | | | | 170 | | | | | 175 | |
| Asp | Val | Leu | Asn | Ala | Gly | Trp | Asn | Ile | Lys | Gly | Val | Lys | Pro | Gly | Thr |
| | | | 180 | | | | | 185 | | | | | 190 | | |
| Thr | Ala | Ser | Asp | Asn | Val | Asp | Phe | Val | Arg | Thr | Tyr | Asp | Thr | Val | Glu |
| | 195 | | | | | 200 | | | | | 205 | | | | |
| Phe | Leu | Ser | Ala | Asp | Thr | Lys | Thr | Thr | Thr | Val | Asn | Val | Glu | Ser | Lys |
| 210 | | | | | 215 | | | | | 220 | | | | | |
| Asp | Asn | Gly | Lys | Lys | Thr | Glu | Val | Lys | Ile | Gly | Ala | Lys | Thr | Ser | Val |
| 225 | | | | | 230 | | | | | 235 | | | | | 240 |
| Ile | Lys | Glu | Lys | Asp | | | | | | | | | | | |
| | | | | 245 | | | | | | | | | | | |

```
<210> SEQ ID NO 3
<211> LENGTH: 1776
<212> TYPE: DNA
<213> ORGANISM: Neisseria meningitidis
<400> SEQUENCE: 3
atgaacaaaa taccgcat catttggaat agtgccctca atgcctgggt cgtcgtatcc      60
gagctcacac gcaaccacac caaacgcgcc tccgcaaccg tgaagaccgc cgtattggcg    120
acactgttgt ttgcaacggt tcaggcaagt gctaacaatg aagagcaaga agaagattta   180
tatttagacc ccgtacaacg cactgttgcc gtgttgatag tcaattccga taagaaggc    240
acgggagaaa agaaaaaagt agaagaaaat tcagattggg cagtatattt caacgagaaa   300
ggagtactaa cagccagaga aatcaccctc aaagccggcg acaacctgaa atcaaacaa   360
aacggcacaa acttcaccta ctcgctgaaa aagaccctca cagatctgac cagtgttgga   420
actgaaaaat tatcgtttag cgcaaacggc aataaagtca acatcacaag cgacaccaaa   480
ggcttgaatt ttgcgaaaga aacggctggg acgaacggcg acaccacggt tcatctgaac   540
```

-continued

```
ggtattggtt cgactttgac cgatacgctg ctgaataccg agcgaccac aaacgtaacc      600 aacgacaacg ttaccgatga cgagaaaaaa cgtgcggcaa gcgttaaaga cgtattaaac    660
gctggctgga acattaaagg cgttaaaccc ggtacaacag cttccgataa cgttgatttc    720
gtccgcactt acgacacagt cgagttcttg agcgcagata cgaaaacaac gactgttaat    780
gtggaaagca agacaacgg caagaaaacc gaagttaaaa tcggtgcgaa gacttctgtt     840
attaaagaaa aagacggtaa gttggttact ggtaaagaca aaggcgagaa tggttcttct    900
acagacgaag gcgaaggctt agtgactgca aagaagtga ttgatgcagt aaacaaggct     960
ggttggagaa tgaaaacaac aaccgctaat ggtcaaacag gtcaagctga caagtttgaa    1020
accgttacat caggcacaaa tgtaaccttt gctagtggta aggtacaac tgcgactgta     1080 agtaaagatg atcaaggcaa catcactgtt atgtatgatg taaatgtcgg cgatgcccta   1140
aacgtcaatc agctgcaaaa cagcggttgg aatttggatt ccaaagcggt tgcaggttct   1200
tcgggcaaag tcatcagcgg caatgtttcg ccgagcaagg gaaagatgga tgaaaccgtc    1260
aacattaatg ccggcaacaa catcgagatt acccgcaacg gtaaaaatat cgacatcgcc   1320
acttcgatga ccccgcagtt ttccagcgtt tcgctcggcg cggggcgga tgcgcccact     1380 ttgagcgtgg atggggacgc attgaatgtc ggcagcaaga aggacaacaa acccgtccgc   1440
attaccaatg tcgccccggg cgttaaagag ggggatgtta caaacgtcgc acaacttaaa   1500
ggcgtggcgc aaaacttgaa caaccgcatc gacaatgtgg acggcaacgc gcgtgcgggc    1560
atcgcccaag cgattgcaac cgcaggtctg gttcaggcgt atttgcccgg caagagtatg    1620
atggcgatcg gcggcggcac ttatcgcggc gaagccggtt acgccatcgg ctactccagt   1680
atttccgacg gcggaaattg gattatcaaa ggcacggctt ccggcaattc gcgcggccat   1740
ttcggtgctt ccgcatctgt cggttatcag tggtaa                              1776
```

<210> SEQ ID NO 4
<211> LENGTH: 591
<212> TYPE: PRT
<213> ORGANISM: Neisseria meningitidis

<400> SEQUENCE: 4

```
Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
```

```
                    145                 150                 155                 160
Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
                195                 200                 205

Lys Lys Arg Ala Ala Ser Val Lys Asp Val Leu Asn Ala Gly Trp Asn
                210                 215                 220

Ile Lys Gly Val Lys Pro Gly Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270

Lys Ile Gly Ala Lys Thr Ser Val Ile Lys Glu Lys Asp Gly Lys Leu
                275                 280                 285

Val Thr Gly Lys Asp Lys Gly Glu Asn Gly Ser Ser Thr Asp Glu Gly
                290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Gln Gly Asn Ile
                355                 360                 365

Thr Val Met Tyr Asp Val Asn Val Gly Asp Ala Leu Asn Val Asn Gln
                370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
                450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
                515                 520                 525

Gly Leu Val Gln Ala Tyr Leu Pro Gly Lys Ser Met Met Ala Ile Gly
                530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575
```

Ser Arg Gly His Phe Gly Ala Ser Ala Ser Val Gly Tyr Gln Trp
        580                 585                 590

<210> SEQ ID NO 5
<211> LENGTH: 1779
<212> TYPE: DNA
<213> ORGANISM: Neisseria meningitidis
<220> FEATURE:
<221> NAME/KEY: misc_feature
<222> LOCATION: (48)
<223> OTHER INFORMATION: any nucleotide
<221> NAME/KEY: misc_feature
<222> LOCATION: (420)
<223> OTHER INFORMATION: any nucleotide
<221> NAME/KEY: misc_feature
<222> LOCATION: (608)
<223> OTHER INFORMATION: any nucleotide
<221> NAME/KEY: misc_feature
<222> LOCATION: (682)..(684)
<223> OTHER INFORMATION: any nucleotide
<221> NAME/KEY: misc_feature
<222> LOCATION: (763)
<223> OTHER INFORMATION: any nucleotide
<221> NAME/KEY: misc_feature
<222> LOCATION: (774)
<223> OTHER INFORMATION: any nucleotide
<221> NAME/KEY: misc_feature
<222> LOCATION: (1473)
<223> OTHER INFORMATION: any nucleotide
<221> NAME/KEY: misc_feature
<222> LOCATION: (1492)
<223> OTHER INFORMATION: any nucleotide
<221> NAME/KEY: misc_feature
<222> LOCATION: (1560)
<223> OTHER INFORMATION: any nucleotide

<400> SEQUENCE: 5

| | | | | | |
|---|---|---|---|---|---|
| atgaacaaaa | tataccgcat | catttggaat | agtgccctca | atgcctgngt | cgccgtatcc | 60 |
| gagctcacac | gcaaccacac | caaacgcgcc | tccgcaaccg | tgaagaccgc | cgtattggcg | 120 |
| acactgttgt | ttgcaacggt | tcaggcgaat | gctaccgatg | aagatgaaga | agaagagtta | 180 |
| gaatccgtac | aacgctctgt | cgtagggagc | attcaagcca | gtatggaagg | cagcggcgaa | 240 |
| ttggaaacga | tatcattatc | aatgactaac | gacagcaagg | aatttgtaga | cccatacata | 300 |
| gtagttaccc | tcaaagccgg | cgacaacctg | aaaatcaaac | aaaacaccaa | tgaaaacacc | 360 |
| aatgccagta | gcttcaccta | ctcgctgaaa | aaagacctca | caggcctgat | caatgttgan | 420 |
| actgaaaaat | tatcgtttgg | cgcaaacggc | aagaaagtca | acatcataag | cgacaccaaa | 480 |
| ggcttgaatt | tcgcgaaaga | aacggctggg | acgaacggcg | acaccacggt | tcatctgaac | 540 |
| ggtatcggtt | cgactttgac | cgatacgctt | gcgggttctt | ctgcttctca | cgttgatgcg | 600 |
| ggtaaccnaa | gtacacatta | cactcgtgca | gcaagtatta | aggatgtgtt | gaatgcgggt | 660 |
| tggaatatta | agggtgttaa | annnggctca | acaactggtc | aatcagaaaa | tgtcgatttc | 720 |
| gtccgcactt | acgacacagt | cgagttcttg | agcgcagata | cgnaaacaac | gacngttaat | 780 |
| gtggaaagca | agacaacgg | caagagaacc | gaagttaaaa | tcggtgcgaa | gacttctgtt | 840 |
| attaaagaaa | aagacggtaa | gttggttact | ggtaaaggca | aggcgagaa | tggttcttct | 900 |
| acagacgaag | gcgaaggctt | agtgactgca | aagaagtga | ttgatgcagt | aaacaaggct | 960 |
| ggttggagaa | tgaaaacaac | aaccgctaat | ggtcaaacag | gtcaagctga | caagtttgaa | 1020 |
| accgttacat | caggcacaaa | tgtaacctt | gctagtggta | aagtacaac | tgcgactgta | 1080 |
| agtaaagatg | atcaaggcaa | catcactgtt | atgtatgatg | taaatgtcgg | cgatgcccta | 1140 |
| aacgtcaatc | agctgcaaaa | cagcggttgg | aatttggatt | ccaaagcggt | tgcaggttct | 1200 |

```
tcgggcaaag tcatcagcgg caatgtttcg ccgagcaagg gaaagatgga tgaaaccgtc   1260
aacattaatg ccggcaacaa catcgagatt agccgcaacg gtaaaaatat cgacatcgcc   1320
acttcgatgg cgccgcagtt ttccagcgtt tcgctcggcg cgggggcaga tgcgcccact   1380
ttaagcgtgg atgacgaggg cgcgttgaat gtcggcagca aggatgccaa caaacccgtc   1440
cgcattacca atgtcgcccc gggcgttaaa gangggatg ttacaaacgt cncacaactt    1500
aaaggcgtgg cgcaaaactt gaacaaccgc atcgacaatg tggacggcaa cgcgcgtgcn   1560
ggcatcgccc aagcgattgc aaccgcaggt ctggttcagg cgtatctgcc cggcaagagt   1620
atgatggcga tcggcggcgg cacttatcgc ggcgaagccg gttacgccat cggctactcc   1680
agtatttccg acggcggaaa ttggattatc aaaggcacgg cttccggcaa ttcgcgcggc   1740
catttcggtg cttccgcatc tgtcggttat cagtggtaa                          1779
```

<210> SEQ ID NO 6
<211> LENGTH: 592
<212> TYPE: PRT
<213> ORGANISM: Neisseria meningitidis
<220> FEATURE:
<221> NAME/KEY: SITE
<222> LOCATION: (16)
<223> OTHER INFORMATION: unknown
<221> NAME/KEY: SITE
<222> LOCATION: (140)
<223> OTHER INFORMATION: unknown
<221> NAME/KEY: SITE
<222> LOCATION: (203)
<223> OTHER INFORMATION: unknown
<221> NAME/KEY: SITE
<222> LOCATION: (228)
<223> OTHER INFORMATION: unknown
<221> NAME/KEY: SITE
<222> LOCATION: (255)
<223> OTHER INFORMATION: unknown
<221> NAME/KEY: SITE
<222> LOCATION: (491)
<223> OTHER INFORMATION: unknown
<221> NAME/KEY: SITE
<222> LOCATION: (498)
<223> OTHER INFORMATION: unknown

<400> SEQUENCE: 6

```
Met Asn Lys Ile Tyr Arg Ile Ile Trp Asn Ser Ala Leu Asn Ala Xaa
  1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Asn Ala Thr Asp Glu Asp Glu Glu Glu Leu Glu Ser Val Gln
     50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Xaa Thr Glu Lys Leu
    130                 135                 140

Ser Phe Gly Ala Asn Gly Lys Lys Val Asn Ile Ile Ser Asp Thr Lys
```

-continued

```
             145                 150                 155                 160
        Gly Leu Asn Phe Ala Lys Glu Thr Ala Gly Thr Asn Gly Asp Thr Thr
                        165                 170                 175
        Val His Leu Asn Gly Ile Gly Ser Thr Leu Thr Asp Thr Leu Ala Gly
                        180                 185                 190
        Ser Ser Ala Ser His Val Asp Ala Gly Asn Xaa Ser Thr His Tyr Thr
                        195                 200                 205
        Arg Ala Ala Ser Ile Lys Asp Val Leu Asn Ala Gly Trp Asn Ile Lys
                        210                 215                 220
        Gly Val Lys Xaa Gly Ser Thr Thr Gly Gln Ser Glu Asn Val Asp Phe
        225                 230                 235                 240
        Val Arg Thr Tyr Asp Thr Val Glu Phe Leu Ser Ala Asp Thr Xaa Thr
                        245                 250                 255
        Thr Thr Val Asn Val Glu Ser Lys Asp Asn Gly Lys Arg Thr Glu Val
                        260                 265                 270
        Lys Ile Gly Ala Lys Thr Ser Val Ile Lys Glu Lys Asp Gly Lys Leu
                        275                 280                 285
        Val Thr Gly Lys Gly Lys Gly Glu Asn Gly Ser Ser Thr Asp Glu Gly
                        290                 295                 300
        Glu Gly Leu Val Thr Ala Lys Glu Val Ile Asp Ala Val Asn Lys Ala
        305                 310                 315                 320
        Gly Trp Arg Met Lys Thr Thr Ala Asn Gly Gln Thr Gly Gln Ala
                        325                 330                 335
        Asp Lys Phe Glu Thr Val Thr Ser Gly Thr Asn Val Thr Phe Ala Ser
                        340                 345                 350
        Gly Lys Gly Thr Thr Ala Thr Val Ser Lys Asp Gln Gly Asn Ile
                        355                 360                 365
        Thr Val Met Tyr Asp Val Asn Val Gly Asp Ala Leu Asn Val Asn Gln
                        370                 375                 380
        Leu Gln Asn Ser Gly Trp Asn Leu Asp Ser Lys Ala Val Ala Gly Ser
        385                 390                 395                 400
        Ser Gly Lys Val Ile Ser Gly Asn Val Ser Pro Ser Lys Gly Lys Met
                        405                 410                 415
        Asp Glu Thr Val Asn Ile Asn Ala Gly Asn Asn Ile Glu Ile Ser Arg
                        420                 425                 430
        Asn Gly Lys Asn Ile Asp Ile Ala Thr Ser Met Ala Pro Gln Phe Ser
                        435                 440                 445
        Ser Val Ser Leu Gly Ala Gly Ala Asp Ala Pro Thr Leu Ser Val Asp
                        450                 455                 460
        Asp Glu Gly Ala Leu Asn Val Gly Ser Lys Asp Ala Asn Lys Pro Val
        465                 470                 475                 480
        Arg Ile Thr Asn Val Ala Pro Gly Val Lys Xaa Gly Asp Val Thr Asn
                        485                 490                 495
        Val Xaa Gln Leu Lys Gly Val Ala Gln Asn Leu Asn Asn Arg Ile Asp
                        500                 505                 510
        Asn Val Asp Gly Asn Ala Arg Ala Gly Ile Ala Gln Ala Ile Ala Thr
                        515                 520                 525
        Ala Gly Leu Val Gln Ala Tyr Leu Pro Gly Lys Ser Met Met Ala Ile
                        530                 535                 540
        Gly Gly Gly Thr Tyr Arg Gly Glu Ala Gly Tyr Ala Ile Gly Tyr Ser
        545                 550                 555                 560
        Ser Ile Ser Asp Gly Gly Asn Trp Ile Ile Lys Gly Thr Ala Ser Gly
                        565                 570                 575
```

```
Asn Ser Arg Gly His Phe Gly Ala Ser Ala Ser Val Gly Tyr Gln Trp
        580                 585                 590
```

```
<210> SEQ ID NO 7
<211> LENGTH: 492
<212> TYPE: DNA
<213> ORGANISM: Neisseria meningitidis

<400> SEQUENCE: 7
atgttacgtt tgactgcttt agccgtatgc accgccctcg ctttgggcgc gtgttcgccg      60
caaaattccg actctgcccc acaagccaaa gaacaggcgg tttcgccgc acaaaccgaa     120 ggcgcgtccg ttaccgtcaa aaccgcgcgc ggcgacgttc aaataccgca aaaccccgaa    180
cgcatcgccg tttacgattt gggtatgctc gacaccttga gcaaactggg cgtgaaaacc    240
ggtttgtccg tcgataaaaa ccgcctgccg tatttagagg aatatttcaa acgacaaaa    300 cctgccggca ctttgttcga gccggattac gaaacgctca acgcttacaa accgcagctc    360
atcatcatcg gcagccgcgc cgccaaggcg tttgacaaat tgaacgaaat cgcgccgacc    420
atcgrmwtga ccgccgatac cgccaacctc aaagaaagtg ccaargaggc atcgacgctg    480
gcgcaaatct tc                                                         492
```

```
<210> SEQ ID NO 8
<211> LENGTH: 164
<212> TYPE: PRT
<213> ORGANISM: Neisseria meningitidis
<220> FEATURE:
<221> NAME/KEY: SITE
<222> LOCATION: (142)..(143)
<223> OTHER INFORMATION: unknown

<400> SEQUENCE: 8

Met Leu Arg Leu Thr Ala Leu Ala Val Cys Thr Ala Leu Ala Leu Gly
  1               5                  10                  15

Ala Cys Ser Pro Gln Asn Ser Asp Ser Ala Pro Gln Ala Lys Glu Gln
                 20                  25                  30

Ala Val Ser Ala Ala Gln Thr Glu Gly Ala Ser Val Thr Val Lys Thr
             35                  40                  45

Ala Arg Gly Asp Val Gln Ile Pro Gln Asn Pro Glu Arg Ile Ala Val
         50                  55                  60

Tyr Asp Leu Gly Met Leu Asp Thr Leu Ser Lys Leu Gly Val Lys Thr
 65                  70                  75                  80

Gly Leu Ser Val Asp Lys Asn Arg Leu Pro Tyr Leu Glu Glu Tyr Phe
                 85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
        115                 120                 125

Lys Ala Phe Asp Lys Leu Asn Glu Ile Ala Pro Thr Ile Xaa Xaa Thr
    130                 135                 140

Ala Asp Thr Ala Asn Leu Lys Glu Ser Ala Lys Glu Ala Ser Thr Leu
145                 150                 155                 160

Ala Gln Ile Phe
```

```
<210> SEQ ID NO 9
<211> LENGTH: 966
<212> TYPE: DNA
<213> ORGANISM: Neisseria meningitidis
```

```
<400> SEQUENCE: 9
atgttacgtt tgactgcttt agccgtatgc accgccctcg ctttgggcgc gtgttcgccg     60
caaaattccg actctgcccc acaagccaaa gaacaggcgg tttccgccgc acaaaccgaa    120
ggcgcgtccg ttaccgtcaa aaccgcgcgc ggcgacgttc aaataccgca aaaccccgaa    180
cgcatcgccg tttacgattt gggtatgctc gacaccttga gcaaactggg cgtgaaaacc    240
ggtttgtccg tcgataaaaa ccgcctgccg tatttagagg aatatttcaa aacgacaaaa    300
cctgccggca ctttgttcga gccggattac gaaacgctca acgcttacaa accgcagctc    360
atcatcatcg gcagccgcgc cgccaaggcg tttgacaaat tgaacgaaat cgcgccgacc    420
atcgaaatga ccgccgatac cgccaacctc aagaaagtg ccaaagagcg catcgacgcg     480
ctggcgcaaa tcttcggcaa acaggcggaa gccgacaagc tgaaggcgga aatcgacgcg    540
tcttttgaag ccgcgaaaac tgccgcacaa ggtaagggca aggtttggt gattttggtc     600
aacggcggca agatgtcggc tttcggcccg tcttcacgct gggcggctg gctgcacaaa     660
gacatcggcg ttcccgctgt cgatgaatca attaaagaag gcagccacgg tcagcctatc    720
agctttgaat acctgaaaga gaaaaatccc gactggctgt tgtccttga ccgaagcgcg     780
gccatcggcg aagagggtca ggcggcgaaa gacgtgttgg ataatccgct ggttgccgaa    840
acaaccgctt ggaaaaaagg acaggtcgtg tacctcgttc ctgaaactta tttggcagcc    900
ggtggcgcgc aagagctgct gaatgcaagc aaacaggttg ccgacgcttt taacgcggca    960
aaataa                                                               966

<210> SEQ ID NO 10
<211> LENGTH: 321
<212> TYPE: PRT
<213> ORGANISM: Neisseria meningitidis

<400> SEQUENCE: 10

Met Leu Arg Leu Thr Ala Leu Ala Val Cys Thr Ala Leu Ala Leu Gly
  1               5                  10                  15

Ala Cys Ser Pro Gln Asn Ser Asp Ser Ala Pro Gln Ala Lys Glu Gln
                 20                  25                  30

Ala Val Ser Ala Ala Gln Thr Glu Gly Ala Ser Val Thr Val Lys Thr
             35                  40                  45

Ala Arg Gly Asp Val Gln Ile Pro Gln Asn Pro Glu Arg Ile Ala Val
         50                  55                  60

Tyr Asp Leu Gly Met Leu Asp Thr Leu Ser Lys Leu Gly Val Lys Thr
 65                  70                  75                  80

Gly Leu Ser Val Asp Lys Asn Arg Leu Pro Tyr Leu Glu Glu Tyr Phe
                 85                  90                  95

Lys Thr Thr Lys Pro Ala Gly Thr Leu Phe Glu Pro Asp Tyr Glu Thr
                100                 105                 110

Leu Asn Ala Tyr Lys Pro Gln Leu Ile Ile Ile Gly Ser Arg Ala Ala
            115                 120                 125

Lys Ala Phe Asp Lys Leu Asn Glu Ile Ala Pro Thr Ile Glu Met Thr
        130                 135                 140

Ala Asp Thr Ala Asn Leu Lys Glu Ser Ala Lys Glu Arg Ile Asp Ala
145                 150                 155                 160

Leu Ala Gln Ile Phe Gly Lys Gln Ala Glu Ala Asp Lys Leu Lys Ala
                165                 170                 175

Glu Ile Asp Ala Ser Phe Glu Ala Ala Lys Thr Ala Ala Gln Gly Lys
```

```
                    180                185                190
Gly Lys Gly Leu Val Ile Leu Val Asn Gly Gly Lys Met Ser Ala Phe
            195                200                205
Gly Pro Ser Ser Arg Leu Gly Gly Trp Leu His Lys Asp Ile Gly Val
    210                215                220
Pro Ala Val Asp Glu Ser Ile Lys Glu Gly Ser His Gly Gln Pro Ile
225                230                235                240
Ser Phe Glu Tyr Leu Lys Glu Lys Asn Pro Asp Trp Leu Phe Val Leu
                245                250                255
Asp Arg Ser Ala Ala Ile Gly Glu Glu Gly Gln Ala Ala Lys Asp Val
            260                265                270
Leu Asp Asn Pro Leu Val Ala Glu Thr Thr Ala Trp Lys Lys Gly Gln
        275                280                285
Val Val Tyr Leu Val Pro Glu Thr Tyr Leu Ala Ala Gly Gly Ala Gln
    290                295                300
Glu Leu Leu Asn Ala Ser Lys Gln Val Ala Asp Ala Phe Asn Ala Ala
305                310                315                320
Lys

<210> SEQ ID NO 11
<211> LENGTH: 966
<212> TYPE: DNA
<213> ORGANISM: Neisseria meningitidis

<400> SEQUENCE: 11
atgttacgtt tgactgcttt agccgtatgc accgccctcg ctttgggcgc gtgttcgccg     60
caaaattccg actctgcccc acaagccaaa gaacaggcgg tttccgccgc acaatccgaa    120
ggcgtgtccg ttaccgtcaa acggcgcgc ggcgatgttc aaataccgca aaccccgaa     180 cgtatcgccg tttacgattt gggtatgctc gacaccttga gcaaactggg cgtgaaaacc    240
ggtttgtccg tcgataaaaa ccgcctgccg tatttagagg aatatttcaa acgacaaaa    300 cctgccggaa ctttgttcga gccggattac gaaacgctca acgcttacaa accgcagctc    360
atcatcatcg gcagccgcgc agccaaagcg tttgacaaat gaacgaaat cgcgccgacc     420 atcgaaatga ccgccgatac cgccaacctc aagaaagtg ccaagagcg tatcgacgcg     480 ctggcgcaaa tcttcggcaa aaaggcggaa gccgacaagc tgaaggcgga atcgacgcg     540 tcttttgaag ccgcgaaaac tgccgcgcaa ggcaaaggca agggtttggt gattttggtc    600
aacggcggca agatgtccgc cttcggcccg tcttcacgac tgggcggctg gctgcacaaa    660
gacatcggcg ttcccgctgt tgacgaagcc atcaaagaag cagccacgg tcagcctatc    720 agctttgaat acctgaaaga gaaaaatccc gactggctgt tgtccttga ccgcagcgcg    780 gccatcggcg aagagggtca ggcggcgaaa gacgtgttga caatccgct ggttgccgaa    840 acaccgcttt ggaaaaaagg acaagtcgtt taccttgttc ctgaaactta tttggcagcc    900
ggtggcgcgc aagagctact gaatgcaagc aaacaggttg ccgacgcttt taacgcggca    960
aaataa                                                                966

<210> SEQ ID NO 12
<211> LENGTH: 321
<212> TYPE: PRT
<213> ORGANISM: Neisseria meningitidis

<400> SEQUENCE: 12

Met Leu Arg Leu Thr Ala Leu Ala Val Cys Thr Ala Leu Ala Leu Gly
```

```
              1               5                  10                 15
Ala Cys Ser Pro Gln Asn Ser Asp Ser Ala Pro Gln Ala Lys Glu Gln
                20                  25                  30
Ala Val Ser Ala Ala Gln Ser Glu Gly Val Ser Val Thr Val Lys Thr
            35                  40                  45
Ala Arg Gly Asp Val Gln Ile Pro Gln Asn Pro Glu Arg Ile Ala Val
        50                  55                  60
Tyr Asp Leu Gly Met Leu Asp Thr Leu Ser Lys Leu Gly Val Lys Thr
65                  70                  75                  80
Gly Leu Ser Val Asp Lys Asn Arg Leu Pro Tyr Leu Glu Glu Tyr Phe
                85                  90                  95
Lys Thr Thr Lys Pro Ala Gly Thr Leu Phe Glu Pro Asp Tyr Glu Thr
            100                 105                 110
Leu Asn Ala Tyr Lys Pro Gln Leu Ile Ile Ile Gly Ser Arg Ala Ala
        115                 120                 125
Lys Ala Phe Asp Lys Leu Asn Glu Ile Ala Pro Thr Ile Glu Met Thr
    130                 135                 140
Ala Asp Thr Ala Asn Leu Lys Glu Ser Ala Lys Glu Arg Ile Asp Ala
145                 150                 155                 160
Leu Ala Gln Ile Phe Gly Lys Lys Ala Glu Ala Asp Lys Leu Lys Ala
                165                 170                 175
Glu Ile Asp Ala Ser Phe Glu Ala Ala Lys Thr Ala Ala Gln Gly Lys
            180                 185                 190
Gly Lys Gly Leu Val Ile Leu Val Asn Gly Gly Lys Met Ser Ala Phe
        195                 200                 205
Gly Pro Ser Ser Arg Leu Gly Gly Trp Leu His Lys Asp Ile Gly Val
    210                 215                 220
Pro Ala Val Asp Glu Ala Ile Lys Glu Gly Ser His Gly Gln Pro Ile
225                 230                 235                 240
Ser Phe Glu Tyr Leu Lys Glu Lys Asn Pro Asp Trp Leu Phe Val Leu
                245                 250                 255
Asp Arg Ser Ala Ala Ile Gly Glu Glu Gly Gln Ala Ala Lys Asp Val
            260                 265                 270
Leu Asn Asn Pro Leu Val Ala Glu Thr Thr Ala Trp Lys Lys Gly Gln
        275                 280                 285
Val Val Tyr Leu Val Pro Glu Thr Tyr Leu Ala Ala Gly Gly Ala Gln
    290                 295                 300
Glu Leu Leu Asn Ala Ser Lys Gln Val Ala Asp Ala Phe Asn Ala Ala
305                 310                 315                 320
Lys
```

<210> SEQ ID NO 13
<211> LENGTH: 375
<212> TYPE: DNA
<213> ORGANISM: Neisseria meningitidis

<400> SEQUENCE: 13

```
atgaaacttc tgaccaccgc aatcctgtct tccgcaatcg cgctcagcag tatggctgcc      60
gccgctggca cggacaaccc cactgttgca aaaaaaaccg tcagctacgt ctgccagcaa     120
ggtaaaaaag tcaaagtaac ctacggcttc aacaaacagg gtctgaccac atacgcttcc     180
gccgtcatca acggcaaacg cgtgcaaatg cctgtcaatt tggacaaatc cgacaatgtg     240
gaaacattct acggcaaaga aggcggttat gttttgggta ccggcgtgat ggatggcaaa     300
```

```
tcctaccgca aacagcccat tatgattacc gcacctgaca accaaatcgt cttcaaagac      360
tgttccccac gttaa                                                       375
```

<210> SEQ ID NO 14
<211> LENGTH: 124
<212> TYPE: PRT
<213> ORGANISM: Neisseria meningitidis

<400> SEQUENCE: 14

```
Met Lys Leu Leu Thr Thr Ala Ile Leu Ser Ser Ala Ile Ala Leu Ser
 1               5                  10                  15

Ser Met Ala Ala Ala Ala Gly Thr Asp Asn Pro Thr Val Ala Lys Lys
            20                  25                  30

Thr Val Ser Tyr Val Cys Gln Gln Gly Lys Lys Val Lys Val Thr Tyr
        35                  40                  45

Gly Phe Asn Lys Gln Gly Leu Thr Thr Tyr Ala Ser Ala Val Ile Asn
    50                  55                  60

Gly Lys Arg Val Gln Met Pro Val Asn Leu Asp Lys Ser Asp Asn Val
65                  70                  75                  80

Glu Thr Phe Tyr Gly Lys Glu Gly Gly Tyr Val Leu Gly Thr Gly Val
                85                  90                  95

Met Asp Gly Lys Ser Tyr Arg Lys Gln Pro Ile Met Ile Thr Ala Pro
            100                 105                 110

Asp Asn Gln Ile Val Phe Lys Asp Cys Ser Pro Arg
        115                 120
```

<210> SEQ ID NO 15
<211> LENGTH: 375
<212> TYPE: DNA
<213> ORGANISM: Neisseria meningitidis

<400> SEQUENCE: 15

```
atgaaacttc tgaccaccgc aatcctgtct tccgcaatcg cgctcagcag tatggctgct      60
gctgccggca cgaacaaccc caccgttgcc aaaaaaaccg tcagctacgt ctgccagcaa     120
ggtaaaaaag tcaaagtaac ctacggcttt aacaaacagg gcctgaccac atacgcttcc     180
gccgtcatca cggcaaacg tgtgcaaatg cctgtcaatt tggacaaatc cgacaatgtg     240
gaaacattct acggcaaaga aggcggttat gttttgggta ccggcgtgat ggatggcaaa     300
tcctatcgca aacagcctat tatgattacc gcacctgaca accaaatcgt cttcaaagac     360
tgttccccac gttaa                                                      375
```

<210> SEQ ID NO 16
<211> LENGTH: 124
<212> TYPE: PRT
<213> ORGANISM: Neisseria meningitidis

<400> SEQUENCE: 16

```
Met Lys Leu Leu Thr Thr Ala Ile Leu Ser Ser Ala Ile Ala Leu Ser
 1               5                  10                  15

Ser Met Ala Ala Ala Ala Gly Thr Asn Asn Pro Thr Val Ala Lys Lys
            20                  25                  30

Thr Val Ser Tyr Val Cys Gln Gln Gly Lys Lys Val Lys Val Thr Tyr
        35                  40                  45

Gly Phe Asn Lys Gln Gly Leu Thr Thr Tyr Ala Ser Ala Val Ile Asn
    50                  55                  60

Gly Lys Arg Val Gln Met Pro Val Asn Leu Asp Lys Ser Asp Asn Val
```

```
65                  70                  75                  80
Glu Thr Phe Tyr Gly Lys Glu Gly Tyr Val Leu Gly Thr Gly Val
                85                  90                  95

Met Asp Gly Lys Ser Tyr Arg Lys Gln Pro Ile Met Ile Thr Ala Pro
            100                 105                 110

Asp Asn Gln Ile Val Phe Lys Asp Cys Ser Pro Arg
        115                 120
```

<210> SEQ ID NO 17
<211> LENGTH: 519
<212> TYPE: DNA
<213> ORGANISM: Neisseria meningitidis
<220> FEATURE:
<221> NAME/KEY: misc_feature
<222> LOCATION: (425)
<223> OTHER INFORMATION: any nucleotide
<221> NAME/KEY: misc_feature
<222> LOCATION: (485)
<223> OTHER INFORMATION: any nucleotide
<221> NAME/KEY: misc_feature
<222> LOCATION: (489)
<223> OTHER INFORMATION: any nucleotide

<400> SEQUENCE: 17

```
ggcaccgaat tcaaaaccac cctttccgga gccgacatac aggcagggt gggtgaaaaa      60 gcccgagccg atgcgaaaat tatcctaaaa ggcatcgtta accgcatcca aaccgaagaa     120
aagctggaat ccaactcgac cgtatggcaa aagcaggccg gaagcggcag cacggttgaa     180
acgctgaagc taccgagctt tgaagggccg gcactgccta agctgaccgc tcccggcggc     240
tatatcgccg acatccccaa aggcaacctc aaaaccgaaa tcgaaaagct ggccaaacag     300
cccgaatatg cctatctgaa acagcttcag acggtcaagg acgtgaactg gaaccaagta     360
cagctcgctt acgacaaatg ggactataaa caggaaggcc taaccggagc cggagccgca     420
attancgcac tggccgttac cgtggtcacc tcaggcgcag gaaccggagc cgtattggga     480
ttaanacgng tggccgccgc cgcaaccgat gcagcattt                           519
```

<210> SEQ ID NO 18
<211> LENGTH: 173
<212> TYPE: PRT
<213> ORGANISM: Neisseria meningitidis
<220> FEATURE:
<221> NAME/KEY: SITE
<222> LOCATION: (142)
<223> OTHER INFORMATION: unknown
<221> NAME/KEY: SITE
<222> LOCATION: (162)
<223> OTHER INFORMATION: unknown

<400> SEQUENCE: 18

```
Gly Thr Glu Phe Lys Thr Thr Leu Ser Gly Ala Asp Ile Gln Ala Gly
 1               5                  10                  15

Val Gly Glu Lys Ala Arg Ala Asp Ala Lys Ile Ile Leu Lys Gly Ile
                20                  25                  30

Val Asn Arg Ile Gln Thr Glu Gly Lys Leu Glu Ser Asn Ser Thr Val
            35                  40                  45

Trp Gln Lys Gln Ala Gly Ser Gly Ser Thr Val Glu Thr Leu Lys Leu
        50                  55                  60

Pro Ser Phe Glu Gly Pro Ala Leu Pro Lys Leu Thr Ala Pro Gly Gly
 65                 70                  75                  80

Tyr Ile Ala Asp Ile Pro Lys Gly Asn Leu Lys Thr Glu Ile Glu Lys
                85                  90                  95
```

```
Leu Ala Lys Gln Pro Glu Tyr Ala Tyr Leu Lys Gln Leu Gln Thr Val
            100                 105                 110

Lys Asp Val Asn Trp Asn Gln Val Gln Leu Ala Tyr Asp Lys Trp Asp
        115                 120                 125

Tyr Lys Gln Glu Gly Leu Thr Gly Ala Gly Ala Ala Ile Xaa Ala Leu
130                 135                 140

Ala Val Thr Val Val Thr Ser Gly Ala Gly Thr Gly Ala Val Leu Gly
145                 150                 155                 160

Leu Xaa Arg Val Ala Ala Ala Thr Asp Ala Ala Phe
                165                 170
```

<210> SEQ ID NO 19
<211> LENGTH: 1923
<212> TYPE: DNA
<213> ORGANISM: Neisseria meningitidis

<400> SEQUENCE: 19

```
atgcaactgc tggcagccga aggcattcac caacaccaat tgaatgttca gaaaagtacc      60
cgtttcatcg gcatcaaagt gggtaaaagc aattacagca aaaacgagct gaacgaaacc     120
aaactgcccg tacgcgttat cgcccaaaca gccaaaaccc gttccggctg ggataccgta     180
ctcgaaggca ccgaattcaa aaccacccct tccggagcca catacaggc agggtgggt      240
gaaaaagccc gagccgatgc gaaaattatc ctaaaggca tcgttaaccg catccaaacc     300
gaagaaaagc tggaatccaa ctcgaccgta tggcaaaagc aggccggaag cggcagcacg     360
gttgaaacgc tgaagctacc gagctttgaa gggccggcac tgcctaagct gaccgctccc     420
ggcggctata tcgccgacat ccccaaaggc aacctcaaaa ccgaaatcga aagctggcc      480
aaacagcccg aatatgccta tctgaaacag cttcagacgg tcaaggacgt gaactggaac     540
caagtacagc tcgcttacga caatgggac tataaacagg aaggcctaac cggagccgga     600
gccgcaatta tcgcactggc cgttaccgtg gtcacctcag gcgcaggaac cggagccgta     660
ttgggattaa acgtgcggc cgccgccgca accgatgcag catttgcctc tttggccagc     720
caggcttccg tatcgttcat caacaacaaa ggcaatatcg gtaacaccct gaaagagctg     780
ggcagaagca gcacggtgaa aaatctgatg gttgccgtcg ctaccgcagg cgtagccgac     840
aaaatcggtg cttcggcact gaacaatgtc agcgataagc agtggatcaa caacctgacc     900
gtcaacctgg ccaatgcggg cagtgccgca ctgattaata ccgctgtcaa cggcggcagc     960
ctgaaagaca atctggaagc gaatatcctt gcggctttgg tgaatactgc gcatggagag    1020
gcagcaagta aaatcaaaca gttggatcag cactacattg cccataagat tgcccatgcc    1080
atagcgggct gtgcggcagc ggcggcgaat aagggcaagt gtcaagatgg tgcgatcggt    1140
gcggcggtcg gtgaaatcct tggcgaaacc ctactggacg cagagaccc tggcagcctg    1200
aatgtgaagg acagggcaaa atcattgct aaggcgaagc tggcagcagg gcggttgcg      1260
gcgttgagta aggggatgt gagtacggcg gcgaatgcgg ctgctgtggc ggtagagaat    1320
aattctttaa atgatataca ggatcgtttg ttgagtggaa attatgcttt atgtatagt      1380
gcaggaggag cagaaagctt ttgtgagtct tatcgaccac tgggcttgcc acactttgta    1440
agtgtttcag gagaaatgaa attacctaat aaattcggga atcgtatggt taatggaaaa    1500
ttaattatta acactagaaa tggcaatgta tatttctctg taggtaaaat atggagtact    1560
gtaaaatcaa caaatcaaa tataagtggg gtatctgtcg gttgggtttt aaatgtttcc     1620
cctaatgatt atttaaaaga agcatctatg aatgatttca gaaatagtaa tcaaaataaa    1680
```

```
gcctatgcag aaatgatttc ccagactttg gtaggtgaga gtgttggtgg tagtctttgt    1740
ctgacaagag cctgcttttc ggtaagttca acaatatcta aatctaaatc tccttttaaa    1800
gattcaaaaa ttattgggga aatcggtttg ggaagtggtg ttgctgcagg agtagaaaaa    1860
acaatataca taggtaacat aaaagatatt gataaattta ttagtgcaaa cataaaaaaa    1920
tag                                                                 1923

<210> SEQ ID NO 20
<211> LENGTH: 640
<212> TYPE: PRT
<213> ORGANISM: Neisseria meningitidis

<400> SEQUENCE: 20

Met Gln Leu Leu Ala Ala Glu Gly Ile His Gln His Gln Leu Asn Val
 1               5                  10                  15

Gln Lys Ser Thr Arg Phe Ile Gly Ile Lys Val Gly Lys Ser Asn Tyr
             20                  25                  30

Ser Lys Asn Glu Leu Asn Glu Thr Lys Leu Pro Val Arg Val Ile Ala
         35                  40                  45

Gln Thr Ala Lys Thr Arg Ser Gly Trp Asp Thr Val Leu Glu Gly Thr
     50                  55                  60

Glu Phe Lys Thr Thr Leu Ser Gly Ala Asp Ile Gln Ala Gly Val Gly
 65                  70                  75                  80

Glu Lys Ala Arg Ala Asp Ala Lys Ile Ile Leu Lys Gly Ile Val Asn
                 85                  90                  95

Arg Ile Gln Thr Glu Glu Lys Leu Glu Ser Asn Ser Thr Val Trp Gln
            100                 105                 110

Lys Gln Ala Gly Ser Gly Ser Thr Val Glu Thr Leu Lys Leu Pro Ser
        115                 120                 125

Phe Glu Gly Pro Ala Leu Pro Lys Leu Thr Ala Pro Gly Gly Tyr Ile
    130                 135                 140

Ala Asp Ile Pro Lys Gly Asn Leu Lys Thr Glu Ile Glu Lys Leu Ala
145                 150                 155                 160

Lys Gln Pro Glu Tyr Ala Tyr Leu Lys Gln Leu Gln Thr Val Lys Asp
                165                 170                 175

Val Asn Trp Asn Gln Val Gln Leu Ala Tyr Asp Lys Trp Asp Tyr Lys
            180                 185                 190

Gln Glu Gly Leu Thr Gly Ala Gly Ala Ala Ile Ile Ala Leu Ala Val
        195                 200                 205

Thr Val Val Thr Ser Gly Ala Gly Thr Gly Ala Val Leu Gly Leu Asn
    210                 215                 220

Gly Ala Ala Ala Ala Thr Asp Ala Ala Phe Ala Ser Leu Ala Ser
225                 230                 235                 240

Gln Ala Ser Val Ser Phe Ile Asn Asn Lys Gly Asn Ile Gly Asn Thr
                245                 250                 255

Leu Lys Glu Leu Gly Arg Ser Ser Thr Val Lys Asn Leu Met Val Ala
            260                 265                 270

Val Ala Thr Ala Gly Val Ala Asp Lys Ile Gly Ala Ser Ala Leu Asn
        275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305                 310                 315                 320
```

-continued

```
Leu Lys Asp Asn Leu Glu Ala Asn Ile Leu Ala Ala Leu Val Asn Thr
            325                 330                 335

Ala His Gly Glu Ala Ala Ser Lys Ile Lys Gln Leu Asp Gln His Tyr
            340                 345                 350

Ile Ala His Lys Ile Ala His Ala Ile Ala Gly Cys Ala Ala Ala Ala
            355                 360                 365

Ala Asn Lys Gly Lys Cys Gln Asp Gly Ala Ile Gly Ala Ala Val Gly
            370                 375                 380

Glu Ile Leu Gly Glu Thr Leu Leu Asp Gly Arg Asp Pro Gly Ser Leu
385                 390                 395                 400

Asn Val Lys Asp Arg Ala Lys Ile Ile Ala Lys Ala Lys Leu Ala Ala
            405                 410                 415

Gly Ala Val Ala Ala Leu Ser Lys Gly Asp Val Ser Thr Ala Ala Asn
            420                 425                 430

Ala Ala Ala Val Ala Val Glu Asn Asn Ser Leu Asn Asp Ile Gln Asp
            435                 440                 445

Arg Leu Leu Ser Gly Asn Tyr Ala Leu Cys Met Ser Ala Gly Gly Ala
450                 455                 460

Glu Ser Phe Cys Glu Ser Tyr Arg Pro Leu Gly Leu Pro His Phe Val
465                 470                 475                 480

Ser Val Ser Gly Glu Met Lys Leu Pro Asn Lys Phe Gly Asn Arg Met
            485                 490                 495

Val Asn Gly Lys Leu Ile Ile Asn Thr Arg Asn Gly Asn Val Tyr Phe
            500                 505                 510

Ser Val Gly Lys Ile Trp Ser Thr Val Lys Ser Thr Lys Ser Asn Ile
            515                 520                 525

Ser Gly Val Ser Val Gly Trp Val Leu Asn Val Ser Pro Asn Asp Tyr
            530                 535                 540

Leu Lys Glu Ala Ser Met Asn Asp Phe Arg Asn Ser Asn Gln Asn Lys
545                 550                 555                 560

Ala Tyr Ala Glu Met Ile Ser Gln Thr Leu Val Gly Glu Ser Val Gly
            565                 570                 575

Gly Ser Leu Cys Leu Thr Arg Ala Cys Phe Ser Val Ser Ser Thr Ile
            580                 585                 590
Ser Lys Ser Lys Ser Pro Phe Lys Asp Ser Lys Ile Ile Gly Glu Ile
            595                 600                 605
Gly Leu Gly Ser Gly Val Ala Ala Gly Val Glu Lys Thr Ile Tyr Ile
            610                 615                 620

Gly Asn Ile Lys Asp Ile Asp Lys Phe Ile Ser Ala Asn Ile Lys Lys
625                 630                 635                 640
```

<210> SEQ ID NO 21
<211> LENGTH: 2291
<212> TYPE: DNA
<213> ORGANISM: Neisseria meningitidis
<220> FEATURE:
<221> NAME/KEY: misc_feature
<222> LOCATION: (1)
<223> OTHER INFORMATION: any nucleotide
<221> NAME/KEY: misc_feature
<222> LOCATION: (85)
<223> OTHER INFORMATION: any nucleotide
<221> NAME/KEY: misc_feature
<222> LOCATION: (149)
<223> OTHER INFORMATION: any nucleotide
<221> NAME/KEY: misc_feature
<222> LOCATION: (238)
<223> OTHER INFORMATION: any nucleotide
<221> NAME/KEY: misc_feature
<222> LOCATION: (426)

-continued

```
<223> OTHER INFORMATION: any nucleotide
<221> NAME/KEY: misc_feature
<222> LOCATION: (679)
<223> OTHER INFORMATION: any nucleotide
<221> NAME/KEY: misc_feature
<222> LOCATION: (863)
<223> OTHER INFORMATION: any nucleotide
<221> NAME/KEY: misc_feature
<222> LOCATION: (971)
<223> OTHER INFORMATION: any nucleotide
<221> NAME/KEY: misc_feature
<222> LOCATION: (1336)
<223> OTHER INFORMATION: any nucleotide
<221> NAME/KEY: misc_feature
<222> LOCATION: (1388)
<223> OTHER INFORMATION: any nucleotide
<221> NAME/KEY: misc_feature
<222> LOCATION: (1837)
<223> OTHER INFORMATION: any nucleotide
<221> NAME/KEY: misc_feature
<222> LOCATION: (1909)
<223> OTHER INFORMATION: any nucleotide
<221> NAME/KEY: misc_feature
<222> LOCATION: (1939)
<223> OTHER INFORMATION: any nucleotide
<221> NAME/KEY: misc_feature
<222> LOCATION: (1941)
<223> OTHER INFORMATION: any nucleotide
<221> NAME/KEY: misc_feature
<222> LOCATION: (1959)
<223> OTHER INFORMATION: any nucleotide
<221> NAME/KEY: misc_feature
<222> LOCATION: (2079)
<223> OTHER INFORMATION: any nucleotide
<221> NAME/KEY: misc_feature
<222> LOCATION: (2084)..(2085)
<223> OTHER INFORMATION: any nucleotide
<221> NAME/KEY: misc_feature
<222> LOCATION: (2113)
<223> OTHER INFORMATION: any nucleotide
<221> NAME/KEY: misc_feature
<222> LOCATION: (2120)
<223> OTHER INFORMATION: any nucleotide
<221> NAME/KEY: misc_feature
<222> LOCATION: (2236)..(2238)
<223> OTHER INFORMATION: any nucleotide
<221> NAME/KEY: misc_feature
<222> LOCATION: (2242)
<223> OTHER INFORMATION: any nucleotide
<221> NAME/KEY: misc_feature
<222> LOCATION: (2244)
<223> OTHER INFORMATION: any nucleotide

<400> SEQUENCE: 21
ntgcaactgc tggcagaaga aggcatccac aagcacgagt tggatgtcca aaaaagccgc      60
cgctttatcg gcatcaaggt aggtnagagc aattacagta aaaacgaact gaacgaaacc     120
aaattgcctg tccgcgtcgt cgcccaaant gcagccaccc gttcaggctg ggataccgtg     180
ctcgaaggta ccgaattcaa aaccacgctg gccggtgccg acattcaggc aggtgtangc     240
gaaaaagccc gtgtcgatgc gaaaattatc ctcaaaggca ttgtgaaccg tatccagtcg     300
gaagaaaaat tagaaaccaa ctcaaccgta tggcagaaac aggccggacg cggcagcact     360
atcgaaacgc taaaactgcc cagcttcgaa agccctactc cgcccaaatt gtccgcaccc     420
ggcggntata tcgtcgacat tccgaaaggc aatctgaaaa ccgaaatcga aagctgtcc      480 aaacagcccg agtatgccta tctgaaacag ctccaagtag cgaaaaacat caactggaat     540
caggtgcagc ttgcttacga cagatgggac tacaaacagg agggcttaac cgaagcaggt     600
gcggcgatta tcgcactggc cgttaccgtg gtcacctcag gcgcaggaac cggagccgta     660
ttgggattaa acggtgcgnc cgccgccgca accgatgcag cattcgcctc tttggccagc     720
```

-continued

```
caggcttccg tatcgttcat caacaacaaa ggcgatgtcg gcaaaccct gaaagagctg     780 ggcagaagca gcacggtgaa aaatctggtg gttgccgccg ctaccgcagg cgtagccgac    840
aaaatcggcg cttcggcact gancaatgtc agcgataagc agtggatcaa caacctgacc    900
gtcaacctag ccaatgcggg cagtgccgca ctgattaata ccgctgtcaa cggcggcagc    960
ctgaaagaca ntctggaagc gaatatcctt gcggctttgg tcaataccgc gcatggagaa   1020
gcagccagta aaatcaaaca gttggatcag cactacatag tccacaagat tgcccatgcc   1080
atagcgggct gtgcggcagc ggcggcgaat aagggcaagt gtcaggatgg tgcgataggt   1140
gcggctgtgg gcgagatagt cggggaggct ttgacaaacg gcaaaaatcc tgacactttg   1200
acagctaaag aacgcgaaca gattttggca tacagcaaac tggttgccgg tacggtaagc   1260
ggtgtggtcg gcggcgatgt aaatgcggcg gcgaatgcgg ctgaggtagc ggtgaaaaat   1320
aatcagctta gcgacnaaga gggtagagaa tttgataacg aaatgactgc atgcgccaaa   1380
cagaatantc ctcaactgtg cagaaaaaat actgtaaaaa agtatcaaaa tgttgctgat   1440
aaaagacttg ctgcttcgat tgcaatatgt acggatatat cccgtagtac tgaatgtaga   1500
acaatcagaa acaacatttt gatcgatagt agaagccttc attcatcttg ggaagcaggt   1560
ctaattggta agatgatga atggtataaa ttattcagca aatcttacac ccaagcagat   1620
ttggctttac agtcttatca tttgaatact gctgctaaat cttggcttca atcgggcaat   1680
acaaagcctt tatccgaatg gatgtccgac caaggttata cacttatttc aggagttaat   1740
cctagattca ttccaatacc aagagggttt gtaaaacaaa atacacctat tactaatgtc   1800
aaatacccgg aaggcatcag tttcgataca aacctanaaa gacatctggc aaatgctgat   1860
ggttttagtc aagaacaggg cattaaagga gcccataacc gcaccaatnt tatggcagaa   1920
ctaaattcac gaggaggang ngtaaaatct gaaacccana ctgatattga aggcattacc   1980
cgaattaaat atgagattcc tacactagac aggacaggta aacctgatgg tggatttaag   2040
gaaatttcaa gtataaaaac tgtttataat cctaaaaant tttnngatga taaaatactt   2100
caaatggctc aanatgctgn ttcacaagga tattcaaaag cctctaaaat tgctcaaaat   2160
gaaagaacta aatcaatatc ggaaagaaaa aatgtcattc aattctcaga aacctttgac   2220
ggaatcaaat ttagannnta tntngatgta aatacaggaa gaattacaaa cattcaccca   2280
gaataattta a                                                         2291
```

<210> SEQ ID NO 22
<211> LENGTH: 761
<212> TYPE: PRT
<213> ORGANISM: Neisseria meningitidis
<220> FEATURE:
<221> NAME/KEY: SITE
<222> LOCATION: (1)
<223> OTHER INFORMATION: unknown
<221> NAME/KEY: SITE
<222> LOCATION: (29)
<223> OTHER INFORMATION: unknown
<221> NAME/KEY: SITE
<222> LOCATION: (50)
<223> OTHER INFORMATION: unknown
<221> NAME/KEY: SITE
<222> LOCATION: (80)
<223> OTHER INFORMATION: unknown
<221> NAME/KEY: SITE
<222> LOCATION: (227)
<223> OTHER INFORMATION: unknown
<221> NAME/KEY: SITE
<222> LOCATION: (288)
<223> OTHER INFORMATION: unknown
<221> NAME/KEY: SITE

```
<222> LOCATION: (324)
<223> OTHER INFORMATION: unknown
<221> NAME/KEY: SITE
<222> LOCATION: (446)
<223> OTHER INFORMATION: unknown
<221> NAME/KEY: SITE
<222> LOCATION: (463)
<223> OTHER INFORMATION: unknown
<221> NAME/KEY: SITE
<222> LOCATION: (613)
<223> OTHER INFORMATION: unknown
<221> NAME/KEY: SITE
<222> LOCATION: (637)
<223> OTHER INFORMATION: unknown
<221> NAME/KEY: SITE
<222> LOCATION: (647)
<223> OTHER INFORMATION: unknown
<221> NAME/KEY: SITE
<222> LOCATION: (653)
<223> OTHER INFORMATION: unknown
<221> NAME/KEY: SITE
<222> LOCATION: (693)
<223> OTHER INFORMATION: unknown
<221> NAME/KEY: SITE
<222> LOCATION: (695)
<223> OTHER INFORMATION: unknown
<221> NAME/KEY: SITE
<222> LOCATION: (705)
<223> OTHER INFORMATION: unknown
<221> NAME/KEY: SITE
<222> LOCATION: (707)
<223> OTHER INFORMATION: unknown
<221> NAME/KEY: SITE
<222> LOCATION: (746)
<223> OTHER INFORMATION: unknown
<221> NAME/KEY: SITE
<222> LOCATION: (748)
<223> OTHER INFORMATION: unknown

<400> SEQUENCE: 22

Xaa Gln Leu Leu Ala Glu Glu Gly Ile His Lys His Glu Leu Asp Val
 1               5                  10                  15

Gln Lys Ser Arg Arg Phe Ile Gly Ile Lys Val Gly Xaa Ser Asn Tyr
            20                  25                  30

Ser Lys Asn Glu Leu Asn Glu Thr Lys Leu Pro Val Arg Val Val Ala
        35                  40                  45

Gln Xaa Ala Ala Thr Arg Ser Gly Trp Asp Thr Val Leu Glu Gly Thr
    50                  55                  60

Glu Phe Lys Thr Thr Leu Ala Gly Ala Asp Ile Gln Ala Gly Val Xaa
65                  70                  75                  80

Glu Lys Ala Arg Val Asp Ala Lys Ile Ile Leu Lys Gly Ile Val Asn
                85                  90                  95

Arg Ile Gln Ser Glu Glu Lys Leu Glu Thr Asn Ser Thr Val Trp Gln
            100                 105                 110

Lys Gln Ala Gly Arg Gly Ser Thr Ile Glu Thr Leu Lys Leu Pro Ser
        115                 120                 125

Phe Glu Ser Pro Thr Pro Lys Leu Ser Ala Pro Gly Gly Tyr Ile
    130                 135                 140

Val Asp Ile Pro Lys Gly Asn Leu Lys Thr Glu Ile Glu Lys Leu Ser
145                 150                 155                 160

Lys Gln Pro Glu Tyr Ala Tyr Leu Lys Gln Leu Gln Val Ala Lys Asn
                165                 170                 175

Ile Asn Trp Asn Gln Val Gln Leu Ala Tyr Asp Arg Trp Asp Tyr Lys
            180                 185                 190

Gln Glu Gly Leu Thr Glu Ala Gly Ala Ala Ile Ile Ala Leu Ala Val
        195                 200                 205
```

```
Thr Val Val Thr Ser Gly Ala Gly Thr Gly Ala Val Leu Gly Leu Asn
    210                 215                 220

Gly Ala Xaa Ala Ala Ala Thr Asp Ala Ala Phe Ala Ser Leu Ala Ser
225             230                 235                 240

Gln Ala Ser Val Ser Phe Ile Asn Asn Lys Gly Asp Val Gly Lys Thr
                245                 250                 255

Leu Lys Glu Leu Gly Arg Ser Ser Thr Val Lys Asn Leu Val Val Ala
            260                 265                 270

Ala Ala Thr Ala Gly Val Ala Asp Lys Ile Gly Ala Ser Ala Leu Xaa
            275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305             310                 315                 320

Leu Lys Asp Xaa Leu Glu Ala Asn Ile Leu Ala Ala Leu Val Asn Thr
            325                 330                 335

Ala His Gly Glu Ala Ala Ser Lys Ile Lys Gln Leu Asp Gln His Tyr
            340                 345                 350

Ile Val His Lys Ile Ala His Ala Ile Ala Gly Cys Ala Ala Ala Ala
            355                 360                 365

Ala Asn Lys Gly Lys Cys Gln Asp Gly Ala Ile Gly Ala Ala Val Gly
    370                 375                 380

Glu Ile Val Gly Glu Ala Leu Thr Asn Gly Lys Asn Pro Asp Thr Leu
385                 390                 395                 400

Thr Ala Lys Glu Arg Glu Gln Ile Leu Ala Tyr Ser Lys Leu Val Ala
                405                 410                 415

Gly Thr Val Ser Gly Val Val Gly Gly Asp Val Asn Ala Ala Ala Asn
            420                 425                 430

Ala Ala Glu Val Ala Val Lys Asn Asn Gln Leu Ser Asp Xaa Glu Gly
            435                 440                 445

Arg Glu Phe Asp Asn Glu Met Thr Ala Cys Ala Lys Gln Asn Xaa Pro
    450                 455                 460

Gln Leu Cys Arg Lys Asn Thr Val Lys Lys Tyr Gln Asn Val Ala Asp
465                 470                 475                 480

Lys Arg Leu Ala Ala Ser Ile Ala Ile Cys Thr Asp Ile Ser Arg Ser
                485                 490                 495

Thr Glu Cys Arg Thr Ile Arg Lys Gln His Leu Ile Asp Ser Arg Ser
            500                 505                 510

Leu His Ser Ser Trp Glu Ala Gly Leu Ile Gly Lys Asp Asp Glu Trp
            515                 520                 525

Tyr Lys Leu Phe Ser Lys Ser Tyr Thr Gln Ala Asp Leu Ala Leu Gln
    530                 535                 540

Ser Tyr His Leu Asn Thr Ala Ala Lys Ser Trp Leu Gln Ser Gly Asn
545             550                 555                 560

Thr Lys Pro Leu Ser Glu Trp Met Ser Asp Gln Gly Tyr Thr Leu Ile
                565                 570                 575

Ser Gly Val Asn Pro Arg Phe Ile Pro Ile Pro Arg Gly Phe Val Lys
            580                 585                 590

Gln Asn Thr Pro Ile Thr Asn Val Lys Tyr Pro Glu Gly Ile Ser Phe
            595                 600                 605

Asp Thr Asn Leu Xaa Arg His Leu Ala Asn Ala Asp Gly Phe Ser Gln
610             615                 620
```

```
Glu Gln Gly Ile Lys Gly Ala His Asn Arg Thr Asn Xaa Met Ala Glu
625                 630                 635                 640

Leu Asn Ser Arg Gly Gly Xaa Val Lys Ser Glu Thr Xaa Thr Asp Ile
                645                 650                 655

Glu Gly Ile Thr Arg Ile Lys Tyr Glu Ile Pro Thr Leu Asp Arg Thr
                660                 665                 670

Gly Lys Pro Asp Gly Gly Phe Lys Glu Ile Ser Ile Lys Thr Val
            675                 680                 685

Tyr Asn Pro Lys Xaa Phe Xaa Asp Asp Lys Ile Leu Gln Met Ala Gln
            690                 695                 700

Xaa Ala Xaa Ser Gln Gly Tyr Ser Lys Ala Ser Lys Ile Ala Gln Asn
705                 710                 715                 720

Glu Arg Thr Lys Ser Ile Ser Glu Arg Lys Asn Val Ile Gln Phe Ser
                725                 730                 735

Glu Thr Phe Asp Gly Ile Lys Phe Arg Xaa Tyr Xaa Asp Val Asn Thr
                740                 745                 750

Gly Arg Ile Thr Asn Ile His Pro Glu
                755             760

<210> SEQ ID NO 23
<211> LENGTH: 336
<212> TYPE: DNA
<213> ORGANISM: Neisseria meningitidis

<400> SEQUENCE: 23
cggatcgttg taggtttgcg gatttcttgc gccgtagtca ccgtagtccc aagtataacc      60
caaggctttg tcttcgcctt tcattccgat aagggatatg acgctttggt cggtatagcc     120
gtcttgggaa cctttgtcca cccaacgcat atctgcctgc ggattctcat tgccgcttct     180
tggctgctga ttttctgcc ttcgcgtttt tcaacttcgc gcttgagggc ttcggcatat     240
ttgtcggcca acgccatttc tttcggatgc agctgcctat tgttccaatc tacattcgca     300
cccaccacag caccaccact accaccagtt gcatag                               336

<210> SEQ ID NO 24
<211> LENGTH: 111
<212> TYPE: PRT
<213> ORGANISM: Neisseria meningitidis

<400> SEQUENCE: 24

Arg Ile Val Val Gly Leu Arg Ile Ser Cys Ala Val Val Thr Val Val
1               5                   10                  15

Pro Ser Ile Thr Gln Gly Phe Val Phe Ala Phe His Ser Asp Lys Gly
                20                  25                  30

Tyr Asp Ala Leu Val Gly Ile Ala Val Leu Gly Thr Phe Val His Pro
            35                  40                  45

Thr His Ile Cys Leu Arg Ile Leu Ala Ala Ser Trp Leu Leu Ile
        50                  55                  60

Phe Leu Pro Ser Arg Phe Ser Thr Ser Arg Leu Arg Ala Ser Ala Tyr
65              70                  75                  80

Leu Ser Ala Asn Ala Ile Ser Phe Gly Cys Ser Cys Leu Leu Phe Gln
                85                  90                  95

Ser Thr Phe Ala Pro Thr Thr Ala Pro Pro Leu Pro Pro Val Ala
            100                 105                 110

<210> SEQ ID NO 25
<211> LENGTH: 1716
```

```
<212> TYPE: DNA
<213> ORGANISM: Neisseria meningitidis
<220> FEATURE:
<221> NAME/KEY: unsure
<222> LOCATION: (496)..(1542)
<223> OTHER INFORMATION: N = Unknown
<221> NAME/KEY: unsure
<222> LOCATION: (1673)..(1674)
<223> OTHER INFORMATION: N= Unknown

<400> SEQUENCE: 25
aagtttgact ttacctggtt tattccggcg gtaatcaaat accgccggtt gttttttgaa      60
gtattggtgg tgtcggtggt gttgcagctg tttgcgctga ttacgcctct gttttttcaa     120
gtggtgatgg acaaggtgct ggtacatcgg ggattctcta ctttggatgt ggtgtcggtg     180
gctttgttgg tggtgtcgct gtttgagatt gtgttgggcg gtttgcggac gtatctgttt     240
gcacatacga cttcacgtat tgatgtggaa ttgggcgcgc gtttgttccg gcatctgctt     300
tccctgcctt tatcctattt cgagcacaga cgagtgggtg atacggtggc tcgggtgcgg     360
gaattggagc agattcgcaa tttcttgacc ggtcaggcgc tgacttcggt gttggatttg     420
gcgttttcgt ttatctttct ggcggtgatg tggtattaca gctccactct gacttgggtg     480
gtattggctt cgttgnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnatttgcgc caaccggacg    1560
gtgctgatta tcgcccaccg tctgtccact gttaaaacgg cacaccggat cattgccatg    1620
gataaaggca ggattgtgga agcgggaaca cagcaggaat tgctggcgaa cgnnaacgga    1680
tattaccgct atctgtatga tttacagaac gggtag                              1716

<210> SEQ ID NO 26
<211> LENGTH: 571
<212> TYPE: PRT
<213> ORGANISM: Neisseria meningitidis
<220> FEATURE:
<221> NAME/KEY: UNSURE
<222> LOCATION: (166)..(514)
<223> OTHER INFORMATION: x = Unknown
```

```
<221> NAME/KEY: SITE
<222> LOCATION: (558)
<223> OTHER INFORMATION: unknown

<400> SEQUENCE: 26
```

| | | | | | | | | | | | | | | | |
|---|---|---|---|---|---|---|---|---|---|---|---|---|---|---|---|
| Lys | Phe | Asp | Phe | Thr | Trp | Phe | Ile | Pro | Ala | Val | Ile | Lys | Tyr | Arg | Arg |
| 1 | | | | 5 | | | | | 10 | | | | | 15 | |
| Leu | Phe | Phe | Glu | Val | Leu | Val | Val | Ser | Val | Val | Leu | Gln | Leu | Phe | Ala |
| | | | 20 | | | | | 25 | | | | | 30 | | |
| Leu | Ile | Thr | Pro | Leu | Phe | Phe | Gln | Val | Val | Met | Asp | Lys | Val | Leu | Val |
| | | 35 | | | | | 40 | | | | | 45 | | | |
| His | Arg | Gly | Phe | Ser | Thr | Leu | Asp | Val | Val | Ser | Val | Ala | Leu | Leu | Val |
| | | 50 | | | | 55 | | | | | 60 | | | | |
| Val | Ser | Leu | Phe | Glu | Ile | Val | Leu | Gly | Gly | Leu | Arg | Thr | Tyr | Leu | Phe |
| 65 | | | | | 70 | | | | | 75 | | | | | 80 |
| Ala | His | Thr | Thr | Ser | Arg | Ile | Asp | Val | Glu | Leu | Gly | Ala | Arg | Leu | Phe |
| | | | | 85 | | | | | 90 | | | | | 95 | |
| Arg | His | Leu | Leu | Ser | Leu | Pro | Leu | Ser | Tyr | Phe | Glu | His | Arg | Arg | Val |
| | | | 100 | | | | | 105 | | | | | 110 | | |
| Gly | Asp | Thr | Val | Ala | Arg | Val | Arg | Glu | Leu | Glu | Gln | Ile | Arg | Asn | Phe |
| | | 115 | | | | | 120 | | | | | 125 | | | |
| Leu | Thr | Gly | Gln | Ala | Leu | Thr | Ser | Val | Leu | Asp | Leu | Ala | Phe | Ser | Phe |
| | | 130 | | | | 135 | | | | | 140 | | | | |
| Ile | Phe | Leu | Ala | Val | Met | Trp | Tyr | Tyr | Ser | Ser | Thr | Leu | Thr | Trp | Val |
| 145 | | | | | 150 | | | | | 155 | | | | | 160 |
| Val | Leu | Ala | Ser | Leu | Xaa | Xaa | Xaa | Xaa | Xaa | Xaa | Xaa | Xaa | Xaa | Xaa | Xaa |
| | | | | 165 | | | | | 170 | | | | | 175 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 180 | | | | | 185 | | | | | 190 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 195 | | | | | 200 | | | | | 205 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 210 | | | | | 215 | | | | | 220 | | | |
| Xaa | Xaa | Xaa | Xaa | Xaa | Xaa | Xaa | Xaa | Xaa | Xaa | Xaa | Xaa | Xaa | Xaa | Xaa | Xaa |
| 225 | | | | | 230 | | | | | 235 | | | | | 240 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 245 | | | | | 250 | | | | | 255 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 260 | | | | | 265 | | | | | 270 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 275 | | | | | 280 | | | | | 285 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 290 | | | | | 295 | | | | | 300 | | | |
| Xaa | Xaa | Xaa | Xaa | Xaa | Xaa | Xaa | Xaa | Xaa | Xaa | Xaa | Xaa | Xaa | Xaa | Xaa | Xaa |
| 305 | | | | | 310 | | | | | 315 | | | | | 320 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 325 | | | | | 330 | | | | | 335 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 340 | | | | | 345 | | | | | 350 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 355 | | | | | 360 | | | | | 365 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 370 | | | | | 375 | | | | | 380 | | | |
| Xaa | Xaa | Xaa | Xaa | Xaa | Xaa | Xaa | Xaa | Xaa | Xaa | Xaa | Xaa | Xaa | Xaa | Xaa | Xaa |

-continued

```
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa Xaa
                485                 490                 495
Xaa Xaa Xaa Xaa Xaa Xaa Xaa Xaa Xaa Xaa Xaa Xaa Xaa Xaa Xaa Xaa
            500                 505                 510

Xaa Xaa Ile Cys Ala Asn Arg Thr Val Leu Ile Ile Ala His Arg Leu
        515                 520                 525
Ser Thr Val Lys Thr Ala His Arg Ile Ile Ala Met Asp Lys Gly Arg
    530                 535                 540
Ile Val Glu Ala Gly Thr Gln Gln Glu Leu Leu Ala Asn Xaa Asn Gly
545                 550                 555                 560

Tyr Tyr Arg Tyr Leu Tyr Asp Leu Gln Asn Gly
                565                 570
```

<210> SEQ ID NO 27
<211> LENGTH: 2133
<212> TYPE: DNA
<213> ORGANISM: Neisseria meningitidis

<400> SEQUENCE: 27

```
atgtctatcg tatccgcacc gctccccgcc ctttccgccc tcatcatcct cgcccattac     60
cacggcattg ccgccaatcc tgccgatata cagcatgaat tttgtacttc cgcacagagc    120
gatttaaatg aaacgcaatg gctgttagcc gccaaatctt tgggattgaa ggcaaaggta    180
gtccgccagc ctattaaacg tttggctatg gcgactttac ccgcattggt atggtgtgat    240
gacggcaacc atttcatttt ggccaaaaca gacggtgagg gtgagcatgc ccaatttttg    300
atacaggatt tggttacgaa taagtctgcg gtattgtctt ttgccgaatt ttctaacaga    360
tattcgggca aactgatatt ggttgcttcc cgcgcttcgg tattgggcag tttggcaaag    420
tttgacttta cctggtttat tccggcggta atcaaatacc gccggttgtt ttttgaagta    480
ttggtggtgt cggtggtgtt gcagctgttt gcgctgatta cgcctctgtt tttccaagtg    540
gtgatggaca aggtgctggt acatcgggga ttctctactt tggatgtggt gtcggtggct    600
ttgttggtgg tgtcgctgtt tgagattgtg ttgggcggtt tgcggacgta tctgtttgca    660
catacgactt cacgtattga tgtggaattg ggcgcgcgtt tgttccggca tctgctttcc    720
ctgcctttat cctatttcga gcacagacga gtgggtgata cggtggctcg ggtgcgggaa    780
ttggagcaga ttcgcaattt cttgaccggt caggcgctga cttcggtgtt ggatttggcg    840
ttttcgttta tctttctggc ggtgatgtgg tattacagct ccactctgac ttgggtggta    900
ttggcttcgt tgcctgccta tgcgttttgg tcggcattta tcagtccgat actgcggacg    960
cgtctgaacg ataagttcgc gcgcaatgca gacaaccagt cgtttttagt agaaagcatc   1020
actgcggtgg gtacggtaaa ggcgatggcg gtggagccgc agatgacgca gcgttgggac   1080
```

```
aatcagttgg cggcttatgt ggcttcggga tttcgggtaa cgaagttggc ggtggtcggc    1140 cagcagggggg tgcagctgat tcagaagctg gtgacggtgg cgacgttgtg gattggcgca   1200
cggctggtaa ttgagagcaa gctgacggtg gggcagctga ttgcgtttaa tatgctctcg   1260
ggacaggtgg cggcgcctgt tatccgtttg gcgcagttgt ggcaggattt ccagcaggtg   1320
gggatttcgg tggcgcgttt ggggatatt ctgaatgcgc cgaccgagaa tgcgtcttcg    1380
catttggctt tgcccgatat ccgggggag attacgttcg aacatgtcga tttccgctat    1440
aaggcggacg gcaggctgat tttgcaggat ttgaacctgc ggattcgggc ggggaagtg    1500 ctggggattg tgggacgttc ggggtcgggc aaatccacac tcaccaaatt ggtgcagcgt   1560
ctgtatgtac cggagcaggg acgggtgttg gtggacggca acgatttggc tttggccgct   1620
cctgcctggc tgcggcggca ggtcggcgtg gtcttgcagg agaatgtgct gctcaaccgc   1680
agcatacgcg acaatatcgc gctgacggat acgggtatgc cgctggaacg cattatcgaa   1740
gcagccaaac tggcgggcgc acacgagttt attatggagc tgccggaagg ctacggcacc   1800
gtggtgggcg aacaaggggc cggcttgtcg gcggacagc ggcagcgtat tgcgattgcc    1860
cgcgcgttaa tcaccaatcc gcgcattctg atttttgatg aagccaccag cgcgctggat   1920
tatgaaagtg aacagcgat tatgcagaac atgcaggcca tttgcgccaa ccggacggtg    1980
ctgattatcg cccaccgtct gtccactgtt aaaacggcac accggatcat tgccatggat   2040
aaaggcagga ttgtggaagc gggaacacag caggaattgc tggcgaagcc gaacggatat   2100
taccgctatc tgtatgattt acagaacggg tag                                2133
```

<210> SEQ ID NO 28
<211> LENGTH: 710
<212> TYPE: PRT
<213> ORGANISM: Neisseria meningitidis

<400> SEQUENCE: 28

```
Met Ser Ile Val Ser Ala Pro Leu Pro Ala Leu Ser Ala Leu Ile Ile
  1               5                  10                  15

Leu Ala His Tyr His Gly Ile Ala Ala Asn Pro Ala Asp Ile Gln His
                 20                  25                  30

Glu Phe Cys Thr Ser Ala Gln Ser Asp Leu Asn Glu Thr Gln Trp Leu
             35                  40                  45

Leu Ala Ala Lys Ser Leu Gly Leu Lys Ala Lys Val Val Arg Gln Pro
         50                  55                  60

Ile Lys Arg Leu Ala Met Ala Thr Leu Pro Ala Leu Val Trp Cys Asp
 65                  70                  75                  80

Asp Gly Asn His Phe Ile Leu Ala Lys Thr Asp Gly Glu Gly Glu His
                 85                  90                  95

Ala Gln Phe Leu Ile Gln Asp Leu Val Thr Asn Lys Ser Ala Val Leu
            100                 105                 110

Ser Phe Ala Glu Phe Ser Asn Arg Tyr Ser Gly Lys Leu Ile Leu Val
        115                 120                 125

Ala Ser Arg Ala Ser Val Leu Gly Ser Leu Ala Lys Phe Asp Phe Thr
    130                 135                 140

Trp Phe Ile Pro Ala Val Ile Lys Tyr Arg Arg Leu Phe Phe Glu Val
145                 150                 155                 160

Leu Val Val Ser Val Val Leu Gln Leu Phe Ala Leu Ile Thr Pro Leu
                165                 170                 175

Phe Phe Gln Val Val Met Asp Lys Val Leu Val His Arg Gly Phe Ser
            180                 185                 190
```

```
Thr Leu Asp Val Val Ser Val Ala Leu Leu Val Ser Leu Phe Glu
            195                 200                 205
Ile Val Leu Gly Gly Leu Arg Thr Tyr Leu Phe Ala His Thr Thr Ser
            210                 215                 220
Arg Ile Asp Val Glu Leu Gly Ala Arg Leu Phe Arg His Leu Leu Ser
225                 230                 235                 240
Leu Pro Leu Ser Tyr Phe Glu His Arg Arg Val Gly Asp Thr Val Ala
                245                 250                 255
Arg Val Arg Glu Leu Glu Gln Ile Arg Asn Phe Leu Thr Gly Gln Ala
            260                 265                 270
Leu Thr Ser Val Leu Asp Leu Ala Phe Ser Phe Ile Phe Leu Ala Val
            275                 280                 285
Met Trp Tyr Tyr Ser Ser Thr Leu Thr Trp Val Val Leu Ala Ser Leu
            290                 295                 300
Pro Ala Tyr Ala Phe Trp Ser Ala Phe Ile Ser Pro Ile Leu Arg Thr
305                 310                 315                 320
Arg Leu Asn Asp Lys Phe Ala Arg Asn Ala Asp Asn Gln Ser Phe Leu
                325                 330                 335
Val Glu Ser Ile Thr Ala Val Gly Thr Val Lys Ala Met Ala Val Glu
            340                 345                 350
Pro Gln Met Thr Gln Arg Trp Asp Asn Gln Leu Ala Ala Tyr Val Ala
            355                 360                 365
Ser Gly Phe Arg Val Thr Lys Leu Ala Val Val Gly Gln Gln Gly Val
            370                 375                 380
Gln Leu Ile Gln Lys Leu Val Thr Val Ala Thr Leu Trp Ile Gly Ala
385                 390                 395                 400
Arg Leu Val Ile Glu Ser Lys Leu Thr Val Gly Gln Leu Ile Ala Phe
                405                 410                 415
Asn Met Leu Ser Gly Gln Val Ala Ala Pro Val Ile Arg Leu Ala Gln
            420                 425                 430
Leu Trp Gln Asp Phe Gln Gln Val Gly Ile Ser Val Ala Arg Leu Gly
            435                 440                 445
Asp Ile Leu Asn Ala Pro Thr Glu Asn Ala Ser Ser His Leu Ala Leu
450                 455                 460
Pro Asp Ile Arg Gly Glu Ile Thr Phe Glu His Val Asp Phe Arg Tyr
465                 470                 475                 480
Lys Ala Asp Gly Arg Leu Ile Leu Gln Asp Leu Asn Leu Arg Ile Arg
                485                 490                 495
Ala Gly Glu Val Leu Gly Ile Val Gly Arg Ser Gly Ser Gly Lys Ser
            500                 505                 510
Thr Leu Thr Lys Leu Val Gln Arg Leu Tyr Val Pro Glu Gln Gly Arg
            515                 520                 525
Val Leu Val Asp Gly Asn Asp Leu Ala Leu Ala Ala Pro Ala Trp Leu
            530                 535                 540
Arg Arg Gln Val Gly Val Val Leu Gln Glu Asn Val Leu Leu Asn Arg
545                 550                 555                 560
Ser Ile Arg Asp Asn Ile Ala Leu Thr Asp Thr Gly Met Pro Leu Glu
                565                 570                 575
Arg Ile Ile Glu Ala Ala Lys Leu Ala Gly Ala His Glu Phe Ile Met
            580                 585                 590
Glu Leu Pro Glu Gly Tyr Gly Thr Val Val Gly Glu Gln Gly Ala Gly
            595                 600                 605
```

```
Leu Ser Gly Gly Gln Arg Gln Arg Ile Ala Ile Ala Arg Ala Leu Ile
    610                 615                 620

Thr Asn Pro Arg Ile Leu Ile Phe Asp Glu Ala Thr Ser Ala Leu Asp
625                 630                 635                 640

Tyr Glu Ser Glu Arg Ala Ile Met Gln Asn Met Gln Ala Ile Cys Ala
                645                 650                 655

Asn Arg Thr Val Leu Ile Ile Ala His Arg Leu Ser Thr Val Lys Thr
            660                 665                 670

Ala His Arg Ile Ile Ala Met Asp Lys Gly Arg Ile Val Glu Ala Gly
            675                 680                 685

Thr Gln Gln Glu Leu Leu Ala Lys Pro Asn Gly Tyr Tyr Arg Tyr Leu
    690                 695                 700

Tyr Asp Leu Gln Asn Gly
705                 710

<210> SEQ ID NO 29
<211> LENGTH: 2133
<212> TYPE: DNA
<213> ORGANISM: Neisseria meningitidis

<400> SEQUENCE: 29
atgtctatcg tatccgcacc gctccccgcc ctttccgccc tcatcatcct cgcccattac      60
cacggcattg ccgccaatcc tgccgatata cagcatgaat tttgtacttc cgcacagagc     120
gatttaaatg aaacgcaatg gctgttagcc gccaaatctt tgggattgaa ggcaaaggta     180
gtccgccagc ctattaaacg tttggctatg gcgactttac ccgcattggt atggtgtgat     240
gacggcaacc atttatttt ggctaaaaca gacggtgggg gtgagcatgc ccaatatcta     300
atacaggatt taactacgaa taagtctgcg gtattgtctt ttgccgaatt ttctaacaga     360
tattcgggca aactgatatt ggttgcttcc cgcgcttcgg tattgggcag tttggcaaag     420 tttgactta cctggtttat tccggcggta atcaaatacc gccggttgtt ttttgaagta     480
ttggtggtgt cggtggtgtt gcagctgttt gcgctgatta cgcctctgtt tttccaagtg     540
gtgatggaca aggtgctggt acatcgggga ttctctactt tggatgtggt gtcggtggct     600
ttgttggtgg tgtcgctgtt tgagattgtg tgggcggtt tgcggacgta tctgtttgca     660
catacgactt cacgtattga tgtggaattg ggcgcgcgtt tgttccggca tctgctttcc     720
ctgcctttat cctatttcga gcacagacga gtgggtgata cggtggctcg ggtgcgggaa     780
ttggagcaga ttcgcaattt cttgaccggt caggcgctga cttcggtgtt ggatttggcg     840
ttttcgttta tctttctggc ggtgatgtgg tattacagct ccactctgac ttgggtggta     900
ttggcttcgt tgcctgccta tgcgttttgg tcggcattta tcagtccgat actgcggacg     960
cgtctgaacg ataagttcgc gcgcaatgca gacaaccagt cgttttttagt agaaagcatc    1020 actgcggtgg gtacggtaaa ggcgatggcg gtggagccgc agatgacgca gcgttgggac    1080
aatcagttgg cggcttatgt ggcttcggga tttcgggtaa cgaagttggc ggtggtcggc    1140 cagcagggggg tgcagctgat tcagaagctg gtgacggtgg cgacgttgtg gattggcgca    1200
cggctggtaa ttgagagcaa gctgacggtg gggcagctga ttgcgtttaa tatgctctcg    1260
ggacaggtgg cggcgcctgt tatccgtttg gcgcagttgt ggcaggattt ccagcaggtg    1320
gggatttcgg tggcgcgttt gggggatatt ctgaatgcgc cgaccgagaa tgcgtcttcg    1380
catttggctt tgcccgatat ccgggggggag attacgttcg aacatgtcga tttccgctat    1440
aaggcggacg gcaggctgat tttgcaggat ttgaacctgc ggattcgggc gggggaagtg    1500
```

-continued

```
ctggggattg tgggacgttc ggggtcgggc aaatccacac tcaccaaatt ggtgcagcgt    1560
ctgtatgtac cggcgcaggg acgggtgttg gtggacggca acgatttggc tttggccgct    1620
cctgcttggc tgcggcggca ggtcggcgtg gtcttgcagg agaatgtgct gctcaaccgc    1680
agcatacgcg acaatatcgc gctgacggat acgggtatgc cgctggaacg cattatcgaa    1740
gcagccaaac tggcgggcgc acacgagttt attatggagc tgccggaagg ctacggcacc    1800
gtggtgggcg aacaaggggc cggcttgtcg ggcggacagc ggcagcgtat tgcgattgcc    1860
cgcgcgttaa tcaccaatcc gcgcattctg attttttgatg aagccaccag cgcgctggat    1920
tatgaaagtg aacgagcgat tatgcagaac atgcaggcca tttgcgccaa ccggacggtg    1980
ctgattatcg cccaccgtct gtccactgtt aaaacggcac accggatcat tgccatggat    2040
aaaggcagga ttgtggaagc gggaacacag caggaattgc tggcgaagcc gaacggatat    2100
taccgctatc tgtatgattt acagaacggg tag                                  2133
```

<210> SEQ ID NO 30
<211> LENGTH: 710
<212> TYPE: PRT
<213> ORGANISM: Neisseria meningitidis

<400> SEQUENCE: 30

```
Met Ser Ile Val Ser Ala Pro Leu Pro Ala Leu Ser Ala Leu Ile Ile
  1               5                  10                  15

Leu Ala His Tyr His Gly Ile Ala Ala Asn Pro Ala Asp Ile Gln His
                 20                  25                  30

Glu Phe Cys Thr Ser Ala Gln Ser Asp Leu Asn Glu Thr Gln Trp Leu
             35                  40                  45

Leu Ala Ala Lys Ser Leu Gly Leu Lys Ala Lys Val Arg Gln Pro
         50                  55                  60

Ile Lys Arg Leu Ala Met Ala Thr Leu Pro Ala Leu Val Trp Cys Asp
 65                  70                  75                  80

Asp Gly Asn His Phe Ile Leu Ala Lys Thr Asp Gly Gly Glu His
                 85                  90                  95

Ala Gln Tyr Leu Ile Gln Asp Leu Thr Thr Asn Lys Ser Ala Val Leu
            100                 105                 110

Ser Phe Ala Glu Phe Ser Asn Arg Tyr Ser Gly Lys Leu Ile Leu Val
        115                 120                 125

Ala Ser Arg Ala Ser Val Leu Gly Ser Leu Ala Lys Phe Asp Phe Thr
    130                 135                 140

Trp Phe Ile Pro Ala Val Ile Lys Tyr Arg Arg Leu Phe Phe Glu Val
145                 150                 155                 160

Leu Val Val Ser Val Val Leu Gln Leu Phe Ala Leu Ile Thr Pro Leu
                165                 170                 175

Phe Phe Gln Val Val Met Asp Lys Val Leu Val His Arg Gly Phe Ser
            180                 185                 190

Thr Leu Asp Val Val Ser Val Ala Leu Leu Val Ser Leu Phe Glu
        195                 200                 205

Ile Val Leu Gly Gly Leu Arg Thr Tyr Leu Phe Ala His Thr Thr Ser
    210                 215                 220

Arg Ile Asp Val Glu Leu Gly Ala Arg Leu Phe Arg His Leu Leu Ser
225                 230                 235                 240

Leu Pro Leu Ser Tyr Phe Glu His Arg Val Gly Asp Thr Val Ala
                245                 250                 255

Arg Val Arg Glu Leu Glu Gln Ile Arg Asn Phe Leu Thr Gly Gln Ala
```

-continued

```
                260                 265                 270
Leu Thr Ser Val Leu Asp Leu Ala Phe Ser Phe Ile Phe Leu Ala Val
            275                 280                 285
Met Trp Tyr Tyr Ser Ser Thr Leu Thr Trp Val Val Leu Ala Ser Leu
            290                 295                 300
Pro Ala Tyr Ala Phe Trp Ser Ala Phe Ile Ser Pro Ile Leu Arg Thr
305                 310                 315                 320
Arg Leu Asn Asp Lys Phe Ala Arg Asn Ala Asp Asn Gln Ser Phe Leu
            325                 330                 335
Val Glu Ser Ile Thr Ala Val Gly Thr Val Lys Ala Met Ala Val Glu
            340                 345                 350
Pro Gln Met Thr Gln Arg Trp Asp Asn Gln Leu Ala Ala Tyr Val Ala
            355                 360                 365
Ser Gly Phe Arg Val Thr Lys Leu Ala Val Val Gly Gln Gln Gly Val
            370                 375                 380
Gln Leu Ile Gln Lys Leu Val Thr Val Ala Thr Leu Trp Ile Gly Ala
385                 390                 395                 400
Arg Leu Val Ile Glu Ser Lys Leu Thr Val Gly Gln Leu Ile Ala Phe
                405                 410                 415
Asn Met Leu Ser Gly Gln Val Ala Ala Pro Val Ile Arg Leu Ala Gln
            420                 425                 430
Leu Trp Gln Asp Phe Gln Gln Val Gly Ile Ser Val Ala Arg Leu Gly
            435                 440                 445
Asp Ile Leu Asn Ala Pro Thr Glu Asn Ala Ser Ser His Leu Ala Leu
            450                 455                 460
Pro Asp Ile Arg Gly Glu Ile Thr Phe Glu His Val Asp Phe Arg Tyr
465                 470                 475                 480
Lys Ala Asp Gly Arg Leu Ile Leu Gln Asp Leu Asn Leu Arg Ile Arg
            485                 490                 495
Ala Gly Glu Val Leu Gly Ile Val Gly Arg Ser Gly Ser Gly Lys Ser
            500                 505                 510
Thr Leu Thr Lys Leu Val Gln Arg Leu Tyr Val Pro Ala Gln Gly Arg
            515                 520                 525
Val Leu Val Asp Gly Asn Asp Leu Ala Leu Ala Ala Pro Ala Trp Leu
            530                 535                 540
Arg Arg Gln Val Gly Val Val Leu Gln Glu Asn Val Leu Leu Asn Arg
545                 550                 555                 560
Ser Ile Arg Asp Asn Ile Ala Leu Thr Asp Thr Gly Met Pro Leu Glu
                565                 570                 575
Arg Ile Ile Glu Ala Ala Lys Leu Ala Gly Ala His Glu Phe Ile Met
            580                 585                 590
Glu Leu Pro Glu Gly Tyr Gly Thr Val Val Gly Glu Gln Gly Ala Gly
            595                 600                 605
Leu Ser Gly Gly Gln Arg Gln Arg Ile Ala Ile Ala Arg Ala Leu Ile
            610                 615                 620
Thr Asn Pro Arg Ile Leu Ile Phe Asp Glu Ala Thr Ser Ala Leu Asp
625                 630                 635                 640
Tyr Glu Ser Glu Arg Ala Ile Met Gln Asn Met Gln Ala Ile Cys Ala
                645                 650                 655
Asn Arg Thr Val Leu Ile Ile Ala His Arg Leu Ser Thr Val Lys Thr
            660                 665                 670
Ala His Arg Ile Ile Ala Met Asp Lys Gly Arg Ile Val Glu Ala Gly
            675                 680                 685
```

```
Thr Gln Gln Glu Leu Leu Ala Lys Pro Asn Gly Tyr Tyr Arg Tyr Leu
        690                 695                 700

Tyr Asp Leu Gln Asn Gly
705                 710

<210> SEQ ID NO 31
<211> LENGTH: 186
<212> TYPE: DNA
<213> ORGANISM: Neisseria meningitidis

<400> SEQUENCE: 31
atgaaatact tgatccgcac cgccttactc gcagtcgcag ccgccggcat ctacgcctgc      60
caaccgcaat ccgaagccgc agtgcaagtc aaggctgaaa acagcctgac cgctatgcgc     120
ttagccgtcg ccgacaaaca ggcagagatt gacgggttga acgcccaaak sgacgccgaa    180
atcaga                                                                186

<210> SEQ ID NO 32
<211> LENGTH: 62
<212> TYPE: PRT
<213> ORGANISM: Neisseria meningitidis
<220> FEATURE:
<221> NAME/KEY: SITE
<222> LOCATION: (57)
<223> OTHER INFORMATION: unknown

<400> SEQUENCE: 32

Met Lys Tyr Leu Ile Arg Thr Ala Leu Leu Ala Val Ala Ala Ala Gly
  1               5                  10                  15

Ile Tyr Ala Cys Gln Pro Gln Ser Glu Ala Ala Val Gln Val Lys Ala
                 20                  25                  30

Glu Asn Ser Leu Thr Ala Met Arg Leu Ala Val Ala Asp Lys Gln Ala
            35                  40                  45

Glu Ile Asp Gly Leu Asn Ala Gln Xaa Asp Ala Glu Ile Arg
        50                  55                  60

<210> SEQ ID NO 33
<211> LENGTH: 261
<212> TYPE: DNA
<213> ORGANISM: Neisseria meningitidis

<400> SEQUENCE: 33
atgaaatact tgatccgcac cgccttactc gcagtcgcag ccgccggcat ctacgcctgc      60
caaccgcaat ccgaagccgc agtgcaagtc aaggctgaaa acagcctgac cgctatgcgc     120
ttagccgtcg ccgacaaaca ggcagagatt gacgggttga acgcccaaat cgacgccgaa    180
atcagacaac gcgaagccga agaattgaaa gactaccgat ggatacacgg cgacgcggaa    240
gtgccggagc tggaaaaatg a                                              261

<210> SEQ ID NO 34
<211> LENGTH: 86
<212> TYPE: PRT
<213> ORGANISM: Neisseria meningitidis

<400> SEQUENCE: 34

Met Lys Tyr Leu Ile Arg Thr Ala Leu Leu Ala Val Ala Ala Ala Gly
  1               5                  10                  15

Ile Tyr Ala Cys Gln Pro Gln Ser Glu Ala Ala Val Gln Val Lys Ala
                 20                  25                  30
```

Glu Asn Ser Leu Thr Ala Met Arg Leu Ala Val Ala Asp Lys Gln Ala
             35                  40                  45

Glu Ile Asp Gly Leu Asn Ala Gln Ile Asp Ala Glu Ile Arg Gln Arg
 50                  55                  60

Glu Ala Glu Glu Leu Lys Asp Tyr Arg Trp Ile His Gly Asp Ala Glu
 65                  70                  75                  80

Val Pro Glu Leu Glu Lys
             85

<210> SEQ ID NO 35
<211> LENGTH: 279
<212> TYPE: DNA
<213> ORGANISM: Neisseria meningitidis

<400> SEQUENCE: 35
atggttatcg aatattact cgcatcaagc aagcatgctc ttgtcattac tctattgtta      60
aatcccgtct tccatgcatc cagttgcgta tcgcgttsgg caatacggaa taaaatctgc    120
tgttctgctt tggctaaatt tgccaaattg tttattgttt ctttaggagc agcttgctta    180
gccgccttcg ctttcgacaa cgcccccaca ggcgcttccc aagcgttgcc taccgttacc    240
gcacccgtgg cgattcccgc gcccgcttcg gcagcctga                           279

<210> SEQ ID NO 36
<211> LENGTH: 92
<212> TYPE: PRT
<213> ORGANISM: Neisseria meningitidis
<220> FEATURE:
<221> NAME/KEY: SITE
<222> LOCATION: (33)
<223> OTHER INFORMATION: unknown

<400> SEQUENCE: 36

Met Val Ile Gly Ile Leu Leu Ala Ser Ser Lys His Ala Leu Val Ile
 1               5                  10                  15

Thr Leu Leu Leu Asn Pro Val Phe His Ala Ser Ser Cys Val Ser Arg
             20                  25                  30

Xaa Ala Ile Arg Asn Lys Ile Cys Cys Ser Ala Leu Ala Lys Phe Ala
             35                  40                  45

Lys Leu Phe Ile Val Ser Leu Gly Ala Ala Cys Leu Ala Ala Phe Ala
 50                  55                  60

Phe Asp Asn Ala Pro Thr Gly Ala Ser Gln Ala Leu Pro Thr Val Thr
 65                  70                  75                  80

Ala Pro Val Ala Ile Pro Ala Pro Ala Ser Ala Ala
             85                  90

<210> SEQ ID NO 37
<211> LENGTH: 312
<212> TYPE: DNA
<213> ORGANISM: Neisseria meningitidis

<400> SEQUENCE: 37
atggcttgta caggttttgat ggttttttccg ttaatggtta tcggaatatt acttgcatca    60
agcaagcctg ctcctttcct tactctattg ttaaatcccg tcttccatgc atccagttgc   120
gtatcgcgtt gggcaatacg gaataaaatc tgctgttctg ctttggctaa atttgccaaa   180
ttgtttattg tttctttagg agcagcttgc ttagccgcct tcgctttcga caacgccccc   240
acaggcgctt cccaagcgtt gcctaccgtt accgcacccg tggcgattcc cgcgcccgct   300
tcggcagcct ga                                                        312

<210> SEQ ID NO 38
<211> LENGTH: 103
<212> TYPE: PRT
<213> ORGANISM: Neisseria meningitidis

<400> SEQUENCE: 38

Met Ala Cys Thr Gly Leu Met Val Phe Pro Leu Met Val Ile Gly Ile
1               5                   10                  15

Leu Leu Ala Ser Ser Lys Pro Ala Pro Phe Leu Thr Leu Leu Leu Asn
            20                  25                  30

Pro Val Phe His Ala Ser Ser Cys Val Ser Arg Trp Ala Ile Arg Asn
        35                  40                  45

Lys Ile Cys Cys Ser Ala Leu Ala Lys Phe Ala Lys Leu Phe Ile Val
    50                  55                  60

Ser Leu Gly Ala Ala Cys Leu Ala Ala Phe Ala Phe Asp Asn Ala Pro
65                  70                  75                  80

Thr Gly Ala Ser Gln Ala Leu Pro Thr Val Thr Ala Pro Val Ala Ile
                85                  90                  95

Pro Ala Pro Ala Ser Ala Ala
            100

<210> SEQ ID NO 39
<211> LENGTH: 255
<212> TYPE: DNA
<213> ORGANISM: Neisseria meningitidis

<400> SEQUENCE: 39
atgttcagta ttttaaatgt gtttcttcat tgtattctgg cttgtgtagt ctctggtgag      60
acgcctacta tatttggtat ccttgctctt ttttacttat tgtatctttc ttatcttgct     120
gtttttaaga ttttctttc ttttttctta gacagagttt cactccggtc tcccaggctg     180
gagtgcaaat ggcatgaccc tttggctcac tggctcacgg ccacttctgc tattctgccg     240
cctcagcctc caggg                                                      255

<210> SEQ ID NO 40
<211> LENGTH: 85
<212> TYPE: PRT
<213> ORGANISM: Neisseria meningitidis

<400> SEQUENCE: 40

Met Phe Ser Ile Leu Asn Val Phe Leu His Cys Ile Leu Ala Cys Val
1               5                   10                  15

Val Ser Gly Glu Thr Pro Thr Ile Phe Gly Ile Leu Ala Leu Phe Tyr
            20                  25                  30

Leu Leu Tyr Leu Ser Tyr Leu Ala Val Phe Lys Ile Phe Phe Ser Phe
        35                  40                  45

Phe Leu Asp Arg Val Ser Leu Arg Ser Pro Arg Leu Glu Cys Lys Trp
    50                  55                  60

His Asp Pro Leu Ala His Trp Leu Thr Ala Thr Ser Ala Ile Leu Pro
65                  70                  75                  80

Pro Gln Pro Pro Gly
                85

<210> SEQ ID NO 41
<211> LENGTH: 237
<212> TYPE: DNA
<213> ORGANISM: Neisseria meningitidis

<400> SEQUENCE: 41

```
gtgcggacgt ggttggtttt ttggttgcag cgtttgaaat acccgttgtt gctttggatt      60
gcggatatgt tgctgtaccg gttgttgggc ggcgcggaaa tcgaatgcgg ccgttgccct     120
gtgccgccga tgacggattg gcagcatttt ttgccggcga tgggaacggt gtcggcttgg     180
gtggcggtga tttgggcata cctgatgatt gaaagtgaaa aaaacggaag atattga        237
```

<210> SEQ ID NO 42
<211> LENGTH: 78
<212> TYPE: PRT
<213> ORGANISM: Neisseria meningitidis

<400> SEQUENCE: 42

Val Arg Thr Trp Leu Val Phe Trp Leu Gln Arg Leu Lys Tyr Pro Leu
1               5                   10                  15
Leu Leu Trp Ile Ala Asp Met Leu Leu Tyr Arg Leu Leu Gly Gly Ala
            20                  25                  30
Glu Ile Glu Cys Gly Arg Cys Pro Val Pro Pro Met Thr Asp Trp Gln
        35                  40                  45
His Phe Leu Pro Ala Met Gly Thr Val Ser Ala Trp Val Ala Val Ile
    50                  55                  60
Trp Ala Tyr Leu Met Ile Glu Ser Glu Lys Asn Gly Arg Tyr
65                  70                  75

<210> SEQ ID NO 43
<211> LENGTH: 237
<212> TYPE: DNA
<213> ORGANISM: Neisseria meningitidis

<400> SEQUENCE: 43

```
gtgcggacgt ggttggtttt ttggttgcag cgtttgaaat acccgttgtt gctttgtatt      60
gcggatatgc tgctgtaccg gttgttgggc ggcgcggaaa tcgaatgcgg ccgttgccct     120
gtaccgccga tgacggattg gcagcatttt ttgccgacga tgggaacggt ggcggcttgg     180
gtggcggtga tttgggcata cctgatgatt gaaagtgaaa aaaacggaag atattga        237
```

<210> SEQ ID NO 44
<211> LENGTH: 78
<212> TYPE: PRT
<213> ORGANISM: Neisseria meningitidis

<400> SEQUENCE: 44

Val Arg Thr Trp Leu Val Phe Trp Leu Gln Arg Leu Lys Tyr Pro Leu
1               5                   10                  15
Leu Leu Cys Ile Ala Asp Met Leu Leu Tyr Arg Leu Leu Gly Gly Ala
            20                  25                  30
Glu Ile Glu Cys Gly Arg Cys Pro Val Pro Pro Met Thr Asp Trp Gln
        35                  40                  45
His Phe Leu Pro Thr Met Gly Thr Val Ala Ala Trp Val Ala Val Ile
    50                  55                  60
Trp Ala Tyr Leu Met Ile Glu Ser Glu Lys Asn Gly Arg Tyr
65                  70                  75

<210> SEQ ID NO 45
<211> LENGTH: 660
<212> TYPE: DNA
<213> ORGANISM: Neisseria meningitidis -continued

```
<400> SEQUENCE: 45
atgtttcaaa attttgattt gggcgtgttc ctgcttgccg tcctcccgt gctgccctcc      60 attaccgtct cgcacgtggc gcgcggctat acggcgcgct actggggaga caacactgcc    120
gaacaatacg gcaggctgac actgaacccc ctgccccata tcgatttggt cggcacaatc    180
atcgtaccgc tgcttacttt gatgttcacg cccttcctgt tcggctgggc gcgtccgatt    240
cctatcgatt cgcgcaactt ccgcaacccg cgccttgcct ggcgttgcgt tgccgcgtcc    300
ggcccgctgt cgaatctagc gatggctgtw ctgtggggcg tggttttggt gctgactccg    360
tatgtcggcg gggcgtatca gatgccgttg gctcaaatgg caaactacgg tattctgatc    420
aatgcgattc tgttcgcgct caacatcatc cccatcctgc cttgggacgg cggcatttc     480 atcgacacct tcctgtcggc gaaatattcg caagcgttcc gcaaaatcga accttatggg    540
acgtggatta tcctactgct gatgctgacc sgggttttgg gtgcgtttat wgcaccgatt    600
stgcggmtgc gtgattgcrt ttgtgcagat gtwcgtctga ctggctttca gacggcataa    660

<210> SEQ ID NO 46
<211> LENGTH: 219
<212> TYPE: PRT
<213> ORGANISM: Neisseria meningitidis
<220> FEATURE:
<221> NAME/KEY: SITE
<222> LOCATION: (191)
<223> OTHER INFORMATION: unknown
<221> NAME/KEY: SITE
<222> LOCATION: (201)
<223> OTHER INFORMATION: unknown
<221> NAME/KEY: SITE
<222> LOCATION: (203)
<223> OTHER INFORMATION: unknown
<221> NAME/KEY: SITE
<222> LOCATION: (207)
<223> OTHER INFORMATION: unknown

<400> SEQUENCE: 46

Met Phe Gln Asn Phe Asp Leu Gly Val Phe Leu Leu Ala Val Leu Pro
  1               5                  10                  15

Val Leu Pro Ser Ile Thr Val Ser His Val Ala Arg Gly Tyr Thr Ala
             20                  25                  30

Arg Tyr Trp Gly Asp Asn Thr Ala Glu Gln Tyr Gly Arg Leu Thr Leu
         35                  40                  45

Asn Pro Leu Pro His Ile Asp Leu Val Gly Thr Ile Ile Val Pro Leu
     50                  55                  60

Leu Thr Leu Met Phe Thr Pro Phe Leu Phe Gly Trp Ala Arg Pro Ile
 65                  70                  75                  80

Pro Ile Asp Ser Arg Asn Phe Arg Asn Pro Arg Leu Ala Trp Arg Cys
                 85                  90                  95

Val Ala Ala Ser Gly Pro Leu Ser Asn Leu Ala Met Ala Val Leu Trp
            100                 105                 110

Gly Val Val Leu Val Leu Thr Pro Tyr Val Gly Gly Ala Tyr Gln Met
        115                 120                 125

Pro Leu Ala Gln Met Ala Asn Tyr Gly Ile Leu Ile Asn Ala Ile Leu
    130                 135                 140

Phe Ala Leu Asn Ile Ile Pro Ile Leu Pro Trp Asp Gly Gly Ile Phe
145                 150                 155                 160

Ile Asp Thr Phe Leu Ser Ala Lys Tyr Ser Gln Ala Phe Arg Lys Ile
                165                 170                 175

Glu Pro Tyr Gly Thr Trp Ile Ile Leu Leu Leu Met Leu Thr Xaa Val
```

```
                    180              185              190
Leu Gly Ala Phe Ile Ala Pro Ile Xaa Arg Xaa Arg Asp Cys Xaa Cys
        195              200              205
Ala Asp Val Arg Leu Thr Gly Phe Gln Thr Ala
        210              215

<210> SEQ ID NO 47
<211> LENGTH: 639
<212> TYPE: DNA
<213> ORGANISM: Neisseria meningitidis

<400> SEQUENCE: 47
atgtttcaaa attttgattt gggcgtgttt ctgcttgccg tcctgcccgt gctgctctcc      60
attaccgtca gggaggtggc gcgcggctat acggcgcgct actggggaga caacactgcc     120
gaacaatacg gcaggctgac actgaacccc ctgccccata tcgatttggt cggcacaatc     180
atcgtaccgc tgcttacttt gatgttcacg cccttcctgt tcggctgggc gcgtccgatt     240
cctatcgatt cgcgcaactt ccgcaacccg cgccttgcct ggcgttgcgt tgccgcgtcc     300
ggcccgctgt cgaatctagc gatggctgtt ctgtggggcg tggttttggt gctgactccg     360
tatgtcggcg gggcgtatca gatgccgttg gctcaaatgg caaactacgg tattctgatc     420
aatgcgattc tgttcgcgct caacatcatc cccatcctgc cttgggacgg cggcattttc     480
atcgacacct tcctgtcggc gaaatattcg caagcgttcc gcaaaatcga accttatggg     540
acgtggatta tcctactgct gatgctgacc ggggttttgg gtgcgtttat tgcaccgatt     600
gtgcggctgg tgattgcgtt tgtgcagatg ttcgtctga                            639

<210> SEQ ID NO 48
<211> LENGTH: 212
<212> TYPE: PRT
<213> ORGANISM: Neisseria meningitidis

<400> SEQUENCE: 48

Met Phe Gln Asn Phe Asp Leu Gly Val Phe Leu Leu Ala Val Leu Pro
 1               5                  10                  15
Val Leu Leu Ser Ile Thr Val Arg Glu Val Ala Arg Gly Tyr Thr Ala
                20                  25                  30
Arg Tyr Trp Gly Asp Asn Thr Ala Glu Gln Tyr Gly Arg Leu Thr Leu
            35                  40                  45
Asn Pro Leu Pro His Ile Asp Leu Val Gly Thr Ile Val Pro Leu
        50                  55                  60
Leu Thr Leu Met Phe Thr Pro Phe Leu Phe Gly Trp Ala Arg Pro Ile
65                  70                  75                  80
Pro Ile Asp Ser Arg Asn Phe Arg Asn Pro Arg Leu Ala Trp Arg Cys
                85                  90                  95
Val Ala Ala Ser Gly Pro Leu Ser Asn Leu Ala Met Ala Val Leu Trp
                100                 105                 110
Gly Val Val Leu Val Leu Thr Pro Tyr Val Gly Ala Tyr Gln Met
            115                 120                 125
Pro Leu Ala Gln Met Ala Asn Tyr Gly Ile Leu Ile Asn Ala Ile Leu
        130                 135                 140
Phe Ala Leu Asn Ile Ile Pro Ile Leu Pro Trp Asp Gly Gly Ile Phe
145                 150                 155                 160
Ile Asp Thr Phe Leu Ser Ala Lys Tyr Ser Gln Ala Phe Arg Lys Ile
                165                 170                 175
```

```
Glu Pro Tyr Gly Thr Trp Ile Ile Leu Leu Met Leu Thr Gly Val
            180                 185                 190

Leu Gly Ala Phe Ile Ala Pro Ile Val Arg Leu Val Ile Ala Phe Val
        195                 200                 205

Gln Met Phe Val
    210

<210> SEQ ID NO 49
<211> LENGTH: 558
<212> TYPE: DNA
<213> ORGANISM: Neisseria meningitidis
<220> FEATURE:
<221> NAME/KEY: misc_feature
<222> LOCATION: (312)
<223> OTHER INFORMATION: any nucleotide
<221> NAME/KEY: misc_feature
<222> LOCATION: (328)..(330)
<223> OTHER INFORMATION: any nucleotide
<221> NAME/KEY: misc_feature
<222> LOCATION: (353)
<223> OTHER INFORMATION: any nucleotide
<221> NAME/KEY: misc_feature
<222> LOCATION: (420)
<223> OTHER INFORMATION: any nucleotide
<221> NAME/KEY: misc_feature
<222> LOCATION: (426)
<223> OTHER INFORMATION: any nucleotide
<221> NAME/KEY: misc_feature
<222> LOCATION: (473)
<223> OTHER INFORMATION: any nucleotide
<221> NAME/KEY: misc_feature
<222> LOCATION: (506)
<223> OTHER INFORMATION: any nucleotide

<400> SEQUENCE: 49
cgcggctata cagcgcgcta ctggggtgac aacactgccg aacaatacgg caggctgaca     60
ctgaaccccc tgccccatat cgatttggtc ggcacaatca tcgtaccgct gcttactttg    120
atgtttacgc ccttcctgtt cggctgggcg cgtccgattc ctatcgattc gcgcaacttc    180
cgcaacccgc gccttgcctg gcgttgcgtt gccgcgtccg gcccgctgtc gaatctggcg    240
atggctgttc tgtggggcgt ggttttggtg ctgactccgt atgtcggtgg ggcgtatcag    300
atgccgttgg cncaaatggc aaactacnnn attctgatca atgcgattct gtncgcgctc    360
aacatcatcc ccatcctgcc ttgggacggc ggcattttca tcgacacctt cctgtcggcn    420
aaatantcgc aagcgttccg caaaatcgaa ccttatggga cgtggattat ccngctgctt    480
atgctgaccg gggttttggg tgcgtntatt gcaccgattg tgcagctggt gattgcgttt    540
gtgcagatgt tcgtctga                                                 558

<210> SEQ ID NO 50
<211> LENGTH: 185
<212> TYPE: PRT
<213> ORGANISM: Neisseria meningitidis
<220> FEATURE:
<221> NAME/KEY: SITE
<222> LOCATION: (110)
<223> OTHER INFORMATION: unknown
<221> NAME/KEY: SITE
<222> LOCATION: (118)
<223> OTHER INFORMATION: unknown
<221> NAME/KEY: SITE
<222> LOCATION: (142)
<223> OTHER INFORMATION: unknown
<221> NAME/KEY: SITE
<222> LOCATION: (158)
<223> OTHER INFORMATION: unknown
<221> NAME/KEY: SITE
<222> LOCATION: (169)
```

<223> OTHER INFORMATION: unknown

<400> SEQUENCE: 50

Arg Gly Tyr Thr Ala Arg Tyr Trp Gly Asp Asn Thr Ala Glu Gln Tyr
1               5                   10                  15

Gly Arg Leu Thr Leu Asn Pro Leu Pro His Ile Asp Leu Val Gly Thr
            20                  25                  30

Ile Ile Val Pro Leu Leu Thr Leu Met Phe Thr Pro Phe Leu Phe Gly
        35                  40                  45

Trp Ala Arg Pro Ile Pro Ile Asp Ser Arg Asn Phe Arg Asn Pro Arg
    50                  55                  60

Leu Ala Trp Arg Cys Val Ala Ser Gly Pro Leu Ser Asn Leu Ala
65                  70                  75                  80

Met Ala Val Leu Trp Gly Val Val Leu Thr Pro Tyr Val Gly
                85                  90                  95

Gly Ala Tyr Gln Met Pro Leu Ala Gln Met Ala Asn Tyr Xaa Ile Leu
                100                 105                 110

Ile Asn Ala Ile Leu Xaa Ala Leu Asn Ile Ile Pro Ile Leu Pro Trp
            115                 120                 125

Asp Gly Gly Ile Phe Ile Asp Thr Phe Leu Ser Ala Lys Xaa Ser Gln
        130                 135                 140

Ala Phe Arg Lys Ile Glu Pro Tyr Gly Thr Trp Ile Ile Xaa Leu Leu
145                 150                 155                 160

Met Leu Thr Gly Val Leu Gly Ala Xaa Ile Ala Pro Ile Val Gln Leu
                165                 170                 175

Val Ile Ala Phe Val Gln Met Phe Val
                180                 185

<210> SEQ ID NO 51
<211> LENGTH: 498
<212> TYPE: DNA
<213> ORGANISM: Neisseria meningitidis

<400> SEQUENCE: 51
atgaacctga tttcacgtta catcatccgt caaatggcgg ttatggcggt ttacgcgctc      60
cttgccttcc tcgcttttgta cagcttttttt gaaatcctgt acgaaaccgg caacctcggc    120
aaaggcagtt acggcatatg ggaaatgctg gctacaccg ccctcaaaat gcccgcccgc      180
gcctacgaac tgattcccct cgccgtcctt atcggcggac tggtctccct cagccagctt     240
gccgccggca gcgaactgac cgtcatcaaa gccagcggca tgagcaccaa aaagctgctg     300
ttgattctgt cgcagttcgg ttttattttt gctattgcca ccgtcgcgct cggcgaatgg     360
gttgcgccca cactgagcca aaagccgaa acatcaaag ccgccgccat caacggcaaa       420
atcagcaccg gcaataccgg cctttggctg aaagaaaaaa acagcgtgat caatgtgcgc     480
gaaatgttgc ccgaccat                                                   498

<210> SEQ ID NO 52
<211> LENGTH: 166
<212> TYPE: PRT
<213> ORGANISM: Neisseria meningitidis

<400> SEQUENCE: 52

Met Asn Leu Ile Ser Arg Tyr Ile Ile Arg Gln Met Ala Val Met Ala
1               5                   10                  15

Val Tyr Ala Leu Leu Ala Phe Leu Ala Leu Tyr Ser Phe Phe Glu Ile
            20                  25                  30

```
Leu Tyr Glu Thr Gly Asn Leu Gly Lys Gly Ser Tyr Gly Ile Trp Glu
        35                  40                  45

Met Leu Gly Tyr Thr Ala Leu Lys Met Pro Ala Arg Ala Tyr Glu Leu
    50                  55                  60

Ile Pro Leu Ala Val Leu Ile Gly Gly Leu Val Ser Leu Ser Gln Leu
65                  70                  75                  80

Ala Ala Gly Ser Glu Leu Thr Val Ile Lys Ala Ser Gly Met Ser Thr
                85                  90                  95

Lys Lys Leu Leu Leu Ile Leu Ser Gln Phe Gly Phe Ile Phe Ala Ile
                100                 105                 110

Ala Thr Val Ala Leu Gly Glu Trp Val Ala Pro Thr Leu Ser Gln Lys
                115                 120                 125

Ala Glu Asn Ile Lys Ala Ala Ile Asn Gly Lys Ile Ser Thr Gly
130                 135                 140

Asn Thr Gly Leu Trp Leu Lys Glu Lys Asn Ser Val Ile Asn Val Arg
145                 150                 155                 160

Glu Met Leu Pro Asp His
                165
```

<210> SEQ ID NO 53
<211> LENGTH: 980
<212> TYPE: DNA
<213> ORGANISM: Neisseria meningitidis

<400> SEQUENCE: 53

```
atgaacctga tttcacgtta catcatccgt caaatggcgg ttatggcggt ttacgcgctc      60
cttgccttcc tcgctttgta cagcttttt gaaatcctgt acgaaaccgg caacctcggc     120
aaaggcagtt acggcatatg gaaatgctg gctacaccg ccctcaaaat gcccgcccgc      180
gcctacgaac tgattcccct cgccgtcctt atcggcggac tggtctccct cagccagctt     240
gccgccggca gcgaactgac cgtcatcaaa gccagcggca tgagcaccaa aaagctgctg     300
ttgattctgt cgcagttcgg tttatttt gctattgcca ccgtcgcgct cggcgaatgg       360
gttgcgccca cactgagcca aaaagccgaa acatcaaag ccgccgccat aacggcaaa      420
atcagcaccg gcaataccgg cctttggctg aagaaaaaa acagcrtkat caatgtgcgc     480
gaaatgttgc ccgaccatac gcttttgggc atcaaaattt gggcgcgcaa cgataaaaac     540
gaattggcag aggcagtgga agccgattcc gccgttttga cagcgacgg cagttggcag      600
ttgaaaaaca tccgccgcag cacgcttggc gaagacaaag tcgaggtctc tattgcggct     660
gaagaaaact ggccgatttc cgtcaaacgc aacctgatgg acgtattgct cgtcaaaccc     720
gaccaaatgt ccgtcggcga actgaccacc tacatccgcc acctccaaaa caacagccaa     780
aacacccgaa tctacgccat cgcatggtgg cgcaaattgg tttaccccgc cgcagcctgg     840
gtgatggcgc tcgtcgccct tgcctttacc ccgcaaacca cccgccacgg caatatgggc     900
ttaaaactct tcggcggcat ctgtstcgga ttgctgttcc accttgccgg acggctcttt     960
gggtttacca gccaactcgg                                                 980
```

<210> SEQ ID NO 54
<211> LENGTH: 326
<212> TYPE: PRT
<213> ORGANISM: Neisseria meningitidis
<220> FEATURE:
<221> NAME/KEY: SITE
<222> LOCATION: (156)
<223> OTHER INFORMATION: unknown

```
<221> NAME/KEY: SITE
<222> LOCATION: (309)
<223> OTHER INFORMATION: unknown

<400> SEQUENCE: 54
```

| | | | | | | | | | | | | | | | |
|---|---|---|---|---|---|---|---|---|---|---|---|---|---|---|---|
| Met | Asn | Leu | Ile | Ser | Arg | Tyr | Ile | Ile | Arg | Gln | Met | Ala | Val | Met | Ala |
| 1 | | | | 5 | | | | | 10 | | | | | 15 | |
| Val | Tyr | Ala | Leu | Leu | Ala | Phe | Leu | Ala | Leu | Tyr | Ser | Phe | Phe | Glu | Ile |
| | | | 20 | | | | | 25 | | | | | 30 | | |
| Leu | Tyr | Glu | Thr | Gly | Asn | Leu | Gly | Lys | Gly | Ser | Tyr | Gly | Ile | Trp | Glu |
| | | | 35 | | | | | 40 | | | | | 45 | | |
| Met | Leu | Gly | Tyr | Thr | Ala | Leu | Lys | Met | Pro | Ala | Arg | Ala | Tyr | Glu | Leu |
| | | 50 | | | | | 55 | | | | | 60 | | | |
| Ile | Pro | Leu | Ala | Val | Leu | Ile | Gly | Gly | Leu | Val | Ser | Leu | Ser | Gln | Leu |
| 65 | | | | | 70 | | | | | 75 | | | | | 80 |
| Ala | Ala | Gly | Ser | Glu | Leu | Thr | Val | Ile | Lys | Ala | Ser | Gly | Met | Ser | Thr |
| | | | | 85 | | | | | 90 | | | | | 95 | |
| Lys | Lys | Leu | Leu | Leu | Ile | Leu | Ser | Gln | Phe | Gly | Phe | Ile | Phe | Ala | Ile |
| | | | 100 | | | | | 105 | | | | | 110 | | |
| Ala | Thr | Val | Ala | Leu | Gly | Glu | Trp | Val | Ala | Pro | Thr | Leu | Ser | Gln | Lys |
| | | 115 | | | | | 120 | | | | | 125 | | | |
| Ala | Glu | Asn | Ile | Lys | Ala | Ala | Ile | Asn | Gly | Lys | Ile | Ser | Thr | Gly |
| | 130 | | | | | 135 | | | | | 140 | | | | |
| Asn | Thr | Gly | Leu | Trp | Leu | Lys | Glu | Lys | Asn | Ser | Xaa | Ile | Asn | Val | Arg |
| 145 | | | | | 150 | | | | | 155 | | | | | 160 |
| Glu | Met | Leu | Pro | Asp | His | Thr | Leu | Leu | Gly | Ile | Lys | Ile | Trp | Ala | Arg |
| | | | | 165 | | | | | 170 | | | | | 175 | |
| Asn | Asp | Lys | Asn | Glu | Leu | Ala | Glu | Ala | Val | Glu | Ala | Asp | Ser | Ala | Val |
| | | | 180 | | | | | 185 | | | | | 190 | | |
| Leu | Asn | Ser | Asp | Gly | Ser | Trp | Gln | Leu | Lys | Asn | Ile | Arg | Arg | Ser | Thr |
| | | | 195 | | | | | 200 | | | | | 205 | | |
| Leu | Gly | Glu | Asp | Lys | Val | Glu | Val | Ser | Ile | Ala | Ala | Glu | Glu | Asn | Trp |
| | 210 | | | | | 215 | | | | | 220 | | | | |
| Pro | Ile | Ser | Val | Lys | Arg | Asn | Leu | Met | Asp | Val | Leu | Leu | Val | Lys | Pro |
| 225 | | | | | 230 | | | | | 235 | | | | | 240 |
| Asp | Gln | Met | Ser | Val | Gly | Glu | Leu | Thr | Thr | Tyr | Ile | Arg | His | Leu | Gln |
| | | | | 245 | | | | | 250 | | | | | 255 | |
| Asn | Asn | Ser | Gln | Asn | Thr | Arg | Ile | Tyr | Ala | Ile | Ala | Trp | Trp | Arg | Lys |
| | | | 260 | | | | | 265 | | | | | 270 | | |
| Leu | Val | Tyr | Pro | Ala | Ala | Ala | Trp | Val | Met | Ala | Leu | Val | Ala | Phe | Ala |
| | | 275 | | | | | 280 | | | | | 285 | | | |
| Phe | Thr | Pro | Gln | Thr | Thr | Arg | His | Gly | Asn | Met | Gly | Leu | Lys | Leu | Phe |
| | | 290 | | | | | 295 | | | | | 300 | | | |
| Gly | Gly | Ile | Cys | Xaa | Gly | Leu | Leu | Phe | His | Leu | Ala | Gly | Arg | Leu | Phe |
| 305 | | | | | 310 | | | | | 315 | | | | | 320 |
| Gly | Phe | Thr | Ser | Gln | Leu |
| | | | | 325 | |

```
<210> SEQ ID NO 55
<211> LENGTH: 1071
<212> TYPE: DNA
<213> ORGANISM: Neisseria meningitidis
<220> FEATURE:
<221> NAME/KEY: misc_feature
<222> LOCATION: (148)
<223> OTHER INFORMATION: any nucleotide
<221> NAME/KEY: misc_feature
```

<222> LOCATION: (153)
<223> OTHER INFORMATION: any nucleotide
<221> NAME/KEY: misc_feature
<222> LOCATION: (172)
<223> OTHER INFORMATION: any nucleotide
<221> NAME/KEY: misc_feature
<222> LOCATION: (229)
<223> OTHER INFORMATION: any nucleotide
<221> NAME/KEY: misc_feature
<222> LOCATION: (260)
<223> OTHER INFORMATION: any nucleotide
<221> NAME/KEY: misc_feature
<222> LOCATION: (669)
<223> OTHER INFORMATION: any nucleotide
<221> NAME/KEY: misc_feature
<222> LOCATION: (770)..(772)
<223> OTHER INFORMATION: any nucleotide
<221> NAME/KEY: misc_feature
<222> LOCATION: (907)
<223> OTHER INFORMATION: any nucleotide
<221> NAME/KEY: misc_feature
<222> LOCATION: (951)
<223> OTHER INFORMATION: any nucleotide
<221> NAME/KEY: misc_feature
<222> LOCATION: (961)
<223> OTHER INFORMATION: any nucleotide
<221> NAME/KEY: misc_feature
<222> LOCATION: (1001)
<223> OTHER INFORMATION: any nucleotide

<400> SEQUENCE: 55

| | | | | | |
|---|---|---|---|---|---|
| atgaacctga | tttcacgtta | catcatccgt | caaatggcgg | ttatggcggt | ttacgcgctc | 60 |
| cttgccttcc | tcgctttgta | cagctttttt | gaaatcctgt | acgaaaccgg | caacctcggc | 120 |
| aaaggcagtt | acggcatatg | ggaaatgntg | ggntacaccg | ccctcaaaat | gnccgcccgc | 180 |
| gcctacgaac | tgatgcccct | cgccgtcctt | atcggcggac | tggtctctnt | cagccagctt | 240 |
| gccgccggca | gcgaactgan | cgtcatcaaa | gccagcggca | tgagcaccaa | aaagctgctg | 300 |
| ttgattctgt | cgcagttcgg | ttttattttt | gctattgcca | ccgtcgcgct | cggcgaatgg | 360 |
| gttgcgccca | cactgagcca | aaaagccgaa | acatcaaag | ccgcggccat | caacggcaaa | 420 |
| atcagtaccg | gcaataccgg | cctttggctg | aaagaaaaaa | acagcattat | caatgtgcgc | 480 |
| gaaatgttgc | ccgaccatac | cctgctgggc | attaaaatct | gggcccgcaa | cgataaaaac | 540 |
| gaactggcag | aggcagtgga | agccgattcc | gccgttttga | cagcgacgg | cagttggcag | 600 |
| ttgaaaaaca | tccgccgcag | cacgcttggc | gaagacaaag | tcgaggtctc | tattgcggct | 660 |
| gaagaaaant | ggccgatttc | cgtcaaacgc | aacctgatgg | acgtattgct | cgtcaaaccc | 720 |
| gaccaaatgt | ccgtcggcga | actgaccacc | tacatccgcc | acctccaaan | nnacagccaa | 780 |
| aacacccgaa | tctacgccat | cgcatggtgg | cgcaaattgg | tttacccgc | cgcagcctgg | 840 |
| gtgatggcgc | tcgtcgcctt | tgcctttacc | ccgcaaacca | cccgccacgg | caatatgggc | 900 |
| ttaaaantct | tcggcggcat | ctgtctcgga | ttgctgttcc | accttgccgg | ncggctcttc | 960 |
| nggtttacca | gccaactcta | cggcatcccg | cccttcctcg | ncggcgcact | acctaccata | 1020 |
| gccttcgcct | tgctcgccgt | ttggctgata | cgcaaacagg | aaaaacgcta | a | 1071 |

<210> SEQ ID NO 56
<211> LENGTH: 356
<212> TYPE: PRT
<213> ORGANISM: Neisseria meningitidis
<220> FEATURE:
<221> NAME/KEY: SITE
<222> LOCATION: (50)
<223> OTHER INFORMATION: unknown
<221> NAME/KEY: SITE
<222> LOCATION: (58)

```
<223> OTHER INFORMATION: unknown
<221> NAME/KEY: SITE
<222> LOCATION: (77)
<223> OTHER INFORMATION: unknown
<221> NAME/KEY: SITE
<222> LOCATION: (87)
<223> OTHER INFORMATION: unknown
<221> NAME/KEY: SITE
<222> LOCATION: (223)
<223> OTHER INFORMATION: unknown
<221> NAME/KEY: SITE
<222> LOCATION: (257)..(258)
<223> OTHER INFORMATION: unknown
<221> NAME/KEY: SITE
<222> LOCATION: (303)
<223> OTHER INFORMATION: unknown
<221> NAME/KEY: SITE
<222> LOCATION: (321)
<223> OTHER INFORMATION: unknown
<221> NAME/KEY: SITE
<222> LOCATION: (334)
<223> OTHER INFORMATION: unknown

<400> SEQUENCE: 56
```

Met Asn Leu Ile Ser Arg Tyr Ile Ile Arg Gln Met Ala Val Met Ala
 1               5                  10                  15

Val Tyr Ala Leu Leu Ala Phe Leu Ala Leu Tyr Ser Phe Phe Glu Ile
             20                  25                  30

Leu Tyr Glu Thr Gly Asn Leu Gly Lys Gly Ser Tyr Gly Ile Trp Glu
         35                  40                  45

Met Xaa Gly Tyr Thr Ala Leu Lys Met Xaa Ala Arg Ala Tyr Glu Leu
     50                  55                  60

Met Pro Leu Ala Val Leu Ile Gly Gly Leu Val Ser Xaa Ser Gln Leu
65                  70                  75                  80

Ala Ala Gly Ser Glu Leu Xaa Val Ile Lys Ala Ser Gly Met Ser Thr
                 85                  90                  95

Lys Lys Leu Leu Leu Ile Leu Ser Gln Phe Gly Phe Ile Phe Ala Ile
            100                 105                 110

Ala Thr Val Ala Leu Gly Glu Trp Val Ala Pro Thr Leu Ser Gln Lys
        115                 120                 125

Ala Glu Asn Ile Lys Ala Ala Ile Asn Gly Lys Ile Ser Thr Gly
    130                 135                 140

Asn Thr Gly Leu Trp Leu Lys Glu Lys Asn Ser Ile Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

Leu Asn Ser Asp Gly Ser Trp Gln Leu Lys Asn Ile Arg Arg Ser Thr
        195                 200                 205

Leu Gly Glu Asp Lys Val Glu Val Ser Ile Ala Ala Glu Glu Xaa Trp
    210                 215                 220

Pro Ile Ser Val Lys Arg Asn Leu Met Asp Val Leu Val Lys Pro
225                 230                 235                 240

Asp Gln Met Ser Val Gly Glu Leu Thr Thr Tyr Ile Arg His Leu Gln
                245                 250                 255

Xaa Xaa Ser Gln Asn Thr Arg Ile Tyr Ala Ile Ala Trp Trp Arg Lys
            260                 265                 270

Leu Val Tyr Pro Ala Ala Ala Trp Val Met Ala Leu Val Ala Phe Ala
        275                 280                 285

```
Phe Thr Pro Gln Thr Thr Arg His Gly Asn Met Gly Leu Lys Xaa Phe
    290                 295                 300
Gly Gly Ile Cys Leu Gly Leu Leu Phe His Leu Ala Gly Arg Leu Phe
305                 310                 315                 320
Xaa Phe Thr Ser Gln Leu Tyr Gly Ile Pro Pro Phe Leu Xaa Gly Ala
                325                 330                 335
Leu Pro Thr Ile Ala Phe Ala Leu Leu Ala Val Trp Leu Ile Arg Lys
            340                 345                 350
Gln Glu Lys Arg
        355

<210> SEQ ID NO 57
<211> LENGTH: 854
<212> TYPE: DNA
<213> ORGANISM: Neisseria meningitidis

<400> SEQUENCE: 57
gcagtagccg aaactgccaa cagccagggc aaaggtaaac aggcaggcag ttcggtttct      60
gtttcactga aaacttcagg cgacctttgc ggcaaactca aaaccaccct taaaactttg     120
gtctgctctt tggtttccct gagtatggta ttgcctgccc atgcccaaat taccaccgac     180
aaatcagcac ctaaaaacca gcaggtcgtt atccttaaaa ccaacactgg tgcccccttg     240
gtgaatatcc aaactccgaa tggacgcgga ttgagccaca accgctatac gcatttgatg     300
ttgacaacaa aggggcagtg ttaaacaacg accgtaacaa taatccgttt gtggtcaaag     360
gcagtgcgca attgattttg aacgaggtac gcggtacggc tagcaaactc aacggcatcg     420
ttaccgtagg cggtcaaaag gccgacgtga ttattgccaa ccccaacggc attaccgtta     480
atggcggcgg cttaaaaaat gtcggtcggg gcatcttaac taccggtgcg ccccaaatcg     540
gcaaagacgg tgcactgaca ggatttgatg tgcgtcaagg cacattggac cgtagragca     600
gcaggttgga atgataaagg cggagcmrmy tacaccgggg tacttgctcg tgcagttgct     660
ttgcagggga aattwmmggg taaaaactgg cggtttctac cggtcctcag aaagtagatt     720
acgccagcgg cgaaatcagt gcaggtacgg cagcgggtac gaaaccgact attgcccttg     780
atactgccgc actgggcggt atgtacgccg acagcatcac actgattgcc aatgaaaaag     840
gcgtaggcgt ctaa                                                      854

<210> SEQ ID NO 58
<211> LENGTH: 284
<212> TYPE: PRT
<213> ORGANISM: Neisseria meningitidis
<220> FEATURE:
<221> NAME/KEY: SITE
<222> LOCATION: (96)
<223> OTHER INFORMATION: unknown
<221> NAME/KEY: SITE
<222> LOCATION: (199)
<223> OTHER INFORMATION: unknown
<221> NAME/KEY: SITE
<222> LOCATION: (210)
<223> OTHER INFORMATION: unknown
<221> NAME/KEY: SITE
<222> LOCATION: (225)..(226)
<223> OTHER INFORMATION: unknown
<221> NAME/KEY: SITE
<222> LOCATION: (229)
<223> OTHER INFORMATION: unknown

<400> SEQUENCE: 58

Ala Val Ala Glu Thr Ala Asn Ser Gln Gly Lys Gly Lys Gln Ala Gly
  1               5                  10                  15
```

```
Ser Ser Val Ser Val Ser Leu Lys Thr Ser Gly Asp Leu Cys Gly Lys
             20                  25                  30

Leu Lys Thr Thr Leu Lys Thr Leu Val Cys Ser Leu Val Ser Leu Ser
         35                  40                  45

Met Val Leu Pro Ala His Ala Gln Ile Thr Thr Asp Lys Ser Ala Pro
     50                  55                  60

Lys Asn Gln Gln Val Val Ile Leu Lys Thr Asn Thr Gly Ala Pro Leu
 65                  70                  75                  80

Val Asn Ile Gln Thr Pro Asn Gly Arg Gly Leu Ser His Asn Arg Xaa
                 85                  90                  95

Tyr Ala Phe Asp Val Asp Asn Lys Gly Ala Val Leu Asn Asn Asp Arg
            100                 105                 110

Asn Asn Asn Pro Phe Val Val Lys Gly Ser Ala Gln Leu Ile Leu Asn
        115                 120                 125

Glu Val Arg Gly Thr Ala Ser Lys Leu Asn Gly Ile Val Thr Val Gly
    130                 135                 140

Gly Gln Lys Ala Asp Val Ile Ile Ala Asn Pro Asn Gly Ile Thr Val
145                 150                 155                 160

Asn Gly Gly Phe Lys Asn Val Gly Arg Gly Ile Leu Thr Thr Gly
                165                 170                 175

Ala Pro Gln Ile Gly Lys Asp Gly Ala Leu Thr Gly Phe Asp Val Val
            180                 185                 190

Lys Ala His Trp Thr Val Xaa Ala Ala Gly Trp Asn Asp Lys Gly Gly
        195                 200                 205

Ala Xaa Tyr Thr Gly Val Leu Ala Arg Ala Val Ala Leu Gln Gly Lys
    210                 215                 220

Xaa Xaa Gly Lys Xaa Leu Ala Val Ser Thr Gly Pro Gln Lys Val Asp
225                 230                 235                 240

Tyr Ala Ser Gly Glu Ile Ser Ala Gly Thr Ala Ala Gly Thr Lys Pro
                245                 250                 255

Thr Ile Ala Leu Asp Thr Ala Ala Leu Gly Gly Met Tyr Ala Asp Ser
        260                 265                 270

Ile Thr Leu Ile Ala Asn Glu Lys Gly Val Gly Val
    275                 280

<210> SEQ ID NO 59
<211> LENGTH: 5937
<212> TYPE: DNA
<213> ORGANISM: Neisseria meningitidis

<400> SEQUENCE: 59
atgaataaag gtttacatcg cattatcttt agtaaaaagc acagcaccat ggttgcagta      60
gccgaaactg ccaacagcca gggcaaaggt aaacaggcag gcagttcggt ttctgtttca     120
ctgaaaactt caggcgacct tgcggcaaa ctcaaaacca cccttaaaac tttggtctgc     180
tctttggttt ccctgagtat ggtattgcct gcccatgccc aaattaccac cgacaaatca     240
gcacctaaaa accagcaggt cgttatcctt aaaaccaaca ctggtgcccc cttggtgaat     300
atccaaactc cgaatggacg cggattgagc cacaaccgct atacgcagtt tgatgttgac     360
aacaaggggg cagtgttaaa caacgaccgt aacaataatc cgtttgtggt caaaggcagt     420
gcgcaattga ttttgaacga ggtacgcggt acggctagca aactcaacgg catcgttacc     480
gtaggcggtc aaaaggccga cgtgattatt gccaacccca cggcattac cgttaatggc     540 ggcggcttta aaaatgtcgg tcgggcatc ttaactaccg gtgcgcccca atcggcaaa     600
```

-continued

```
gacggtgcac tgacaggatt tgatgtgcgt caaggcacat tgaccgtagg agcagcaggt    660
tggaatgata aaggcggagc cgactacacc ggggtacttg ctcgtgcagt tgctttgcag    720
gggaaattac agggtaaaaa cctggcggtt tctaccggtc ctcagaaagt agattacgcc    780
agcggcgaaa tcagtgcagg tacggcagcg ggtacgaaac cgactattgc ccttgatact    840
gccgcactgg gcggtatgta cgccgacagc atcacactga ttgccaatga aaaggcgta     900 ggcgtcaaaa atgccggcac actcgaagcg gccaagcaat tgattgtgac ttcgtcaggc    960
cgcattgaaa acagcggccg catcgccacc actgccgacg gcaccgaagc ttcaccgact   1020
tatctctcca tcgaaaccac cgaaaaagga gcggcaggca catttatctc caatggtggt   1080
cggatcgaga gcaaaggctt attggttatt gagacgggag aagatatcag cttgcgtaac   1140
ggagccgtgg tgcagaataa cggcagtcgc ccagctacca cggtattaaa tgctggtcat   1200
aatttggtga ttgagagcaa aactaatgtg aacaatgcca aaggcccggc tactctgtcg   1260
gccgacggcc gtaccgtcat caaggaggcc agtattcaga ctggcactac cgtatacagt   1320
tccagcaaag gcaacgccga attaggcaat aacacacgca ttaccggggc agatgttacc   1380
gtattatcca acggcaccat cagcagttcc gccgtaatag atgccaaaga caccgcacac   1440
atcgaagcag gcaaaccgct ttctttggaa gcttcaacag ttacctccga tatccgctta   1500
aacggaggca gtatcaaggg cggcaagcag cttgctttac tggcagacga taacattact   1560
gccaaaacta ccaatctgaa tactcccggc aatctgtatg ttcatacagg taaagatctg   1620
aatttgaatg ttgataaaga tttgtctgcc gccagcatcc atttgaaatc ggataacgct   1680
gcccatatta ccggcaccag taaaaccctc actgcctcaa aagacatggg tgtggaggca   1740
ggctcgctga atgttaccaa taccaatctg cgtaccaact cgggtaatct gcacattcag   1800
gcagccaaag gcaatattca gcttcgcaat accaagctga acgcagccaa ggctctcgaa   1860
accaccgcat tgcagggcaa tatcgtttca gacggccttc atgctgtttc tgcagacggt   1920
catgtatcct tattggccaa cggtaatgcc gactttaccg gtcacaatac cctgacagcc   1980
aaggccgatg tcaatgcagg atcggttggt aaaggccgtc tgaaagcaga caataccaat   2040
atcacttcat cttcaggaga tattacgttg gttgccggca acggtattca gcttggtgac   2100
ggaaaacaac gcaattcaat caacggaaaa cacatcagca tcaaaaacaa cggtggtaat   2160
gccgacttaa aaaaccttaa cgtccatgcc aaaagcgggg cattgaacat tcattccgac   2220
cgggcattga gcatagaaaa taccaagctg gagtctaccc ataatacgca tcttaatgca   2280
caacacgagc gggtaacgct caaccaagta gatgcctacg cacaccgtca tctaagcatt   2340
accggcagcc agatttggca aaacgacaaa ctgccttctg ccaacaagct ggtggctaac   2400
ggtgtattgg cactcaatgc gcgctattcc caaattgccg acaacaccac gctgagagcg   2460
ggtgcaatca accttactgc cggtaccgcc ctagtcaagc gcggcaacat caattggagt   2520
accgtttcga ccaaaacttt ggaagataat gccgaattaa aaccattggc cggacggctg   2580
aatattgaag caggtagcgg cacattaacc atcgaacctg ccaaccgcat cagtgcgcat   2640
accgacctga gcatcaaaac aggcggaaaa ttgctgttgt ctgcaaaagg aggaaatgca   2700
ggtgcgccta gtgctcaagt ttcctcattg gaagcaaaag gcaatatccg tctggttaca   2760
ggagaaacag atttaagagg ttctaaaatt acagccggta aaaacttggt tgtcgccacc   2820
accaaaggca agttgaatat cgaagccgta acaactcat tcagcaatta ttttcctaca   2880
caaaaagcgg ctgaactcaa ccaaaaatcc aaagaattgg aacagcagat tgcgcagttg   2940
```

```
aaaaaaagct cgcctaaaag caagctgatt ccaaccctgc aagaagaacg cgaccgtctc    3000
gctttctata ttcaagccat caacaaggaa gttaaaggta aaaacccaa aggcaaagaa     3060 tacctgcaag ccaagctttc tgcacaaaat attgacttga tttccgcaca aggcatcgaa    3120
atcagcggtt ccgatattac cgcttccaaa aaactgaacc ttcacgccgc aggcgtattg    3180
ccaaaggcag cagattcaga ggcggctgct attctgattg acggcataac cgaccaatat    3240
gaaattggca agcccaccta caagagtcac tacgacaaag ctgctctgaa caagccttca    3300
cgtttgaccg gacgtacagg ggtaagtatt catgcagctg cggcactcga tgatgcacgt    3360
attattatcg gtgcatccga aatcaaagct ccctcaggca gcatagacat caaagcccat    3420
agtgatattg tactggaggc tggacaaaac gatgcctata ccttcttaaa aaccaaaggt    3480 aaagcggca aaatcatcag aaaaaccaag tttaccagca cccgcgacca cctgattatg     3540
ccagcccccg tcgagctgac cgccaacggc ataacgcttc aggcaggcgg caacatcgaa    3600
gctaatacca cccgcttcaa tgcccctgca ggtaaagtta ccctggttgc gggtgaagag    3660
ctgcaactgc tggcagaaga aggcatccac aagcacgagt tggatgtcca aaaaagccgc    3720
cgctttatcg gcatcaaggt aggcaagagc aattacagta aaaacgaact gaacgaaacc    3780
aaattgcctg tccgcgtcgt cgcccaaact gcagccaccc gttcaggctg ggataccgtg    3840
ctcgaaggta ccgaattcaa aaccacgctg gccggtgcgg acattcaggc aggtgtaggc    3900 gaaaagccc gtgccgatgc gaaaattatc ctcaaaggca ttgtgaaccg tatccagtcg     3960
gaagaaaaat tagaaaccaa ctcaaccgta tggcagaaac aggccggacg cggcagcact    4020
atcgaaacgc tgaaactgcc cagcttcgaa agccctactc cgcccaaact gaccgccccc    4080
ggtggctata tcgtcgacat tccgaaaggc aatttgaaaa ccgaaatcga aaagctggcc    4140
aaacagcccg agtatgccta tctgaaacag ctccaagtag cgaaaaacgt caactggaac    4200
caggtgcaac tggcttacga taatgggac tataagcagg aaggcttaac cagagccggt      4260
gcagcgattg ttaccataat cgtaaccgca ctgacttatg gatacggcgc aaccgcagcg    4320
ggcggtgtag ccgcttcagg aagtagtaca gccgcagctg ccggaacagc cgccacaacg    4380
acagcagcag ctactaccgt ttctacagcg actgccatgc aaaccgctgc tttagcctcc    4440
ttgtatagcc aagcagctgt atccatcatc aataataaag gtgatgtcgg caaagcgttg    4500
aaagatctcg gcaccagtga tacggtcaag cagattgtca cttctgccct gacggcgggt    4560
gcattaaatc agatgggcgc agatattgcc caattgaaca gcaaggtaag aaccgaactg    4620
ttcagcagta cggcaatca aactattgcc aaccttggag gcagactggc taccaatctc      4680
agtaatgcag gtatctcagc tggtatcaat accgccgtca acggcggcag cctgaaagac    4740
aacttaggca atgccgcatt aggagcattg gttaatagct tccaaggaga gccgccagc      4800 aaaatcaaaa caaccttcag cgacgattat gttgccaaac agttcgccca cgctttggct    4860
gggtgtgtta gcggattggt acaaggaaaa tgtaaagacg gggcaattgg cgcagcagtt    4920
ggggaaatcg tagccgactc catgcttggc ggcagaaacc ctgctacact cagcgatgcg    4980
gaaaagcata aggttatcag ttactcgaag attattgccg gcagcgtggc ggcactcaac    5040
ggcggcgatg tgaatactgc ggcgaatgcg gctgaggtgg cggtagtgaa taatgctttg    5100
aattttgaca gtaccccctac caatgcgaaa aagcatcaac cgcagaagcc cgacaaaacc    5160
gcactggaaa aaattatcca aggtattatg cctgcacatg cagcaggtgc gatgactaat    5220
ccgcaggata aggatgctgc catttggata agcaatatcc gtaatggcat cacaggcccg    5280
attgtgatta ccagctatgg ggtttatgct gcaggttgga cagctccgct gatcggtaca    5340
```

-continued

```
gcgggtaaat tagctatcag cacctgcatg gctaatcctt ctggttgtac tgtcatggtc     5400
actcaggctg ccgaagcggg cgcgggaatc gccacgggtg cggtaacggt aggcaacgct     5460
tgggaagcgc ctgtggggc gttgtcgaaa gcgaaggcgg ccaagcaggc tataccaacc      5520
cagacagtta agaacttga tggcttacta caagaatcaa aaaatatagg tgctgtaaat      5580
acacgaatta atatagcgaa tagtactact cgatatacac caatgagaca acgggacaa      5640 ccggtatctg ctggctttga gcatgttctt gagggcact tccataggcc tattgcgaat      5700
aaccgttcag tttttaccat ctccccaaat gaattgaagg ttatacttca agtaataaa      5760 gtagtttctt ctcccgtatc gatgactcct gatggccaat atatgcggac tgtcgatgta     5820
ggaaaagtta ttggtactac ttctattaaa gaaggtggaa acccacaac tacaattaaa      5880 gtatttacag ataagtcagg aaatttgatt actacatacc cagtaaaagg aaactaa       5937
```

<210> SEQ ID NO 60
<211> LENGTH: 1978
<212> TYPE: PRT
<213> ORGANISM: Neisseria meningitidis

<400> SEQUENCE: 60

```
Met Asn Lys Gly Leu His Arg Ile Ile Phe Ser Lys Lys His Ser Thr
  1               5                   10                  15

Met Val Ala Val Ala Glu Thr Ala Asn Ser Gln Gly Lys Gly Lys Gln
                 20                  25                  30

Ala Gly Ser Ser Val Ser Val Ser Leu Lys Thr Ser Gly Asp Leu Cys
             35                  40                  45

Gly Lys Leu Lys Thr Thr Leu Lys Thr Leu Val Cys Ser Leu Val Ser
     50                  55                  60

Leu Ser Met Val Leu Pro Ala His Ala Gln Ile Thr Thr Asp Lys Ser
 65                  70                  75                  80

Ala Pro Lys Asn Gln Gln Val Val Ile Leu Lys Thr Asn Thr Gly Ala
                 85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Val Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Gly Phe Lys Asn Val Gly Arg Gly Ile Leu Thr
            180                 185                 190

Thr Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270
```

-continued

```
Lys Pro Thr Ile Ala Leu Asp Thr Ala Ala Leu Gly Gly Met Tyr Ala
        275                 280                 285
Asp Ser Ile Thr Leu Ile Ala Asn Glu Lys Gly Val Gly Val Lys Asn
290                 295                 300
Ala Gly Thr Leu Glu Ala Ala Lys Gln Leu Ile Val Thr Ser Ser Gly
305                 310                 315                 320
Arg Ile Glu Asn Ser Gly Arg Ile Ala Thr Thr Ala Asp Gly Thr Glu
                325                 330                 335
Ala Ser Pro Thr Tyr Leu Ser Ile Glu Thr Thr Glu Lys Gly Ala Ala
                340                 345                 350
Gly Thr Phe Ile Ser Asn Gly Gly Arg Ile Glu Ser Lys Gly Leu Leu
                355                 360                 365
Val Ile Glu Thr Gly Glu Asp Ile Ser Leu Arg Asn Gly Ala Val Val
370                 375                 380
Gln Asn Asn Gly Ser Arg Pro Ala Thr Thr Val Leu Asn Ala Gly His
385                 390                 395                 400
Asn Leu Val Ile Glu Ser Lys Thr Asn Val Asn Asn Ala Lys Gly Pro
                405                 410                 415
Ala Thr Leu Ser Ala Asp Gly Arg Thr Val Ile Lys Glu Ala Ser Ile
                420                 425                 430
Gln Thr Gly Thr Thr Val Tyr Ser Ser Lys Gly Asn Ala Glu Leu
                435                 440                 445
Gly Asn Asn Thr Arg Ile Thr Gly Ala Asp Val Thr Val Leu Ser Asn
        450                 455                 460
Gly Thr Ile Ser Ser Ala Val Ile Asp Ala Lys Asp Thr Ala His
465                 470                 475                 480
Ile Glu Ala Gly Lys Pro Leu Ser Leu Glu Ala Ser Thr Val Thr Ser
                485                 490                 495
Asp Ile Arg Leu Asn Gly Gly Ser Ile Lys Gly Gly Lys Gln Leu Ala
                500                 505                 510
Leu Leu Ala Asp Asp Asn Ile Thr Ala Lys Thr Thr Asn Leu Asn Thr
        515                 520                 525
Pro Gly Asn Leu Tyr Val His Thr Gly Lys Asp Leu Asn Leu Asn Val
        530                 535                 540
Asp Lys Asp Leu Ser Ala Ala Ser Ile His Leu Lys Ser Asp Asn Ala
545                 550                 555                 560
Ala His Ile Thr Gly Thr Ser Lys Thr Leu Thr Ala Ser Lys Asp Met
                565                 570                 575
Gly Val Glu Ala Gly Ser Leu Asn Val Thr Asn Thr Asn Leu Arg Thr
                580                 585                 590
Asn Ser Gly Asn Leu His Ile Gln Ala Ala Lys Gly Asn Ile Gln Leu
                595                 600                 605
Arg Asn Thr Lys Leu Asn Ala Ala Lys Ala Leu Glu Thr Thr Ala Leu
                610                 615                 620
Gln Gly Asn Ile Val Ser Asp Gly Leu His Ala Val Ser Ala Asp Gly
625                 630                 635                 640
His Val Ser Leu Leu Ala Asn Gly Asn Ala Asp Phe Thr Gly His Asn
                645                 650                 655
Thr Leu Thr Ala Lys Ala Asp Val Asn Ala Gly Ser Val Gly Lys Gly
                660                 665                 670
Arg Leu Lys Ala Asp Asn Thr Asn Ile Thr Ser Ser Ser Gly Asp Ile
                675                 680                 685
```

```
Thr Leu Val Ala Gly Asn Gly Ile Gln Leu Gly Asp Gly Lys Gln Arg
    690                 695                 700
Asn Ser Ile Asn Gly Lys His Ile Ser Ile Lys Asn Asn Gly Gly Asn
705                 710                 715                 720
Ala Asp Leu Lys Asn Leu Asn Val His Ala Lys Ser Gly Ala Leu Asn
                725                 730                 735
Ile His Ser Asp Arg Ala Leu Ser Ile Glu Asn Thr Lys Leu Glu Ser
            740                 745                 750
Thr His Asn Thr His Leu Asn Ala Gln His Glu Arg Val Thr Leu Asn
        755                 760                 765
Gln Val Asp Ala Tyr Ala His Arg His Leu Ser Ile Thr Gly Ser Gln
    770                 775                 780
Ile Trp Gln Asn Asp Lys Leu Pro Ser Ala Asn Lys Leu Val Ala Asn
785                 790                 795                 800
Gly Val Leu Ala Leu Asn Ala Arg Tyr Ser Gln Ile Ala Asp Asn Thr
                805                 810                 815
Thr Leu Arg Ala Gly Ala Ile Asn Leu Thr Ala Gly Thr Ala Leu Val
            820                 825                 830
Lys Arg Gly Asn Ile Asn Trp Ser Thr Val Ser Thr Lys Thr Leu Glu
        835                 840                 845
Asp Asn Ala Glu Leu Lys Pro Leu Ala Gly Arg Leu Asn Ile Glu Ala
    850                 855                 860
Gly Ser Gly Thr Leu Thr Ile Glu Pro Ala Asn Arg Ile Ser Ala His
865                 870                 875                 880
Thr Asp Leu Ser Ile Lys Thr Gly Gly Lys Leu Leu Leu Ser Ala Lys
                885                 890                 895
Gly Gly Asn Ala Gly Ala Pro Ser Ala Gln Val Ser Ser Leu Glu Ala
            900                 905                 910
Lys Gly Asn Ile Arg Leu Val Thr Gly Glu Thr Asp Leu Arg Gly Ser
        915                 920                 925
Lys Ile Thr Ala Gly Lys Asn Leu Val Val Ala Thr Thr Lys Gly Lys
    930                 935                 940
Leu Asn Ile Glu Ala Val Asn Asn Ser Phe Ser Asn Tyr Phe Pro Thr
945                 950                 955                 960
Gln Lys Ala Ala Glu Leu Asn Gln Lys Ser Lys Glu Leu Glu Gln Gln
                965                 970                 975
Ile Ala Gln Leu Lys Lys Ser Ser Pro Lys Ser Lys Leu Ile Pro Thr
            980                 985                 990
Leu Gln Glu Glu Arg Asp Arg Leu Ala Phe Tyr Ile Gln Ala Ile Asn
        995                 1000                1005
Lys Glu Val Lys Gly Lys Lys Pro Lys Gly Lys Glu Tyr Leu Gln Ala
    1010                1015                1020
Lys Leu Ser Ala Gln Asn Ile Asp Leu Ile Ser Ala Gln Gly Ile Glu
1025                1030                1035                1040
Ile Ser Gly Ser Asp Ile Thr Ala Ser Lys Lys Leu Asn Leu His Ala
                1045                1050                1055
Ala Gly Val Leu Pro Lys Ala Ala Asp Ser Glu Ala Ala Ile Leu
            1060                1065                1070
Ile Asp Gly Ile Thr Asp Gln Tyr Glu Ile Gly Lys Pro Thr Tyr Lys
        1075                1080                1085
Ser His Tyr Asp Lys Ala Ala Leu Asn Lys Pro Ser Arg Leu Thr Gly
    1090                1095                1100
Arg Thr Gly Val Ser Ile His Ala Ala Ala Ala Leu Asp Asp Ala Arg
```

-continued

```
1105                1110                1115                1120
Ile Ile Ile Gly Ala Ser Glu Ile Lys Ala Pro Ser Gly Ser Ile Asp
                1125                1130                1135
Ile Lys Ala His Ser Asp Ile Val Leu Glu Ala Gly Gln Asn Asp Ala
            1140                1145                1150
Tyr Thr Phe Leu Lys Thr Lys Gly Lys Ser Gly Lys Ile Ile Arg Lys
            1155                1160                1165
Thr Lys Phe Thr Ser Thr Arg Asp His Leu Ile Met Pro Ala Pro Val
        1170                1175                1180
Glu Leu Thr Ala Asn Gly Ile Thr Leu Gln Ala Gly Asn Ile Glu
1185                1190                1195                1200
Ala Asn Thr Thr Arg Phe Asn Ala Pro Ala Gly Lys Val Thr Leu Val
                1205                1210                1215
Ala Gly Glu Glu Leu Gln Leu Leu Ala Glu Gly Ile His Lys His
        1220                1225                1230
Glu Leu Asp Val Gln Lys Ser Arg Arg Phe Ile Gly Ile Lys Val Gly
        1235                1240                1245
Lys Ser Asn Tyr Ser Lys Asn Glu Leu Asn Glu Thr Lys Leu Pro Val
        1250                1255                1260
Arg Val Val Ala Gln Thr Ala Ala Thr Arg Ser Gly Trp Asp Thr Val
1265                1270                1275                1280
Leu Glu Gly Thr Glu Phe Lys Thr Thr Leu Ala Gly Ala Asp Ile Gln
                1285                1290                1295
Ala Gly Val Gly Glu Lys Ala Arg Ala Asp Ala Lys Ile Ile Leu Lys
            1300                1305                1310
Gly Ile Val Asn Arg Ile Gln Ser Glu Glu Lys Leu Glu Thr Asn Ser
        1315                1320                1325
Thr Val Trp Gln Lys Gln Ala Gly Arg Gly Ser Thr Ile Glu Thr Leu
        1330                1335                1340
Lys Leu Pro Ser Phe Glu Ser Pro Thr Pro Lys Leu Thr Ala Pro
1345                1350                1355                1360
Gly Gly Tyr Ile Val Asp Ile Pro Lys Gly Asn Leu Lys Thr Glu Ile
            1365                1370                1375
Glu Lys Leu Ala Lys Gln Pro Glu Tyr Ala Tyr Leu Lys Gln Leu Gln
        1380                1385                1390
Val Ala Lys Asn Val Asn Trp Asn Gln Val Gln Leu Ala Tyr Asp Lys
            1395                1400                1405
Trp Asp Tyr Lys Gln Glu Gly Leu Thr Arg Ala Gly Ala Ala Ile Val
        1410                1415                1420
Thr Ile Ile Val Thr Ala Leu Thr Tyr Gly Tyr Gly Ala Thr Ala Ala
1425                1430                1435                1440
Gly Gly Val Ala Ala Ser Gly Ser Ser Thr Ala Ala Ala Ala Gly Thr
                1445                1450                1455
Ala Ala Thr Thr Thr Ala Ala Ala Thr Thr Val Ser Thr Ala Thr Ala
            1460                1465                1470
Met Gln Thr Ala Ala Leu Ala Ser Leu Tyr Ser Gln Ala Ala Val Ser
        1475                1480                1485
Ile Ile Asn Asn Lys Gly Asp Val Gly Lys Ala Leu Lys Asp Leu Gly
        1490                1495                1500
Thr Ser Asp Thr Val Lys Gln Ile Val Thr Ser Ala Leu Thr Ala Gly
1505                1510                1515                1520
Ala Leu Asn Gln Met Gly Ala Asp Ile Ala Gln Leu Asn Ser Lys Val
            1525                1530                1535
```

-continued

```
Arg Thr Glu Leu Phe Ser Ser Thr Gly Asn Gln Thr Ile Ala Asn Leu
            1540                1545                1550
Gly Gly Arg Leu Ala Thr Asn Leu Ser Asn Ala Gly Ile Ser Ala Gly
        1555                1560                1565
Ile Asn Thr Ala Val Asn Gly Gly Ser Leu Lys Asp Asn Leu Gly Asn
    1570                1575                1580
Ala Ala Leu Gly Ala Leu Val Asn Ser Phe Gln Gly Glu Ala Ala Ser
1585                1590                1595                1600
Lys Ile Lys Thr Thr Phe Ser Asp Asp Tyr Val Ala Lys Gln Phe Ala
            1605                1610                1615
His Ala Leu Ala Gly Cys Val Ser Gly Leu Val Gln Gly Lys Cys Lys
        1620                1625                1630
Asp Gly Ala Ile Gly Ala Ala Val Gly Glu Ile Val Ala Asp Ser Met
    1635                1640                1645
Leu Gly Gly Arg Asn Pro Ala Thr Leu Ser Asp Ala Glu Lys His Lys
    1650                1655                1660
Val Ile Ser Tyr Ser Lys Ile Ile Ala Gly Ser Val Ala Ala Leu Asn
1665                1670                1675                1680
Gly Gly Asp Val Asn Thr Ala Ala Asn Ala Ala Glu Val Ala Val Val
            1685                1690                1695
Asn Asn Ala Leu Asn Phe Asp Ser Thr Pro Thr Asn Ala Lys Lys His
        1700                1705                1710
Gln Pro Gln Lys Pro Asp Lys Thr Ala Leu Glu Lys Ile Ile Gln Gly
        1715                1720                1725
Ile Met Pro Ala His Ala Ala Gly Ala Met Thr Asn Pro Gln Asp Lys
        1730                1735                1740
Asp Ala Ala Ile Trp Ile Ser Asn Ile Arg Asn Gly Ile Thr Gly Pro
1745                1750                1755                1760
Ile Val Ile Thr Ser Tyr Gly Val Tyr Ala Ala Gly Trp Thr Ala Pro
            1765                1770                1775
Leu Ile Gly Thr Ala Gly Lys Leu Ala Ile Ser Thr Cys Met Ala Asn
            1780                1785                1790
Pro Ser Gly Cys Thr Val Met Val Thr Gln Ala Ala Glu Ala Gly Ala
        1795                1800                1805
Gly Ile Ala Thr Gly Ala Val Thr Val Gly Asn Ala Trp Glu Ala Pro
    1810                1815                1820
Val Gly Ala Leu Ser Lys Ala Lys Ala Ala Lys Gln Ala Ile Pro Thr
1825                1830                1835                1840
Gln Thr Val Lys Glu Leu Asp Gly Leu Leu Gln Glu Ser Lys Asn Ile
            1845                1850                1855
Gly Ala Val Asn Thr Arg Ile Asn Ile Ala Asn Ser Thr Thr Arg Tyr
        1860                1865                1870
Thr Pro Met Arg Gln Thr Gly Gln Pro Val Ser Ala Gly Phe Glu His
        1875                1880                1885
Val Leu Glu Gly His Phe His Arg Pro Ile Ala Asn Asn Arg Ser Val
    1890                1895                1900
Phe Thr Ile Ser Pro Asn Glu Leu Lys Val Ile Leu Gln Ser Asn Lys
1905                1910                1915                1920
Val Val Ser Ser Pro Val Ser Met Thr Pro Asp Gly Gln Tyr Met Arg
            1925                1930                1935
Thr Val Asp Val Gly Lys Val Ile Gly Thr Thr Ser Ile Lys Glu Gly
        1940                1945                1950
```

```
Gly Gln Pro Thr Thr Thr Ile Lys Val Phe Thr Asp Lys Ser Gly Asn
    1955                1960                1965

Leu Ile Thr Thr Tyr Pro Val Lys Gly Asn
   1970                1975

<210> SEQ ID NO 61
<211> LENGTH: 4599
<212> TYPE: DNA
<213> ORGANISM: Neisseria meningitidis
<220> FEATURE:
<221> NAME/KEY: misc_feature
<222> LOCATION: (203)
<223> OTHER INFORMATION: any nucleotide
<221> NAME/KEY: misc_feature
<222> LOCATION: (207)
<223> OTHER INFORMATION: any nucleotide
<221> NAME/KEY: misc_feature
<222> LOCATION: (209)..(212)
<223> OTHER INFORMATION: any nucleotide
<221> NAME/KEY: misc_feature
<222> LOCATION: (214)..(215)
<223> OTHER INFORMATION: any nucleotide
<221> NAME/KEY: misc_feature
<222> LOCATION: (217)
<223> OTHER INFORMATION: any nucleotide
<221> NAME/KEY: misc_feature
<222> LOCATION: (255)
<223> OTHER INFORMATION: any nucleotide
<221> NAME/KEY: misc_feature
<222> LOCATION: (887)
<223> OTHER INFORMATION: any nucleotide
<221> NAME/KEY: misc_feature
<222> LOCATION: (1026)..(1027)
<223> OTHER INFORMATION: any nucleotide
<221> NAME/KEY: misc_feature
<222> LOCATION: (1029)
<223> OTHER INFORMATION: any nucleotide
<221> NAME/KEY: misc_feature
<222> LOCATION: (1053)..(1054)
<223> OTHER INFORMATION: any nucleotide
<221> NAME/KEY: misc_feature
<222> LOCATION: (1130)
<223> OTHER INFORMATION: any nucleotide
<221> NAME/KEY: misc_feature
<222> LOCATION: (1249)
<223> OTHER INFORMATION: any nucleotide
<221> NAME/KEY: misc_feature
<222> LOCATION: (1341)
<223> OTHER INFORMATION: any nucleotide
<221> NAME/KEY: misc_feature
<222> LOCATION: (1993)
<223> OTHER INFORMATION: any nucleotide
<221> NAME/KEY: misc_feature
<222> LOCATION: (2078)..(2081)
<223> OTHER INFORMATION: any nucleotide
<221> NAME/KEY: misc_feature
<222> LOCATION: (2244)
<223> OTHER INFORMATION: any nucleotide
<221> NAME/KEY: misc_feature
<222> LOCATION: (2342)
<223> OTHER INFORMATION: any nucleotide
<221> NAME/KEY: misc_feature
<222> LOCATION: (2413)
<223> OTHER INFORMATION: any nucleotide
<221> NAME/KEY: misc_feature
<222> LOCATION: (2708)
<223> OTHER INFORMATION: any nucleotide
<221> NAME/KEY: misc_feature
<222> LOCATION: (2765)
<223> OTHER INFORMATION: any nucleotide
<221> NAME/KEY: misc_feature
<222> LOCATION: (2876)
<223> OTHER INFORMATION: any nucleotide
<221> NAME/KEY: misc_feature
<222> LOCATION: (2888)
<223> OTHER INFORMATION: any nucleotide
<221> NAME/KEY: misc_feature
```

-continued

```
<222> LOCATION: (2890)..(2892)
<223> OTHER INFORMATION: any nucleotide
<221> NAME/KEY: misc_feature
<222> LOCATION: (2894)..(2895)
<223> OTHER INFORMATION: any nucleotide
<221> NAME/KEY: misc_feature
<222> LOCATION: (2954)
<223> OTHER INFORMATION: any nucleotide
<221> NAME/KEY: misc_feature
<222> LOCATION: (3469)
<223> OTHER INFORMATION: any nucleotide
<221> NAME/KEY: misc_feature
<222> LOCATION: (3491)
<223> OTHER INFORMATION: any nucleotide
<221> NAME/KEY: misc_feature
<222> LOCATION: (3495)
<223> OTHER INFORMATION: any nucleotide
<221> NAME/KEY: misc_feature
<222> LOCATION: (3507)
<223> OTHER INFORMATION: any nucleotide
<221> NAME/KEY: misc_feature
<222> LOCATION: (3523)
<223> OTHER INFORMATION: any nucleotide
<221> NAME/KEY: misc_feature
<222> LOCATION: (3528)
<223> OTHER INFORMATION: any nucleotide
<221> NAME/KEY: misc_feature
<222> LOCATION: (3549)
<223> OTHER INFORMATION: any nucleotide
<221> NAME/KEY: misc_feature
<222> LOCATION: (3658)
<223> OTHER INFORMATION: any nucleotide
<221> NAME/KEY: misc_feature
<222> LOCATION: (3661)
<223> OTHER INFORMATION: any nucleotide
<221> NAME/KEY: misc_feature
<222> LOCATION: (3745)
<223> OTHER INFORMATION: any nucleotide
<221> NAME/KEY: misc_feature
<222> LOCATION: (3809)
<223> OTHER INFORMATION: any nucleotide
<221> NAME/KEY: misc_feature
<222> LOCATION: (3898)
<223> OTHER INFORMATION: any nucleotide
<221> NAME/KEY: misc_feature
<222> LOCATION: (4086)
<223> OTHER INFORMATION: any nucleotide
<221> NAME/KEY: misc_feature
<222> LOCATION: (4339)
<223> OTHER INFORMATION: any nucleotide
<221> NAME/KEY: misc_feature
<222> LOCATION: (4523)
<223> OTHER INFORMATION: any nucleotide
<221> NAME/KEY: misc_feature
<222> LOCATION: (4577)
<223> OTHER INFORMATION: any nucleotide

<400> SEQUENCE: 61
atgaataaag gtttacatcg cattatcttt agtaaaaagc acagcaccat ggttgcagta      60
gccgaaactg ccaacagcca gggcaaaggt aaacaggcag gcagttcggt ttctgtttca     120
ctgaaaactt caggcgacct tgcggcaaa ctcaaaacca cccttaaaac cttggtctgc     180
tctttggttt ccctgagtat ggnattncnn nncnntnccc aaattaccac cgacaaatca     240
gcacctaaaa accancaggt cgttatcctt aaaaccaaca ctggtgcccc cttggtgaat     300
atccaaactc cgaatggacg cggattgagc cacaaccgct atacgcagtt tgatgttgac     360
aacaaagggg cagtgttaaa caacgaccgt aacaataatc cgtttctggt caaaggcagt     420
gcgcaattga ttttgaacga ggtacgcggt acggctagca aactcaacgg catcgttacc     480
gtaggcggtc aaaaggccga cgtgattatt gccaacccca cggcattac cgttaatggc     540 ggcggcttta aaaatgtcgg tcgggcatc ttaactatcg gtgcgcccca aatcggcaaa     600
```

-continued

```
gacggtgcac tgacaggatt tgatgtgcgt caaggcacat tgaccgtagg agcagcaggt    660
tggaatgata aaggcggagc cgactacacc ggggtacttg ctcgtgcagt tgctttgcag    720
gggaaattac agggtaaaaa cctggcggtt tctaccggtc ctcagaaagt agattacgcc    780
agcggcgaaa tcagtgcagg tacggcagcg ggtacgaaac cgactattgc ccttgatact    840
gccgcactgg gcgtatgta cgccgacagc atcacactga ttgccantga aaaaggcgta    900
ggcgtcaaaa atgccggcac actcgaagcg gccaagcaat tgattgtgac ttcgtcaggc    960
cgcattgaaa acagcggccg catcgccacc actgccgacg gcaccgaagc ttcaccgact    1020
tatctnncna tcgaaaccac cgaaaaagga gcnncaggca catttatctc caatggtggt    1080
cggatcgaga gcaaaggctt attggttatt gagacgggag aagatatcan cttgcgtaac    1140
ggagccgtgg tgcagaataa cggcagtcgc ccagctacca cggtattaaa tgctggtcat    1200
aatttggtga ttgagagtaa aactaatgtg aacaatgcca aaggctcgnc taatctgtcg    1260
gccggcggtc gtactacgat caatgatgct actattcaag cgggcagttc cgtgtacagc    1320
tccaccaaag gcgatactga nttgggtgaa aatacccgta ttattgctga aaacgtaacc    1380
gtattatcta acggtagtat tggcagtgct gctgtaattg aggctaaaga cactgcacac    1440
attgaatcgg gcaaaccgct ttctttagaa acctcgaccg ttgcctccaa catccgtttg    1500
aacaacggta acattaaagg cggaaagcag cttgctttac tggcagacga taacattact    1560
gccaaaacta ccaatctgaa tactcccggc aatctgtatg ttcatacagg taagatctg    1620 aatttgaatg ttgataaaga tttgtctgcc gccagcatcc atttgaaatc ggataacgct    1680
gcccatatta ccggcaccag taaaaccctc actgcctcaa agacatggg tgtggaggca    1740 ggcttgctga atgttaccaa taccaatctg cgtaccaact cgggtaatct gcacattcag    1800
gcagccaaag gcaatattca gcttcgcaat accaagctga acgcagccaa ggctctcgaa    1860
accaccgcat tgcagggcaa tatcgtttca gacggccttc atgctgtttc tgcagacggt    1920
catgtatcct tattggccaa cggtaatgcc gactttaccg gtcacaatac cctgacagcc    1980
aaggccgatg tcnatgcagg atcggttggt aaaggccgtc tgaaagcaga caataccaat    2040
atcacttcat cttcaggaga tattacgttg gttgccgnnn ncggtattca gcttggtgac    2100
ggaaaacaac gcaattcaat caacggaaaa cacatcagca tcaaaaacaa cggtggtaat    2160
gccgacttaa aaaaccttaa cgtccatgcc aaaagcgggg cattgaacat tcattccgac    2220
cgggcattga gcatagaaaa tacnaagctg gagtctaccc ataatacgca tcttaatgca    2280
caacacgagc gggtaacgct caaccaagta gatgcctacg cacaccgtca tctaagcatt    2340
ancggcagcc agatttggca aaacgacaaa ctgccttctg ccaacaagct ggtggctaac    2400
ggtgtattgg cantcaatgc gcgctattcc caaattgccg acaacaccac gctgagagcg    2460
ggtgcaatca accttactgc cggtaccgcc ctagtcaagc gcggcaacat caattggagt    2520
accgtttcga ccaagacttt ggaagataat gccgaattaa accattggc cggacggctg    2580 aatattgaag caggtagcgg cacattaacc atcgaacctg ccaaccgcat cagtgcgcat    2640
accgacctga gcatcaaaac aggcggaaaa ttgctgttgt ctgcaaaagg aggaaatgca    2700
ggtgcgcnta gtgctcaagt ttcctcattg gaagcaaaag gcaatatccg tctggttaca    2760
ggagnaacag atttaagagg ttctaaaatt acagccggta aaaacttggt tgtcgccacc    2820
accaaaggca agttgaatat cgaagccgta acaactcat tcagcaatta ttttcntaca    2880
caaaaagngn nngnnctcaa ccaaaaatcc aaagaattgg aacagcagat tgcgcagttg    2940
aaaaaaagct cgcntaaaag caagctgatt ccaacccctgc aagaagaacg cgaccgtctc    3000
```

```
gctttctata ttcaagccat caacaaggaa gttaaaggta aaaacccaa aggcaaagaa      3060 tacctgcaag ccaagctttc tgcacaaaat attgacttga tttccgcaca aggcatcgaa      3120
atcagcggtt ccgatattac cgcttccaaa aaactgaacc ttcacgccgc aggcgtattg      3180
ccaaaggcag cagattcaga ggcggctgct attctgattg acggcataac cgaccaatat      3240
gaaattggca agcccaccta caagagtcac tacgacaaag ctgctctgaa caagccttca      3300
cgtttgaccg gacgtacggg ggtaagtatt catgcagctg cggcactcga tgatgcacgt      3360
attattatcg gtgcatccga aatcaaagct ccctcaggca gcatagacat caaagcccat      3420
agtgatattg tactggaggc tggacaaaac gatgcctata ccttcttana aaccaaaggt      3480
aaaagcggca naatnatcag aaaaacnaag tttaccagca ccngcganca cctgattatg      3540
ccagccccng tcgagctgac cgccaacggt atcacgcttc aggcaggcgg caacatcgaa      3600
gctaatacca cccgcttcaa tgcccctgca ggtaaagtta ccctggttgc gggtgaanag      3660
ntgcaactgc tggcagaaga aggcatccac aagcacgagt tggatgtcca aaaaagccgc      3720
cgctttatcg gcatcaaggt aggtnagagc aattacagta aaaacgaact gaacgaaacc      3780
aaattgcctg tccgcgtcgt cgcccaaant gcagccaccc gttcaggctg ggataccgtg      3840
ctcgaaggta ccgaattcaa aaccacgctg gccggtgccg acattcaggc aggtgtangc      3900
gaaaaagccc gtgtcgatgc gaaaattatc ctcaaaggca ttgtgaaccg tatccagtcg      3960
gaagaaaaat tagaaaccaa ctcaaccgta tggcagaaac aggccggacg cggcagcact      4020
atcgaaacgc taaaactgcc cagcttcgaa agccctactc cgcccaaatt gtccgcaccc      4080
ggcggntata tcgtcgacat tccgaaaggc aatctgaaaa ccgaaatcga aaagctgtcc      4140
aaacagcccg agtatgccta tctgaaacag ctccaagtag cgaaaaacat caactggaat      4200
caggtgcagc ttgcttacga cagatgggac tacaaacagg agggcttaac cgaagcaggt      4260
gcggcgatta tcgcactggc cgttaccgtg gtcacctcag gcgcaggaac cggagccgta      4320
ttgggattaa acgtgcgnc cgccgccgca accgatgcag cattcgcctc tttggccagc      4380
caggcttccg tatcgttcat caacaacaaa ggcgatgtcg gcaaaaccct gaaagagctg      4440
ggcagaagca gcacggtgaa aaatctggtg gttgccgccg ctaccgcagg cgtagccgac      4500
aaaatcggcg cttcggcact gancaatgtc agcgataagc agtggatcaa caacctgacc      4560
gtcaacctag ccaatgncgg gcagtgccgc actgattaa                            4599
```

```
<210> SEQ ID NO 62
<211> LENGTH: 1532
<212> TYPE: PRT
<213> ORGANISM: Neisseria meningitidis
<220> FEATURE:
<221> NAME/KEY: SITE
<222> LOCATION: (68)..(73)
<223> OTHER INFORMATION: unknown
<221> NAME/KEY: SITE
<222> LOCATION: (85)
<223> OTHER INFORMATION: unknown
<221> NAME/KEY: SITE
<222> LOCATION: (296)
<223> OTHER INFORMATION: unknown
<221> NAME/KEY: SITE
<222> LOCATION: (343)
<223> OTHER INFORMATION: unknown
<221> NAME/KEY: SITE
<222> LOCATION: (352)
<223> OTHER INFORMATION: unknown
<221> NAME/KEY: SITE
<222> LOCATION: (377)
<223> OTHER INFORMATION: unknown
```

```
<221> NAME/KEY: SITE
<222> LOCATION: (417)
<223> OTHER INFORMATION: unknown
<221> NAME/KEY: SITE
<222> LOCATION: (477)
<223> OTHER INFORMATION: unknown
<221> NAME/KEY: SITE
<222> LOCATION: (665)
<223> OTHER INFORMATION: unknown
<221> NAME/KEY: SITE
<222> LOCATION: (693)..(694)
<223> OTHER INFORMATION: unknown
<221> NAME/KEY: SITE
<222> LOCATION: (781)
<223> OTHER INFORMATION: unknown
<221> NAME/KEY: SITE
<222> LOCATION: (805)
<223> OTHER INFORMATION: unknown
<221> NAME/KEY: SITE
<222> LOCATION: (903)
<223> OTHER INFORMATION: unknown
<221> NAME/KEY: SITE
<222> LOCATION: (922)
<223> OTHER INFORMATION: unknown
<221> NAME/KEY: SITE
<222> LOCATION: (959)
<223> OTHER INFORMATION: unknown
<221> NAME/KEY: SITE
<222> LOCATION: (963)..(965)
<223> OTHER INFORMATION: unknown
<221> NAME/KEY: SITE
<222> LOCATION: (985)
<223> OTHER INFORMATION: unknown
<221> NAME/KEY: SITE
<222> LOCATION: (1157)
<223> OTHER INFORMATION: unknown
<221> NAME/KEY: SITE
<222> LOCATION: (1164)..(1165)
<223> OTHER INFORMATION: unknown
<221> NAME/KEY: SITE
<222> LOCATION: (1175)..(1176)
<223> OTHER INFORMATION: unknown
<221> NAME/KEY: SITE
<222> LOCATION: (1220)..(1221)
<223> OTHER INFORMATION: unknown
<221> NAME/KEY: SITE
<222> LOCATION: (1249)
<223> OTHER INFORMATION: unknown
<221> NAME/KEY: SITE
<222> LOCATION: (1270)
<223> OTHER INFORMATION: unknown
<221> NAME/KEY: SITE
<222> LOCATION: (1300)
<223> OTHER INFORMATION: unknown
<221> NAME/KEY: SITE
<222> LOCATION: (1447)
<223> OTHER INFORMATION: unknown
<221> NAME/KEY: SITE
<222> LOCATION: (1508)
<223> OTHER INFORMATION: unknown
<221> NAME/KEY: SITE
<222> LOCATION: (1526)
<223> OTHER INFORMATION: unknown

<400> SEQUENCE: 62

Met Asn Lys Gly Leu His Arg Ile Ile Phe Ser Lys Lys His Ser Thr
  1               5                  10                  15

Met Val Ala Val Ala Glu Thr Ala Asn Ser Gln Gly Lys Gly Lys Gln
             20                  25                  30

Ala Gly Ser Ser Val Ser Val Ser Leu Lys Thr Ser Gly Asp Leu Cys
         35                  40                  45

Gly Lys Leu Lys Thr Thr Leu Lys Thr Leu Val Cys Ser Leu Val Ser
     50                  55                  60

Leu Ser Met Xaa Xaa Xaa Xaa Xaa Xaa Gln Ile Thr Thr Asp Lys Ser
```

-continued

```
            65                  70                  75                  80
Ala Pro Lys Asn Xaa Gln Val Val Ile Leu Lys Thr Asn Thr Gly Ala
                    85                  90                  95
Pro Leu Val Asn Ile Gln Thr Pro Asn Gly Arg Gly Leu Ser His Asn
                    100                 105                 110
Arg Tyr Thr Gln Phe Asp Val Asp Asn Lys Gly Ala Val Leu Asn Asn
                    115                 120                 125
Asp Arg Asn Asn Asn Pro Phe Leu Val Lys Gly Ser Ala Gln Leu Ile
    130                 135                 140
Leu Asn Glu Val Arg Gly Thr Ala Ser Lys Leu Asn Gly Ile Val Thr
145                 150                 155                 160
Val Gly Gly Gln Lys Ala Asp Val Ile Ile Ala Asn Pro Asn Gly Ile
                    165                 170                 175
Thr Val Asn Gly Gly Phe Lys Asn Val Gly Arg Gly Ile Leu Thr
                    180                 185                 190
Ile Gly Ala Pro Gln Ile Gly Lys Asp Gly Ala Leu Thr Gly Phe Asp
                    195                 200                 205
Val Arg Gln Gly Thr Leu Thr Val Gly Ala Ala Gly Trp Asn Asp Lys
    210                 215                 220
Gly Gly Ala Asp Tyr Thr Gly Val Leu Ala Arg Ala Val Ala Leu Gln
225                 230                 235                 240
Gly Lys Leu Gln Gly Lys Asn Leu Ala Val Ser Thr Gly Pro Gln Lys
                    245                 250                 255
Val Asp Tyr Ala Ser Gly Glu Ile Ser Ala Gly Thr Ala Ala Gly Thr
                    260                 265                 270
Lys Pro Thr Ile Ala Leu Asp Thr Ala Ala Leu Gly Gly Met Tyr Ala
                    275                 280                 285
Asp Ser Ile Thr Leu Ile Ala Xaa Glu Lys Gly Val Gly Val Lys Asn
    290                 295                 300
Ala Gly Thr Leu Glu Ala Ala Lys Gln Leu Ile Val Thr Ser Ser Gly
305                 310                 315                 320
Arg Ile Glu Asn Ser Gly Arg Ile Ala Thr Thr Ala Asp Gly Thr Glu
                    325                 330                 335
Ala Ser Pro Thr Tyr Leu Xaa Ile Glu Thr Thr Glu Lys Gly Ala Xaa
                    340                 345                 350
Gly Thr Phe Ile Ser Asn Gly Gly Arg Ile Glu Ser Lys Gly Leu Leu
                    355                 360                 365
Val Ile Glu Thr Gly Glu Asp Ile Xaa Leu Arg Asn Gly Ala Val Val
    370                 375                 380
Gln Asn Asn Gly Ser Arg Pro Ala Thr Thr Val Leu Asn Ala Gly His
385                 390                 395                 400
Asn Leu Val Ile Glu Ser Lys Thr Asn Val Asn Asn Ala Lys Gly Ser
                    405                 410                 415
Xaa Asn Leu Ser Ala Gly Gly Arg Thr Thr Ile Asn Asp Ala Thr Ile
                    420                 425                 430
Gln Ala Gly Ser Ser Val Tyr Ser Thr Lys Gly Asp Thr Xaa Leu
                    435                 440                 445
Gly Glu Asn Thr Arg Ile Ile Ala Glu Asn Val Thr Val Leu Ser Asn
    450                 455                 460
Gly Ser Ile Gly Ser Ala Ala Val Ile Glu Ala Lys Asp Thr Ala His
465                 470                 475                 480
Ile Glu Ser Gly Lys Pro Leu Ser Leu Glu Thr Ser Thr Val Ala Ser
                    485                 490                 495
```

```
Asn Ile Arg Leu Asn Asn Gly Asn Ile Lys Gly Gly Lys Gln Leu Ala
            500                 505                 510

Leu Leu Ala Asp Asp Asn Ile Thr Ala Lys Thr Thr Asn Leu Asn Thr
            515                 520                 525

Pro Gly Asn Leu Tyr Val His Thr Gly Lys Asp Leu Asn Leu Asn Val
            530                 535                 540

Asp Lys Asp Leu Ser Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Leu Leu Asn Val Thr Asn Thr Asn Leu Arg Thr
            580                 585                 590

Asn Ser Gly Asn Leu His Ile Gln Ala Ala Lys Gly Asn Ile Gln Leu
            595                 600                 605

Arg Asn Thr Lys Leu Asn Ala Ala Lys Ala Leu Glu Thr Thr Ala Leu
            610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
                645                 650                 655

Thr Leu Thr Ala Lys Ala Asp Val Xaa Ala Gly Ser Val Gly Lys Gly
                660                 665                 670

Arg Leu Lys Ala Asp Asn Thr Asn Ile Thr Ser Ser Gly Asp Ile
            675                 680                 685

Thr Leu Val Ala Xaa Xaa Gly Ile Gln Leu Gly Asp Gly Lys Gln Arg
            690                 695                 700

Asn Ser Ile Asn Gly Lys His Ile Ser Ile Lys Asn Asn Gly Gly Asn
705                 710                 715                 720

Ala Asp Leu Lys Asn Leu Asn Val His Ala Lys Ser Gly Ala Leu Asn
                725                 730                 735

Ile His Ser Asp Arg Ala Leu Ser Ile Glu Asn Thr Lys Leu Glu Ser
                740                 745                 750

Thr His Asn Thr His Leu Asn Ala Gln His Glu Arg Val Thr Leu Asn
            755                 760                 765

Gln Val Asp Ala Tyr Ala His Arg His Leu Ser Ile Xaa Gly Ser Gln
770                 775                 780

Ile Trp Gln Asn Asp Lys Leu Pro Ser Ala Asn Lys Leu Val Ala Asn
785                 790                 795                 800

Gly Val Leu Ala Xaa Asn Ala Arg Tyr Ser Gln Ile Ala Asp Asn Thr
            805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
            835                 840                 845

Asp Asn Ala Glu Leu Lys Pro Leu Ala Gly Arg Leu Asn Ile Glu Ala
            850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Leu Ser Ala Lys
                885                 890                 895

Gly Gly Asn Ala Gly Ala Xaa Ser Ala Gln Val Ser Ser Leu Glu Ala
            900                 905                 910
```

```
Lys Gly Asn Ile Arg Leu Val Thr Gly Xaa Thr Asp Leu Arg Gly Ser
            915                 920                 925

Lys Ile Thr Ala Gly Lys Asn Leu Val Val Ala Thr Thr Lys Gly Lys
            930                 935                 940

Leu Asn Ile Glu Ala Val Asn Asn Ser Phe Ser Asn Tyr Phe Xaa Thr
945                 950                 955                 960

Gln Lys Xaa Xaa Xaa Leu Asn Gln Lys Ser Lys Glu Leu Glu Gln Gln
                965                 970                 975

Ile Ala Gln Leu Lys Lys Ser Ser Xaa Lys Ser Lys Leu Ile Pro Thr
            980                 985                 990

Leu Gln Glu Glu Arg Asp Arg Leu Ala Phe Tyr Ile Gln Ala Ile Asn
            995                 1000                1005

Lys Glu Val Lys Gly Lys Lys Pro Lys Gly Lys Glu Tyr Leu Gln Ala
    1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
            1045                1050                1055

Ala Gly Val Leu Pro Lys Ala Ala Asp Ser Glu Ala Ala Ala Ile Leu
            1060                1065                1070

Ile Asp Gly Ile Thr Asp Gln Tyr Glu Ile Gly Lys Pro Thr Tyr Lys
            1075                1080                1085

Ser His Tyr Asp Lys Ala Ala Leu Asn Lys Pro Ser Arg Leu Thr Gly
            1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
            1125                1130                1135

Ile Lys Ala His Ser Asp Ile Val Leu Glu Ala Gly Gln Asn Asp Ala
            1140                1145                1150

Tyr Thr Phe Leu Xaa Thr Lys Gly Lys Ser Gly Xaa Xaa Ile Arg Lys
            1155                1160                1165

Thr Lys Phe Thr Ser Thr Xaa Xaa His Leu Ile Met Pro Ala Pro Val
    1170                1175                1180

Glu Leu Thr Ala Asn Gly Ile Thr Leu Gln Ala Gly Asn Ile Glu
1185                1190                1195                1200

Ala Asn Thr Thr Arg Phe Asn Ala Pro Ala Gly Lys Val Thr Leu Val
            1205                1210                1215

Ala Gly Glu Xaa Xaa Gln Leu Leu Ala Glu Glu Gly Ile His Lys His
            1220                1225                1230

Glu Leu Asp Val Gln Lys Ser Arg Arg Phe Ile Gly Ile Lys Val Gly
            1235                1240                1245

Xaa Ser Asn Tyr Ser Lys Asn Glu Leu Asn Glu Thr Lys Leu Pro Val
    1250                1255                1260

Arg Val Val Ala Gln Xaa Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
            1285                1290                1295

Ala Gly Val Xaa Glu Lys Ala Arg Val Asp Ala Lys Ile Ile Leu Lys
            1300                1305                1310

Gly Ile Val Asn Arg Ile Gln Ser Glu Glu Lys Leu Glu Thr Asn Ser
    1315                1320                1325

Thr Val Trp Gln Lys Gln Ala Gly Arg Gly Ser Thr Ile Glu Thr Leu
```

-continued

Lys Leu Pro Ser Phe Glu Ser Pro Thr Pro Pro Lys Leu Ser Ala Pro
1345                 1350                 1355                 1360

Gly Gly Tyr Ile Val Asp Ile Pro Lys Gly Asn Leu Lys Thr Glu Ile
            1365                 1370                 1375

Glu Lys Leu Ser Lys Gln Pro Glu Tyr Ala Tyr Leu Lys Gln Leu Gln
        1380                 1385                 1390

Val Ala Lys Asn Ile Asn Trp Asn Gln Val Gln Leu Ala Tyr Asp Arg
    1395                 1400                 1405

Trp Asp Tyr Lys Gln Glu Gly Leu Thr Glu Ala Gly Ala Ala Ile Ile
1410                 1415                 1420

Ala Leu Ala Val Thr Val Val Thr Ser Gly Ala Gly Thr Gly Ala Val
1425                 1430                 1435                 1440

Leu Gly Leu Asn Gly Ala Xaa Ala Ala Ala Thr Asp Ala Ala Phe Ala
            1445                 1450                 1455

Ser Leu Ala Ser Gln Ala Ser Val Ser Phe Ile Asn Asn Lys Gly Asp
        1460                 1465                 1470

Val Gly Lys Thr Leu Lys Glu Leu Gly Arg Ser Ser Thr Val Lys Asn
    1475                 1480                 1485

Leu Val Val Ala Ala Ala Thr Ala Gly Val Ala Asp Lys Ile Gly Ala
    1490                 1495                 1500

Ser Ala Leu Xaa Asn Val Ser Asp Lys Gln Trp Ile Asn Asn Leu Thr
1505                 1510                 1515                 1520

Val Asn Leu Ala Asn Xaa Gly Gln Cys Arg Thr Asp
            1525                 1530

<210> SEQ ID NO 63
<211> LENGTH: 1782
<212> TYPE: DNA
<213> ORGANISM: Neisseria meningitidis
<220> FEATURE:
<221> NAME/KEY: misc_feature
<222> LOCATION: (89)
<223> OTHER INFORMATION: any nucleotide
<221> NAME/KEY: unsure
<222> LOCATION: (697)
<223> OTHER INFORMATION: N = Unknown
<221> NAME/KEY: unsure
<222> LOCATION: (862)
<223> OTHER INFORMATION: N = Unknown
<221> NAME/KEY: misc_feature
<222> LOCATION: (959)..(960)
<223> OTHER INFORMATION: any nucleotide

<400> SEQUENCE: 63

```
cgcttcattc atgatgaagc agtcggcagc aacatcggcg gcggcaaaat gattgttgca     60
gccgggcagg atatcaatgt acgcggcana agccttattt ctgataaggg cattgtttta    120
aaagcaggac acgacatcga tatttctact gcccataatc gctataccgg caatgaatac    180
cacgagagca waaawtcagg cgtcatgggt actggcggat tgggctttac tatcggtaac    240
cggaaaacta ccgatgacac tgatcgtacc aatattgtsc atacaggcag cattataggc    300
agcctgaatg gagacaccgt tacagttgca ggaaaccgct accgacaaac cggcagtacc    360
gtctccagcc ccgaggggcg caataccgtc acagccaaaw gcatagatgt agagttcgca    420
aacaaccggt atgccactga ctacgcccat acccagggaa caaaaaggcc ttaccgtcgc    480
cctcaatgtc ccggttgtcc aagctgcaca aaacttcata caagcagccc aaaatgtggg    540
caaaagtaaa aataaacgcg ttaatgccat ggctgcagcc aatgctgcat ggcagagtta    600
```

-continued

```
tcaagcaacc caacaaatgc aacaatttgc tccaagcagc agtgcgggac aaggtcaaaa      660
ctacaatcaa agccccagta tcagtgtgtc cattacntac ggcgaacaga aaagtcgtaa      720
cgagcaaaaa agacattaca ccgaagcggc agcaagtcaa attatcggca aagggcaaac      780
cacacttgcg gcaacaggaa gtggggagca gtccaatatc aatattacag gttccgatgt      840
catcggccat gcaggtactc cnctcattgc cgacaaccat atcagactcc aatctgccaa      900
acaggacggc agcgagcaaa gcaaaaacaa agcagtggt tggaatgcag gcgtacgtnn       960
caaaataggc aacggcatca ggtttggaat taccgccgga ggaaatatcg gtaaaggtaa     1020
agagcaaggg ggaagtacta cccaccgcca cacccatgtc ggcagcacaa ccggcaaaac     1080
taccatccga agcggcgggg gataccaccc tcaaaggtgt gcagctcatc ggcaaaggca     1140
tacaggcaga tacgcgcaac ctgcatatag aaagtgttca agatactgaa acctatcaga     1200
gcaaacagca aaacggcaat gtccaagttt actgtcggtt acggattcag tgcaagcggc     1260
agttaccgcc aaagcaaagt caaagcagac catgcctccg taaccgggca agcggtatt     1320 tatgccggag aagacggcta tcaaatyaaa gtyagagaca cacagacct yaagggcgt      1380 atcatcacgt ctagccaaag cgcagaagat aagggcaaaa accttttca gacggccacc     1440 cttactgcca gcgacattca aaccacagc cgctacgaag cagaagctt cggcataggc      1500 ggcagtttcg acctgaacgg cggctgggac ggcacggtta ccgacaaaca aggcaggcct     1560
accgacagga taagcccggc agccggctac ggcagcgacg gagacagcaa aaacagcacc     1620
acccgcagcg cgtcaacac ccacaacata cacatcaccg acgaagcggg acaacttgcc     1680
cgaacaggca ggactgcaaa agaaaccgaa gcgcgtatct acaccggcat cgacaccgaa     1740
actgcggatc aacactcagg ccatctgaaa aacagcttcg ac                        1782
```

<210> SEQ ID NO 64
<211> LENGTH: 593
<212> TYPE: PRT
<213> ORGANISM: Neisseria meningitidis
<220> FEATURE:
<221> NAME/KEY: SITE
<222> LOCATION: (30)
<223> OTHER INFORMATION: unknown
<221> NAME/KEY: SITE
<222> LOCATION: (64)..(65)
<223> OTHER INFORMATION: unknown
<221> NAME/KEY: SITE
<222> LOCATION: (134)
<223> OTHER INFORMATION: unknown
<221> NAME/KEY: SITE
<222> LOCATION: (232)
<223> OTHER INFORMATION: unknown
<221> NAME/KEY: SITE
<222> LOCATION: (287)
<223> OTHER INFORMATION: unknown
<221> NAME/KEY: SITE
<222> LOCATION: (320)
<223> OTHER INFORMATION: unknown

<400> SEQUENCE: 64

```
Arg Phe Ile His Asp Glu Ala Val Gly Ser Asn Ile Gly Gly Lys
 1               5                  10                  15

Met Ile Val Ala Ala Gly Gln Asp Ile Asn Val Arg Gly Xaa Ser Leu
                20                  25                  30

Ile Ser Asp Lys Gly Ile Val Leu Lys Ala Gly His Asp Ile Asp Ile
            35                  40                  45

Ser Thr Ala His Asn Arg Tyr Thr Gly Asn Glu Tyr His Glu Ser Xaa
        50                  55                  60
```

```
Xaa Ser Gly Val Met Gly Thr Gly Leu Gly Phe Thr Ile Gly Asn
 65                  70                  75                  80

Arg Lys Thr Thr Asp Asp Thr Asp Arg Thr Asn Ile Val His Thr Gly
                 85                  90                  95

Ser Ile Ile Gly Ser Leu Asn Gly Asp Thr Val Thr Val Ala Gly Asn
            100                 105                 110

Arg Tyr Arg Gln Thr Gly Ser Thr Val Ser Ser Pro Glu Gly Arg Asn
        115                 120                 125

Thr Val Thr Ala Lys Xaa Ile Asp Val Glu Phe Ala Asn Asn Arg Tyr
    130                 135                 140

Ala Thr Asp Tyr Ala His Thr Gln Glu Gln Lys Gly Leu Thr Val Ala
145                 150                 155                 160

Leu Asn Val Pro Val Gln Ala Ala Gln Asn Phe Ile Gln Ala Ala
                165                 170                 175

Gln Asn Val Gly Lys Ser Lys Asn Lys Arg Val Asn Ala Met Ala Ala
                180                 185                 190

Ala Asn Ala Ala Trp Gln Ser Tyr Gln Ala Thr Gln Gln Met Gln Gln
            195                 200                 205

Phe Ala Pro Ser Ser Ser Ala Gly Gln Gly Gln Asn Tyr Asn Gln Ser
    210                 215                 220

Pro Ser Ile Ser Val Ser Ile Xaa Tyr Gly Gln Lys Ser Arg Asn
225                 230                 235                 240

Glu Gln Lys Arg His Tyr Thr Glu Ala Ala Ser Gln Ile Ile Gly
                245                 250                 255

Lys Gly Gln Thr Thr Leu Ala Ala Thr Gly Ser Gly Glu Gln Ser Asn
                260                 265                 270

Ile Asn Ile Thr Gly Ser Asp Val Ile Gly His Ala Gly Thr Xaa Leu
            275                 280                 285

Ile Ala Asp Asn His Ile Arg Leu Gln Ser Ala Lys Gln Asp Gly Ser
    290                 295                 300

Glu Gln Ser Lys Asn Lys Ser Ser Gly Trp Asn Ala Gly Val Arg Xaa
305                 310                 315                 320

Lys Ile Gly Asn Gly Ile Arg Phe Gly Ile Thr Ala Gly Gly Asn Ile
                325                 330                 335

Gly Lys Gly Lys Glu Gln Gly Gly Ser Thr Thr His Arg His Thr His
            340                 345                 350

Val Gly Ser Thr Thr Gly Lys Thr Thr Ile Arg Ser Gly Gly Asp Thr
        355                 360                 365

Thr Leu Lys Gly Val Gln Leu Ile Gly Lys Gly Ile Gln Ala Asp Thr
    370                 375                 380

Arg Asn Leu His Ile Glu Ser Val Gln Asp Thr Glu Thr Tyr Gln Ser
385                 390                 395                 400

Lys Gln Gln Asn Gly Asn Val Gln Val Thr Val Gly Tyr Gly Phe Ser
                405                 410                 415

Ala Ser Gly Ser Tyr Arg Gln Ser Lys Val Lys Ala Asp His Ala Ser
            420                 425                 430

Val Thr Gly Gln Ser Gly Ile Tyr Ala Gly Glu Asp Gly Tyr Gln Ile
        435                 440                 445

Lys Val Arg Asp Asn Thr Asp Leu Lys Gly Gly Ile Ile Thr Ser Ser
    450                 455                 460

Gln Ser Ala Glu Asp Lys Gly Lys Asn Leu Phe Gln Thr Ala Thr Leu
465                 470                 475                 480

Thr Ala Ser Asp Ile Gln Asn His Ser Arg Tyr Glu Gly Arg Ser Phe
```

```
                        485                 490                 495
Gly Ile Gly Gly Ser Phe Asp Leu Asn Gly Gly Trp Asp Gly Thr Val
                500                 505                 510
Thr Asp Lys Gln Gly Arg Pro Thr Asp Arg Ile Ser Pro Ala Ala Gly
            515                 520                 525
Tyr Gly Ser Asp Gly Asp Ser Lys Asn Ser Thr Thr Arg Ser Gly Val
        530                 535                 540
Asn Thr His Asn Ile His Ile Thr Asp Glu Ala Gly Gln Leu Ala Arg
545                 550                 555                 560
Thr Gly Arg Thr Ala Lys Glu Thr Glu Ala Arg Ile Tyr Thr Gly Ile
                565                 570                 575
Asp Thr Glu Thr Ala Asp Gln His Ser Gly His Leu Lys Asn Ser Phe
            580                 585                 590
Asp

<210> SEQ ID NO 65
<211> LENGTH: 390
<212> TYPE: DNA
<213> ORGANISM: Neisseria meningitidis

<400> SEQUENCE: 65
acgaccggca gcctcggcgg catactggcc ggcggcggca cttcccttgc cgcaccgtat      60
ttggacaaag cggcgaaaaa cctcggtccg gcgggcaaag cggcggtcaa cgcactgggc     120
ggtgcggcca tcggctatgc aactggtggt agtggtggtg ctgtggtggg tgcgaatgta     180
gattggaaca ataggcagct gcatccgaaa gaaatggcgt tggccgacaa atatgccgaa     240
gccctcaagc gcgaagttga aaacgcgaa ggcagaaaaa tcagcagcca agaagcggca     300
atgagaatcc gcaggcagat atgcgttggg tggacaaagg ttcccaagac ggctataccg     360
accaaagcgt catatccctt atcggaatga                                     390

<210> SEQ ID NO 66
<211> LENGTH: 129
<212> TYPE: PRT
<213> ORGANISM: Neisseria meningitidis

<400> SEQUENCE: 66

Thr Thr Gly Ser Leu Gly Gly Ile Leu Ala Gly Gly Thr Ser Leu
 1               5                  10                  15
Ala Ala Pro Tyr Leu Asp Lys Ala Ala Glu Asn Leu Gly Pro Ala Gly
             20                  25                  30
Lys Ala Ala Val Asn Ala Leu Gly Gly Ala Ala Ile Gly Tyr Ala Thr
         35                  40                  45
Gly Gly Ser Gly Gly Ala Val Val Gly Ala Asn Val Asp Trp Asn Asn
     50                  55                  60
Arg Gln Leu His Pro Lys Glu Met Ala Leu Ala Asp Lys Tyr Ala Glu
 65                  70                  75                  80
Ala Leu Lys Arg Glu Val Glu Lys Arg Glu Gly Arg Lys Ile Ser Ser
                 85                  90                  95
Gln Glu Ala Ala Met Arg Ile Arg Arg Gln Ile Cys Val Gly Trp Thr
            100                 105                 110
Lys Val Pro Lys Thr Ala Ile Pro Thr Lys Ala Ser Tyr Pro Leu Ser
        115                 120                 125
Glu
```

-continued

```
<210> SEQ ID NO 67
<211> LENGTH: 960
<212> TYPE: DNA
<213> ORGANISM: Neisseria meningitidis

<400> SEQUENCE: 67
caatgccgtc tgaaaagctc acaattttac agacggcatt tgttatgcaa gtacatatac      60
agattcccta tatactgccc agrkgcgtgc gtggctgaag cacccccta cgcttgctat     120 ttgraacagc tccaagtcac caaagacgtc aactggaacc aggtacwact ggcgtacgac     180
aaatgggact ataaacagga aggcttaacc ggagccggaa cagcgattat tgcgctggct     240
gttaccgtgg ttactgcggg cgcgggagcc ggagccgcac tgggcttaaa cggcgcggcc     300
gcagcggcaa ccgatgccgc attcgcctcg ctggccagcc aggcttccgt atcgctcatc     360
aacaacaaag gcaatatcgg taacaccctg aaagagctgg gcagaagcag cacggtgaaa     420 atctgatgg ttgccgtcgc taccgcaggc gtagccgaca aaatcggtgc ttcggcactg     480
aacaatgtca gcgataagca gtggatcaac aacctgaccg tcaacctggc caatgcgggc     540
agtgccgcac tgattaatac cgctgtcaac ggcggcagcc tgaaagacaa tctggaagcg     600
aatatccttg cggctttggt gaatactgcg catggagaag cagccagtaa atcaaacag      660 ttggatcagc actacattac ccacaagatt gcccatgcca tagcgggctg tgcggctgcg     720
gcggcgaata agggcaagtg tcaggatggt gcgataggtg cggctgtggg cgagatagtc     780
ggggaggctt tgacaaacgg caaaaatcct gacactttga cagctaaaga acgcgaacag     840
attttggcat acagcaaact ggttgccggt acggtaagcg gtgtggtcgg cggcgatgta     900
aatgcggcgg cgaatgcggc tgaggtagcg gtgaaaaata atcagcttag cgacaaatga     960

<210> SEQ ID NO 68
<211> LENGTH: 319
<212> TYPE: PRT
<213> ORGANISM: Neisseria meningitidis
<220> FEATURE:
<221> NAME/KEY: SITE
<222> LOCATION: (28)
<223> OTHER INFORMATION: unknown
<221> NAME/KEY: SITE
<222> LOCATION: (42)
<223> OTHER INFORMATION: unknown
<221> NAME/KEY: SITE
<222> LOCATION: (56)
<223> OTHER INFORMATION: unknown

<400> SEQUENCE: 68

Gln Cys Arg Leu Lys Ser Ser Gln Phe Tyr Arg Arg His Leu Leu Cys
  1               5                  10                  15

Lys Tyr Ile Tyr Arg Phe Pro Ile Tyr Cys Pro Xaa Ala Cys Val Ala
             20                  25                  30

Glu Asp Thr Pro Tyr Ala Cys Tyr Leu Xaa Gln Leu Gln Val Thr Lys
         35                  40                  45

Asp Val Asn Trp Asn Gln Val Xaa Leu Ala Tyr Asp Lys Trp Asp Tyr
     50                  55                  60

Lys Gln Glu Gly Leu Thr Gly Ala Gly Ala Ala Ile Ile Ala Leu Ala
 65                  70                  75                  80

Val Thr Val Val Thr Ala Gly Ala Gly Ala Gly Ala Ala Leu Gly Leu
                 85                  90                  95

Asn Gly Ala Ala Ala Ala Ala Thr Asp Ala Ala Phe Ala Ser Leu Ala
            100                 105                 110

Ser Gln Ala Ser Val Ser Leu Ile Asn Asn Lys Gly Asn Ile Gly Asn
```

```
            115                 120                 125
Thr Leu Lys Glu Leu Gly Arg Ser Ser Thr Val Lys Asn Leu Met Val
        130                 135                 140
Ala Val Ala Thr Ala Gly Val Ala Asp Lys Ile Gly Ala Ser Ala Leu
145                 150                 155                 160
Asn Asn Val Ser Asp Lys Gln Trp Ile Asn Asn Leu Thr Val Asn Leu
                165                 170                 175
Ala Asn Ala Gly Ser Ala Ala Leu Ile Asn Thr Ala Val Asn Gly Gly
            180                 185                 190
Ser Leu Lys Asp Asn Leu Glu Ala Asn Ile Leu Ala Ala Leu Val Asn
        195                 200                 205
Thr Ala His Gly Glu Ala Ala Ser Lys Ile Lys Gln Leu Asp Gln His
        210                 215                 220
Tyr Ile Thr His Lys Ile Ala His Ala Ile Ala Gly Cys Ala Ala Ala
225                 230                 235                 240
Ala Ala Asn Lys Gly Lys Cys Gln Asp Gly Ala Ile Gly Ala Ala Val
                245                 250                 255
Gly Glu Ile Val Gly Glu Ala Leu Thr Asn Gly Lys Asn Pro Asp Thr
            260                 265                 270
Leu Thr Ala Lys Glu Arg Glu Gln Ile Leu Ala Tyr Ser Lys Leu Val
        275                 280                 285
Ala Gly Thr Val Ser Gly Val Val Gly Gly Asp Val Asn Ala Ala Ala
        290                 295                 300
Asn Ala Ala Glu Val Ala Val Lys Asn Asn Gln Leu Ser Asp Lys
305                 310                 315

<210> SEQ ID NO 69
<211> LENGTH: 1860
<212> TYPE: DNA
<213> ORGANISM: Neisseria meningitidis

<400> SEQUENCE: 69
atgcaagtaa atattcagat tccctatata ctgcccagat gcgtgcgtgc tgaagacacc      60
ccctacgctt gctatttgaa acagctccaa gtcaccaaag acgtcaactg gaaccaggta     120
caactggcgt acgacaaatg ggactataaa caggaaggct taaccggagc cggagcagcg     180
attattgcgc tggctgttac cgtggttact gcgggcgcgg gagccggagc cgcactgggc     240
ttaaacggcg cggccgcagc ggcaaccgat gccgcattcg cctcgctggc cagccaggct     300
tccgtatcgc tcatcaacaa caaaggcaat atcggtaaca ccctgaaaga gctgggcaga     360
agcagcacgg tgaaaaatct gatggttgcc gtcgctaccg caggcgtagc cgacaaaatc     420
ggtgcttcgg cactgaacaa tgtcagcgat aagcagtgga tcaacaacct gaccgtcaac     480
ctggccaatg cgggcagtgc cgcactgatt aataccgctg tcaacggcgg cagcctgaaa     540
gacaatctgg aagcgaatat ccttgcggct ttggtgaata ctgcgcatgg agaagcagcc     600
agtaaaatca acagttgga tcagcactac attacccaca gattgcccca tgccatagcg     660
ggctgtgcgg ctgcggcggc gaataagggc aagtgtcagg atggtgcgat aggtgcggct     720
gtgggcgaga tagtcgggga ggcttttgaca acggcaaaa atcctgacac tttgacagct     780
aaagaacgcg aacagatttt ggcatacagc aaactggttg ccggtacggt aagcggtgtg     840
gtcggcggcg atgtaaatgc ggcggcgaat gcggctgagg tagcggtgaa aaataatcag     900
cttagcgaca agagggtag agaatttgat aacgaaatga ctgcatgcgc caaacagaat     960
aatcctcaac tgtgcagaaa aaatactgta aaaagtatc aaaatgttgc tgataaaaga    1020
```

-continued

```
cttgctgctt cgattgcaat atgtacggat atatcccgta gtactgaatg tagaacaatc    1080
agaaaacaac atttgatcga tagtagaagc cttcattcat cttgggaagc aggtctaatt    1140
ggtaaagatg atgaatggta taaattattc agcaaatctt acacccaagc agatttggct    1200
ttacagtctt atcatttgaa tactgctgct aaatcttggc ttcaatcggg caatacaaag    1260
cctttatccg aatggatgtc cgaccaaggt tatacactta tttcaggagt taatcctaga    1320
ttcattccaa taccaagagg gtttgtaaaa caaaatacac ctattactaa tgtcaaatac    1380
ccggaaggca tcagtttcga tacaaaccta aaaagacatc tggcaaatgc tgatggtttt    1440
agtcaaaaac agggcattaa aggagcccat aaccgcacca attttatggc agaactaaat    1500
tcacgaggag gacgcgtaaa atctgaaacc caaactgata ttgaaggcat tacccgaatt    1560
aaatatgaga ttcctacact agacaggaca ggtaaacctg atggtggatt taaggaaatt    1620
tcaagtataa aaactgttta taatcctaaa aaattttctg atgataaaat acttcaaatg    1680
gctcaaaatg ctgcttcaca aggatattca aaagcctcta aaattgctca aatgaaaga    1740 actaaatcaa tatcggaaag aaaaaatgtc attcaattct cagaaaccctt tgacggaatc    1800 aaatttagat catattttga tgtaaataca ggaagaatta caaacattca cccagaataa    1860
```

<210> SEQ ID NO 70
<211> LENGTH: 619
<212> TYPE: PRT
<213> ORGANISM: Neisseria meningitidis

<400> SEQUENCE: 70

```
Met Gln Val Asn Ile Gln Ile Pro Tyr Ile Leu Pro Arg Cys Val Arg
 1               5                  10                  15

Ala Glu Asp Thr Pro Tyr Ala Cys Tyr Leu Lys Gln Leu Gln Val Thr
                20                  25                  30

Lys Asp Val Asn Trp Asn Gln Val Gln Leu Ala Tyr Asp Lys Trp Asp
            35                  40                  45

Tyr Lys Gln Glu Gly Leu Thr Gly Ala Gly Ala Ala Ile Ile Ala Leu
        50                  55                  60

Ala Val Thr Val Thr Ala Gly Ala Gly Ala Ala Leu Gly
 65                  70                  75                  80

Leu Asn Gly Ala Ala Ala Ala Thr Asp Ala Ala Phe Ala Ser Leu
                85                  90                  95

Ala Ser Gln Ala Ser Val Ser Leu Ile Asn Asn Lys Gly Asn Ile Gly
            100                 105                 110

Asn Thr Leu Lys Glu Leu Gly Arg Ser Ser Thr Val Lys Asn Leu Met
        115                 120                 125

Val Ala Val Ala Thr Ala Gly Val Ala Asp Lys Ile Gly Ala Ser Ala
    130                 135                 140

Leu Asn Asn Val Ser Asp Lys Gln Trp Ile Asn Asn Leu Thr Val Asn
145                 150                 155                 160

Leu Ala Asn Ala Gly Ser Ala Ala Leu Ile Asn Thr Ala Val Asn Gly
                165                 170                 175

Gly Ser Leu Lys Asp Asn Leu Glu Ala Asn Ile Leu Ala Ala Leu Val
            180                 185                 190

Asn Thr Ala His Gly Glu Ala Ala Ser Lys Ile Lys Gln Leu Asp Gln
        195                 200                 205

His Tyr Ile Thr His Lys Ile Ala His Ala Ile Ala Gly Cys Ala Ala
    210                 215                 220
```

-continued

```
Ala Ala Ala Asn Lys Gly Lys Cys Gln Asp Gly Ala Ile Gly Ala Ala
225                 230                 235                 240

Val Gly Glu Ile Val Gly Glu Ala Leu Thr Asn Gly Lys Asn Pro Asp
            245                 250                 255

Thr Leu Thr Ala Lys Glu Arg Glu Gln Ile Leu Ala Tyr Ser Lys Leu
                260                 265                 270

Val Ala Gly Thr Val Ser Gly Val Val Gly Asp Val Asn Ala Ala
            275                 280                 285

Ala Asn Ala Ala Glu Val Ala Val Lys Asn Asn Gln Leu Ser Asp Lys
        290                 295                 300

Glu Gly Arg Glu Phe Asp Asn Glu Met Thr Ala Cys Ala Lys Gln Asn
305                 310                 315                 320

Asn Pro Gln Leu Cys Arg Lys Asn Thr Val Lys Lys Tyr Gln Asn Val
                325                 330                 335

Ala Asp Lys Arg Leu Ala Ala Ser Ile Ala Ile Cys Thr Asp Ile Ser
            340                 345                 350

Arg Ser Thr Glu Cys Arg Thr Ile Arg Lys Gln His Leu Ile Asp Ser
        355                 360                 365

Arg Ser Leu His Ser Ser Trp Glu Ala Gly Leu Ile Gly Lys Asp Asp
    370                 375                 380

Glu Trp Tyr Lys Leu Phe Ser Lys Ser Tyr Thr Gln Ala Asp Leu Ala
385                 390                 395                 400

Leu Gln Ser Tyr His Leu Asn Thr Ala Ala Lys Ser Trp Leu Gln Ser
                405                 410                 415

Gly Asn Thr Lys Pro Leu Ser Glu Trp Met Ser Asp Gln Gly Tyr Thr
            420                 425                 430

Leu Ile Ser Gly Val Asn Pro Arg Phe Ile Pro Ile Pro Arg Gly Phe
        435                 440                 445

Val Lys Gln Asn Thr Pro Ile Thr Asn Val Lys Tyr Pro Glu Gly Ile
    450                 455                 460

Ser Phe Asp Thr Asn Leu Lys Arg His Leu Ala Asn Ala Asp Gly Phe
465                 470                 475                 480

Ser Gln Lys Gln Gly Ile Lys Gly Ala His Asn Arg Thr Asn Phe Met
                485                 490                 495

Ala Glu Leu Asn Ser Arg Gly Gly Arg Val Lys Ser Glu Thr Gln Thr
            500                 505                 510

Asp Ile Glu Gly Ile Thr Arg Ile Lys Tyr Glu Ile Pro Thr Leu Asp
        515                 520                 525

Arg Thr Gly Lys Pro Asp Gly Phe Lys Glu Ile Ser Ser Ile Lys
    530                 535                 540

Thr Val Tyr Asn Pro Lys Lys Phe Ser Asp Asp Lys Ile Leu Gln Met
545                 550                 555                 560

Ala Gln Asn Ala Ala Ser Gln Gly Tyr Ser Lys Ala Ser Lys Ile Ala
                565                 570                 575

Gln Asn Glu Arg Thr Lys Ser Ile Ser Glu Arg Lys Asn Val Ile Gln
            580                 585                 590

Phe Ser Glu Thr Phe Asp Gly Ile Lys Phe Arg Ser Tyr Phe Asp Val
        595                 600                 605

Asn Thr Gly Arg Ile Thr Asn Ile His Pro Glu
    610                 615

<210> SEQ ID NO 71
<211> LENGTH: 1788
<212> TYPE: DNA
```

```
<213> ORGANISM: Neisseria meningitidis
<220> FEATURE:
<221> NAME/KEY: misc_feature
<222> LOCATION: (181)
<223> OTHER INFORMATION: any nucleotide
<221> NAME/KEY: misc_feature
<222> LOCATION: (365)
<223> OTHER INFORMATION: any nucleotide
<221> NAME/KEY: misc_feature
<222> LOCATION: (473)
<223> OTHER INFORMATION: any nucleotide
<221> NAME/KEY: misc_feature
<222> LOCATION: (838)
<223> OTHER INFORMATION: any nucleotide
<221> NAME/KEY: misc_feature
<222> LOCATION: (890)
<223> OTHER INFORMATION: any nucleotide
<221> NAME/KEY: misc_feature
<222> LOCATION: (1339)
<223> OTHER INFORMATION: any nucleotide
<221> NAME/KEY: misc_feature
<222> LOCATION: (1411)
<223> OTHER INFORMATION: any nucleotide
<221> NAME/KEY: misc_feature
<222> LOCATION: (1441)
<223> OTHER INFORMATION: any nucleotide
<221> NAME/KEY: misc_feature
<222> LOCATION: (1443)
<223> OTHER INFORMATION: any nucleotide
<221> NAME/KEY: misc_feature
<222> LOCATION: (1461)
<223> OTHER INFORMATION: any nucleotide
<221> NAME/KEY: misc_feature
<222> LOCATION: (1581)
<223> OTHER INFORMATION: any nucleotide
<221> NAME/KEY: misc_feature
<222> LOCATION: (1586)..(1587)
<223> OTHER INFORMATION: any nucleotide
<221> NAME/KEY: misc_feature
<222> LOCATION: (1615)
<223> OTHER INFORMATION: any nucleotide
<221> NAME/KEY: misc_feature
<222> LOCATION: (1622)
<223> OTHER INFORMATION: any nucleotide
<221> NAME/KEY: misc_feature
<222> LOCATION: (1738)..(1740)
<223> OTHER INFORMATION: any nucleotide
<221> NAME/KEY: misc_feature
<222> LOCATION: (1744)
<223> OTHER INFORMATION: any nucleotide
<221> NAME/KEY: misc_feature
<222> LOCATION: (1746)
<223> OTHER INFORMATION: any nucleotide

<400> SEQUENCE: 71
tatctgaaac agctccaagt agcgaaaaac atcaactgga atcaggtgca gcttgcttac      60
gacagatggg actacaaaca ggagggctta accgaagcag gtgcggcgat tatcgcactg     120
gccgttaccg tggtcacctc aggcgcagga accggagccg tattgggatt aaacggtgcg     180
nccgccgccg caaccgatgc agcattcgcc tctttggcca gccaggcttc cgtatcgttc     240
atcaacaaca aaggcgatgt cggcaaaacc ctgaaagagc tgggcagaag cagcacggtg     300
aaaaatctgg tggttgccgc cgctaccgca ggcgtagccg acaaaatcgg cgcttcggca     360
ctgancaatg tcagcgataa gcagtggatc aacaacctga ccgtcaacct agccaatgcg     420
ggcagtgccg cactgattaa taccgctgtc aacggcggca gcctgaaaga cantctggaa     480
gcgaatatcc ttgcggcttt ggtcaatacc gcgcatgag aagcagccag taaaatcaaa      540
cagttggatc agcactacat agtccacaag attgcccatg ccatagcggg ctgtgcggca     600
gcggcggcga ataagggcaa gtgtcaggat ggtgcgatag gtgcggctgt gggcgagata     660
gtcggggagg ctttgacaaa cggcaaaaat cctgacactt tgacagctaa agaacgcgaa     720
```

```
cagattttgg catacagcaa actggttgcc ggtacggtaa gcggtgtggt cggcggcgat      780
gtaaatgcgg cggcgaatgc ggctgaggta gcggtgaaaa ataatcagct tagcgacnaa      840
gagggtagag aatttgataa cgaaatgact gcatgcgcca aacagaatan tcctcaactg      900
tgcagaaaaa atactgtaaa aaagtatcaa aatgttgctg ataaaagact tgctgcttcg      960
attgcaatat gtacggatat atcccgtagt actgaatgta gaacaatcag aaaacaacat     1020
ttgatcgata gtagaagcct tcattcatct tgggaagcag gtctaattgg taagatgat      1080 gaatggtata aattattcag caaatcttac acccaagcag atttggcttt acagtcttat     1140
catttgaata ctgctgctaa atcttggctt caatcgggca atacaaagcc tttatccgaa     1200
tggatgtccg accaaggtta tacacttatt tcaggagtta atcctagatt cattccaata     1260
ccaagagggt ttgtaaaaca aaatacacct attactaatg tcaaataccc ggaaggcatc     1320
agtttcgata caaacctana aagacatctg gcaaatgcta atggttttag tcaagaacag     1380
ggcattaaag gagcccataa ccgcaccaat nttatggcag aactaaattc acgaggagga     1440
ngngtaaaat ctgaaaccca nactgatatt gaaggcatta cccgaattaa atatgagatt     1500
cctacactag acaggacagg taaacctgat ggtggattta aggaaatttc aagtataaaa     1560
actgtttata atcctaaaaa nttttnngat gataaaaatac ttcaaatggc tcaanatgct     1620
gnttcacaag gatattcaaa agcctctaaa attgctcaaa atgaaagaac taaatcaata     1680
tcggaaagaa aaaatgtcat tcaattctca gaaacctttg acggaatcaa atttagannn     1740
tatntngatg taaatacagg aagaattaca aacattcacc cagaataa                  1788
```

<210> SEQ ID NO 72
<211> LENGTH: 595
<212> TYPE: PRT
<213> ORGANISM: Neisseria meningitidis
<220> FEATURE:
<221> NAME/KEY: SITE
<222> LOCATION: (61)
<223> OTHER INFORMATION: unknown
<221> NAME/KEY: SITE
<222> LOCATION: (122)
<223> OTHER INFORMATION: unknown
<221> NAME/KEY: SITE
<222> LOCATION: (158)
<223> OTHER INFORMATION: unknown
<221> NAME/KEY: SITE
<222> LOCATION: (280)
<223> OTHER INFORMATION: unknown
<221> NAME/KEY: SITE
<222> LOCATION: (297)
<223> OTHER INFORMATION: unknown
<221> NAME/KEY: SITE
<222> LOCATION: (447)
<223> OTHER INFORMATION: unknown
<221> NAME/KEY: SITE
<222> LOCATION: (471)
<223> OTHER INFORMATION: unknown
<221> NAME/KEY: SITE
<222> LOCATION: (481)
<223> OTHER INFORMATION: unknown
<221> NAME/KEY: SITE
<222> LOCATION: (487)
<223> OTHER INFORMATION: unknown
<221> NAME/KEY: SITE
<222> LOCATION: (527)
<223> OTHER INFORMATION: unknown
<221> NAME/KEY: SITE
<222> LOCATION: (529)
<223> OTHER INFORMATION: unknown
<221> NAME/KEY: SITE
<222> LOCATION: (539)
<223> OTHER INFORMATION: unknown

```
<221> NAME/KEY: SITE
<222> LOCATION: (541)
<223> OTHER INFORMATION: unknown
<221> NAME/KEY: SITE
<222> LOCATION: (580)
<223> OTHER INFORMATION: unknown
<221> NAME/KEY: SITE
<222> LOCATION: (582)
<223> OTHER INFORMATION: unknown

<400> SEQUENCE: 72

Tyr Leu Lys Gln Leu Gln Val Ala Lys Asn Ile Asn Trp Asn Gln Val
 1               5                  10                  15

Gln Leu Ala Tyr Asp Arg Trp Asp Tyr Lys Gln Glu Gly Leu Thr Glu
             20                  25                  30

Ala Gly Ala Ala Ile Ile Ala Leu Ala Val Thr Val Val Thr Ser Gly
         35                  40                  45

Ala Gly Thr Gly Ala Val Leu Gly Leu Asn Gly Ala Xaa Ala Ala Ala
     50                  55                  60

Thr Asp Ala Ala Phe Ala Ser Leu Ala Ser Gln Ala Ser Val Ser Phe
 65                  70                  75                  80

Ile Asn Asn Lys Gly Asp Val Gly Lys Thr Leu Lys Glu Leu Gly Arg
                 85                  90                  95

Ser Ser Thr Val Lys Asn Leu Val Ala Ala Thr Ala Gly Val
            100                 105                 110

Ala Asp Lys Ile Gly Ala Ser Ala Leu Xaa Asn Val Ser Asp Lys Gln
            115                 120                 125

Trp Ile Asn Asn Leu Thr Val Asn Leu Ala Asn Ala Gly Ser Ala Ala
        130                 135                 140

Leu Ile Asn Thr Ala Val Asn Gly Gly Ser Leu Lys Asp Xaa Leu Glu
145                 150                 155                 160

Ala Asn Ile Leu Ala Ala Leu Val Asn Thr Ala His Gly Glu Ala Ala
                165                 170                 175

Ser Lys Ile Lys Gln Leu Asp Gln His Tyr Ile Val His Lys Ile Ala
            180                 185                 190

His Ala Ile Ala Gly Cys Ala Ala Ala Ala Asn Lys Gly Lys Cys
        195                 200                 205

Gln Asp Gly Ala Ile Gly Ala Val Gly Glu Ile Val Gly Glu Ala
    210                 215                 220

Leu Thr Asn Gly Lys Asn Pro Asp Thr Leu Thr Ala Lys Glu Arg Glu
225                 230                 235                 240

Gln Ile Leu Ala Tyr Ser Lys Leu Val Ala Gly Thr Val Ser Gly Val
                245                 250                 255

Val Gly Gly Asp Val Asn Ala Ala Asn Ala Ala Glu Val Ala Val
            260                 265                 270

Lys Asn Asn Gln Leu Ser Asp Xaa Glu Gly Arg Glu Phe Asp Asn Glu
            275                 280                 285

Met Thr Ala Cys Ala Lys Gln Asn Xaa Pro Gln Leu Cys Arg Lys Asn
    290                 295                 300

Thr Val Lys Lys Tyr Gln Asn Val Ala Asp Lys Arg Leu Ala Ala Ser
305                 310                 315                 320

Ile Ala Ile Cys Thr Asp Ile Ser Arg Ser Thr Glu Cys Arg Thr Ile
                325                 330                 335

Arg Lys Gln His Leu Ile Asp Ser Arg Ser Leu His Ser Ser Trp Glu
            340                 345                 350
```

```
Ala Gly Leu Ile Gly Lys Asp Asp Glu Trp Tyr Lys Leu Phe Ser Lys
        355                 360                 365

Ser Tyr Thr Gln Ala Asp Leu Ala Leu Gln Ser Tyr His Leu Asn Thr
    370                 375                 380

Ala Ala Lys Ser Trp Leu Gln Ser Gly Asn Thr Lys Pro Leu Ser Glu
385                 390                 395                 400

Trp Met Ser Asp Gln Gly Tyr Thr Leu Ile Ser Gly Val Asn Pro Arg
                405                 410                 415

Phe Ile Pro Ile Pro Arg Gly Phe Val Lys Gln Asn Thr Pro Ile Thr
            420                 425                 430

Asn Val Lys Tyr Pro Glu Gly Ile Ser Phe Asp Thr Asn Leu Xaa Arg
        435                 440                 445

His Leu Ala Asn Ala Asp Gly Phe Ser Gln Glu Gln Gly Ile Lys Gly
    450                 455                 460

Ala His Asn Arg Thr Asn Xaa Met Ala Glu Leu Asn Ser Arg Gly Gly
465                 470                 475                 480

Xaa Val Lys Ser Glu Thr Xaa Thr Asp Ile Glu Gly Ile Thr Arg Ile
                485                 490                 495

Lys Tyr Glu Ile Pro Thr Leu Asp Arg Thr Gly Lys Pro Asp Gly Gly
            500                 505                 510

Phe Lys Glu Ile Ser Ser Ile Lys Thr Val Tyr Asn Pro Lys Xaa Phe
        515                 520                 525

Xaa Asp Asp Lys Ile Leu Gln Met Ala Gln Xaa Ala Xaa Ser Gln Gly
    530                 535                 540

Tyr Ser Lys Ala Ser Lys Ile Ala Gln Asn Glu Arg Thr Lys Ser Ile
545                 550                 555                 560

Ser Glu Arg Lys Asn Val Ile Gln Phe Ser Glu Thr Phe Asp Gly Ile
                565                 570                 575

Lys Phe Arg Xaa Tyr Xaa Asp Val Asn Thr Gly Arg Ile Thr Asn Ile
            580                 585                 590

His Pro Glu
        595

<210> SEQ ID NO 73
<211> LENGTH: 453
<212> TYPE: DNA
<213> ORGANISM: Neisseria meningitidis

<400> SEQUENCE: 73
atggcaatca ttacattgta ttattctgtc aatggtattt taaatgtatg tgcaaaagca      60
aaaaatattc aagtagttgc caataataag aatatggttc tttttgggtt tttggsmrgc    120
atcatcggcg gttcaaccaa tgccatgtct cccatattgt taatattttt gcttagcgaa    180
acagaaaata aaaatcgtat cgtaaaatca agcaatctat gctatctttt ggcgaaaatt    240
gttcaaatat atatgctaag agaccagtat tggttattaa ataagagtga atacgdttta    300
atatttttac tgtccgtatt gtctgttatt ggattgtatg ttggaattcg gttaaggact    360
aagattagcc caattttttt taaaatgtta attttttattg ttttattggt attggctctg    420
aaaatcgggc attcgggttt aatcaaactt taa                                 453

<210> SEQ ID NO 74
<211> LENGTH: 150
<212> TYPE: PRT
<213> ORGANISM: Neisseria meningitidis
<220> FEATURE:
<221> NAME/KEY: SITE
```

```
<222> LOCATION: (39)..(40)
<223> OTHER INFORMATION: unknown
<221> NAME/KEY: SITE
<222> LOCATION: (99)
<223> OTHER INFORMATION: unknown

<400> SEQUENCE: 74
```

Met Ala Ile Ile Thr Leu Tyr Tyr Ser Val Asn Gly Ile Leu Asn Val
1               5                   10                  15

Cys Ala Lys Ala Lys Asn Ile Gln Val Val Ala Asn Asn Lys Asn Met
                20                  25                  30

Val Leu Phe Gly Phe Leu Xaa Xaa Ile Ile Gly Gly Ser Thr Asn Ala
            35                  40                  45

Met Ser Pro Ile Leu Leu Ile Phe Leu Leu Ser Glu Thr Glu Asn Lys
        50                  55                  60

Asn Arg Ile Val Lys Ser Ser Asn Leu Cys Tyr Leu Leu Ala Lys Ile
65                  70                  75                  80

Val Gln Ile Tyr Met Leu Arg Asp Gln Tyr Trp Leu Leu Asn Lys Ser
                85                  90                  95

Glu Tyr Xaa Leu Ile Phe Leu Leu Ser Val Leu Ser Val Ile Gly Leu
            100                 105                 110

Tyr Val Gly Ile Arg Leu Arg Thr Lys Ile Ser Pro Asn Phe Phe Lys
        115                 120                 125

Met Leu Ile Phe Ile Val Leu Leu Val Leu Ala Leu Lys Ile Gly His
    130                 135                 140

Ser Gly Leu Ile Lys Leu
145                 150

```
<210> SEQ ID NO 75
<211> LENGTH: 768
<212> TYPE: DNA
<213> ORGANISM: Neisseria meningitidis

<400> SEQUENCE: 75
```

| | | | | | |
|---|---|---|---|---|---|
| atgcaagaaa | taatgcaatc | tatcgttttt | gttgctgccg | caatactgca | cggaattaca | 60 |
| ggcatgggat | ttccgatgct | cggtacaacc | gcattggctt | ttatcatgcc | attgtctaag | 120 |
| gttgttgcct | tggtggcatt | accaagcctg | ttaatgagct | tgttggttct | atgcagcaat | 180 |
| aacaaaaagg | ttttttggca | agagattgtt | tattatttaa | aaacctataa | attgcttgct | 240 |
| atcggcagcg | tcgttggcag | catttggggg | gtgaagttgc | ttttgatact | tccagtgtct | 300 |
| tggctgcttt | tactgatggc | aatcattaca | ttgtattatt | ctgtcaatgg | tattttaaat | 360 |
| gtatgtgcaa | aagcaaaaaa | tattcaagta | gttgccaata | taagaatat | ggttcttttt | 420 |
| gggtttttgg | caggcatcat | cggcggttca | accaatgcca | tgtctcccat | attgttaata | 480 |
| ttttttgctta | gcgaaacaga | aaataaaaat | cgtatcgtaa | atcaagcaa | tctatgctat | 540 |
| cttttggcga | aaattgttca | atatatatg | ctaagagacc | agtattggtt | attaaataag | 600 |
| agtgaatacg | tttaatatt | tttactgtcc | gtattgtctg | ttattggatt | gtatgttgga | 660 |
| attcggttaa | ggactaagat | tagcccaaat | tttttaaaa | tgttaattt | tattgtttta | 720 |
| ttggtattgg | ctctgaaaat | cgggcattcg | ggtttaatca | aactttaa | | 768 |

```
<210> SEQ ID NO 76
<211> LENGTH: 255
<212> TYPE: PRT
<213> ORGANISM: Neisseria meningitidis

<400> SEQUENCE: 76
```

```
Met Gln Glu Ile Met Gln Ser Ile Val Phe Val Ala Ala Ala Ile Leu
 1               5                  10                  15

His Gly Ile Thr Gly Met Gly Phe Pro Met Leu Gly Thr Thr Ala Leu
                20                  25                  30

Ala Phe Ile Met Pro Leu Ser Lys Val Val Ala Leu Val Ala Leu Pro
            35                  40                  45

Ser Leu Leu Met Ser Leu Leu Val Leu Cys Ser Asn Asn Lys Lys Gly
        50                  55                  60

Phe Trp Gln Glu Ile Val Tyr Tyr Leu Lys Thr Tyr Lys Leu Leu Ala
 65                 70                  75                  80

Ile Gly Ser Val Val Gly Ser Ile Leu Gly Val Lys Leu Leu Leu Ile
                85                  90                  95

Leu Pro Val Ser Trp Leu Leu Leu Met Ala Ile Ile Thr Leu Tyr
                100                 105                 110

Tyr Ser Val Asn Gly Ile Leu Asn Val Cys Ala Lys Ala Lys Asn Ile
            115                 120                 125

Gln Val Val Ala Asn Asn Lys Asn Met Val Leu Phe Gly Phe Leu Ala
        130                 135                 140

Gly Ile Ile Gly Gly Ser Thr Asn Ala Met Ser Pro Ile Leu Leu Ile
145                 150                 155                 160

Phe Leu Leu Ser Glu Thr Glu Asn Lys Asn Arg Ile Val Lys Ser Ser
                165                 170                 175

Asn Leu Cys Tyr Leu Leu Ala Lys Ile Val Gln Ile Tyr Met Leu Arg
            180                 185                 190

Asp Gln Tyr Trp Leu Leu Asn Lys Ser Glu Tyr Gly Leu Ile Phe Leu
        195                 200                 205

Leu Ser Val Leu Ser Val Ile Gly Leu Tyr Val Gly Ile Arg Leu Arg
        210                 215                 220

Thr Lys Ile Ser Pro Asn Phe Phe Lys Met Leu Ile Phe Ile Val Leu
225                 230                 235                 240

Leu Val Leu Ala Leu Lys Ile Gly His Ser Gly Leu Ile Lys Leu
                245                 250                 255
```

<210> SEQ ID NO 77
<211> LENGTH: 768
<212> TYPE: DNA
<213> ORGANISM: Neisseria meningitidis

<400> SEQUENCE: 77

| | | | | | |
|---|---|---|---|---|---|
| atgcaagaaa | taatgcaatc | tatcgttttt | gttgctgccg | caatactgca | cggaattaca | 60 |
| ggcatgggat | tccgatgct | cggtacaacc | gcattggctt | ttatcatgcc | attgtctaag | 120 |
| gttgttgcct | tggtggcatt | accaagcctg | ttaatgagct | tgttggttct | atgcagcaat | 180 |
| aacaaaaagg | ttttttggca | agagattgtt | tattatttaa | aaacctataa | attgcttgct | 240 |
| atcggcagcg | tcgttggcag | catttggggg | gtgaagttgc | ttttgatact | tccagtgtct | 300 |
| tggctgcttt | tactgatggc | aatcattaca | ttgtattatt | ctgtcaatgg | tattttaaat | 360 |
| gtatgtgcaa | aagcaaaaaa | tattcaagta | gttgccaata | ataagaatat | ggttcttttt | 420 |
| gggttttttgg | caggcatcat | cggcggttca | accaatgcca | tgtctcccat | attgttaata | 480 |
| ttttgctta | gcgaaacaga | gaataaaaat | cgtatcgcaa | atcaagcaa | tctatgctat | 540 |
| cttttggcaa | aaattgttca | atatatatg | ctaagagacc | agtattggtt | attaaataag | 600 |
| agtgaatacg | gtttaatatt | tttactgtcc | gtattgtctg | ttattggatt | gtatgttgga | 660 |

```
attcggttaa ggactaagat tagcccaaat ttttttaaaa tgttaatttt tattgtttta    720
ttggtattgg ctctgaaaat cgggtattca ggtttaatca aactttaa                 768
```

<210> SEQ ID NO 78
<211> LENGTH: 255
<212> TYPE: PRT
<213> ORGANISM: Neisseria meningitidis

<400> SEQUENCE: 78

```
Met Gln Glu Ile Met Gln Ser Ile Val Phe Val Ala Ala Ala Ile Leu
  1               5                  10                  15

His Gly Ile Thr Gly Met Gly Phe Pro Met Leu Gly Thr Thr Ala Leu
             20                  25                  30

Ala Phe Ile Met Pro Leu Ser Lys Val Val Ala Leu Val Ala Leu Pro
         35                  40                  45

Ser Leu Leu Met Ser Leu Leu Val Leu Cys Ser Asn Asn Lys Lys Gly
     50                  55                  60

Phe Trp Gln Glu Ile Val Tyr Tyr Leu Lys Thr Tyr Lys Leu Leu Ala
 65                  70                  75                  80

Ile Gly Ser Val Val Gly Ser Ile Leu Gly Val Lys Leu Leu Leu Ile
                 85                  90                  95

Leu Pro Val Ser Trp Leu Leu Leu Met Ala Ile Ile Thr Leu Tyr
            100                 105                 110

Tyr Ser Val Asn Gly Ile Leu Asn Val Cys Ala Lys Ala Lys Asn Ile
        115                 120                 125

Gln Val Val Ala Asn Asn Lys Asn Met Val Leu Phe Gly Phe Leu Ala
    130                 135                 140

Gly Ile Ile Gly Gly Ser Thr Asn Ala Met Ser Pro Ile Leu Leu Ile
145                 150                 155                 160

Phe Leu Leu Ser Glu Thr Glu Asn Lys Asn Arg Ile Ala Lys Ser Ser
                165                 170                 175

Asn Leu Cys Tyr Leu Leu Ala Lys Ile Val Gln Ile Tyr Met Leu Arg
            180                 185                 190

Asp Gln Tyr Trp Leu Leu Asn Lys Ser Glu Tyr Gly Leu Ile Phe Leu
        195                 200                 205

Leu Ser Val Leu Ser Val Ile Gly Leu Tyr Val Gly Ile Arg Leu Arg
    210                 215                 220

Thr Lys Ile Ser Pro Asn Phe Phe Lys Met Leu Ile Phe Ile Val Leu
225                 230                 235                 240

Leu Val Leu Ala Leu Lys Ile Gly Tyr Ser Gly Leu Ile Lys Leu
                245                 250                 255
```

<210> SEQ ID NO 79
<211> LENGTH: 516
<212> TYPE: DNA
<213> ORGANISM: Neisseria meningitidis

<400> SEQUENCE: 79

```
atgagacata tgaaaataca aaattattta ctagtattta tagttttaca tatagccttg     60
atagtaatta atatagtgtt tggttatttt gttttctat ttgatttttt tgcgttttg     120 tttttgcaa acgtctttct tgctgtaaat ttattatttt tagaaaaaaa cataaaaaac    180
aaattattgt ttttattgcc gatttctatt attatatgga tggtaattca tattagtatg    240
ataaatataa aattttataa atttgagcat caaataaagg aacaaatat atcctcgatt     300 actggggtga taaaaccaca tgatagttat aattatgttt atgactcaaa tggatatgct    360
```

```
aaattaaaag ataatcatag atatggtagg gtaattagag aaacacctta tattgatgta      420
gttgcatctg atgttaaaaa taaatccata agattaagct tggtttgtgg tattcattca      480
tatgctccat gtgccaattt tataaaattt gtcagg                                516
```

<210> SEQ ID NO 80
<211> LENGTH: 172
<212> TYPE: PRT
<213> ORGANISM: Neisseria meningitidis

<400> SEQUENCE: 80

```
Met Arg His Met Lys Ile Gln Asn Tyr Leu Leu Val Phe Ile Val Leu
  1               5                  10                  15

His Ile Ala Leu Ile Val Ile Asn Ile Val Phe Gly Tyr Phe Val Phe
             20                  25                  30

Leu Phe Asp Phe Phe Ala Phe Leu Phe Phe Ala Asn Val Phe Leu Ala
         35                  40                  45

Val Asn Leu Leu Phe Leu Glu Lys Asn Ile Lys Asn Lys Leu Leu Phe
     50                  55                  60

Leu Leu Pro Ile Ser Ile Ile Trp Met Val Ile His Ile Ser Met
 65                  70                  75                  80

Ile Asn Ile Lys Phe Tyr Lys Phe Glu His Gln Ile Lys Glu Gln Asn
                 85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Val Arg
                165                 170
```

<210> SEQ ID NO 81
<211> LENGTH: 729
<212> TYPE: DNA
<213> ORGANISM: Neisseria meningitidis

<400> SEQUENCE: 81

```
atgagacata tgaaaaataa aaattattta ctagtattta tagttttaca tatagccttg       60
atagtaatta atatagtgtt tggttatttt gttttctat ttgattttt tgcgttttg         120 tttttttgcaa acgtctttct tgctgtaaat ttattatttt tagaaaaaaa cataaaaaac     180
aaattattgt ttttattgcc gatttctatt attatatgga tggtaattca tattagtatg     240
ataaatataa aattttataa atttgagcat caaataaagg aacaaaatat atcctcgatt     300
actggggtga taaaaccaca tgatagttat aattatgttt atgactcaaa tggatatgct     360
aaattaaaag ataatcatag atatggtagg gtaattagag aaacacctta tattgatgta     420
gttgcatctg atgttaaaaa taaatccata agattaagct tggtttgtgg tattcattca     480
tatgctccat gtgccaattt tataaaattt gcaaaaaaac ctgttaaaat ttattttat    540 aatcaacctc aaggagattt tatagataat gtaatatttg aaattaatga tggaaacaaa    600
agtttgtact tgttagataa gtataaaaca ttttttctta ttgaaaacag tgtttgtatc     660
gtattaatta ttttatattt aaaatttaat ttgcttttat ataggactta cttcaatgag    720
```

```
ttggaatag                                                               729
```

<210> SEQ ID NO 82
<211> LENGTH: 242
<212> TYPE: PRT
<213> ORGANISM: Neisseria meningitidis

<400> SEQUENCE: 82

```
Met Arg His Met Lys Asn Lys Asn Tyr Leu Leu Val Phe Ile Val Leu
 1               5                  10                  15

His Ile Ala Leu Ile Val Ile Asn Ile Val Phe Gly Tyr Phe Val Phe
            20                  25                  30

Leu Phe Asp Phe Phe Ala Phe Leu Phe Phe Ala Asn Val Phe Leu Ala
        35                  40                  45

Val Asn Leu Leu Phe Leu Glu Lys Asn Ile Lys Asn Lys Leu Leu Phe
    50                  55                  60

Leu Leu Pro Ile Ser Ile Ile Trp Met Val Ile His Ile Ser Met
65                  70                  75                  80

Ile Asn Ile Lys Phe Tyr Lys Phe Glu His Gln Ile Lys Glu Gln Asn
                85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Ala Lys Lys Pro Val Lys
                165                 170                 175

Ile Tyr Phe Tyr Asn Gln Pro Gln Gly Asp Phe Ile Asp Asn Val Ile
            180                 185                 190

Phe Glu Ile Asn Asp Gly Asn Lys Ser Leu Tyr Leu Leu Asp Lys Tyr
        195                 200                 205

Lys Thr Phe Phe Leu Ile Glu Asn Ser Val Cys Ile Val Leu Ile Ile
    210                 215                 220

Leu Tyr Leu Lys Phe Asn Leu Leu Tyr Arg Thr Tyr Phe Asn Glu
225                 230                 235                 240

Leu Glu
```

<210> SEQ ID NO 83
<211> LENGTH: 729
<212> TYPE: DNA
<213> ORGANISM: Neisseria meningitidis

<400> SEQUENCE: 83

```
atgagacata tgaaaaataa aaattattta ctagtattta gtttttaca tataaccttg        60 atagtaatta atatagtgtt tggttatttt gtttttctat ttgattttt tgcgttttg        120 ttttttgcaa acgtctttct tgctgtaaat ttattatttt tagaaaaaaa cataaaaaac       180
aaattattgt ttttattgcc gatttctatt attatatgga tggtaattca tattagtatg       240
ataaatataa aattttataa atttgagcat caaataaagg aacaaaatat atcctcgatt       300
actggggtga taaaaccaca tgatagttat aattatgttt atgactcaaa tggatatgct       360
aaattaaaag ataatcatag atatggtagg gtaattagag aaacacctta tattgatgta       420
```

-continued

```
gttgcatctg atgttaaaaa taaatccata agattaagct tggtttgtgg tattcattca    480
tatgctccat gtgccaattt tataaaattt gcaaaaaaac ctgttaaaat ttatttttat    540
aatcaacctc aaggagattt tatagataat gtaatatttg aaattaatga tggaaaaaaa    600
agtttgtact tgttagataa gtataaaaca tttttctta ttgaaaacag tgtttgtatc     660
gtattaatta ttttatattt aaaatttaat ttgcttttat ataggactta cttcaatgag    720
ttggaatag                                                            729
```

<210> SEQ ID NO 84
<211> LENGTH: 242
<212> TYPE: PRT
<213> ORGANISM: Neisseria meningitidis

<400> SEQUENCE: 84

```
Met Arg His Met Lys Asn Lys Asn Tyr Leu Leu Val Phe Ile Val Leu
  1               5                  10                  15

His Ile Thr Leu Ile Val Ile Asn Ile Val Phe Gly Tyr Phe Val Phe
             20                  25                  30

Leu Phe Asp Phe Phe Ala Phe Leu Phe Phe Ala Asn Val Phe Leu Ala
         35                  40                  45

Val Asn Leu Leu Phe Leu Glu Lys Asn Ile Lys Asn Lys Leu Leu Phe
     50                  55                  60

Leu Leu Pro Ile Ser Ile Ile Trp Met Val Ile His Ile Ser Met
 65                  70                  75                  80

Ile Asn Ile Lys Phe Tyr Lys Phe Glu His Gln Ile Lys Glu Gln Asn
                 85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Ala Lys Lys Pro Val Lys
                165                 170                 175

Ile Tyr Phe Tyr Asn Gln Pro Gln Gly Asp Phe Ile Asp Asn Val Ile
            180                 185                 190

Phe Glu Ile Asn Asp Gly Lys Lys Ser Leu Tyr Leu Leu Asp Lys Tyr
        195                 200                 205

Lys Thr Phe Phe Leu Ile Glu Asn Ser Val Cys Ile Val Leu Ile Ile
    210                 215                 220

Leu Tyr Leu Lys Phe Asn Leu Leu Leu Tyr Arg Thr Tyr Phe Asn Glu
225                 230                 235                 240

Leu Glu
```

<210> SEQ ID NO 85
<211> LENGTH: 552
<212> TYPE: DNA
<213> ORGANISM: Neisseria meningitidis

<400> SEQUENCE: 85

```
accccccaaca gcgtgaccgt cttgccgtct tcggcggat cgggcgtac cggcgcgacc     60 atcaatgcag caggcggggt cggcatgact gccttttcga caaccttaat ttccgtagcc   120
```

```
gagggcgcgg ttgtagagct gcaggccgtg agagccaaag ccgtcaatgc aaccgccgct    180
tgcattttta cggtcttgag taaggacatt ttcgatttcc ttttatttt ccgttttcag     240 acggctgact tccgcctgta ttttcgccaa agccatgccg acagcgtgcg ccttgacttc    300
atatttaaaa gcttccgcgc gtgccagttc cagttcgcgc gcatagtttt gagccgacaa    360
cagcagggct tgcgccttgt cgcgctccat cttgtcgatg accgcctgca gcttcgcaaa    420
tgccgacttg tagccttgat ggtgcgacac agccaagccc gtgccgacaa gcgcgataat    480
ggcaatcggt tgccagtaat tcgccagcag tttcacgaga ttcattctcg acctcctgac    540
gcttcacgct ga                                                         552
```

<210> SEQ ID NO 86
<211> LENGTH: 183
<212> TYPE: PRT
<213> ORGANISM: Neisseria meningitidis

<400> SEQUENCE: 86

```
Thr Pro Asn Ser Val Thr Val Leu Pro Ser Phe Gly Gly Phe Gly Arg
 1               5                  10                  15

Thr Gly Ala Thr Ile Asn Ala Ala Gly Gly Val Gly Met Thr Ala Phe
            20                  25                  30

Ser Thr Thr Leu Ile Ser Val Ala Glu Gly Ala Val Val Glu Leu Gln
        35                  40                  45

Ala Val Arg Ala Lys Ala Val Asn Ala Thr Ala Ala Cys Ile Phe Thr
    50                  55                  60

Val Leu Ser Lys Asp Ile Phe Asp Phe Leu Phe Ile Phe Arg Phe Gln
65                  70                  75                  80

Thr Ala Asp Phe Arg Leu Tyr Phe Arg Gln Ser His Ala Asp Ser Val
                85                  90                  95

Arg Leu Asp Phe Ile Phe Lys Ser Phe Arg Ala Cys Gln Phe Gln Phe
            100                 105                 110

Ala Arg Ile Val Leu Ser Arg Gln Gln Gln Gly Leu Arg Leu Val Ala
        115                 120                 125

Leu His Leu Val Asp Asp Arg Leu Gln Leu Arg Lys Cys Arg Leu Val
    130                 135                 140

Ala Leu Met Val Arg His Ser Gln Ala Arg Ala Asp Lys Arg Asp Asn
145                 150                 155                 160

Gly Asn Arg Leu Pro Val Ile Arg Gln Gln Phe His Glu Ile His Ser
                165                 170                 175

Arg Pro Pro Asp Ala Ser Arg
            180
```

<210> SEQ ID NO 87
<211> LENGTH: 468
<212> TYPE: DNA
<213> ORGANISM: Neisseria meningitidis

<400> SEQUENCE: 87

```
atgactgcct tttcgacaac cttaatttcc gtagccgagg gcgcggttgt agagctgcag    60
gccgtgagag ccaaagccgt caatgcaacc gccgcttgca ttttttacggt cttgagtaag   120 gacattttcg atttcctttt tattttccgt tttcagacgg ctgacttccg cctgttttt    180 cgccaaagcc atgccgacag cgtgcgcctt gacttcatat ttttagctt ccgcgcgtgc    240 cagttccagt tcgcgcgcat agttttgagc cgacaacagc agggcttgcg ccttgtcgcg   300
```

-continued

| | |
|---|---|
| ctccatcttg tcgatgaccg cctgctgctt cgcaaatgcc gacttgtagc cttgatggtg | 360 |
| cgacacagcc aagcccgtgc cgacaagcgc gataatggca atcggttgcc agttattcgc | 420 |
| cagcagtttc acgagattca ttctcgacct cctgacgctt cacgctga | 468 |

<210> SEQ ID NO 88
<211> LENGTH: 155
<212> TYPE: PRT
<213> ORGANISM: Neisseria meningitidis

<400> SEQUENCE: 88

Met Thr Ala Phe Ser Thr Thr Leu Ile Ser Val Ala Glu Gly Ala Val
1               5                   10                  15

Val Glu Leu Gln Ala Val Arg Ala Lys Ala Val Asn Ala Thr Ala Ala
            20                  25                  30

Cys Ile Phe Thr Val Leu Ser Lys Asp Ile Phe Asp Phe Leu Phe Ile
        35                  40                  45

Phe Arg Phe Gln Thr Ala Asp Phe Arg Leu Phe Phe Arg Gln Ser His
    50                  55                  60

Ala Asp Ser Val Arg Leu Asp Phe Ile Phe Phe Ser Phe Arg Ala Cys
65                  70                  75                  80

Gln Phe Gln Phe Ala Arg Ile Val Leu Ser Arg Gln Gln Gln Gly Leu
                85                  90                  95

Arg Leu Val Ala Leu His Leu Val Asp Asp Arg Leu Leu Leu Arg Lys
            100                 105                 110

Cys Arg Leu Val Ala Leu Met Val Arg His Ser Gln Ala Arg Ala Asp
        115                 120                 125

Lys Arg Asp Asn Gly Asn Arg Leu Pro Val Ile Arg Gln Gln Phe His
    130                 135                 140

Glu Ile His Ser Arg Pro Pro Asp Ala Ser Arg
145                 150                 155

<210> SEQ ID NO 89
<211> LENGTH: 462
<212> TYPE: DNA
<213> ORGANISM: Neisseria meningitidis

<400> SEQUENCE: 89

| | |
|---|---|
| atgaccgcct tttcgacaac cttaatttcc gtagccgagg gcgcgcttgt agagctgcaa | 60 |
| gccgtgatgg ccaaagccgt caatacaacc gccgcctgca tttttacggt cttgagtaag | 120 |
| gacattttcg atttcctttt tatttccgt tttcagacgg ctgacttccg cctgtttttt | 180 |
| cgccaaagcc atgccgacgg cgtgcgcctt gacttcatat ttttagctt ccgcacgcgc | 240 |
| ctgttccagt tcgcgggcgt agttttgagc cgacaacagc agggcttgcg ccttgtcgcg | 300 |
| cttcattttc tcaatgaccg cctgctgctt cgcaaaagcc gacttgtagc cttgatggtg | 360 |
| cgacaccgcc aaacccgtgc cgacaagcgc gatgatggca atcggttgcc agttattcgc | 420 |
| cagcagtttc acgagattca ttctcgacct cctgacgttt ga | 462 |

<210> SEQ ID NO 90
<211> LENGTH: 153
<212> TYPE: PRT
<213> ORGANISM: Neisseria meningitidis

<400> SEQUENCE: 90

Met Thr Ala Phe Ser Thr Thr Leu Ile Ser Val Ala Glu Gly Ala Leu
1               5                   10                  15

```
Val Glu Leu Gln Ala Val Met Ala Lys Ala Val Asn Thr Thr Ala Ala
             20                  25                  30

Cys Ile Phe Thr Val Leu Ser Lys Asp Ile Phe Asp Phe Leu Phe Ile
         35                  40                  45

Phe Arg Phe Gln Thr Ala Asp Phe Arg Leu Phe Phe Arg Gln Ser His
     50                  55                  60

Ala Asp Gly Val Arg Leu Asp Phe Ile Phe Phe Ser Arg Phe Thr Arg
 65                  70                  75                  80

Leu Phe Gln Phe Ala Gly Val Val Leu Ser Arg Gln Gln Gly Leu
                 85                  90                  95

Arg Leu Val Ala Leu His Phe Leu Asn Asp Arg Leu Leu Arg Lys
             100                 105                 110

Ser Arg Leu Val Ala Leu Met Val Arg His Arg Gln Thr Arg Ala Asp
         115                 120                 125

Lys Arg Asp Asp Gly Asn Arg Leu Pro Val Ile Arg Gln Gln Phe His
130                 135                 140

Glu Ile His Ser Arg Pro Pro Asp Val
145                 150
```

<210> SEQ ID NO 91
<211> LENGTH: 592
<212> TYPE: PRT
<213> ORGANISM: Neisseria meningitidis

<400> SEQUENCE: 91

```
Met Asn Lys Ile Tyr Arg Ile Ile Trp Asn Ser Ala Leu Asn Ala Trp
  1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Asn Ala Thr Asp Glu Asp Glu Glu Glu Leu Glu Ser Val Gln
     50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
             100                 105                 110

Lys Gln Asn Thr Asn Glu Asn Thr Asn Ala Ser Ser Phe Thr Tyr Ser
         115                 120                 125

Leu Lys Lys Asp Leu Thr Gly Leu Ile Asn Val Glu Thr Glu Lys Leu
     130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                 165                 170                 175

Val His Leu Asn Gly Ile Gly Ser Thr Leu Thr Asp Thr Leu Ala Gly
             180                 185                 190

Ser Ser Ala Ser His Val Asp Ala Gly Asn Gln Ser Thr His Tyr Thr
         195                 200                 205

Arg Ala Ala Ser Ile Lys Asp Val Leu Asn Ala Gly Trp Asn Ile Lys
     210                 215                 220

Gly Val Lys Thr Gly Ser Thr Thr Gly Gln Ser Glu Asn Val Asp Phe
225                 230                 235                 240
```

```
Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
        370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Ser Arg
                420                 425                 430

Asn Gly Lys Asn Ile Asp Ile Ala Thr Ser Met Ala Pro Gln Phe Ser
            435                 440                 445

Ser Val Ser Leu Gly Ala Gly Ala Asp Ala Pro Thr Leu Ser Val Asp
        450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
                500                 505                 510

Asn Val Asp Gly Asn Ala Arg Ala Gly Ile Ala Gln Ala Ile Ala Thr
            515                 520                 525

Ala Gly Leu Val Gln Ala Tyr Leu Pro Gly Lys Ser Met Met Ala Ile
        530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
            580                 585                 590

<210> SEQ ID NO 92
<211> LENGTH: 594
<212> TYPE: PRT
<213> ORGANISM: Neisseria meningitidis

<400> SEQUENCE: 92

Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
```

-continued

```
                20                  25                  30
Thr Val Ala Thr Ala Val Leu Ala Thr Leu Leu Phe Ala Thr Val Gln
            35                  40                  45

Ala Asn Ala Thr Asp Asp Asp Leu Tyr Leu Glu Pro Val Gln Arg
 50                  55                  60

Thr Ala Val Val Leu Ser Phe Arg Ser Asp Lys Glu Gly Thr Gly Glu
 65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
                100                 105                 110

Lys Ile Lys Gln Asn Thr Asn Glu Asn Thr Asn Asp Ser Ser Phe Thr
                115                 120                 125

Tyr Ser Leu Lys Lys Asp Leu Thr Asp Leu Thr Ser Val Glu Thr Glu
                130                 135                 140

Lys Leu Ser Phe Gly Ala Asn Gly Asn Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Pro Thr Val His Leu Asn Gly Ile Gly Ser Thr Leu Thr Asp Thr Leu
                180                 185                 190

Leu Asn Thr Gly Ala Thr Thr Asn Val Thr Asn Asp Asn Val Thr Asp
                195                 200                 205

Asp Glu Lys Lys Arg Ala Ala Ser Val Lys Asp Val Leu Asn Ala Gly
                210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
                260                 265                 270

Glu Val Lys Ile Gly Ala Lys Thr Ser Val Ile Lys Glu Lys Asp Gly
                275                 280                 285

Lys Leu Val Thr Gly Lys Gly Lys Asp Glu Asn Gly Ser Ser Thr Asp
                290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Asn Val Thr Phe
                340                 345                 350

Ala Ser Gly Lys Gly Thr Thr Ala Thr Val Ser Lys Asp Asp Gln Gly
                355                 360                 365

Asn Ile Thr Val Lys Tyr Asp Val Asn Val Gly Asp Ala Leu Asn Val
                370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
                420                 425                 430

Thr Arg Asn Gly Lys Asn Ile Asp Ile Ala Thr Ser Met Ala Pro Gln
                435                 440                 445
```

```
Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Thr Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn Arg
            500                 505                 510

Ile Asp Asn Val Asp Gly Asn Ala Arg Ala Gly Ile Ala Gln Ala Ile
            515                 520                 525

Ala Thr Ala Gly Leu Val Gln Ala Tyr Leu Pro Gly Lys Ser Met Met
        530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 93
<211> LENGTH: 594
<212> TYPE: PRT
<213> ORGANISM: Neisseria meningitidis

<400> SEQUENCE: 93

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Asp Asp Leu Tyr Leu Glu Pro Val Gln Arg
    50                  55                  60

Thr Ala Pro Val Leu Ser Phe His Ala Asp Ser Glu Gly Thr Gly Glu
65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220
```

```
Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
            245                 250                 255

Lys Thr Thr Thr Val Asn Val Glu Ser Lys Asp Asn Gly Lys Lys Thr
                260                 265                 270

Glu Val Lys Ile Gly Ala Lys Ser Val Ile Glu Lys Asp Gly
            275                 280                 285

Lys Leu Val Thr Gly Lys Asp Lys Gly Glu Asn Gly Ser Ser Thr Asp
            290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Ala Asn Gly Gln Thr Gly
                325                 330                 335

Gln Ala Asp Lys Phe Glu Thr Val Thr Ser Gly Thr Lys Val Thr Phe
                340                 345                 350

Ala Ser Gly Asn Gly Thr Thr Ala Thr Val Ser Lys Asp Asp Gln Gly
            355                 360                 365

Asn Ile Thr Val Lys Tyr Asp Val Asn Val Gly Asp Ala Leu Asn Val
370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
                420                 425                 430

Thr Arg Asn Gly Lys Asn Ile Asp Ile Ala Thr Ser Met Thr Pro Gln
            435                 440                 445

Phe Ser Ser Val Ser Leu Gly Ala Gly Ala Asp Ala Pro Thr Leu Ser
            450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
                500                 505                 510

Ile Asp Asn Val Asp Gly Asn Ala Arg Ala Gly Ile Ala Gln Ala Ile
            515                 520                 525

Ala Thr Ala Gly Leu Val Gln Ala Tyr Leu Pro Gly Lys Ser Met Met
530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 94
<211> LENGTH: 594
<212> TYPE: PRT
<213> ORGANISM: Neisseria meningitidis

<400> SEQUENCE: 94
```

-continued

```
Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
             20                  25                  30

Thr Val Ala Thr Ala Val Leu Ala Thr Leu Leu Phe Ala Thr Val Gln
         35                  40                  45

Ala Asn Ala Thr Asp Asp Asp Leu Tyr Leu Glu Pro Val Gln Arg
     50                  55                  60

Thr Ala Val Val Leu Ser Phe Arg Ser Asp Lys Glu Gly Thr Gly Glu
 65                  70                  75                  80

Lys Glu Gly Thr Glu Asp Ser Asn Trp Ala Val Tyr Phe Asp Glu Lys
                 85                  90                  95

Arg Val Leu Lys Ala Gly Ala Ile Thr Leu Lys Ala Gly Asp Asn Leu
             100                 105                 110

Lys Ile Lys Gln Asn Thr Asn Glu Asn Thr Asn Asp Ser Ser Phe Thr
             115                 120                 125

Tyr Ser Leu Lys Lys Asp Leu Thr Asp Leu Thr Ser Val Glu Thr Glu
 130                 135                 140

Lys Leu Ser Phe Gly Ala Asn Gly Asn Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Pro Thr Val His Leu Asn Gly Ile Gly Ser Thr Leu Thr Asp Thr Leu
             180                 185                 190

Leu Asn Thr Gly Ala Thr Thr Asn Val Thr Asn Asp Asn Val Thr Asp
         195                 200                 205

Asp Glu Lys Lys Arg Ala Ala Ser Val Lys Asp Val Leu Asn Ala Gly
     210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
                260                 265                 270

Glu Val Lys Ile Gly Ala Lys Thr Ser Val Ile Lys Glu Lys Asp Gly
             275                 280                 285

Lys Leu Val Thr Gly Lys Gly Lys Asp Glu Asn Gly Ser Ser Thr Asp
         290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Asn Val Thr Phe
             340                 345                 350

Ala Ser Gly Lys Gly Thr Thr Ala Thr Val Ser Lys Asp Asp Gln Gly
         355                 360                 365

Asn Ile Thr Val Lys Tyr Asp Val Asn Val Gly Asp Ala Leu Asn Val
     370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
```

-continued

```
                420                 425                 430
Thr Arg Asn Gly Lys Asn Ile Asp Ile Ala Thr Ser Met Ala Pro Gln
            435                 440                 445
Phe Ser Ser Val Ser Leu Gly Ala Gly Ala Asp Ala Pro Thr Leu Ser
450                 455                 460
Val Asp Asp Glu Gly Ala Leu Asn Val Gly Ser Lys Asp Thr Asn Lys
465                 470                 475                 480
Pro Val Arg Ile Thr Asn Val Ala Pro Gly Val Lys Glu Gly Asp Val
                485                 490                 495
Thr Asn Val Ala Gln Leu Lys Gly Val Ala Gln Asn Leu Asn Asn Arg
            500                 505                 510
Ile Asp Asn Val Asp Gly Asn Ala Arg Ala Gly Ile Ala Gln Ala Ile
        515                 520                 525
Ala Thr Ala Gly Leu Val Gln Ala Tyr Leu Pro Gly Lys Ser Met Met
530                 535                 540
Ala Ile Gly Gly Asp Thr Tyr Arg Gly Glu Ala Gly Tyr Ala Ile Gly
545                 550                 555                 560
Tyr Ser Ser Ile Ser Asp Gly Gly Asn Trp Ile Ile Lys Gly Thr Ala
                565                 570                 575
Ser Gly Asn Ser Arg Gly His Phe Gly Ala Ser Ala Ser Val Gly Tyr
            580                 585                 590
Gln Trp

<210> SEQ ID NO 95
<211> LENGTH: 591
<212> TYPE: PRT
<213> ORGANISM: Neisseria meningitidis

<400> SEQUENCE: 95

Met Asn Lys Ile Tyr Arg Ile Ile Trp Asn Ser Ala Leu Asn Ala Trp
1               5                   10                  15
Val Val Val Ser Glu Leu Thr Arg Asn His Thr Lys Arg Ala Ser Ala
                20                  25                  30
Thr Val Glu Thr Ala Val Leu Ala Thr Leu Leu Phe Ala Thr Val Gln
            35                  40                  45
Ala Ser Ala Asn Asn Glu Glu Gln Glu Glu Asp Leu Tyr Leu Asp Pro
        50                  55                  60
Val Gln Arg Thr Val Ala Val Leu Ile Val Asn Ser Asp Lys Glu Gly
65                  70                  75                  80
Thr Gly Glu Lys Glu Lys Val Glu Glu Asn Ser Asp Trp Ala Val Tyr
                85                  90                  95
Phe Asn Glu Lys Gly Val Leu Thr Ala Arg Glu Ile Thr Leu Lys Ala
                100                 105                 110
Gly Asp Asn Leu Lys Ile Lys Gln Asn Gly Thr Asn Phe Thr Tyr Ser
            115                 120                 125
Leu Lys Lys Asp Leu Thr Asp Leu Thr Ser Val Gly Thr Glu Lys Leu
        130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Asp Thr Leu Leu Asn
                180                 185                 190
Thr Gly Ala Thr Thr Asn Val Thr Asn Asp Asn Val Thr Asp Asp Glu
```

```
                195                 200                 205
Lys Lys Arg Ala Ala Ser Val Lys Asp Val Leu Asn Ala Gly Trp Asn
            210                 215                 220
Ile Lys Gly Val Lys Pro Gly Thr Thr Ala Ser Asp Asn Val Asp Phe
225                 230                 235                 240
Val Arg Thr Tyr Asp Thr Val Glu Phe Leu Ser Ala Asp Thr Lys Thr
                245                 250                 255
Thr Thr Val Asn Val Glu Ser Lys Asp Asn Gly Lys Lys Thr Glu Val
            260                 265                 270
Lys Ile Gly Ala Lys Thr Ser Val Ile Lys Glu Lys Asp Gly Lys Leu
            275                 280                 285
Val Thr Gly Lys Asp Lys Gly Glu Asn Gly Ser Ser Thr Asp Glu Gly
            290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Gln Gly Asn Ile
            355                 360                 365
Thr Val Met Tyr Asp Val Asn Val Gly Asp Ala Leu Asn Val Asn Gln
370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
            435                 440                 445
Ser Val Ser Leu Gly Ala Gly Ala Asp Ala Pro Thr Leu Ser Val Asp
            450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
Val Asp Gly Asn Ala Arg Ala Gly Ile Ala Gln Ala Ile Ala Thr Ala
            515                 520                 525
Gly Leu Val Gln Ala Tyr Leu Pro Gly Lys Ser Met Met Ala Ile Gly
            530                 535                 540
Gly Gly Thr Tyr Arg Gly Glu Ala Gly Tyr Ala Ile Gly Tyr Ser Ser
545                 550                 555                 560
Ile Ser Asp Gly Gly Asn Trp Ile Ile Lys Gly Thr Ala Ser Gly Asn
                565                 570                 575
Ser Arg Gly His Phe Gly Ala Ser Ala Ser Val Gly Tyr Gln Trp
            580                 585                 590

<210> SEQ ID NO 96
<211> LENGTH: 591
<212> TYPE: PRT
<213> ORGANISM: Neisseria meningitidis
```

-continued

```
<400> SEQUENCE: 96

Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Ser Ala Asn Asn Glu Glu Gln Glu Glu Asp Leu Tyr Leu Asp Pro
     50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
```

-continued

```
                405                 410                 415
Asp Glu Thr Val Asn Ile Asn Ala Gly Asn Asn Ile Glu Ile Thr Arg
                420                 425                 430
Asn Gly Lys Asn Ile Asp Ile Ala Thr Ser Met Thr Pro Gln Phe Ser
                435                 440                 445
Ser Val Ser Leu Gly Ala Gly Ala Asp Ala Pro Thr Leu Ser Val Asp
                450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                    485                 490                 495
Ala Gln Leu Lys Gly Val Ala Gln Asn Leu Asn Asn Arg Ile Asp Asn
                500                 505                 510
Val Asp Gly Asn Ala Arg Ala Gly Ile Ala Gln Ala Ile Ala Thr Ala
                515                 520                 525
Gly Leu Val Gln Ala Tyr Leu Pro Gly Lys Ser Met Met Ala Ile Gly
                530                 535                 540
Gly Gly Thr Tyr Arg Gly Glu Ala Gly Tyr Ala Ile Gly Tyr Ser Ser
545                 550                 555                 560
Ile Ser Asp Gly Gly Asn Trp Ile Ile Lys Gly Thr Ala Ser Gly Asn
                565                 570                 575
Ser Arg Gly His Phe Gly Ala Ser Ala Ser Val Gly Tyr Gln Trp
                580                 585                 590

<210> SEQ ID NO 97
<211> LENGTH: 595
<212> TYPE: PRT
<213> ORGANISM: Neisseria meningitidis

<400> SEQUENCE: 97

Met Asn Lys Ile Tyr Arg Ile Ile Trp Asn Ser Ala Leu Asn Ala Trp
1               5                   10                  15
Val Val Val Ser Glu Leu Thr Arg Asn His Thr Lys Arg Ala Ser Ala
                20                  25                  30
Thr Val Glu Thr Ala Val Leu Ala Thr Leu Leu Phe Ala Thr Val Gln
            35                  40                  45
Ala Asn Ala Thr Asp Thr Asp Glu Asp Asp Glu Leu Glu Pro Val Val
        50                  55                  60
Arg Ser Ala Leu Val Leu Gln Phe Met Ile Asp Lys Glu Gly Asn Gly
65                  70                  75                  80
Glu Ile Glu Ser Thr Gly Asp Ile Gly Trp Ser Ile Tyr Tyr Asp Asp
                85                  90                  95
His Asn Thr Leu His Gly Ala Thr Val Thr Leu Lys Ala Gly Asp Asn
                100                 105                 110
Leu Lys Ile Lys Gln Asn Thr Asp Glu Asn Thr Asn Ala Ser Ser Phe
            115                 120                 125
Thr Tyr Ser Leu Lys Lys Asp Leu Thr Asp Leu Thr Ser Val Gly Thr
        130                 135                 140
Glu Glu Leu Ser Phe Gly Ala Asn Gly Asn Lys Val Asn Ile Thr Ser
145                 150                 155                 160
Asp Thr Lys Gly Leu Asn Phe Ala Lys Lys Thr Ala Gly Thr Asn Gly
                165                 170                 175
Asp Thr Thr Val His Leu Asn Gly Ile Gly Ser Thr Leu Thr Asp Thr
                180                 185                 190
```

-continued

```
Leu Ala Gly Ser Ser Ala Ser His Val Asp Ala Gly Asn Gln Ser Thr
        195                 200                 205
His Tyr Thr Arg Ala Ala Ser Ile Lys Asp Val Leu Asn Ala Gly Trp
    210                 215                 220
Asn Ile Lys Gly Val Lys Thr Gly Ser Thr Thr Gly Gln Ser Glu Asn
225                 230                 235                 240
Val Asp Phe Val Arg Thr Tyr Asp Thr Val Glu Phe Leu Ser Ala Asp
                245                 250                 255
Thr Lys Thr Thr Thr Val Asn Val Glu Ser Lys Asp Asn Gly Lys Arg
            260                 265                 270
Thr Glu Val Lys Ile Gly Ala Lys Thr Ser Val Ile Lys Glu Lys Asp
        275                 280                 285
Gly Lys Leu Val Thr Gly Lys Gly Gly Glu Asn Gly Ser Ser Thr
    290                 295                 300
Asp Glu Gly Glu Gly Leu Val Thr Ala Lys Glu Val Ile Asp Ala Val
305                 310                 315                 320
Asn Lys Ala Gly Trp Arg Met Lys Thr Thr Ala Asn Gly Gln Thr
                325                 330                 335
Gly Gln Ala Asp Lys Phe Glu Thr Val Thr Ser Gly Thr Asn Val Thr
            340                 345                 350
Phe Ala Ser Gly Lys Gly Thr Ala Thr Val Ser Lys Asp Asp Gln
        355                 360                 365
Gly Asn Ile Thr Val Lys Tyr Asp Val Asn Val Gly Asp Ala Leu Asn
    370                 375                 380
Val Asn Gln Leu Gln Asn Ser Gly Trp Asn Leu Asp Ser Lys Ala Val
385                 390                 395                 400
Ala Gly Ser Ser Gly Lys Val Ile Ser Gly Asn Val Ser Pro Ser Lys
                405                 410                 415
Gly Lys Met Asp Glu Thr Val Asn Ile Asn Ala Gly Asn Asn Ile Glu
            420                 425                 430
Ile Thr Arg Asn Gly Lys Asn Ile Asp Ile Ala Thr Ser Met Thr Pro
        435                 440                 445
Gln Phe Ser Ser Val Ser Leu Gly Ala Gly Ala Asp Ala Pro Thr Leu
    450                 455                 460
Ser Val Asp Asp Glu Gly Ala Leu Asn Val Gly Ser Lys Asp Ala Asn
465                 470                 475                 480
Lys Pro Val Arg Ile Thr Asn Val Ala Pro Gly Val Lys Glu Gly Asp
                485                 490                 495
Val Thr Asn Val Ala Gln Leu Lys Gly Val Ala Gln Asn Leu Asn Asn
            500                 505                 510
His Ile Asp Asn Val Asp Gly Asn Ala Arg Ala Gly Ile Ala Gln Ala
        515                 520                 525
Ile Ala Thr Ala Gly Leu Val Gln Ala Tyr Leu Pro Gly Lys Ser Met
    530                 535                 540
Met Ala Ile Gly Gly Gly Thr Tyr Arg Gly Glu Ala Gly Tyr Ala Ile
545                 550                 555                 560
Gly Tyr Ser Ser Ile Ser Asp Gly Gly Asn Trp Ile Ile Lys Gly Thr
                565                 570                 575
Ala Ser Gly Asn Ser Arg Gly His Phe Gly Ala Ser Ala Ser Val Gly
            580                 585                 590
Tyr Gln Trp
    595
```

-continued

```
<210> SEQ ID NO 98
<211> LENGTH: 592
<212> TYPE: PRT
<213> ORGANISM: Neisseria meningitidis

<400> SEQUENCE: 98

Met Asn Lys Ile Tyr Arg Ile Ile Trp Asn Ser Ala Leu Asn Ala Trp
  1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Asn Ala Thr Asp Glu Asp Glu Glu Glu Leu Glu Ser Val Gln
     50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380
```

-continued

```
Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
            435                 440                 445

Ser Val Ser Leu Gly Ala Gly Ala Asp Ala Pro Thr Leu Ser Val Asp
        450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
            500                 505                 510

Asn Val Asp Gly Asn Ala Arg Ala Gly Ile Ala Gln Ala Ile Ala Thr
            515                 520                 525

Ala Gly Leu Val Gln Ala Tyr Leu Pro Gly Lys Ser Met Met Ala Ile
        530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
            580                 585                 590
```

<210> SEQ ID NO 99
<211> LENGTH: 594
<212> TYPE: PRT
<213> ORGANISM: Neisseria meningitidis

<400> SEQUENCE: 99

```
Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
            20                  25                  30

Thr Val Ala Thr Ala Val Leu Ala Thr Leu Phe Ala Thr Val Gln
        35                  40                  45

Ala Ser Thr Thr Asp Asp Asp Leu Tyr Leu Glu Pro Val Gln Arg
    50                  55                  60

Thr Ala Pro Val Leu Ser Phe His Ala Asp Ser Glu Gly Thr Gly Glu
 65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
            115                 120                 125

Tyr Ser Leu Lys Lys Asp Leu Thr Asp Leu Thr Ser Val Glu Thr Glu
        130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175
```

-continued

```
Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
                260                 265                 270

Glu Val Lys Ile Gly Ala Lys Thr Ser Val Ile Lys Glu Lys Asp Gly
            275                 280                 285

Lys Leu Val Thr Gly Lys Asp Lys Gly Glu Asn Gly Ser Ser Thr Asp
        290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Lys Val Thr Phe
                340                 345                 350

Ala Ser Gly Asn Gly Thr Thr Ala Thr Val Ser Lys Asp Asp Gln Gly
            355                 360                 365

Asn Ile Thr Val Lys Tyr Asp Val Asn Val Gly Asp Ala Leu Asn Val
        370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
                420                 425                 430

Thr Arg Asn Gly Lys Asn Ile Asp Ile Ala Thr Ser Met Thr Pro Gln
            435                 440                 445

Phe Ser Ser Val Ser Leu Gly Ala Gly Ala Asp Ala Pro Thr Leu Ser
        450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Ser Leu Val Gln Ala Tyr Leu Pro Gly Lys Ser Met Met
        530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590
```

Gln Trp

<210> SEQ ID NO 100
<211> LENGTH: 599
<212> TYPE: PRT
<213> ORGANISM: Neisseria meningitidis

<400> SEQUENCE: 100

```
Met Asn Lys Ile Tyr Arg Ile Ile Trp Asn Ser Ala Leu Asn Ala Trp
  1               5                  10                  15

Val Ala Val Ser Glu Leu Thr Arg Asn His Thr Lys Arg Ala Ser Ala
                 20                  25                  30

Thr Val Lys Thr Ala Val Leu Ala Thr Leu Leu Phe Ala Thr Val Gln
             35                  40                  45

Ala Asn Ala Thr Asp Glu Asp Glu Glu Glu Leu Glu Pro Val Val
         50                  55                  60

Arg Ser Ala Leu Val Leu Gln Phe Met Ile Asp Lys Glu Gly Asn Gly
 65                  70                  75                  80

Glu Asn Glu Ser Thr Gly Asn Ile Gly Trp Ser Ile Tyr Tyr Asp Asn
                 85                  90                  95

His Asn Thr Leu His Gly Ala Thr Val Thr Leu Lys Ala Gly Asp Asn
                100                 105                 110

Leu Lys Ile Lys Gln Asn Thr Asn Lys Asn Thr Asn Glu Asn Thr Asn
            115                 120                 125

Asp Ser Ser Phe Thr Tyr Ser Leu Lys Lys Asp Leu Thr Asp Leu Thr
        130                 135                 140

Ser Val Glu Thr Glu Lys Leu Ser Phe Gly Ala Asn Gly Asn Lys Val
145                 150                 155                 160

Asn Ile Thr Ser Asp Thr Lys Gly Leu Asn Phe Ala Lys Glu Thr Ala
                165                 170                 175

Gly Thr Asn Gly Asp Thr Thr Val His Leu Asn Gly Ile Gly Ser Thr
            180                 185                 190

Leu Thr Asp Thr Leu Leu Asn Thr Gly Ala Thr Thr Asn Val Thr Asn
        195                 200                 205

Asp Asn Val Thr Asp Asp Lys Lys Arg Ala Ala Ser Val Lys Asp
    210                 215                 220

Val Leu Asn Ala Gly Trp Asn Ile Lys Gly Val Lys Pro Gly Thr Thr
225                 230                 235                 240

Ala Ser Asp Asn Val Asp Phe Val His Thr Tyr Asp Thr Val Glu Phe
                245                 250                 255

Leu Ser Ala Asp Thr Lys Thr Thr Val Asn Val Glu Ser Lys Asp
            260                 265                 270

Asn Gly Lys Arg Thr Glu Val Lys Ile Gly Ala Lys Thr Ser Val Ile
        275                 280                 285

Lys Glu Lys Asp Gly Lys Leu Val Thr Gly Lys Gly Lys Gly Glu Asn
    290                 295                 300

Gly Ser Ser Thr Asp Glu Gly Glu Gly Leu Val Thr Ala Lys Glu Val
305                 310                 315                 320

Ile Asp Ala Val Asn Lys Ala Gly Trp Arg Met Lys Thr Thr Thr Ala
                325                 330                 335

Asn Gly Gln Thr Gly Gln Ala Asp Lys Phe Glu Thr Val Thr Ser Gly
            340                 345                 350

Thr Asn Val Thr Phe Ala Ser Gly Lys Gly Thr Thr Ala Thr Val Ser
        355                 360                 365
```

```
Lys Asp Asp Gln Gly Asn Ile Thr Val Lys Tyr Asp Val Asn Val Gly
    370                 375                 380

Asp Ala Leu Asn Val Asn Gln Leu Gln Asn Ser Gly Trp Asn Leu Asp
385                 390                 395                 400

Ser Lys Ala Val Ala Gly Ser Ser Gly Lys Val Ile Ser Gly Asn Val
                405                 410                 415

Ser Pro Ser Lys Gly Lys Met Asp Glu Thr Val Asn Ile Asn Ala Gly
            420                 425                 430

Asn Asn Ile Glu Ile Thr Arg Asn Gly Lys Asn Ile Asp Ile Ala Thr
        435                 440                 445

Ser Met Thr Pro Gln Phe Ser Ser Val Ser Leu Gly Ala Gly Ala Asp
    450                 455                 460

Ala Pro Thr Leu Ser Val Asp Asp Lys Gly Ala Leu Asn Val Gly Ser
465                 470                 475                 480

Lys Asp Ala Asn Lys Pro Val Arg Ile Thr Asn Val Ala Pro Gly Val
                485                 490                 495

Lys Glu Gly Asp Val Thr Asn Val Ala Gln Leu Lys Gly Val Ala Gln
            500                 505                 510

Asn Leu Asn Asn Arg Ile Asp Asn Val Asp Gly Asn Ala Arg Ala Gly
        515                 520                 525

Ile Ala Gln Ala Ile Ala Thr Ala Gly Leu Val Gln Ala Tyr Leu Pro
    530                 535                 540

Gly Lys Ser Met Met Ala Ile Gly Gly Gly Thr Tyr Arg Gly Glu Ala
545                 550                 555                 560

Gly Tyr Ala Ile Gly Tyr Ser Ser Ile Ser Asp Gly Gly Asn Trp Ile
                565                 570                 575

Ile Lys Gly Thr Ala Ser Gly Asn Ser Arg Gly His Phe Gly Ala Ser
            580                 585                 590

Ala Ser Val Gly Tyr Gln Trp
            595
```

<210> SEQ ID NO 101
<211> LENGTH: 598
<212> TYPE: PRT
<213> ORGANISM: Neisseria meningitidis

<400> SEQUENCE: 101

```
Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Phe Ala Thr Val Gln
            35                  40                  45

Ala Asn Ala Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
                100                 105                 110

Lys Ile Lys Gln Asn Thr Asn Glu Asn Thr Asn Glu Asn Thr Asn Asp
            115                 120                 125

Ser Ser Phe Thr Tyr Ser Leu Lys Lys Asp Leu Thr Asp Leu Thr Ser
    130                 135                 140
```

-continued

```
Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
            165                 170                 175

Thr Asn Gly Asp Pro Thr Val His Leu Asn Gly Ile Gly Ser Thr Leu
        180                 185                 190

Thr Asp Thr Leu Leu Asn Thr Gly Ala Thr Thr Asn Val Thr Asn Asp
    195                 200                 205

Asn Val Thr Asp Asp Glu Lys Lys Arg Ala Ala Ser Val Lys Asp Val
210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
            245                 250                 255

Ser Ala Asp Thr Lys Thr Thr Thr Val Asn Val Glu Ser Lys Asp Asn
        260                 265                 270

Gly Lys Lys Thr Glu Val Lys Ile Gly Ala Lys Thr Ser Val Ile Lys
    275                 280                 285

Glu Lys Asp Gly Lys Leu Val Thr Gly Lys Gly Lys Asp Glu Asn Gly
290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Thr Ala Asn
            325                 330                 335

Gly Gln Thr Gly Gln Ala Asp Lys Phe Glu Thr Val Thr Ser Gly Thr
        340                 345                 350

Lys Val Thr Phe Ala Ser Gly Asn Gly Thr Thr Ala Thr Val Ser Lys
    355                 360                 365

Asp Asp Gln Gly Asn Ile Thr Val Lys Tyr Asp Val Asn Val Gly Asp
    370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
            405                 410                 415

Pro Ser Lys Gly Lys Met Asp Glu Thr Val Asn Ile Asn Ala Gly Asn
        420                 425                 430

Asn Ile Glu Ile Thr Arg Asn Gly Lys Asn Ile Asp Ile Ala Thr Ser
    435                 440                 445

Met Thr Pro Gln Phe Ser Ser Val Ser Leu Gly Ala Gly Ala Asp Ala
450                 455                 460

Pro Thr Leu Ser Val Asp Asp Glu Gly Ala Leu Asn Val Gly Ser Lys
465                 470                 475                 480

Asp Ala Asn Lys Pro Val Arg Ile Thr Asn Val Ala Pro Gly Val Lys
            485                 490                 495

Glu Gly Asp Val Thr Asn Val Ala Gln Leu Lys Gly Val Ala Gln Asn
        500                 505                 510

Leu Asn Asn Arg Ile Asp Asn Val Asp Gly Asn Ala Arg Ala Gly Ile
    515                 520                 525

Ala Gln Ala Ile Ala Thr Ala Gly Leu Ala Gln Ala Tyr Leu Pro Gly
    530                 535                 540

Lys Ser Met Met Ala Ile Gly Gly Gly Thr Tyr Arg Gly Glu Ala Gly
545                 550                 555                 560
```

-continued

```
Tyr Ala Ile Gly Tyr Ser Ser Ile Ser Asp Thr Gly Asn Trp Val Ile
            565                 570                 575

Lys Gly Thr Ala Ser Gly Asn Ser Arg Gly His Phe Gly Ala Ser Ala
            580                 585                 590

Ser Val Gly Tyr Gln Trp
        595

<210> SEQ ID NO 102
<211> LENGTH: 594
<212> TYPE: PRT
<213> ORGANISM: Neisseria meningitidis

<400> SEQUENCE: 102

Met Asn Lys Ile Tyr Arg Ile Ile Trp Asn Ser Ala Leu Asn Ala Trp
  1               5                  10                  15

Val Ala Val Ser Glu Leu Thr Arg Asn His Thr Lys Arg Ala Ser Ala
             20                  25                  30

Thr Val Ala Thr Ala Val Leu Ala Thr Leu Leu Phe Ala Thr Val Gln
         35                  40                  45

Ala Ser Thr Thr Asp Asp Asp Leu Tyr Leu Glu Pro Val Gln Arg
     50                  55                  60

Thr Ala Pro Val Leu Ser Phe His Ala Asp Ser Glu Gly Thr Gly Glu
 65                  70                  75                  80

Lys Glu Val Thr Glu Asp Ser Asn Trp Gly Val Tyr Phe Asp Lys Lys
                 85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285

Lys Leu Val Thr Gly Lys Asp Lys Gly Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335
```

Gln Ala Asp Lys Phe Glu Thr Val Thr Ser Gly Thr Lys Val Thr Phe
                340                 345                 350

Ala Ser Gly Asn Gly Thr Thr Ala Thr Val Ser Lys Asp Asp Gln Gly
            355                 360                 365

Asn Ile Thr Val Lys Tyr Asp Val Asn Val Gly Asp Ala Leu Asn Val
        370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 103
<211> LENGTH: 591
<212> TYPE: PRT
<213> ORGANISM: Neisseria meningitidis

<400> SEQUENCE: 103

Met Asn Lys Ile Tyr Arg Ile Ile Trp Asn Ser Ala Leu Asn Ala Trp
1               5                   10                  15

Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

-continued

```
Gly Asp Asn Leu Lys Ile Lys Gln Asn Gly Thr Asn Phe Thr Tyr Ser
            115                 120                 125
Leu Lys Lys Asp Leu Thr Asp Leu Thr Ser Val Gly Thr Glu Lys Leu
    130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Thr Asp Thr Leu Leu Asn
                180                 185                 190
Thr Gly Ala Thr Thr Asn Val Thr Asn Asp Asn Val Thr Asp Asp Glu
            195                 200                 205
Lys Lys Arg Ala Ala Ser Val Lys Asp Val Leu Asn Ala Gly Trp Asn
    210                 215                 220
Ile Lys Gly Val Lys Pro Gly Thr Ala Ser Asp Asn Val Asp Phe
225                 230                 235                 240
Val Arg Thr Tyr Asp Thr Val Glu Phe Leu Ser Ala Asp Thr Lys Thr
                245                 250                 255
Thr Thr Val Asn Val Glu Ser Lys Asp Asn Gly Lys Lys Thr Glu Val
            260                 265                 270
Lys Ile Gly Ala Lys Thr Ser Val Ile Lys Glu Lys Asp Gly Lys Leu
    275                 280                 285
Val Thr Gly Lys Asp Lys Gly Glu Asn Gly Ser Ser Thr Asp Glu Gly
                290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Asp Gln Gly Asn Ile
    355                 360                 365
Thr Val Met Tyr Asp Val Asn Val Gly Asp Ala Leu Asn Val Asn His
                370                 375                 380
Leu Gln Asn Ser Gly Trp Asp Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
    435                 440                 445
Ser Val Ser Leu Gly Ala Gly Ala Asp Ala Pro Thr Leu Ser Val Asp
    450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
Val Asp Gly Asn Ala Arg Ala Gly Ile Ala Gln Ala Ile Ala Thr Ala
    515                 520                 525
```

```
Gly Leu Val Gln Ala Tyr Leu Pro Gly Lys Ser Met Met Ala Ile Gly
        530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
        580                 585                 590

<210> SEQ ID NO 104
<211> LENGTH: 591
<212> TYPE: PRT
<213> ORGANISM: Neisseria meningitidis

<400> SEQUENCE: 104

Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
        50                  55                  60

Val Gln Arg Thr Val Ala Val Leu Ile Val Asn Ser Asp Lys Glu Gly
65                  70                  75                  80

Thr Gly Glu Lys Glu Lys Val Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320
```

```
Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 105
<211> LENGTH: 591
<212> TYPE: PRT
<213> ORGANISM: Neisseria meningitidis

<400> SEQUENCE: 105

Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
                 20                  25                  30

Thr Val Lys Thr Ala Val Leu Ala Thr Leu Phe Ala Thr Val Gln
             35                  40                  45

Ala Ser Ala Asn Asn Glu Glu Gln Glu Glu Asp Leu Tyr Leu Asp Pro
     50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
```

-continued

```
                100                 105                 110
Gly Asp Asn Leu Lys Ile Lys Gln Asn Gly Thr Asn Phe Thr Tyr Ser
            115                 120                 125
Leu Lys Lys Asp Leu Thr Asp Leu Thr Ser Val Gly Thr Glu Lys Leu
130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Thr Asp Thr Leu Leu Asn
                180                 185                 190
Thr Gly Ala Thr Thr Asn Val Thr Asn Asp Asn Val Thr Asp Asp Glu
                195                 200                 205
Lys Lys Arg Ala Ala Ser Val Lys Asp Val Leu Asn Ala Gly Trp Asn
210                 215                 220
Ile Lys Gly Val Lys Pro Gly Thr Thr Ala Ser Asp Asn Val Asp Phe
225                 230                 235                 240
Val Arg Thr Tyr Asp Thr Val Glu Phe Leu Ser Ala Asp Thr Lys Thr
                245                 250                 255
Thr Thr Val Asn Val Glu Ser Lys Asp Asn Gly Lys Lys Thr Glu Val
                260                 265                 270
Lys Ile Gly Ala Lys Thr Ser Val Ile Lys Glu Lys Asp Gly Lys Leu
            275                 280                 285
Val Thr Gly Lys Asp Lys Gly Glu Asn Gly Ser Ser Thr Asp Glu Gly
            290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
                340                 345                 350
Gly Lys Gly Thr Thr Ala Thr Val Ser Lys Asp Asp Gln Gly Asn Ile
            355                 360                 365
Thr Val Met Tyr Asp Val Asn Val Gly Asp Ala Leu Asn Val Asn Gln
            370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
                420                 425                 430
Asn Gly Lys Asn Ile Asp Ile Ala Thr Ser Met Thr Pro Gln Phe Ser
            435                 440                 445
Ser Val Ser Leu Gly Ala Gly Ala Asp Ala Pro Thr Leu Ser Val Asp
450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
Val Asp Gly Asn Ala Arg Ala Gly Ile Ala Gln Ala Ile Ala Thr Ala
            515                 520                 525
```

```
Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 106
<211> LENGTH: 592
<212> TYPE: PRT
<213> ORGANISM: Neisseria meningitidis

<400> SEQUENCE: 106

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Asn Ala Thr Asp Glu Asp Glu Glu Glu Leu Glu Ser Val Gln
 50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
    130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
```

-continued

```
305                 310                 315                 320
Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
                355                 360                 365

Thr Val Met Tyr Asp Val Asn Val Gly Asp Ala Leu Asn Val Asn Gln
                370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Ser Arg
                420                 425                 430

Asn Gly Lys Asn Ile Asp Ile Ala Thr Ser Met Ala Pro Gln Phe Ser
                435                 440                 445

Ser Val Ser Leu Gly Ala Gly Ala Asp Ala Pro Thr Leu Ser Val Asp
                450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
                500                 505                 510

Asn Val Asp Gly Asn Ala Arg Ala Gly Ile Ala Gln Ala Ile Ala Thr
                515                 520                 525

Ala Gly Leu Val Gln Ala Tyr Leu Pro Gly Lys Ser Met Met Ala Ile
                530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
                580                 585                 590

<210> SEQ ID NO 107
<211> LENGTH: 592
<212> TYPE: PRT
<213> ORGANISM: Neisseria meningitidis

<400> SEQUENCE: 107

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
                35                  40                  45

Ala Asn Ala Thr Asp Glu Asp Glu Glu Glu Leu Glu Ser Val Gln
                50                  55                  60

Arg Ser Val Val Gly Ser Ile Gln Ala Ser Met Gly Ser Gly Glu
 65                 70                  75                  80

Leu Glu Thr Ile Ser Leu Ser Met Thr Asn Asp Ser Lys Glu Phe Val
                85                  90                  95
```

-continued

```
Asp Pro Tyr Ile Val Val Thr Leu Lys Ala Gly Asp Asn Leu Lys Ile
            100                 105                 110
Lys Gln Asn Thr Asn Glu Asn Thr Asn Ala Ser Ser Phe Thr Tyr Ser
        115                 120                 125
Leu Lys Lys Asp Leu Thr Gly Leu Ile Asn Val Glu Thr Glu Lys Leu
    130                 135                 140
Ser Phe Gly Ala Asn Gly Lys Lys Val Asn Ile Ile Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Thr Asp Thr Leu Ala Gly
            180                 185                 190
Ser Ser Ala Ser His Val Asp Ala Gly Asn Gln Ser Thr His Tyr Thr
        195                 200                 205
Arg Ala Ala Ser Ile Lys Asp Val Leu Asn Ala Gly Trp Asn Ile Lys
    210                 215                 220
Gly Val Lys Thr Gly Ser Thr Thr Gly Gln Ser Glu Asn Val Asp Phe
225                 230                 235                 240
Val Arg Thr Tyr Asp Thr Val Glu Phe Leu Ser Ala Asp Thr Lys Thr
                245                 250                 255
Thr Thr Val Asn Val Glu Ser Lys Asp Asn Gly Lys Arg Thr Glu Val
            260                 265                 270
Lys Ile Gly Ala Lys Thr Ser Val Ile Lys Glu Lys Asp Gly Lys Leu
        275                 280                 285
Val Thr Gly Lys Gly Lys Gly Glu Asn Gly Ser Ser Thr Asp Glu Gly
    290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Asp Gln Gly Asn Ile
        355                 360                 365
Thr Val Met Tyr Asp Val Asn Val Gly Asp Ala Leu Asn Val Asn Gln
    370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Ser Arg
            420                 425                 430
Asn Gly Lys Asn Ile Asp Ile Ala Thr Ser Met Ala Pro Gln Phe Ser
        435                 440                 445
Ser Val Ser Leu Gly Ala Gly Ala Asp Ala Pro Thr Leu Ser Val Asp
    450                 455                 460
Asp Glu Gly Ala Leu Asn Val Gly Ser Lys Asp Ala Asn Lys Pro Val
465                 470                 475                 480
Arg Ile Thr Asn Val Ala Pro Gly Val Lys Glu Gly Asp Val Thr Asn
                485                 490                 495
Val Ala Gln Leu Lys Gly Val Ala Gln Asn Leu Asn Asn Arg Ile Asp
            500                 505                 510
Asn Val Asp Gly Asn Ala Arg Ala Gly Ile Ala Gln Ala Ile Ala Thr
```

```
            515                 520                 525
Ala Gly Leu Val Gln Ala Tyr Leu Pro Gly Lys Ser Met Met Ala Ile
        530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
                580                 585                 590

<210> SEQ ID NO 108
<211> LENGTH: 589
<212> TYPE: PRT
<213> ORGANISM: Neisseria meningitidis

<400> SEQUENCE: 108

Met Asn Lys Ile Tyr Arg Ile Ile Trp Asn Ser Ala Leu Asn Ala Trp
  1                 5                  10                  15

Val Val Val Ser Glu Leu Thr Arg Asn His Thr Lys Arg Ala Ser Ala
                 20                  25                  30

Thr Val Ala Thr Ala Val Leu Ala Thr Leu Leu Ser Ala Thr Val Gln
             35                  40                  45

Ala Asn Ala Thr Asp Thr Asp Glu Asp Glu Glu Leu Glu Ser Val Val
         50                  55                  60

Arg Ser Ala Leu Val Leu Gln Phe Met Ile Asp Lys Glu Gly Asn Gly
 65                  70                  75                  80

Glu Ile Glu Ser Thr Gly Asp Ile Gly Trp Ser Ile Tyr Tyr Asp Asp
                 85                  90                  95

His Asn Thr Leu His Gly Ala Thr Val Thr Leu Lys Ala Gly Asp Asn
            100                 105                 110

Leu Lys Ile Lys Gln Ser Gly Lys Asp Phe Thr Tyr Ser Leu Lys Lys
        115                 120                 125

Glu Leu Lys Asp Leu Thr Ser Val Glu Thr Glu Lys Leu Ser Phe Gly
    130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175

Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
        195                 200                 205

Ser Ile Lys Asp Val Leu Asn Ala Gly Trp Asn Ile Lys Gly Val Lys
    210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
        275                 280                 285

Lys Gly Lys Gly Glu Asn Gly Ser Ser Thr Asp Glu Gly Glu Gly Leu
    290                 295                 300
```

```
Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
            340                 345                 350

Thr Thr Ala Thr Val Ser Lys Asp Asp Gln Gly Asn Ile Thr Val Lys
        355                 360                 365

Tyr Asp Val Asn Val Gly Asp Ala Leu Asn Val Asn Gln Leu Gln Asn
370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
        435                 440                 445

Leu Gly Ala Gly Ala Asp Ala Pro Thr Leu Ser Val Asp Asp Glu Gly
450                 455                 460

Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
                485                 490                 495

Leu Lys Gly Val Ala Gln Asn Leu Asn Asn Arg Ile Asp Asn Val Asp
            500                 505                 510

Gly Asn Ala Arg Ala Gly Ile Ala Gln Ala Ile Ala Thr Ala Gly Leu
        515                 520                 525

Ala Gln Ala Tyr Leu Pro Gly Lys Ser Met Met Ala Ile Gly Gly Gly
530                 535                 540

Thr Tyr Arg Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585

<210> SEQ ID NO 109
<211> LENGTH: 589
<212> TYPE: PRT
<213> ORGANISM: Neisseria meningitidis

<400> SEQUENCE: 109

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Ser Ala Thr Val Gln
            35                  40                  45

Ala Asn Ala Thr Asp Thr Asp Glu Asp Glu Leu Glu Ser Val Val
        50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
                85                  90                  95
```

-continued

```
His Asn Thr Leu His Gly Ala Thr Val Thr Leu Lys Ala Gly Asp Asn
            100                 105                 110
Leu Lys Ile Lys Gln Ser Gly Lys Asp Phe Thr Tyr Ser Leu Lys Lys
            115                 120                 125
Glu Leu Lys Asp Leu Thr Ser Val Glu Thr Glu Lys Leu Ser Phe Gly
            130                 135                 140
Ala Asn Gly Asn Lys Val Asn Ile Thr Ser Asp Thr Lys Gly Leu Asn
145                 150                 155                 160
Phe Ala Lys Glu Thr Ala Gly Thr Asn Gly Asp Pro Thr Val His Leu
                165                 170                 175
Asn Gly Ile Gly Ser Thr Leu Thr Asp Thr Leu Ala Gly Ser Ser Ala
                180                 185                 190
Ser His Val Asp Ala Gly Asn Gln Ser Thr His Tyr Thr Arg Ala Ala
            195                 200                 205
Ser Ile Lys Asp Val Leu Asn Ala Gly Trp Asn Ile Lys Gly Val Lys
            210                 215                 220
Thr Gly Ser Thr Thr Gly Gln Ser Glu Asn Val Asp Phe Val Arg Thr
225                 230                 235                 240
Tyr Asp Thr Val Glu Phe Leu Ser Ala Asp Thr Lys Thr Thr Thr Val
                245                 250                 255
Asn Val Glu Ser Lys Asp Asn Gly Lys Arg Thr Glu Val Lys Ile Gly
                260                 265                 270
Ala Lys Thr Ser Val Ile Lys Glu Lys Asp Gly Lys Leu Val Thr Gly
            275                 280                 285
Lys Gly Lys Gly Glu Asn Gly Ser Ser Thr Asp Glu Gly Glu Gly Leu
            290                 295                 300
Val Thr Ala Lys Glu Val Ile Asp Ala Val Asn Lys Ala Gly Trp Arg
305                 310                 315                 320
Met Lys Thr Thr Thr Ala Asn Gly Gln Thr Gly Gln Ala Asp Lys Phe
                325                 330                 335
Glu Thr Val Thr Ser Gly Thr Lys Val Thr Phe Ala Ser Gly Asn Gly
            340                 345                 350
Thr Thr Ala Thr Val Ser Lys Asp Asp Gln Gly Asn Ile Thr Val Lys
            355                 360                 365
Tyr Asp Val Asn Val Gly Asp Ala Leu Asn Val Asn Gln Leu Gln Asn
370                 375                 380
Ser Gly Trp Asn Leu Asp Ser Lys Ala Val Ala Gly Ser Ser Gly Lys
385                 390                 395                 400
Val Ile Ser Gly Asn Val Ser Pro Ser Lys Gly Lys Met Asp Glu Thr
                405                 410                 415
Val Asn Ile Asn Ala Gly Asn Asn Ile Glu Ile Thr Arg Asn Gly Lys
                420                 425                 430
Asn Ile Asp Ile Ala Thr Ser Met Thr Pro Gln Phe Ser Ser Val Ser
            435                 440                 445
Leu Gly Ala Gly Ala Asp Ala Pro Thr Leu Ser Val Asp Asp Glu Gly
            450                 455                 460
Ala Leu Asn Val Gly Ser Lys Asp Ala Asn Lys Pro Val Arg Ile Thr
465                 470                 475                 480
Asn Val Ala Pro Gly Val Lys Glu Gly Asp Val Thr Asn Val Ala Gln
                485                 490                 495
Leu Lys Gly Val Ala Gln Asn Leu Asn Asn Arg Ile Asp Asn Val Asp
            500                 505                 510
```

-continued

```
Gly Asn Ala Arg Ala Gly Ile Ala Gln Ala Ile Ala Thr Ala Gly Leu
            515                 520                 525

Ala Gln Ala Tyr Leu Pro Gly Lys Ser Met Met Ala Ile Gly Gly Gly
        530                 535                 540

Thr Tyr Arg Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585

<210> SEQ ID NO 110
<211> LENGTH: 592
<212> TYPE: PRT
<213> ORGANISM: Neisseria meningitidis

<400> SEQUENCE: 110

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Asn Ala Thr Asp Glu Asp Glu Glu Glu Leu Glu Ser Val Gln
     50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
    130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Met Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300
```

```
Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
                355                 360                 365

Thr Val Met Tyr Asp Val Asn Val Gly Asp Ala Leu Asn Val Asn Gln
                370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
                450                 455                 460

Asp Lys Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
                500                 505                 510

Asn Val Asp Gly Asn Ala Arg Ala Gly Ile Ala Gln Ala Ile Ala Thr
                515                 520                 525

Ala Gly Leu Val Gln Ala Tyr Leu Pro Gly Lys Ser Met Met Ala Ile
                530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
                580                 585                 590

<210> SEQ ID NO 111
<211> LENGTH: 600
<212> TYPE: PRT
<213> ORGANISM: Neisseria meningitidis

<400> SEQUENCE: 111

Met Asn Lys Ile Tyr Arg Ile Ile Trp Asn Ile Ala Leu Asn Ala Trp
1               5                   10                  15

Val Val Ser Glu Leu Thr Arg Asn His Thr Lys Arg Ala Ser Ala
                20                  25                  30

Thr Val Ala Thr Ala Val Leu Ala Thr Leu Leu Ser Ala Thr Val Gln
                35                  40                  45

Ala Asn Ala Thr Asp Glu Glu Asp Asn Glu Asp Leu Glu Pro Val Val
                50                  55                  60

Arg Thr Ala Pro Val Leu Ser Phe His Ser Asp Lys Glu Gly Thr Gly
65                  70                  75                  80

Glu Lys Glu Glu Val Gly Ala Ser Ser Asn Leu Thr Val Tyr Phe Asp
```

-continued

```
                    85                  90                  95
Lys Asn Arg Val Leu Lys Ala Gly Thr Ile Thr Leu Lys Ala Gly Asp
                100                 105                 110
Asn Leu Lys Ile Lys Gln Asn Thr Asn Glu Asn Thr Asn Glu Asn Thr
            115                 120                 125
Asn Ala Ser Ser Phe Thr Tyr Ser Leu Lys Lys Asp Leu Thr Gly Leu
        130                 135                 140
Ile Asn Val Glu Thr Glu Lys Leu Ser Phe Gly Ala Asn Gly Lys Lys
145                 150                 155                 160
Val Asn Ile Ile Ser Asp Thr Lys Gly Leu Asn Phe Ala Lys Glu Thr
                165                 170                 175
Ala Gly Thr Asn Gly Asp Pro Thr Val His Leu Asn Gly Ile Gly Ser
                180                 185                 190
Thr Leu Thr Asp Thr Leu Ala Gly Ser Ser Ala Ser His Val Asp Ala
            195                 200                 205
Gly Asn Gln Ser Thr His Tyr Thr Arg Ala Ala Ser Ile Lys Asp Val
        210                 215                 220
Leu Asn Ala Gly Trp Asn Ile Lys Gly Val Lys Thr Gly Ser Thr Thr
225                 230                 235                 240
Gly Gln Ser Glu Asn Val Asp Phe Val Arg Thr Tyr Asp Thr Val Glu
                245                 250                 255
Phe Leu Ser Ala Asp Thr Lys Thr Thr Val Asn Val Glu Ser Lys
                260                 265                 270
Asp Asn Gly Lys Arg Thr Glu Val Lys Ile Gly Ala Lys Thr Ser Val
            275                 280                 285
Ile Lys Glu Lys Asp Gly Lys Leu Val Thr Gly Lys Gly Lys Gly Glu
        290                 295                 300
Asn Gly Ser Ser Thr Asp Glu Gly Gly Leu Val Thr Ala Lys Glu
305                 310                 315                 320
Val Ile Asp Ala Val Asn Lys Ala Gly Trp Arg Met Lys Thr Thr Thr
                325                 330                 335
Ala Asn Gly Gln Thr Gly Gln Ala Asp Lys Phe Glu Thr Val Thr Ser
                340                 345                 350
Gly Thr Lys Val Thr Phe Ala Ser Gly Asn Gly Thr Thr Ala Thr Val
            355                 360                 365
Ser Lys Asp Asp Gln Gly Asn Ile Thr Val Lys Tyr Asp Val Asn Val
        370                 375                 380
Gly Asp Ala Leu Asn Val Asn Gln Leu Gln Asn Ser Gly Trp Asn Leu
385                 390                 395                 400
Asp Ser Lys Ala Val Ala Gly Ser Ser Lys Val Ile Ser Gly Asn
                405                 410                 415
Val Ser Pro Ser Lys Gly Lys Met Asp Glu Thr Val Asn Ile Asn Ala
                420                 425                 430
Gly Asn Asn Ile Glu Ile Thr Arg Asn Gly Lys Asn Ile Asp Ile Ala
            435                 440                 445
Thr Ser Met Thr Pro Gln Phe Ser Ser Val Ser Leu Gly Ala Gly Ala
        450                 455                 460
Asp Ala Pro Thr Leu Ser Val Asp Asp Glu Gly Ala Leu Asn Val Gly
465                 470                 475                 480
Ser Lys Asp Ala Asn Lys Pro Val Arg Ile Thr Asn Val Ala Pro Gly
                485                 490                 495
Val Lys Glu Gly Asp Val Thr Asn Val Ala Gln Leu Lys Gly Val Ala
                500                 505                 510
```

```
Gln Asn Leu Asn Asn Arg Ile Asp Asn Val Asp Gly Asn Ala Arg Ala
        515                 520                 525

Gly Ile Ala Gln Ala Ile Ala Thr Ala Gly Leu Val Gln Ala Tyr Leu
    530                 535                 540

Pro Gly Lys Ser Met Met Ala Ile Gly Gly Thr Tyr Arg Gly Glu
545                 550                 555                 560

Ala Gly Tyr Ala Ile Gly Tyr Ser Ser Ile Ser Asp Gly Gly Asn Trp
                565                 570                 575

Ile Ile Lys Gly Thr Ala Ser Gly Asn Ser Arg Gly His Phe Gly Ala
                580                 585                 590

Ser Ala Ser Val Gly Tyr Gln Trp
            595                 600

<210> SEQ ID NO 112
<211> LENGTH: 32
<212> TYPE: DNA
<213> ORGANISM: Neisseria meningitidis

<400> SEQUENCE: 112
cgcggatccc atatgtcgcc gcaaaattcc ga                                      32

<210> SEQ ID NO 113
<211> LENGTH: 28
<212> TYPE: DNA
<213> ORGANISM: Neisseria meningitidis

<400> SEQUENCE: 113
cccgctcgag ttttgccgcg ttaaaagc                                           28

<210> SEQ ID NO 114
<211> LENGTH: 30
<212> TYPE: DNA
<213> ORGANISM: Neisseria meningitidis

<400> SEQUENCE: 114
cgcggatccc atatgaccgt gaagaccgcc                                         30

<210> SEQ ID NO 115
<211> LENGTH: 28
<212> TYPE: DNA
<213> ORGANISM: Neisseria meningitidis

<400> SEQUENCE: 115
cccgctcgag ccactgataa ccgacaga                                           28

<210> SEQ ID NO 116
<211> LENGTH: 34
<212> TYPE: DNA
<213> ORGANISM: Neisseria meningitidis

<400> SEQUENCE: 116
cgcggatccc atatgtattt gaaacagctc caag                                    34

<210> SEQ ID NO 117
<211> LENGTH: 26
<212> TYPE: DNA
<213> ORGANISM: Neisseria meningitidis

<400> SEQUENCE: 117
cccgctcgag ttctgggtga atgtta                                             26
```

<210> SEQ ID NO 118
<211> LENGTH: 29
<212> TYPE: DNA
<213> ORGANISM: Neisseria meningitidis

<400> SEQUENCE: 118
gcggatccca tgggcacg gacaacccc                                    29

<210> SEQ ID NO 119
<211> LENGTH: 26
<212> TYPE: DNA
<213> ORGANISM: Neisseria meningitidis

<400> SEQUENCE: 119
cccgctcgag acgtggggaa cagtct                                     26

<210> SEQ ID NO 120
<211> LENGTH: 34
<212> TYPE: DNA
<213> ORGANISM: Neisseria meningitidis

<400> SEQUENCE: 120
gcggatccca tgaaaaat attcaagtag ttgc                              34

<210> SEQ ID NO 121
<211> LENGTH: 27
<212> TYPE: DNA
<213> ORGANISM: Neisseria meningitidis

<400> SEQUENCE: 121
cccgctcgag aagtttgatt aaacccg                                    27

<210> SEQ ID NO 122
<211> LENGTH: 31
<212> TYPE: DNA
<213> ORGANISM: Neisseria meningitidis

<400> SEQUENCE: 122
cgcggatccc atatgtgcca accgcaatcc g                               31

<210> SEQ ID NO 123
<211> LENGTH: 27
<212> TYPE: DNA
<213> ORGANISM: Neisseria meningitidis

<400> SEQUENCE: 123
cccgctcgag tttttccagc tccggca                                    27

<210> SEQ ID NO 124
<211> LENGTH: 33
<212> TYPE: DNA
<213> ORGANISM: Neisseria meningitidis

<400> SEQUENCE: 124
gcggatccca tggttatc ggaatattac tcg                               33

<210> SEQ ID NO 125
<211> LENGTH: 25
<212> TYPE: DNA
<213> ORGANISM: Neisseria meningitidis

<400> SEQUENCE: 125
cccgctcgag ggctgcagaa gctgg                                      25

```
<210> SEQ ID NO 126
<211> LENGTH: 32
<212> TYPE: DNA
<213> ORGANISM: Neisseria meningitidis

<400> SEQUENCE: 126
cgcggatccc atatgcggac gtggttggtt tt                           32

<210> SEQ ID NO 127
<211> LENGTH: 30
<212> TYPE: DNA
<213> ORGANISM: Neisseria meningitidis

<400> SEQUENCE: 127
cccgctcgag atatcttccg ttttttttcac                            30

<210> SEQ ID NO 128
<211> LENGTH: 36
<212> TYPE: DNA
<213> ORGANISM: Neisseria meningitidis

<400> SEQUENCE: 128
cgcggatccg ctagcgtaaa tttattattt ttagaa                      36

<210> SEQ ID NO 129
<211> LENGTH: 28
<212> TYPE: DNA
<213> ORGANISM: Neisseria meningitidis

<400> SEQUENCE: 129
cccgctcgag ttccaactca ttgaagta                               28

<210> SEQ ID NO 130
<211> LENGTH: 35
<212> TYPE: DNA
<213> ORGANISM: Neisseria meningitidis

<400> SEQUENCE: 130
cgcggatccc atatgaataa aggtttacat cgcat                       35

<210> SEQ ID NO 131
<211> LENGTH: 26
<212> TYPE: DNA
<213> ORGANISM: Neisseria meningitidis

<400> SEQUENCE: 131
cccgctcgag aatcgctgca ccggct                                 26

<210> SEQ ID NO 132
<211> LENGTH: 30
<212> TYPE: DNA
<213> ORGANISM: Neisseria meningitidis

<400> SEQUENCE: 132
cgcggatccc atatgactgc cttttcgaca                             30

<210> SEQ ID NO 133
<211> LENGTH: 26
<212> TYPE: DNA
<213> ORGANISM: Neisseria meningitidis

<400> SEQUENCE: 133
```

```
cccgctcgag gcgtgaagcg tcagga                                              26

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence:  BamHI -
      NdeI

<400> SEQUENCE: 134
cgcggatccc atatg                                                          15

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence:  BamHI -
      NheI

<400> SEQUENCE: 135
cgcggatccg ctagc                                                          15

<210> SEQ ID NO 136
<211> LENGTH: 17
<212> TYPE: DNA
<213> ORGANISM: Artificial Sequence
<220> FEATURE:
<223> OTHER INFORMATION: Description of Artificial Sequence:  EcoRI -
      NheI

<400> SEQUENCE: 136
ccggaattct agctagc                                                        17

<210> SEQ ID NO 137
<211> LENGTH: 10
<212> TYPE: DNA
<213> ORGANISM: Artificial Sequence
<220> FEATURE:
<223> OTHER INFORMATION: Description of Artificial Sequence:  XhoI

<400> SEQUENCE: 137
cccgctcgag                                                                10

<210> SEQ ID NO 138
<211> LENGTH: 291
<212> TYPE: PRT
<213> ORGANISM: Artificial Sequence
<220> FEATURE:
<223> OTHER INFORMATION: Description of Artificial Sequence: ORF40a
<221> NAME/KEY: SITE
<222> LOCATION: (6)
<223> OTHER INFORMATION: place-holder
<221> NAME/KEY: SITE
<222> LOCATION: (130)
<223> OTHER INFORMATION: place-holder
<221> NAME/KEY: SITE
<222> LOCATION: (193)
<223> OTHER INFORMATION: place-holder
<221> NAME/KEY: SITE
<222> LOCATION: (218)
<223> OTHER INFORMATION: place-holder
<221> NAME/KEY: SITE
<222> LOCATION: (245)
<223> OTHER INFORMATION: place-holder

<400> SEQUENCE: 138

Ser Ala Leu Asn Ala Xaa Val Ala Val Ser Glu Leu Thr Arg Asn His
```

-continued

```
                1               5                      10                     15
            Thr Lys Arg Ala Ser Ala Thr Val Lys Thr Ala Val Leu Ala Thr Leu
                            20                     25                     30

Leu Phe Ala Thr Val Gln Ala Asn Ala Thr Asp Glu Asp Glu Glu
                        35                     40                     45

Glu Leu Glu Ser Val Gln Arg Ser Val Gly Ser Ile Gln Ala Ser
                    50                     55                     60

Met Glu Gly Ser Gly Glu Leu Glu Thr Ile Ser Leu Ser Met Thr Asn
            65                     70                     75                     80

Asp Ser Lys Glu Phe Val Asp Pro Tyr Ile Val Thr Leu Lys Ala
                            85                     90                     95

Gly Asp Asn Leu Lys Ile Lys Gln Asn Thr Asn Glu Asn Thr Asn Ala
                            100                    105                    110

Ser Ser Phe Thr Tyr Ser Leu Lys Lys Asp Leu Thr Gly Leu Ile Asn
                            115                    120                    125

Val Xaa Thr Glu Lys Leu Ser Phe Gly Ala Asn Gly Lys Lys Val Asn
                    130                    135                    140

Ile Ile Ser Asp Thr Lys Gly Leu Asn Phe Ala Lys Glu Thr Ala Gly
            145                    150                    155                    160

Thr Asn Gly Asp Thr Thr Val His Leu Asn Gly Ile Gly Ser Thr Leu
                            165                    170                    175

Thr Asp Thr Leu Ala Gly Ser Ser Ala Ser His Val Asp Ala Gly Asn
                        180                    185                    190

Xaa Ser Thr His Tyr Thr Arg Ala Ala Ser Ile Lys Asp Val Leu Asn
                        195                    200                    205

Ala Gly Trp Asn Ile Lys Gly Val Lys Xaa Gly Ser Thr Thr Gly Gln
                    210                    215                    220

Ser Glu Asn Val Asp Phe Val Arg Thr Tyr Asp Thr Val Glu Phe Leu
            225                    230                    235                    240

Ser Ala Asp Thr Xaa Thr Thr Val Asn Val Glu Ser Lys Asp Asn
                            245                    250                    255

Gly Lys Arg Thr Glu Val Lys Ile Gly Ala Lys Thr Ser Val Ile Lys
                            260                    265                    270

Glu Lys Asp Gly Lys Leu Val Thr Gly Lys Lys Gly Glu Asn Gly
                            275                    280                    285

Ser Ser Thr
                290

<210> SEQ ID NO 139
<211> LENGTH: 240
<212> TYPE: PRT
<213> ORGANISM: Artificial Sequence
<220> FEATURE:
<223> OTHER INFORMATION: Description of Artificial Sequence: Hsf

<400> SEQUENCE: 139

Thr Leu Leu Phe Ala Thr Val Gln Ala Asn Ala Thr Asp Glu Asp Glu
            1                   5                      10                     15

Glu Leu Asp Pro Val Val Arg Thr Ala Pro Val Leu Ser Phe His Ser
                            20                     25                     30

Asp Lys Glu Gly Thr Gly Glu Lys Glu Val Thr Glu Asn Ser Asn Trp
                        35                     40                     45

Gly Ile Tyr Phe Asp Asn Lys Gly Val Leu Lys Ala Gly Ala Ile Thr
                    50                     55                     60

Leu Lys Ala Gly Asp Asn Leu Lys Ile Lys Gln Asn Thr Asp Glu Ser
```

-continued

```
                65                  70                  75                  80
Thr Asn Ala Ser Ser Phe Thr Tyr Ser Leu Lys Lys Asp Leu Thr Asp
                    85                  90                  95
Leu Thr Ser Val Ala Thr Glu Lys Leu Ser Phe Gly Ala Asn Gly Asp
                100                 105                 110
Lys Val Asp Ile Thr Ser Asp Ala Asn Gly Leu Lys Leu Ala Lys Thr
                115                 120                 125
Gly Asn Gly Asn Val His Leu Asn Gly Leu Asp Ser Thr Leu Pro Asp
            130                 135                 140
Ala Val Thr Asn Thr Gly Val Leu Ser Ser Ser Ser Phe Thr Pro Asn
145                 150                 155                 160
Asp Val Glu Lys Thr Arg Ala Ala Thr Val Lys Asp Val Leu Asn Ala
                165                 170                 175
Gly Trp Asn Ile Lys Gly Ala Lys Thr Ala Gly Gly Asn Val Glu Ser
                180                 185                 190
Val Asp Leu Val Ser Ala Tyr Asn Asn Val Glu Phe Ile Thr Gly Asp
                195                 200                 205
Lys Asn Thr Leu Asp Val Val Leu Thr Ala Lys Glu Asn Gly Lys Thr
            210                 215                 220
Thr Glu Val Lys Phe Thr Pro Lys Thr Ser Val Ile Lys Glu Lys Asp
225                 230                 235                 240

<210> SEQ ID NO 140
<211> LENGTH: 251
<212> TYPE: PRT
<213> ORGANISM: Artificial Sequence
<220> FEATURE:
<223> OTHER INFORMATION: Description of Artificial Sequence: overlap
      identity
<221> NAME/KEY: SITE
<222> LOCATION: (10)
<223> OTHER INFORMATION: absent or positive
<221> NAME/KEY: SITE
<222> LOCATION: (12)..(13)
<223> OTHER INFORMATION: absent or positive
<221> NAME/KEY: SITE
<222> LOCATION: (15)..(16)
<223> OTHER INFORMATION: absent or positive
<221> NAME/KEY: SITE
<222> LOCATION: (18)..(21)
<223> OTHER INFORMATION: absent or positive
<221> NAME/KEY: SITE
<222> LOCATION: (26)
<223> OTHER INFORMATION: absent or positive
<221> NAME/KEY: SITE
<222> LOCATION: (29)..(30)
<223> OTHER INFORMATION: absent or positive
<221> NAME/KEY: SITE
<222> LOCATION: (33)..(35)
<223> OTHER INFORMATION: absent or positive
<221> NAME/KEY: SITE
<222> LOCATION: (38)..(49)
<223> OTHER INFORMATION: absent or positive
<221> NAME/KEY: SITE
<222> LOCATION: (52)
<223> OTHER INFORMATION: absent or positive
<221> NAME/KEY: SITE
<222> LOCATION: (54)..(55)
<223> OTHER INFORMATION: absent or positive
<221> NAME/KEY: SITE
<222> LOCATION: (58)..(59)
<223> OTHER INFORMATION: absent or positive
<221> NAME/KEY: SITE
<222> LOCATION: (64)
<223> OTHER INFORMATION: absent or positive
<221> NAME/KEY: SITE
<222> LOCATION: (66)..(67)
<223> OTHER INFORMATION: absent or positive
```

-continued

```
<221> NAME/KEY: SITE
<222> LOCATION: (70)
<223> OTHER INFORMATION: absent or positive
<221> NAME/KEY: SITE
<222> LOCATION: (82)..(90)
<223> OTHER INFORMATION: absent or positive
<221> NAME/KEY: SITE
<222> LOCATION: (106)
<223> OTHER INFORMATION: absent or positive
<221> NAME/KEY: SITE
<222> LOCATION: (113)
<223> OTHER INFORMATION: absent or positive
<221> NAME/KEY: SITE
<222> LOCATION: (117)
<223> OTHER INFORMATION: absent or positive
<221> NAME/KEY: SITE
<222> LOCATION: (120)
<223> OTHER INFORMATION: absent or positive
<221> NAME/KEY: SITE
<222> LOCATION: (125)..(126)
<223> OTHER INFORMATION: absent or positive
<221> NAME/KEY: SITE
<222> LOCATION: (129)..(130)
<223> OTHER INFORMATION: absent or positive
<221> NAME/KEY: SITE
<222> LOCATION: (133)..(138)
<223> OTHER INFORMATION: absent or positive
<221> NAME/KEY: SITE
<222> LOCATION: (140)..(142)
<223> OTHER INFORMATION: absent or positive
<221> NAME/KEY: SITE
<222> LOCATION: (148)..(149)
<223> OTHER INFORMATION: absent or positive
<221> NAME/KEY: SITE
<222> LOCATION: (153)
<223> OTHER INFORMATION: absent or positive
<221> NAME/KEY: SITE
<222> LOCATION: (155)..(157)
<223> OTHER INFORMATION: absent or positive
<221> NAME/KEY: SITE
<222> LOCATION: (161)..(173)
<223> OTHER INFORMATION: absent or positive
<221> NAME/KEY: SITE
<222> LOCATION: (176)
<223> OTHER INFORMATION: absent or positive
<221> NAME/KEY: SITE
<222> LOCATION: (180)
<223> OTHER INFORMATION: absent or positive
<221> NAME/KEY: SITE
<222> LOCATION: (194)
<223> OTHER INFORMATION: absent or positive
<221> NAME/KEY: SITE
<222> LOCATION: (196)..(203)
<223> OTHER INFORMATION: absent or positive
<221> NAME/KEY: SITE
<222> LOCATION: (206)
<223> OTHER INFORMATION: absent or positive
<221> NAME/KEY: SITE
<222> LOCATION: (208)..(209)
<223> OTHER INFORMATION: absent or positive
<221> NAME/KEY: SITE
<222> LOCATION: (211)..(212)
<223> OTHER INFORMATION: absent or positive
<221> NAME/KEY: SITE
<222> LOCATION: (216)..(218)
<223> OTHER INFORMATION: absent or positive
<221> NAME/KEY: SITE
<222> LOCATION: (220)..(221)
<223> OTHER INFORMATION: absent or positive
<221> NAME/KEY: SITE
<222> LOCATION: (223)..(224)
<223> OTHER INFORMATION: absent or positive
<221> NAME/KEY: SITE
<222> LOCATION: (226)..(229)
<223> OTHER INFORMATION: absent or positive
<221> NAME/KEY: SITE
<222> LOCATION: (231)
<223> OTHER INFORMATION: absent or positive
<221> NAME/KEY: SITE
```

```
<222> LOCATION: (235)
<223> OTHER INFORMATION: absent or positive
<221> NAME/KEY: SITE
<222> LOCATION: (240)..(242)
<223> OTHER INFORMATION: absent or positive

<400> SEQUENCE: 140
```

Thr Leu Leu Phe Ala Thr Val Gln Ala Xaa Ala Xaa Xaa Glu Xaa Xaa
1               5                   10                  15

Glu Xaa Xaa Xaa Xaa Leu Asp Pro Val Xaa Arg Thr Xaa Xaa Val Leu
            20                  25                  30

Xaa Xaa Xaa Ser Asp Xaa Xaa Xaa Xaa Xaa Xaa Xaa Xaa Xaa Xaa Xaa
            35                  40                  45

Xaa Asn Ser Xaa Trp Xaa Xaa Tyr Phe Xaa Xaa Lys Gly Val Leu Xaa
    50                  55                  60

Ala Xaa Xaa Ile Thr Xaa Lys Ala Gly Asp Asn Leu Lys Ile Lys Gln
65              70                  75                  80

Asn Xaa Xaa Xaa Xaa Xaa Xaa Xaa Xaa Phe Thr Tyr Ser Leu Lys
        85                  90                  95

Lys Asp Leu Thr Asp Leu Thr Ser Val Xaa Thr Glu Lys Leu Ser Phe
            100                 105                 110

Xaa Ala Asn Gly Xaa Lys Val Xaa Ile Thr Ser Asp Xaa Xaa Gly Leu
    115                 120                 125

Xaa Xaa Ala Lys Xaa Xaa Xaa Xaa Xaa Gly Xaa Xaa Xaa Val His
130                 135                 140

Leu Asn Gly Xaa Xaa Ser Thr Leu Xaa Asp Xaa Xaa Xaa Asn Thr Gly
145                 150                 155                 160

Xaa Xaa Xaa Xaa Xaa Xaa Xaa Xaa Xaa Xaa Xaa Xaa Glu Lys Xaa
                165                 170                 175

Arg Ala Ala Xaa Val Lys Asp Val Leu Asn Ala Gly Trp Asn Ile Lys
            180                 185                 190

Gly Xaa Lys Xaa Xaa Xaa Xaa Xaa Xaa Xaa Val Asp Xaa Val Xaa
        195                 200                 205

Xaa Tyr Xaa Xaa Val Glu Phe Xaa Xaa Xaa Asp Xaa Xaa Thr Xaa Xaa
    210                 215                 220

Val Xaa Xaa Xaa Xaa Lys Xaa Asn Gly Lys Xaa Thr Glu Val Lys Xaa
225                 230                 235                 240

Xaa Xaa Lys Thr Ser Val Ile Lys Glu Lys Asp
            245                 250

```
<210> SEQ ID NO 141
<211> LENGTH: 36
<212> TYPE: PRT
<213> ORGANISM: Artificial Sequence
<220> FEATURE:
<223> OTHER INFORMATION: Description of Artificial Sequence: ORF40a

<400> SEQUENCE: 141
```

Val Ala Val Ser Glu Leu Thr Arg Asn His Thr Lys Arg Ala Ser Ala
1               5                   10                  15

Thr Val Lys Thr Ala Val Leu Ala Thr Leu Leu Phe Ala Thr Val Gln
            20                  25                  30

Ala Asn Ala Thr
        35

```
<210> SEQ ID NO 142
<211> LENGTH: 36
<212> TYPE: PRT
```

<213> ORGANISM: Artificial Sequence
<220> FEATURE:
<223> OTHER INFORMATION: Description of Artificial Sequence: homology
<221> NAME/KEY: SITE
<222> LOCATION: (2)
<223> OTHER INFORMATION: absent or positive
<221> NAME/KEY: SITE
<222> LOCATION: (9)
<223> OTHER INFORMATION: absent or positive
<221> NAME/KEY: SITE
<222> LOCATION: (19)
<223> OTHER INFORMATION: absent or positive

<400> SEQUENCE: 142

Val Xaa Val Ser Glu Leu Thr Arg Xaa His Thr Lys Arg Ala Ser Ala
 1               5                  10                  15

Thr Val Xaa Thr Ala Val Leu Ala Thr Leu Leu Phe Ala Thr Val Gln
            20                  25                  30

Ala Asn Ala Thr
        35

<210> SEQ ID NO 143
<211> LENGTH: 36
<212> TYPE: PRT
<213> ORGANISM: Artificial Sequence
<220> FEATURE:
<223> OTHER INFORMATION: Description of Artificial Sequence: Hsf

<400> SEQUENCE: 143

Val Val Val Ser Glu Leu Thr Arg Thr His Thr Lys Arg Ala Ser Ala
 1               5                  10                  15

Thr Val Glu Thr Ala Val Leu Ala Thr Leu Leu Phe Ala Thr Val Gln
            20                  25                  30

Ala Asn Ala Thr
        35

<210> SEQ ID NO 144
<211> LENGTH: 38
<212> TYPE: PRT
<213> ORGANISM: Artificial Sequence
<220> FEATURE:
<223> OTHER INFORMATION: Description of Artificial Sequence: Orf40a

<400> SEQUENCE: 144

Val Thr Leu Lys Ala Gly Asp Asn Leu Lys Ile Lys Gln Asn Thr Asn
 1               5                  10                  15

Glu Asn Thr Asn Ala Ser Ser Phe Thr Tyr Ser Leu Lys Lys Asp Leu
            20                  25                  30

Thr Gly Leu Ile Asn Val
        35

<210> SEQ ID NO 145
<211> LENGTH: 38
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (1)
<223> OTHER INFORMATION: absent or positive
<221> NAME/KEY: SITE
<222> LOCATION: (16)
<223> OTHER INFORMATION: absent or positive
<221> NAME/KEY: SITE
<222> LOCATION: (18)
<223> OTHER INFORMATION: absent or positive
<221> NAME/KEY: SITE

```
<222> LOCATION: (34)
<223> OTHER INFORMATION: absent or positive
<221> NAME/KEY: SITE
<222> LOCATION: (36)..(37)
<223> OTHER INFORMATION: absent or positive

<400> SEQUENCE: 145

Xaa Thr Leu Lys Ala Gly Asp Asn Leu Lys Ile Lys Gln Asn Thr Xaa
  1               5                  10                  15

Glu Xaa Thr Asn Ala Ser Ser Phe Thr Tyr Ser Leu Lys Lys Asp Leu
             20                  25                  30

Thr Xaa Leu Xaa Xaa Val
         35

<210> SEQ ID NO 146
<211> LENGTH: 38
<212> TYPE: PRT
<213> ORGANISM: Artificial Sequence
<220> FEATURE:
<223> OTHER INFORMATION: Description of Artificial Sequence: Hsf

<400> SEQUENCE: 146

Ile Thr Leu Lys Ala Gly Asp Asn Leu Lys Ile Lys Gln Asn Thr Asp
  1               5                  10                  15

Glu Ser Thr Asn Ala Ser Ser Phe Thr Tyr Ser Leu Lys Lys Asp Leu
             20                  25                  30

Thr Asp Leu Thr Ser Val
         35

<210> SEQ ID NO 147
<211> LENGTH: 29
<212> TYPE: PRT
<213> ORGANISM: Artificial Sequence
<220> FEATURE:
<223> OTHER INFORMATION: Description of Artificial Sequence: Orf40a

<400> SEQUENCE: 147

Val Thr Glu Lys Leu Ser Phe Gly Ala Asn Gly Lys Lys Val Asn Ile
  1               5                  10                  15

Ile Ser Asp Thr Lys Gly Leu Asn Phe Ala Lys Glu Thr
             20                  25

<210> SEQ ID NO 148
<211> LENGTH: 29
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (2)..(3)
<223> OTHER INFORMATION: absent or positive
<221> NAME/KEY: SITE
<222> LOCATION: (7)
<223> OTHER INFORMATION: absent or positive
<221> NAME/KEY: SITE
<222> LOCATION: (9)
<223> OTHER INFORMATION: absent or positive
<221> NAME/KEY: SITE
<222> LOCATION: (12)
<223> OTHER INFORMATION: absent or positive
<221> NAME/KEY: SITE
<222> LOCATION: (17)
<223> OTHER INFORMATION: absent or positive
<221> NAME/KEY: SITE
<222> LOCATION: (28)..(29)
<223> OTHER INFORMATION: absent or positive

<400> SEQUENCE: 148
```

-continued

```
Val Xaa Xaa Lys Leu Ser Xaa Gly Xaa Asn Gly Xaa Lys Val Asn Ile
 1               5                  10                  15

Xaa Ser Asp Thr Lys Gly Leu Asn Phe Ala Lys Xaa Xaa
                20                  25

<210> SEQ ID NO 149
<211> LENGTH: 29
<212> TYPE: PRT
<213> ORGANISM: Artificial Sequence
<220> FEATURE:
<223> OTHER INFORMATION: Description of Artificial Sequence: Hsf

<400> SEQUENCE: 149

Val Ser Asp Lys Leu Ser Leu Gly Thr Asn Gly Asn Lys Val Asn Ile
 1               5                  10                  15

Thr Ser Asp Thr Lys Gly Leu Asn Phe Ala Lys Asp Ser
                20                  25

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: ORF40a

<400> SEQUENCE: 150

Thr Asn Gly Asp Thr Thr Val His Leu Asn Gly Ile Gly Ser Thr Leu
 1               5                  10                  15

Thr Asp Thr Leu Ala Gly Ser Ser Ala Ser His Val Asp Ala Gly Asn
                20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (2)..(3)
<223> OTHER INFORMATION: absent or positive
<221> NAME/KEY: SITE
<222> LOCATION: (5)..(7)
<223> OTHER INFORMATION: absent or positive
<221> NAME/KEY: SITE
<222> LOCATION: (13)
<223> OTHER INFORMATION: absent or positive
<221> NAME/KEY: SITE
<222> LOCATION: (21)..(22)
<223> OTHER INFORMATION: absent or positive
<221> NAME/KEY: SITE
<222> LOCATION: (24)
<223> OTHER INFORMATION: absent or positive
<221> NAME/KEY: SITE
<222> LOCATION: (26)..(30)
<223> OTHER INFORMATION: absent or positive

<400> SEQUENCE: 151

Thr Xaa Xaa Asp Xaa Xaa Xaa His Leu Asn Gly Ile Xaa Ser Thr Leu
 1               5                  10                  15

Thr Asp Thr Leu Xaa Xaa Ser Xaa Ala Xaa Xaa Xaa Xaa Xaa Gly Asn
                20                  25                  30

<210> SEQ ID NO 152
<211> LENGTH: 32
<212> TYPE: PRT
<213> ORGANISM: Artificial Sequence
<220> FEATURE:
```

```
<223> OTHER INFORMATION: Description of Artificial Sequence: Hsf

<400> SEQUENCE: 152

Thr Gly Asp Asp Ala Asn Ile His Leu Asn Gly Ile Ala Ser Thr Leu
 1               5                  10                  15

Thr Asp Thr Leu Leu Asn Ser Gly Ala Thr Thr Asn Leu Gly Gly Asn
             20                  25                  30

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: ORF40a

<400> SEQUENCE: 153

Arg Ala Ala Ser Ile Lys Asp Val Leu Asn Ala Gly Trp Asn Ile Lys
 1               5                  10                  15

Gly Val Lys

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (5)
<223> OTHER INFORMATION: absent or positive
<221> NAME/KEY: SITE
<222> LOCATION: (15)..(16)
<223> OTHER INFORMATION: absent or positive

<400> SEQUENCE: 154

Arg Ala Ala Ser Xaa Lys Asp Val Leu Asn Ala Gly Trp Asn Xaa Xaa
 1               5                  10                  15

Gly Val Lys

<210> SEQ ID NO 155
<211> LENGTH: 19
<212> TYPE: PRT
<213> ORGANISM: Artificial Sequence
<220> FEATURE:
<223> OTHER INFORMATION: Description of Artificial Sequence: Hsf

<400> SEQUENCE: 155

Arg Ala Ala Ser Val Lys Asp Val Leu Asn Ala Gly Trp Asn Val Arg
 1               5                  10                  15

Gly Val Lys

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: ORF40a

<400> SEQUENCE: 156

Ser Thr Thr Gly Gln Ser Glu Asn Val Asp Phe Val Arg Thr Tyr Asp
 1               5                  10                  15

Thr Val Glu Phe Leu Ser Ala Asp Thr Thr Thr Thr
             20                  25

<210> SEQ ID NO 157
```

```
<211> LENGTH: 28
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (2)..(4)
<223> OTHER INFORMATION: absent or positive
<221> NAME/KEY: SITE
<222> LOCATION: (6)
<223> OTHER INFORMATION: absent or positive
<221> NAME/KEY: SITE
<222> LOCATION: (9)
<223> OTHER INFORMATION: absent or positive
<221> NAME/KEY: SITE
<222> LOCATION: (13)
<223> OTHER INFORMATION: absent or positive
<221> NAME/KEY: SITE
<222> LOCATION: (19)
<223> OTHER INFORMATION: absent or positive
<221> NAME/KEY: SITE
<222> LOCATION: (21)
<223> OTHER INFORMATION: absent or positive
<221> NAME/KEY: SITE
<222> LOCATION: (23)
<223> OTHER INFORMATION: absent or positive
<221> NAME/KEY: SITE
<222> LOCATION: (25)..(26)
<223> OTHER INFORMATION: absent or positive

<400> SEQUENCE: 157

Ser Xaa Xaa Xaa Gln Xaa Glu Asn Xaa Asp Phe Val Xaa Thr Tyr Asp
  1               5                  10                  15

Thr Val Xaa Phe Xaa Ser Xaa Asp Xaa Xaa Thr Thr
             20                  25

<210> SEQ ID NO 158
<211> LENGTH: 28
<212> TYPE: PRT
<213> ORGANISM: Artificial Sequence
<220> FEATURE:
<223> OTHER INFORMATION: Description of Artificial Sequence: Hsf

<400> SEQUENCE: 158

Ser Ala Asn Asn Gln Val Glu Asn Ile Asp Phe Val Ala Thr Tyr Asp
  1               5                  10                  15

Thr Val Asp Phe Val Ser Gly Asp Lys Asp Thr Thr
             20                  25

<210> SEQ ID NO 159
<211> LENGTH: 240
<212> TYPE: PRT
<213> ORGANISM: Artificial Sequence
<220> FEATURE:
<223> OTHER INFORMATION: Description of Artificial Sequence: ORF38a

<400> SEQUENCE: 159

Met Leu Arg Leu Thr Ala Leu Ala Val Cys Thr Ala Leu Ala Leu Gly
  1               5                  10                  15

Ala Cys Ser Pro Gln Asn Ser Asp Ser Ala Pro Gln Ala Lys Glu Gln
             20                  25                  30

Ala Val Ser Ala Ala Gln Ser Glu Gly Val Ser Val Thr Val Lys Thr
         35                  40                  45

Ala Arg Gly Asp Val Gln Ile Pro Gln Asn Pro Glu Arg Ile Ala Val
     50                  55                  60

Tyr Asp Leu Gly Met Leu Asp Thr Leu Ser Lys Leu Gly Val Lys Thr
 65                  70                  75                  80
```

```
Gly Leu Ser Val Asp Lys Asn Arg Leu Pro Tyr Leu Glu Glu Tyr Phe
                 85                  90                  95
Lys Thr Thr Lys Pro Ala Gly Thr Leu Phe Glu Pro Asp Tyr Glu Thr
            100                 105                 110
Leu Asn Ala Tyr Lys Pro Gln Leu Ile Ile Ile Gly Ser Arg Ala Ala
        115                 120                 125
Lys Ala Phe Asp Lys Leu Asn Glu Ile Ala Pro Thr Ile Glu Met Thr
130                 135                 140
Ala Asp Thr Ala Asn Leu Lys Glu Ser Ala Lys Glu Arg Ile Asp Ala
145                 150                 155                 160
Leu Ala Gln Ile Phe Gly Lys Ala Glu Ala Asp Lys Leu Lys Ala
                165                 170                 175
Glu Ile Asp Ala Ser Phe Glu Ala Ala Lys Thr Ala Ala Gln Gly Lys
            180                 185                 190
Gly Lys Gly Leu Val Ile Leu Val Asn Gly Gly Lys Met Ser Ala Phe
        195                 200                 205
Gly Pro Ser Ser Arg Leu Gly Gly Trp Leu His Lys Asp Ile Gly Val
    210                 215                 220
Pro Ala Val Asp Glu Ala Ile Lys Glu Gly Ser His Gly Gln Pro Ile
225                 230                 235                 240
```

<210> SEQ ID NO 160
<211> LENGTH: 94
<212> TYPE: PRT
<213> ORGANISM: Artificial Sequence
<220> FEATURE:
<223> OTHER INFORMATION: Description of Artificial Sequence: ORF38

<400> SEQUENCE: 160

```
Glu Gly Ala Ser Val Thr Val Lys Thr Ala Arg Gly Asp Val Gln Ile
1               5                   10                  15
Pro Gln Asn Pro Glu Arg Ile Ala Val Tyr Asp Leu Gly Met Leu Asp
            20                  25                  30
Thr Leu Ser Lys Leu Gly Val Lys Thr Gly Leu Ser Val Asp Lys Asn
        35                  40                  45
Arg Leu Pro Tyr Leu Glu Glu Tyr Phe Lys Thr Thr Lys Pro Ala Gly
    50                  55                  60
Thr Leu Phe Glu Pro Asp Tyr Glu Thr Leu Asn Ala Tyr Lys Pro Gln
65                  70                  75                  80
Leu Ile Ile Ile Gly Ser Arg Ala Ala Lys Ala Phe Asp Lys
                85                  90
```

<210> SEQ ID NO 161
<211> LENGTH: 96
<212> TYPE: PRT
<213> ORGANISM: Artificial Sequence
<220> FEATURE:
<223> OTHER INFORMATION: Description of Artificial Sequence: overlap
      identity
<221> NAME/KEY: SITE
<222> LOCATION: (3)
<223> OTHER INFORMATION: absent or positive
<221> NAME/KEY: SITE
<222> LOCATION: (5)..(6)
<223> OTHER INFORMATION: absent or positive
<221> NAME/KEY: SITE
<222> LOCATION: (9)..(11)
<223> OTHER INFORMATION: absent or positive
<221> NAME/KEY: SITE
<222> LOCATION: (13)..(16)
<223> OTHER INFORMATION: absent or positive
<221> NAME/KEY: SITE

```
<222> LOCATION: (18)
<223> OTHER INFORMATION: absent or positive
<221> NAME/KEY: SITE
<222> LOCATION: (21)..(26)
<223> OTHER INFORMATION: absent or positive
<221> NAME/KEY: SITE
<222> LOCATION: (30)
<223> OTHER INFORMATION: absent or positive
<221> NAME/KEY: SITE
<222> LOCATION: (34)..(36)
<223> OTHER INFORMATION: absent or positive
<221> NAME/KEY: SITE
<222> LOCATION: (38)..(45)
<223> OTHER INFORMATION: absent or positive
<221> NAME/KEY: SITE
<222> LOCATION: (47)..(50)
<223> OTHER INFORMATION: absent or positive
<221> NAME/KEY: SITE
<222> LOCATION: (53)..(57)
<223> OTHER INFORMATION: absent or positive
<221> NAME/KEY: SITE
<222> LOCATION: (60)..(64)
<223> OTHER INFORMATION: absent or positive
<221> NAME/KEY: SITE
<222> LOCATION: (66)..(70)
<223> OTHER INFORMATION: absent or positive
<221> NAME/KEY: SITE
<222> LOCATION: (72)
<223> OTHER INFORMATION: absent or positive
<221> NAME/KEY: SITE
<222> LOCATION: (74)..(75)
<223> OTHER INFORMATION: absent or positive
<221> NAME/KEY: SITE
<222> LOCATION: (78)
<223> OTHER INFORMATION: absent or positive
<221> NAME/KEY: SITE
<222> LOCATION: (81)
<223> OTHER INFORMATION: absent or positive
<221> NAME/KEY: SITE
<222> LOCATION: (86)..(87)
<223> OTHER INFORMATION: absent or positive
<221> NAME/KEY: SITE
<222> LOCATION: (89)..(90)
<223> OTHER INFORMATION: absent or positive
<221> NAME/KEY: SITE
<222> LOCATION: (92)..(93)
<223> OTHER INFORMATION: absent or positive

<400> SEQUENCE: 161

Glu Gly Xaa Ser Xaa Xaa Val Lys Xaa Xaa Xaa Gly Xaa Xaa Xaa Xaa
 1               5                  10                  15

Pro Xaa Asn Pro Xaa Xaa Xaa Xaa Xaa Asp Leu Gly Xaa Leu Asp
             20                  25                  30

Thr Xaa Xaa Xaa Leu Xaa Xaa Xaa Xaa Xaa Xaa Xaa Val Xaa Xaa
         35                  40                  45

Xaa Xaa Leu Pro Xaa Xaa Xaa Xaa Xaa Phe Lys Xaa Xaa Xaa Xaa Xaa
     50                  55                  60

Gly Xaa Xaa Xaa Xaa Xaa Asp Xaa Glu Xaa Xaa Asn Ala Xaa Lys Pro
 65                  70                  75                  80

Xaa Leu Ile Ile Ile Xaa Xaa Arg Xaa Xaa Lys Xaa Xaa Asp Lys Leu
                 85                  90                  95

<210> SEQ ID NO 162
<211> LENGTH: 96
<212> TYPE: PRT
<213> ORGANISM: Artificial Sequence
<220> FEATURE:
<223> OTHER INFORMATION: Description of Artificial Sequence: Lipo

<400> SEQUENCE: 162

Glu Gly Asp Ser Phe Leu Val Lys Asp Ser Leu Gly Glu Asn Lys Thr
```

-continued

```
                 1               5                  10                 15
Pro Lys Asn Pro Ser Lys Val Val Ile Leu Asp Leu Gly Ile Leu Asp
                 20                  25                 30

Thr Phe Asp Ala Leu Lys Leu Asn Asp Lys Val Ala Gly Val Pro Ala
         35                  40                 45

Lys Asn Leu Pro Lys Tyr Leu Gln Gln Phe Lys Asn Lys Pro Ser Val
     50                  55                 60

Gly Gly Val Gln Gln Val Asp Phe Glu Ala Ile Asn Ala Leu Lys Pro
65                  70                  75                  80

Asp Leu Ile Ile Ile Ser Gly Arg Gln Ser Lys Phe Tyr Asp Lys Leu
                 85                  90                  95
```

<210> SEQ ID NO 163
<211> LENGTH: 91
<212> TYPE: PRT
<213> ORGANISM: Artificial Sequence
<220> FEATURE:
<223> OTHER INFORMATION: Description of Artificial Sequence: ORF44

<400> SEQUENCE: 163

```
Thr Val Ser Tyr Val Cys Gln Gln Gly Lys Lys Val Lys Val Thr Tyr
1               5                  10                 15

Gly Phe Asn Lys Gln Gly Leu Thr Thr Tyr Ala Ser Ala Val Ile Asn
                 20                  25                 30

Gly Lys Arg Val Gln Met Pro Val Asn Leu Asp Lys Ser Asp Asn Val
         35                  40                 45

Glu Thr Phe Tyr Gly Lys Glu Gly Tyr Val Leu Gly Thr Gly Val
     50                  55                 60

Met Asp Gly Lys Ser Tyr Arg Lys Gln Pro Ile Met Ile Thr Ala Pro
65                  70                  75                  80

Asp Asn Gln Ile Val Phe Lys Asp Cys Ser Pro
                 85                  90
```

<210> SEQ ID NO 164
<211> LENGTH: 91
<212> TYPE: PRT
<213> ORGANISM: Artificial Sequence
<220> FEATURE:
<223> OTHER INFORMATION: Description of Artificial Sequence: overlap
      identity
<221> NAME/KEY: SITE
<222> LOCATION: (1)
<223> OTHER INFORMATION: absent or positive
<221> NAME/KEY: SITE
<222> LOCATION: (3)
<223> OTHER INFORMATION: absent or positive
<221> NAME/KEY: SITE
<222> LOCATION: (10)..(13)
<223> OTHER INFORMATION: absent or positive
<221> NAME/KEY: SITE
<222> LOCATION: (15)
<223> OTHER INFORMATION: absent or positive
<221> NAME/KEY: SITE
<222> LOCATION: (17)
<223> OTHER INFORMATION: absent or positive
<221> NAME/KEY: SITE
<222> LOCATION: (20)..(21)
<223> OTHER INFORMATION: absent or positive
<221> NAME/KEY: SITE
<222> LOCATION: (23)..(24)
<223> OTHER INFORMATION: absent or positive
<221> NAME/KEY: SITE
<222> LOCATION: (26)
<223> OTHER INFORMATION: absent or positive
<221> NAME/KEY: SITE
<222> LOCATION: (28)..(31)

```
<223> OTHER INFORMATION: absent or positive
<221> NAME/KEY: SITE
<222> LOCATION: (33)..(38)
<223> OTHER INFORMATION: absent or positive
<221> NAME/KEY: SITE
<222> LOCATION: (40)
<223> OTHER INFORMATION: absent or positive
<221> NAME/KEY: SITE
<222> LOCATION: (43)..(44)
<223> OTHER INFORMATION: absent or positive
<221> NAME/KEY: SITE
<222> LOCATION: (49)
<223> OTHER INFORMATION: absent or positive
<221> NAME/KEY: SITE
<222> LOCATION: (51)..(56)
<223> OTHER INFORMATION: absent or positive
<221> NAME/KEY: SITE
<222> LOCATION: (59)
<223> OTHER INFORMATION: absent or positive
<221> NAME/KEY: SITE
<222> LOCATION: (61)
<223> OTHER INFORMATION: absent or positive
<221> NAME/KEY: SITE
<222> LOCATION: (63)..(64)
<223> OTHER INFORMATION: absent or positive
<221> NAME/KEY: SITE
<222> LOCATION: (67)..(69)
<223> OTHER INFORMATION: absent or positive
<221> NAME/KEY: SITE
<222> LOCATION: (72)
<223> OTHER INFORMATION: absent or positive
<221> NAME/KEY: SITE
<222> LOCATION: (74)
<223> OTHER INFORMATION: absent or positive
<221> NAME/KEY: SITE
<222> LOCATION: (76)..(78)
<223> OTHER INFORMATION: absent or positive
<221> NAME/KEY: SITE
<222> LOCATION: (81)..(82)
<223> OTHER INFORMATION: absent or positive
<221> NAME/KEY: SITE
<222> LOCATION: (84)..(86)
<223> OTHER INFORMATION: absent or positive

<400> SEQUENCE: 164

Xaa Val Xaa Tyr Val Cys Gln Gln Gly Xaa Xaa Xaa Xaa Val Xaa Tyr
 1               5                   10                  15

Xaa Phe Asn Xaa Xaa Gly Xaa Xaa Thr Xaa Ala Xaa Xaa Xaa Xaa Asn
            20                  25                  30

Xaa Xaa Xaa Xaa Xaa Xaa Pro Xaa Asn Leu Xaa Xaa Ser Asp Asn Val
        35                  40                  45

Xaa Thr Xaa Xaa Xaa Xaa Xaa Xaa Gly Tyr Xaa Leu Xaa Thr Xaa Xaa
    50                  55                  60

Met Asp Xaa Xaa Xaa Tyr Arg Xaa Gln Xaa Ile Xaa Xaa Xaa Ala Pro
65                  70                  75                  80

Xaa Xaa Gln Xaa Xaa Xaa Lys Asp Cys Ser Pro
                85                  90

<210> SEQ ID NO 165
<211> LENGTH: 90
<212> TYPE: PRT
<213> ORGANISM: Artificial Sequence
<220> FEATURE:
<223> OTHER INFORMATION: Description of Artificial Sequence: LecA

<400> SEQUENCE: 165

Ser Val Ala Tyr Val Cys Gln Gln Gly Arg Arg Leu Asn Val Asn Tyr
 1               5                   10                  15

Arg Phe Asn Ser Ala Gly Val Pro Thr Ser Ala Glu Leu Arg Val Asn
            20                  25                  30
```

Asn Arg Asn Leu Arg Leu Pro Tyr Asn Leu Ser Ala Ser Asp Asn Val
            35                  40                  45

Asp Thr Val Phe Ser Ala Asn Gly Tyr Arg Leu Thr Thr Asn Ala Met
         50                  55                  60

Asp Ser Ala Asn Tyr Arg Ser Gln Asp Ile Ile Val Ser Ala Pro Asn
 65                  70                  75                  80

Gly Gln Met Leu Tyr Lys Asp Cys Ser Pro
                 85                  90

<210> SEQ ID NO 166
<211> LENGTH: 240
<212> TYPE: PRT
<213> ORGANISM: Artificial Sequence
<220> FEATURE:
<223> OTHER INFORMATION: Description of Artificial Sequence: ORF49a
<221> NAME/KEY: SITE
<222> LOCATION: (18)
<223> OTHER INFORMATION: place-holder
<221> NAME/KEY: SITE
<222> LOCATION: (48)
<223> OTHER INFORMATION: place-holder
<221> NAME/KEY: SITE
<222> LOCATION: (195)
<223> OTHER INFORMATION: place-holder

<400> SEQUENCE: 166

Ser Lys Asn Glu Leu Asn Glu Thr Lys Leu Pro Val Arg Val Val Ala
 1               5                  10                  15

Gln Xaa Ala Ala Thr Arg Ser Gly Trp Asp Thr Val Leu Glu Gly Thr
                 20                  25                  30

Glu Phe Lys Thr Thr Leu Ala Gly Ala Asp Ile Gln Ala Gly Val Xaa
             35                  40                  45

Glu Lys Ala Arg Val Asp Ala Lys Ile Ile Leu Lys Gly Ile Val Asn
 50                  55                  60

Arg Ile Gln Ser Glu Glu Lys Leu Glu Thr Asn Ser Thr Val Trp Gln
 65                  70                  75                  80

Lys Gln Ala Gly Arg Gly Ser Thr Ile Glu Thr Leu Lys Leu Pro Ser
                 85                  90                  95

Phe Glu Ser Pro Thr Pro Lys Leu Ser Ala Pro Gly Gly Tyr Ile
             100                 105                 110

Val Asp Ile Pro Lys Gly Asn Leu Lys Thr Glu Ile Glu Lys Leu Ser
         115                 120                 125

Lys Gln Pro Glu Tyr Ala Tyr Leu Lys Gln Leu Gln Val Ala Lys Asn
 130                 135                 140

Ile Asn Trp Asn Gln Val Gln Leu Ala Tyr Asp Arg Trp Asp Tyr Lys
145                 150                 155                 160

Gln Glu Gly Leu Thr Glu Ala Gly Ala Ile Ile Ala Leu Ala Val
                 165                 170                 175

Thr Val Val Thr Ser Gly Ala Gly Thr Gly Ala Val Leu Gly Leu Asn
             180                 185                 190

Gly Ala Xaa Ala Ala Thr Asp Ala Ala Phe Ala Ser Leu Ala Ser
         195                 200                 205

Gln Ala Ser Val Ser Phe Ile Asn Asn Lys Gly Asp Val Gly Lys Thr
     210                 215                 220

Leu Lys Glu Leu Gly Arg Ser Ser Thr Val Lys Asn Leu Val Val Ala
225                 230                 235                 240

<210> SEQ ID NO 167

```
<211> LENGTH: 540
<212> TYPE: PRT
<213> ORGANISM: Artificial Sequence
<220> FEATURE:
<223> OTHER INFORMATION: Description of Artificial Sequence: ORF49a
<221> NAME/KEY: SITE
<222> LOCATION: (1)
<223> OTHER INFORMATION: place-holder
<221> NAME/KEY: SITE
<222> LOCATION: (29)
<223> OTHER INFORMATION: place-holder
<221> NAME/KEY: SITE
<222> LOCATION: (50)
<223> OTHER INFORMATION: place-holder
<221> NAME/KEY: SITE
<222> LOCATION: (80)
<223> OTHER INFORMATION: place-holder
<221> NAME/KEY: SITE
<222> LOCATION: (227)
<223> OTHER INFORMATION: place-holder
<221> NAME/KEY: SITE
<222> LOCATION: (288)
<223> OTHER INFORMATION: place-holder
<221> NAME/KEY: SITE
<222> LOCATION: (324)
<223> OTHER INFORMATION: place-holder
<221> NAME/KEY: SITE
<222> LOCATION: (446)
<223> OTHER INFORMATION: place-holder
<221> NAME/KEY: SITE
<222> LOCATION: (463)
<223> OTHER INFORMATION: place-holder

<400> SEQUENCE: 167

Xaa Gln Leu Leu Ala Glu Glu Gly Ile His Lys His Glu Leu Asp Val
  1               5                  10                  15

Gln Lys Ser Arg Arg Phe Ile Gly Ile Lys Val Gly Xaa Ser Asn Tyr
             20                  25                  30

Ser Lys Asn Glu Leu Asn Glu Thr Lys Leu Pro Val Arg Val Val Ala
         35                  40                  45

Gln Xaa Ala Ala Thr Arg Ser Gly Trp Asp Thr Val Leu Glu Gly Thr
     50                  55                  60

Glu Phe Lys Thr Thr Leu Ala Gly Ala Asp Ile Gln Ala Gly Val Xaa
 65                  70                  75                  80

Glu Lys Ala Arg Val Asp Ala Lys Ile Ile Leu Lys Gly Ile Val Asn
                 85                  90                  95

Arg Ile Gln Ser Glu Glu Lys Leu Glu Thr Asn Ser Thr Val Trp Gln
            100                 105                 110

Lys Gln Ala Gly Arg Gly Ser Thr Ile Glu Thr Leu Lys Leu Pro Ser
        115                 120                 125

Phe Glu Ser Pro Thr Pro Pro Lys Leu Ser Ala Pro Gly Gly Tyr Ile
    130                 135                 140

Val Asp Ile Pro Lys Gly Asn Leu Lys Thr Glu Ile Glu Lys Leu Ser
145                 150                 155                 160

Lys Gln Pro Glu Tyr Ala Tyr Leu Lys Gln Leu Gln Val Ala Lys Asn
                165                 170                 175

Ile Asn Trp Asn Gln Val Gln Leu Ala Tyr Asp Arg Trp Asp Tyr Lys
            180                 185                 190

Gln Glu Gly Leu Thr Glu Ala Gly Ala Ile Ile Ala Leu Ala Val
        195                 200                 205

Thr Val Val Thr Ser Gly Ala Gly Thr Gly Ala Val Leu Gly Leu Asn
    210                 215                 220

Gly Ala Xaa Ala Ala Ala Thr Asp Ala Ala Phe Ala Ser Leu Ala Ser
225                 230                 235                 240
```

-continued

```
Gln Ala Ser Val Ser Phe Ile Asn Asn Lys Gly Asp Val Gly Lys Thr
                245                 250                 255

Leu Lys Glu Leu Gly Arg Ser Ser Thr Val Lys Asn Leu Val Val Ala
            260                 265                 270

Ala Ala Thr Ala Gly Val Ala Asp Lys Ile Gly Ala Ser Ala Leu Xaa
        275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305                 310                 315                 320

Leu Lys Asp Xaa Leu Glu Ala Asn Ile Leu Ala Ala Leu Val Asn Thr
                325                 330                 335

Ala His Gly Glu Ala Ala Ser Lys Ile Lys Gln Leu Asp Gln His Tyr
            340                 345                 350

Ile Val His Lys Ile Ala His Ala Ile Ala Gly Cys Ala Ala Ala Ala
        355                 360                 365

Ala Asn Lys Gly Lys Cys Gln Asp Gly Ala Ile Gly Ala Ala Val Gly
    370                 375                 380

Glu Ile Val Gly Glu Ala Leu Thr Asn Gly Lys Asn Pro Asp Thr Leu
385                 390                 395                 400

Thr Ala Lys Glu Arg Glu Gln Ile Leu Ala Tyr Ser Lys Leu Val Ala
                405                 410                 415

Gly Thr Val Ser Gly Val Val Gly Gly Asp Val Asn Ala Ala Ala Asn
            420                 425                 430

Ala Ala Glu Val Ala Val Lys Asn Asn Gln Leu Ser Asp Xaa Glu Gly
        435                 440                 445

Arg Glu Phe Asp Asn Glu Met Thr Ala Cys Ala Lys Gln Asn Xaa Pro
    450                 455                 460

Gln Leu Cys Arg Lys Asn Thr Val Lys Lys Tyr Gln Asn Val Ala Asp
465                 470                 475                 480

Lys Arg Leu Ala Ala Ser Ile Ala Ile Cys Thr Asp Ile Ser Arg Ser
                485                 490                 495

Thr Glu Cys Arg Thr Ile Arg Lys Gln His Leu Ile Asp Ser Arg Ser
            500                 505                 510

Leu His Ser Ser Trp Glu Ala Gly Leu Ile Gly Lys Asp Asp Glu Trp
        515                 520                 525

Tyr Lys Leu Phe Ser Lys Ser Tyr Thr Gln Ala Asp
    530                 535                 540

<210> SEQ ID NO 168
<211> LENGTH: 540
<212> TYPE: PRT
<213> ORGANISM: Artificial Sequence
<220> FEATURE:
<223> OTHER INFORMATION: Description of Artificial Sequence: ORF49-1

<400> SEQUENCE: 168

Met Gln Leu Leu Ala Ala Glu Gly Ile His Gln His Gln Leu Asn Val
  1               5                  10                  15

Gln Lys Ser Thr Arg Phe Ile Gly Ile Lys Val Gly Lys Ser Asn Tyr
             20                  25                  30

Ser Lys Asn Glu Leu Asn Glu Thr Lys Leu Pro Val Arg Val Ile Ala
         35                  40                  45

Gln Thr Ala Lys Thr Arg Ser Gly Trp Asp Thr Val Leu Glu Gly Thr
     50                  55                  60
```

-continued

```
Glu Phe Lys Thr Thr Leu Ser Gly Ala Asp Ile Gln Ala Gly Val Gly
 65                  70                  75                  80

Glu Lys Ala Arg Ala Asp Ala Lys Ile Ile Leu Lys Gly Ile Val Asn
                 85                  90                  95

Arg Ile Gln Thr Glu Glu Lys Leu Glu Ser Asn Ser Thr Val Trp Gln
                100                 105                 110

Lys Gln Ala Gly Ser Gly Ser Thr Val Glu Thr Leu Lys Leu Pro Ser
                115                 120                 125

Phe Glu Gly Pro Ala Leu Pro Lys Leu Thr Ala Pro Gly Gly Tyr Ile
130                 135                 140

Ala Asp Ile Pro Lys Gly Asn Leu Lys Thr Glu Ile Glu Lys Leu Ala
145                 150                 155                 160

Lys Gln Pro Glu Tyr Ala Tyr Leu Lys Gln Leu Gln Thr Val Lys Asp
                165                 170                 175

Val Asn Trp Asn Gln Val Gln Leu Ala Tyr Asp Lys Trp Asp Tyr Lys
                180                 185                 190

Gln Glu Gly Leu Thr Gly Ala Gly Ala Ile Ile Ala Leu Ala Val
                195                 200                 205

Thr Val Val Thr Ser Gly Ala Gly Thr Gly Ala Val Leu Gly Leu Asn
210                 215                 220

Gly Ala Ala Ala Ala Thr Asp Ala Ala Phe Ala Ser Leu Ala Ser
225                 230                 235                 240

Gln Ala Ser Val Ser Phe Ile Asn Asn Lys Gly Asn Ile Gly Asn Thr
                245                 250                 255

Leu Lys Glu Leu Gly Arg Ser Ser Thr Val Lys Asn Leu Met Val Ala
                260                 265                 270

Val Ala Thr Ala Gly Val Ala Asp Lys Ile Gly Ala Ser Ala Leu Asn
                275                 280                 285

Asn Val Ser Asp Lys Gln Trp Ile Asn Asn Leu Thr Val Asn Leu Ala
                290                 295                 300

Asn Ala Gly Ser Ala Ala Leu Ile Asn Thr Ala Val Asn Gly Gly Ser
305                 310                 315                 320

Leu Lys Asp Asn Leu Glu Ala Asn Ile Leu Ala Ala Leu Val Asn Thr
                325                 330                 335

Ala His Gly Glu Ala Ala Ser Lys Ile Lys Gln Leu Asp Gln His Tyr
                340                 345                 350

Ile Ala His Lys Ile Ala His Ala Ile Ala Gly Cys Ala Ala Ala Ala
                355                 360                 365

Ala Asn Lys Gly Lys Cys Gln Asp Gly Ala Ile Gly Ala Ala Val Gly
370                 375                 380

Glu Ile Leu Gly Glu Thr Leu Leu Asp Gly Arg Asp Pro Gly Ser Leu
385                 390                 395                 400

Asn Val Lys Asp Arg Ala Lys Ile Ile Ala Lys Ala Lys Leu Ala Ala
                405                 410                 415

Gly Ala Val Ala Ala Leu Ser Lys Gly Asp Val Ser Thr Ala Ala Asn
                420                 425                 430

Ala Ala Ala Val Ala Val Glu Asn Asn Ser Leu Asn Asp Ile Gln Asp
                435                 440                 445

Arg Leu Leu Ser Gly Asn Tyr Ala Leu Cys Met Ser Ala Gly Gly Ala
                450                 455                 460

Glu Ser Phe Cys Glu Ser Tyr Arg Pro Leu Gly Leu Pro His Phe Val
465                 470                 475                 480
```

```
Ser Val Ser Gly Glu Met Lys Leu Pro Asn Lys Phe Gly Asn Arg Met
                485                 490                 495

Val Asn Gly Lys Leu Ile Ile Asn Thr Arg Asn Gly Asn Val Tyr Phe
            500                 505                 510

Ser Val Gly Lys Ile Trp Ser Thr Val Lys Ser Thr Lys Ser Asn Ile
            515                 520                 525

Ser Gly Val Ser Val Gly Trp Val Leu Asn Val Ser
        530                 535                 540

<210> SEQ ID NO 169
<211> LENGTH: 210
<212> TYPE: PRT
<213> ORGANISM: Artificial Sequence
<220> FEATURE:
<223> OTHER INFORMATION: Description of Artificial Sequence: ORF39
<221> NAME/KEY: SITE
<222> LOCATION: (166)..(193)
<223> OTHER INFORMATION: place-holder

<400> SEQUENCE: 169

Lys Phe Asp Phe Thr Trp Phe Ile Pro Ala Val Ile Lys Tyr Arg Arg
  1               5                  10                  15

Leu Phe Phe Glu Val Leu Val Val Ser Val Val Leu Gln Leu Phe Ala
                20                  25                  30

Leu Ile Thr Pro Leu Phe Phe Gln Val Val Met Asp Lys Val Leu Val
            35                  40                  45

His Arg Gly Phe Ser Thr Leu Asp Val Val Ser Val Ala Leu Leu Val
 50                  55                  60

Val Ser Leu Phe Glu Ile Val Leu Gly Gly Leu Arg Thr Tyr Leu Phe
 65                  70                  75                  80

Ala His Thr Thr Ser Arg Ile Asp Val Glu Leu Gly Ala Arg Leu Phe
                85                  90                  95

Arg His Leu Leu Ser Leu Pro Leu Ser Tyr Phe Glu His Arg Arg Val
               100                 105                 110

Gly Asp Thr Val Ala Arg Val Arg Glu Leu Glu Gln Ile Arg Asn Phe
           115                 120                 125

Leu Thr Gly Gln Ala Leu Thr Ser Val Leu Asp Leu Ala Phe Ser Phe
130                 135                 140

Ile Phe Leu Ala Val Met Trp Tyr Tyr Ser Ser Thr Leu Thr Trp Val
145                 150                 155                 160

Val Leu Ala Ser Leu Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Ile Cys Ala Asn Arg Thr Val Leu Ile Ile Ala His Arg Leu Ser
        195                 200                 205

Thr Val
    210

<210> SEQ ID NO 170
<211> LENGTH: 240
<212> TYPE: PRT
<213> ORGANISM: Artificial Sequence
<220> FEATURE:
<223> OTHER INFORMATION: Description of Artificial Sequence: ORF39a

<400> SEQUENCE: 170

Ala Val Leu Ser Phe Ala Glu Phe Ser Asn Arg Tyr Ser Gly Lys Leu
  1               5                  10                  15
```

-continued

```
Ile Leu Val Ala Ser Arg Ala Ser Val Leu Gly Ser Leu Ala Lys Phe
             20                  25                  30

Asp Phe Thr Trp Phe Ile Pro Ala Val Ile Lys Tyr Arg Arg Leu Phe
         35                  40                  45

Phe Glu Val Leu Val Val Ser Val Leu Gln Leu Phe Ala Leu Ile
     50                  55                  60

Thr Pro Leu Phe Phe Gln Val Val Met Asp Lys Val Leu Val His Arg
 65                  70                  75                  80

Gly Phe Ser Thr Leu Asp Val Val Ser Val Ala Leu Leu Val Val Ser
                 85                  90                  95

Leu Phe Glu Ile Val Leu Gly Gly Leu Arg Thr Tyr Leu Phe Ala His
             100                 105                 110

Thr Thr Ser Arg Ile Asp Val Glu Leu Gly Ala Arg Leu Phe Arg His
             115                 120                 125

Leu Leu Ser Leu Pro Leu Ser Tyr Phe Glu His Arg Arg Val Gly Asp
         130                 135                 140

Thr Val Ala Arg Val Arg Glu Leu Glu Gln Ile Arg Asn Phe Leu Thr
145                 150                 155                 160

Gly Gln Ala Leu Thr Ser Val Leu Asp Leu Ala Phe Ser Phe Ile Phe
                 165                 170                 175

Leu Ala Val Met Trp Tyr Tyr Ser Ser Thr Leu Thr Trp Val Val Leu
             180                 185                 190

Ala Ser Leu Pro Ala Tyr Ala Phe Trp Ser Ala Phe Ile Ser Pro Ile
         195                 200                 205

Leu Arg Thr Arg Leu Asn Asp Lys Phe Ala Arg Asn Ala Asp Asn Gln
     210                 215                 220

Ser Phe Leu Val Glu Ser Ile Thr Ala Val Gly Thr Val Lys Ala Met
225                 230                 235                 240

<210> SEQ ID NO 171
<211> LENGTH: 690
<212> TYPE: PRT
<213> ORGANISM: Artificial Sequence
<220> FEATURE:
<223> OTHER INFORMATION: Description of Artificial Sequence: ORF39a
<221> NAME/KEY: SITE
<222> LOCATION: (29)..(40)
<223> OTHER INFORMATION: place-holder
<221> NAME/KEY: SITE
<222> LOCATION: (137)..(153)
<223> OTHER INFORMATION: place-holder
<221> NAME/KEY: SITE
<222> LOCATION: (173)..(187)
<223> OTHER INFORMATION: place-holder

<400> SEQUENCE: 171

Tyr His Gly Ile Ala Ala Asn Pro Ala Asp Ile Gln His Glu Phe Cys
 1               5                  10                  15

Thr Ser Ala Gln Ser Asp Leu Asn Glu Thr Gln Trp Xaa Xaa Xaa Xaa
             20                  25                  30

Xaa Xaa Xaa Xaa Xaa Xaa Xaa Val Val Arg Gln Pro Ile Lys Arg
         35                  40                  45

Leu Ala Met Ala Thr Leu Pro Ala Leu Val Trp Cys Asp Asp Gly Asn
     50                  55                  60

His Phe Ile Leu Ala Lys Thr Asp Gly Gly Glu His Ala Gln Tyr
 65                  70                  75                  80

Leu Ile Gln Asp Leu Thr Thr Asn Lys Ser Ala Val Leu Ser Phe Ala
                 85                  90                  95
```

-continued

```
Glu Phe Ser Asn Arg Tyr Ser Gly Lys Leu Ile Leu Val Ala Ser Arg
                100                 105                 110

Ala Ser Val Leu Gly Ser Leu Ala Lys Phe Asp Phe Thr Trp Phe Ile
            115                 120                 125

Pro Ala Val Ile Lys Tyr Arg Arg Xaa Xaa Xaa Xaa Xaa Xaa Xaa Xaa
130                 135                 140

Xaa Xaa Xaa Xaa Xaa Xaa Xaa Xaa Ile Thr Pro Leu Phe Phe Gln
145                 150                 155                 160

Val Val Met Asp Lys Val Leu Val His Arg Gly Phe Xaa Xaa Xaa Xaa
            165                 170                 175

Xaa Xaa Xaa Xaa Xaa Xaa Xaa Xaa Xaa Xaa Phe Glu Ile Val Leu
            180                 185                 190

Gly Gly Leu Arg Thr Tyr Leu Phe Ala His Thr Thr Ser Arg Ile Asp
            195                 200                 205

Val Glu Leu Gly Ala Arg Leu Phe Arg His Leu Leu Ser Leu Pro Leu
            210                 215                 220

Ser Tyr Phe Glu His Arg Arg Val Gly Asp Thr Val Ala Arg Val Arg
225                 230                 235                 240

Glu Leu Glu Gln Ile Arg Asn Phe Leu Thr Gly Gln Ala Leu Thr Ser
                245                 250                 255

Val Leu Asp Leu Ala Phe Ser Phe Ile Phe Leu Ala Val Met Trp Tyr
            260                 265                 270

Tyr Ser Ser Thr Leu Thr Trp Val Val Leu Ala Ser Leu Pro Ala Tyr
            275                 280                 285

Ala Phe Trp Ser Ala Phe Ile Ser Pro Ile Leu Arg Thr Arg Leu Asn
            290                 295                 300

Asp Lys Phe Ala Arg Asn Ala Asp Asn Gln Ser Phe Leu Val Glu Ser
305                 310                 315                 320

Ile Thr Ala Val Gly Thr Val Lys Ala Met Ala Val Glu Pro Gln Met
                325                 330                 335

Thr Gln Arg Trp Asp Asn Gln Leu Ala Ala Tyr Val Ala Ser Gly Phe
            340                 345                 350

Arg Val Thr Lys Leu Ala Val Val Gly Gln Gln Gly Val Gln Leu Ile
            355                 360                 365

Gln Lys Leu Val Thr Val Ala Thr Leu Trp Ile Gly Ala Arg Leu Val
370                 375                 380

Ile Glu Ser Lys Leu Thr Val Gly Gln Leu Ile Ala Phe Asn Met Leu
385                 390                 395                 400

Ser Gly Gln Val Ala Ala Pro Val Ile Arg Leu Ala Gln Leu Trp Gln
            405                 410                 415

Asp Phe Gln Gln Val Gly Ile Ser Val Ala Arg Leu Gly Asp Ile Leu
            420                 425                 430

Asn Ala Pro Thr Glu Asn Ala Ser His Leu Ala Leu Pro Asp Ile
            435                 440                 445

Arg Gly Glu Ile Thr Phe Glu His Val Asp Phe Arg Tyr Lys Ala Asp
            450                 455                 460

Gly Arg Leu Ile Leu Gln Asp Leu Asn Leu Arg Ile Arg Ala Gly Glu
465                 470                 475                 480

Val Leu Gly Ile Val Gly Arg Ser Gly Ser Gly Lys Ser Thr Leu Thr
            485                 490                 495

Lys Leu Val Gln Arg Leu Tyr Val Pro Ala Gln Gly Arg Val Leu Val
                500                 505                 510
```

```
Asp Gly Asn Asp Leu Ala Leu Ala Ala Pro Ala Trp Leu Arg Arg Gln
            515                 520                 525
Val Gly Val Val Leu Gln Glu Asn Val Leu Leu Asn Arg Ser Ile Arg
        530                 535                 540
Asp Asn Ile Ala Leu Thr Asp Thr Gly Met Pro Leu Glu Arg Ile Ile
545                 550                 555                 560
Glu Ala Ala Lys Leu Ala Gly Ala His Glu Phe Ile Met Glu Leu Pro
                565                 570                 575
Glu Gly Tyr Gly Thr Val Val Gly Glu Gln Gly Ala Gly Leu Ser Gly
            580                 585                 590
Gly Gln Arg Gln Arg Ile Ala Ile Ala Arg Ala Leu Ile Thr Asn Pro
        595                 600                 605
Arg Ile Leu Ile Phe Asp Glu Ala Thr Ser Ala Leu Asp Tyr Glu Ser
    610                 615                 620
Glu Arg Ala Ile Met Gln Asn Met Gln Ala Ile Cys Ala Asn Arg Thr
625                 630                 635                 640
Val Leu Ile Ile Ala His Arg Leu Ser Thr Val Lys Thr Ala His Arg
                645                 650                 655
Ile Ile Ala Met Asp Lys Gly Arg Ile Val Glu Ala Gly Thr Gln Gln
            660                 665                 670
Glu Leu Leu Ala Lys Pro Asn Gly Tyr Tyr Arg Tyr Leu Tyr Asp Leu
        675                 680                 685
Gln Asn
    690

<210> SEQ ID NO 172
<211> LENGTH: 690
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (3)
<223> OTHER INFORMATION: absent or positive
<221> NAME/KEY: SITE
<222> LOCATION: (6)
<223> OTHER INFORMATION: absent or positive
<221> NAME/KEY: SITE
<222> LOCATION: (9)..(12)
<223> OTHER INFORMATION: absent or positive
<221> NAME/KEY: SITE
<222> LOCATION: (14)
<223> OTHER INFORMATION: absent or positive
<221> NAME/KEY: SITE
<222> LOCATION: (16)..(22)
<223> OTHER INFORMATION: absent or positive
<221> NAME/KEY: SITE
<222> LOCATION: (24)..(25)
<223> OTHER INFORMATION: absent or positive
<221> NAME/KEY: SITE
<222> LOCATION: (27)
<223> OTHER INFORMATION: absent or positive
<221> NAME/KEY: SITE
<222> LOCATION: (29)..(41)
<223> OTHER INFORMATION: absent or positive
<221> NAME/KEY: SITE
<222> LOCATION: (43)..(45)
<223> OTHER INFORMATION: absent or positive
<221> NAME/KEY: SITE
<222> LOCATION: (47)
<223> OTHER INFORMATION: absent or positive
<221> NAME/KEY: SITE
<222> LOCATION: (51)..(53)
<223> OTHER INFORMATION: absent or positive
<221> NAME/KEY: SITE
<222> LOCATION: (60)..(61)
```

-continued

```
<223> OTHER INFORMATION: absent or positive
<221> NAME/KEY: SITE
<222> LOCATION: (64)
<223> OTHER INFORMATION: absent or positive
<221> NAME/KEY: SITE
<222> LOCATION: (69)
<223> OTHER INFORMATION: absent or positive
<221> NAME/KEY: SITE
<222> LOCATION: (71)
<223> OTHER INFORMATION: absent or positive
<221> NAME/KEY: SITE
<222> LOCATION: (73)..(75)
<223> OTHER INFORMATION: absent or positive
<221> NAME/KEY: SITE
<222> LOCATION: (77)..(79)
<223> OTHER INFORMATION: absent or positive
<221> NAME/KEY: SITE
<222> LOCATION: (83)
<223> OTHER INFORMATION: absent or positive
<221> NAME/KEY: SITE
<222> LOCATION: (86)
<223> OTHER INFORMATION: absent or positive
<221> NAME/KEY: SITE
<222> LOCATION: (88)..(92)
<223> OTHER INFORMATION: absent or positive
<221> NAME/KEY: SITE
<222> LOCATION: (94)..(95)
<223> OTHER INFORMATION: absent or positive
<221> NAME/KEY: SITE
<222> LOCATION: (99)..(101)
<223> OTHER INFORMATION: absent or positive
<221> NAME/KEY: SITE
<222> LOCATION: (103)
<223> OTHER INFORMATION: absent or positive
<221> NAME/KEY: SITE
<222> LOCATION: (115)..(116)
<223> OTHER INFORMATION: absent or positive
<221> NAME/KEY: SITE
<222> LOCATION: (118)
<223> OTHER INFORMATION: absent or positive
<221> NAME/KEY: SITE
<222> LOCATION: (136)..(153)
<223> OTHER INFORMATION: absent or positive
<221> NAME/KEY: SITE
<222> LOCATION: (173)..(187)
<223> OTHER INFORMATION: absent or positive
<221> NAME/KEY: SITE
<222> LOCATION: (193)
<223> OTHER INFORMATION: absent or positive
<221> NAME/KEY: SITE
<222> LOCATION: (199)
<223> OTHER INFORMATION: absent or positive
<221> NAME/KEY: SITE
<222> LOCATION: (203)
<223> OTHER INFORMATION: absent or positive
<221> NAME/KEY: SITE
<222> LOCATION: (221)
<223> OTHER INFORMATION: absent or positive
<221> NAME/KEY: SITE
<222> LOCATION: (224)
<223> OTHER INFORMATION: absent or positive
<221> NAME/KEY: SITE
<222> LOCATION: (229)
<223> OTHER INFORMATION: absent or positive
<221> NAME/KEY: SITE
<222> LOCATION: (243)
<223> OTHER INFORMATION: absent or positive
<221> NAME/KEY: SITE
<222> LOCATION: (261)
<223> OTHER INFORMATION: absent or positive
<221> NAME/KEY: SITE
<222> LOCATION: (267)
<223> OTHER INFORMATION: absent or positive
<221> NAME/KEY: SITE
<222> LOCATION: (275)..(276)
<223> OTHER INFORMATION: absent or positive
<221> NAME/KEY: SITE
<222> LOCATION: (279)
<223> OTHER INFORMATION: absent or positive
```

-continued

```
<221> NAME/KEY: SITE
<222> LOCATION: (281)
<223> OTHER INFORMATION: absent or positive
<221> NAME/KEY: SITE
<222> LOCATION: (283)
<223> OTHER INFORMATION: absent or positive
<221> NAME/KEY: SITE
<222> LOCATION: (287)
<223> OTHER INFORMATION: absent or positive
<221> NAME/KEY: SITE
<222> LOCATION: (289)..(290)
<223> OTHER INFORMATION: absent or positive
<221> NAME/KEY: SITE
<222> LOCATION: (293)
<223> OTHER INFORMATION: absent or positive
<221> NAME/KEY: SITE
<222> LOCATION: (301)
<223> OTHER INFORMATION: absent or positive
<221> NAME/KEY: SITE
<222> LOCATION: (304)..(305)
<223> OTHER INFORMATION: absent or positive
<221> NAME/KEY: SITE
<222> LOCATION: (310)
<223> OTHER INFORMATION: absent or positive
<221> NAME/KEY: SITE
<222> LOCATION: (321)
<223> OTHER INFORMATION: absent or positive
<221> NAME/KEY: SITE
<222> LOCATION: (324)..(325)
<223> OTHER INFORMATION: absent or positive
<221> NAME/KEY: SITE
<222> LOCATION: (327)
<223> OTHER INFORMATION: absent or positive
<221> NAME/KEY: SITE
<222> LOCATION: (330)
<223> OTHER INFORMATION: absent or positive
<221> NAME/KEY: SITE
<222> LOCATION: (333)
<223> OTHER INFORMATION: absent or positive
<221> NAME/KEY: SITE
<222> LOCATION: (338)..(339)
<223> OTHER INFORMATION: absent or positive
<221> NAME/KEY: SITE
<222> LOCATION: (342)
<223> OTHER INFORMATION: absent or positive
<221> NAME/KEY: SITE
<222> LOCATION: (346)
<223> OTHER INFORMATION: absent or positive
<221> NAME/KEY: SITE
<222> LOCATION: (349)..(350)
<223> OTHER INFORMATION: absent or positive
<221> NAME/KEY: SITE
<222> LOCATION: (356)
<223> OTHER INFORMATION: absent or positive
<221> NAME/KEY: SITE
<222> LOCATION: (359)..(360)
<223> OTHER INFORMATION: absent or positive
<221> NAME/KEY: SITE
<222> LOCATION: (367)
<223> OTHER INFORMATION: absent or positive
<221> NAME/KEY: SITE
<222> LOCATION: (371)
<223> OTHER INFORMATION: absent or positive
<221> NAME/KEY: SITE
<222> LOCATION: (373)
<223> OTHER INFORMATION: absent or positive
<221> NAME/KEY: SITE
<222> LOCATION: (375)
<223> OTHER INFORMATION: absent or positive
<221> NAME/KEY: SITE
<222> LOCATION: (379)
<223> OTHER INFORMATION: absent or positive
<221> NAME/KEY: SITE
<222> LOCATION: (382)
<223> OTHER INFORMATION: absent or positive
<221> NAME/KEY: SITE
<222> LOCATION: (386)..(388)
<223> OTHER INFORMATION: absent or positive
<221> NAME/KEY: SITE
```

-continued

```
<222> LOCATION: (390)..(391)
<223> OTHER INFORMATION: absent or positive
<221> NAME/KEY: SITE
<222> LOCATION: (405)
<223> OTHER INFORMATION: absent or positive
<221> NAME/KEY: SITE
<222> LOCATION: (426)
<223> OTHER INFORMATION: absent or positive
<221> NAME/KEY: SITE
<222> LOCATION: (431)
<223> OTHER INFORMATION: absent or positive
<221> NAME/KEY: SITE
<222> LOCATION: (434)
<223> OTHER INFORMATION: absent or positive
<221> NAME/KEY: SITE
<222> LOCATION: (438)..(442)
<223> OTHER INFORMATION: absent or positive
<221> NAME/KEY: SITE
<222> LOCATION: (447)
<223> OTHER INFORMATION: absent or positive
<221> NAME/KEY: SITE
<222> LOCATION: (449)
<223> OTHER INFORMATION: absent or positive
<221> NAME/KEY: SITE
<222> LOCATION: (451)
<223> OTHER INFORMATION: absent or positive
<221> NAME/KEY: SITE
<222> LOCATION: (455)..(458)
<223> OTHER INFORMATION: absent or positive
<221> NAME/KEY: SITE
<222> LOCATION: (463)
<223> OTHER INFORMATION: absent or positive
<221> NAME/KEY: SITE
<222> LOCATION: (465)..(467)
<223> OTHER INFORMATION: absent or positive
<221> NAME/KEY: SITE
<222> LOCATION: (470)
<223> OTHER INFORMATION: absent or positive
<221> NAME/KEY: SITE
<222> LOCATION: (472)
<223> OTHER INFORMATION: absent or positive
<221> NAME/KEY: SITE
<222> LOCATION: (475)
<223> OTHER INFORMATION: absent or positive
<221> NAME/KEY: SITE
<222> LOCATION: (477)..(478)
<223> OTHER INFORMATION: absent or positive
<221> NAME/KEY: SITE
<222> LOCATION: (482)
<223> OTHER INFORMATION: absent or positive
<221> NAME/KEY: SITE
<222> LOCATION: (499)
<223> OTHER INFORMATION: absent or positive
<221> NAME/KEY: SITE
<222> LOCATION: (502)
<223> OTHER INFORMATION: absent or positive
<221> NAME/KEY: SITE
<222> LOCATION: (504)
<223> OTHER INFORMATION: absent or positive
<221> NAME/KEY: SITE
<222> LOCATION: (506)..(507)
<223> OTHER INFORMATION: absent or positive
<221> NAME/KEY: SITE
<222> LOCATION: (509)
<223> OTHER INFORMATION: absent or positive
<221> NAME/KEY: SITE
<222> LOCATION: (512)
<223> OTHER INFORMATION: absent or positive
<221> NAME/KEY: SITE
<222> LOCATION: (515)
<223> OTHER INFORMATION: absent or positive
<221> NAME/KEY: SITE
<222> LOCATION: (521)
<223> OTHER INFORMATION: absent or positive
<221> NAME/KEY: SITE
<222> LOCATION: (523)
<223> OTHER INFORMATION: absent or positive
<221> NAME/KEY: SITE
<222> LOCATION: (535)
```

-continued

```
<223> OTHER INFORMATION: absent or positive
<221> NAME/KEY: SITE
<222> LOCATION: (550)
<223> OTHER INFORMATION: absent or positive
<221> NAME/KEY: SITE
<222> LOCATION: (552)
<223> OTHER INFORMATION: absent or positive
<221> NAME/KEY: SITE
<222> LOCATION: (556)
<223> OTHER INFORMATION: absent or positive
<221> NAME/KEY: SITE
<222> LOCATION: (558)
<223> OTHER INFORMATION: absent or positive
<221> NAME/KEY: SITE
<222> LOCATION: (560)..(561)
<223> OTHER INFORMATION: absent or positive
<221> NAME/KEY: SITE
<222> LOCATION: (573)
<223> OTHER INFORMATION: absent or positive
<221> NAME/KEY: SITE
<222> LOCATION: (576)
<223> OTHER INFORMATION: absent or positive
<221> NAME/KEY: SITE
<222> LOCATION: (580)
<223> OTHER INFORMATION: absent or positive
<221> NAME/KEY: SITE
<222> LOCATION: (582)
<223> OTHER INFORMATION: absent or positive
<221> NAME/KEY: SITE
<222> LOCATION: (605)..(606)
<223> OTHER INFORMATION: absent or positive
<221> NAME/KEY: SITE
<222> LOCATION: (609)
<223> OTHER INFORMATION: absent or positive
<221> NAME/KEY: SITE
<222> LOCATION: (626)..(6272)
<223> OTHER INFORMATION: absent or positive
<221> NAME/KEY: SITE
<222> LOCATION: (630)
<223> OTHER INFORMATION: absent or positive
<221> NAME/KEY: SITE
<222> LOCATION: (633)..(634)
<223> OTHER INFORMATION: absent or positive
<221> NAME/KEY: SITE
<222> LOCATION: (637)..(638)
<223> OTHER INFORMATION: absent or positive
<221> NAME/KEY: SITE
<222> LOCATION: (642)
<223> OTHER INFORMATION: absent or positive
<221> NAME/KEY: SITE
<222> LOCATION: (653)
<223> OTHER INFORMATION: absent or positive
<221> NAME/KEY: SITE
<222> LOCATION: (655)
<223> OTHER INFORMATION: absent or positive
<221> NAME/KEY: SITE
<222> LOCATION: (659)
<223> OTHER INFORMATION: absent or positive
<221> NAME/KEY: SITE
<222> LOCATION: (661)
<223> OTHER INFORMATION: absent or positive
<221> NAME/KEY: SITE
<222> LOCATION: (664)
<223> OTHER INFORMATION: absent or positive
<221> NAME/KEY: SITE
<222> LOCATION: (668)
<223> OTHER INFORMATION: absent or positive
<221> NAME/KEY: SITE
<222> LOCATION: (670)..(672)
<223> OTHER INFORMATION: absent or positive
<221> NAME/KEY: SITE
<222> LOCATION: (677)
<223> OTHER INFORMATION: absent or positive
<221> NAME/KEY: SITE
<222> LOCATION: (681)
<223> OTHER INFORMATION: absent or positive
<221> NAME/KEY: SITE
<222> LOCATION: (683)
<223> OTHER INFORMATION: absent or positive
```

-continued

```
<221> NAME/KEY: SITE
<222> LOCATION: (686)..(687)
<223> OTHER INFORMATION: absent or positive
<221> NAME/KEY: SITE
<222> LOCATION: (690)
<223> OTHER INFORMATION: absent or positive

<400> SEQUENCE: 172

Tyr His Xaa Ile Ala Xaa Asn Pro Xaa Xaa Xaa His Xaa Phe Xaa
 1               5                  10                  15

Xaa Xaa Xaa Xaa Xaa Xaa Leu Xaa Xaa Thr Xaa Trp Xaa Xaa Xaa Xaa
             20                  25                  30

Xaa Xaa Xaa Xaa Xaa Xaa Xaa Xaa Val Xaa Xaa Xaa Ile Xaa Arg
         35                  40                  45

Leu Ala Xaa Xaa Xaa Leu Pro Ala Leu Val Trp Xaa Asp Gly Xaa
     50                  55                  60

His Phe Ile Leu Xaa Lys Xaa Asp Xaa Xaa Glu Xaa Xaa Xaa Tyr
 65                  70                  75                  80

Leu Ile Xaa Asp Leu Xaa Thr Xaa Xaa Xaa Xaa Leu Xaa Xaa Ala
                 85                  90                  95

Glu Phe Xaa Xaa Xaa Tyr Xaa Gly Lys Leu Ile Leu Val Ala Ser Arg
             100                 105                 110

Ala Ser Xaa Xaa Gly Xaa Leu Ala Lys Phe Asp Phe Thr Trp Phe Ile
         115                 120                 125

Pro Ala Val Ile Lys Tyr Arg Xaa Xaa Xaa Xaa Xaa Xaa Xaa Xaa
     130                 135                 140

Xaa Xaa Xaa Xaa Xaa Xaa Xaa Xaa Ile Thr Pro Leu Phe Phe Gln
145                 150                 155                 160

Val Val Met Asp Lys Val Leu Val His Arg Gly Phe Xaa Xaa Xaa Xaa
                 165                 170                 175

Xaa Xaa Xaa Xaa Xaa Xaa Xaa Xaa Xaa Xaa Phe Glu Ile Val Leu
             180                 185                 190

Xaa Gly Leu Arg Thr Tyr Xaa Phe Ala His Xaa Thr Ser Arg Ile Asp
         195                 200                 205

Val Glu Leu Gly Ala Arg Leu Phe Arg His Leu Leu Xaa Leu Pro Xaa
     210                 215                 220

Ser Tyr Phe Glu Xaa Arg Arg Val Gly Asp Thr Val Ala Arg Val Arg
225                 230                 235                 240

Glu Leu Xaa Gln Ile Arg Asn Phe Leu Thr Gly Gln Ala Leu Thr Ser
                 245                 250                 255

Val Leu Asp Leu Xaa Phe Ser Phe Ile Phe Xaa Ala Val Met Trp Tyr
                 260                 265                 270

Tyr Ser Xaa Xaa Leu Thr Xaa Val Xaa Leu Xaa Ser Leu Pro Xaa Tyr
             275                 280                 285

Xaa Xaa Trp Ser Xaa Phe Ile Ser Pro Ile Leu Arg Xaa Arg Leu Xaa
     290                 295                 300

Xaa Lys Phe Ala Arg Xaa Ala Asp Asn Gln Ser Phe Leu Val Glu Ser
305                 310                 315                 320

Xaa Thr Ala Xaa Xaa Thr Xaa Lys Ala Xaa Ala Val Xaa Pro Gln Met
                 325                 330                 335

Thr Xaa Xaa Trp Asp Xaa Gln Leu Ala Tyr Val Xaa Xaa Gly Phe
             340                 345                 350

Arg Val Thr Xaa Leu Ala Xaa Xaa Gly Gln Gln Gly Val Gln Xaa Ile
     355                 360                 365

Gln Lys Xaa Val Xaa Val Xaa Thr Leu Trp Xaa Gly Ala Xaa Leu Val
```

-continued

```
    370                 375                 380

Ile Xaa Xaa Xaa Leu Xaa Xaa Gly Gln Leu Ile Ala Phe Asn Met Leu
385                 390                 395                 400

Ser Gly Gln Val Xaa Ala Pro Val Ile Arg Leu Ala Gln Leu Trp Gln
                405                 410                 415

Asp Phe Gln Gln Val Gly Ile Ser Val Xaa Arg Leu Gly Asp Xaa Leu
            420                 425                 430

Asn Xaa Pro Thr Glu Xaa Xaa Xaa Xaa Xaa Leu Ala Leu Pro Xaa Ile
        435                 440                 445

Xaa Gly Xaa Ile Thr Phe Xaa Xaa Xaa Xaa Phe Arg Tyr Lys Xaa Asp
    450                 455                 460

Xaa Xaa Xaa Ile Leu Xaa Asp Xaa Asn Leu Xaa Ile Xaa Xaa Gly Glu
465                 470                 475                 480

Val Xaa Gly Ile Val Gly Arg Ser Gly Ser Gly Lys Ser Thr Leu Thr
                485                 490                 495

Lys Leu Xaa Gln Arg Xaa Tyr Xaa Pro Xaa Xaa Gly Xaa Val Leu Xaa
            500                 505                 510

Asp Gly Xaa Asp Leu Ala Leu Ala Xaa Pro Xaa Trp Leu Arg Arg Gln
        515                 520                 525

Val Gly Val Val Leu Gln Xaa Asn Val Leu Leu Asn Arg Ser Ile Arg
    530                 535                 540

Asp Asn Ile Ala Leu Xaa Asp Xaa Gly Met Pro Xaa Glu Xaa Ile Xaa
545                 550                 555                 560

Xaa Ala Ala Lys Leu Ala Gly Ala His Glu Phe Ile Xaa Glu Leu Xaa
                565                 570                 575

Glu Gly Tyr Xaa Thr Xaa Val Gly Glu Gln Gly Ala Gly Leu Ser Gly
            580                 585                 590

Gly Gln Arg Gln Arg Ile Ala Ile Ala Arg Ala Leu Xaa Xaa Asn Pro
        595                 600                 605

Xaa Ile Leu Ile Phe Asp Glu Ala Thr Ser Ala Leu Asp Tyr Glu Ser
    610                 615                 620

Glu Xaa Xaa Ile Met Xaa Asn Met Xaa Xaa Ile Cys Xaa Xaa Arg Thr
625                 630                 635                 640

Val Xaa Ile Ile Ala His Arg Leu Ser Thr Val Lys Xaa Ala Xaa Arg
                645                 650                 655

Ile Ile Xaa Met Xaa Lys Gly Xaa Ile Val Glu Xaa Gly Xaa Xaa Xaa
            660                 665                 670

Glu Leu Leu Ala Xaa Pro Asn Gly Xaa Tyr Xaa Tyr Leu Xaa Xaa Leu
        675                 680                 685

Gln Xaa
    690

<210> SEQ ID NO 173
<211> LENGTH: 687
<212> TYPE: PRT
<213> ORGANISM: Artificial Sequence
<220> FEATURE:
<223> OTHER INFORMATION: Description of Artificial Sequence: cytolysin
      from A. pleuropneumoniae

<400> SEQUENCE: 173

Tyr His Asn Ile Ala Val Asn Pro Glu Glu Leu Lys His Lys Phe Asp
  1               5                  10                  15

Leu Glu Gly Lys Gly Leu Asp Leu Thr Ala Trp Leu Leu Ala Ala Lys
             20                  25                  30
```

-continued

```
Ser Leu Glu Leu Lys Ala Lys Gln Val Lys Ala Ile Asp Arg Leu
         35                  40                  45

Ala Phe Ile Ala Leu Pro Ala Leu Val Trp Arg Glu Asp Gly Lys His
     50                  55                  60

Phe Ile Leu Thr Lys Ile Asp Asn Glu Ala Lys Lys Tyr Leu Ile Phe
 65                  70                  75                  80

Asp Leu Glu Thr His Asn Pro Arg Ile Leu Glu Gln Ala Glu Phe Glu
                 85                  90                  95

Ser Leu Tyr Gln Gly Lys Leu Ile Leu Val Ala Ser Arg Ala Ser Ile
             100                 105                 110

Val Gly Lys Leu Ala Lys Phe Asp Phe Thr Trp Phe Ile Pro Ala Val
         115                 120                 125

Ile Lys Tyr Arg Lys Ile Phe Ile Glu Thr Leu Ile Val Ser Ile Phe
         130                 135                 140

Leu Gln Ile Phe Ala Leu Ile Thr Pro Leu Phe Phe Gln Val Val Met
145                 150                 155                 160

Asp Lys Val Leu His Arg Gly Phe Ser Thr Leu Asn Val Ile Thr
                 165                 170                 175

Val Ala Leu Ala Ile Val Val Leu Phe Glu Ile Val Leu Asn Gly Leu
             180                 185                 190

Arg Thr Tyr Ile Phe Ala His Ser Thr Ser Arg Ile Asp Val Glu Leu
         195                 200                 205

Gly Ala Arg Leu Phe Arg His Leu Leu Ala Leu Pro Ile Ser Tyr Phe
     210                 215                 220

Glu Asn Arg Arg Val Gly Asp Thr Val Ala Arg Val Arg Glu Leu Asp
225                 230                 235                 240

Gln Ile Arg Asn Phe Leu Thr Gly Gln Ala Leu Thr Ser Val Leu Asp
                 245                 250                 255

Leu Met Phe Ser Phe Ile Phe Phe Ala Val Met Trp Tyr Tyr Ser Pro
             260                 265                 270

Lys Leu Thr Leu Val Ile Leu Gly Ser Leu Pro Phe Tyr Met Gly Trp
         275                 280                 285

Ser Ile Phe Ile Ser Pro Ile Leu Arg Arg Arg Leu Asp Glu Lys Phe
     290                 295                 300

Ala Arg Gly Ala Asp Asn Gln Ser Phe Leu Val Glu Ser Val Thr Ala
305                 310                 315                 320

Ile Asn Thr Ile Lys Ala Leu Ala Val Thr Pro Gln Met Thr Asn Thr
                 325                 330                 335

Trp Asp Lys Gln Leu Ala Ser Tyr Val Ser Ala Gly Phe Arg Val Thr
             340                 345                 350

Thr Leu Ala Thr Ile Gly Gln Gln Gly Val Gln Phe Ile Gln Lys Val
         355                 360                 365

Val Met Val Ile Thr Leu Trp Leu Gly Ala His Leu Val Ile Ser Gly
     370                 375                 380

Asp Leu Ser Ile Gly Gln Leu Ile Ala Phe Asn Met Leu Ser Gly Gln
385                 390                 395                 400

Val Ile Ala Pro Val Ile Arg Leu Ala Gln Leu Trp Gln Asp Phe Gln
                 405                 410                 415

Gln Val Gly Ile Ser Val Thr Arg Leu Gly Asp Val Leu Asn Ser Pro
             420                 425                 430

Thr Glu Ser Tyr Gln Gly Lys Leu Ala Leu Pro Glu Ile Lys Gly Asp
         435                 440                 445

Ile Thr Phe Arg Asn Ile Arg Phe Arg Tyr Lys Pro Asp Ala Pro Val
```

```
                450                 455                 460
Ile Leu Asn Asp Val Asn Leu Ser Ile Gln Gln Gly Glu Val Ile Gly
465                 470                 475                 480

Ile Val Gly Arg Ser Gly Ser Gly Lys Ser Thr Leu Thr Lys Leu Ile
                485                 490                 495

Gln Arg Phe Tyr Ile Pro Glu Asn Gly Gln Val Leu Ile Asp Gly His
                500                 505                 510

Asp Leu Ala Leu Ala Asp Pro Asn Trp Leu Arg Arg Gln Val Gly Val
                515                 520                 525

Val Leu Gln Asp Asn Val Leu Leu Asn Arg Ser Ile Arg Asp Asn Ile
            530                 535                 540

Ala Leu Ala Asp Pro Gly Met Pro Met Glu Lys Ile Val His Ala Ala
545                 550                 555                 560

Lys Leu Ala Gly Ala His Glu Phe Ile Ser Glu Leu Arg Glu Gly Tyr
                565                 570                 575

Asn Thr Ile Val Gly Glu Gln Gly Ala Gly Leu Ser Gly Gly Gln Arg
                580                 585                 590

Gln Arg Ile Ala Ile Ala Arg Ala Leu Val Asn Asn Pro Lys Ile Leu
            595                 600                 605

Ile Phe Asp Glu Ala Thr Ser Ala Leu Asp Tyr Glu Ser Glu His Ile
610                 615                 620

Ile Met Arg Asn Met His Gln Ile Cys Lys Gly Arg Thr Val Ile Ile
625                 630                 635                 640

Ile Ala His Arg Leu Ser Thr Val Lys Asn Ala Asp Arg Ile Ile Val
                645                 650                 655

Met Glu Lys Gly Gln Ile Val Glu Gln Gly Lys His Lys Glu Leu Leu
                660                 665                 670

Ala Asp Pro Asn Gly Leu Tyr His Tyr Leu His Gln Leu Gln Ser
            675                 680                 685

<210> SEQ ID NO 174
<211> LENGTH: 222
<212> TYPE: PRT
<213> ORGANISM: Artificial Sequence
<220> FEATURE:
<223> OTHER INFORMATION: Description of Artificial Sequence: ORF39
<221> NAME/KEY: SITE
<222> LOCATION: (17)..(33)
<223> OTHER INFORMATION: place-holder
<221> NAME/KEY: SITE
<222> LOCATION: (53)..(67)
<223> OTHER INFORMATION: place-holder
<221> NAME/KEY: SITE
<222> LOCATION: (211)
<223> OTHER INFORMATION: place-holder

<400> SEQUENCE: 174

Lys Phe Asp Phe Thr Trp Phe Ile Pro Ala Val Ile Lys Tyr Arg Arg
  1               5                  10                  15

Xaa Xaa Xaa Xaa Xaa Xaa Xaa Xaa Xaa Xaa Xaa Xaa Xaa Xaa Xaa
                20                  25                  30

Xaa Ile Thr Pro Leu Phe Phe Gln Val Val Met Asp Lys Val Leu Val
        35                  40                  45

His Arg Gly Phe Xaa Xaa Xaa Xaa Xaa Xaa Xaa Xaa Xaa Xaa Xaa
        50                  55                  60

Xaa Xaa Xaa Phe Glu Ile Val Leu Gly Gly Leu Arg Thr Tyr Leu Phe
65                  70                  75                  80

Ala His Thr Thr Ser Arg Ile Asp Val Glu Leu Gly Ala Arg Leu Phe
```

```
                    85                  90                  95
Arg His Leu Leu Ser Leu Pro Leu Ser Tyr Phe Glu His Arg Arg Val
            100                 105                 110

Gly Asp Thr Val Ala Arg Val Arg Glu Leu Glu Gln Ile Arg Asn Phe
        115                 120                 125

Leu Thr Gly Gln Ala Leu Thr Ser Val Leu Asp Leu Ala Phe Ser Phe
    130                 135                 140

Ile Phe Leu Ala Val Met Trp Tyr Tyr Ser Ser Thr Leu Thr Trp Val
145                 150                 155                 160

Val Leu Ala Ser Leu Ile Cys Ile Cys Ala Asn Arg Thr Val Leu Ile
                165                 170                 175

Ile Ala His Arg Leu Ser Thr Val Lys Thr Ala His Arg Ile Ile Ala
            180                 185                 190

Met Asp Lys Gly Arg Ile Val Glu Ala Gly Thr Gln Gln Glu Leu Leu
        195                 200                 205

Ala Asn Xaa Asn Gly Tyr Tyr Arg Tyr Leu Tyr Asp Leu Gln
    210                 215                 220

<210> SEQ ID NO 175
<211> LENGTH: 222
<212> TYPE: PRT
<213> ORGANISM: Artificial Sequence
<220> FEATURE:
<223> OTHER INFORMATION: Description of Artificial Sequence: overlap
      identity
<221> NAME/KEY: SITE
<222> LOCATION: (16)..(33)
<223> OTHER INFORMATION: absent or positive
<221> NAME/KEY: SITE
<222> LOCATION: (53)..(67)
<223> OTHER INFORMATION: absent or positive
<221> NAME/KEY: SITE
<222> LOCATION: (71)
<223> OTHER INFORMATION: absent or positive
<221> NAME/KEY: SITE
<222> LOCATION: (79)
<223> OTHER INFORMATION: absent or positive
<221> NAME/KEY: SITE
<222> LOCATION: (83)
<223> OTHER INFORMATION: absent or positive
<221> NAME/KEY: SITE
<222> LOCATION: (101)
<223> OTHER INFORMATION: absent or positive
<221> NAME/KEY: SITE
<222> LOCATION: (104)
<223> OTHER INFORMATION: absent or positive
<221> NAME/KEY: SITE
<222> LOCATION: (109)
<223> OTHER INFORMATION: absent or positive
<221> NAME/KEY: SITE
<222> LOCATION: (123)
<223> OTHER INFORMATION: absent or positive
<221> NAME/KEY: SITE
<222> LOCATION: (137)
<223> OTHER INFORMATION: absent or positive
<221> NAME/KEY: SITE
<222> LOCATION: (141)
<223> OTHER INFORMATION: absent or positive
<221> NAME/KEY: SITE
<222> LOCATION: (147)
<223> OTHER INFORMATION: absent or positive
<221> NAME/KEY: SITE
<222> LOCATION: (155)..(156)
<223> OTHER INFORMATION: absent or positive
<221> NAME/KEY: SITE
<222> LOCATION: (159)
<223> OTHER INFORMATION: absent or positive
<221> NAME/KEY: SITE
<222> LOCATION: (163)
<223> OTHER INFORMATION: absent or positive
```

```
<221> NAME/KEY: SITE
<222> LOCATION: (166)
<223> OTHER INFORMATION: absent or positive
<221> NAME/KEY: SITE
<222> LOCATION: (170)
<223> OTHER INFORMATION: absent or positive
<221> NAME/KEY: SITE
<222> LOCATION: (186)
<223> OTHER INFORMATION: absent or positive
<221> NAME/KEY: SITE
<222> LOCATION: (188)
<223> OTHER INFORMATION: absent or positive
<221> NAME/KEY: SITE
<222> LOCATION: (192)
<223> OTHER INFORMATION: absent or positive
<221> NAME/KEY: SITE
<222> LOCATION: (197)
<223> OTHER INFORMATION: absent or positive
<221> NAME/KEY: SITE
<222> LOCATION: (199)
<223> OTHER INFORMATION: absent or positive
<221> NAME/KEY: SITE
<222> LOCATION: (201)
<223> OTHER INFORMATION: absent or positive
<221> NAME/KEY: SITE
<222> LOCATION: (203)..(204)
<223> OTHER INFORMATION: absent or positive
<221> NAME/KEY: SITE
<222> LOCATION: (209)..(212)
<223> OTHER INFORMATION: absent or positive
<221> NAME/KEY: SITE
<222> LOCATION: (214)
<223> OTHER INFORMATION: absent or positive
<221> NAME/KEY: SITE
<222> LOCATION: (216)
<223> OTHER INFORMATION: absent or positive
<221> NAME/KEY: SITE
<222> LOCATION: (219)..(220)
<223> OTHER INFORMATION: absent or positive

<400> SEQUENCE: 175

Lys Phe Asp Phe Thr Trp Phe Ile Pro Ala Val Ile Lys Tyr Arg Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Ile Thr Pro Leu Phe Phe Gln Val Val Met Asp Lys Val Leu Val
         35                  40                  45

His Arg Gly Phe Xaa Xaa Xaa Xaa Xaa Xaa Xaa Xaa Xaa Xaa Xaa Xaa
     50                  55                  60

Xaa Xaa Xaa Phe Glu Ile Xaa Leu Gly Gly Leu Arg Thr Tyr Xaa Phe
 65                  70                  75                  80

Ala His Xaa Thr Ser Arg Ile Asp Val Glu Leu Gly Ala Arg Leu Phe
             85                  90                  95

Arg His Leu Leu Xaa Leu Pro Xaa Ser Tyr Phe Glu Xaa Arg Arg Val
            100                 105                 110

Gly Asp Thr Val Ala Arg Val Arg Glu Leu Xaa Gln Ile Arg Asn Phe
            115                 120                 125

Leu Thr Gly Gln Ala Leu Thr Ser Xaa Leu Asp Leu Xaa Phe Ser Phe
            130                 135                 140

Ile Phe Xaa Ala Val Met Trp Tyr Tyr Ser Xaa Xaa Leu Thr Xaa Val
145                 150                 155                 160

Val Leu Xaa Ser Leu Xaa Cys Ile Cys Xaa Asn Arg Thr Val Leu Ile
            165                 170                 175

Ile Ala His Arg Leu Ser Thr Val Lys Xaa Ala Xaa Arg Ile Ile Xaa
            180                 185                 190

Met Asp Lys Gly Xaa Ile Xaa Glu Xaa Gly Xaa Xaa Gln Glu Leu Leu
```

```
            195                 200                 205
Xaa Xaa Xaa Xaa Gly Xaa Tyr Xaa Tyr Leu Xaa Xaa Leu Gln
        210                 215                 220

<210> SEQ ID NO 176
<211> LENGTH: 222
<212> TYPE: PRT
<213> ORGANISM: Artificial Sequence
<220> FEATURE:
<223> OTHER INFORMATION: Description of Artificial Sequence: HlyB

<400> SEQUENCE: 176

Lys Phe Asp Phe Thr Trp Phe Ile Pro Ala Val Ile Lys Tyr Arg Lys
 1               5                  10                  15

Ile Phe Ile Glu Thr Leu Ile Val Ser Ile Phe Leu Gln Ile Phe Ala
            20                  25                  30

Leu Ile Thr Pro Leu Phe Phe Gln Val Val Met Asp Lys Val Leu Val
        35                  40                  45

His Arg Gly Phe Ser Thr Leu Asn Val Ile Thr Val Ala Leu Ala Ile
    50                  55                  60

Val Val Leu Phe Glu Ile Ile Leu Gly Gly Leu Arg Thr Tyr Val Phe
65                  70                  75                  80

Ala His Ser Thr Ser Arg Ile Asp Val Glu Leu Gly Ala Arg Leu Phe
                85                  90                  95

Arg His Leu Leu Ala Leu Pro Ile Ser Tyr Phe Glu Ala Arg Arg Val
            100                 105                 110

Gly Asp Thr Val Ala Arg Val Arg Glu Leu Asp Gln Ile Arg Asn Phe
        115                 120                 125

Leu Thr Gly Gln Ala Leu Thr Ser Ile Leu Asp Leu Leu Phe Ser Phe
    130                 135                 140

Ile Phe Phe Ala Val Met Trp Tyr Tyr Ser Pro Lys Leu Thr Leu Val
145                 150                 155                 160

Val Leu Gly Ser Leu Pro Cys Ile Cys Gln Asn Arg Thr Val Leu Ile
                165                 170                 175

Ile Ala His Arg Leu Ser Thr Val Lys Asn Ala Asp Arg Ile Ile Val
            180                 185                 190

Met Asp Lys Gly Glu Ile Ile Glu Gln Gly Lys His Gln Glu Leu Leu
        195                 200                 205

Lys Asp Glu Lys Gly Leu Tyr Ser Tyr Leu His Gln Leu Gln
    210                 215                 220

<210> SEQ ID NO 177
<211> LENGTH: 240
<212> TYPE: PRT
<213> ORGANISM: Artificial Sequence
<220> FEATURE:
<223> OTHER INFORMATION: Description of Artificial Sequence: ORF112a
<221> NAME/KEY: SITE
<222> LOCATION: (50)
<223> OTHER INFORMATION: place-holder
<221> NAME/KEY: SITE
<222> LOCATION: (58)
<223> OTHER INFORMATION: place-holder
<221> NAME/KEY: SITE
<222> LOCATION: (77)
<223> OTHER INFORMATION: place-holder
<221> NAME/KEY: SITE
<222> LOCATION: (87)
<223> OTHER INFORMATION: place-holder
<221> NAME/KEY: SITE
<222> LOCATION: (223)
<223> OTHER INFORMATION: place-holder
```

-continued

```
<400> SEQUENCE: 177

Met Asn Leu Ile Ser Arg Tyr Ile Ile Arg Gln Met Ala Val Met Ala
1               5                   10                  15

Val Tyr Ala Leu Leu Ala Phe Leu Ala Leu Tyr Ser Phe Phe Glu Ile
                20                  25                  30

Leu Tyr Glu Thr Gly Asn Leu Gly Lys Gly Ser Tyr Gly Ile Trp Glu
            35                  40                  45

Met Xaa Gly Tyr Thr Ala Leu Lys Met Xaa Ala Arg Ala Tyr Glu Leu
        50                  55                  60

Met Pro Leu Ala Val Leu Ile Gly Gly Leu Val Ser Xaa Ser Gln Leu
65                  70                  75                  80

Ala Ala Gly Ser Glu Leu Xaa Val Ile Lys Ala Ser Gly Met Ser Thr
                85                  90                  95

Lys Lys Leu Leu Leu Ile Leu Ser Gln Phe Gly Phe Ile Phe Ala Ile
                100                 105                 110

Ala Thr Val Ala Leu Gly Glu Trp Val Ala Pro Thr Leu Ser Gln Lys
            115                 120                 125

Ala Glu Asn Ile Lys Ala Ala Ala Ile Asn Gly Lys Ile Ser Thr Gly
        130                 135                 140

Asn Thr Gly Leu Trp Leu Lys Glu Lys Asn Ser Ile Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

Leu Asn Ser Asp Gly Ser Trp Gln Leu Lys Asn Ile Arg Arg Ser Thr
        195                 200                 205

Leu Gly Glu Asp Lys Val Glu Val Ser Ile Ala Ala Glu Glu Xaa Trp
    210                 215                 220

Pro Ile Ser Val Lys Arg Asn Leu Met Asp Val Leu Leu Val Lys Pro
225                 230                 235                 240

<210> SEQ ID NO 178
<211> LENGTH: 360
<212> TYPE: PRT
<213> ORGANISM: Artificial Sequence
<220> FEATURE:
<223> OTHER INFORMATION: Description of Artificial Sequence: ORF114a
<221> NAME/KEY: SITE
<222> LOCATION: (68)..(73)
<223> OTHER INFORMATION: place-holder
<221> NAME/KEY: SITE
<222> LOCATION: (85)
<223> OTHER INFORMATION: place-holder
<221> NAME/KEY: SITE
<222> LOCATION: (296)
<223> OTHER INFORMATION: place-holder
<221> NAME/KEY: SITE
<222> LOCATION: (343)
<223> OTHER INFORMATION: place-holder
<221> NAME/KEY: SITE
<222> LOCATION: (352)
<223> OTHER INFORMATION: place-holder

<400> SEQUENCE: 178

Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
                20                  25                  30
```

```
Ala Gly Ser Ser Val Ser Val Ser Leu Lys Thr Ser Gly Asp Leu Cys
            35                  40                  45

Gly Lys Leu Lys Thr Thr Leu Lys Thr Leu Val Cys Ser Leu Val Ser
     50                  55                  60

Leu Ser Met Xaa Xaa Xaa Xaa Xaa Gln Ile Thr Thr Asp Lys Ser
 65                  70                  75                  80

Ala Pro Lys Asn Xaa Gln Val Val Ile Leu Lys Thr Asn Thr Gly Ala
                 85                  90                  95

Pro Leu Val Asn Ile Gln Thr Pro Asn Gly Arg Gly Leu Ser His Asn
                100                 105                 110

Arg Tyr Thr Gln Phe Asp Val Asp Asn Lys Gly Ala Val Leu Asn Asn
            115                 120                 125

Asp Arg Asn Asn Pro Phe Leu Val Lys Gly Ser Ala Gln Leu Ile
130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
                180                 185                 190

Ile Gly Ala Pro Gln Ile Gly Lys Asp Gly Ala Leu Thr Gly Phe Asp
    195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
                260                 265                 270

Lys Pro Thr Ile Ala Leu Asp Thr Ala Ala Leu Gly Gly Met Tyr Ala
    275                 280                 285

Asp Ser Ile Thr Leu Ile Ala Xaa Glu Lys Gly Val Gly Val Lys Asn
    290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Xaa Ile Glu Thr Thr Glu Lys Gly Ala Xaa
            340                 345                 350

Gly Thr Phe Ile Ser Asn Gly Gly
            355                 360

<210> SEQ ID NO 179
<211> LENGTH: 1574
<212> TYPE: PRT
<213> ORGANISM: Artificial Sequence
<220> FEATURE:
<223> OTHER INFORMATION: Description of Artificial Sequence: ORF114-1

<400> SEQUENCE: 179

Met Asn Lys Gly Leu His Arg Ile Ile Phe Ser Lys Lys His Ser Thr
 1               5                  10                  15

Met Val Ala Val Ala Glu Thr Ala Asn Ser Gln Gly Lys Gly Lys Gln
                20                  25                  30
```

```
Ala Gly Ser Ser Val Ser Val Ser Leu Lys Thr Ser Gly Asp Leu Cys
            35                  40                  45

Gly Lys Leu Lys Thr Thr Leu Lys Thr Leu Val Cys Ser Leu Val Ser
        50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
                100                 105                 110

Arg Tyr Thr Gln Phe Asp Val Asp Asn Lys Gly Ala Val Leu Asn Asn
            115                 120                 125

Asp Arg Asn Asn Pro Phe Val Val Lys Gly Ser Ala Gln Leu Ile
130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
            180                 185                 190

Thr Gly Ala Pro Gln Ile Gly Lys Asp Gly Ala Leu Thr Gly Phe Asp
            195                 200                 205

Val Arg Gln Gly Thr Leu Thr Val Gly Ala Ala Gly Trp Asn Asp Lys
210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
            275                 280                 285

Asp Ser Ile Thr Leu Ile Ala Asn Glu Lys Gly Val Gly Val Lys Asn
290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Ser Ile Glu Thr Thr Glu Lys Gly Ala Ala
            340                 345                 350

Gly Thr Phe Ile Ser Asn Gly Gly Arg Ile Glu Ser Lys Gly Leu Leu
            355                 360                 365

Val Ile Glu Thr Gly Glu Asp Ile Ser Leu Arg Asn Gly Ala Val Val
        370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Pro
                405                 410                 415

Ala Thr Leu Ser Ala Asp Gly Arg Thr Val Ile Lys Glu Ala Ser Ile
            420                 425                 430

Gln Thr Gly Thr Thr Val Tyr Ser Ser Lys Gly Asn Ala Glu Leu
            435                 440                 445

Gly Asn Asn Thr Arg Ile Thr Gly Ala Asp Val Thr Val Leu Ser Asn
```

-continued

```
            450                 455                 460
Gly Thr Ile Ser Ser Ser Ala Val Ile Asp Ala Lys Asp Thr Ala His
465                 470                 475                 480

Ile Glu Ala Gly Lys Pro Leu Ser Leu Glu Ala Ser Thr Val Thr Ser
                485                 490                 495

Asp Ile Arg Leu Asn Gly Gly Ser Ile Lys Gly Gly Lys Gln Leu Ala
            500                 505                 510

Leu Leu Ala Asp Asp Asn Ile Thr Ala Lys Thr Thr Asn Leu Asn Thr
            515                 520                 525

Pro Gly Asn Leu Tyr Val His Thr Gly Lys Asp Leu Asn Leu Asn Val
            530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Ser Leu Asn Val Thr Asn Thr Asn Leu Arg Thr
                580                 585                 590

Asn Ser Gly Asn Leu His Ile Gln Ala Ala Lys Gly Asn Ile Gln Leu
            595                 600                 605

Arg Asn Thr Lys Leu Asn Ala Ala Lys Ala Leu Glu Thr Thr Ala Leu
            610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
                645                 650                 655

Thr Leu Thr Ala Lys Ala Asp Val Asn Ala Gly Ser Val Gly Lys Gly
                660                 665                 670

Arg Leu Lys Ala Asp Asn Thr Asn Ile Thr Ser Ser Gly Asp Ile
            675                 680                 685

Thr Leu Val Ala Gly Asn Gly Ile Gln Leu Gly Asp Gly Lys Gln Arg
690                 695                 700

Asn Ser Ile Asn Gly Lys His Ile Ser Ile Lys Asn Asn Gly Gly Asn
705                 710                 715                 720

Ala Asp Leu Lys Asn Leu Asn Val His Ala Lys Ser Gly Ala Leu Asn
                725                 730                 735

Ile His Ser Asp Arg Ala Leu Ser Ile Glu Asn Thr Lys Leu Glu Ser
                740                 745                 750

Thr His Asn Thr His Leu Asn Ala Gln His Glu Arg Val Thr Leu Asn
                755                 760                 765

Gln Val Asp Ala Tyr Ala His Arg His Leu Ser Ile Thr Gly Ser Gln
770                 775                 780

Ile Trp Gln Asn Asp Lys Leu Pro Ser Ala Asn Lys Leu Val Ala Asn
785                 790                 795                 800

Gly Val Leu Ala Leu Asn Ala Arg Tyr Ser Gln Ile Ala Asp Asn Thr
                805                 810                 815

Thr Leu Arg Ala Gly Ala Ile Asn Leu Thr Ala Gly Thr Ala Leu Val
                820                 825                 830

Lys Arg Gly Asn Ile Asn Trp Ser Thr Val Ser Thr Lys Thr Leu Glu
            835                 840                 845

Asp Asn Ala Glu Leu Lys Pro Leu Ala Gly Arg Leu Asn Ile Glu Ala
            850                 855                 860

Gly Ser Gly Thr Leu Thr Ile Glu Pro Ala Asn Arg Ile Ser Ala His
865                 870                 875                 880
```

-continued

```
Thr Asp Leu Ser Ile Lys Thr Gly Gly Lys Leu Leu Ser Ala Lys
                885                 890                 895

Gly Gly Asn Ala Gly Ala Pro Ser Ala Gln Val Ser Ser Leu Glu Ala
            900                 905                 910

Lys Gly Asn Ile Arg Leu Val Thr Gly Glu Thr Asp Leu Arg Gly Ser
        915                 920                 925

Lys Ile Thr Ala Gly Lys Asn Leu Val Val Ala Thr Thr Lys Gly Lys
    930                 935                 940

Leu Asn Ile Glu Ala Val Asn Asn Ser Phe Ser Asn Tyr Phe Pro Thr
945                 950                 955                 960

Gln Lys Ala Ala Glu Leu Asn Gln Lys Ser Lys Glu Leu Glu Gln Gln
                965                 970                 975

Ile Ala Gln Leu Lys Lys Ser Ser Pro Lys Ser Lys Leu Ile Pro Thr
            980                 985                 990

Leu Gln Glu Glu Arg Asp Arg Leu Ala Phe Tyr Ile Gln Ala Ile Asn
        995                 1000                1005

Lys Glu Val Lys Gly Lys Lys Pro Lys Gly Lys Glu Tyr Leu Gln Ala
    1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
                1045                1050                1055

Ala Gly Val Leu Pro Lys Ala Ala Asp Ser Glu Ala Ala Ile Leu
            1060                1065                1070

Ile Asp Gly Ile Thr Asp Gln Tyr Glu Ile Gly Lys Pro Thr Tyr Lys
        1075                1080                1085

Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
                1125                1130                1135

Ile Lys Ala His Ser Asp Ile Val Leu Glu Ala Gly Gln Asn Asp Ala
            1140                1145                1150

Tyr Thr Phe Leu Lys Thr Lys Gly Lys Ser Gly Lys Ile Ile Arg Lys
        1155                1160                1165

Thr Lys Phe Thr Ser Thr Arg Asp His Leu Ile Met Pro Ala Pro Val
    1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
                1205                1210                1215

Ala Gly Glu Glu Leu Gln Leu Leu Ala Glu Gly Ile His Lys His
            1220                1225                1230

Glu Leu Asp Val Gln Lys Ser Arg Arg Phe Ile Gly Ile Lys Val Gly
        1235                1240                1245

Lys Ser Asn Tyr Ser Lys Asn Glu Leu Asn Glu Thr Lys Leu Pro Val
    1250                1255                1260

Arg Val Val Ala Gln Thr Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
                1285                1290                1295
```

```
Ala Gly Val Gly Glu Lys Ala Arg Ala Asp Ala Lys Ile Ile Leu Lys
        1300                1305                1310

Gly Ile Val Asn Arg Ile Gln Ser Glu Glu Lys Leu Glu Thr Asn Ser
    1315                1320                1325

Thr Val Trp Gln Lys Gln Ala Gly Arg Gly Ser Thr Ile Glu Thr Leu
   1330                1335                1340

Lys Leu Pro Ser Phe Glu Ser Pro Thr Pro Lys Leu Thr Ala Pro
1345                1350                1355                1360

Gly Gly Tyr Ile Val Asp Ile Pro Lys Gly Asn Leu Lys Thr Glu Ile
        1365                1370                1375

Glu Lys Leu Ala Lys Gln Pro Glu Tyr Ala Tyr Leu Lys Gln Leu Gln
            1380                1385                1390

Val Ala Lys Asn Val Asn Trp Asn Gln Val Gln Leu Ala Tyr Asp Lys
        1395                1400                1405

Trp Asp Tyr Lys Gln Glu Gly Leu Thr Arg Ala Gly Ala Ala Ile Val
    1410                1415                1420

Thr Ile Ile Val Thr Ala Leu Thr Tyr Gly Tyr Gly Ala Thr Ala Ala
1425                1430                1435                1440

Gly Gly Val Ala Ala Ser Gly Ser Ser Thr Ala Ala Ala Ala Gly Thr
            1445                1450                1455

Ala Ala Thr Thr Thr Ala Ala Ala Thr Thr Val Ser Thr Ala Thr Ala
            1460                1465                1470

Met Gln Thr Ala Ala Leu Ala Ser Leu Tyr Ser Gln Ala Ala Val Ser
    1475                1480                1485

Ile Ile Asn Asn Lys Gly Asp Val Gly Lys Ala Leu Lys Asp Leu Gly
        1490                1495                1500

Thr Ser Asp Thr Val Lys Gln Ile Val Thr Ser Ala Leu Thr Ala Gly
1505                1510                1515                1520

Ala Leu Asn Gln Met Gly Ala Asp Ile Ala Gln Leu Asn Ser Lys Val
            1525                1530                1535

Arg Thr Glu Leu Phe Ser Ser Thr Gly Asn Gln Thr Ile Ala Asn Leu
        1540                1545                1550

Gly Gly Arg Leu Ala Thr Asn Leu Ser Asn Ala Gly Ile Ser Ala Gly
    1555                1560                1565

Ile Asn Thr Ala Val Asn
    1570

<210> SEQ ID NO 180
<211> LENGTH: 281
<212> TYPE: PRT
<213> ORGANISM: Artificial Sequence
<220> FEATURE:
<223> OTHER INFORMATION: Description of Artificial Sequence: ORF114
<221> NAME/KEY: SITE
<222> LOCATION: (29)..(51)
<223> OTHER INFORMATION: place-holder
<221> NAME/KEY: SITE
<222> LOCATION: (96)
<223> OTHER INFORMATION: place-holder
<221> NAME/KEY: SITE
<222> LOCATION: (199)
<223> OTHER INFORMATION: place-holder
<221> NAME/KEY: SITE
<222> LOCATION: (210)
<223> OTHER INFORMATION: place-holder
<221> NAME/KEY: SITE
<222> LOCATION: (225)..(226)
<223> OTHER INFORMATION: place-holder
<221> NAME/KEY: SITE
<222> LOCATION: (229)
<223> OTHER INFORMATION: place-holder
```

<400> SEQUENCE: 180

| Ala | Val | Ala | Glu | Thr | Ala | Asn | Ser | Gln | Gly | Lys | Gly | Lys | Gln | Ala | Gly |
|---|---|---|---|---|---|---|---|---|---|---|---|---|---|---|---|
| 1 | | | | 5 | | | | | 10 | | | | | 15 | |

Ser Ser Val Ser Val Ser Leu Lys Thr Ser Gly Asp Xaa Xaa Xaa Xaa
              20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Pro Ala His Ala Gln Ile Thr Thr Asp Lys Ser Ala Pro
     50                  55                  60

Lys Asn Gln Gln Val Val Ile Leu Lys Thr Asn Thr Gly Ala Pro Leu
 65                  70                  75                  80

Val Asn Ile Gln Thr Pro Asn Gly Arg Gly Leu Ser His Asn Arg Xaa
             85                  90                  95

Tyr Ala Phe Asp Val Asp Asn Lys Gly Ala Val Leu Asn Asn Asp Arg
            100                 105                 110

Asn Asn Asn Pro Phe Val Val Lys Gly Ser Ala Gln Leu Ile Leu Asn
            115                 120                 125

Glu Val Arg Gly Thr Ala Ser Lys Leu Asn Gly Ile Val Thr Val Gly
        130                 135                 140

Gly Gln Lys Ala Asp Val Ile Ile Ala Asn Pro Asn Gly Ile Thr Val
145                 150                 155                 160

Asn Gly Gly Phe Lys Asn Val Gly Arg Gly Ile Leu Thr Thr Gly
                165                 170                 175

Ala Pro Gln Ile Gly Lys Asp Gly Ala Leu Thr Gly Phe Asp Val Val
            180                 185                 190

Lys Ala His Trp Thr Val Xaa Ala Ala Gly Trp Asn Asp Lys Gly Gly
        195                 200                 205

Ala Xaa Tyr Thr Gly Val Leu Ala Arg Ala Val Ala Leu Gln Gly Lys
    210                 215                 220

Xaa Xaa Gly Lys Xaa Leu Ala Val Ser Thr Gly Pro Gln Lys Val Asp
225                 230                 235                 240

Tyr Ala Ser Gly Glu Ile Ser Ala Gly Thr Ala Ala Gly Thr Lys Pro
                245                 250                 255

Thr Ile Ala Leu Asp Thr Ala Ala Leu Gly Gly Met Tyr Ala Asp Ser
            260                 265                 270

Ile Thr Leu Ile Ala Asn Glu Lys Gly
        275                 280

<210> SEQ ID NO 181
<211> LENGTH: 302
<212> TYPE: PRT
<213> ORGANISM: Artificial Sequence
<220> FEATURE:
<223> OTHER INFORMATION: Description of Artificial Sequence: overlap
      identity
<221> NAME/KEY: SITE
<222> LOCATION: (5)..(9)
<223> OTHER INFORMATION: absent or positive
<221> NAME/KEY: SITE
<222> LOCATION: (12)..(13)
<223> OTHER INFORMATION: absent or positive
<221> NAME/KEY: SITE
<222> LOCATION: (15)..(19)
<223> OTHER INFORMATION: absent or positive
<221> NAME/KEY: SITE
<222> LOCATION: (22)..(29)
<223> OTHER INFORMATION: absent or positive
<221> NAME/KEY: SITE
<222> LOCATION: (31)..(55)

-continued

```
<223> OTHER INFORMATION: absent or positive
<221> NAME/KEY: SITE
<222> LOCATION: (58)
<223> OTHER INFORMATION: absent or positive
<221> NAME/KEY: SITE
<222> LOCATION: (60)..(61)
<223> OTHER INFORMATION: absent or positive
<221> NAME/KEY: SITE
<222> LOCATION: (63)..(64)
<223> OTHER INFORMATION: absent or positive
<221> NAME/KEY: SITE
<222> LOCATION: (74)
<223> OTHER INFORMATION: absent or positive
<221> NAME/KEY: SITE
<222> LOCATION: (78)
<223> OTHER INFORMATION: absent or positive
<221> NAME/KEY: SITE
<222> LOCATION: (80)..(81)
<223> OTHER INFORMATION: absent or positive
<221> NAME/KEY: SITE
<222> LOCATION: (83)
<223> OTHER INFORMATION: absent or positive
<221> NAME/KEY: SITE
<222> LOCATION: (85)
<223> OTHER INFORMATION: absent or positive
<221> NAME/KEY: SITE
<222> LOCATION: (92)..(94)
<223> OTHER INFORMATION: absent or positive
<221> NAME/KEY: SITE
<222> LOCATION: (96)
<223> OTHER INFORMATION: absent or positive
<221> NAME/KEY: SITE
<222> LOCATION: (98)
<223> OTHER INFORMATION: absent or positive
<221> NAME/KEY: SITE
<222> LOCATION: (101)..(103)
<223> OTHER INFORMATION: absent or positive
<221> NAME/KEY: SITE
<222> LOCATION: (108)
<223> OTHER INFORMATION: absent or positive
<221> NAME/KEY: SITE
<222> LOCATION: (111)..(112)
<223> OTHER INFORMATION: absent or positive
<221> NAME/KEY: SITE
<222> LOCATION: (116)
<223> OTHER INFORMATION: absent or positive
<221> NAME/KEY: SITE
<222> LOCATION: (118)
<223> OTHER INFORMATION: absent or positive
<221> NAME/KEY: SITE
<222> LOCATION: (120)..(130)
<223> OTHER INFORMATION: absent or positive
<221> NAME/KEY: SITE
<222> LOCATION: (133)..(136)
<223> OTHER INFORMATION: absent or positive
<221> NAME/KEY: SITE
<222> LOCATION: (138)
<223> OTHER INFORMATION: absent or positive
<221> NAME/KEY: SITE
<222> LOCATION: (140)..(141)
<223> OTHER INFORMATION: absent or positive
<221> NAME/KEY: SITE
<222> LOCATION: (143)
<223> OTHER INFORMATION: absent or positive
<221> NAME/KEY: SITE
<222> LOCATION: (145)..(151)
<223> OTHER INFORMATION: absent or positive
<221> NAME/KEY: SITE
<222> LOCATION: (153)
<223> OTHER INFORMATION: absent or positive
<221> NAME/KEY: SITE
<222> LOCATION: (157)..(159)
<223> OTHER INFORMATION: absent or positive
<221> NAME/KEY: SITE
<222> LOCATION: (163)..(164)
<223> OTHER INFORMATION: absent or positive
<221> NAME/KEY: SITE
<222> LOCATION: (166)
<223> OTHER INFORMATION: absent or positive
```

-continued

```
<221> NAME/KEY: SITE
<222> LOCATION: (168)..(169)
<223> OTHER INFORMATION: absent or positive
<221> NAME/KEY: SITE
<222> LOCATION: (173)
<223> OTHER INFORMATION: absent or positive
<221> NAME/KEY: SITE
<222> LOCATION: (176)
<223> OTHER INFORMATION: absent or positive
<221> NAME/KEY: SITE
<222> LOCATION: (182)..(183)
<223> OTHER INFORMATION: absent or positive
<221> NAME/KEY: SITE
<222> LOCATION: (185)..(189)
<223> OTHER INFORMATION: absent or positive
<221> NAME/KEY: SITE
<222> LOCATION: (192)
<223> OTHER INFORMATION: absent or positive
<221> NAME/KEY: SITE
<222> LOCATION: (194)
<223> OTHER INFORMATION: absent or positive
<221> NAME/KEY: SITE
<222> LOCATION: (196)..(200)
<223> OTHER INFORMATION: absent or positive
<221> NAME/KEY: SITE
<222> LOCATION: (202)
<223> OTHER INFORMATION: absent or positive
<221> NAME/KEY: SITE
<222> LOCATION: (209)..(218)
<223> OTHER INFORMATION: absent or positive
<221> NAME/KEY: SITE
<222> LOCATION: (220)..(221)
<223> OTHER INFORMATION: absent or positive
<221> NAME/KEY: SITE
<222> LOCATION: (223)..(225)
<223> OTHER INFORMATION: absent or positive
<221> NAME/KEY: SITE
<222> LOCATION: (227)
<223> OTHER INFORMATION: absent or positive
<221> NAME/KEY: SITE
<222> LOCATION: (230)..(231)
<223> OTHER INFORMATION: absent or positive
<221> NAME/KEY: SITE
<222> LOCATION: (233)
<223> OTHER INFORMATION: absent or positive
<221> NAME/KEY: SITE
<222> LOCATION: (236)..(243)
<223> OTHER INFORMATION: absent or positive
<221> NAME/KEY: SITE
<222> LOCATION: (246)..(248)
<223> OTHER INFORMATION: absent or positive
<221> NAME/KEY: SITE
<222> LOCATION: (250)..(251)
<223> OTHER INFORMATION: absent or positive
<221> NAME/KEY: SITE
<222> LOCATION: (253)..(254)
<223> OTHER INFORMATION: absent or positive
<221> NAME/KEY: SITE
<222> LOCATION: (256)
<223> OTHER INFORMATION: absent or positive
<221> NAME/KEY: SITE
<222> LOCATION: (258)..(267)
<223> OTHER INFORMATION: absent or positive
<221> NAME/KEY: SITE
<222> LOCATION: (269)..(276)
<223> OTHER INFORMATION: absent or positive
<221> NAME/KEY: SITE
<222> LOCATION: (279)
<223> OTHER INFORMATION: absent or positive
<221> NAME/KEY: SITE
<222> LOCATION: (281)
<223> OTHER INFORMATION: absent or positive
<221> NAME/KEY: SITE
<222> LOCATION: (285)
<223> OTHER INFORMATION: absent or positive
<221> NAME/KEY: SITE
<222> LOCATION: (293)
<223> OTHER INFORMATION: absent or positive
<221> NAME/KEY: SITE
```

```
<222> LOCATION: (298)..(301)
<223> OTHER INFORMATION: absent or positive

<400> SEQUENCE: 181

Ala Val Ala Glu Xaa Xaa Xaa Xaa Gly Lys Xaa Xaa Gln Xaa Xaa
 1               5                  10                  15

Xaa Xaa Xaa Ser Val Xaa Xaa Xaa Xaa Xaa Xaa Ser Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Pro Ala Xaa Ala Xaa Ile Xaa Xaa
    50                  55                  60

Asp Lys Ser Ala Pro Lys Asn Gln Gln Xaa Val Ile Leu Xaa Thr Xaa
 65                  70                  75                  80

Xaa Gly Xaa Pro Xaa Val Asn Ile Gln Thr Pro Xaa Xaa Xaa Gly Xaa
                85                  90                  95

Ser Xaa Asn Arg Xaa Xaa Xaa Phe Asp Val Asp Xaa Lys Gly Xaa Xaa
            100                 105                 110

Leu Asn Asn Xaa Arg Xaa Asn Xaa Xaa Xaa Xaa Xaa Xaa Xaa Xaa
        115                 120                 125

Xaa Xaa Asn Pro Xaa Xaa Xaa Xaa Gly Xaa Ala Xaa Xaa Ile Xaa Asn
    130                 135                 140

Xaa Xaa Xaa Xaa Xaa Xaa Xaa Ser Xaa Leu Asn Gly Xaa Xaa Xaa Val
145                 150                 155                 160

Gly Gly Xaa Xaa Ala Xaa Val Xaa Xaa Ala Asn Pro Xaa Gly Ile Xaa
                165                 170                 175

Val Asn Gly Gly Gly Xaa Xaa Asn Xaa Xaa Xaa Xaa Xaa Leu Thr Xaa
                180                 185                 190

Gly Xaa Pro Xaa Xaa Xaa Xaa Xaa Gly Xaa Leu Thr Gly Phe Asp Val
        195                 200                 205

Xaa Xaa Xaa Xaa Xaa Xaa Xaa Xaa Xaa Gly Xaa Xaa Asp Xaa Xaa
        210                 215                 220

Xaa Ala Xaa Tyr Thr Xaa Xaa Leu Xaa Arg Ala Xaa Xaa Xaa Xaa Xaa
225                 230                 235                 240

Xaa Xaa Xaa Gly Lys Xaa Xaa Xaa Val Xaa Xaa Gly Xaa Xaa Lys Xaa
                245                 250                 255

Asp Xaa Xaa Xaa Xaa Xaa Xaa Xaa Xaa Xaa Ala Xaa Xaa Xaa Xaa
            260                 265                 270

Xaa Xaa Xaa Xaa Pro Thr Xaa Ala Xaa Asp Thr Ala Xaa Leu Gly Gly
        275                 280                 285

Met Tyr Ala Asp Xaa Ile Thr Leu Ile Xaa Xaa Xaa Xaa Gly
    290                 295                 300

<210> SEQ ID NO 182
<211> LENGTH: 300
<212> TYPE: PRT
<213> ORGANISM: Artificial Sequence
<220> FEATURE:
<223> OTHER INFORMATION: Description of Artificial Sequence: pspA

<400> SEQUENCE: 182

Ala Val Ala Glu Asn Val His Arg Asp Gly Lys Ser Met Gln Asp Ser
 1               5                  10                  15

Glu Ala Ala Ser Val Arg Val Thr Gly Ala Ala Ser Val Ser Ser Ala
            20                  25                  30

Arg Ala Ala Phe Gly Phe Arg Met Ala Ala Phe Ser Val Met Leu Ala
```

```
                35                  40                  45
Leu Gly Val Ala Ala Phe Ser Pro Ala Pro Ala Ser Gly Ile Ile Ala
         50                  55                  60
Asp Lys Ser Ala Pro Lys Asn Gln Gln Ala Val Ile Leu Gln Thr Ala
 65                  70                  75                  80
Asn Gly Leu Pro Gln Val Asn Ile Gln Thr Pro Ser Ser Gln Gly Val
                 85                  90                  95
Ser Val Asn Arg Phe Lys Gln Phe Asp Val Asp Glu Lys Gly Val Ile
            100                 105                 110
Leu Asn Asn Ser Arg Ser Asn Thr Gln Thr Gln Leu Gly Gly Trp Ile
            115                 120                 125
Gln Gly Asn Pro His Leu Ala Arg Gly Glu Ala Arg Val Ile Val Asn
        130                 135                 140
Gln Ile Asp Ser Ser Asn Pro Ser Leu Leu Asn Gly Tyr Ile Glu Val
145                 150                 155                 160
Gly Gly Lys Arg Ala Glu Val Val Ala Asn Pro Ser Gly Ile Arg
                165                 170                 175
Val Asn Gly Gly Gly Leu Ile Asn Ala Ala Ser Val Thr Leu Thr Ser
            180                 185                 190
Gly Val Pro Val Leu Asn Asn Gly Asn Leu Thr Gly Phe Asp Val Ser
        195                 200                 205
Ser Gly Lys Val Val Ile Gly Gly Lys Gly Leu Asp Thr Ser Asp Ala
    210                 215                 220
Asp Tyr Thr Arg Ile Leu Ser Arg Ala Ala Glu Ile Asn Ala Gly Val
225                 230                 235                 240
Trp Gly Lys Asp Val Lys Val Val Ser Gly Lys Asn Lys Leu Asp Phe
                245                 250                 255
Asp Gly Ser Leu Ala Lys Thr Ala Ser Ala Pro Ser Ser Ser Asp Ser
            260                 265                 270
Val Thr Pro Thr Val Ala Ile Asp Thr Ala Thr Leu Gly Gly Met Tyr
        275                 280                 285
Ala Asp Lys Ile Thr Leu Ile Ser Thr Asp Asn Gly
    290                 295                 300

<210> SEQ ID NO 183
<211> LENGTH: 628
<212> TYPE: PRT
<213> ORGANISM: Artificial Sequence
<220> FEATURE:
<223> OTHER INFORMATION: Description of Artificial Sequence: ORF114a
<221> NAME/KEY: SITE
<222> LOCATION: (47)..(73)
<223> OTHER INFORMATION: place-holder
<221> NAME/KEY: SITE
<222> LOCATION: (85)
<223> OTHER INFORMATION: place-holder
<221> NAME/KEY: SITE
<222> LOCATION: (296)
<223> OTHER INFORMATION: place-holder
<221> NAME/KEY: SITE
<222> LOCATION: (343)
<223> OTHER INFORMATION: place-holder
<221> NAME/KEY: SITE
<222> LOCATION: (352)
<223> OTHER INFORMATION: place-holder
<221> NAME/KEY: SITE
<222> LOCATION: (377)
<223> OTHER INFORMATION: place-holder
<221> NAME/KEY: SITE
<222> LOCATION: (417)
<223> OTHER INFORMATION: place-holder
<221> NAME/KEY: SITE
```

```
<222> LOCATION: (447)
<223> OTHER INFORMATION: place-holder
<221> NAME/KEY: SITE
<222> LOCATION: (582)..(593)
<223> OTHER INFORMATION: place-holder

<400> SEQUENCE: 183
```

| | | | | | | | | | | | | | | |
|---|---|---|---|---|---|---|---|---|---|---|---|---|---|---|
| Met | Asn | Lys | Gly | Leu | His | Arg | Ile | Ile | Phe | Ser | Lys | Lys | His | Ser | Thr |
| 1 | | | | 5 | | | | | 10 | | | | | 15 | |
| Met | Val | Ala | Val | Ala | Glu | Thr | Ala | Asn | Ser | Gln | Gly | Lys | Gly | Lys | Gln |
| | | | 20 | | | | | 25 | | | | | 30 | | |
| Ala | Gly | Ser | Ser | Val | Ser | Val | Ser | Leu | Lys | Thr | Ser | Gly | Asp | Xaa | Xaa |
| | | 35 | | | | | 40 | | | | | 45 | | | |
| Xaa | Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | 60 | | | | |
| Xaa | Xaa | Xaa | Xaa | Xaa | Xaa | Xaa | Xaa | Gln | Ile | Thr | Thr | Asp | Lys | Ser |
| 65 | | | | | 70 | | | | | 75 | | | | | 80 |
| Ala | Pro | Lys | Asn | Xaa | Gln | Val | Val | Ile | Leu | Lys | Thr | Asn | Thr | Gly | Ala |
| | | | | 85 | | | | | 90 | | | | | 95 | |
| Pro | Leu | Val | Asn | Ile | Gln | Thr | Pro | Asn | Gly | Arg | Gly | Leu | Ser | His | Asn |
| | | | 100 | | | | | 105 | | | | | 110 | | |
| Arg | Tyr | Thr | Gln | Phe | Asp | Val | Asp | Asn | Lys | Gly | Ala | Val | Leu | Asn | Asn |
| | | 115 | | | | | 120 | | | | | 125 | | | |
| Asp | Arg | Asn | Asn | Asn | Pro | Phe | Leu | Val | Lys | Gly | Ser | Ala | Gln | Leu | Ile |
| 130 | | | | | 135 | | | | | 140 | | | | | |
| Leu | Asn | Glu | Val | Arg | Gly | Thr | Ala | Ser | Lys | Leu | Asn | Gly | Ile | Val | Thr |
| 145 | | | | | 150 | | | | | 155 | | | | | 160 |
| Val | Gly | Gly | Gln | Lys | Ala | Asp | Val | Ile | Ile | Ala | Asn | Pro | Asn | Gly | Ile |
| | | | | 165 | | | | | 170 | | | | | 175 | |
| Thr | Val | Asn | Gly | Gly | Gly | Phe | Lys | Asn | Val | Gly | Arg | Gly | Ile | Leu | Thr |
| | | | 180 | | | | | 185 | | | | | 190 | | |
| Ile | Gly | Ala | Pro | Gln | Ile | Gly | Lys | Asp | Gly | Ala | Leu | Thr | Gly | Phe | Asp |
| | | 195 | | | | | 200 | | | | | 205 | | | |
| Val | Arg | Gln | Gly | Thr | Leu | Thr | Val | Gly | Ala | Ala | Gly | Trp | Asn | Asp | Lys |
| 210 | | | | | 215 | | | | | 220 | | | | | |
| Gly | Gly | Ala | Asp | Tyr | Thr | Gly | Val | Leu | Ala | Arg | Ala | Val | Ala | Leu | Gln |
| 225 | | | | | 230 | | | | | 235 | | | | | 240 |
| Gly | Lys | Leu | Gln | Gly | Lys | Asn | Leu | Ala | Val | Ser | Thr | Gly | Pro | Gln | Lys |
| | | | | 245 | | | | | 250 | | | | | 255 | |
| Val | Asp | Tyr | Ala | Ser | Gly | Glu | Ile | Ser | Ala | Gly | Thr | Ala | Ala | Gly | Thr |
| | | | 260 | | | | | 265 | | | | | 270 | | |
| Lys | Pro | Thr | Ile | Ala | Leu | Asp | Thr | Ala | Ala | Leu | Gly | Gly | Met | Tyr | Ala |
| | | 275 | | | | | 280 | | | | | 285 | | | |
| Asp | Ser | Ile | Thr | Leu | Ile | Ala | Xaa | Glu | Lys | Gly | Val | Gly | Val | Lys | Asn |
| 290 | | | | | 295 | | | | | 300 | | | | | |
| Ala | Gly | Thr | Leu | Glu | Ala | Ala | Lys | Gln | Leu | Ile | Val | Thr | Ser | Ser | Gly |
| 305 | | | | | 310 | | | | | 315 | | | | | 320 |
| Arg | Ile | Glu | Asn | Ser | Gly | Arg | Ile | Ala | Thr | Thr | Ala | Asp | Gly | Thr | Glu |
| | | | | 325 | | | | | 330 | | | | | 335 | |
| Ala | Ser | Pro | Thr | Tyr | Leu | Xaa | Ile | Glu | Thr | Thr | Glu | Lys | Gly | Ala | Xaa |
| | | | 340 | | | | | 345 | | | | | 350 | | |
| Gly | Thr | Phe | Ile | Ser | Asn | Gly | Gly | Arg | Ile | Glu | Ser | Lys | Gly | Leu | Leu |
| | | 355 | | | | | 360 | | | | | 365 | | | |
| Val | Ile | Glu | Thr | Gly | Glu | Asp | Ile | Xaa | Leu | Arg | Asn | Gly | Ala | Val | Val |
| 370 | | | | | 375 | | | | | 380 | | | | | |

```
Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
            405                 410                 415

Xaa Asn Leu Ser Ala Gly Gly Arg Thr Thr Ile Asn Asp Ala Thr Ile
            420                 425                 430

Gln Ala Gly Ser Ser Val Tyr Ser Ser Thr Lys Gly Asp Thr Xaa Leu
            435                 440                 445

Gly Glu Asn Thr Arg Ile Ile Ala Glu Asn Val Thr Val Leu Ser Asn
        450                 455                 460

Gly Ser Ile Gly Ser Ala Ala Val Ile Glu Ala Lys Asp Thr Ala His
465                 470                 475                 480

Ile Glu Ser Gly Lys Pro Leu Ser Leu Glu Thr Ser Thr Val Ala Ser
            485                 490                 495

Asn Ile Arg Leu Asn Asn Gly Asn Ile Lys Gly Lys Gln Leu Ala
            500                 505                 510

Leu Leu Ala Asp Asp Asn Ile Thr Ala Lys Thr Thr Asn Leu Asn Thr
            515                 520                 525

Pro Gly Asn Leu Tyr Val His Thr Gly Lys Asp Leu Asn Leu Asn Val
            530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
            565                 570                 575

Gly Val Glu Ala Gly Xaa Xaa Xaa Xaa Xaa Xaa Xaa Xaa Xaa Xaa
            580                 585                 590

Xaa Ser Gly Asn Leu His Ile Gln Ala Ala Lys Gly Asn Ile Gln Leu
            595                 600                 605

Arg Asn Thr Lys Leu Asn Ala Ala Lys Ala Leu Glu Thr Thr Ala Leu
            610                 615                 620

Gln Gly Asn Ile
625

<210> SEQ ID NO 184
<211> LENGTH: 663
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (4)..(8)
<223> OTHER INFORMATION: absent or positive
<221> NAME/KEY: SITE
<222> LOCATION: (11)
<223> OTHER INFORMATION: absent or positive
<221> NAME/KEY: SITE
<222> LOCATION: (14)
<223> OTHER INFORMATION: absent or positive
<221> NAME/KEY: SITE
<222> LOCATION: (16)
<223> OTHER INFORMATION: absent or positive
<221> NAME/KEY: SITE
<222> LOCATION: (18)
<223> OTHER INFORMATION: absent or positive
<221> NAME/KEY: SITE
<222> LOCATION: (23)..(27)
<223> OTHER INFORMATION: absent or positive
<221> NAME/KEY: SITE
<222> LOCATION: (30)..(31)
<223> OTHER INFORMATION: absent or positive
<221> NAME/KEY: SITE
<222> LOCATION: (33)..(37)
```

-continued

```
<223> OTHER INFORMATION: absent or positive
<221> NAME/KEY: SITE
<222> LOCATION: (40)..(48)
<223> OTHER INFORMATION: absent or positive
<221> NAME/KEY: SITE
<222> LOCATION: (50)..(79)
<223> OTHER INFORMATION: absent or positive
<221> NAME/KEY: SITE
<222> LOCATION: (81)..(82)
<223> OTHER INFORMATION: absent or positive
<221> NAME/KEY: SITE
<222> LOCATION: (90)
<223> OTHER INFORMATION: absent or positive
<221> NAME/KEY: SITE
<222> LOCATION: (92)
<223> OTHER INFORMATION: absent or positive
<221> NAME/KEY: SITE
<222> LOCATION: (96)
<223> OTHER INFORMATION: absent or positive
<221> NAME/KEY: SITE
<222> LOCATION: (98)..(99)
<223> OTHER INFORMATION: absent or positive
<221> NAME/KEY: SITE
<222> LOCATION: (101)
<223> OTHER INFORMATION: absent or positive
<221> NAME/KEY: SITE
<222> LOCATION: (103)
<223> OTHER INFORMATION: absent or positive
<221> NAME/KEY: SITE
<222> LOCATION: (110)..(112)
<223> OTHER INFORMATION: absent or positive
<221> NAME/KEY: SITE
<222> LOCATION: (114)
<223> OTHER INFORMATION: absent or positive
<221> NAME/KEY: SITE
<222> LOCATION: (116)
<223> OTHER INFORMATION: absent or positive
<221> NAME/KEY: SITE
<222> LOCATION: (119)..(120)
<223> OTHER INFORMATION: absent or positive
<221> NAME/KEY: SITE
<222> LOCATION: (126)
<223> OTHER INFORMATION: absent or positive
<221> NAME/KEY: SITE
<222> LOCATION: (129)..(130)
<223> OTHER INFORMATION: absent or positive
<221> NAME/KEY: SITE
<222> LOCATION: (134)
<223> OTHER INFORMATION: absent or positive
<221> NAME/KEY: SITE
<222> LOCATION: (136)
<223> OTHER INFORMATION: absent or positive
<221> NAME/KEY: SITE
<222> LOCATION: (138)..(148)
<223> OTHER INFORMATION: absent or positive
<221> NAME/KEY: SITE
<222> LOCATION: (151)
<223> OTHER INFORMATION: absent or positive
<221> NAME/KEY: SITE
<222> LOCATION: (153)..(154)
<223> OTHER INFORMATION: absent or positive
<221> NAME/KEY: SITE
<222> LOCATION: (156)
<223> OTHER INFORMATION: absent or positive
<221> NAME/KEY: SITE
<222> LOCATION: (158)..(159)
<223> OTHER INFORMATION: absent or positive
<221> NAME/KEY: SITE
<222> LOCATION: (161)
<223> OTHER INFORMATION: absent or positive
<221> NAME/KEY: SITE
<222> LOCATION: (163)..(169)
<223> OTHER INFORMATION: absent or positive
<221> NAME/KEY: SITE
<222> LOCATION: (171)
<223> OTHER INFORMATION: absent or positive
<221> NAME/KEY: SITE
<222> LOCATION: (175)..(177)
<223> OTHER INFORMATION: absent or positive
```

```
<221> NAME/KEY: SITE
<222> LOCATION: (181)..(182)
<223> OTHER INFORMATION: absent or positive
<221> NAME/KEY: SITE
<222> LOCATION: (184)
<223> OTHER INFORMATION: absent or positive
<221> NAME/KEY: SITE
<222> LOCATION: (186)..(187)
<223> OTHER INFORMATION: absent or positive
<221> NAME/KEY: SITE
<222> LOCATION: (191)
<223> OTHER INFORMATION: absent or positive
<221> NAME/KEY: SITE
<222> LOCATION: (194)
<223> OTHER INFORMATION: absent or positive
<221> NAME/KEY: SITE
<222> LOCATION: (200)..(201)
<223> OTHER INFORMATION: absent or positive
<221> NAME/KEY: SITE
<222> LOCATION: (203)..(207)
<223> OTHER INFORMATION: absent or positive
<221> NAME/KEY: SITE
<222> LOCATION: (210)
<223> OTHER INFORMATION: absent or positive
<221> NAME/KEY: SITE
<222> LOCATION: (212)
<223> OTHER INFORMATION: absent or positive
<221> NAME/KEY: SITE
<222> LOCATION: (214)..(218)
<223> OTHER INFORMATION: absent or positive
<221> NAME/KEY: SITE
<222> LOCATION: (220)
<223> OTHER INFORMATION: absent or positive
<221> NAME/KEY: SITE
<222> LOCATION: (227)..(228)
<223> OTHER INFORMATION: absent or positive
<221> NAME/KEY: SITE
<222> LOCATION: (230)..(233)
<223> OTHER INFORMATION: absent or positive
<221> NAME/KEY: SITE
<222> LOCATION: (235)..(236)
<223> OTHER INFORMATION: absent or positive
<221> NAME/KEY: SITE
<222> LOCATION: (238)..(239)
<223> OTHER INFORMATION: absent or positive
<221> NAME/KEY: SITE
<222> LOCATION: (241)..(243)
<223> OTHER INFORMATION: absent or positive
<221> NAME/KEY: SITE
<222> LOCATION: (248)..(249)
<223> OTHER INFORMATION: absent or positive
<221> NAME/KEY: SITE
<222> LOCATION: (251)
<223> OTHER INFORMATION: absent or positive
<221> NAME/KEY: SITE
<222> LOCATION: (254)..(261)
<223> OTHER INFORMATION: absent or positive
<221> NAME/KEY: SITE
<222> LOCATION: (264)..(266)
<223> OTHER INFORMATION: absent or positive
<221> NAME/KEY: SITE
<222> LOCATION: (268)..(269)
<223> OTHER INFORMATION: absent or positive
<221> NAME/KEY: SITE
<222> LOCATION: (271)..(272)
<223> OTHER INFORMATION: absent or positive
<221> NAME/KEY: SITE
<222> LOCATION: (274)
<223> OTHER INFORMATION: absent or positive
<221> NAME/KEY: SITE
<222> LOCATION: (276)..(285)
<223> OTHER INFORMATION: absent or positive
<221> NAME/KEY: SITE
<222> LOCATION: (287)..(294)
<223> OTHER INFORMATION: absent or positive
<221> NAME/KEY: SITE
<222> LOCATION: (297)
<223> OTHER INFORMATION: absent or positive
<221> NAME/KEY: SITE
```

-continued

```
<222> LOCATION: (299)
<223> OTHER INFORMATION: absent or positive
<221> NAME/KEY: SITE
<222> LOCATION: (303)
<223> OTHER INFORMATION: absent or positive
<221> NAME/KEY: SITE
<222> LOCATION: (311)
<223> OTHER INFORMATION: absent or positive
<221> NAME/KEY: SITE
<222> LOCATION: (316)..(319)
<223> OTHER INFORMATION: absent or positive
<221> NAME/KEY: SITE
<222> LOCATION: (321)..(324)
<223> OTHER INFORMATION: absent or positive
<221> NAME/KEY: SITE
<222> LOCATION: (326)
<223> OTHER INFORMATION: absent or positive
<221> NAME/KEY: SITE
<222> LOCATION: (328)..(330)
<223> OTHER INFORMATION: absent or positive
<221> NAME/KEY: SITE
<222> LOCATION: (333)..(341)
<223> OTHER INFORMATION: absent or positive
<221> NAME/KEY: SITE
<222> LOCATION: (343)..(345)
<223> OTHER INFORMATION: absent or positive
<221> NAME/KEY: SITE
<222> LOCATION: (349)
<223> OTHER INFORMATION: absent or positive
<221> NAME/KEY: SITE
<222> LOCATION: (351)..(358)
<223> OTHER INFORMATION: absent or positive
<221> NAME/KEY: SITE
<222> LOCATION: (360)..(367)
<223> OTHER INFORMATION: absent or positive
<221> NAME/KEY: SITE
<222> LOCATION: (369)..(381)
<223> OTHER INFORMATION: absent or positive
<221> NAME/KEY: SITE
<222> LOCATION: (383)
<223> OTHER INFORMATION: absent or positive
<221> NAME/KEY: SITE
<222> LOCATION: (385)
<223> OTHER INFORMATION: absent or positive
<221> NAME/KEY: SITE
<222> LOCATION: (387)..(390)
<223> OTHER INFORMATION: absent or positive
<221> NAME/KEY: SITE
<222> LOCATION: (392)..(397)
<223> OTHER INFORMATION: absent or positive
<221> NAME/KEY: SITE
<222> LOCATION: (399)..(402)
<223> OTHER INFORMATION: absent or positive
<221> NAME/KEY: SITE
<222> LOCATION: (404)..(409)
<223> OTHER INFORMATION: absent or positive
<221> NAME/KEY: SITE
<222> LOCATION: (412)..(420)
<223> OTHER INFORMATION: absent or positive
<221> NAME/KEY: SITE
<222> LOCATION: (422)..(427)
<223> OTHER INFORMATION: absent or positive
<221> NAME/KEY: SITE
<222> LOCATION: (429)..(432)
<223> OTHER INFORMATION: absent or positive
<221> NAME/KEY: SITE
<222> LOCATION: (435)..(436)
<223> OTHER INFORMATION: absent or positive
<221> NAME/KEY: SITE
<222> LOCATION: (438)..(445)
<223> OTHER INFORMATION: absent or positive
<221> NAME/KEY: SITE
<222> LOCATION: (447)..(453)
<223> OTHER INFORMATION: absent or positive
<221> NAME/KEY: SITE
<222> LOCATION: (456)..(459)
<223> OTHER INFORMATION: absent or positive
<221> NAME/KEY: SITE
<222> LOCATION: (461)..(463)
```

```
<223> OTHER INFORMATION: absent or positive
<221> NAME/KEY: SITE
<222> LOCATION: (465)
<223> OTHER INFORMATION: absent or positive
<221> NAME/KEY: SITE
<222> LOCATION: (467)..(470)
<223> OTHER INFORMATION: absent or positive
<221> NAME/KEY: SITE
<222> LOCATION: (472)..(474)
<223> OTHER INFORMATION: absent or positive
<221> NAME/KEY: SITE
<222> LOCATION: (476)..(485)
<223> OTHER INFORMATION: absent or positive
<221> NAME/KEY: SITE
<222> LOCATION: (487)..(490)
<223> OTHER INFORMATION: absent or positive
<221> NAME/KEY: SITE
<222> LOCATION: (492)..(498)
<223> OTHER INFORMATION: absent or positive
<221> NAME/KEY: SITE
<222> LOCATION: (500)
<223> OTHER INFORMATION: absent or positive
<221> NAME/KEY: SITE
<222> LOCATION: (502)
<223> OTHER INFORMATION: absent or positive
<221> NAME/KEY: SITE
<222> LOCATION: (505)..(521)
<223> OTHER INFORMATION: absent or positive
<221> NAME/KEY: SITE
<222> LOCATION: (523)..(524)
<223> OTHER INFORMATION: absent or positive
<221> NAME/KEY: SITE
<222> LOCATION: (526)..(532)
<223> OTHER INFORMATION: absent or positive
<221> NAME/KEY: SITE
<222> LOCATION: (534)..(538)
<223> OTHER INFORMATION: absent or positive
<221> NAME/KEY: SITE
<222> LOCATION: (540)..(544)
<223> OTHER INFORMATION: absent or positive
<221> NAME/KEY: SITE
<222> LOCATION: (547)..(551)
<223> OTHER INFORMATION: absent or positive
<221> NAME/KEY: SITE
<222> LOCATION: (554)..(555)
<223> OTHER INFORMATION: absent or positive
<221> NAME/KEY: SITE
<222> LOCATION: (557)..(558)
<223> OTHER INFORMATION: absent or positive
<221> NAME/KEY: SITE
<222> LOCATION: (560)
<223> OTHER INFORMATION: absent or positive
<221> NAME/KEY: SITE
<222> LOCATION: (562)..(563)
<223> OTHER INFORMATION: absent or positive
<221> NAME/KEY: SITE
<222> LOCATION: (565)..(567)
<223> OTHER INFORMATION: absent or positive
<221> NAME/KEY: SITE
<222> LOCATION: (569)..(575)
<223> OTHER INFORMATION: absent or positive
<221> NAME/KEY: SITE
<222> LOCATION: (577)..(578)
<223> OTHER INFORMATION: absent or positive
<221> NAME/KEY: SITE
<222> LOCATION: (580)..(590)
<223> OTHER INFORMATION: absent or positive
<221> NAME/KEY: SITE
<222> LOCATION: (593)..(602)
<223> OTHER INFORMATION: absent or positive
<221> NAME/KEY: SITE
<222> LOCATION: (604)..(610)
<223> OTHER INFORMATION: absent or positive
<221> NAME/KEY: SITE
<222> LOCATION: (612)..(624)
<223> OTHER INFORMATION: absent or positive
<221> NAME/KEY: SITE
<222> LOCATION: (627)
<223> OTHER INFORMATION: absent or positive
```

```
<221> NAME/KEY: SITE
<222> LOCATION: (631)..(632)
<223> OTHER INFORMATION: absent or positive
<221> NAME/KEY: SITE
<222> LOCATION: (634)..(640)
<223> OTHER INFORMATION: absent or positive
<221> NAME/KEY: SITE
<222> LOCATION: (642)..(643)
<223> OTHER INFORMATION: absent or positive
<221> NAME/KEY: SITE
<222> LOCATION: (646)
<223> OTHER INFORMATION: absent or positive
<221> NAME/KEY: SITE
<222> LOCATION: (648)
<223> OTHER INFORMATION: absent or positive
<221> NAME/KEY: SITE
<222> LOCATION: (650)..(652)
<223> OTHER INFORMATION: absent or positive
<221> NAME/KEY: SITE
<222> LOCATION: (654)
<223> OTHER INFORMATION: absent or positive
<221> NAME/KEY: SITE
<222> LOCATION: (656)..(660)
<223> OTHER INFORMATION: absent or positive

<400> SEQUENCE: 184

Met Asn Lys Xaa Xaa Xaa Xaa Ile Phe Xaa Lys Lys Xaa Ser Xaa
  1               5                  10                  15

Met Xaa Ala Val Ala Glu Xaa Xaa Xaa Xaa Xaa Gly Lys Xaa Xaa Gln
             20                  25                  30

Xaa Xaa Xaa Xaa Xaa Ser Val Xaa Xaa Xaa Xaa Xaa Xaa Xaa Xaa
         35                  40                  45

Ser Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Ile
 65                  70                  75                  80

Xaa Xaa Asp Lys Ser Ala Pro Lys Asn Xaa Gln Xaa Val Ile Leu Xaa
                 85                  90                  95

Thr Xaa Xaa Gly Xaa Pro Xaa Val Asn Ile Gln Thr Pro Xaa Xaa Xaa
            100                 105                 110

Gly Xaa Ser Xaa Asn Arg Xaa Xaa Gln Phe Asp Val Asp Xaa Lys Gly
        115                 120                 125

Xaa Xaa Leu Asn Asn Xaa Arg Xaa Asn Xaa Xaa Xaa Xaa Xaa Xaa
    130                 135                 140

Xaa Xaa Xaa Xaa Asn Pro Xaa Leu Xaa Xaa Gly Xaa Ala Xaa Xaa Ile
145                 150                 155                 160

Xaa Asn Xaa Xaa Xaa Xaa Xaa Xaa Ser Xaa Leu Asn Gly Xaa Xaa
                165                 170                 175

Xaa Val Gly Gly Xaa Xaa Ala Xaa Val Xaa Xaa Ala Asn Pro Xaa Gly
            180                 185                 190

Ile Xaa Val Asn Gly Gly Xaa Xaa Asn Xaa Xaa Xaa Xaa Xaa Leu
        195                 200                 205

Thr Xaa Gly Xaa Pro Xaa Xaa Xaa Xaa Xaa Gly Xaa Leu Thr Gly Phe
    210                 215                 220

Asp Val Xaa Xaa Gly Xaa Xaa Xaa Xaa Gly Xaa Xaa Gly Xaa Xaa Asp
225                 230                 235                 240

Xaa Xaa Xaa Ala Asp Tyr Thr Xaa Xaa Leu Xaa Arg Ala Xaa Xaa Xaa
                245                 250                 255

Xaa Xaa Xaa Xaa Xaa Gly Lys Xaa Xaa Xaa Val Xaa Xaa Gly Xaa Xaa
            260                 265                 270

Lys Xaa Asp Xaa Xaa Xaa Xaa Xaa Xaa Xaa Xaa Xaa Xaa Ala Xaa Xaa
```

-continued

```
                275                 280                 285
Xaa Xaa Xaa Xaa Xaa Xaa Pro Thr Xaa Ala Xaa Asp Thr Ala Xaa Leu
            290                 295                 300
Gly Gly Met Tyr Ala Asp Xaa Ile Thr Leu Ile Xaa Xaa Xaa Xaa Gly
305                 310                 315                 320
Xaa Xaa Xaa Xaa Asn Gly Xaa Xaa Xaa Ala Ala Xaa Xaa Xaa Xaa
            325                 330                 335
Xaa Xaa Xaa Xaa Xaa Gly Xaa Xaa Xaa Asn Ser Gly Xaa Ile Xaa
            340                 345                 350
Xaa Xaa Xaa Xaa Xaa Ala Xaa Xaa Xaa Xaa Xaa Xaa Xaa Xaa Thr
            355                 360                 365
Xaa Xaa Xaa Xaa Xaa Xaa Xaa Xaa Xaa Xaa Xaa Xaa Gly Xaa Ile
370                 375                 380
Xaa Ser Xaa Xaa Xaa Xaa Val Xaa Xaa Xaa Xaa Xaa Xaa Ile Xaa Xaa
385                 390                 395                 400
Xaa Xaa Gly Xaa Xaa Xaa Xaa Xaa Gly Ser Xaa Xaa Xaa Xaa Xaa
            405                 410                 415
Xaa Xaa Xaa Xaa Gly Xaa Xaa Xaa Xaa Xaa Ser Xaa Xaa Xaa Xaa
            420                 425                 430
Asn Asn Xaa Xaa Gly Xaa Xaa Xaa Xaa Xaa Xaa Xaa Ser Xaa Xaa
            435                 440                 445
Xaa Xaa Xaa Xaa Xaa Asn Asp Xaa Xaa Xaa Xaa Ala Xaa Xaa Xaa Val
            450                 455                 460
Xaa Ser Xaa Xaa Xaa Xaa Asp Xaa Xaa Xaa Gly Xaa Xaa Xaa Xaa
465                 470                 475                 480
Xaa Xaa Xaa Xaa Xaa Thr Xaa Xaa Xaa Xaa Gly Xaa Xaa Xaa Xaa
            485                 490                 495
Xaa Xaa Ile Xaa Ala Xaa Asp Thr Xaa Xaa Xaa Xaa Xaa Xaa Xaa
            500                 505                 510
Xaa Xaa Xaa Xaa Xaa Xaa Xaa Xaa Xaa Ser Xaa Xaa Arg Xaa Xaa Xaa
            515                 520                 525
Xaa Xaa Xaa Xaa Gly Xaa Xaa Xaa Xaa Xaa Leu Xaa Xaa Xaa Xaa
            530                 535                 540
Ile Thr Xaa Xaa Xaa Xaa Xaa Ala Lys Xaa Xaa Asn Xaa Xaa Thr Xaa
545                 550                 555                 560
Gly Xaa Xaa Tyr Xaa Xaa Xaa Gly Xaa Xaa Xaa Xaa Xaa Xaa Asp
            565                 570                 575
Xaa Xaa Leu Xaa Xaa Xaa Xaa Xaa Xaa Xaa Xaa Xaa Xaa Ala Ala
            580                 585                 590
Xaa Xaa Xaa Xaa Xaa Xaa Xaa Xaa Xaa Ala Xaa Xaa Xaa Xaa
            595                 600                 605
Xaa Xaa Ala Xaa Xaa Xaa Xaa Xaa Xaa Xaa Xaa Xaa Xaa Xaa
            610                 615                 620
Ser Gly Xaa Leu His Ile Xaa Xaa Ala Xaa Xaa Xaa Xaa Xaa Xaa
625                 630                 635                 640
Gln Xaa Xaa Asn Thr Xaa Leu Xaa Asn Xaa Xaa Xaa Ala Xaa Glu Xaa
            645                 650                 655
Xaa Xaa Xaa Xaa Gly Asn Ile
            660

<210> SEQ ID NO 185
<211> LENGTH: 622
<212> TYPE: PRT
<213> ORGANISM: Artificial Sequence
```

<220> FEATURE:
<223> OTHER INFORMATION: Description of Artificial Sequence: pspA

<400> SEQUENCE: 185

| | | | | | | | | | | | | | | |
|---|---|---|---|---|---|---|---|---|---|---|---|---|---|---|
| Met | Asn | Lys | Arg | Cys | Tyr | Lys | Val | Ile | Phe | Asn | Lys | Lys | Arg | Ser | Cys |
| 1 | | | | 5 | | | | | 10 | | | | | 15 | |
| Met | Met | Ala | Val | Ala | Glu | Asn | Val | His | Arg | Asp | Gly | Lys | Ser | Met | Gln |
| | | | 20 | | | | | 25 | | | | | 30 | | |
| Asp | Ser | Glu | Ala | Ala | Ser | Val | Arg | Val | Thr | Gly | Ala | Ala | Ser | Val | Ser |
| | | 35 | | | | | 40 | | | | | 45 | | | |
| Ser | Ala | Arg | Ala | Ala | Phe | Gly | Phe | Arg | Met | Ala | Ala | Phe | Ser | Val | Met |
| | 50 | | | | | 55 | | | | | 60 | | | | |
| Leu | Ala | Leu | Gly | Val | Ala | Ala | Phe | Ser | Pro | Ala | Pro | Ala | Ser | Gly | Ile |
| 65 | | | | | 70 | | | | | 75 | | | | | 80 |
| Ile | Ala | Asp | Lys | Ser | Ala | Pro | Lys | Asn | Gln | Gln | Ala | Val | Ile | Leu | Gln |
| | | | | 85 | | | | | 90 | | | | | 95 | |
| Thr | Ala | Asn | Gly | Leu | Pro | Gln | Val | Asn | Ile | Gln | Thr | Pro | Ser | Ser | Gln |
| | | | 100 | | | | | 105 | | | | | 110 | | |
| Gly | Val | Ser | Val | Asn | Arg | Phe | Lys | Gln | Phe | Asp | Val | Asp | Glu | Lys | Gly |
| | | 115 | | | | | 120 | | | | | 125 | | | |
| Val | Ile | Leu | Asn | Asn | Ser | Arg | Ser | Asn | Thr | Gln | Thr | Gln | Leu | Gly | Gly |
| | 130 | | | | | 135 | | | | | 140 | | | | |
| Trp | Ile | Gln | Gly | Asn | Pro | His | Leu | Ala | Arg | Gly | Glu | Ala | Arg | Val | Ile |
| 145 | | | | | 150 | | | | | 155 | | | | | 160 |
| Val | Asn | Gln | Ile | Asp | Ser | Ser | Asn | Pro | Ser | Leu | Leu | Asn | Gly | Tyr | Ile |
| | | | | 165 | | | | | 170 | | | | | 175 | |
| Glu | Val | Gly | Gly | Lys | Arg | Ala | Glu | Val | Val | Ala | Asn | Pro | Ser | Gly | |
| | | | 180 | | | | | 185 | | | | | 190 | | |
| Ile | Arg | Val | Asn | Gly | Gly | Leu | Ile | Asn | Ala | Ala | Ser | Val | Thr | Leu | |
| | | 195 | | | | | 200 | | | | | 205 | | | |
| Thr | Ser | Gly | Val | Pro | Val | Leu | Asn | Asn | Gly | Asn | Leu | Thr | Gly | Phe | Asp |
| | 210 | | | | | 215 | | | | | 220 | | | | |
| Val | Ser | Ser | Gly | Lys | Val | Val | Ile | Gly | Gly | Lys | Gly | Leu | Asp | Thr | Ser |
| 225 | | | | | 230 | | | | | 235 | | | | | 240 |
| Asp | Ala | Asp | Tyr | Thr | Arg | Ile | Leu | Ser | Arg | Ala | Ala | Glu | Ile | Asn | Ala |
| | | | | 245 | | | | | 250 | | | | | 255 | |
| Gly | Val | Trp | Gly | Lys | Asp | Val | Lys | Val | Val | Ser | Gly | Lys | Asn | Lys | Leu |
| | | | 260 | | | | | 265 | | | | | 270 | | |
| Asp | Phe | Asp | Gly | Ser | Leu | Ala | Lys | Thr | Ala | Ser | Ala | Pro | Ser | Ser | Ser |
| | | 275 | | | | | 280 | | | | | 285 | | | |
| Asp | Ser | Val | Thr | Pro | Thr | Val | Ala | Ile | Asp | Thr | Ala | Thr | Leu | Gly | Gly |
| | 290 | | | | | 295 | | | | | 300 | | | | |
| Met | Tyr | Ala | Asp | Lys | Ile | Thr | Leu | Ile | Ser | Thr | Asp | Asn | Gly | Ala | Val |
| 305 | | | | | 310 | | | | | 315 | | | | | 320 |
| Ile | Arg | Asn | Lys | Gly | Arg | Ile | Phe | Ala | Ala | Thr | Gly | Val | Thr | Leu | |
| | | | | 325 | | | | | 330 | | | | | 335 | |
| Ser | Ala | Asp | Gly | Lys | Leu | Ser | Asn | Ser | Gly | Ser | Ile | Asp | Ala | Ala | Glu |
| | | | 340 | | | | | 345 | | | | | 350 | | |
| Ile | Thr | Ile | Ser | Ala | Gln | Thr | Val | Asp | Asn | Arg | Gln | Gly | Phe | Ile | Arg |
| | | | 355 | | | | | 360 | | | | | 365 | | |
| Ser | Gly | Lys | Gly | Ser | Val | Leu | Lys | Val | Ser | Asp | Gly | Ile | Asn | Asn | Gln |
| | 370 | | | | | 375 | | | | | 380 | | | | |
| Ala | Gly | Leu | Ile | Gly | Ser | Ala | Gly | Leu | Leu | Asp | Ile | Arg | Asp | Thr | Gly |
| 385 | | | | | 390 | | | | | 395 | | | | | 400 |

```
Lys Ser Ser Leu His Ile Asn Asn Thr Asp Gly Thr Ile Ile Ala Gly
                405                 410                 415

Lys Asp Val Ser Leu Gln Ala Lys Ser Leu Asp Asn Asp Gly Ile Leu
            420                 425                 430

Thr Ala Ala Arg Asp Val Ser Val Ser Leu His Asp Asp Phe Ala Gly
        435                 440                 445

Lys Arg Asp Ile Glu Ala Gly Arg Thr Leu Thr Phe Ser Thr Gln Gly
    450                 455                 460

Arg Leu Lys Asn Thr Arg Ile Ile Gln Ala Gly Asp Thr Val Ser Leu
465                 470                 475                 480

Thr Ala Ala Gln Ile Asp Asn Thr Val Ser Gly Lys Ile Gln Ser Gly
                485                 490                 495

Asn Arg Thr Gly Leu Asn Gly Lys Asn Gly Ile Thr Asn Arg Gly Leu
                500                 505                 510

Ile Asn Ser Asn Gly Ile Thr Leu Leu Gln Thr Glu Ala Lys Ser Asp
                515                 520                 525

Asn Ala Gly Thr Gly Arg Ile Tyr Gly Ser Arg Val Ala Val Glu Ala
                530                 535                 540

Asp Thr Leu Leu Asn Arg Glu Glu Thr Val Asn Gly Glu Thr Lys Ala
545                 550                 555                 560

Ala Val Ile Ala Ala Arg Glu Arg Leu Asp Ile Gly Ala Arg Glu Ile
                565                 570                 575

Glu Asn Arg Glu Ala Ala Leu Leu Ser Ser Ser Gly Asp Leu His Ile
                580                 585                 590

Gly Ser Ala Leu Asn Gly Ser Arg Gln Val Gln Gly Ala Asn Thr Ser
                595                 600                 605

Leu His Asn Arg Ser Ala Ala Ile Glu Ser Ser Gly Asn Ile
                610                 615                 620

<210> SEQ ID NO 186
<211> LENGTH: 400
<212> TYPE: PRT
<213> ORGANISM: Artificial Sequence
<220> FEATURE:
<223> OTHER INFORMATION: Description of Artificial Sequence: ORF114a
<221> NAME/KEY: SITE
<222> LOCATION: (58)
<223> OTHER INFORMATION: place-holder
<221> NAME/KEY: SITE
<222> LOCATION: (105)
<223> OTHER INFORMATION: place-holder
<221> NAME/KEY: SITE
<222> LOCATION: (114)
<223> OTHER INFORMATION: place-holder
<221> NAME/KEY: SITE
<222> LOCATION: (139)
<223> OTHER INFORMATION: place-holder
<221> NAME/KEY: SITE
<222> LOCATION: (179)
<223> OTHER INFORMATION: place-holder
<221> NAME/KEY: SITE
<222> LOCATION: (209)
<223> OTHER INFORMATION: place-holder
<221> NAME/KEY: SITE
<222> LOCATION: (344)..(355)
<223> OTHER INFORMATION: place-holder

<400> SEQUENCE: 186

Leu Gln Gly Lys Leu Gln Gly Lys Asn Leu Ala Val Ser Thr Gly Pro
1               5                   10                  15

Gln Lys Val Asp Tyr Ala Ser Gly Glu Ile Ser Ala Gly Thr Ala Ala
            20                  25                  30
```

```
Gly Thr Lys Pro Thr Ile Ala Leu Asp Thr Ala Ala Leu Gly Gly Met
         35                  40                  45

Tyr Ala Asp Ser Ile Thr Leu Ile Ala Xaa Glu Lys Gly Val Gly Val
 50                  55                  60

Lys Asn Ala Gly Thr Leu Glu Ala Ala Lys Gln Leu Ile Val Thr Ser
 65                  70                  75                  80

Ser Gly Arg Ile Glu Asn Ser Gly Arg Ile Ala Thr Thr Ala Asp Gly
                 85                  90                  95

Thr Glu Ala Ser Pro Thr Tyr Leu Xaa Ile Glu Thr Thr Glu Lys Gly
            100                 105                 110

Ala Xaa Gly Thr Phe Ile Ser Asn Gly Gly Arg Ile Glu Ser Lys Gly
        115                 120                 125

Leu Leu Val Ile Glu Thr Gly Glu Asp Ile Xaa Leu Arg Asn Gly Ala
    130                 135                 140

Val Val Gln Asn Asn Gly Ser Arg Pro Ala Thr Thr Val Leu Asn Ala
145                 150                 155                 160

Gly His Asn Leu Val Ile Glu Ser Lys Thr Asn Val Asn Asn Ala Lys
                165                 170                 175

Gly Ser Xaa Asn Leu Ser Ala Gly Gly Arg Thr Thr Ile Asn Asp Ala
            180                 185                 190

Thr Ile Gln Ala Gly Ser Ser Val Tyr Ser Ser Thr Lys Gly Asp Thr
        195                 200                 205

Xaa Leu Gly Glu Asn Thr Arg Ile Ile Ala Glu Asn Val Thr Val Leu
    210                 215                 220

Ser Asn Gly Ser Ile Gly Ser Ala Ala Val Ile Glu Ala Lys Asp Thr
225                 230                 235                 240

Ala His Ile Glu Ser Gly Lys Pro Leu Ser Leu Glu Thr Ser Thr Val
                245                 250                 255

Ala Ser Asn Ile Arg Leu Asn Asn Gly Asn Ile Lys Gly Gly Lys Gln
            260                 265                 270

Leu Ala Leu Leu Ala Asp Asp Asn Ile Thr Ala Lys Thr Thr Asn Leu
        275                 280                 285

Asn Thr Pro Gly Asn Leu Tyr Val His Thr Gly Lys Asp Leu Asn Leu
290                 295                 300

Asn Val Asp Lys Asp Leu Ser Ala Ala Ser Ile His Leu Lys Ser Asp
305                 310                 315                 320

Asn Ala Ala His Ile Thr Gly Thr Ser Lys Thr Leu Thr Ala Ser Lys
                325                 330                 335

Asp Met Gly Val Glu Ala Gly Xaa Xaa Xaa Xaa Xaa Xaa Xaa Xaa Xaa
            340                 345                 350

Xaa Xaa Xaa Ser Gly Asn Leu His Ile Gln Ala Ala Lys Gly Asn Ile
        355                 360                 365

Gln Leu Arg Asn Thr Lys Leu Asn Ala Ala Lys Ala Leu Glu Thr Thr
    370                 375                 380

Ala Leu Gln Gly Asn Ile Val Ser Asp Gly Leu His Ala Val Ser Ala
385                 390                 395                 400

<210> SEQ ID NO 187
<211> LENGTH: 432
<212> TYPE: PRT
<213> ORGANISM: Artificial Sequence
<220> FEATURE:
<223> OTHER INFORMATION: Description of Artificial Sequence: homology
<221> NAME/KEY: SITE
<222> LOCATION: (4)
```

-continued

```
<223> OTHER INFORMATION: absent or positive
<221> NAME/KEY: SITE
<222> LOCATION: (10)..(14)
<223> OTHER INFORMATION: absent or positive
<221> NAME/KEY: SITE
<222> LOCATION: (16)..(23)
<223> OTHER INFORMATION: absent or positive
<221> NAME/KEY: SITE
<222> LOCATION: (25)
<223> OTHER INFORMATION: absent or positive
<221> NAME/KEY: SITE
<222> LOCATION: (27)
<223> OTHER INFORMATION: absent or positive
<221> NAME/KEY: SITE
<222> LOCATION: (29)..(30)
<223> OTHER INFORMATION: absent or positive
<221> NAME/KEY: SITE
<222> LOCATION: (32)..(34)
<223> OTHER INFORMATION: absent or positive
<221> NAME/KEY: SITE
<222> LOCATION: (36)..(43)
<223> OTHER INFORMATION: absent or positive
<221> NAME/KEY: SITE
<222> LOCATION: (45)..(51)
<223> OTHER INFORMATION: absent or positive
<221> NAME/KEY: SITE
<222> LOCATION: (53)
<223> OTHER INFORMATION: absent or positive
<221> NAME/KEY: SITE
<222> LOCATION: (55)..(63)
<223> OTHER INFORMATION: absent or positive
<221> NAME/KEY: SITE
<222> LOCATION: (65)
<223> OTHER INFORMATION: absent or positive
<221> NAME/KEY: SITE
<222> LOCATION: (67)
<223> OTHER INFORMATION: absent or positive
<221> NAME/KEY: SITE
<222> LOCATION: (69)..(71)
<223> OTHER INFORMATION: absent or positive
<221> NAME/KEY: SITE
<222> LOCATION: (73)..(75)
<223> OTHER INFORMATION: absent or positive
<221> NAME/KEY: SITE
<222> LOCATION: (77)..(81)
<223> OTHER INFORMATION: absent or positive
<221> NAME/KEY: SITE
<222> LOCATION: (83)..(91)
<223> OTHER INFORMATION: absent or positive
<221> NAME/KEY: SITE
<222> LOCATION: (93)..(94)
<223> OTHER INFORMATION: absent or positive
<221> NAME/KEY: SITE
<222> LOCATION: (97)..(108)
<223> OTHER INFORMATION: absent or positive
<221> NAME/KEY: SITE
<222> LOCATION: (110)
<223> OTHER INFORMATION: absent or positive
<221> NAME/KEY: SITE
<222> LOCATION: (112)..(116)
<223> OTHER INFORMATION: absent or positive
<221> NAME/KEY: SITE
<222> LOCATION: (118)
<223> OTHER INFORMATION: absent or positive
<221> NAME/KEY: SITE
<222> LOCATION: (120)..(123)
<223> OTHER INFORMATION: absent or positive
<221> NAME/KEY: SITE
<222> LOCATION: (126)
<223> OTHER INFORMATION: absent or positive
<221> NAME/KEY: SITE
<222> LOCATION: (128)
<223> OTHER INFORMATION: absent or positive
<221> NAME/KEY: SITE
<222> LOCATION: (130)..(140)
<223> OTHER INFORMATION: absent or positive
<221> NAME/KEY: SITE
<222> LOCATION: (142)..(147)
<223> OTHER INFORMATION: absent or positive
```

-continued

```
<221> NAME/KEY: SITE
<222> LOCATION: (149)..(158)
<223> OTHER INFORMATION: absent or positive
<221> NAME/KEY: SITE
<222> LOCATION: (160)..(163)
<223> OTHER INFORMATION: absent or positive
<221> NAME/KEY: SITE
<222> LOCATION: (165)
<223> OTHER INFORMATION: absent or positive
<221> NAME/KEY: SITE
<222> LOCATION: (168)..(171)
<223> OTHER INFORMATION: absent or positive
<221> NAME/KEY: SITE
<222> LOCATION: (173)..(181)
<223> OTHER INFORMATION: absent or positive
<221> NAME/KEY: SITE
<222> LOCATION: (183)..(186)
<223> OTHER INFORMATION: absent or positive
<221> NAME/KEY: SITE
<222> LOCATION: (188)..(190)
<223> OTHER INFORMATION: absent or positive
<221> NAME/KEY: SITE
<222> LOCATION: (192)
<223> OTHER INFORMATION: absent or positive
<221> NAME/KEY: SITE
<222> LOCATION: (195)..(200)
<223> OTHER INFORMATION: absent or positive
<221> NAME/KEY: SITE
<222> LOCATION: (202)..(205)
<223> OTHER INFORMATION: absent or positive
<221> NAME/KEY: SITE
<222> LOCATION: (208)..(218)
<223> OTHER INFORMATION: absent or positive
<221> NAME/KEY: SITE
<222> LOCATION: (220)..(223)
<223> OTHER INFORMATION: absent or positive
<221> NAME/KEY: SITE
<222> LOCATION: (225)..(231)
<223> OTHER INFORMATION: absent or positive
<221> NAME/KEY: SITE
<222> LOCATION: (234)..(244)
<223> OTHER INFORMATION: absent or positive
<221> NAME/KEY: SITE
<222> LOCATION: (246)..(252)
<223> OTHER INFORMATION: absent or positive
<221> NAME/KEY: SITE
<222> LOCATION: (254)..(263)
<223> OTHER INFORMATION: absent or positive
<221> NAME/KEY: SITE
<222> LOCATION: (265)..(272)
<223> OTHER INFORMATION: absent or positive
<221> NAME/KEY: SITE
<222> LOCATION: (274)..(275)
<223> OTHER INFORMATION: absent or positive
<221> NAME/KEY: SITE
<222> LOCATION: (277)..(280)
<223> OTHER INFORMATION: absent or positive
<221> NAME/KEY: SITE
<222> LOCATION: (283)..(285)
<223> OTHER INFORMATION: absent or positive
<221> NAME/KEY: SITE
<222> LOCATION: (287)..(294)
<223> OTHER INFORMATION: absent or positive
<221> NAME/KEY: SITE
<222> LOCATION: (296)..(297)
<223> OTHER INFORMATION: absent or positive
<221> NAME/KEY: SITE
<222> LOCATION: (299)..(301)
<223> OTHER INFORMATION: absent or positive
<221> NAME/KEY: SITE
<222> LOCATION: (303)..(309)
<223> OTHER INFORMATION: absent or positive
<221> NAME/KEY: SITE
<222> LOCATION: (311)..(318)
<223> OTHER INFORMATION: absent or positive
<221> NAME/KEY: SITE
<222> LOCATION: (321)..(323)
<223> OTHER INFORMATION: absent or positive
<221> NAME/KEY: SITE
```

```
<222> LOCATION: (325)..(329)
<223> OTHER INFORMATION: absent or positive
<221> NAME/KEY: SITE
<222> LOCATION: (331)..(337)
<223> OTHER INFORMATION: absent or positive
<221> NAME/KEY: SITE
<222> LOCATION: (339)
<223> OTHER INFORMATION: absent or positive
<221> NAME/KEY: SITE
<222> LOCATION: (341)..(349)
<223> OTHER INFORMATION: absent or positive
<221> NAME/KEY: SITE
<222> LOCATION: (351)
<223> OTHER INFORMATION: absent or positive
<221> NAME/KEY: SITE
<222> LOCATION: (353)
<223> OTHER INFORMATION: absent or positive
<221> NAME/KEY: SITE
<222> LOCATION: (355)..(356)
<223> OTHER INFORMATION: absent or positive
<221> NAME/KEY: SITE
<222> LOCATION: (358)..(363)
<223> OTHER INFORMATION: absent or positive
<221> NAME/KEY: SITE
<222> LOCATION: (365)
<223> OTHER INFORMATION: absent or positive
<221> NAME/KEY: SITE
<222> LOCATION: (367)..(369)
<223> OTHER INFORMATION: absent or positive
<221> NAME/KEY: SITE
<222> LOCATION: (371)..(391)
<223> OTHER INFORMATION: absent or positive
<221> NAME/KEY: SITE
<222> LOCATION: (394)..(403)
<223> OTHER INFORMATION: absent or positive
<221> NAME/KEY: SITE
<222> LOCATION: (406)..(408)
<223> OTHER INFORMATION: absent or positive
<221> NAME/KEY: SITE
<222> LOCATION: (410)..(411)
<223> OTHER INFORMATION: absent or positive
<221> NAME/KEY: SITE
<222> LOCATION: (413)..(419)
<223> OTHER INFORMATION: absent or positive
<221> NAME/KEY: SITE
<222> LOCATION: (421)..(428)
<223> OTHER INFORMATION: absent or positive
<221> NAME/KEY: SITE
<222> LOCATION: (430)..(431)
<223> OTHER INFORMATION: absent or positive

<400> SEQUENCE: 187

Leu Gln Gly Xaa Leu Gln Gly Lys Asn Xaa Xaa Xaa Xaa Xaa Gly Xaa
  1               5                  10                  15

Xaa Xaa Xaa Xaa Xaa Xaa Xaa Gly Xaa Ile Xaa Ala Xaa Xaa Ala Xaa
             20                  25                  30

Xaa Xaa Lys Xaa Xaa Xaa Xaa Xaa Xaa Xaa Ala Xaa Xaa Xaa Xaa
         35                  40                  45

Xaa Xaa Xaa Ser Xaa Thr Xaa Xaa Xaa Xaa Xaa Xaa Xaa Val
     50                  55                  60

Xaa Asn Xaa Gly Xaa Xaa Xaa Ala Xaa Xaa Xaa Leu Xaa Xaa Xaa Xaa
 65                  70                  75                  80

Xaa Gly Xaa Xaa Xaa Xaa Xaa Xaa Xaa Xaa Ile Xaa Xaa Thr Ala
             85                  90                  95

Xaa Xaa Xaa Xaa Xaa Xaa Xaa Xaa Xaa Xaa Xaa Glu Xaa Thr Xaa
            100                 105                 110

Xaa Xaa Xaa Xaa Gly Xaa Thr Xaa Xaa Xaa Xaa Gly Gly Xaa Ile Xaa
            115                 120                 125

Ser Xaa Xaa Xaa Xaa Xaa Xaa Xaa Xaa Xaa Ile Xaa Xaa Xaa
            130                 135             140
```

```
Xaa Xaa Xaa Val Xaa Xaa Xaa Xaa Xaa Xaa Xaa Xaa Thr Xaa
145                 150                 155                 160

Xaa Xaa Xaa Gly Xaa Asn Leu Xaa Xaa Xaa Xaa Lys Xaa Xaa Xaa Xaa
                165             170                 175

Xaa Xaa Xaa Xaa Xaa Val Xaa Xaa Xaa Gly Xaa Xaa Xaa Leu Xaa
            180             185                 190

Ala Gly Xaa Xaa Xaa Xaa Xaa Asp Xaa Xaa Xaa Xaa Ala Gly Xaa
        195                 200                 205

Xaa Xaa Xaa Xaa Xaa Xaa Xaa Xaa Xaa Tyr Xaa Xaa Xaa Xaa Gly
    210                 215                 220

Xaa Xaa Xaa Xaa Xaa Xaa Xaa Thr Arg Xaa Xaa Xaa Xaa Xaa Xaa
225                 230                 235                 240

Xaa Xaa Xaa Xaa Gly Xaa Xaa Xaa Xaa Xaa Xaa Ile Xaa Xaa Xaa
                245                 250                 255

Xaa Xaa Xaa Xaa Xaa Xaa Gly Xaa Xaa Xaa Xaa Xaa Xaa Xaa
                260             265                 270

Thr Xaa Xaa Ser Xaa Xaa Xaa Xaa Asn Asn Xaa Xaa Xaa Lys Xaa Xaa
        275                 280                 285

Xaa Xaa Xaa Xaa Xaa Xaa Ala Xaa Xaa Asn Xaa Xaa Xaa Lys Xaa Xaa
    290                 295                 300

Xaa Xaa Xaa Xaa Xaa Gly Xaa Xaa Xaa Xaa Xaa Xaa Xaa Lys Asp
305                 310                 315                 320

Xaa Xaa Xaa Asn Xaa Xaa Xaa Xaa Ser Xaa Xaa Xaa Xaa Xaa Xaa
                325                 330                 335

Xaa Ser Xaa Asn Xaa Xaa Xaa Xaa Xaa Xaa Xaa Xaa His Xaa Thr
        340                 345                 350

Xaa Thr Xaa Xaa Thr Xaa Xaa Xaa Xaa Xaa Asp Xaa Gly Xaa Xaa
        355                 360                 365

Xaa Gly Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Lys Gly Xaa Xaa Xaa Xaa Xaa Xaa
385                 390                 395                 400

Xaa Xaa Xaa Asn Thr Xaa Xaa Xaa Ala Xaa Xaa Ala Xaa Xaa Xaa
                405                 410                 415

Xaa Xaa Xaa Gly Xaa Xaa Xaa Xaa Xaa Xaa Xaa Ala Xaa Xaa Ala
            420                 425                 430

<210> SEQ ID NO 188
<211> LENGTH: 402
<212> TYPE: PRT
<213> ORGANISM: Artificial Sequence
<220> FEATURE:
<223> OTHER INFORMATION: Description of Artificial Sequence: pspA

<400> SEQUENCE: 188

Leu Gln Gly Asp Leu Gln Gly Lys Asn Ile Phe Ala Ala Ala Gly Ser
  1               5                  10                  15

Asp Ile Thr Asn Thr Gly Ser Ile Gly Ala Glu Asn Ala Leu Leu Leu
             20                  25                  30

Lys Ala Ser Asn Ile Glu Ser Arg Ser Glu Thr Arg Ser Asn Gln
         35                  40                  45

Asn Glu Gln Gly Ser Val Arg Asn Ile Gly Arg Val Ala Gly Ile Tyr
     50                  55                  60

Leu Thr Gly Arg Gln Asn Gly Ser Val Leu Leu Asp Ala Gly Asn Asn
 65                  70                  75                  80
```

-continued

```
Ile Val Leu Thr Ala Ser Glu Leu Thr Asn Gln Ser Glu Asp Gly Gln
                 85                  90                  95

Thr Val Leu Asn Ala Gly Gly Asp Ile Arg Ser Asp Thr Thr Gly Ile
            100                 105                 110

Ser Arg Asn Gln Asn Thr Ile Phe Asp Ser Asp Asn Tyr Val Ile Arg
        115                 120                 125

Lys Glu Gln Asn Glu Val Gly Ser Thr Ile Arg Thr Arg Gly Asn Leu
    130                 135                 140

Ser Leu Asn Ala Lys Gly Asp Ile Arg Ile Arg Ala Ala Glu Val Gly
145                 150                 155                 160

Ser Glu Gln Gly Arg Leu Lys Leu Ala Ala Gly Arg Asp Ile Lys Val
                165                 170                 175

Glu Ala Gly Lys Ala His Thr Glu Thr Glu Asp Ala Leu Lys Tyr Thr
            180                 185                 190

Gly Arg Ser Gly Gly Gly Ile Lys Gln Lys Met Thr Arg His Leu Lys
        195                 200                 205

Asn Gln Asn Gly Gln Ala Val Ser Gly Thr Leu Asp Gly Lys Glu Ile
    210                 215                 220

Ile Leu Val Ser Gly Arg Asp Ile Thr Val Thr Gly Ser Asn Ile Ile
225                 230                 235                 240

Ala Asp Asn His Thr Ile Leu Ser Ala Lys Asn Asn Ile Val Leu Lys
                245                 250                 255

Ala Ala Glu Thr Arg Ser Arg Ser Ala Glu Met Asn Lys Lys Glu Lys
            260                 265                 270

Ser Gly Leu Met Gly Ser Gly Gly Ile Gly Phe Thr Ala Gly Ser Lys
        275                 280                 285

Lys Asp Thr Gln Thr Asn Arg Ser Glu Thr Val Ser His Thr Glu Ser
    290                 295                 300

Val Val Gly Ser Leu Asn Gly Asn Thr Leu Ile Ser Ala Gly Lys His
305                 310                 315                 320

Tyr Thr Gln Thr Gly Ser Thr Ile Ser Ser Pro Gln Gly Asp Val Gly
                325                 330                 335

Ile Ser Ser Gly Lys Ile Ser Ile Asp Ala Ala Gln Asn Arg Tyr Ser
            340                 345                 350

Gln Glu Ser Lys Gln Val Tyr Glu Gln Lys Gly Val Thr Val Ala Ile
        355                 360                 365

Ser Val Pro Val Val Asn Thr Val Met Gly Ala Val Asp Ala Val Lys
    370                 375                 380

Ala Val Gln Thr Val Gly Lys Ser Lys Asn Ser Arg Val Asn Ala Met
385                 390                 395                 400

Ala Ala
```

<210> SEQ ID NO 189
<211> LENGTH: 497
<212> TYPE: PRT
<213> ORGANISM: Artificial Sequence
<220> FEATURE:
<223> OTHER INFORMATION: Description of Artificial Sequence: ORF116
<221> NAME/KEY: SITE
<222> LOCATION: (25)
<223> OTHER INFORMATION: place-holder
<221> NAME/KEY: SITE
<222> LOCATION: (59)..(74)
<223> OTHER INFORMATION: place-holder
<221> NAME/KEY: SITE
<222> LOCATION: (78)..(83)
<223> OTHER INFORMATION: place-holder

```
<221> NAME/KEY: SITE
<222> LOCATION: (129)
<223> OTHER INFORMATION: place-holder
<221> NAME/KEY: SITE
<222> LOCATION: (160)..(174)
<223> OTHER INFORMATION: place-holder
<221> NAME/KEY: SITE
<222> LOCATION: (183)..(191)
<223> OTHER INFORMATION: place-holder
<221> NAME/KEY: SITE
<222> LOCATION: (227)
<223> OTHER INFORMATION: place-holder
<221> NAME/KEY: SITE
<222> LOCATION: (282)
<223> OTHER INFORMATION: place-holder
<221> NAME/KEY: SITE
<222> LOCATION: (315)
<223> OTHER INFORMATION: place-holder
<221> NAME/KEY: SITE
<222> LOCATION: (328)..(339)
<223> OTHER INFORMATION: place-holder

<400> SEQUENCE: 189
```

Glu Ala Val Gly Ser Asn Ile Gly Gly Lys Met Ile Val Ala Ala
 1               5                  10                  15

Gly Gln Asp Ile Asn Val Arg Gly Xaa Ser Leu Ile Ser Asp Lys Gly
            20                  25                  30

Ile Val Leu Lys Ala Gly His Asp Ile Asp Ile Ser Thr Ala His Asn
        35                  40                  45

Arg Tyr Thr Gly Asn Glu Tyr His Glu Ser Xaa Xaa Xaa Xaa Xaa
 50                  55                  60

Xaa Xaa Xaa Xaa Xaa Xaa Xaa Xaa Xaa Xaa Asn Arg Lys Xaa Xaa Xaa
 65                  70                  75                  80

Xaa Xaa Xaa Arg Thr Asn Ile Val His Thr Gly Ser Ile Ile Gly Ser
            85                  90                  95

Leu Asn Gly Asp Thr Val Thr Val Ala Gly Asn Arg Tyr Arg Gln Thr
            100                 105                 110

Gly Ser Thr Val Ser Ser Pro Glu Gly Arg Asn Thr Val Thr Ala Lys
        115                 120                 125

Xaa Ile Asp Val Glu Phe Ala Asn Asn Arg Tyr Ala Thr Asp Tyr Ala
130                 135                 140

His Thr Gln Glu Gln Lys Gly Leu Thr Val Ala Leu Asn Val Pro Xaa
145                 150                 155                 160

Xaa Xaa Xaa Xaa Xaa Xaa Xaa Xaa Xaa Xaa Xaa Xaa Xaa Xaa Gly Lys
                165                 170                 175

Ser Lys Asn Lys Arg Val Xaa Xaa Xaa Xaa Xaa Xaa Xaa Xaa Xaa Trp
            180                 185                 190

Gln Ser Tyr Gln Ala Thr Gln Gln Met Gln Gln Phe Ala Pro Ser Ser
        195                 200                 205

Ser Ala Gly Gln Gly Gln Asn Tyr Asn Gln Ser Pro Ser Ile Ser Val
    210                 215                 220

Ser Ile Xaa Tyr Gly Glu Gln Lys Ser Arg Asn Glu Gln Lys Arg His
225                 230                 235                 240

Tyr Thr Glu Ala Ala Ala Ser Gln Ile Ile Gly Lys Gly Gln Thr Thr
                245                 250                 255

Leu Ala Ala Thr Gly Ser Gly Glu Gln Ser Asn Ile Asn Ile Thr Gly
            260                 265                 270

Ser Asp Val Ile Gly His Ala Gly Thr Xaa Leu Ile Ala Asp Asn His
        275                 280                 285

Ile Arg Leu Gln Ser Ala Lys Gln Asp Gly Ser Glu Gln Ser Lys Asn

```
                  290             295                 300

Lys Ser Ser Gly Trp Asn Ala Gly Val Arg Xaa Lys Ile Gly Asn Gly
305                 310                 315                 320

Ile Arg Phe Gly Ile Thr Ala Xaa Xaa Xaa Xaa Xaa Xaa Xaa Xaa Xaa
                325                 330                 335

Xaa Xaa Xaa Ser Thr Thr His Arg His Thr His Val Gly Ser Thr Thr
            340                 345                 350

Gly Lys Thr Thr Ile Arg Ser Gly Gly Asp Thr Thr Leu Lys Gly Val
        355                 360                 365

Gln Leu Ile Gly Lys Gly Ile Gln Ala Asp Thr Arg Asn Leu His Ile
    370                 375                 380

Glu Ser Val Gln Asp Thr Glu Thr Tyr Gln Ser Lys Gln Gln Asn Gly
385                 390                 395                 400

Asn Val Gln Val Thr Val Gly Tyr Gly Phe Ser Ala Ser Gly Ser Tyr
                405                 410                 415

Arg Gln Ser Lys Val Lys Ala Asp His Ala Ser Val Thr Gly Gln Ser
                420                 425                 430

Gly Ile Tyr Ala Gly Glu Asp Gly Tyr Gln Ile Lys Val Arg Asp Asn
            435                 440                 445

Thr Asp Leu Lys Gly Gly Ile Ile Thr Ser Ser Gln Ser Ala Glu Asp
450                 455                 460

Lys Gly Lys Asn Leu Phe Gln Thr Ala Thr Leu Thr Ala Ser Asp Ile
465                 470                 475                 480

Gln Asn His Ser Arg Tyr Glu Gly Arg Ser Phe Gly Ile Gly Gly Ser
                485                 490                 495

Phe

<210> SEQ ID NO 190
<211> LENGTH: 502
<212> TYPE: PRT
<213> ORGANISM: Artificial Sequence
<220> FEATURE:
<223> OTHER INFORMATION: Description of Artificial Sequence: overlap
      identity
<221> NAME/KEY: SITE
<222> LOCATION: (1)
<223> OTHER INFORMATION: absent or positive
<221> NAME/KEY: SITE
<222> LOCATION: (4)..(8)
<223> OTHER INFORMATION: absent or positive
<221> NAME/KEY: SITE
<222> LOCATION: (10)..(12)
<223> OTHER INFORMATION: absent or positive
<221> NAME/KEY: SITE
<222> LOCATION: (14)..(16)
<223> OTHER INFORMATION: absent or positive
<221> NAME/KEY: SITE
<222> LOCATION: (18)
<223> OTHER INFORMATION: absent or positive
<221> NAME/KEY: SITE
<222> LOCATION: (21)
<223> OTHER INFORMATION: absent or positive
<221> NAME/KEY: SITE
<222> LOCATION: (23)
<223> OTHER INFORMATION: absent or positive
<221> NAME/KEY: SITE
<222> LOCATION: (25)..(27)
<223> OTHER INFORMATION: absent or positive
<221> NAME/KEY: SITE
<222> LOCATION: (29)
<223> OTHER INFORMATION: absent or positive
<221> NAME/KEY: SITE
<222> LOCATION: (31)..(34)
<223> OTHER INFORMATION: absent or positive
<221> NAME/KEY: SITE
```

```
<222> LOCATION: (36)
<223> OTHER INFORMATION: absent or positive
<221> NAME/KEY: SITE
<222> LOCATION: (38)..(40)
<223> OTHER INFORMATION: absent or positive
<221> NAME/KEY: SITE
<222> LOCATION: (42)..(45)
<223> OTHER INFORMATION: absent or positive
<221> NAME/KEY: SITE
<222> LOCATION: (47)..(48)
<223> OTHER INFORMATION: absent or positive
<221> NAME/KEY: SITE
<222> LOCATION: (50)..(53)
<223> OTHER INFORMATION: absent or positive
<221> NAME/KEY: SITE
<222> LOCATION: (55)..(76)
<223> OTHER INFORMATION: absent or positive
<221> NAME/KEY: SITE
<222> LOCATION: (78)..(88)
<223> OTHER INFORMATION: absent or positive
<221> NAME/KEY: SITE
<222> LOCATION: (91)
<223> OTHER INFORMATION: absent or positive
<221> NAME/KEY: SITE
<222> LOCATION: (93)..(94)
<223> OTHER INFORMATION: absent or positive
<221> NAME/KEY: SITE
<222> LOCATION: (100)
<223> OTHER INFORMATION: absent or positive
<221> NAME/KEY: SITE
<222> LOCATION: (102)..(104)
<223> OTHER INFORMATION: absent or positive
<221> NAME/KEY: SITE
<222> LOCATION: (107)..(108)
<223> OTHER INFORMATION: absent or positive
<221> NAME/KEY: SITE
<222> LOCATION: (110)
<223> OTHER INFORMATION: absent or positive
<221> NAME/KEY: SITE
<222> LOCATION: (116)
<223> OTHER INFORMATION: absent or positive
<221> NAME/KEY: SITE
<222> LOCATION: (120)
<223> OTHER INFORMATION: absent or positive
<221> NAME/KEY: SITE
<222> LOCATION: (122)..(129)
<223> OTHER INFORMATION: absent or positive
<221> NAME/KEY: SITE
<222> LOCATION: (131)..(134)
<223> OTHER INFORMATION: absent or positive
<221> NAME/KEY: SITE
<222> LOCATION: (136)
<223> OTHER INFORMATION: absent or positive
<221> NAME/KEY: SITE
<222> LOCATION: (140)..(147)
<223> OTHER INFORMATION: absent or positive
<221> NAME/KEY: SITE
<222> LOCATION: (152)
<223> OTHER INFORMATION: absent or positive
<221> NAME/KEY: SITE
<222> LOCATION: (156)..(157)
<223> OTHER INFORMATION: absent or positive
<221> NAME/KEY: SITE
<222> LOCATION: (160)..(177)
<223> OTHER INFORMATION: absent or positive
<221> NAME/KEY: SITE
<222> LOCATION: (183)
<223> OTHER INFORMATION: absent or positive
<221> NAME/KEY: SITE
<222> LOCATION: (186)..(207)
<223> OTHER INFORMATION: absent or positive
<221> NAME/KEY: SITE
<222> LOCATION: (209)..(210)
<223> OTHER INFORMATION: absent or positive
<221> NAME/KEY: SITE
<222> LOCATION: (212)..(214)
<223> OTHER INFORMATION: absent or positive
<221> NAME/KEY: SITE
<222> LOCATION: (219)..(226)
```

-continued

```
<223> OTHER INFORMATION: absent or positive
<221> NAME/KEY: SITE
<222> LOCATION: (231)..(232)
<223> OTHER INFORMATION: absent or positive
<221> NAME/KEY: SITE
<222> LOCATION: (238)..(240)
<223> OTHER INFORMATION: absent or positive
<221> NAME/KEY: SITE
<222> LOCATION: (242)..(246)
<223> OTHER INFORMATION: absent or positive
<221> NAME/KEY: SITE
<222> LOCATION: (248)..(253)
<223> OTHER INFORMATION: absent or positive
<221> NAME/KEY: SITE
<222> LOCATION: (255)
<223> OTHER INFORMATION: absent or positive
<221> NAME/KEY: SITE
<222> LOCATION: (257)
<223> OTHER INFORMATION: absent or positive
<221> NAME/KEY: SITE
<222> LOCATION: (259)..(261)
<223> OTHER INFORMATION: absent or positive
<221> NAME/KEY: SITE
<222> LOCATION: (263)
<223> OTHER INFORMATION: absent or positive
<221> NAME/KEY: SITE
<222> LOCATION: (265)
<223> OTHER INFORMATION: absent or positive
<221> NAME/KEY: SITE
<222> LOCATION: (267)
<223> OTHER INFORMATION: absent or positive
<221> NAME/KEY: SITE
<222> LOCATION: (269)..(270)
<223> OTHER INFORMATION: absent or positive
<221> NAME/KEY: SITE
<222> LOCATION: (272)
<223> OTHER INFORMATION: absent or positive
<221> NAME/KEY: SITE
<222> LOCATION: (274)
<223> OTHER INFORMATION: absent or positive
<221> NAME/KEY: SITE
<222> LOCATION: (281)
<223> OTHER INFORMATION: absent or positive
<221> NAME/KEY: SITE
<222> LOCATION: (283)..(284)
<223> OTHER INFORMATION: absent or positive
<221> NAME/KEY: SITE
<222> LOCATION: (287)
<223> OTHER INFORMATION: absent or positive
<221> NAME/KEY: SITE
<222> LOCATION: (289)
<223> OTHER INFORMATION: absent or positive
<221> NAME/KEY: SITE
<222> LOCATION: (291)
<223> OTHER INFORMATION: absent or positive
<221> NAME/KEY: SITE
<222> LOCATION: (293)..(298)
<223> OTHER INFORMATION: absent or positive
<221> NAME/KEY: SITE
<222> LOCATION: (300)
<223> OTHER INFORMATION: absent or positive
<221> NAME/KEY: SITE
<222> LOCATION: (302)..(304)
<223> OTHER INFORMATION: absent or positive
<221> NAME/KEY: SITE
<222> LOCATION: (306)
<223> OTHER INFORMATION: absent or positive
<221> NAME/KEY: SITE
<222> LOCATION: (308)
<223> OTHER INFORMATION: absent or positive
<221> NAME/KEY: SITE
<222> LOCATION: (312)
<223> OTHER INFORMATION: absent or positive
<221> NAME/KEY: SITE
<222> LOCATION: (314)
<223> OTHER INFORMATION: absent or positive
<221> NAME/KEY: SITE
<222> LOCATION: (319)..(321)
<223> OTHER INFORMATION: absent or positive
```

-continued

```
<221> NAME/KEY: SITE
<222> LOCATION: (323)..(324)
<223> OTHER INFORMATION: absent or positive
<221> NAME/KEY: SITE
<222> LOCATION: (327)
<223> OTHER INFORMATION: absent or positive
<221> NAME/KEY: SITE
<222> LOCATION: (330)
<223> OTHER INFORMATION: absent or positive
<221> NAME/KEY: SITE
<222> LOCATION: (333)..(345)
<223> OTHER INFORMATION: absent or positive
<221> NAME/KEY: SITE
<222> LOCATION: (347)..(348)
<223> OTHER INFORMATION: absent or positive
<221> NAME/KEY: SITE
<222> LOCATION: (350)..(351)
<223> OTHER INFORMATION: absent or positive
<221> NAME/KEY: SITE
<222> LOCATION: (353)
<223> OTHER INFORMATION: absent or positive
<221> NAME/KEY: SITE
<222> LOCATION: (356)..(359)
<223> OTHER INFORMATION: absent or positive
<221> NAME/KEY: SITE
<222> LOCATION: (361)
<223> OTHER INFORMATION: absent or positive
<221> NAME/KEY: SITE
<222> LOCATION: (363)
<223> OTHER INFORMATION: absent or positive
<221> NAME/KEY: SITE
<222> LOCATION: (369)..(370)
<223> OTHER INFORMATION: absent or positive
<221> NAME/KEY: SITE
<222> LOCATION: (373)
<223> OTHER INFORMATION: absent or positive
<221> NAME/KEY: SITE
<222> LOCATION: (376)
<223> OTHER INFORMATION: absent or positive
<221> NAME/KEY: SITE
<222> LOCATION: (380)..(386)
<223> OTHER INFORMATION: absent or positive
<221> NAME/KEY: SITE
<222> LOCATION: (392)
<223> OTHER INFORMATION: absent or positive
<221> NAME/KEY: SITE
<222> LOCATION: (396)..(400)
<223> OTHER INFORMATION: absent or positive
<221> NAME/KEY: SITE
<222> LOCATION: (403)
<223> OTHER INFORMATION: absent or positive
<221> NAME/KEY: SITE
<222> LOCATION: (405)..(407)
<223> OTHER INFORMATION: absent or positive
<221> NAME/KEY: SITE
<222> LOCATION: (417)..(418)
<223> OTHER INFORMATION: absent or positive
<221> NAME/KEY: SITE
<222> LOCATION: (422)..(423)
<223> OTHER INFORMATION: absent or positive
<221> NAME/KEY: SITE
<222> LOCATION: (426)..(428)
<223> OTHER INFORMATION: absent or positive
<221> NAME/KEY: SITE
<222> LOCATION: (430)
<223> OTHER INFORMATION: absent or positive
<221> NAME/KEY: SITE
<222> LOCATION: (434)..(435)
<223> OTHER INFORMATION: absent or positive
<221> NAME/KEY: SITE
<222> LOCATION: (440)
<223> OTHER INFORMATION: absent or positive
<221> NAME/KEY: SITE
<222> LOCATION: (443)
<223> OTHER INFORMATION: absent or positive
<221> NAME/KEY: SITE
<222> LOCATION: (447)
<223> OTHER INFORMATION: absent or positive
<221> NAME/KEY: SITE
```

-continued

```
<222> LOCATION: (449)
<223> OTHER INFORMATION: absent or positive
<221> NAME/KEY: SITE
<222> LOCATION: (451)..(453)
<223> OTHER INFORMATION: absent or positive
<221> NAME/KEY: SITE
<222> LOCATION: (455)
<223> OTHER INFORMATION: absent or positive
<221> NAME/KEY: SITE
<222> LOCATION: (457)
<223> OTHER INFORMATION: absent or positive
<221> NAME/KEY: SITE
<222> LOCATION: (459)..(462)
<223> OTHER INFORMATION: absent or positive
<221> NAME/KEY: SITE
<222> LOCATION: (464)..(468)
<223> OTHER INFORMATION: absent or positive
<221> NAME/KEY: SITE
<222> LOCATION: (471)
<223> OTHER INFORMATION: absent or positive
<221> NAME/KEY: SITE
<222> LOCATION: (475)..(476)
<223> OTHER INFORMATION: absent or positive
<221> NAME/KEY: SITE
<222> LOCATION: (478)..(483)
<223> OTHER INFORMATION: absent or positive
<221> NAME/KEY: SITE
<222> LOCATION: (489)..(496)
<223> OTHER INFORMATION: absent or positive
<221> NAME/KEY: SITE
<222> LOCATION: (498)..(499)
<223> OTHER INFORMATION: absent or positive
<221> NAME/KEY: SITE
<222> LOCATION: (501)
<223> OTHER INFORMATION: absent or positive

<400> SEQUENCE: 190

Xaa Ala Val Xaa Xaa Xaa Xaa Gly Xaa Xaa Ile Xaa Xaa Xaa
 1               5                   10                  15

Gly Xaa Asp Ile Xaa Val Xaa Gly Xaa Xaa Ile Xaa Asp Xaa Xaa
            20                  25                  30

Xaa Xaa Leu Xaa Ala Xaa Xaa Xaa Ile Xaa Xaa Xaa Xaa Ala Xaa Xaa
        35                  40                  45

Arg Xaa Xaa Xaa Glu Xaa Xaa Xaa Xaa Xaa Xaa Xaa Xaa
 50                  55                  60

Xaa Xaa Xaa Xaa Xaa Xaa Xaa Xaa Xaa Xaa Xaa Lys Xaa Xaa
65                  70                  75                  80

Xaa Xaa Xaa Xaa Xaa Xaa Xaa Xaa His Thr Xaa Ser Xaa Xaa Gly Ser
                85                  90                  95

Leu Asn Gly Xaa Thr Xaa Xaa Xaa Ala Gly Xaa Xaa Tyr Xaa Gln Thr
            100                 105                 110

Gly Ser Thr Xaa Ser Ser Pro Xaa Gly Xaa Xaa Xaa Xaa Xaa Xaa
        115                 120                 125

Xaa Ile Xaa Xaa Xaa Xaa Ala Xaa Asn Arg Tyr Xaa Xaa Xaa Xaa
130                 135                 140

Xaa Xaa Xaa Glu Gln Lys Gly Xaa Thr Val Ala Xaa Xaa Val Pro Xaa
145                 150                 155                 160

Xaa Xaa Xaa Xaa Xaa Xaa Xaa Xaa Xaa Xaa Xaa Xaa Xaa Xaa
                165                 170                 175

Xaa Gly Lys Ser Lys Asn Xaa Arg Val Xaa Xaa Xaa Xaa Xaa Xaa
            180                 185                 190

Xaa Xaa Xaa Xaa Xaa Xaa Xaa Xaa Xaa Xaa Xaa Xaa Xaa Ala
        195                 200                 205

Xaa Xaa Pro Xaa Xaa Xaa Ala Gly Gln Gly Xaa Xaa Xaa Xaa Xaa
210                 215                 220
```

```
Xaa Xaa Ile Ser Val Ser Xaa Xaa Tyr Gly Glu Gln Lys Xaa Xaa Xaa
225                 230                 235                 240

Glu Xaa Xaa Xaa Xaa Xaa Thr Xaa Xaa Xaa Xaa Xaa Ile Xaa Gly
            245                 250                 255

Xaa Gly Xaa Xaa Xaa Leu Xaa Ala Xaa Gly Xaa Gly Xaa Xaa Ser Xaa
        260                 265                 270

Ile Xaa Ile Thr Gly Ser Asp Val Xaa Gly Xaa Xaa Gly Thr Xaa Leu
        275                 280                 285

Xaa Ala Xaa Asn Xaa Xaa Xaa Xaa Xaa Ala Xaa Gln Xaa Xaa Xaa
        290                 295                 300

Glu Xaa Ser Xaa Asn Lys Ser Xaa Gly Xaa Asn Ala Gly Val Xaa Xaa
305                 310                 315                 320

Xaa Ile Xaa Xaa Gly Ile Xaa Phe Gly Xaa Thr Ala Xaa Xaa Xaa
            325                 330                 335

Xaa Xaa Xaa Xaa Xaa Xaa Xaa Thr Xaa Xaa Arg Xaa Xaa His
            340                 345                 350

Xaa Gly Ser Xaa Xaa Xaa Xaa Thr Xaa Ile Xaa Ser Gly Gly Asp Thr
        355                 360                 365

Xaa Xaa Lys Gly Xaa Gln Leu Xaa Gly Lys Gly Xaa Xaa Xaa Xaa
370                 375                 380

Xaa Xaa Leu His Ile Glu Ser Xaa Gln Asp Thr Xaa Xaa Xaa Xaa
385                 390                 395                 400

Lys Gln Xaa Asn Xaa Xaa Xaa Gln Val Thr Val Gly Tyr Gly Phe Ser
            405                 410                 415

Xaa Xaa Gly Ser Tyr Xaa Xaa Ser Lys Xaa Xaa Xaa Asp Xaa Ala Ser
            420                 425                 430

Val Xaa Xaa Gln Ser Gly Ile Xaa Ala Gly Xaa Asp Gly Tyr Xaa Ile
        435                 440                 445

Xaa Val Xaa Xaa Xaa Thr Xaa Leu Xaa Gly Xaa Xaa Xaa Xaa Ser Xaa
        450                 455                 460

Xaa Xaa Xaa Xaa Asp Lys Xaa Lys Asn Leu Xaa Xaa Thr Xaa Xaa
465                 470                 475                 480

Xaa Xaa Xaa Asp Ile Gln Asn His Xaa Xaa Xaa Xaa Xaa Xaa Xaa
            485                 490                 495

Gly Xaa Xaa Gly Xaa Phe
            500

<210> SEQ ID NO 191
<211> LENGTH: 491
<212> TYPE: PRT
<213> ORGANISM: Artificial Sequence
<220> FEATURE:
<223> OTHER INFORMATION: Description of Artificial Sequence: pspA

<400> SEQUENCE: 191

Gln Ala Val Ser Gly Thr Leu Asp Gly Lys Glu Ile Ile Leu Val Ser
1               5                   10                  15

Gly Arg Asp Ile Thr Val Thr Gly Ser Asn Ile Ile Ala Asp Asn His
            20                  25                  30

Thr Ile Leu Ser Ala Lys Asn Asn Ile Val Leu Lys Ala Ala Glu Thr
        35                  40                  45

Arg Ser Arg Ser Ala Glu Met Asn Lys Lys Glu Lys Ser Gly Leu Met
    50                  55                  60

Gly Ser Gly Gly Ile Gly Phe Thr Ala Gly Ser Lys Lys Asp Thr Gln
65                  70                  75                  80
```

-continued

```
Thr Asn Arg Ser Glu Thr Val Ser His Thr Glu Ser Val Val Gly Ser
                 85                  90                  95
Leu Asn Gly Asn Thr Leu Ile Ser Ala Gly Lys His Tyr Thr Gln Thr
            100                 105                 110
Gly Ser Thr Ile Ser Ser Pro Gln Gly Asp Val Gly Ile Ser Ser Gly
        115                 120                 125
Lys Ile Ser Ile Asp Ala Ala Gln Asn Arg Tyr Ser Gln Glu Ser Lys
    130                 135                 140
Gln Val Tyr Glu Gln Lys Gly Val Thr Val Ala Ile Ser Val Pro Val
145                 150                 155                 160
Val Asn Thr Val Met Gly Ala Val Asp Ala Val Lys Ala Val Gln Thr
                165                 170                 175
Val Gly Lys Ser Lys Asn Ser Arg Val Asn Ala Met Ala Ala Ala Asn
            180                 185                 190
Ala Leu Asn Lys Gly Val Asp Ser Gly Val Ala Leu Tyr Asn Ala Ala
        195                 200                 205
Arg Asn Pro Lys Lys Ala Ala Gly Gln Gly Ile Ser Val Ser Val Thr
    210                 215                 220
Tyr Gly Glu Gln Lys Asn Thr Ser Glu Ser Arg Ile Lys Gly Thr Gln
225                 230                 235                 240
Val Gln Glu Gly Lys Ile Thr Gly Gly Lys Val Ser Leu Thr Ala
                245                 250                 255
Ser Gly Ala Gly Lys Asp Ser Arg Ile Thr Ile Thr Gly Ser Asp Val
            260                 265                 270
Tyr Gly Gly Lys Gly Thr Arg Leu Lys Ala Glu Asn Ala Val Gln Ile
        275                 280                 285
Glu Ala Ala Arg Gln Thr His Gln Glu Arg Ser Glu Asn Lys Ser Ala
    290                 295                 300
Gly Phe Asn Ala Gly Val Ala Ile Ala Ile Asn Lys Gly Ile Ser Phe
305                 310                 315                 320
Gly Phe Thr Ala Gly Ala Asn Tyr Gly Lys Gly Tyr Gly Asn Gly Asp
                325                 330                 335
Glu Thr Ala Tyr Arg Asn Ser His Ile Gly Ser Lys Asp Ser Gln Thr
            340                 345                 350
Ala Ile Glu Ser Gly Gly Asp Thr Val Ile Lys Gly Gly Gln Leu Lys
        355                 360                 365
Gly Lys Gly Val Gly Val Thr Ala Glu Ser Leu His Ile Glu Ser Leu
    370                 375                 380
Gln Asp Thr Ala Val Phe Lys Gly Lys Gln Glu Asn Val Ser Ala Gln
385                 390                 395                 400
Val Thr Val Gly Tyr Gly Phe Ser Val Gly Gly Ser Tyr Asn Arg Ser
                405                 410                 415
Lys Ser Ser Asp Tyr Ala Ser Val Asn Glu Gln Ser Gly Ile Phe
            420                 425                 430
Ala Gly Gly Asp Gly Tyr Arg Ile Arg Val Asn Gly Lys Thr Gly Leu
        435                 440                 445
Val Gly Ala Ala Val Val Ser Asp Ala Asp Lys Ser Lys Asn Leu Leu
    450                 455                 460
Lys Thr Ser Glu Ile Trp His Lys Asp Ile Gln Asn His Ala Ser Ala
465                 470                 475                 480
Ala Ala Ser Ala Leu Gly Leu Ser Gly Gly Phe
                485                 490
```

```
<210> SEQ ID NO 192
<211> LENGTH: 310
<212> TYPE: PRT
<213> ORGANISM: Artificial Sequence
<220> FEATURE:
<223> OTHER INFORMATION: Description of Artificial Sequence: ORF41
<221> NAME/KEY: SITE
<222> LOCATION: (19)
<223> OTHER INFORMATION: place-holder
<221> NAME/KEY: SITE
<222> LOCATION: (33)
<223> OTHER INFORMATION: place-holder
<221> NAME/KEY: SITE
<222> LOCATION: (47)
<223> OTHER INFORMATION: place-holder

<400> SEQUENCE: 192

Tyr Arg Arg His Leu Leu Cys Lys Tyr Ile Tyr Arg Phe Pro Ile Tyr
 1               5                  10                  15

Cys Pro Xaa Ala Cys Val Ala Glu Asp Thr Pro Tyr Ala Cys Tyr Leu
            20                  25                  30

Xaa Gln Leu Gln Val Thr Lys Asp Val Asn Trp Asn Gln Val Xaa Leu
        35                  40                  45

Ala Tyr Asp Lys Trp Asp Tyr Lys Gln Glu Gly Leu Thr Gly Ala Gly
    50                  55                  60

Ala Ala Ile Ile Ala Leu Ala Val Thr Val Thr Ala Gly Ala Gly
65                  70                  75                  80

Ala Gly Ala Ala Leu Gly Leu Asn Gly Ala Ala Ala Thr Asp
                85                  90                  95

Ala Ala Phe Ala Ser Leu Ala Ser Gln Ala Ser Val Ser Leu Ile Asn
            100                 105                 110

Asn Lys Gly Asn Ile Gly Asn Thr Leu Lys Glu Leu Gly Arg Ser Ser
        115                 120                 125

Thr Val Lys Asn Leu Met Val Ala Val Ala Thr Ala Gly Val Ala Asp
    130                 135                 140

Lys Ile Gly Ala Ser Ala Leu Asn Asn Val Ser Asp Lys Gln Trp Ile
145                 150                 155                 160

Asn Asn Leu Thr Val Asn Leu Ala Asn Ala Gly Ser Ala Ala Leu Ile
                165                 170                 175

Asn Thr Ala Val Asn Gly Gly Ser Leu Lys Asp Asn Leu Glu Ala Asn
            180                 185                 190

Ile Leu Ala Ala Leu Val Asn Thr Ala His Gly Glu Ala Ala Ser Lys
        195                 200                 205

Ile Lys Gln Leu Asp Gln His Tyr Ile Thr His Lys Ile Ala His Ala
    210                 215                 220

Ile Ala Gly Cys Ala Ala Ala Ala Asn Lys Gly Lys Cys Gln Asp
225                 230                 235                 240

Gly Ala Ile Gly Ala Ala Val Gly Glu Ile Gly Glu Ala Leu Thr
                245                 250                 255

Asn Gly Lys Asn Pro Asp Thr Leu Thr Ala Lys Glu Arg Glu Gln Ile
            260                 265                 270

Leu Ala Tyr Ser Lys Leu Val Ala Gly Thr Val Ser Gly Val Val Gly
        275                 280                 285

Gly Asp Val Asn Ala Ala Asn Ala Ala Glu Val Ala Val Lys Asn
    290                 295                 300

Asn Gln Leu Ser Asp Lys
305                 310
```

```
<210> SEQ ID NO 193
<211> LENGTH: 330
<212> TYPE: PRT
<213> ORGANISM: Artificial Sequence
<220> FEATURE:
<223> OTHER INFORMATION: Description of Artificial Sequence: ORF41a
<221> NAME/KEY: SITE
<222> LOCATION: (61)
<223> OTHER INFORMATION: place-holder
<221> NAME/KEY: SITE
<222> LOCATION: (122)
<223> OTHER INFORMATION: place-holder
<221> NAME/KEY: SITE
<222> LOCATION: (158)
<223> OTHER INFORMATION: place-holder
<221> NAME/KEY: SITE
<222> LOCATION: (280)
<223> OTHER INFORMATION: place-holder
<221> NAME/KEY: SITE
<222> LOCATION: (297)
<223> OTHER INFORMATION: place-holder

<400> SEQUENCE: 193

Tyr Leu Lys Gln Leu Gln Val Ala Lys Asn Ile Asn Trp Asn Gln Val
  1               5                  10                  15

Gln Leu Ala Tyr Asp Arg Trp Asp Tyr Lys Gln Glu Gly Leu Thr Glu
             20                  25                  30

Ala Gly Ala Ala Ile Ile Ala Leu Ala Val Thr Val Thr Ser Gly
         35                  40                  45

Ala Gly Thr Gly Ala Val Leu Gly Leu Asn Gly Ala Xaa Ala Ala Ala
         50                  55                  60

Thr Asp Ala Ala Phe Ala Ser Leu Ala Ser Gln Ala Ser Val Ser Phe
 65                  70                  75                  80

Ile Asn Asn Lys Gly Asp Val Gly Lys Thr Leu Lys Glu Leu Gly Arg
                 85                  90                  95

Ser Ser Thr Val Lys Asn Leu Val Val Ala Ala Thr Ala Gly Val
            100                 105                 110

Ala Asp Lys Ile Gly Ala Ser Ala Leu Xaa Asn Val Ser Asp Lys Gln
            115                 120                 125

Trp Ile Asn Asn Leu Thr Val Asn Leu Ala Asn Ala Gly Ser Ala Ala
130                 135                 140

Leu Ile Asn Thr Ala Val Asn Gly Gly Ser Leu Lys Asp Xaa Leu Glu
145                 150                 155                 160

Ala Asn Ile Leu Ala Ala Leu Val Asn Thr Ala His Gly Glu Ala Ala
                165                 170                 175

Ser Lys Ile Lys Gln Leu Asp Gln His Tyr Ile Val His Lys Ile Ala
            180                 185                 190

His Ala Ile Ala Gly Cys Ala Ala Ala Ala Asn Lys Gly Lys Cys
            195                 200                 205

Gln Asp Gly Ala Ile Gly Ala Ala Val Gly Glu Ile Val Gly Glu Ala
210                 215                 220

Leu Thr Asn Gly Lys Asn Pro Asp Thr Leu Thr Ala Lys Glu Arg Glu
225                 230                 235                 240

Gln Ile Leu Ala Tyr Ser Lys Leu Val Ala Gly Thr Val Ser Gly Val
                245                 250                 255

Val Gly Gly Asp Val Asn Ala Ala Asn Ala Ala Glu Val Ala Val
            260                 265                 270

Lys Asn Asn Gln Leu Ser Asp Xaa Glu Gly Arg Glu Phe Asp Asn Glu
275                 280                 285
```

Met Thr Ala Cys Ala Lys Gln Asn Xaa Pro Gln Leu Cys Arg Lys Asn
            290                 295                 300

Thr Val Lys Lys Tyr Gln Asn Val Ala Asp Lys Arg Leu Ala Ala Ser
305                 310                 315                 320

Ile Ala Ile Cys Thr Asp Ile Ser Arg Ser
                325                 330

<210> SEQ ID NO 194
<211> LENGTH: 180
<212> TYPE: PRT
<213> ORGANISM: Artificial Sequence
<220> FEATURE:
<223> OTHER INFORMATION: Description of Artificial Sequence: ORF51a

<400> SEQUENCE: 194

Tyr Lys Leu Leu Ala Ile Gly Ser Val Val Gly Ser Ile Leu Gly Val
  1               5                  10                  15

Lys Leu Leu Leu Ile Leu Pro Val Ser Trp Leu Leu Leu Leu Met Ala
                 20                  25                  30

Ile Ile Thr Leu Tyr Tyr Ser Val Asn Gly Ile Leu Asn Val Cys Ala
             35                  40                  45

Lys Ala Lys Asn Ile Gln Val Val Ala Asn Asn Lys Asn Met Val Leu
         50                  55                  60

Phe Gly Phe Leu Ala Gly Ile Ile Gly Gly Ser Thr Asn Ala Met Ser
 65                  70                  75                  80

Pro Ile Leu Leu Ile Phe Leu Leu Ser Glu Thr Glu Asn Lys Asn Arg
                 85                  90                  95

Ile Ala Lys Ser Ser Asn Leu Cys Tyr Leu Leu Ala Lys Ile Val Gln
            100                 105                 110

Ile Tyr Met Leu Arg Asp Gln Tyr Trp Leu Leu Asn Lys Ser Glu Tyr
        115                 120                 125

Gly Leu Ile Phe Leu Leu Ser Val Leu Ser Val Ile Gly Leu Tyr Val
    130                 135                 140

Gly Ile Arg Leu Arg Thr Lys Ile Ser Pro Asn Phe Phe Lys Met Leu
145                 150                 155                 160

Ile Phe Ile Val Leu Leu Val Leu Ala Leu Lys Ile Gly Tyr Ser Gly
                165                 170                 175

Leu Ile Lys Leu
            180

<210> SEQ ID NO 195
<211> LENGTH: 180
<212> TYPE: PRT
<213> ORGANISM: Artificial Sequence
<220> FEATURE:
<223> OTHER INFORMATION: Description of Artificial Sequence: ORF82a

<400> SEQUENCE: 195

Met Arg His Met Lys Asn Lys Asn Tyr Leu Leu Val Phe Ile Val Leu
  1               5                  10                  15

His Ile Thr Leu Ile Val Ile Asn Ile Val Phe Gly Tyr Phe Val Phe
                 20                  25                  30

Leu Phe Asp Phe Phe Ala Phe Leu Phe Ala Asn Val Phe Leu Ala
             35                  40                  45

Val Asn Leu Leu Phe Leu Glu Lys Asn Ile Lys Asn Lys Leu Leu Phe
         50                  55                  60

Leu Leu Pro Ile Ser Ile Ile Trp Met Val Ile His Ile Ser Met
 65                  70                  75                  80

-continued

```
Ile Asn Ile Lys Phe Tyr Lys Phe Glu His Gln Ile Lys Glu Gln Asn
            85              90              95

Ile Ser Ser Ile Thr Gly Val Ile Lys Pro His Asp Ser Tyr Asn Tyr
            100             105             110

Val Tyr Asp Ser Asn Gly Tyr Ala Lys Leu Lys Asp Asn His Arg Tyr
        115             120             125

Gly Arg Val Ile Arg Glu Thr Pro Tyr Ile Asp Val Val Ala Ser Asp
    130             135             140

Val Lys Asn Lys Ser Ile Arg Leu Ser Leu Val Cys Gly Ile His Ser
145             150             155             160

Tyr Ala Pro Cys Ala Asn Phe Ile Lys Phe Ala Lys Lys Pro Val Lys
            165             170             175

Ile Tyr Phe Tyr
            180
```